US012527885B2

(12) United States Patent
Jaafar-Thiel et al.

(10) Patent No.: US 12,527,885 B2
(45) Date of Patent: Jan. 20, 2026

(54) HIGH PURITY COPPER RADIOPHARMACEUTICAL COMPOSITIONS AND DIAGNOSTIC AND THERAPEUTIC USES THEREOF

(71) Applicants: Nuclidium AG, Basel (CH); University of Basel, Basel (CH)

(72) Inventors: Leila Jaafar-Thiel, Erlangen (DE); Melpomeni Fani, Basel (CH); Jacopo Millul, Basel (CH); Francesco De Rose, Munich (DE)

(73) Assignees: Nuclidium AG, Basel (CH); University of Basel, Basel (CH)

( * ) Notice: Subject to any disclaimer, the term of this patent is extended or adjusted under 35 U.S.C. 154(b) by 0 days.

(21) Appl. No.: 18/477,496

(22) Filed: Sep. 28, 2023

(65) Prior Publication Data

US 2024/0173441 A1 May 30, 2024

Related U.S. Application Data

(63) Continuation of application No. 18/474,218, filed on Sep. 25, 2023.

(60) Provisional application No. 63/520,329, filed on Aug. 17, 2023, provisional application No. 63/416,479, filed on Oct. 14, 2022, provisional application No. 63/409,687, filed on Sep. 23, 2022.

(51) Int. Cl.
*A61K 51/04* (2006.01)
*A61B 5/055* (2006.01)
*A61K 31/30* (2006.01)
*A61K 51/08* (2006.01)
*C07B 59/00* (2006.01)

(52) U.S. Cl.
CPC .......... *A61K 51/0482* (2013.01); *A61B 5/055* (2013.01); *A61K 31/30* (2013.01); *A61K 51/0455* (2013.01); *A61K 51/0459* (2013.01); *A61K 51/083* (2013.01); *A61K 51/088* (2013.01); *C07B 59/002* (2013.01); *A61K 2121/00* (2013.01); *A61K 2123/00* (2013.01); *C07B 2200/05* (2013.01)

(58) Field of Classification Search
CPC ............ A61K 51/0482; A61K 51/0455; A61K 51/0459; A61K 51/083; A61K 51/088; A61B 5/055; C07B 59/002
USPC .......................................................... 424/1.69
See application file for complete search history.

(56) References Cited

U.S. PATENT DOCUMENTS

| | | | |
|---|---|---|---|
| 6,011,825 | A | 1/2000 | Welch et al. |
| 6,306,393 | B1 | 10/2001 | Goldenberg |
| 6,875,886 | B2 | 4/2005 | Frangioni |
| 7,960,342 | B2 | 6/2011 | Rivier et al. |
| 8,501,687 | B2 | 8/2013 | Rivier et al. |
| 8,526,561 | B2 | 9/2013 | Ehst et al. |
| 8,691,761 | B2 | 4/2014 | Rivier et al. |
| 9,312,037 | B2 | 4/2016 | Ehst et al. |
| 10,134,497 | B2 | 11/2018 | Ehst et al. |
| 10,522,261 | B2 | 12/2019 | DeGrado et al. |
| 11,049,628 | B2 | 6/2021 | Ehst et al. |
| 11,318,121 | B2 | 5/2022 | Low et al. |
| 11,413,360 | B2 | 8/2022 | Wurzer et al. |
| 11,497,822 | B1 | 11/2022 | Kim et al. |
| 11,661,402 | B2 | 5/2023 | Pomper et al. |
| 2004/0097418 | A1 | 5/2004 | Coy et al. |
| 2008/0199370 | A1 | 8/2008 | Mourtada et al. |
| 2008/0299040 | A1 | 12/2008 | Rivier et al. |
| 2008/0311037 | A1 | 12/2008 | Heston et al. |
| 2010/0183509 | A1 | 7/2010 | Babich et al. |
| 2014/0323718 | A1 | 10/2014 | Donnelly et al. |
| 2016/0228587 | A1 | 8/2016 | Eder et al. |
| 2022/0016274 | A1 | 1/2022 | McCann |
| 2022/0096663 | A1 | 3/2022 | Basilion et al. |
| 2022/0118120 | A1 | 4/2022 | Wurzer et al. |
| 2023/0147962 | A1 | 5/2023 | Biancofiore et al. |

FOREIGN PATENT DOCUMENTS

| | | | |
|---|---|---|---|
| AU | 2018382479 | A1 | 4/2020 |
| EP | 0607103 | A2 | 7/1994 |
| EP | 2076535 | B1 | 3/2013 |
| EP | 2433963 | B1 | 6/2014 |
| EP | 2383289 | B1 | 10/2014 |
| EP | 2801582 | A1 | 11/2014 |
| EP | 2801582 | B1 | 9/2017 |
| EP | 3495355 | A1 | 6/2019 |

(Continued)

OTHER PUBLICATIONS

Svedjehed et al. EJNMMI Radiopharm Chem. May 2020, 1-14. (Year: 2020).*
Gourni et al. PLoS One 2015 10(12), 1-16. (Year: 2015).*
Kohler et al. Appl. Radiat. Iso. 81 (2013) 268-271. (Year: 2013).*
Moon et al. EJNMMI Radiopharm. Chem. 2020, 5(19), 1-20.*

(Continued)

*Primary Examiner* — Michael G. Hartley
*Assistant Examiner* — Sean R Donohue
(74) *Attorney, Agent, or Firm* — Olivia Uitto; Carl Morales; Goodwin Procter LP

(57) ABSTRACT

The present disclosure relates to the field of nuclear imaging and therapy, and more specifically to high purity copper radiotracer compositions useful in imaging, such as positron emission tomography (PET) and single-photon emission computerized tomography (SPECT), and therapy. More specifically, the present disclosure relates to novel compositions useful in imaging and treatment of conditions such as prostate cancer, somatostatin receptor-expressing tumors, like neuroendocrine tumor, epithelial tumors, as well as to methods wherein such compositions are prepared.

69 Claims, 40 Drawing Sheets

(56) References Cited

FOREIGN PATENT DOCUMENTS

| | | | | | |
|---|---|---|---|---|---|
| KR | 2022006286 | A | * | 1/2022 | |
| WO | WO 2008/048942 | A2 | | 4/2008 | |
| WO | WO 2009/129311 | A2 | | 10/2009 | |
| WO | WO 2010/108125 | A2 | | 9/2010 | |
| WO | WO 2013/029616 | A1 | | 3/2013 | |
| WO | 2015/175972 | A2 | | 11/2015 | |
| WO | WO 2018/111989 | A1 | | 6/2018 | |
| WO | WO 2018/215627 | A1 | | 11/2018 | |
| WO | WO-2019083990 | A2 | * | 5/2019 | ......... A61K 49/0032 |
| WO | WO 2019/115547 | A1 | | 6/2019 | |
| WO | WO 2019/154886 | A1 | | 8/2019 | |
| WO | WO 2021/160825 | A1 | | 8/2021 | |
| WO | WO 2021/225760 | A1 | | 11/2021 | |
| WO | WO 2022/090488 | A1 | | 5/2022 | |
| WO | WO-2022099420 | A1 | * | 5/2022 | ............... G21G 1/10 |
| WO | WO 2022/171811 | A1 | | 8/2022 | |
| WO | WO 2022/212958 | A1 | | 10/2022 | |
| WO | WO 2022/266499 | A1 | | 12/2022 | |
| WO | WO 2023/057457 | A1 | | 4/2023 | |
| WO | WO 2023/144379 | A1 | | 8/2023 | |

OTHER PUBLICATIONS

Ahmedova, A. et al. "Copper Radiopharmaceuticals for Theranostic Applications." European Journal of Medicinal Chemistry, vol. 157, Sep. 5, 2018, pp. 1406-1425.
Alberts, I. L. et al. "Comparing the Diagnostic Performance of Radiotracers in Recurrent Prostate Cancer: A Systematic Review and Network Meta-Analysis." European Journal of Nuclear Medicine and Molecular Imaging, vol. 48, Feb. 6, 2021, pp. 2978-2989.
Anderson, R-C. et al. "Management Impact of $^{68}$Ga-DOTATATE PET/CT in Neuroendocrine Tumors." Nuclear Medicine and Molecular Imaging, vol. 55, Jan. 7, 2021, pp. 31-37.
Ballal, S. et al. "First-in-Human Results on the Biodistribution, Pharmacokinetics, and Dosimetry of [$^{177}$Lu]Lu-DOTA.SA.FAPi and [$^{177}$Lu]Lu-DOTAGA.(SA.FAPi)$_2$." Pharmaceuticals, vol. 14, No. 12, Nov. 24, 2021, pp. 1-18.
Banerjee, S. R. et al. "$^{64}$Cu-Labeled Inhibitors of Prostate-Specific Membrane Antigen for PET Imaging of Prostate Cancer." Journal of Medicinal Chemistry, vol. 57, No. 6, Mar. 27, 2014, pp. 2657-2669.
Banerjee, S. R. et al. "$^{68}$Ga-Labeled Inhibitors of Prostate-Specific Membrane Antigen (PSMA) for Imaging Prostate Cancer." Journal of Medicinal Chemistry, vol. 53, No. 14, Jul. 22, 2010, pp. 5333-5341.
Baum, R. P. et al. "Feasibility, Biodistribution and Preliminary Dosimetry in Peptide-Targeted Radionuclide Therapy (PTRT) of Diverse Adenocarcinomas using $^{177}$Lu-FAP-2286: First-in-Human Results." The Journal of Nuclear Medicine, vol. 63, No. 3, Mar. 2022, pp. 1-45.
Baum, R. P. et al. "First-in-Human Study of Novel SSTR Antagonist $^{177}$Lu-DOTA-LM3 for Peptide Receptor Radionuclide Therapy in Patients with Metastatic Neuroendocrine Neoplasms: Dosimetry, Safety and Efficacy." The Journal of Nuclear Medicine, vol. 62, No. 11, Nov. 2021, pp. 1571-1581.
Baum, R. P. et al. "First-in-Human Study of Novel SSTR Antagonist $^{177}$Lu-DOTA-LM3 for Peptide Receptor Radionuclide Therapy in Patients with Metastatic Neuroendocrine Neoplasms: Dosimetry, Safety and Efficacy." The Journal of Nuclear Medicine, Epub, Mar. 5, 2021, pp. 1-30.
Bauer, W. et al. "SMS 201-995: A Very Potent and Selective Octapeptide Analogue of Somatostatin with Prolonged Action." Life Sciences, vol. 31, No. 11, Sep. 13, 1982, pp. 1133-1140.
Bavelaar, B. M. et al. "Subcellular Targeting of Theranostic Radionuclides." Frontiers in Pharmacology, vol. 9, Sep. 2018, pp. 1-17.
Benešová, M. et al. "Albumin-Binding PSMA Ligands: Optimization of the Tissue Distribution Profile." Molecular Pharmaceutics, vol. 15, No. 3, Mar. 5, 2018, pp. 934-946.
Benešová, M. et al. "Linker Modification Strategies to Control the Prostate-Specific Membrane Antigen (PSMA)-Targeting and Pharmacokinetic Properties of DOTA-Conjugated PSMA Inhibitors." Journal of Medicinal Chemistry, vol. 59, No. 5, Mar. 10, 2016, pp. 1761-1775.
Benešová, M. et al. "Preclinical Evaluation of a Tailor-Made DOTA-Conjugated PSMA Inhibitor with Optimized Linker Moiety for Imaging and Endoradiotherapy of Prostate Cancer." The Journal of Nuclear Medicine, vol. 56, No. 6, Jun. 2015, pp. 914-920.
Bernabeu, T. B. et al. "$^{61}$Cu-PSMA Versus $^{68}$Ga-PSMA for PET Imaging of Prostate Cancer." Abstract, European Journal of Nuclear Medicine and Molecular Imaging, vol. 48, Suppl. 1, Oct. 20-23, 2021, pp. S20-S21.
Bernabeu, T. B. et al. "$^{61}$Cu-PSMA: A New Radiotracer for PET Imaging of Prostate Cancer." Abstract, European Journal of Nuclear Medicine and Molecular Imaging, vol. 48, Suppl. 1, Oct. 20-23, 2021, pp. S15.
Bernabeu, T. B. et al. "$^{61}$Cu-PSMA: A New Radiotracer for PET Imaging of Prostate Cancer." 34th Annual Congress of the European Association of Nuclear Medicine, Oct. 20-23, 2021, 10 slides.
Bois, F. et al. "[$^{68}$Ga]Ga-PSMA-11 in Prostate Cancer: A Comprehensive Review." American Journal of Nuclear Medicine and Molecular Imaging, vol. 10, No. 6, Dec. 15, 2020, pp. 349-374.
Brabander, T. et al. "Long-Term Efficacy, Survival, and Safety of [$^{177}$Lu-DOTA$^0$, Tyr$^3$]octreotate in Patients with Gastroenteropancreatic and Bronchial Neuroendocrine Tumors." Clinical Cancer Research, vol. 23, No. 16, Aug. 15, 2017, pp. 4617-4624.
Bughda, R. et al. "Fibroblast Activation Protein (FAP)-Targeted CAR-T Cells: Launching an Attack on Tumor Stroma." ImmunoTargets and Therapy, vol. 10, Aug. 5, 2021, pp. 313-323.
Calais, J. "FAP: The Next Billion Dollar Nuclear Theranostics Target?" The Journal of Nuclear Medicine, vol. 61, No. 2, Feb. 2020, pp. 163-165.
Calderoni, L. et al. "Evaluation of an Automated Module Synthesis and a Sterile Cold Kit-Based Preparation of $^{68}$Ga-PSMA-11 in Patients with Prostate Cancer." The Journal of Nuclear Medicine, vol. 61, No. 5, May 2020, pp. 716-722.
Cardinale, J. et al. "Preclinical Evaluation of $^{18}$F-PSMA-1007, a New Prostate-Specific Membrane Antigen Ligand for Prostate Cancer Imaging." The Journal of Nuclear Medicine, vol. 58, No. 3, Mar. 2017, pp. 425-431.
Cardinale, J. et al. "Procedures for the GMP-Compliant Production and Quality Control of [$^{18}$F]PSMA-1007: A Next Generation Radiofluorinated Tracers for the Detection of Prostate Cancer." Pharmaceuticals, vol. 10, No. 4, Sep. 27, 2017, pp. 1-18.
Casnici, C. et al. "Anti-Inflammatory Effect of Somatostatin Analogue Octreotide on Rheumatoid Arthritis Synoviocytes." Inflammation, vol. 41, No. 5, Oct. 2018, pp. 1648-1660.
Cescato, R. et al. "Design and in vitro Characterization of Highly Sst$_2$-Selective Somatostatin Antagonists Suitable for Radio-Targeting." Journal of Medicinal Chemistry, Author Manuscript, vol. 51, No. 13, Jul. 10, 2008, pp. 4030-4037.
Chatalic, K. L. S. et al. "Towards Personalized Treatment of Postate Cancer: PSMA I&T, a Promising Prostate-Specific Membrane Antigen-Targeted Theranostic Agent." Theranostics, vol. 6, No. 6, Apr. 12, 2016, pp. 849-861.
Chen, H. et al. "Usefulness of [$^{68}$Ga]Ga-DOTA-FAPI-04 PET/CT in Patients Presenting with Inconclusive [$^{18}$F]FDG PET/CT Findings." European Journal of Nuclear Medicine and Molecular Imaging, vol. 48, Jun. 25, 2020, pp. 73-86.
Cremonesi, M. et al. "Dosimetry in Peptide Radionuclide Receptor Therapy: A Review." The Journal of Nuclear Medicine, vol. 47, No. 9, Sep. 2006, pp. 1467-1475.
Cui, C. et al. "Synthesis and Evaluation of [$^{64}$Cu]PSMA-617 Targeted for Prostate-Specific Membrane Antigen in Prostate Cancer." American Journal of Nuclear Medicine and Molecular Imaging, vol. 7, No. 2, Apr. 30, 2017, pp. 40-52.
Cwikla, J. B. et al. "Efficacy of Radionuclide Treatment DOTATATE Y-90 in Patients with Progressive Metastatic Gastroenteropancreatic Neuroendocrine Carcinomas (GEP-NETs): A Phase II Study." Annals of Oncology, vol. 21, No. 4, Apr. 2010, pp. 787-794.
Dalm, S. U. et al. "Comparison of the Therapeutic Response to Treatment with a $^{177}$Lu-Labeled Somatostatin Receptor Agonist and

(56) References Cited

OTHER PUBLICATIONS

Antagonist in Preclinical Models." The Journal of Nuclear Medicine, vol. 57, No. 2, Feb. 2016, pp. 260-265.
Das, S. et al. "$^{177}$Lu-DOTATATE for the Treatment of Gastroenteropancreatic Neuroendocrine Tumors." Expert Review of Gastroenterology & Hepatology, Author Manuscript, vol. 13, No. 11, Nov. 2019, pp. 1-20.
Deng, M. et al. "Comparison of $^{68}$Ga-FAPI and $^{18}$F-FDG PET/CT in the Imaging of Pancreatic Cancer with Liver Metastases." Clinical Nuclear Medicine, vol. 46, No. 7, Jul. 2021, pp. 589-591.
Dietlein, F. et al. "PSA-Stratified Performance of $^{18}$F- and $^{68}$Ga-PSMA PET in Patients with Biochemical Recurrence of Prostate Cancer." The Journal of Nuclear Medicine, vol. 58, No. 6, Jun. 2017, pp. 947-952.
Donin, N. M. et al. "Why Targeting PSMA is a Game Changer in the Management of Prostate Cancer." The Journal of Nuclear Medicine, vol. 59, No. 2, Feb. 2018, pp. 177-182.
Dos Santos, J. C. et al. "Development of Novel PSMA Ligands for Imaging and Therapy with Copper Isotopes." The Journal of Nuclear Medicine, vol. 61, No. 1, Jan. 2020, pp. 70-79.
Dos Santos, J. C. et al. "Development of Novel PSMA Ligands for Imaging and Therapy with Copper Isotopes." The Journal of Nuclear Medicine, Epub, Sep. 20, 2019, pp. 1-55.
Eder, M. et al. "$^{68}$Ga-Complex Lipophilicity and the Targeting Property of a Urea-Based PSMA Inhibitor for PET Imaging." Bioconjugate Chemistry, vol. 23, No. 4, Apr. 18, 2012, pp. 688-697.
Eisenwiener, K-P. et al. "NODAGATOC, a New Chelator-Coupled Somatostatin Analogue Labeled with [$^{67/68}$Ga] and [$^{111}$In] for SPECT, PET, and Targeted Therapeutic Applications of Somatostatin Receptor (hsst2) Expressing Tumors." Bioconjugate Chemistry, vol. 13, No. 3, Apr. 23, 2002, pp. 530-541.
Eychenne, R. et al. "Overview of Radiolabeled Somatostatin Analogs for Cancer Imaging and Therapy." Molecules, vol. 25, No. 17, Sep. 2, 2020, pp. 1-35.
Fani, M. et al. "PET of Somatostatin Receptor-Positive Tumors Using $^{64}$Cu- and $^{68}$Ga-Somatostatin Antagonists: The Chelate Makes the Difference." Supplemental Data, The Journal of Nuclear Medicine, vol. 52, No. 7, Jul. 2011, pp. 1110-1118.
Fani, M. et al. "PET of Somatostatin Receptor-Positive Tumors Using $^{64}$Cu- and $^{68}$Ga-Somatostatin Antagonists: The Chelate Makes the Difference." The Journal of Nuclear Medicine, vol. 52, No. 7, Jul. 2011, pp. 1110-1118.
Fani, M. et al. "Radiolabeled Somatostatin Analogs—A Continuously Evolving Class of Radiopharmaceuticals." Cancers, vol. 14, No. 5, Feb. 24, 2022, pp. 1-14.
Fani, M. et al. "Somatostatin Receptor Antagonists for Imaging and Therapy." The Journal of Nuclear Medicine, vol. 58, No. 9, Sep. 2017, pp. 61S-66S.
Fani, M. et al. "Unexpected Sensitivity of $sst_2$ Antagonists to N-Terminal Radiometal Modifications." The Journal of Nuclear Medicine, vol. 53, No. 9, Sep. 2012, pp. 1481-1489.
Farolfi, A. et al. "Current and Emerging Clinical Applications of PSMA PET Diagnostic Imaging for Prostate Cancer." The Journal of Nuclear Medicine, vol. 62, No. 5, May 2021, pp. 596-604.
Filippi, L. et al. "Recent Advances in PET Probes for Hepatocellular Carcinoma Characterization." Expert Review of Medical Devices, Accepted Manuscript, vol. 16, No. 5, Apr. 28, 2019, pp. 1-34.
Fu, W. et al. "Increased FAPI Uptake in Brain Metastasis from Lung Cancer on $^{68}$Ga-FAPI PET/CT." Clinical Nuclear Medicine, vol. 46, No. 1, Jan. 2021, pp. e1-e2.
Ghosh, A. et al. "Tumor Target Prostate Specific Membrane Antigen (PSMA) and its Regulation in Prostate Cancer." Journal of Cellular Biochemistry, vol. 91, No. 3, Feb. 15, 2004, pp. 528-539.
Giesel, F. L. et al. "F-18 Labelled PSMA-1007: Biodistribution, Radiation Dosimetry and Histopathological Validation of Tumor Lesions in Prostate Cancer Patients." European Journal of Nuclear Medicine and Molecular Imaging, vol. 44, Nov. 26, 2016, pp. 678-688.
Giesel, F. L. et al. "FAPI-74 PET/CT Using Either $^{18}$F-AIF or Cold-Kit $^{68}$Ga-Labeling: Biodistribution, Radiation Dosimetry and Tumor Delineation in Lung Cancer Patients." The Journal of Nuclear Medicine vol. 62, No. 2, Feb. 2021, pp. 1-22.
Giesel, F. L. et al. "FAPI-PET/CT Improves Staging in a Lung Cancer Patient with Cerebral Metastasis." European Journal of Nuclear Medicine and Molecular Imaging, vol. 46, May 22, 2019, pp. 1754-1755.
Ginj, M. et al. "Radiolabeled Somatostatin Receptor Antagonists are Preferable to Agonists for in vivo Peptide Receptor Targeting of Tumors." PNAS, vol. 103, No. 44, Oct. 31, 2006, pp. 16436-16441.
Gomes-Porras, M. et al. "Somatostatin Analogs in Clinical Practice: A Review." International Journal of Molecular Sciences, vol. 21, No. 5, Feb. 29, 2020, pp. 1-27.
Gorges, T. M. et al. "Heterogeneous PSMA Expression on Circulating Tumor Cells—A Potential Basis for Stratification and Monitoring of PSMA-Directed Therapies in Prostate Cancer." Oncotarget, vol. 7, No. 23, Apr. 26, 2016, pp. 34930-34941.
Gourni, E. et al. "Metal-Based PSMA Radioligands." Molecules, vol. 22, No. 4, Mar. 24, 2017, pp. 1-34.
Gourni, E. et al. "(R)-NODAGA-PSMA: A Versatile Precursor for Radiometal Labeling and Nuclear Imaging of PSMA-Positive Tumors." PLoS One, vol. 10, No. 12, Dec. 23, 2015, pp. 1-16.
Graham, M. M. et al. "$^{68}$Ga-DOTATOC Imaging of Neuroendocrine Tumors: A Systematic Review and Metaanalysis." The Journal of Nuclear Medicine, vol. 58, No. 9, Sep. 2017, pp. 1452-1458.
Guo, W. et al. "Imaging Fibroblast Activation Protein in Liver Cancer: A Single-Center Post Hoc Retrospective Analysis to Compare [68Ga]Ga-FAPI-04 PET/CT Versus MRI and [18F]-FDG PET/CT." European Journal of Nuclear Medicine and Molecular Imaging, vol. 48, Nov. 11, 2020, pp. 1604-1617.
Hamson, E. J. et al. "Understanding Fibroblast Activation Protein (FAP): Substrates, Activities, Expression and Targeting for Cancer Therapy." Proteomics Clinical Applications, vol. 8, No. 5-6, Jun. 2014, pp. 454-463.
Helgebostad, R. et al. "Clinical Applications of Somatostatin Receptor (Agonist) PET Tracers Beyond Neuroendocrine Tumors." Diagnostics, vol. 12, No. 2, Feb. 18, 2022, pp. 1-19.
Hennrich, U. et al. "[$^{68}$Ga]Ga-PSMA-11: The First FDA-Approved $^{68}$Ga-Radiopharmaceutical for PET Imaging of Prostate Cancer." Pharmaceuticals, vol. 14, No. 8, Jul. 23, 2021, pp. 1-12.
Heppeler, A. et al. "Radiometal-Labelled Macrocyclic Chelator-Derivatised Somatotstatin Analogue with Superb Tumour-Targeting Properties and Potential for Receptor-Mediated Internal Radiotherapy." Chemistry: A European Journal, vol. 5, No. 7, Jul. 2, 1999, pp. 1974-1981.
Hicks, R. J. et al. "FAPI-PET/CT: Will it End the Hegemony of $^{18}$F-FDG in Oncology?" The Journal of Nuclear Medicine, vol. 62, No. 3, Mar. 2021, pp. 296-302.
Hocart, S. J. et al. "Highly Potent Cyclic Disulfide Antagonists of Somatostatin." Journal of Medicinal Chemistry, vol. 42, No. 11, Jun. 3, 1999, pp. 1863-1871.
Hofland, L. J. et al. "Somatostatin Receptors and Disease: Role of Receptor Subtypes." Baillière's Clinical Endocrinology and Metabolism, vol. 10, No. 1, Jan. 1996, pp. 164.
Hofmann, M. et al. "Biokinetics and Imaging with the Somatostatin Receptor PET Radioligand $^{68}$Ga-DOTATOC: Preliminary Data." European Journal of Nuclear Medicine, vol. 28, No. 12, Dec. 2001, pp. 1751-1757.
Hu, K. et al. "Preclinical Evaluation and Pilot Clinical Study of 18F-AIF-Labeled FAPI-Tracers for PET Imaging of Cancer Associated Fibroblasts." Research Square, Preprint, Mar. 6, 2021, pp. 1-19.
Jansen, K. et al. "Extended Structure-Activity Relationship and Pharmacokinetic Investigation of (4-Quinolinoyl) glycyl-2-cyanopyrrolidine Inhibitors of Fibroblast Activation Protein (FAP)." Journal of Medicinal Chemistry, vol. 57, No. 7, Mar. 11, 2014, pp. 3053-3074.
Jansen, K. et al. "Selective Inhibitors of Fibroblast Activation Protein (FAP) with a (4-Quinolinoyl)-glycyl-2-cyanopyrrolidine Scaffold." ACS Medicinal Chemistry Letters, vol. 4, No. 5, Mar. 18, 2013, pp. 491-496.
Jeitner, T. M. et al. "Advances in PSMA Theranostics." Translational Oncology, vol. 22, Aug. 2022, pp. 1-16.

(56) References Cited

OTHER PUBLICATIONS

Jha, P. et al. "PET/CT for Pancreatic Malignancy: Potential Pitfalls." Journal of Nuclear Medicine Technology, vol. 43, No. 2, Jun. 2015, pp. 92-97.
Jiang, X. et al. "FAPI-04 PET/CT Using [$^{18}$F]AIF Labeling Strategy: Automatic Synthesis, Quality Control, and in vivo Assessment in Patient." Frontiers in Oncology, vol. 11, Mar. 2021, pp. 1-9.
Jiang, Y. et al. "A Novel Molecular Imaging Probe [$^{99m}$Tc]Tc-HYNIC-FAPI Targeting Cancer-Associated Fibroblasts." Scientific Reports, vol. 13, Mar. 3, 2023, pp. 1-7.
Johnbeck, C. B. et al. "Head-to-Head Comparison of $^{64}$Cu-DOTATATE and $^{68}$Ga-DOTATOC PET/CT: A Prospective Study of 59 Patients with Neuroendocrine Tumors." The Journal of Nuclear Medicine, Sep. 22, 2016, pp. 1-30.
Jones, W. et al. "PSMA Theranostics: Review of the Current Status of PSMA-Targeted Imaging and Radioligand Therapy." Cancers, vol. 12, No. 6, May 26, 2020, pp. 1-14.
Joshi, T. et al. "Harnessing the Coordination Chemistry of 1,4,7-Triazacyclononane for Biomimicry and Radiopharmaceutical Applications." ChemPlusChem, vol. 83, No. 7, Apr. 4, 2018, pp. 554-564.
Kaemmerer, D. et al. "Molecular Imaging with $^{68}$Ga-SSTR PET/CT and Correlation to Immunohistochemistry of Somatostatin Receptors in Neuroendocrine Tumours." European Journal of Nuclear Medicine and Molecular Imaging, vol. 38, May 31, 2011, pp. 1659-1668.
Kaemmerer, D. et al. "Somatostatin Receptors in Bronchopulmonary Neuroendocrine Neoplasms: New Diagnostic, Prognostic, and Therapeutic Markers." The Journal of Clinical Endocrinology & Metabolism, vol. 100, No. 3, Mar. 1, 2015, pp. 831-840.
Kelly, J. et al. "Trifunctional PSMA-Targeting Constructs for Prostate Cancer with Unprecedented Localization to LNCaP Tumors." European Journal of Nuclear Medicine and Molecular Imaging, vol. 45, Apr. 6, 2018, pp. 1841-1851.
Kelly, J. M. et al. "Dual-Target Binding Ligands with Modulated Pharmacokinetics for Endoradiotherapy of Prostate Cancer." The Journal of Nuclear Medicine, vol. 58, No. 9, Sep. 2017, pp. 1442-1449.
Kiesewetter, B. et al. "Pulmonary Neuroendocrine Tumours and Somatostatin Receptor Status: An Assessment of Unlicensed Use of Somatostatin Analogues in the Clinical Practice." ESMO Open, vol. 7, No. 3, Jun. 2022, pp. 1-7.
Kim, M. H. et al. "Evaluation of a $^{64}$Cu-Labeled 1,4,7-Triazacyclononane, 1-Glutaric Acid-4,7 Acetic Acid (NODAGA)-Galactose-Bombesin Analogue as a PET Imaging Probe in a Gastrin-Releasing Peptide Receptor-Expressing Prostate Cancer Xenograft Model." International Journal of Oncology, vol. 46, No. 3, Mar. 2015, pp. 1159-1168.
Koerber, S. A. et al. "The Role of FAPI-PET/CT for Patients with Malignancies of the Lower Gastrointestinal Tract—First Clinical Experience." The Journal of Nuclear Medicine, vol. 61, No. 9, Feb. 14, 2020, pp. 1-21.
Kratochwil, C. et al. "$^{68}$Ga-FAPI PET/CT: Tracer Uptake in 28 Different Kinds of Cancer." The Journal of Nuclear Medicine, vol. 60, No. 6, Jun. 2019, pp. 801-805.
Krebs, S. et al. "Biodistribution and Radiation Dose Estimates for $^{68}$Ga-DOTA-JR11 in Patients with Metastatic Neuroendocrine Tumors." European Journal of Nuclear Medicine and Molecular Imaging, Author Manuscript, vol. 46, No. 3, Mar. 2019, pp. 1-19.
Krebs, S. et al. "Comparison of $^{68}$Ga-DOTA-JR11 PET/CT with Dosimetric $^{177}$Lu-Satoreotide Tetraxetan ($^{177}$Lu-DOTA-JR11) SPECT/CT in Patients with Metastatic Neuroendocrine Tumors Undergoing Peptide Receptor Radionuclide Therapy." European Journal of Nuclear Medicine and Molecular Imaging, Author Manuscript, vol. 47, No. 13, Dec. 2020, pp. 1-19.
Kuten, J. et al. "Head-to-Head Comparison of [$^{68}$Ga]Ga-FAPI-04 and [$^{18}$F]-FDG PET/CT in Evaluating the Extent of Disease in Gastric Adenocarcinoma." European Journal of Nuclear Medicine and Molecular Imaging, vol. 49, Jul. 24, 2021, pp. 743-750.
Lafont, M. A. et al. "Radiopharmaceutical Production of [$^{61}$Cu]Cu-(R)NODAGA-LM3 Injection Solution." 36th Annual Congress of the European Association of Nuclear Medicine, Vienna, Sep. 9-13, 2023, 14 slides.
Lafont, M. A. et al. "Radiopharmaceutical Production of [$^{61}$Cu]Cu-(R)NODAGA-LM3 Injection Solution." 36th Annual Congress of the European Association of Nuclear Medicine, Abstract, Vienna, Sep. 9-13, 2023, pp. 1-2.
Łapińska, G. et al. "The Diagnostic Role of $^{68}$Ga-DOTATATE PET/CT in the Detection of Neuroendocrine Tumours." Nuclear Medicine Review, vol. 14, No. 1, Jul. 1, 2011, pp. 16-20.
Lee, S. M. et al. "Emerging Role of $^{18}$F-Fluorodeoxyglucose Positron Emission Tomography for Guiding Management of Hepatocellular Carcinoma." World Journal of Gastroenterology, vol. 25, No. 11, Mar. 21, 2019, pp. 1289-1306.
Li, M. et al. "Clinical Summary of Fibroblast Activation Protein Inhibitor-Based Radiopharmaceuticals: Cancer and Beyond." European Journal of Nuclear Medicine Imaging, vol. 49, Jan. 31, 2022, pp. 2844-2868.
Liermann, J. et al. "Impact of FAPI-PET/CT on Target Volume Definition in Radiation Therapy of Locally Recurrent Pancreatic Cancer." Cancers, vol. 13, No. 4, Feb. 14, 2021, pp. 1-13.
Lindner, T. et al. "Development of Quinoline-Based Theranostic Ligands for the Targeting of Fibroblast Activation Protein." The Journal of Nuclear Medicine, Supplemental Data, vol. 59, No. 9, Sep. 2018, pp. 1-22.
Lindner, T. et al. "Development of Quinoline-Based Theranostic Ligands for the Targeting of Fibroblast Activation Protein." The Journal of Nuclear Medicine, vol. 59, No. 9, Sep. 2018, pp. 1415-1422.
Lindner, T. et al. "Radioligands Targeting Fibroblast Activation Protein (FAP)." Cancers, vol. 13, No. 22, Nov. 16, 2021, pp. 1-12.
Lindner, T. et al. "Targeting of Activated Fibroblasts for Imaging and Therapy." EJNMMI Radiopharmacy and Chemistry, vol. 4, No. 16, Jul. 25, 2019, pp. 1-15.
Liu, H. et al. "Elevated [$^{68}$Ga]Ga-DOTA-FAPI-04 Activity in Degenerative Osteophyte in a Patient with Lung Cancer." European Journal of Nuclear Medicine and Molecular Imaging, vol. 48, Nov. 12, 2020, pp. 1-2.
Liu, T. et al. "Spacer Length Effects on In Vitro Imaging and Surface Accessibility of Fluorescent inhibitors of Prostate Specific Membrane Antigen." Bioorganic and Medicinal Chemistry Letters, Author Manuscript, vol. 21, No. 23, Dec. 1, 2011, pp. 1-10.
Loktev, A. et al. "Development of Fibroblast Activation Protein-Targeted Radiotracers with Improved Tumor Retention." The Journal of Nuclear Medicine, vol. 60, No. 10, Oct. 2019, pp. 1421-1429.
Lowrance, W. et al. "Advanced Prostate Cancer: AUA/SUO Guideline." American Urological Association, Apr. 2023, pp. 1-53.
Lütje, S. et al. "PSMA Ligands for Radionuclide Imaging and Therapy of Prostate Cancer: Clinical Status." Theranostics, vol. 5, No. 12, Oct. 18, 2015, pp. 1388-1401.
Machulkin, A. E. et al. "Small-Molecule PSMA Ligands. Current State, SAR and Perspectives." Journal of Drug Targeting, vol. 24, No. 8, Feb. 11, 2016, pp. 1-44.
Malmberg, C. et al. "$^{64}$Cu-DOTATATE for Noninvasive Assessment of Atherosclerosis in Large Arteries and Its Correlation with Risk Factors: Head-to-Head Comparison with $^{68}$Ga-DOTATOC in 60 Patients." The Journal of Nuclear Medicine, vol. 56, No. 12, Dec. 2015, pp. 1895-1900.
Marciniak, A. et al. "Somatostatin Analogues Labeled with Copper Radioisotopes: Current Status." Journal of Radioanalytical and Nuclear Chemistry, vol. 313, No. 2, Jun. 13, 2017, pp. 279-289.
Martin, M. et al. "Novel Generation of FAP Inhibitor-Based Homodimers for Improved Application in Radiotheranostics." Cancers, vol. 15, No. 6, Mar. 21, 2023, pp. 1-24.
Maurer, T. et al. "Current Use of PSMA-PET in Prostate Cancer Management." Nature Reviews Urology, vol. 13, Feb. 23, 2016, pp. 1-10.
Meester, E. J. et al. "Imaging Inflammation in Atherosclerotic Plaques, Targeting $SST_2$ with [$^{111}$ In]In-DOTA-JR11." Journal of Nuclear Cardiology, vol. 28, Feb. 5, 2020, pp. 2506-2513.

(56) References Cited

OTHER PUBLICATIONS

Millul, J. et al. "An Ultra-High-Affinity Small Organic Ligand of Fibroblast Activation Protein for Tumor-Targeting Applications." PNAS, vol. 118, No. 16, Apr. 13, 2021, pp. 1-10.
Millul, J. et al. "Enhancing the Tumor-to-Background Ratio of FAP-Positive PET/CT Scans with the Novel $^{61}$Cu-Kalios Derivatives: Synthesis, in vitro, and in vivo Characterization." 36th Annual Congress of the European Association of Nuclear Medicine, Abstract, Sep. 9-13, 2023, pp. 1-2.
Millul, J. et al. "Enhancing the Tumor-to-Background Ratio of FAP-Positive PET/CT Scans with the Novel 61Cu-Kalios Derivatives: Synthesis, in vitro, and in vivo Characterization." 36th Annual Congress of the European Association of Nuclear Medicine, Presentation, Sep. 9-13, 2023, slides 1-14.
Millul, J. et al. "Head-to-Head Comparison of Different Classes of FAP Radioligands Designed to Increase Tumor Residence Time: Monomer, Dimer, Albumin Binders, and Small Molecules vs Peptides." European Journal of Nuclear Medicine and Molecular Imaging, vol. 50, Jun. 1, 2023, pp. 3050-3061.
Mishra, P. J. et al. "Carcinoma Associated Fibroblast Like Differentiation of Human Mesenchymal Stem Cells." Cancer Research, Author Manuscript, vol. 68, No. 11, Jun. 1, 2008, pp. 1-21.
Mori, Y. et al. "FAPI PET: Fibroblast Activation Protein Inhibitor Use in Oncologic and Nononcologic Disease." Radiology, vol. 306, No. 2, Feb. 2023, pp. 1-14.
Morris, M. J. et al. "Diagnostic Performance of 18F-DCFPyL-PET/CT in Men with Biochemically Recurrent Prostate Cancer: Results from the CONDOR Phase III, Multicenter Study." Clinical Cancer Research, vol. 27, No. 13, Jul. 1, 2021, pp. 3674-3682.
Nedrow, J. R. et al. "Positron Emission Tomographic Imaging of Copper 64- and Gallium 68-Labeled Chelator Conjugates of the Somatostatin Agonist $Tyr^3$-Octreotate." Molecular Imaging, vol. 13, No. 7, Sep. 2014, pp. 1-13.
Nicolas, G. P. et al. "Safety, Biodistribution, and Radiation Dosimetry of $^{68}$Ga-OPS202 in Patients with Gastroenteropancreatic Neuroendocrine Tumors: A Prospective Phase I Imaging Study." The Journal of Nuclear Medicine, vol. 59, No. 6, Jun. 2018, pp. 909-914.
Nicolas, G. P. et al. "Sensitivity Comparison of $^{68}$Ga-OPS202 and $^{68}$Ga-DOTATOC PET/CT in Patients with Gastroenteropancreatic Neuroendocrine Tumors: A Prospective Phase II Imaging Study." The Journal of Nuclear Medicine, vol. 59, No. 6, Jun. 2018, pp. 915-921.
Nisa, L. et al. "Yttrium-90 DOTATOC Therapy in GEP-NET and Other SST2 Expressing Tumors: A Selected Review." Annals of Nuclear Medicine, vol. 25, Nov. 25, 2010, pp. 75-85.
Pang, Y. et al. "Comparison of $^{68}$Ga-FAPI and $^{18}$F-FDG Uptake in Gastric, Duodenal, and Colorectal Cancers." Radiology, vol. 298, No. 2, Feb. 2021, pp. 393-402.
Parker, C. et al. "Prostate Cancer: ESMO Clinical Practice Guidelines for Diagnosis, Treatment and Follow-Up." Annals of Oncology, vol. 31, No. 9, Sep. 2020, pp. 1119-1134.
Pauwels, E. et al. "Somatostatin Receptor PET Ligands—The Next Generation for Clinical Practice." American Journal of Nuclear Medicine and Molecular Imaging, vol. 8, No. 5, Oct. 20, 2018, pp. 311-331.
Pedersen, S. F. et al. "$^{64}$Cu-DOTATATE PET/MRI for Detection of Activated Macrophages in Carotid Atherosclerotic Plaques: Studies in Patients Undergoing Endarterectomy." Arteriosclerosis, Thrombosis, and Vascular Biology, vol. 35, No. 7, Jul. 2015, pp. 1696-1703.
Perner, S. et al. "Prostate-Specific Membrane Antigen Expression as a Predictor of Prostate Cancer Progression." Human Pathology, vol. 38, No. 5, May 2007, pp. 696-701.
Price, E. W. et al. "Matching Chelators to Radiometals for Radiopharmaceuticals." Chemical Society Reviews, vol. 43, No. 1, Jan. 7, 2014, pp. 260-290.
Privé, B. M. et al. "Fibroblast Activation Protein-Targeted Radionuclide Therapy: Background, Opportunities, and Challenges of First (pre)Clinical Studies." European Journal of Nuclear Medicine and Molecular Imaging, vol. 50, Feb. 23, 2023, pp. 1906-1918.
Privé, B. M. et al. "Lutetium-177-PSMA-I&T as Metastases Directed Therapy in Oligometastatic Hormone Sensitive Prostate Cancer, a Randomized Controlled Trial." BMC Cancer, vol. 20, Sep. 14, 2020, pp. 1-9.
Pyronnet, S. et al. "Antitumor Effects of Somatostatin." Molecular and Cellular Endocrinology, vol. 286, Nos. 1-2, May 14, 2008, pp. 230-237.
Qin, C. et al. "$^{68}$Ga-DOTA-FAPI-04 PET/MR in the Evaluation of Gastric Carcinomas: Comparison with $^{18}$F-FDG PET/CT." The Journal of Nuclear Medicine, vol. 63, No. 1, Jan. 2022, pp. 81-88.
Quigley, N. G. et al. "Click-Chemistry (CuAAC) Trimerization of an $\alpha_v\beta_6$ Integrin Targeting Ga-68-Peptide: Enhanced Contrast for in-Vivo PET Imaging of Human Lung Adenocarcinoma Xenografts." ChemBioChem, vol. 21, No. 19, Oct. 1, 2020, pp. 2836-2843.
Quigley, N. G. et al. "PET/CT Imaging of Head-and-Neck and Pancreatic Cancer in Humans by Targeting the 'Cancer Integrin' $\alpha v\beta 6$ with Ga-68-Trivehexin." European Journal of Nuclear Medicine and Molecular Imaging, vol. 49, Sep. 24, 2021, pp. 1136-1147.
Rajasekaran, S. A. et al. "A Novel Cytoplasmic Tail MXXXL Motif Mediates the Internalization of Prostate-Specific Membrane Antigen." Molecular Biology of the Cell, vol. 14, No. 12, Dec. 2003, pp. 4745-4845.
Ravert, H. T. et al. "An Improved Synthesis of the Radiolabeled Prostate-Specific Membrane Antigen Inhibitor, [$^{18}$F]DCFPyL." Journal of Labelled Compounds and Radiopharmaceuticals, vol. 59, No. 11, Sep. 2016, pp. 439-450.
Reubi, J. C. et al. "Affinity Profiles for Human Somatostatin Receptor Subtypes SST1-SST5 of Somatostatin Radiotracers Selected for Scintigraphic and Radiotherapeutic Use." European Journal of Nuclear Medicine, vol. 27, Mar. 2000, pp. 273-282.
Reubi, J. C. et al. "Highly Increased $^{125}$1-JR11 Antagonist Binding In Vitro Reveals Novel Indications for $sst_2$ Targeting in Human Cancers." The Journal of Nuclear Medicine, vol. 58, No. 2, Feb. 2017, pp. 300-306.
Röhrich, M. et al. "Fibroblast Activation Protein-Specific PET/CT Imaging in Fibrotic Interstitial Lung Diseases and Lung Cancer: A Translational Exploratory Study." The Journal of Nuclear Medicine, vol. 63, No. 1, Jan. 2022, pp. 127-133.
Rowe, S. P. et al. "[18F]DCFPyL PET/CT for Imaging of Prostate Cancer." Nuklearmedizin, vol. 61, No. 3, Jan. 14, 2022, pp. 1-8.
Ryabtsova, O. et al. "Acylated Gly-(2-cyano)pyrrolidines as Inhibitors of Fibroblast Activation Protein (FAP) and the Issue of FAP/prolyl Oligopeptidase (PREP)-Selectivity." Bioorganic & Medicinal Chemistry Letters, vol. 22, No. 10, May 15, 2012, pp. 3412-3417.
Rylova, S. N. et al. "The Somatostatin Receptor 2 Antagonist $^{64}$Cu-NODAGA-JR11 Outperforms $^{64}$Cu-DOTA-TATE in a Mouse Xenograft Model." PLoS One, vol. 13, No. 4, Apr. 18, 2018, pp. 1-16.
Sandach, P. et al. "Molecular Imaging and Therapy of Colorectal and Anal Cancer." Seminars in Nuclear Medicine, vol. 50, No. 5, Sep. 2020, pp. 465-470.
Sarkar, S. et al. "High in Vivo Stability of $^{64}$Cu-Labeled Cross-Bridged Chelators is a Crucial Factor in Improved Tumor Imaging of RGD Peptide Conjugates." Journal of Medicinal Chemistry, vol. 61, No. 1, Jan. 11, 2018, pp. 385-395.
Ševčik, R. et al. "Formation and Decomplexation Kinetics of Copper(II) Complexes with Cyclen Derivatives Having Mixed Carboxylate and Phosphonate Pendant Arms." Dalton Transactions, vol. 45, No. 32, Aug. 1, 2016, pp. 12723-12733.
Shi, X. et al. "Comparison of PET Imaging of Activated Fibroblasts and 18F-FDG for Diagnosis of Primary Hepatic Tumours: A Prospective Pilot Study." European Journal of Nuclear Medicine and Molecular Imaging, vol. 48, Oct. 24, 2020, pp. 1593-1603.
Šimeček, J. et al. "Copper-64 Labelling of Triazacyclononane-Triphosphinate Chelators." Dalton Transactions, vol. 41, No. 45, Dec. 7, 2012, pp. 13803-13806.
Soeda, F. et al. "Impact of $^{18}$F-PSMA-1007 Uptake in Prostate Cancer Using Different Peptide Concentrations: Preclinical PET/CT Study in Mice." The Journal of Nuclear Medicine, Epub, Mar. 22, 2019, pp. 1-31.

(56) References Cited

OTHER PUBLICATIONS

Sollini, M. et al. "State-of-the-art of FAPI-PET Imaging: A Systematic Review and Meta-Analysis." European Journal of Nuclear Medicine and Molecular Imaging, vol. 48, Jun. 25, 2021, pp. 4396-4414.
Strobel, O. et al. "FDG-PET is Not Useful in Early Pancreatic Cancer Diagnosis." Nature Reviews Gastroenterology & Hepatology, vol. 10, Apr. 2013, pp. 203-205.
Szabo, Z. et al. "Initial Evaluation of [$^{18}$F]DCFPyL for Prostate-Specific Membrane Antigen (PSMA)-Targeted PET Imaging of Prostate Cancer." Molecular Imaging and Biology, vol. 17, Apr. 21, 2015, pp. 565-574.
Tarkin, J. M. et al. "Detection of Atherosclerotic Inflammation by $^{68}$Ga-DOTATATE PET Compared to [$^{18}$F]FDG PET Imaging." Journal of the American College of Cardiology, vol. 69, No. 14, Apr. 11, 2017, pp. 1774-1791.
Umbricht, C. A. et al. "Design and Preclinical Evaluation of an Albumin-Binding PSMA Ligand for $^{64}$Cu-Based PET Imaging." Molecular Pharmaceutics, vol. 15, No. 12, Dec. 3, 2018, pp. 5556-5564.
Umbricht, C. A. et al. "Preclinical Development of Novel PSMA-Targeting Radioligands: Modulation of Albumin-Binding Properties to Improve Prostate Cancer Therapy." Molecular Pharmaceutics, Just Accepted Manuscript, Apr. 23, 2018, pp. 1-35.
Uspenskaya, A. A. et al. "The Importance of Linkers in the Structure of PSMA Ligands." Current Medicinal Chemistry, vol. 29, No. 2, Jan. 1, 2022, pp. 268-298.
Van Den Hoven, A. F. et al. "Current Research Topics in FAPI Theranostics: A Bibliometric Analysis." European Journal of Nuclear Medicine and Molecular Imaging, vol. 50, Nov. 28, 2022, pp. 1014-1027.
Veber, D. F. et al. "Highly Active Cyclic and Bicyclic Somatostatin Analogues of Reduced Ring Size." Nature, vol. 280, Aug. 9, 1979, pp. 512-514.
Wadas, T. J. et al. "Coordinating Radiometals of Copper, Gallium, Indium, Yttrium, and Zirconium for PET and SPECT Imaging of Disease." Chemical Reviews, vol. 110, No. 5, Apr. 23, 2010, pp. 2858-2902.
Waldherr, C. et al. "The Clinical Value of [90Y-DOTA]-D-Phe1-Tyr3-Octreotide (90Y-DOTATOC) in the Treatment of Neuroendocrine Tumours: A Clinical Phase II Study." Annals of Oncology, vol. 12, No. 7, Jul. 2001, pp. 941-945.
Wang, L. et al. "Comparison of $^{68}$Ga-FAPI and $^{18}$F-FDG PET/CT in the Evaluation of Advanced Lung Cancer." Radiology, vol. 303, No. 1, Apr. 2022, pp. 1-9.
Wang, Q. et al. "$^{68}$Ga-DOTA-FAPI-04 PET/CT as a Promising Tool for Differentiating Ovarian Physiological Uptake: Preliminary Experience of Comparative Analysis with $^{18}$F-FDG." Frontiers in Medicine, vol. 8, Oct. 2021, pp. 1-7.
Wang, X. et al. "Comprehensive Evaluation of a Somatostatin-Based Radiolabelled Antagonist for Diagnostic Imaging and Radionuclide Therapy." vol. 39, Aug. 29, 2012, pp. 1876-1885.
Weineisen, M. et al. "$^{68}$Ga- and $^{177}$Lu-Labeled PSMA I&T: Optimization of a PSMA-Targeted Theranostic Concept and First Proof-of-Concept Human Studies." The Journal of Nuclear Medicine, vol. 56, No. 8, Aug. 2015, pp. 1169-1176.
Weineisen, M. et al. "Synthesis and Preclinical Evaluation of DOTAGA-Conjugated PSMA Ligands for Functional Imaging and Endoradiotherapy of Prostate Cancer." EJNMMI Research, vol. 4, Nov. 25, 2014, pp. 1-15.
Wiering, B. et al. "Role of FDG-PET in the Diagnosis and Treatment of Colorectal Liver Metastases." Expert Review of Anticancer Therapy, vol. 4, No. 4, Jan. 10, 2004, pp. 607-613.
Wild, D. et al. "A Phase I/II Study of the Safety and Efficacy of [$^{177}$Lu]Lu-Satoreotide Tetraxetan in Advanced Somatostatin Receptor-Positive Neuroendocrine Tumours." European Journal of Nuclear Medicine and Molecular Imaging, Sep. 18, 2023, pp. 1-13.
Wirtz, M. et al. "Synthesis and In Vitro and In Vivo Evaluation of Urea-Based PSMA Inhibitors with Increased Lipophilicity." EJNMMI Research, vol. 8, Aug. 22, 2018, pp. 1-11.
Young, J. R. et al. "$^{18}$F-FDG PET/CT of Hepatocellular Adenoma Subtypes and Review of Literature." Abdominal Radiology, vol. 46, Feb. 8, 2021, pp. 2604-2609.
Zhao, L. et al. "Clinical Evaluation of $^{68}$Ga-FAPI-RGD for Imaging of Fibroblast Activation Protein and Integrin $\alpha_v\beta_3$ in Various Cancer Types." The Journal of Nuclear Medicine, May 2023, pp. 1-8.
Zhang, A. X. et al. "A Remote Arene-Binding Site on Prostate Specific Membrane Antigen Revealed by Antibody-Recruiting Small Molecules." Journal of the American Chemical Society, vol. 132, No. 36, Sep. 15, 2010, pp. 12711-12716.
Zhu, W. et al. "A Prospective, Randomized, Double-Blind Study to Evaluate the Safety, Biodistribution, and Dosimetry of $^{68}$Ga-NODAGA-LM3 and $^{68}$Ga-DOTA-LM3 in Patients with Well-Differentiated Neuroendocrine Tumors." The Journal of Nuclear Medicine, vol. 62, No. 10, Oct. 2021, pp. 1398-1405.
Zhu, W. et al. "Head-to-Head Comparison of $^{68}$Ga-DOTA-JR11 and $^{68}$Ga-DOTATATE PET/CT in Patients with Metastatic, Well-Differentiated Neuroendocrine Tumors: A Prospective Study." The Journal of Nuclear Medicine, vol. 61, No. 6, Jun. 2020, pp. 897-903.
Zippel, C. et al. "Current Status of PSMA-Radiotracers for Prostate Cancer: Data Analysis of Prospective Trials Listed on ClinicalTrials.gov." Pharmaceuticals, vol. 13, No. 1, Jan. 13, 2020, pp. 1-13.
Afshar-Oromieh, A. et al. "Radiation Dosimetry of $^{68}$Ga-PSMA-11 (HBED-CC) and Preliminary Evaluation of Optimal Imaging Timing." European Journal of Nuclear Medicine and Molecular Imaging, vol. 43, vol. 9, Aug. 2016, pp. 1611-1620.
Afshar-Oromieh, A. et al. "The Clinical Impact of Additional Late PET/CT Imaging with $^{68}$Ga-PSMA-11 (HBED-CC) in the Diagnosis of Prostate Cancer." vol. 58, No. 5, May 2017, pp. 750-755.
Berliner, C. et al. "Delayed Imaging Improves Lesion Detectability in [$^{99m}$Tc]Tc-PSMA-I&S SPECT/CT in Recurrent Prostate Cancer." The Journal of Nuclear Medicine, May 2023, pp. 1-7.
Beyer, T. et al. "A 2022 International Survey on the Status of Prostate Cancer Theranostics." The Journal of Nuclear Medicine, vol. 64, No. 1, Jan. 2023, pp. 47-53.
Cerci, J. J. et al. "Diagnostic Performance and Clinical Impact of $^{68}$Ga-PSMA-11 PET/CT Imaging in Early Relapsed Prostate Cancer After Radical Therapy: A Prospective Multicenter Study (IAEA-PSMA Study)." The Journal of Nuclear Medicine, vol. 63, No. 2, Feb. 2022, pp. 240-247.
Debnath, S. et al. "PSMA-Targeting Imaging and Theranostic Agents—Current Status and Future Perspective." International Journal of Molecular Science, vol. 23, No. 3, Jan. 21, 2022, pp.
ESHI. "Map of PET/CT Systems in Europe per City." European Society for Hybrid, Molecular and Translational Imaging, Oct. 18, 2023, 4 pages, [Online] [Retrieved Dec. 12, 2023], Retrieved from the Internet <URL:https://www.eshi-society.org/petct-map/>.
Fani, M. et al. "$^{61}$Cu-Labeled Radiotracers: Alternative or Choice?" The Journal of Nuclear Medicine, vol. 64, No. 12, Dec. 2023, pp. 1855-1857.
Fanti, S. et al. "EAU-EANM Consensus Statements on the Role of Prostate-specific Membrane Antigen Positron Emission Tomography/Computed Tomography in Patients with Prostate Cancer and with Respect to [$^{177}$Lu]Lu-PSMA Radioligand Therapy." European Urology Oncology, vol. 5, No. 5, Oct. 2022, pp. 530-536.
Fendler, W. P. et al. "PSMA PET/CT: Joint EANM Procedure Guideline/SNMMI Procedure Standard for Prostate Cancer Imaging 2.0." European Journal of Nuclear Medicine and Molecular Imaging, vol. 50, Jan. 5, 2023, 1466-1486.
Fonesca, A. I. et al. "Production of GMP-Compliant Clinical Amounts of Copper-61 Radiopharmaceuticals from Liquid Targets." Pharmaceuticals, vol. 15, No. 6, Jun. 7, 2022, pp. 1-13.
Gafita, A. et al. "Predictors and Real-World Use of Prostate-Specific Radioligand Therapy: PSMA and Beyond." American Society of Clinical Oncology Educational Book, vol. 42, May 24, 2022, pp. 366-382.
Hohberg, M. et al. "Combined Early and Late [$^{68}$Ga]PSMA-HBED-CC PET Scans Improve Lesion Detectability in Biochemical Recurrence of Prostate Cancer with Low PSA Levels." Molecular Imaging and Biology, vol. 21, No. 3, Jun. 2019, pp. 558-566.
IAEA. "Copper-64 Radiopharmaceuticals: Production, Quality Control and Clinical Applications." IAEA Radioisotopes and Radiopharmaceuticals Series, No. 7, Vienna, Nov. 2022, pp. 1-140.

(56) References Cited

OTHER PUBLICATIONS

Jadvar, H. et al. "Appropriate Use Criteria for Prostate-Specific Membrane Antigen PET Imaging." The Journal of Nuclear Medicine, vol. 63, No. 1, Jan. 2022, pp. 59-68.
Jalilian, A. R. et al. "Radiosynthesis and Evaluation of [$^{61}$Cu]-9,10-Phenanthrenequinone Thiosemicarbazone in Fibrosarcoma-Bearing Animals for PET Imaging." Radiochimica Acta, vol. 98, No. 3, Mar. 2010, pp. 175-181.
Kálmán-Szabó, I. et al. "$^{61}$Cu-Labelled Radiodiagnostics of Melanoma with NAPamide-Targeted Radiopharmaceutical." International Journal of Pharmaceutics, vol. 632, Feb. 5, 2023, pp. 1-9.
Karimzadeh, A. et al. "The Impact of PSMA PET-Based Eligibility Criteria Used in the Prospective Phase II TheraP Trial in Metastatic Castration-Resistant Prostate Cancer Patients Undergoing Prostate-Specific Membrane Antigen-Targeted Radioligand Therapy." The Journal of Nuclear Medicine, Jun. 2023, pp. 1-7.
Kuppermann, D. et al. "Imaging Prostate Cancer: Clinical Utility of Prostate-Specific Membrane Antigen." The Journal of Urology, vol. 207, No. 4, Apr. 2022, pp. 769-778.
Maisto, C. et al. "On Site Production of [$^{18}$F]PSMA-1007 Using Different [$^{18}$F]fluoride Activities: Practical, Technical and Economical Impact." EJNMMI Radiopharmacy and Chemistry, vol. 6, No. 36, pp. 1-10.
Neels, O. C. et al. "Radiolabeled PSMA Inhibitors." Cancers, vol. 13, No. 24, Dec. 13, 2021, pp. 1-24.
Nucadvisor. "Co-ordinated Approach to the Development and Supply of Radionuclides in the EU." European Commission, Final Report, First Edition, Aug. 2021, pp. 1-260.
Svedjehed, J. et al. "Automated, Cassette-Based Isolation and Formulation of High-Purity [$^{61}$Cu]$CuCl_2$ from Solid Ni Targets." EJNMMI Radiopharmacy and Chemistry, vol. 5, No. 21, Nov. 5, 2020, pp. 1-14.
Williams, H. A. et al. "A Comparison of PET Imaging Characteristics of Various Copper Radioisotopes." European Journal of Nuclear Medicine and Molecular Imaging, vol. 32, No. 12, Dec. 2005, pp. 1473-1480.
Wondergem, M. et al. "$^{18}$F-DCFPyL PET/CT in the Detection of Prostate Cancer at 60 and 120 Minutes: Detection Rate, Image Quality, Activity Kinetics, and Biodistribution." The Journal of Nuclear Medicine, vol. 58, No. 11, Nov. 2017, pp. 1797-1804.
Zhang, Y. et al. "Positron Emission Tomography Imaging of Vascular Endothelial Growth Factor Receptor Expression with $^{61}$Cu-Labeled Lysine-Tagged $VEGF_{121}$." Molecular Pharmaceutics, Author Manuscript, vol. 9, No. 12, Dec. 3, 2012, pp. 1-17.
Backhaus, P. et al. "Translational Imaging of the Fibroblast Activation Protein (FAP) Using the New Ligand [$^{68}$Ga]Ga-OncoFAP-DOTAGA." European Journal of Nuclear Medicine and Molecular Imaging, vol. 49, Dec. 27, 2021, pp. 1822-1832.
Bartoli, F. et al. "Automated Radiosynthesis, Preliminary In Vitro/In Vivo Characterization of OncoFAP-Based Radiopharmaceuticals for Cancer Imaging and Therapy." Pharmaceuticals, vol. 15, No. 8, Aug. 2, 2022, pp. 1-18.
Bernabeu, T. B. et al. "61Cu-PSMA PET in Prostate Cancer: Development and Selection of the First Radioligand for Clinical Translation." European Journal of Nuclear Medicine and Molecular Imaging, vol. 50, No. 1, Sep. 1, 2023, pp. S425-S426.
Coenen, H. H. et al. "Open Letter to Journal Editors on: International Consensus Radiochemistry Nomenclature Guidelines." Annals of Nuclear Medicine, vol. 32, No. 3, Feb. 8, 2018, pp. 236-238.
Do Carmo, S. J. C. et al. "Fast and Cost-Effective Cyclotron Production of 61Cu Using a natZn Liquid Target: An Opportunity for Radiopharmaceutical Production and R&D." Dalton Transactions, vol. 46, No. 42, Jun. 27, 2017, pp. 1-5.
European Medicines Agency. "ICH Guideline Q3D (R1) on Elemental Impurities." ICH: Harmonisation for Better Health, Mar. 28, 2019, pp. 1-86.
Galbiati, A. et al. "A Dimeric FAP-Targeting Small-Molecule Radioconjugate with High and Prolonged Tumor Uptake." The Journal of Nuclear Medicine, vol. 63, No. 12, Dec. 2022, pp. 1852-1858.
Gilardoni, E. et al. "Mass Spectrometry-Based Method for the Determination of the Biodistribution of Tumor-Targeting Small Molecule-Metal Conjugates." Analytical Chemistry, vol. 94, No. 30, Jul. 12, 2022, pp. 10715-10721.
Greifenstein, L. N. "Synthesis, Radiolabeling and in vitro and in vivo Evaluation of Different Chelator Systems with $^{44}$Sc, $^{64}$Cu, $^{68}$Ga and $^{177}$Lu." Dissertation, Johannes Gutenberg-Universität Mainz, May 2019, pp.
Hesterman, J. et al. "Preclinical Characterization of Novel Radiolabeled and Fluorescent-Labeled Fibroblast Activation Protein (FAP)-Targeting Ligands Using Gamma Counting, SPECT Imaging and Cryo-Fluorescence Tomography (CFT)." European Journal of Nuclear Medicine and Molecular Imaging, vol. 50, No. 1, Sep. 1, 2023, pp. S424-S425.
IAEA. "Cyclotron Produced Radionuclides: Emerging Positron Emitters for Medical Applications: $^{64}$Cu and $^{124}$I." IAEA Radioisotopes and Radiopharmaceuticals Reports No. 1, Mar. 2016, pp. 1-79.
IAEA. "Gallium-68 Cyclotron Production." IAEA Tecdoc Series, IAEA-Tecdoc-1863, Feb. 2019, pp. 1-68.
IAEA. "Production of Emerging Radionuclides Towards Theranostic Applications: Copper-61, Scandium-43 and -44, and Yttrium-86." IAEA Tecdoc Series, IAEA-Tecdoc-1955, Apr. 2021, pp. 1-72.
Jalilian, A. R. et al. "Preparation of [$^{61}$Cu]-2-Acetylpyridine Thiosemicarbazone Complex as a Possible PET Tracer for Malignancies." Applied Radiation and Isotopes, vol. 64, No. 3, Mar. 2006, pp. 337-341.
Jauregui-Osoro, M. et al. "Production of Copper-64 Using a Hospital Cyclotron: Targetry, Purification and Quality Analysis." Nuclear Medicine Communications, vol. 42, No. 9, Sep. 2021, pp. 1024-1038.
Kelly, J. M. et al. "Preclinical Evaluation of a High-Affinity Sarcophagine-Containing PSMA Ligand for $^{64}$Cu/$^{67}$Cu-Based Theranostics in Prostate Cancer." Molecular Pharmaceutics, vol. 17, No. 6, Apr. 14, 2020, pp. 1954-1962.
Luurtsema, G. et al. "EANM Guideline for Harmonisation on Molar Activity or Specific Activity of Radiopharmaceuticals: Impact on Safety and Imaging Quality." EJNMMI Radiopharmacy and Chemistry, vol. 6, No. 34, Oct. 9, 2021, pp. 1-16.
Mansour, N. et al. "Evaluation of a Novel GRPR Antagonist for Prostate Cancer PET Imaging: [$^{64}$Cu]-$DOTHA_2$-PEG-RM26." Nuclear Medicine and Biology, vol. 56, Jan. 2018, pp. 31-38.
Mccarthy, D. W. et al. "High Purity Production and Potential Applications of Copper-60 and Copper-61." Nuclear Medicine & Biology, vol. 26, No. 4, May 1999, pp. 351-358.
Millul, J. et al. "Enhancing the Tumor-to-Background Ratio of FAP-Positive PET/CT Scans with the Novel $^{61}$Cu-Kalios Derivatives: Synthesis, in vitro, and in vivo Characterization." European Journal of Nuclear Medicine and Molecular Imaging, vol. 50, No. 1, Sep. 1, 2023, pp. S186.
Nambisan, A. et al. "Preclinical Evaluation of 67Cu-PSMA-617 Theranostic as an Alternative to 177Lu-PSMA-617 for Prostate Cancer." The Journal of Nuclear Medicine, vol. 63, No. 2, Jun. 2022, pp.
Notni, J. et al. "TRAP, a Powerful and Versatile Framework for Gallium-68 Radiopharmaceuticals." Chemistry A European Journal, vol. 17, No. 52, Dec. 23, 2011, pp. 14718-14722.
PCT International Search Report and Written Opinion, PCT Application No. PCT/US2023/075066, Jan. 9, 2024, 20 pages.
PCT Invitation to Pay Additional Fees, PCT Application No. PCT/US2023/075067, Jan. 5, 2024, 25 pages.
Pettersson, J. et al. "Automated, Cassette-Based Isolation and Formulation of High-Purity [$^{61}$Cu]$CuCl_2$ from Solid Ni Targets." Research Square, Preprint, Jul. 15, 2020, pp. 1-23.
Piel, H. et al. "Excitation Functions of (p,xn)-Reactions on $^{nat}$Ni and Highly Enriched $^{62}$Ni: Possibility of Production of Medically Important Radioisotope $^{62}$Cu at a Small Cyclotron." Radiochimica Acta, vol. 57, No. 1, Feb. 1, 1992, pp. 1-6.
Šimeček, J. "Innovative Complexation Strategies for the Introduction of Short-Lived PET Isotopes into Radiopharmaceuticals." Dissertation, Technische Universität München, Dec. 18, 2013, pp. 1-122.

(56) References Cited

OTHER PUBLICATIONS

Šimeček, J. et al. "A Monoreactive Bifunctional Triazacyclononane Phosphinate Chelator with High Selectivity for Gallium-68." ChemMedChem, vol. 7, No. 8, Aug. 2012, pp. 1375-1378.
Šimeček, J. et al. "Complexation of Metal Ions with TRAP (1,4,7-Triazacyclononane Phosphinic Acid) Ligands and 1,4,7-Triazacyclononane-1,4,7-triacetic Acid: Phosphinate-Containing Ligands as Unique Chelators for Trivalent Gallium." Inorganic Chemistry, vol. 51, No. 1, Jan. 2, 2012, pp. 577-590.
Šimeček, J. et al. "How is $^{68}$Ga Labeling of Macrocyclic Chelators Influenced by Metal Ion Contaminants in $^{68}$Ge/$^{68}$Ga Generator Eluates?." ChemMedChem, vol. 8, No. 1, Jan. 2013, pp. 95-103.
Smith, N. A. et al. "The Production, Separation, and Use of 67Cu for Radioimmunotherapy: A Review." Applied Radiation and Isotopes, vol. 70, No. 10, Oct. 2012, pp. 2377-2383.
Szelecsényi, F. et al. "New Cross-Section Data for the $^{66}$Zn(p,n)$^{66}$Ga, $^{68}$Zn(p,3n)$^{66}$Ga, $^{nat}$Zn(p,x)$^{66}$Ga, $^{68}$Zn(p,2n)$^{67}$Ga and $^{nat}$Zn(p,x)$^{67}$Ga Nuclear Reactions up to 100 MeV." Nuclear Instruments and Methods in Physics Research Section B: Beam Interactions with Materials and Atoms, vol. 234, No. 4, Jul. 2005, pp. 375-386.
Web of Pharma. "Gallium ($^{68}$Ga) Chloride Solution for Radiolabelling." European Pharmacopoeia, 10th Edition, Mar. 18, 2021, pp. 1206-1208, [Online] [Retrieved Jan. 15, 2024], Retrieved from the internet <URL:https://www.webofpharma.com/2021/03/ep-10-european-pharmacopoeia-10th.html>.
Zana, A. et al. "Fibroblast Activation Protein Triggers Release of Drug Payload from Non-Internalizing Small Molecule Drug Conjugates in Solid Tumors." Clinical Cancer Research, vol. 28, No. 24, Dec. 15, 2022, pp. 5440-5454.
Asad, A. H. et al. "Production of $^{61}$Cu by the $^{nat}$Zn(p,$\alpha$) Reaction: Improved Separation and Specific Activity Determination by Titration with Three Chelators." Journal of Radioanalytical and Nuclear Chemistry, vol. 307, No. 2, Sep. 1, 2015, pp. 899-906.
Fonseca, A. I. et al. "Production of GMP-Compliant Clinical Amounts of Copper-61 Radiopharmaceuticals from Liquid Targets." Pharmaceuticals, vol. 15, No. 6, Jun. 7, 2022, pp. 1-13.
Nelson, B. et al. "P-222—Cyclotron Production of the $^{64}$Cu Theranostic Radiometal Using a Novel $^{68}$Zn Sealed Solid Target." Nuclear Medicine and Biology, vol. 108-109, May-Jun. 2022, pp. S171.
PCT International Search Report and Written Opinion, PCT Application No. PCT/US2023/075064, Mar. 19, 2024, 20 pages.
Sadeghi, M. et al. "$^{124}$I Production for PET Imaging at a Cyclotron." Kerntechnik, vol. 77, No. 1, Mar. 2012, pp. 45-49.
Sadeghi, M. et al. "Cyclotron Production of $^{68}$Ga via Proton-Induced Reaction on $^{68}$Zn Target." Nukleonika, vol. 54, No. 1, Jul. 2009, pp. 25-28.
Cullinane, C. et al. "Peptide Receptor Radionuclide Therapy with $^{67}$Cu—CuSarTATE is Highly Efficacious Against a Somatostatin-Positive Neuroendocrine Tumor Model." The Journal of Nuclear Medicine, vol. 61, No. 12, Dec. 2020, pp. 1800-1805.
Li, W. P. et al. "DOTA-$_{D}$-Tyr$^{1}$-Octreotate: A Somatostatin Analogue for Labeling with Metal and Halogen Radionuclides for Cancer Imaging and Therapy." Bioconjugate Chemistry, vol. 13, No. 4, May 25, 2002, pp. 721-728.
PCT International Search Report and Written Opinion, PCT Application No. PCT/US2023/075067, Apr. 16, 2024, 45 pages.
Pfeifer, A. et al. "Clinical PET of Neuroendocrine Tumors Using 64Cu-DOTATATE: First-in-Humans Study." The Journal of Nuclear Medicine, vol. 53, No. 8, Aug. 2012, pp. 1207-1215.
Svedjehed, J. et al. "New Extractant-Impregnated iTLC-SG Paper Facilitates Improved TLC Analysis for Cu Radiolabelled Peptides." TERACHEM, Sep. 14-17, 2022, pp. P-80.
Watabe, T. et al. "Theranostics Targeting Fibroblast Activation Protein in the Tumor Stroma: $^{64}$Cu- and $^{225}$Ac-Labeled FAPI-04 in Pancreatic Cancer Xenograft Mouse Models." The Journal of Nuclear Medicine, vol. 61, No. 4, Apr. 2020, pp. 563-569.
Zandi, N. "$^{61}$CU/$^{67}$Cu Theranostic Pair Production, Chemical Separation and Radiolabeling." Inaugural Dissertation, University of Bern, Oct. 29, 2021, pp. 1-192.
PCT Invitation to Pay Additional Fees, PCT Application No. PCT/US2023/075064, Dec. 21, 2023, eight pages.
Moon, E. S. et al. "Targeting Fibroblast Activation Protein (FAP): Next Generation PET Radiotracers Using Squaramide Coupled Bifunctional DOTA and DATA5m Chelators." EJNMMI Radiopharmacy and Chemistry, vol. 5, No. 19, Jul. 29, 2020, pp. 1-20.

* cited by examiner

A B C

A

B

C

D

A

B

A

B

A

B

A

B

H-NMR Shifts of NODAGA-PSMA-I&T

| Group | Atom | Nuc | Shift | SDev | Assignments |
|---|---|---|---|---|---|
| nodaga | c1# | 13C | 49.171 | 0 | 1 |
| nodaga | c2# | 13C | 53.907 | 0 | 1 |
| nodaga | c3# | 13C | 52.331 | 0 | 1 |
| nodaga | ca# | 13C | 60.107 | 0 | 1 |
| nodaga | h1# | 1H | 2.948 | 0.005 | 5 |
| nodaga | h2# | 1H | 3.128 | 0.004 | 4 |
| nodaga | h3# | 1H | 3.272 | 0.003 | 3 |
| nodaga | ha# | 1H | 3.671 | 0.005 | 7 |
| glu1 | ca | 13C | 67.999 | 0 | 1 |
| glu1 | cb | 13C | 27.412 | 0.001 | 2 |
| glu1 | cg | 13C | 35.297 | 0.007 | 2 |
| glu1 | ha | 1H | 3.289 | 0.011 | 19 |
| glu1 | hba | 1H | 1.832 | 0.007 | 13 |
| glu1 | hbb | 1H | 1.713 | 0.007 | 13 |
| glu1 | hga | 1H | 2.333 | 0.009 | 18 |
| glu1 | hgb | 1H | 2.24 | 0.033 | 22 |
| ltyr2 | ca | 13C | 56.988 | 0 | 1 |
| ltyr2 | cb | 13C | 38.222 | 0.004 | 2 |
| ltyr2 | cd1 | 13C | 142.189 | 0 | 1 |
| ltyr2 | cd2 | 13C | 133.453 | 0 | 1 |
| ltyr2 | ce2 | 13C | 117.904 | 0 | 1 |
| ltyr2 | ha | 1H | 4.51 | 0.009 | 16 |
| ltyr2 | hba | 1H | 2.912 | 0.008 | 22 |
| ltyr2 | hbb | 1H | 2.678 | 0.008 | 22 |
| ltyr2 | hd1 | 1H | 7.518 | 0.009 | 11 |
| ltyr2 | hd2 | 1H | 7.034 | 0.009 | 13 |
| ltyr2 | he2 | 1H | 6.813 | 0.006 | 5 |
| ltyr2 | hn | 1H | 8.112 | 0.005 | 20 |
| ltyr2 | n | 15N | 124.781 | 0 | 1 |
| phe3 | ca | 13C | 57.453 | 0 | 1 |
| phe3 | cb | 13C | 39.689 | 0 | 2 |
| phe3 | cd# | 13C | 132.03 | 0 | 1 |
| phe3 | ce# | 13C | 131.348 | 0 | 1 |
| phe3 | cz | 13C | 129.767 | 0 | 1 |
| phe3 | ha | 1H | 4.558 | 0.018 | 12 |
| phe3 | hba | 1H | 3.104 | 0.01 | 18 |
| phe3 | hbb | 1H | 2.929 | 0.012 | 18 |
| phe3 | hd# | 1H | 7.204 | 0.004 | 8 |
| phe3 | he# | 1H | 7.288 | 0.008 | 3 |
| phe3 | hn | 1H | 8.194 | 0.011 | 16 |
| phe3 | hz | 1H | 7.245 | 0 | 1 |

FIG. 32B

H-NMR Shifts of NODAGA-PSMA-I&T (cont.)

| Group | Atom | Nuc | Shift | SDev | Assignments |
|---|---|---|---|---|---|
| phe3 | n | 15N | 122.106 | 0 | 1 |
| lys4 | ca | 13C | 56.619 | 0 | 1 |
| lys4 | cb | 13C | 33.434 | 0.003 | 2 |
| lys4 | cd | 13C | 30.557 | 0 | 1 |
| lys4 | ce | 13C | 41.853 | 0 | 1 |
| lys4 | cg | 13C | 25.13 | 0 | 1 |
| lys4 | ha | 1H | 4.168 | 0.006 | 24 |
| lys4 | hba | 1H | 1.768 | 0.012 | 15 |
| lys4 | hbb | 1H | 1.644 | 0.009 | 16 |
| lys4 | hd# | 1H | 1.46 | 0.007 | 14 |
| lys4 | he# | 1H | 3.105 | 0.015 | 21 |
| lys4 | hg# | 1H | 1.267 | 0.008 | 16 |
| lys4 | hn | 1H | 8.018 | 0.044 | 22 |
| lys4 | hz | 1H | 7.915 | 0.03 | 19 |
| lys4 | n | 15N | 127.014 | 0 | 1 |
| lys4 | nz | 15N | 125.593 | 0 | 1 |
| ole5 | ca# | 13C | 38.458 | 0 | 1 |
| ole5 | cb# | 13C | 27.976 | 0 | 1 |
| ole5 | cg# | 13C | 30.446 | 0 | 1 |
| ole5 | ha# | 1H | 2.111 | 0.005 | 10 |
| ole5 | hb# | 1H | 1.459 | 0.011 | 9 |
| ole5 | hg# | 1H | 1.176 | 0.007 | 7 |
| lys6 | ca | 13C | 56.829 | 0 | 1 |
| lys6 | cb | 13C | 33.833 | 0.001 | 2 |
| lys6 | cd | 13C | 30.666 | 0 | 1 |
| lys6 | ce | 13C | 42.017 | 0 | 1 |
| lys6 | cg | 13C | 25.084 | 0 | 1 |
| lys6 | ha | 1H | 4.038 | 0.008 | 19 |
| lys6 | hba | 1H | 1.71 | 0.01 | 16 |
| lys6 | hbb | 1H | 1.594 | 0.009 | 13 |
| lys6 | hd# | 1H | 1.431 | 0.01 | 11 |
| lys6 | he# | 1H | 3.083 | 0.033 | 21 |
| lys6 | hg# | 1H | 1.306 | 0.006 | 12 |
| lys6 | hz | 1H | 7.889 | 0.016 | 20 |
| lys6 | nz | 15N | 126.825 | 0 | 1 |
| glu7 | ca | 13C | 56.375 | 0 | 1 |
| glu7 | cb | 13C | 29.847 | 0 | 2 |
| glu7 | cg | 13C | 33.346 | 0 | 1 |
| glu7 | ha | 1H | 4.101 | 0.009 | 12 |
| glu7 | hba | 1H | 2.026 | 0.064 | 14 |
| glu7 | hbb | 1H | 1.873 | 0.049 | 14 |
| glu7 | hg# | 1H | 2.382 | 0.005 | 11 |

FIG. 32C

HIGH PURITY COPPER RADIOPHARMACEUTICAL COMPOSITIONS AND DIAGNOSTIC AND THERAPEUTIC USES THEREOF

1. BACKGROUND

The present disclosure is directed to a new class of radiotracers with potential for "true theranostic" use combining cancer diagnostics and therapy with a single chemical entity that meets the requirements of an ideal Positron Emission Tomography (PET) or single-photon emission computerized tomography (SPECT) tracer, based on a novel high purity $^{6x}$Cu radionuclide production platform. More specifically, the present disclosure relates to novel constructs and compositions thereof and their use in imaging, diagnosing, and treatment of conditions such as myocardial infarct, interstitial lung disease, and cancer, including prostate cancer, epithelial tumors expressing FAP, and neuroendocrine tumor, as well as to methods of making these compositions.

In nuclear medicine, radiotracers are used for the diagnosis and therapy of various conditions and diseases. Radiotracers are compounds in which radionuclides are linked to targeting moieties that target specific organs, cells, or biomarkers in the human body.

Radiotracers can be used in targeted radionuclide therapy with the use of targeting moieties that selectively localize in malignant cells, tumors, or the microenvironments associated therewith, and with radionuclides selected to emit low-range highly ionizing radiation, e.g., α or $\beta^-$ particles. The combination of both the diagnosis and the treatment of a disease utilizing the same or similar biological targeting moieties which target a specific biomarker (e.g., a cell surface receptor) with different diagnostic and therapeutic radionuclides is called targeted theranostics. This approach overcomes the difficulty of quantifying the individual dose needed for the therapy through the diagnosis, rendering the treatment of the patient highly individualized. The theranostic approach is further improved using radionuclides of the same element, e.g., copper radionuclides, $^{60}$Cu, $^{61}$Cu, $^{62}$Cu, and $^{64}$Cu as positron emitters in diagnostic imaging and $^{67}$Cu as an electron-emitter in the radiotherapeutic, as the isotopically different radiotracers will bind identically to the biomarker.

The availability of a large portfolio of active and highly pure radiotracers is essential for the development of nuclear medicine. A variety of copper radionuclides have been used in the field of nuclear medicine, and they offer versatile choices for applications in radionuclide imaging (e.g., in radiotracers) and therapy.

Copper radionuclides, including $^{60}$Cu, $^{61}$Cu, $^{62}$Cu, $^{64}$Cu, and $^{67}$Cu, offer versatile choices for applications in imaging and therapy. The short-lived $^{60}$Cu ($t_{1/2}$=23.4 min), $^{61}$Cu ($t_{1/2}$=3.32 h) and $^{62}$Cu ($t_{1/2}$=9.76 min) decay by electron capture and $\beta^+$ emission, and they have been used as to prepare perfusion agents such as Cu-pyruvaldehyde bis($N^4$-methylthiosemicarbazone) (PTSM) and Cu-ethylglyoxal bis (thiosemicarbazone) ETS. The longer-lived $^{67}$Cu ($t_{1/2}$=62.01 h) decays exclusively by $\beta^-$ emission and has been used to label monoclonal antibodies and antibody fragments for radioimmunotherapy. $^{64}$Cu has an intermediate half-life of 12.7 h and unique decay prolife ($\beta^+$: 18%, $\beta^-$: 38%, and electron capture: 44%), making it useful for radiolabeling nanoparticles, antibodies, antibody fragments, peptides, and small molecules for PET imaging and radionuclide therapy. $^{64}$Cu radiopharmaceuticals can thus be used for quantitative PET imaging to calculate radiation dosimetry prior to performing targeted radiotherapy with $^{64}$Cu or its beta-emitting isotopologue $^{67}$Cu. $^{64}$Cu has been incorporated into many labelled radiotracers based on antibodies, peptides and small molecules that target specific receptors or antigens, particularly in oncology applications.

More recently, $^{61}$Cu ($t_{1/2}$=3.33 h, 61% $\beta^+$, $E_{max}$=1.216 MeV) has been considered a better choice for prolonged imaging of processes with slower kinetics due to its longer half-life (3.33 h) than that of $^{60}$Cu and $^{62}$Cu. $^{61}$Cu is a positron-emitting radionuclide presenting decay characteristics comparable to [$^{68}$Ga]Ga but with the advantage of presenting lower maximum positron energy ($E_{max}$=1.216 MeV vs. $E_{max}$=1.899 MeV) and a substantially more practical half-life (3.33 h vs. 68 min). (McCarthy, D. W. et al. High purity production and potential applications of copper-60 and copper-61. Nucl. Med. Biol. 1999, 26, 351-358.) The intermediate half-life and interesting decay properties allow for better image quality and possibly lower radiation dose to patients.

Radionuclides can be used in personalized medicine but their supply in quantity and quality for clinical applications represents a challenge. Production of target "coins" (the often disk-like objects bearing a target metal that is bombarded with subatomic particles in order to produce radionuclides) that can produce radionuclide compositions having activity, at end of bombardment (EoB), end of synthesis (EoB+2 hours), or at calibration, with the required radionuclide purity is crucial. Suitable target coin preparation is one of the most important aspects in cyclotron production of radionuclides.

Currently, PET is the only highly accurate nuclear medical imaging procedure that enables the visualization and measurement of biochemical processes in cancer diagnosis. PET offers detailed information on progression of the disease that is unattainable through other imaging techniques or only via more invasive procedures. Although efficacy of radionuclides as PET tracers is undisputed, there are critical barriers to their widespread use, such as 1) high production costs (>€400 or $400 USD/dose), 2) inflexible chemistry (requiring complex, costly radiochemical infrastructure), 3) a limited distribution radius (short half-lives) and 4) high radiation burden, putting the patient at risk.

US 2006/0004491 describes a functional automated process for isolating and recovering $^{60}$Cu, $^{61}$Cu, and $^{64}$Cu use in preparing radiodiagnostic agent(s), such for use in PET imaging.

U.S. Pat. No. 10,975,089 relates to compounds that are purportedly useful as radiopharmaceuticals, e.g., radioimaging agents, which bear a radionuclide-chelating agent, for use in radiotherapy and diagnostic imaging. More specifically, compounds are described, which are stated to show improved binding affinity to PSMA. According to U.S. Pat. No. 10,975,089, the use of an amino acid-substituted urea bound to a macrocyclic sarcophagine via specific linkers provides compounds that bind to PSMA and when complexed with a radionuclide, provide improved imaging properties.

An object of the present disclosure is to provide compositions and methods that fully or in part overcome one or more of the issues recognized in the prior art encompassing radiopharmaceuticals, such as radiotracers, and their preparation.

2. SUMMARY

In a first aspect of the disclosure, a compound is provided, the compound comprising: a chelating moiety, optionally a chelated copper radionuclide (*Cu), and a targeting moiety covalently linked to the chelating moiety.

In certain embodiments, a compound is provided, wherein the compound is of Formula X:

Formula X

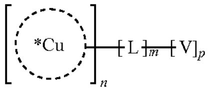

or is a pharmaceutically acceptable salt thereof, wherein:

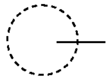

is a chelating moiety;

*Cu is optional, and if present, is selected from $^{61}Cu$, $^{62}Cu$, $^{64}Cu$, and $^{67}Cu$;

L is a bond or a linker moiety;

V is a targeting moiety;

n is an integer from 1 to 10;

m is an integer from 1 to 10;

p is an integer from 1 to 10.

In certain embodiments, a compound is provided, wherein the compound is of Formula A:

Formula A

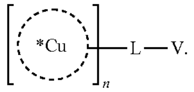

In certain embodiments of the compounds of Formulas X or Formula A, the chelating moiety comprises from 2-8 binding moieties. In certain embodiments, one or more of the binding moieties are selected from thiol groups, amine groups, and carboxylate groups.

In certain embodiments, the chelating moiety comprises: 2,2',2"-(1,4,7-triazonane-1,4,7-triyl)triacetic acid (NOTA); 2-(4,7-bis(carboxymethyl)-1,4,7-triazonan-1-yl)succinic acid (NODASA); 2-(4,7-bis(carboxymethyl)-1,4,7-triazonan-1-yl)pentanedioic acid (NODAGA); or 2,2'((2-(4,7-bis-(carboxymethyl)-1,4,7-triazonan-1-yl)ethyl)azanediyl)di-acetic acid (NETA).

In certain embodiments, the targeting moiety is recognized by a molecular target expressed by malignant or premalignant cells, cells in the tumor microenvironment, inflammatory tissues, or sites of tissue remodeling at sites of a myocardial infarct or fibrosis in interstitial lung disease.

In a second aspect of the present disclosure, a composition is provided comprising a compound is of Formula X or Formula A or is a pharmaceutically acceptable salt thereof. Preferably, the composition has a radiochemical purity of ≥91% or a molar activity of 1 to 250 MBq/nmol. In certain embodiments, the composition has both a radiochemical purity of ≥91% and a molar activity in a range of 1 to 250 MBq/nmol.

In exemplified embodiments, compounds, e.g., novel $^{61}Cu$ radiotracers, and compositions thereof, are provided for (i) the imaging, diagnosis, and staging of cancers, such as: prostate cancer, somatostatin receptor-expressing cancers and epithelial cancers (e.g., using [$^{61}Cu$]Cu-based radiotracers, such as [$^{61}Cu$]Cu-NODAGA-PSMA-I&T, [$^{61}Cu$]Cu-NODAGA-TOC, [$^{61}Cu$]Cu-NODAGA-LM3, [$^{61}Cu$]Cu-NODAGA-F1, [$^{61}Cu$]Cu-NODAGA-F2, [$^{61}Cu$]Cu-NODAGA-F3, and [$^{61}Cu$]Cu-NODAGA-F4). In further contemplated embodiments, (ii) targeted radionuclide therapy of cancers, such as prostate cancer, somatostatin receptor-expressing cancers and epithelial cancers (e.g., using $^{67}Cu$-based radiotracers, such as [$^{67}Cu$]Cu-NODAGA-PSMA-I&T, [$^{67}Cu$]Cu-NODAGA-LM3, [$^{67}Cu$]Cu-NODAGA-F1, [$^{67}Cu$]Cu-NODAGA-F2, [$^{67}Cu$]Cu-NODAGA-F3, and [$^{67}Cu$]Cu-NODAGA-F4.)

In a third aspect of the disclosure, a method of generating an image of a subject is provided, the method comprising administering to the subject a composition according to the first aspect of the present disclosure; and generating an image of ≥ a part of the subject's body, e.g., using positron emission tomography (PET) or single-photon emission computerized tomography (SPECT). In certain embodiments, PET is used and *Cu is $^{61}Cu$. In certain embodiments, SPECT is used and *Cu is $^{67}Cu$.

In a fourth aspect of the disclosure, a method of detecting a disease in a subject is provided, the method comprising administering to the subject a composition according to the first aspect of the present disclosure; detecting the localization of the radiotracer in the subject, e.g., using PET or SPECT. In certain embodiments, PET is used and *Cu is [$^{61}Cu$]Cu. In certain embodiments, SPECT is used and *Cu is $^{67}Cu$.

In certain embodiments, the disease to be detected includes cancers, such as somatostatin receptor-expressing cancer like neuroendocrine tumors, prostate cancer, and malignant meningiomas; epithelial cancers and their respective microenvironments, which overexpress FAP including non-small cell lung cancer, triple-negative breast cancer, colorectal carcinoma, gastric cancer, ovarian cancer, and pancreatic cancer; myocardial infarct; and interstitial lung disease.

In a fifth aspect of the disclosure, a method of monitoring the effect of cancer treatment on a subject afflicted with cancer, is provided, the method comprising administering to the subject a composition according to the first aspect of the present disclosure; and detecting the localization of the radiotracer in the subject, e.g., using PET or SPECT. In certain embodiments, PET is used and *Cu is [$^{61}Cu$]Cu. In certain embodiments, SPECT is used and *Cu is $^{67}Cu$.

In a sixth aspect of the disclosure, a method of providing radionuclide therapy to a cancer patient in need thereof, is provided, the method comprising administering to the subject a composition according to the first aspect of the present disclosure. In certain embodiments, *Cu is $^{67}Cu$.

In a seventh aspect of the disclosure, a method of treating cancer in a patient in need thereof, is provided, the method comprising administering to the subject a composition according to the first aspect of the present disclosure. In certain embodiments, *Cu is $^{67}Cu$.

In certain embodiments of the fifth, sixth, and seventh aspects, the cancer is selected from: somatostatin receptor expressing tumors such as neuroendocrine tumors, prostate cancer, and malignant meningiomas; and epithelial cancers and their respective microenvironments that overexpress FAP, such as non-small cell lung cancer, triple-negative breast cancer, colorectal carcinoma, gastric cancer, ovarian cancer, and pancreatic cancer.

3. BRIEF DESCRIPTION OF THE DRAWINGS

These and other features, aspects, and advantages of the present disclosure will become better understood with regard to the following description, and accompanying drawings, where:

Figure 3:
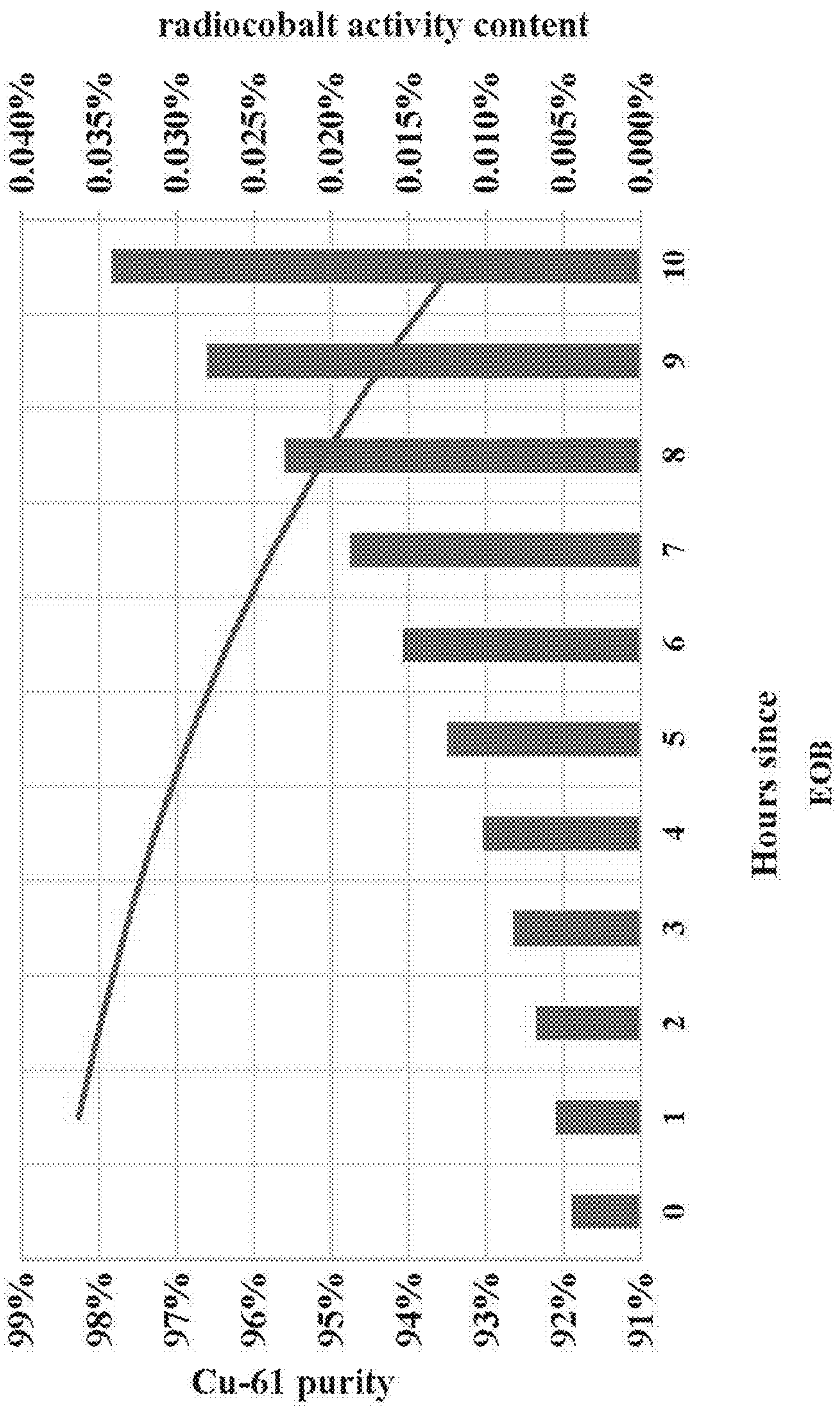

FIG. 3 displays the analysis of $^{61}$Cu purity of [$^{61}$Cu]$CuCl_2$ solution obtained by irradiation of $^{nat}$Ni on Nb backing with deuteron beam at 8.4 MeV for 3 h at 50 μA. The curved line corresponds to reduction in % purity of $^{61}$Cu over time and the bars correspond to radiocobalt activity over time.

Figure 4:
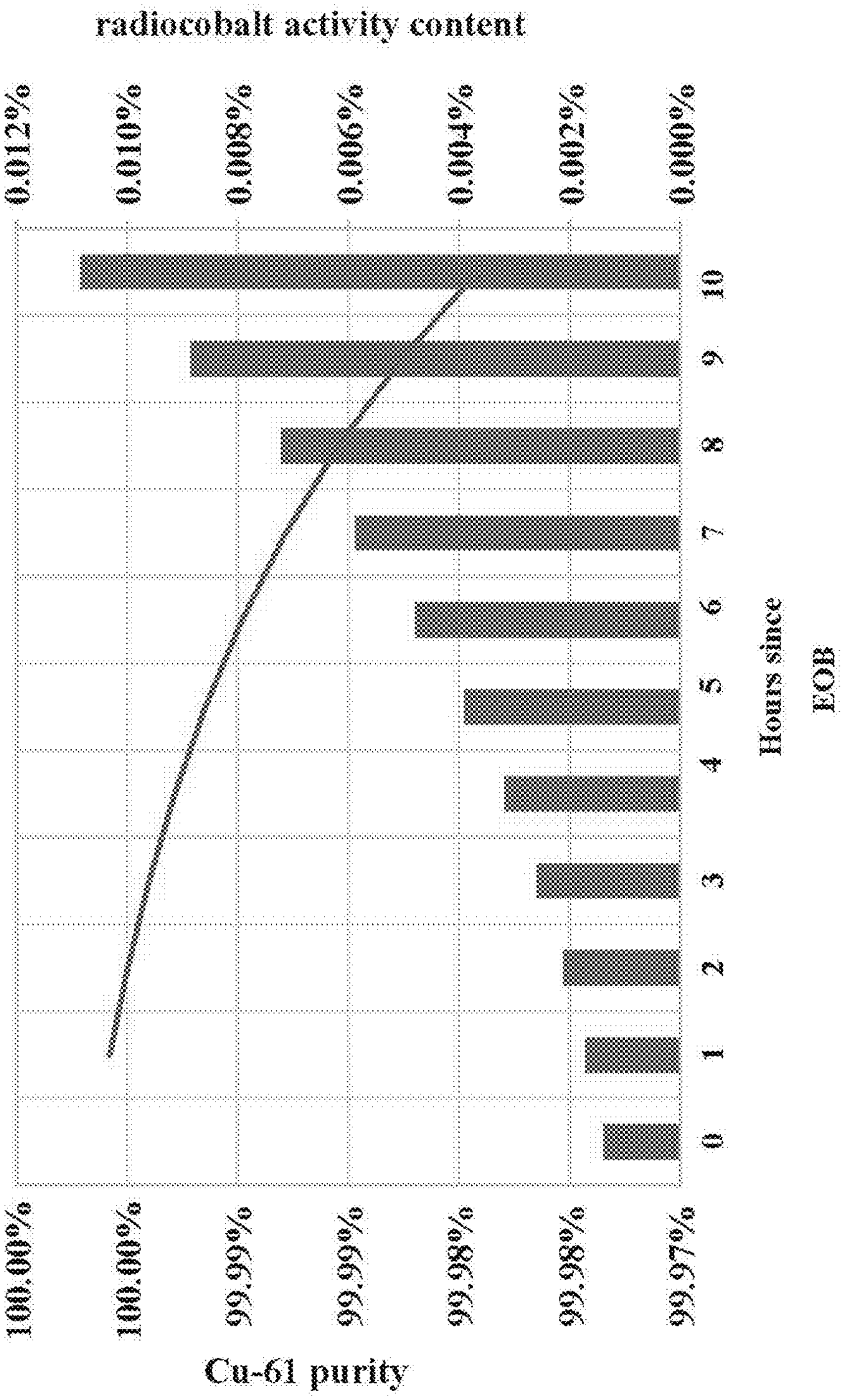

FIG. 4 displays an analysis of $^{61}$Cu purity of [$^{61}$Cu]$CuCl_2$ solution obtained by irradiation of $^{60}$Ni on Nb backing with a deuteron beam at 8.4 MeV for 3 h at 50 μA. The curved line corresponds to the reduction in % purity of $^{61}$Cu over time, and the bars correspond to radiocobalt activity over time.

Figure 5:
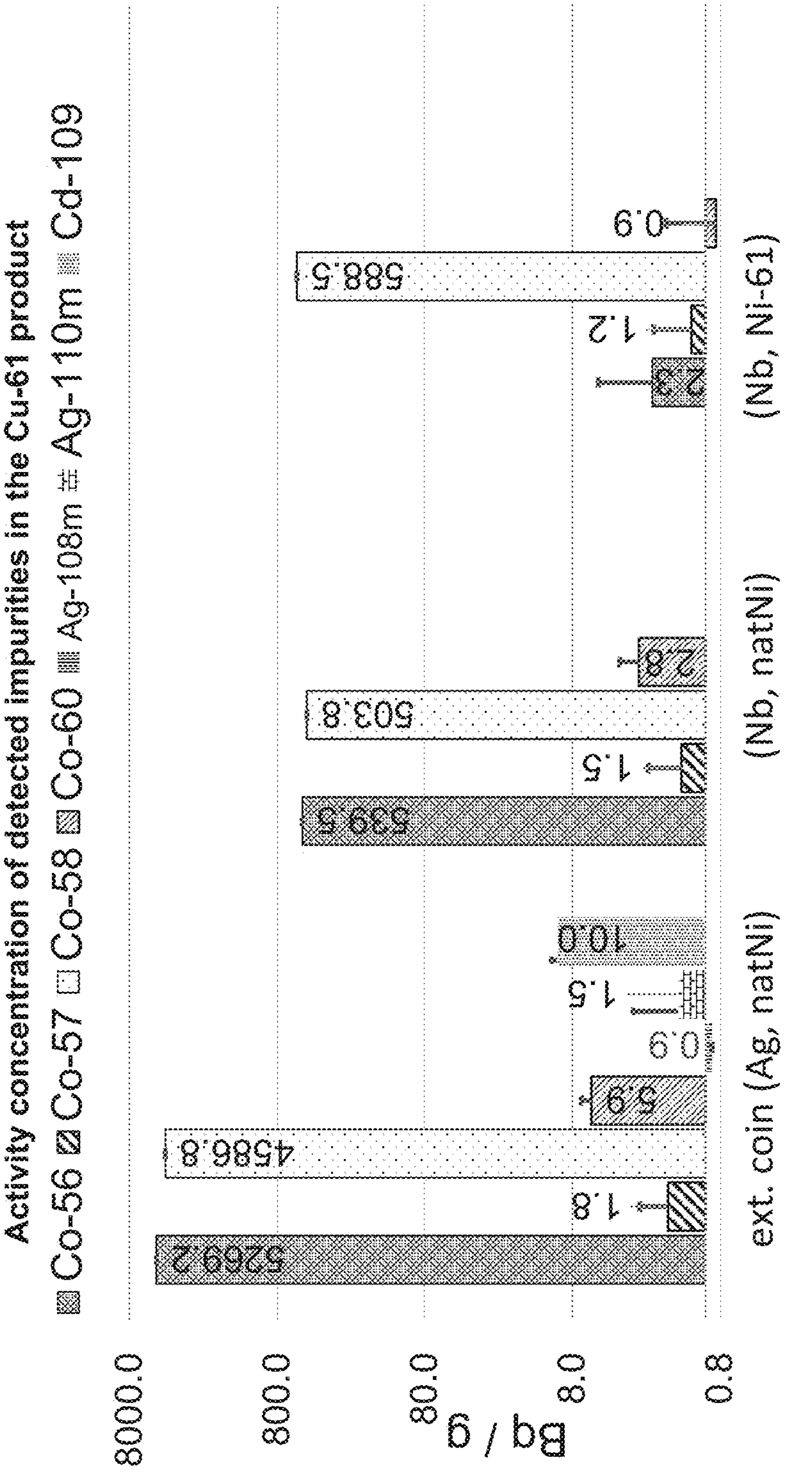

FIG. 5 presents the activity concentration of detected impurities in [$^{61}$Cu]$CuCl_2$ solutions produced according to various methods. The ext. coin (Ag, natNi) data was generated by irradiation of a commercially available $^{nat}$Ni target on Ag backing. The (Nb, natNi) and (Nb, Ni-61) data were generated based on irradiation of Ni targets (natural and isotopically enriched in $^{61}$Ni, respectively) electroplated according to the present disclosure on high-purity Nb backing. The activity concentration was assessed by gamma spectrometry and reported in Bq/g. The data shows that silver and cobalt isotopes are significantly reduced in the [$^{61}$Cu]$CuCl_2$ solution produced by irradiation of Ni targets electroplated according to the present disclosure on high-purity Nb backing.

Figure 6:
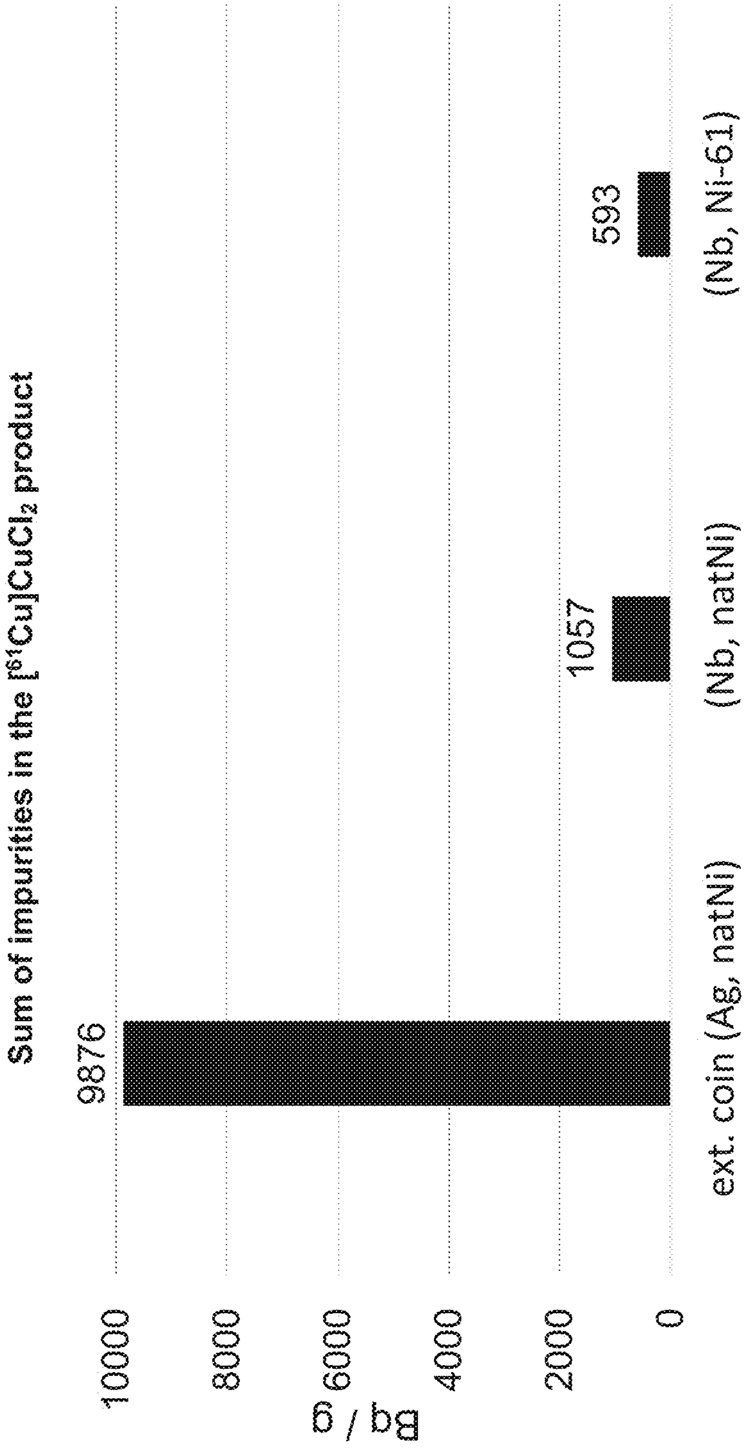

FIG. 6 shows the significant reduction in the sum of radionuclidic impurities present in a [$^{61}$Cu]$CuCl_2$ solutions produced according to various methods. The ext. coin (Ag, natNi) data was generated based on irradiation of a commercially available $^{nat}$Ni target on Ag backing. The (Nb, natNi) and (Nb, Ni-61) data were generated based on irradiation of Ni targets (natural and isotopically enriched in $^{61}$Ni, respectively), electroplated according to the present disclosure on high-purity Nb backing. The radionuclidic impurities were determined by gamma spectrometry and reported in Bq/g (summed radionuclidic impurities). The presented data highlight in particular the reduction of overall impurities in the [$^{61}$Cu]$CuCl_2$ solution when produced in accordance with the present disclosure.

Figure 7:
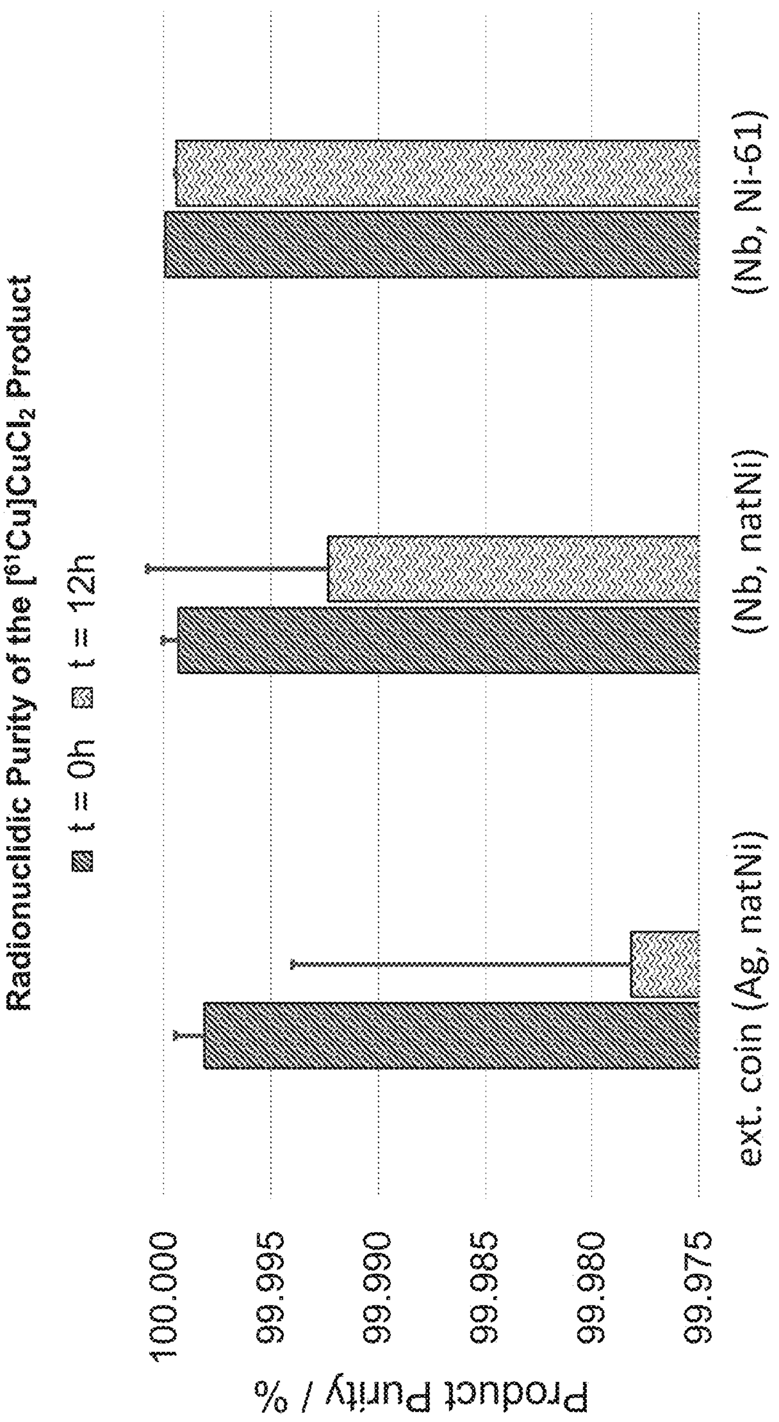

FIG. 7 illustrates the sustained high radionuclidic purity of a [$^{61}$Cu]$CuCl_2$ solution produced according to the present disclosure compared to a commercially available $^{nat}$Ni target on a Ag backing (ext. coin (Ag, natNi)). The (Nb, natNi) and (Nb, Ni-61) coins were prepared by electrodeposition according to the present disclosure on high-purity Nb backing. The data was generated using gamma spectrometry and reported in Bq/g providing the summed radionuclidic purities at t=0 h and at t=12 h. The presented data highlight the superior quality of the [$^{61}$Cu]$CuCl_2$ solution when produced by irradiation of Ni targets electroplated according to the present disclosure on high purity Nb backing, where the purity after 12 hours is still well above the purity limits set by pharmacopeia for similar radionuclides for medical use.

Figure 8:
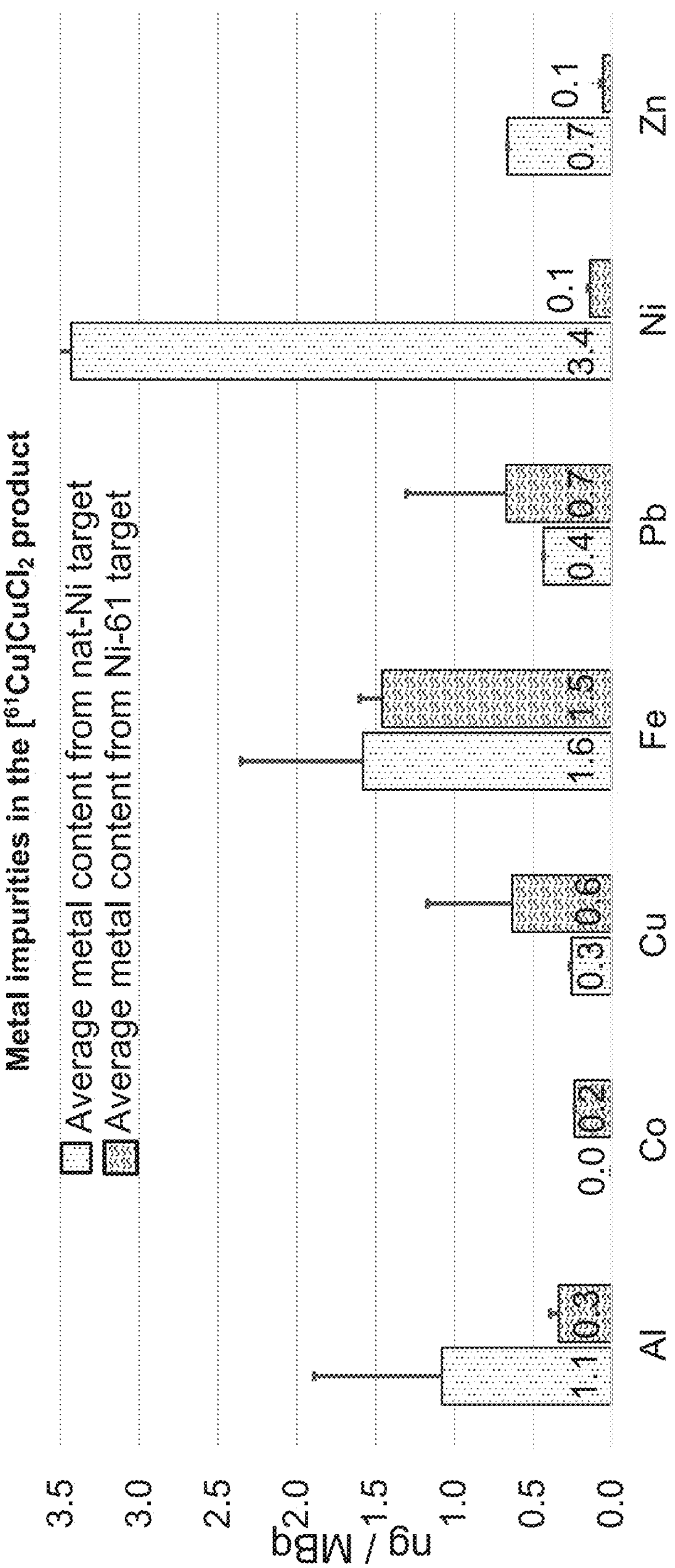

FIG. 8 displays chemical impurities, as measured by ICP-MS, of the [$^{61}$Cu]$CuCl_2$ solution when produced by bombardment of $^{nat}$Ni vs. $^{61}$Ni when produced by irradiation of Ni targets electroplated according to the present disclosure on high-purity Nb backing.

Figure 9:
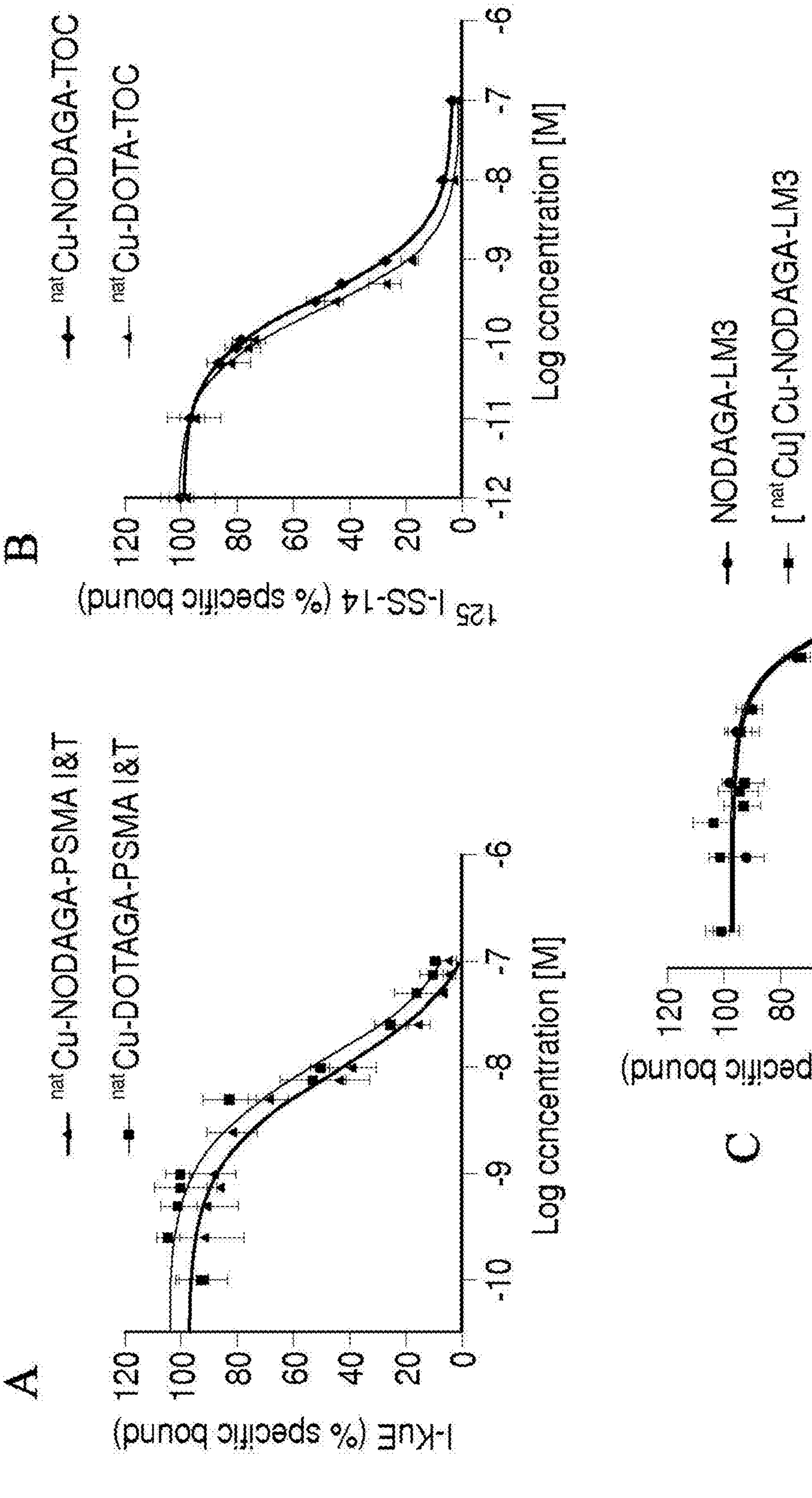

FIG. 9, panels A-C, illustrate the measured affinity for each exemplified construct via the determination of the $IC_{50}$ for various constructs, as described in Example 5. Panels A and B show that between two $^{nat}$Cu-complexed PSMA constructs (panel A) and two $^{nat}$Cu-complexed TOC somatostatin constructs (panel B), the exchange of the chelator from DOTAGA (reference construct DOTAGA-PSMA-I&T used in the clinics) and DOTA (reference construct DOTA-TOC used in the clinics) to the chelator NODAGA (NODAGA-PSMA-I&T and NODAGA-TOC, respectively) does not hamper the affinity of the $^{nat}$Cu-complexed constructs for their molecular target (PSMA and SST2, respectively). Panel C shows that complexation of Cu (or radiolabeling with $^{61}$Cu) does not hamper the affinity of the NODAGA-LM3 construct for its molecular target (SST2), as suggested by the $IC_{50}$ values of the NODAGA-LM3 and $^{nat}$Cu-NODAGA-LM3 that remain the same.

Figure 10:
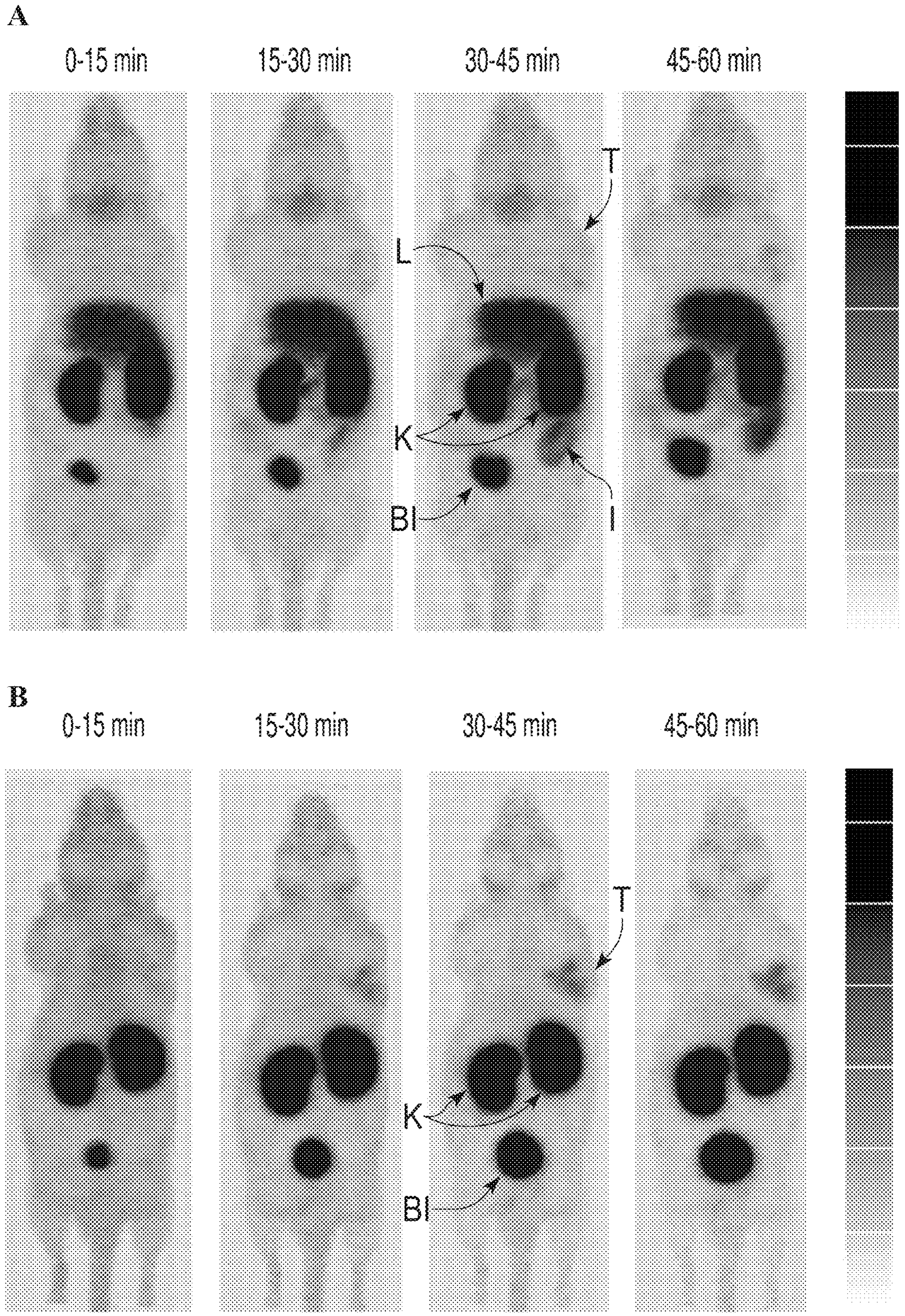

FIG. 10, panels A and B, illustrate the dynamic PET/CT scans of [$^{61}$Cu]Cu-DOTAGA-PSMA-I&T (panel A) and [$^{61}$Cu]Cu-NODAGA-PSMA-I&T (panel B) in PSMA-positive tumor-bearing mice within 1 hour, obtained according to Example 8; L=liver; K=kidney; I=intestine; Bl=bladder; T=tumor; J=joint(s); SG=salivary gland(s).

Figure 11:
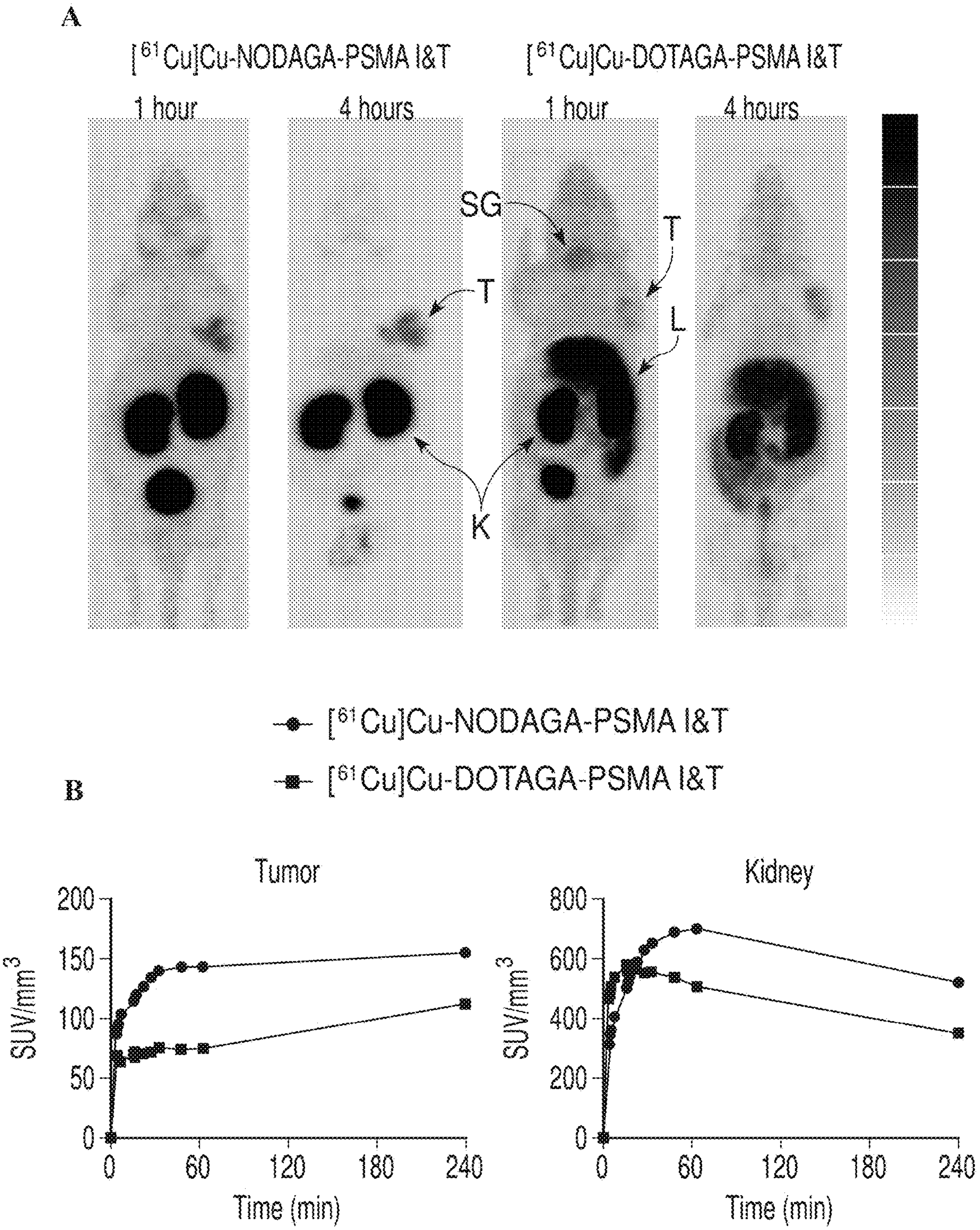

FIG. 11, panels A and B, illustrate PET/CT images of [$^{61}$Cu]Cu-NODAGA-PSMA-I&T and [$^{61}$Cu]Cu-DOTAGA-PSMA-I&T at 1 hour and 4 hours after injection in PSMA-positive tumor-bearing mice (panel A) and the time-activity curves of the tumor and kidneys (panel B; circle is [$^{61}$Cu]Cu-NODAGA-PSMA-I&T and square is [$^{61}$Cu]Cu-DOTAGA-PSMA-I&T), obtained according to Example 8.

Figure 12:
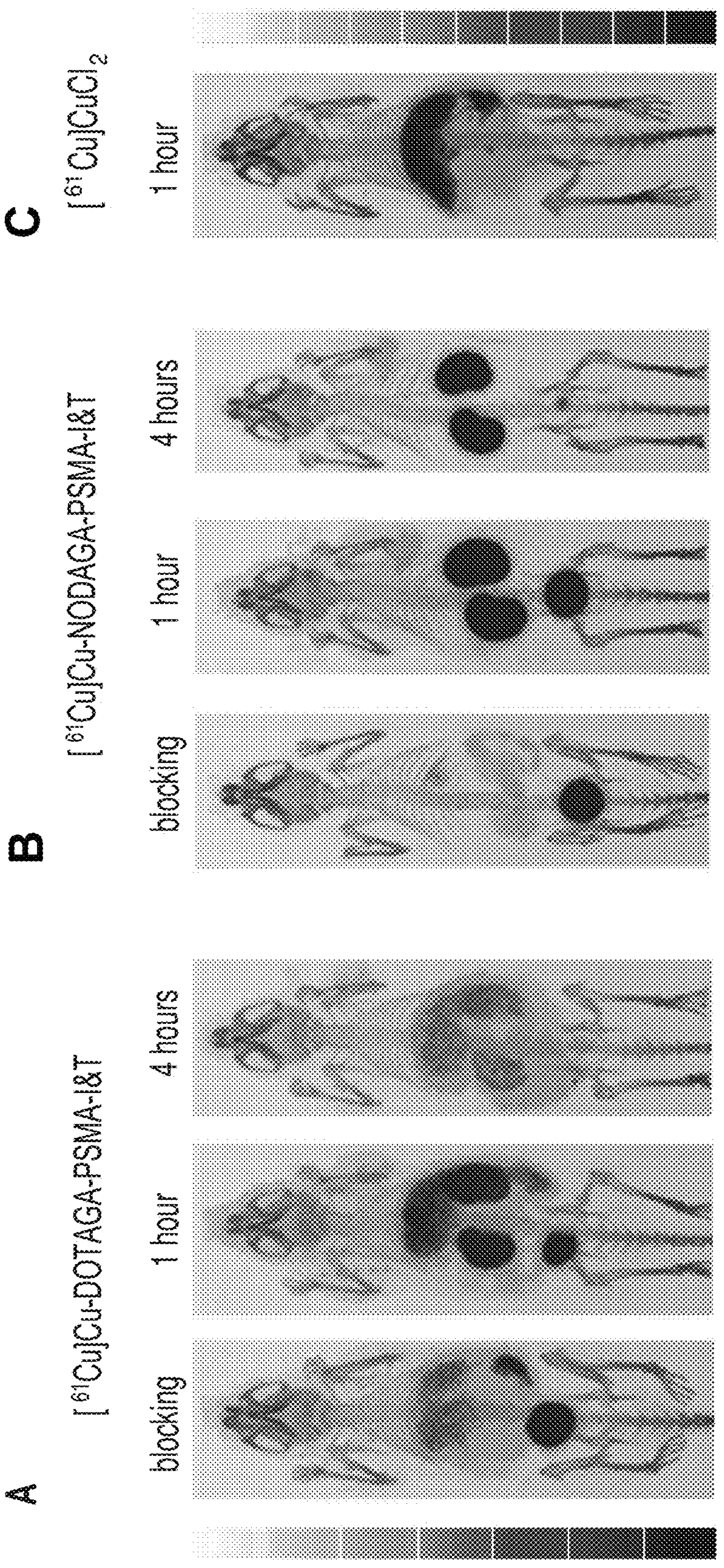

FIG. 12, panels A-C, display progression of biodistribution (1 to 4 hours) of differentially chelated $Cu^{2+}$ ([$^{61}$Cu]Cu-DOTAGA-PSMA-I&T (panel A) vs. [$^{61}$Cu]Cu-NODAGA-PSMA-I&T (panel B) vs. unchelated [$^{61}$Cu]$CuCl_2$).

Figure 13:
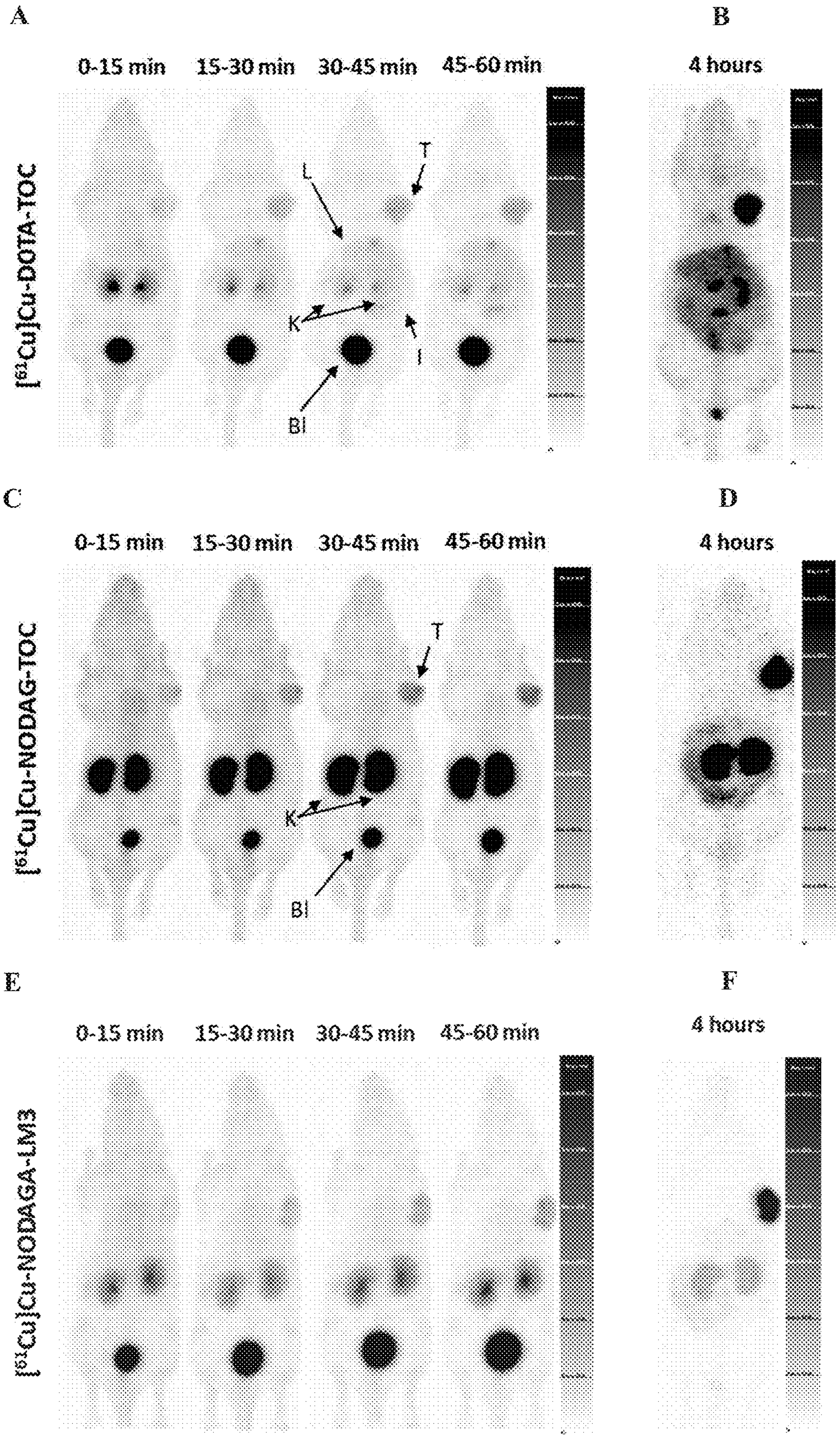

FIG. 13, panels A-F, illustrate the dynamic PET/CT scans within 1 hour and the static PET/CT scans at 4 hours after injection of [$^{61}$Cu]Cu-DOTA-TOC (panels A and B), [$^{61}$Cu]Cu-NODAGA-TOC (panels C and D) in SST2-positive tumor-bearing mice, obtained according to Example 8, and [$^{61}$Cu]Cu-NODAGA-LM3 (panels E and F) in SST2-positive tumor-bearing mice.

Figure 14:
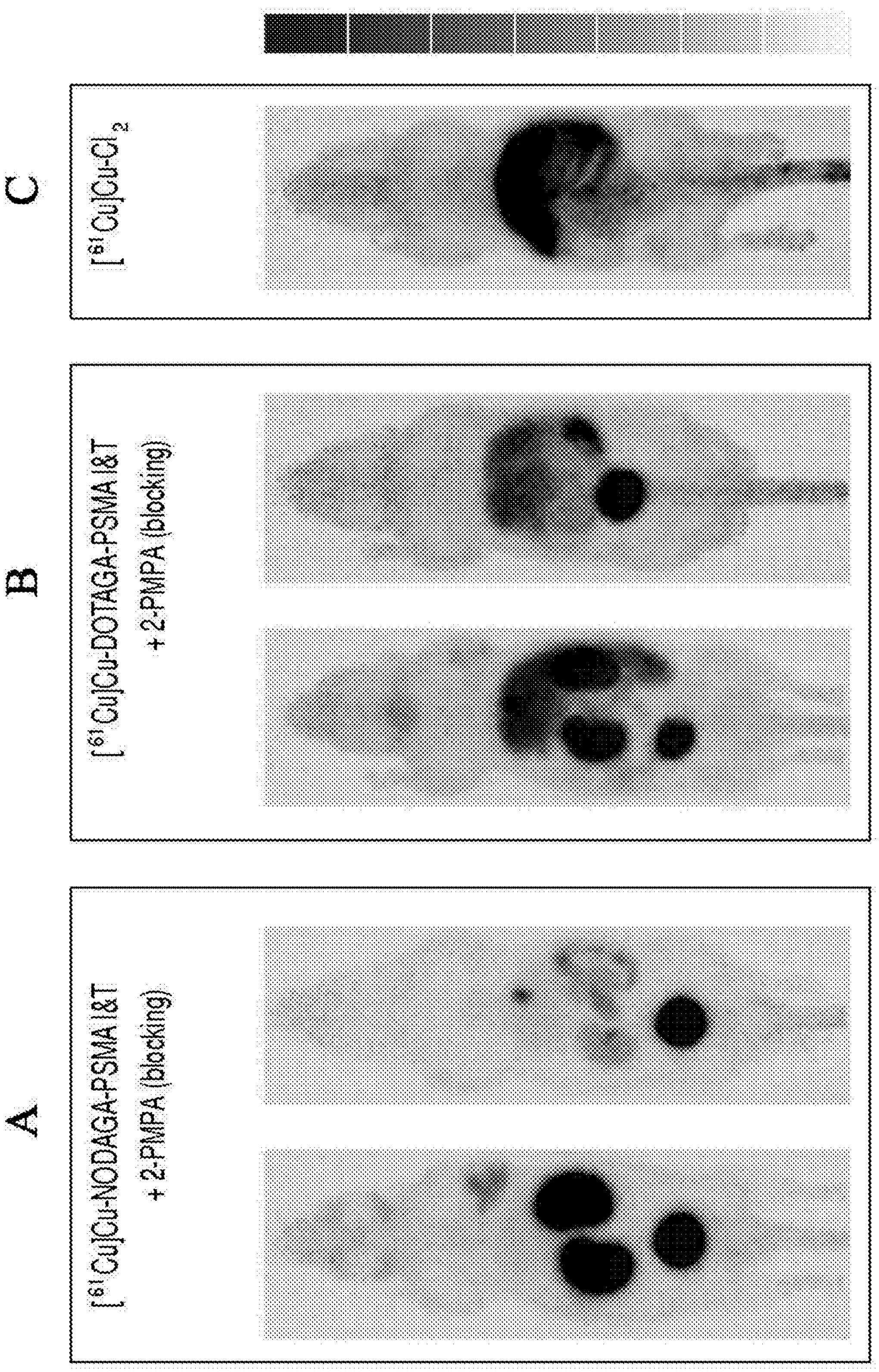

FIG. 14, panels A-C, illustrate the PET/CT scans of [$^{61}$Cu]Cu-NODAGA-PSMA-I&T (panel A) and [$^{61}$Cu]Cu-DOTAGA-PSMA-I&T (panel B) in PSMA-positive tumor-bearing mice at 1 hour after injection of the radiotracer alone or after injection of the blocking agent 2-PMPA and PET/CT scan of [$^{61}$Cu]$CuCl_2$ (panel C) at 1 hour, obtained according to Example 10.

Figure 15:
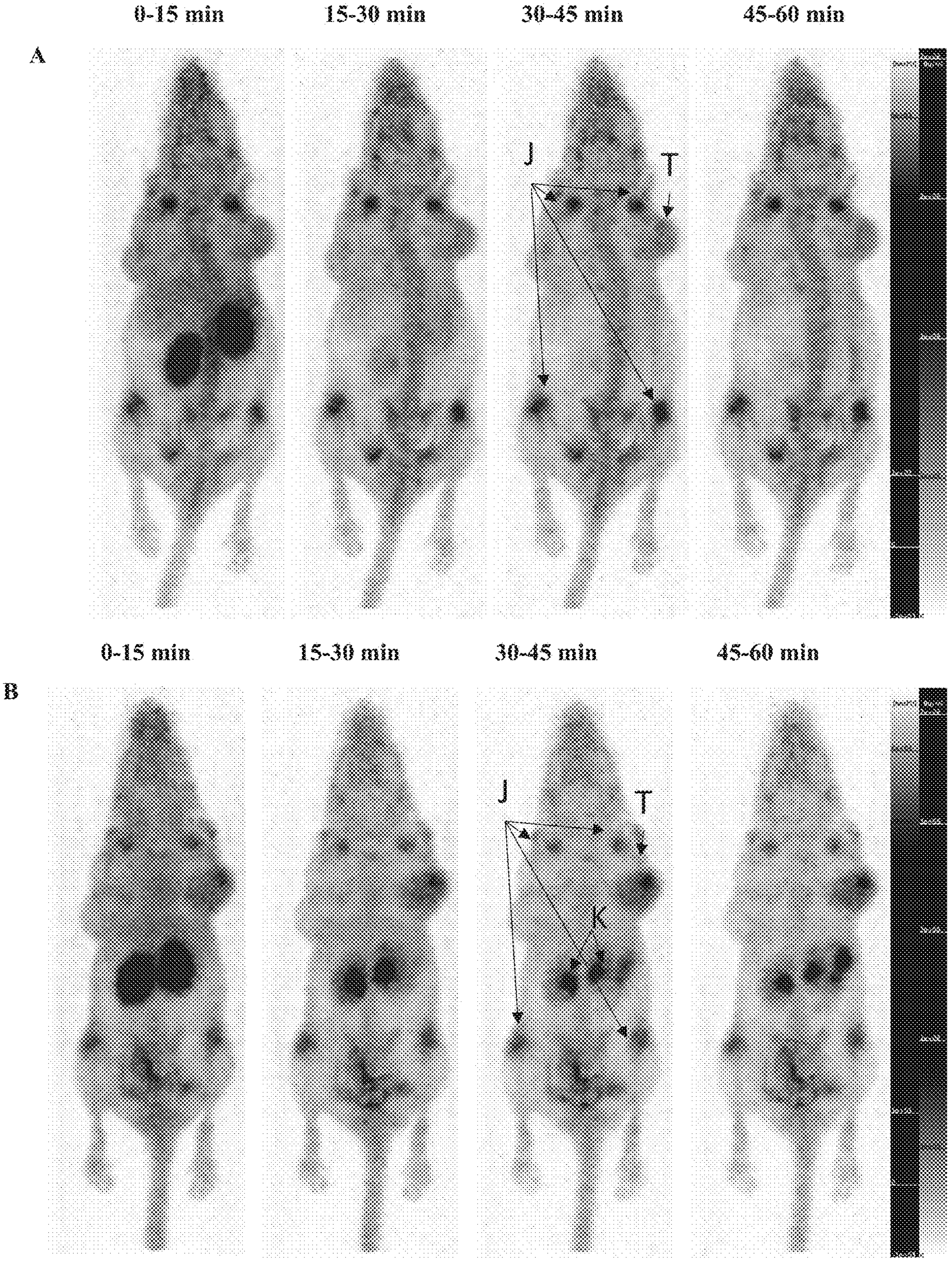

FIG. 15, panels A-B, illustrate the dynamic PET/CT scans of [$^{61}$Cu]Cu-NODAGA-F1 (panel A) and [$^{61}$Cu]Cu-NODAGA-F3 (panel B) in dual HT1080.hFAP and HT1080.wt tumor-bearing mice within 1 hour.

Figure 16:
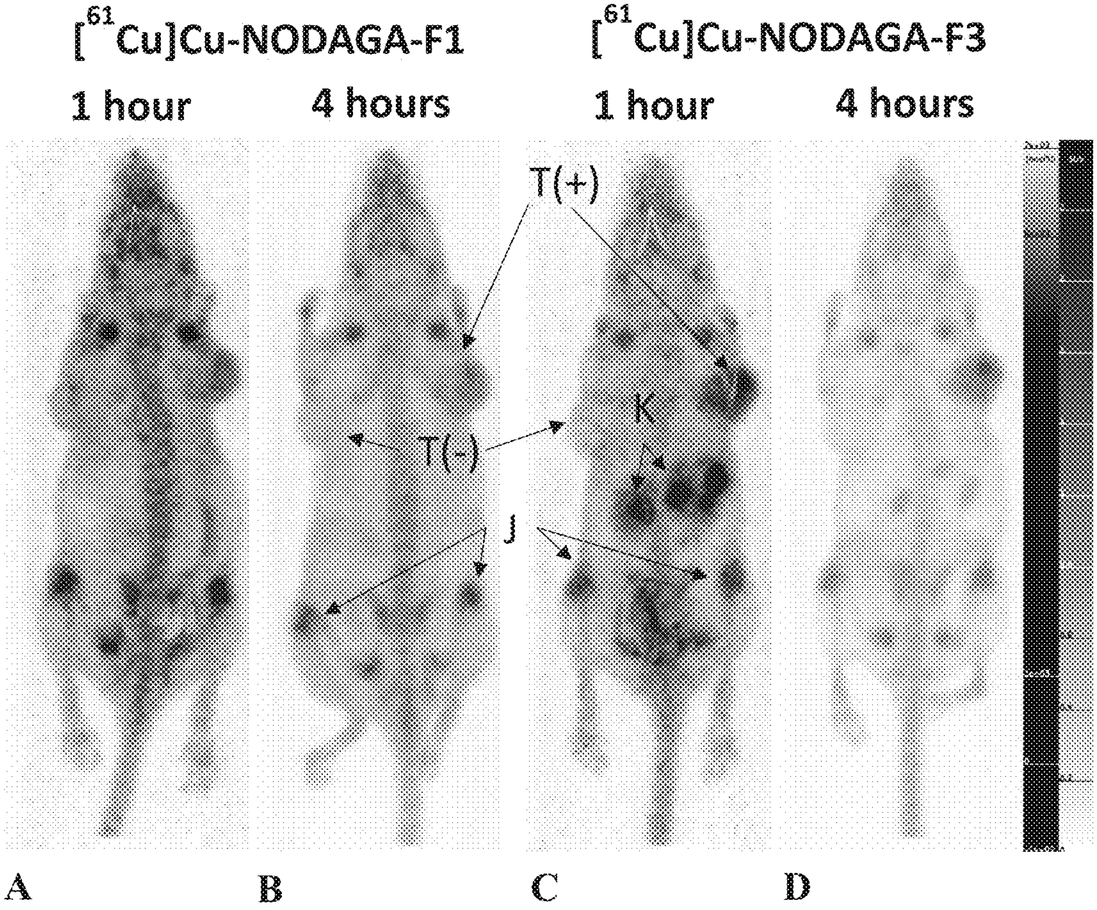

FIG. 16, panels A-D, show the static PET/CT scans of [$^{61}$Cu]Cu-NODAGA-F1 at 1 h (panel A) and at 4 h (panel B) and [$^{61}$Cu]Cu-NODAGA-F3 at 1 h (panel C) and at 4 h (panel D) in mice bearing FAP-positive xenografts.

Figure 17:
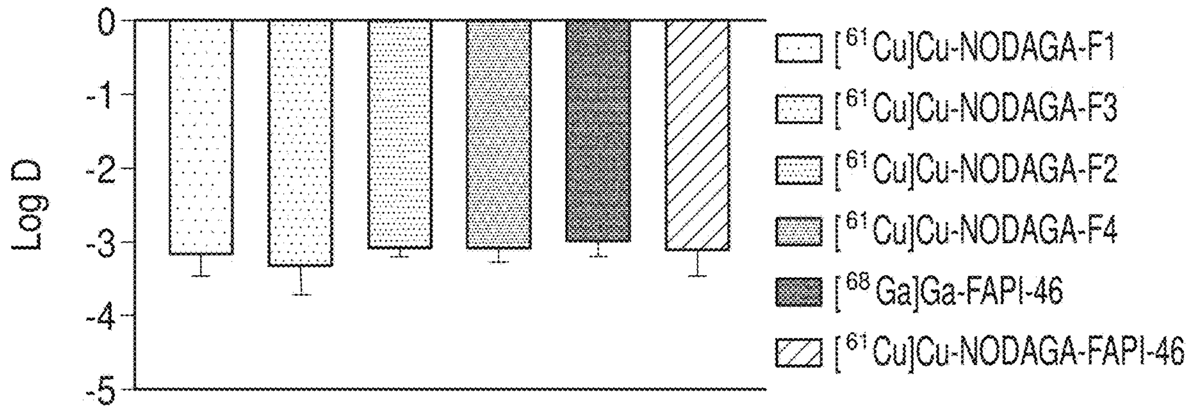

FIG. 17 shows the partition coefficient (log $D_{PBS/octanol,\ pH=7.4}$) of $^{61}$Cu-labeled and $^{68}$Ga-labeled conjugates. From left to right: [$^{61}$Cu]Cu-NODAGA-F1, [$^{61}$Cu]Cu-NODAGA-F3, [$^{61}$Cu]Cu-NODAGA-F2, [$^{61}$Cu]Cu-NODAGA-F4, [$^{68}$Ga]Ga-FAPI-46, and [$^{61}$Cu]Cu-NODAGA-FAPI-46.

Figure 18:
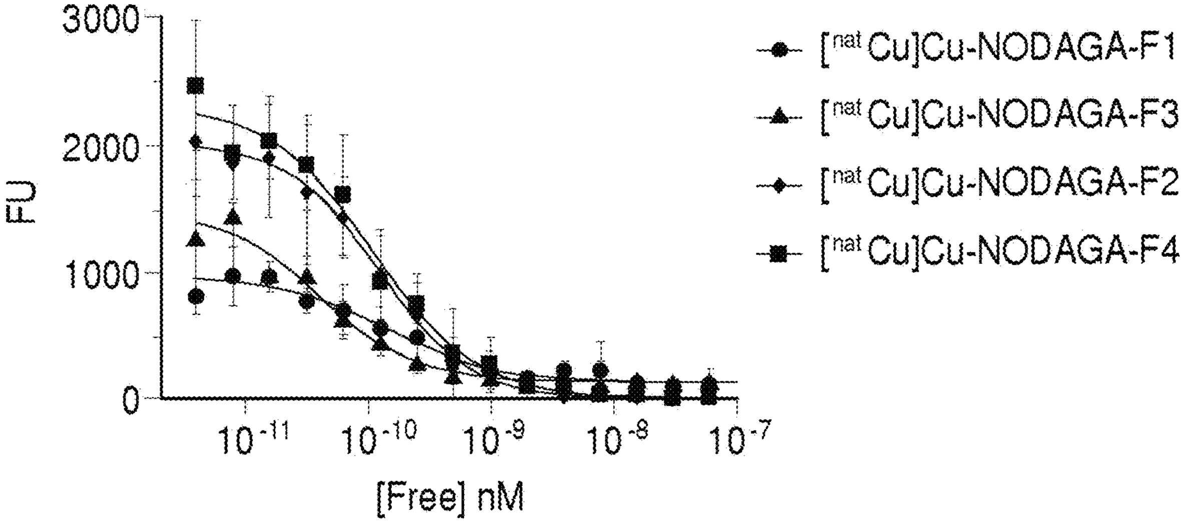

FIG. 18 shows the inhibition ($IC_{50}$) of [$^{nat}$Cu]Cu-NODAGA-F1, [$^{nat}$Cu]Cu-NODAGA-F3, [$^{nat}$Cu]Cu-NODAGA-F2, and [$^{nat}$Cu]Cu-NODAGA-F4.

Figure 19:
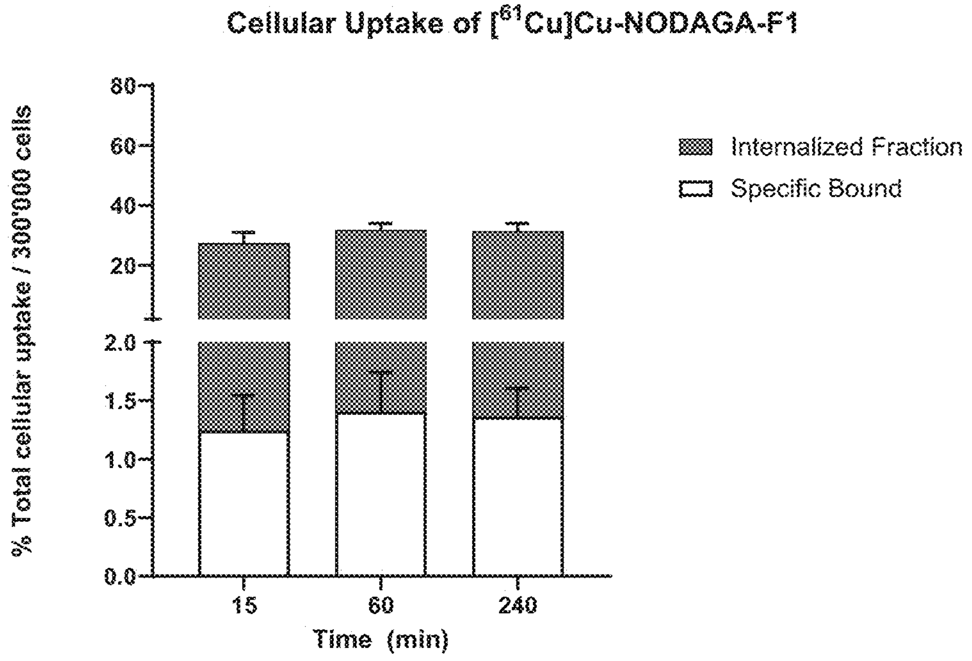
Figure 19:
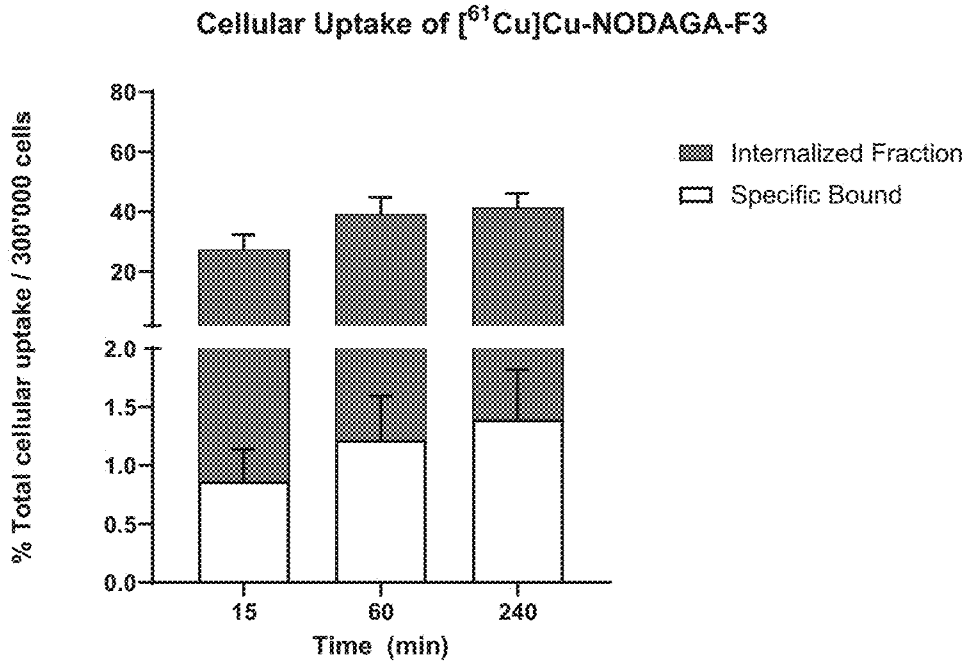
Figure 19:
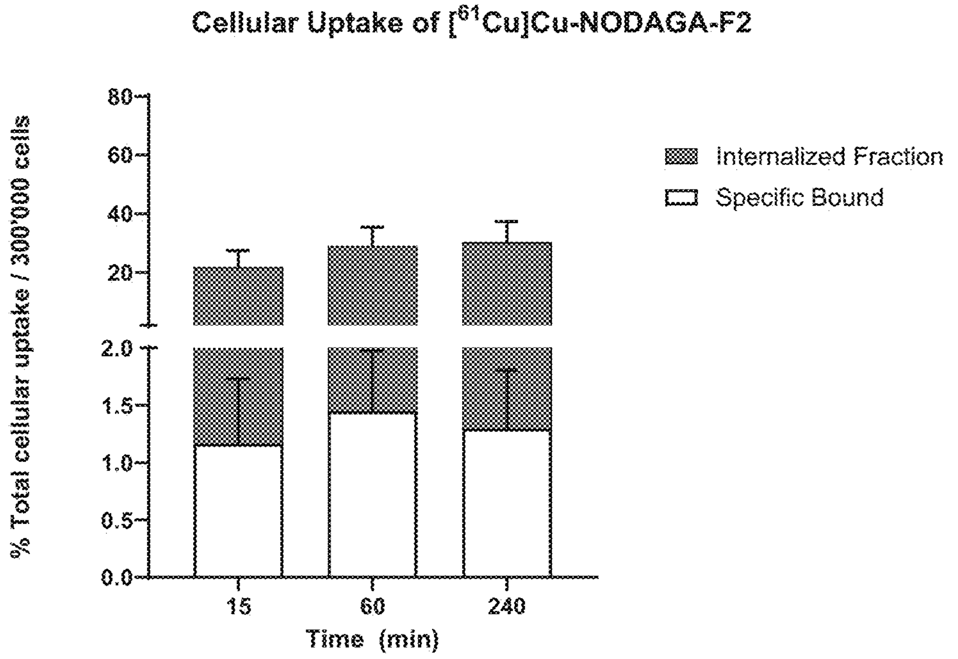
Figure 19:
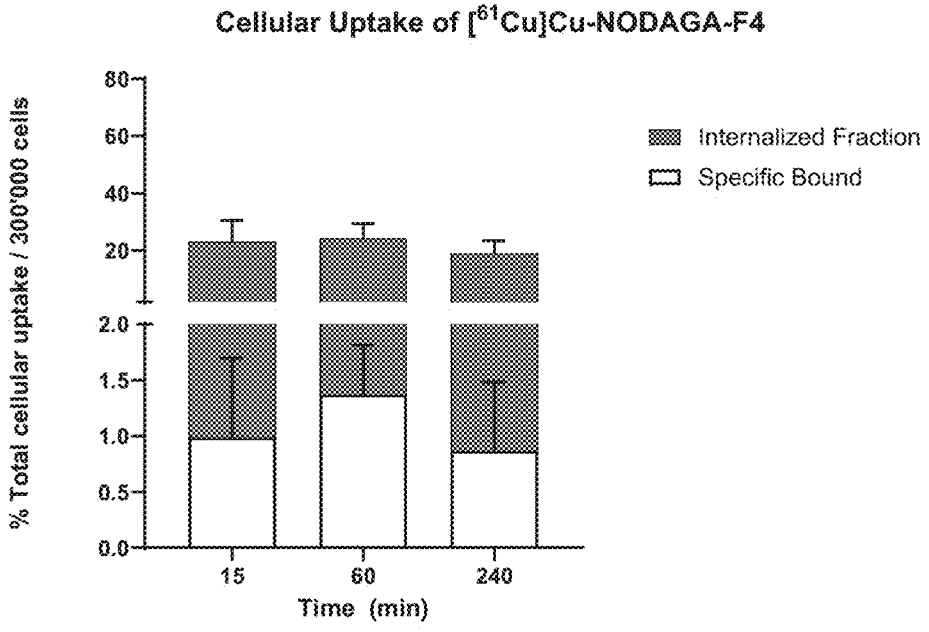

FIG. 19, panels A-D, show cellular uptake of cell surface (cell membrane bound) and internalized fractions of [$^{61}$Cu]

Cu-NODAGA-F1 (panel A), [$^{61}$Cu]Cu-NODAGA-F3 (panel B), [$^{61}$Cu]Cu-NODAGA-F2 (panel C), and [$^{61}$Cu]Cu-NODAGA-F4 (panel D). The values are expressed as % of the applied activity and refer to the specific uptake calculated after subtracting the non-specific values (measured in the presence of the non-FAP expressing cell line HT-1080.wt) from the total values (specific=total−non-specific).

Figure 20:
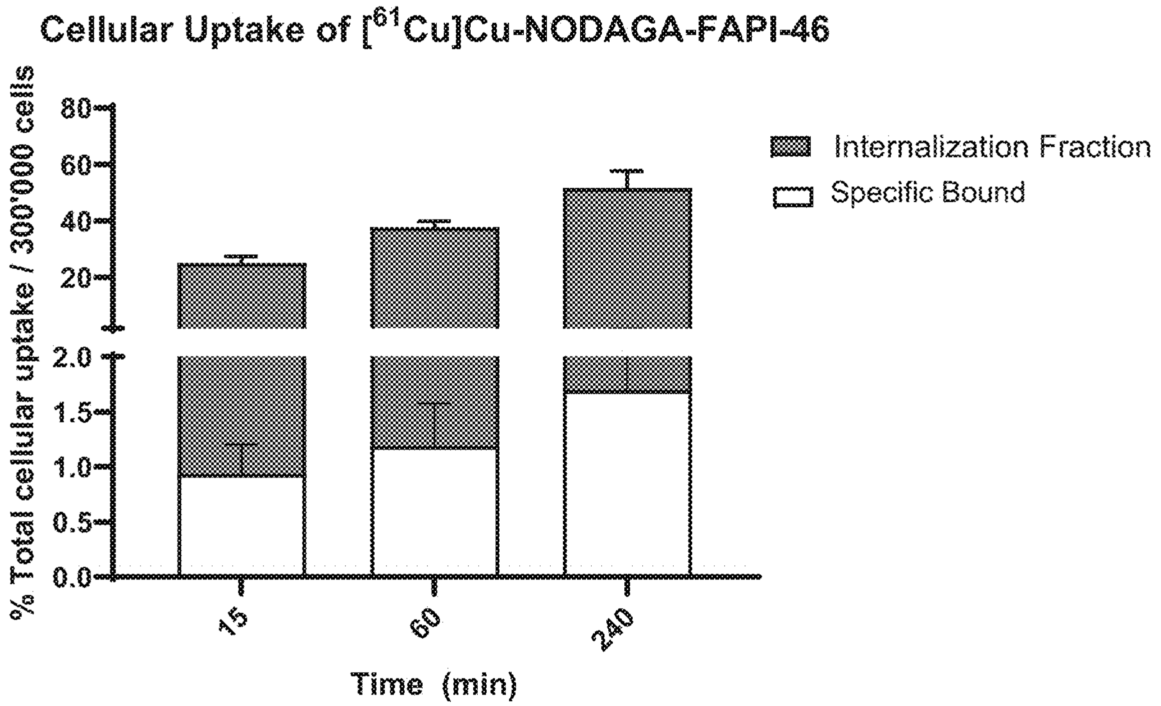

FIG. 20 shows cellular uptake of cell surface (cell membrane bound) and internalized fractions of [$^{61}$Cu]Cu-NODAGA-FAPI-46. The values are expressed as % of the applied activity and refer to the specific uptake calculated after subtracting the non-specific values (measured in the presence of the non-FAP expressing cell line HT-1080.wt) from the total values (specific=total−non-specific).

Figure 21:
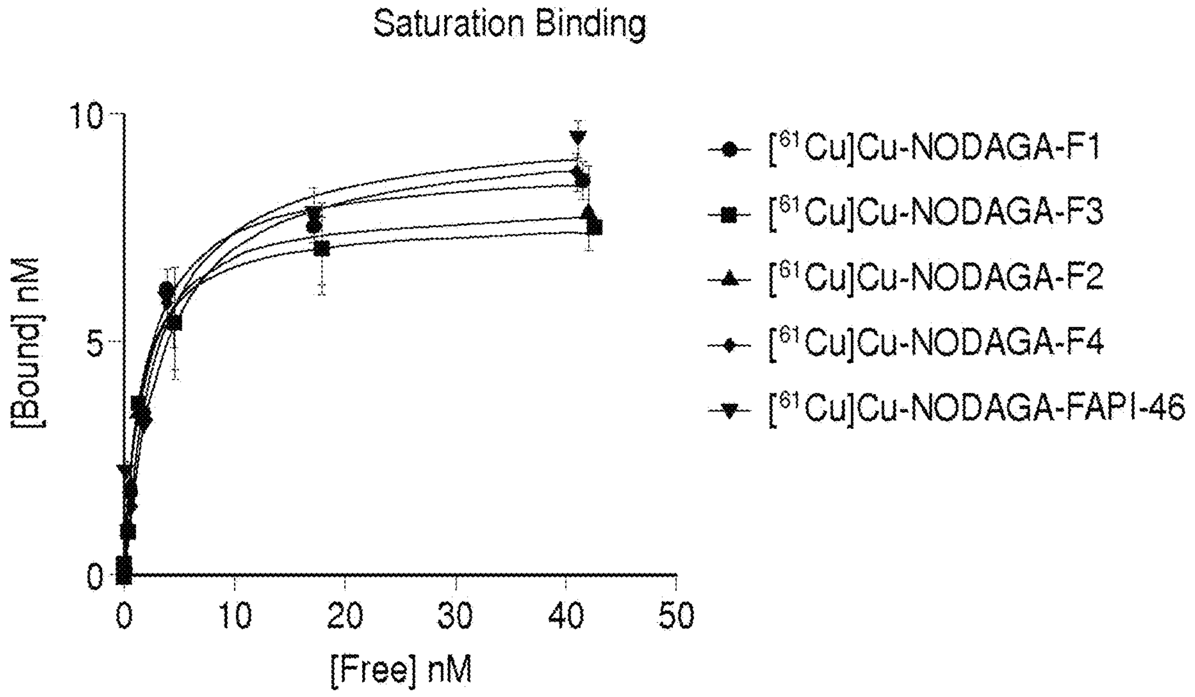

FIG. 21 shows the saturation binding of [$^{61}$Cu]Cu-labeled conjugates, [$^{61}$Cu]Cu-NODAGA-F1, [$^{61}$Cu]Cu-NODAGA-F2, [$^{61}$Cu]Cu-NODAGA-F3, [$^{61}$Cu]Cu-NODAGA-F4, [$^{61}$Cu]Cu-NODAGA-FAPI-46 on isolated HEK-293-hFAP membranes.

Figure 22:
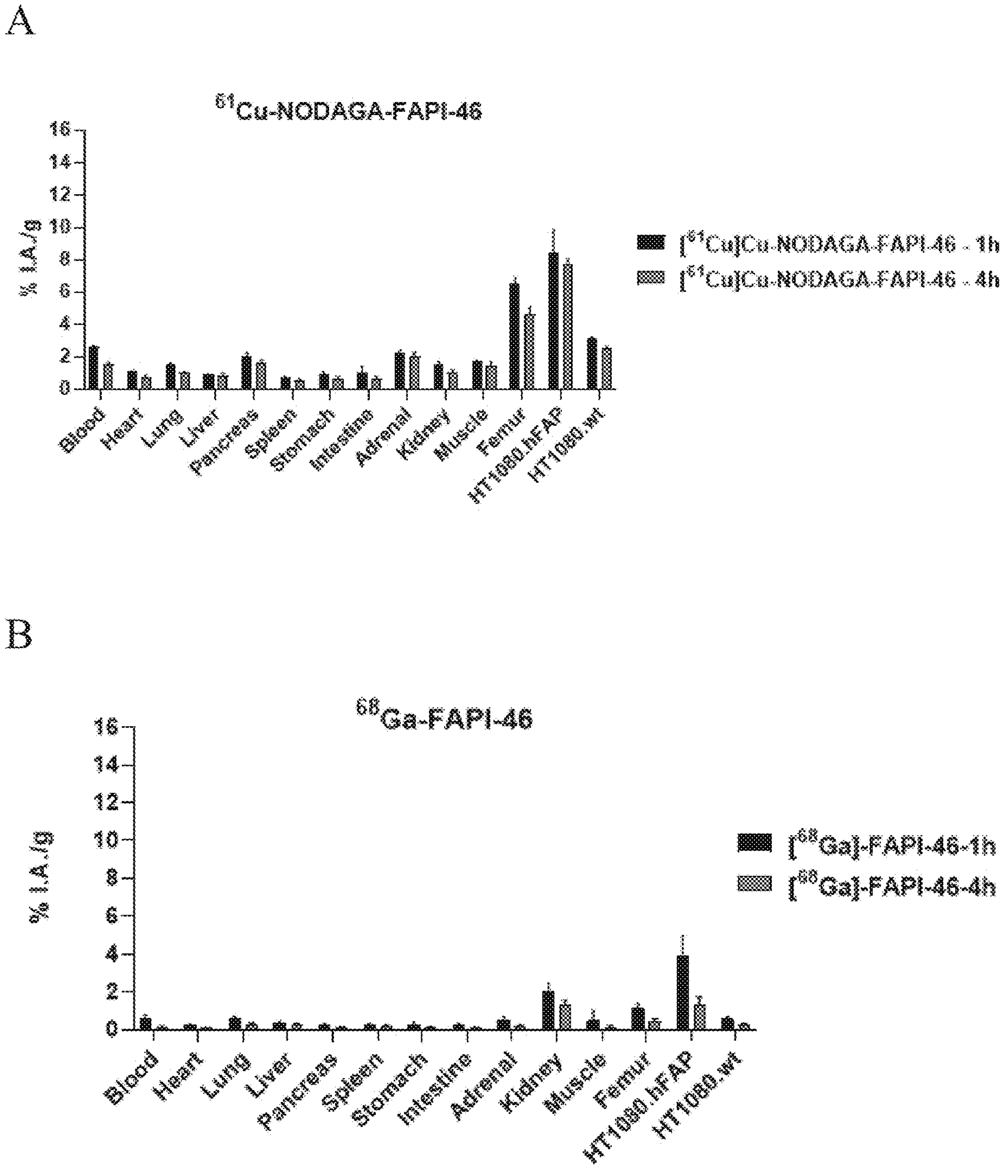

FIG. 22, panels A and B, show the biodistribution profiles of [$^{61}$Cu]Cu-NODAGA-FAPI-46 (panel A) and [$^{68}$Ga]Ga-FAPI-46 (panel B) in HT-1080.hFAP tumor-bearing mice at 1 hour and 4 hours following administration.

Figure 23:
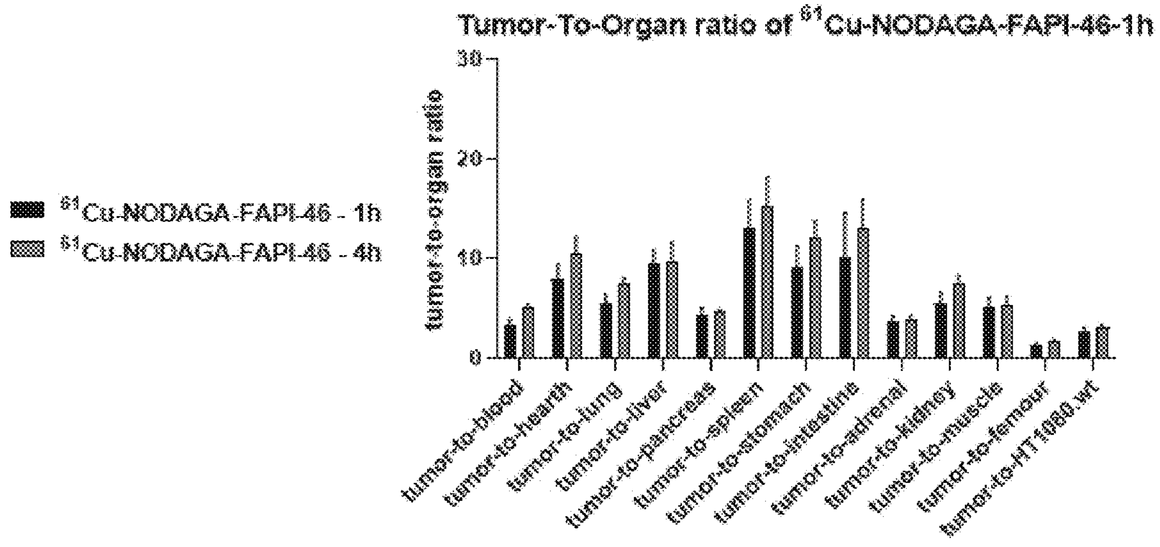
Figure 23:
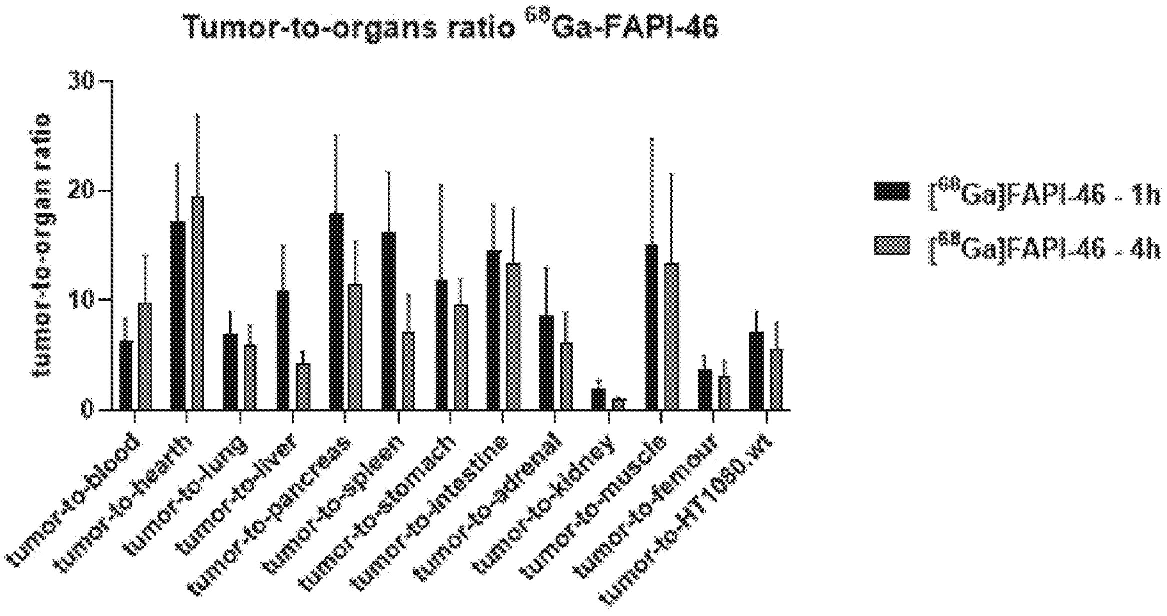

FIG. 23, panels A and B, show the tumor-to-organ ratios of [$^{61}$Cu]Cu-NODAGA-FAPI-46 (panel A) and [$^{68}$Ga]Ga-FAPI-46 (panel B) in HT-1080.hFAP tumor-bearing mice at 1 hour and 4 hours following administration.

Figure 24:
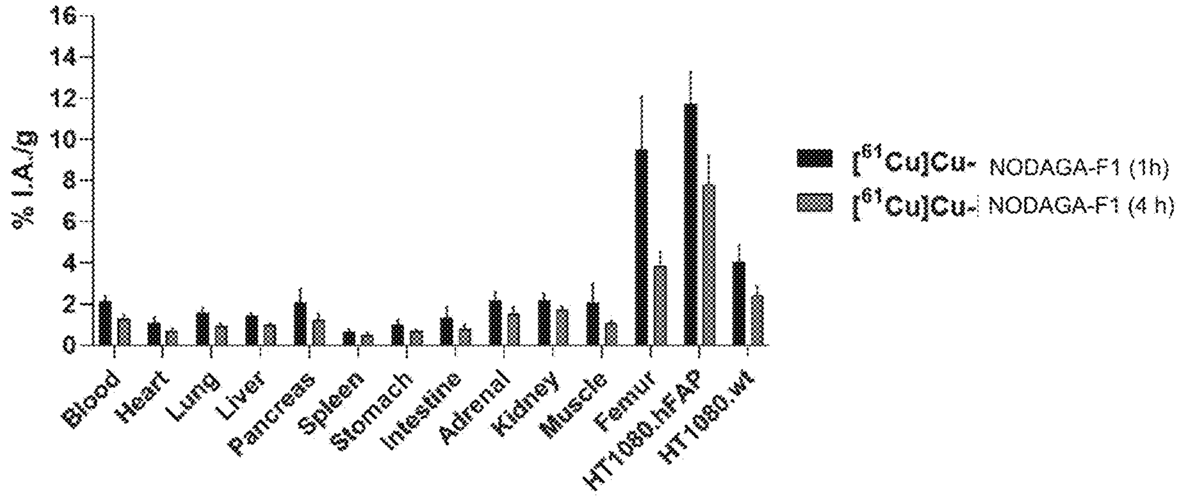
Figure 24:
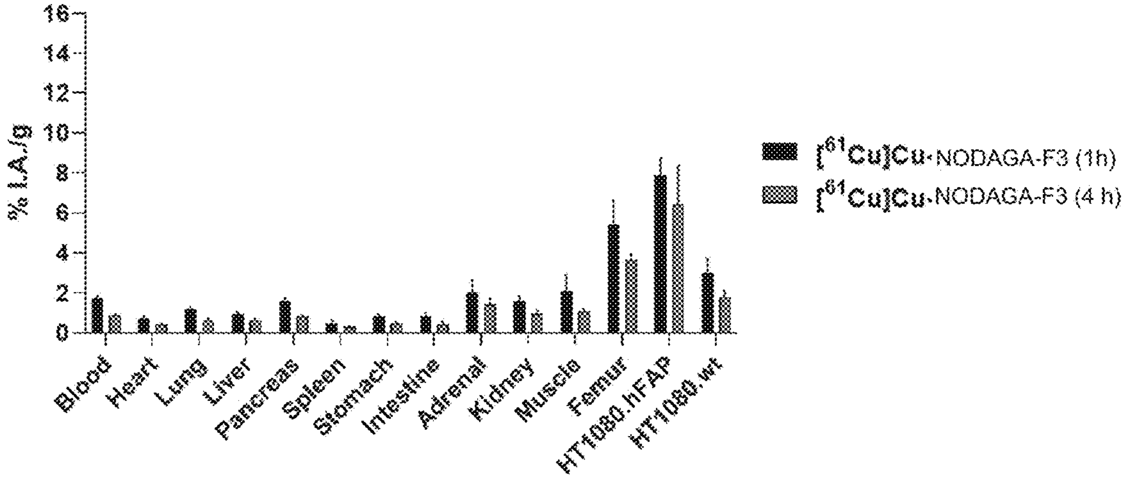

FIG. 24, panels A and B, show biodistribution profiles of [$^{61}$Cu]Cu-NODAGA-F1 (panel A) and [$^{61}$Cu]Cu-NODAGA-F3 (panel B), in HT-1080.hFAP tumor-bearing mice at 1 hour and 4 hours following administration.

Figure 25:
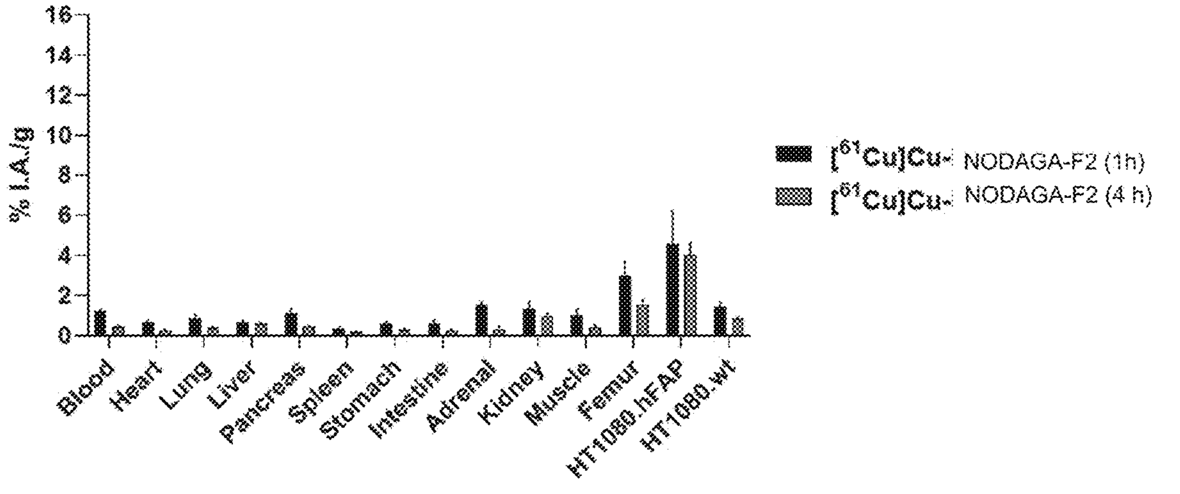
Figure 25:
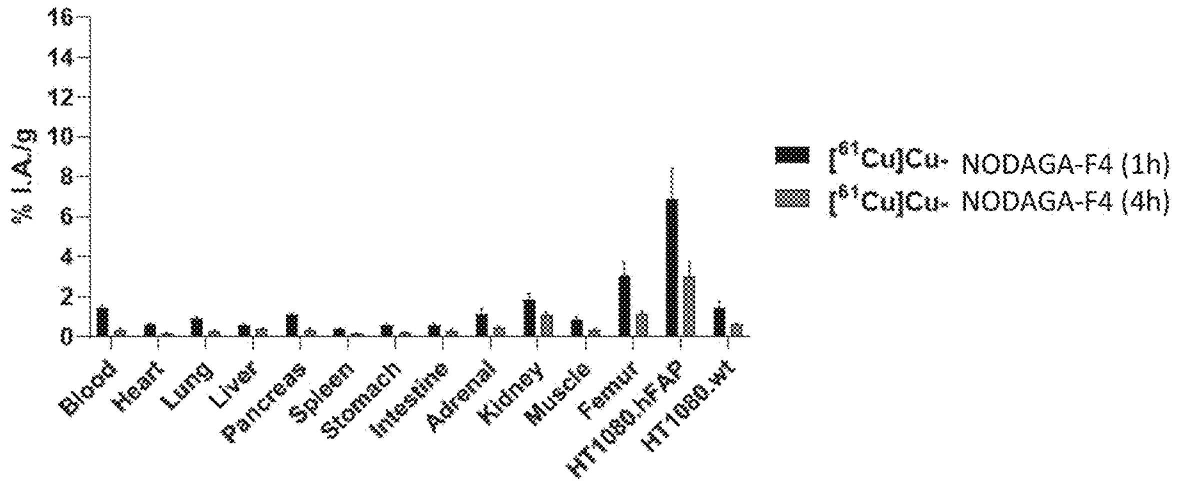

FIG. 25, panels A and B, show biodistribution profiles of [$^{61}$Cu]Cu-NODAGA-F2 (panel A) and [$^{61}$Cu]Cu-NODAGA-F4 (panel B) in HT-1080.hFAP tumor-bearing mice at 1 hour and 4 hours following administration.

Figure 26:
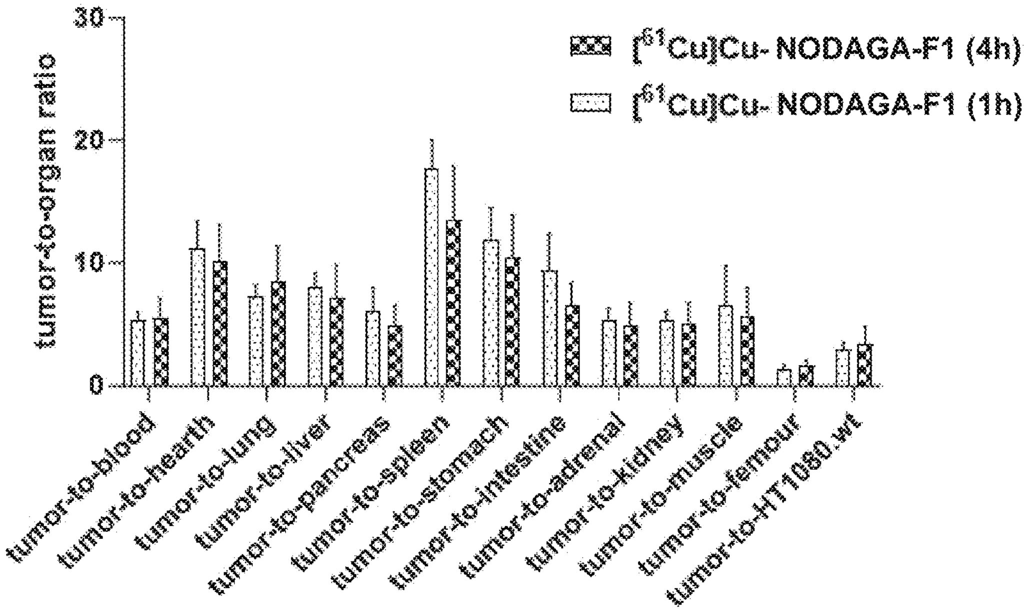
Figure 26:
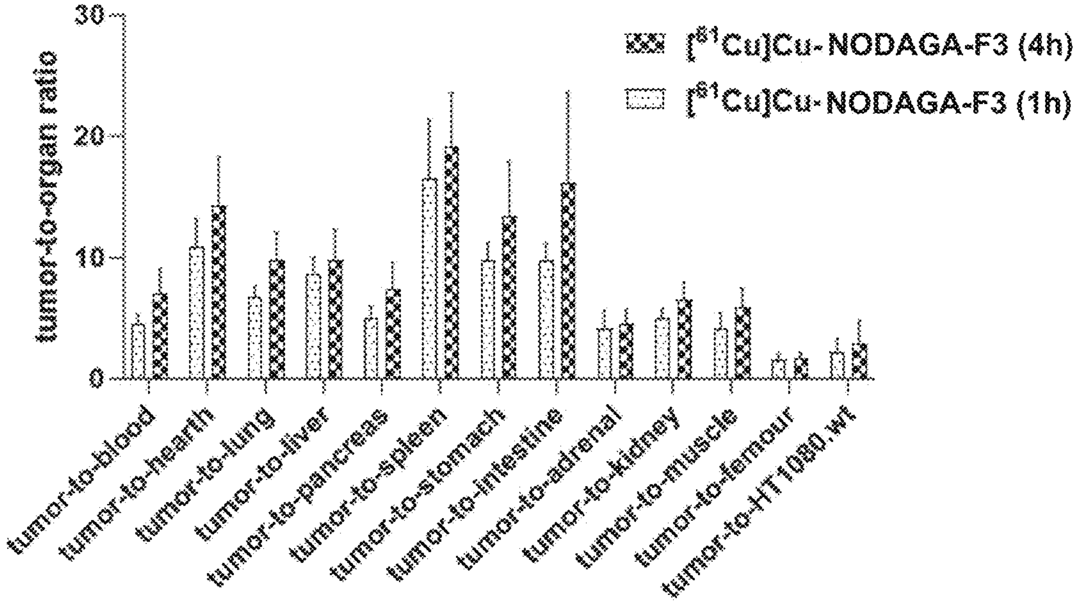

FIG. 26, panels A and B, show the tumor-to-organ ratios of [$^{61}$Cu]Cu-NODAGA-F1 (panel A) and [$^{61}$Cu]Cu-NODAGA-F3 (panel B), in HT-1080.hFAP tumor-bearing mice at 1 hour and 4 hours following administration.

Figure 27:
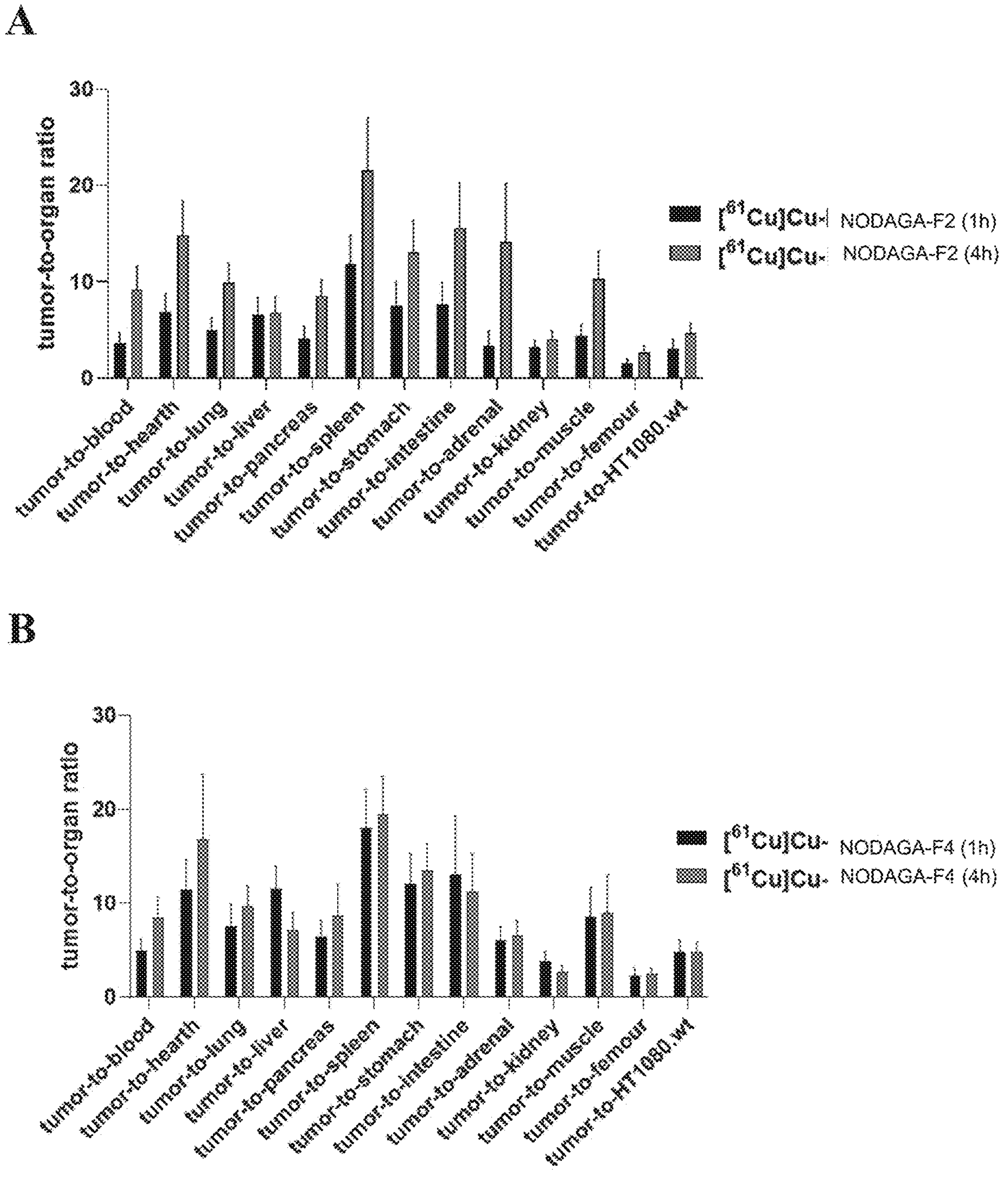

FIG. 27, panels A and B, show the tumor-to-organ ratios of [$^{61}$Cu]Cu-NODAGA-F2 (panel A), and [$^{61}$Cu]Cu-NODAGA-F4 (panel B) in HT-1080.hFAP tumor-bearing mice at 1 hour and hours following administration.

Figure 28:
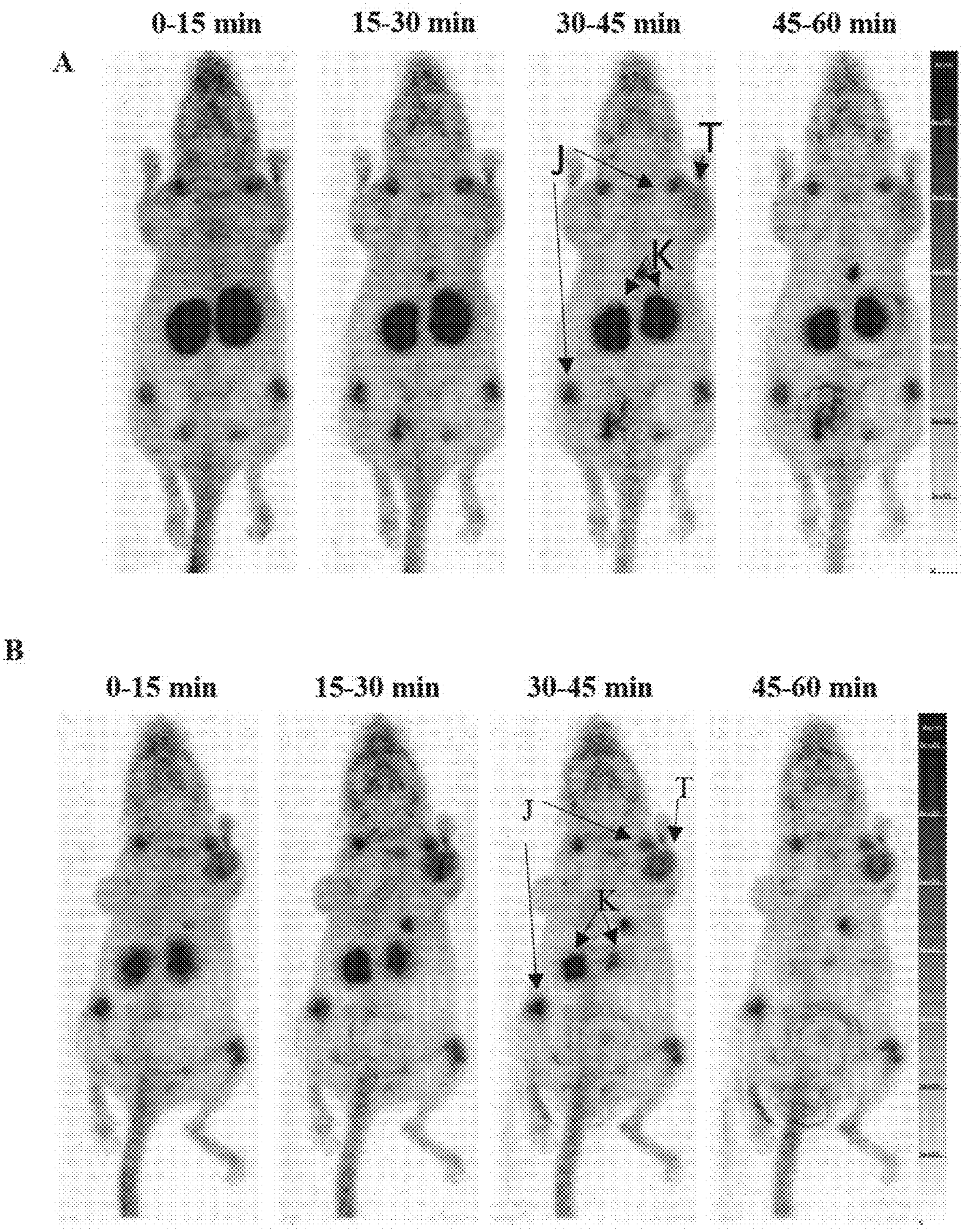

FIG. 28, panels A and B, show the dynamic PET/CT scans of [$^{61}$Cu]Cu-NODAGA-F2 (panel A) and [$^{61}$Cu]Cu-NODAGA-F4 (panel B) in mice bearing FAP-positive xenografts.

Figure 29:
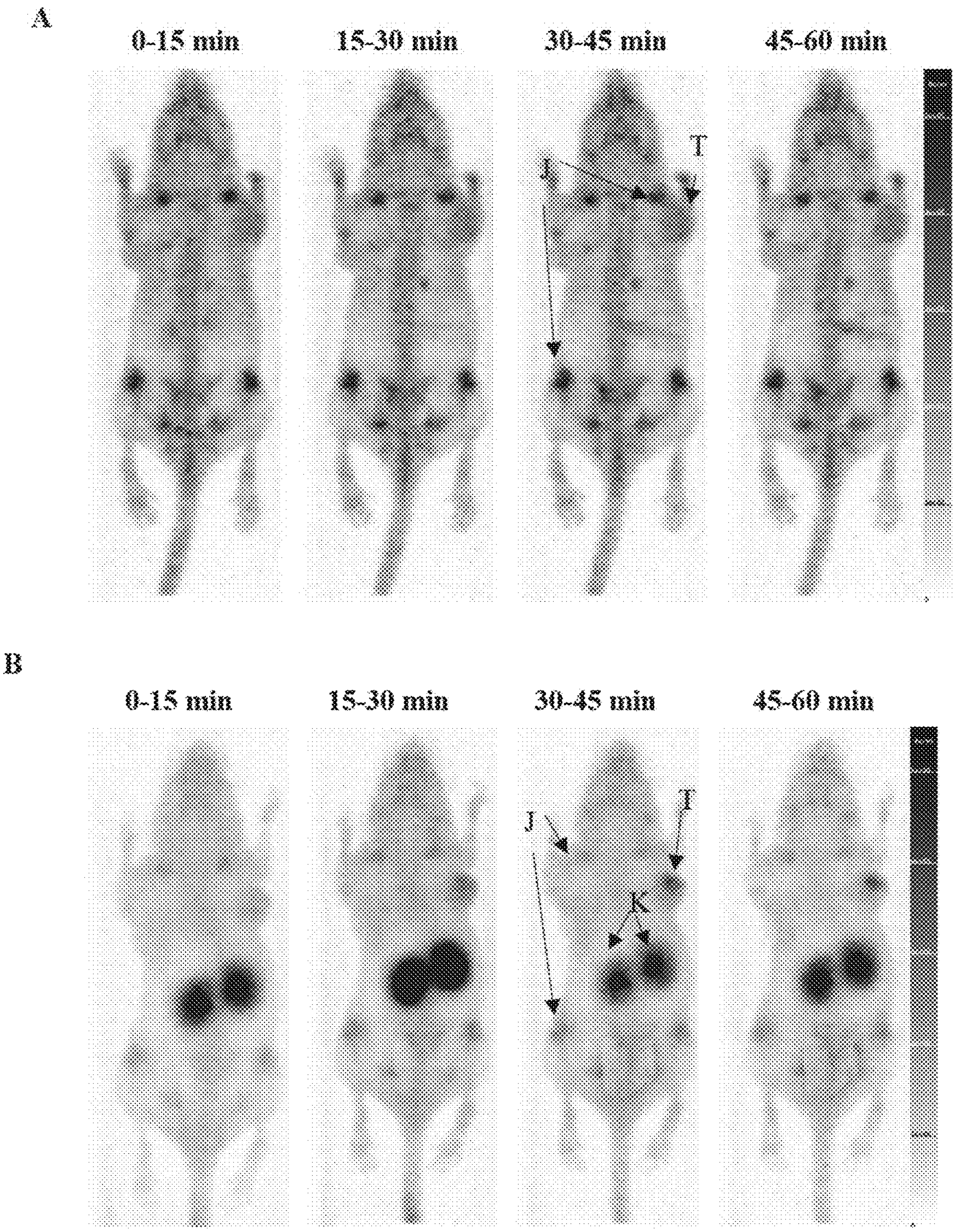

FIG. 29, panels A and B, show the dynamic PET/CT scans of [$^{61}$Cu]Cu-NODAGA-FAPI-46 (panel A) and [$^{68}$Ga]Ga-FAPI-46 (panel B) in mice bearing FAP-positive xenografts.

Figure 30:
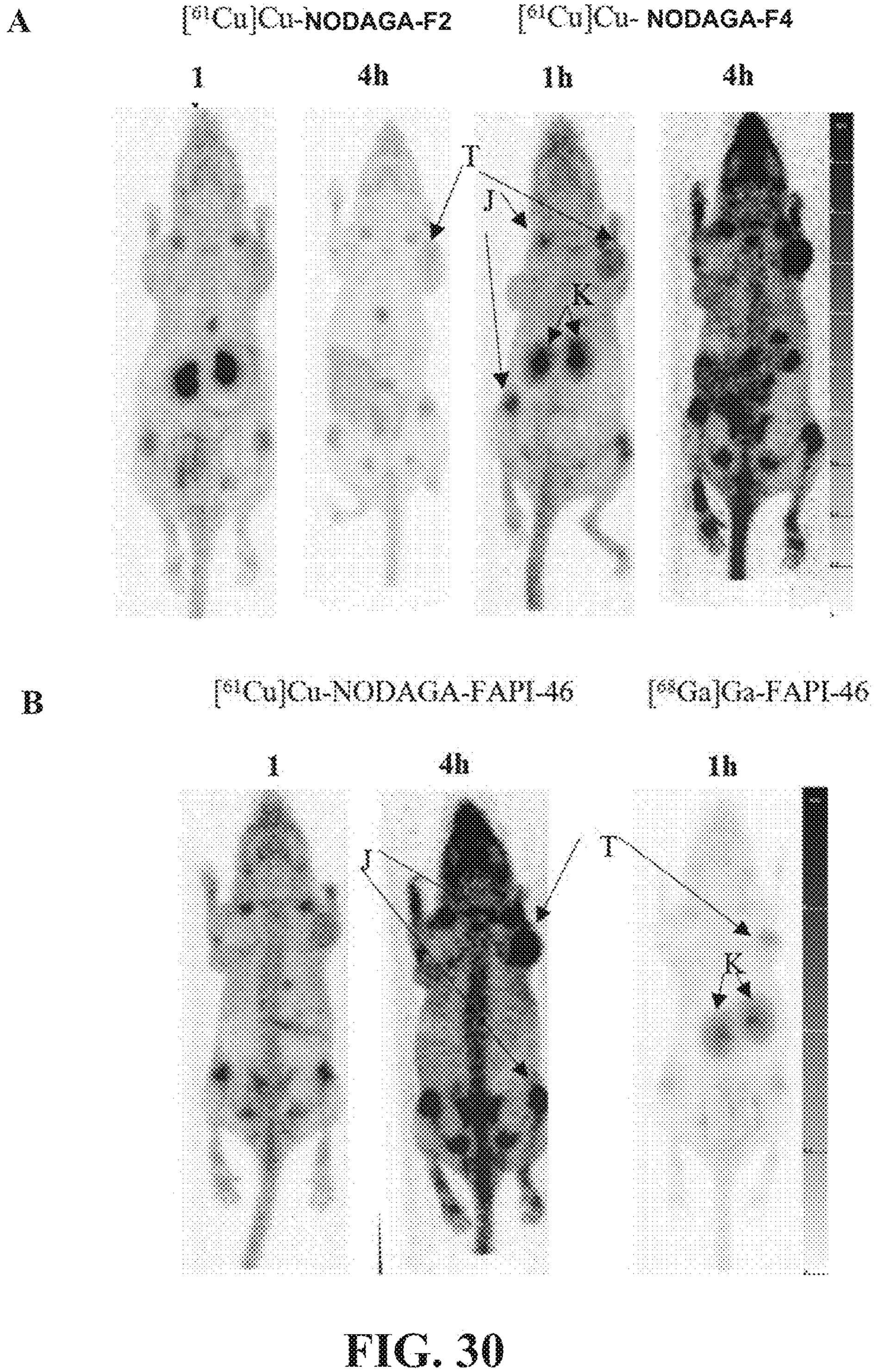

FIG. 30, panels A and B, show SUV PET imaging of [$^{61}$Cu]Cu-NODAGA-F2 vs [$^{61}$Cu]Cu-NODAGA-F4 (1 h and 4 h) (panel A) and [$^{61}$Cu]Cu-NODAGA-FAPI-46 vs $^{68}$Ga-FAPI-46 (1 h and 4 h for [$^{61}$Cu]Cu-NODAGA-FAPI-46 and 1 h only for [$^{68}$Ga]Ga-FAPI-46) (panel B).

Figure 31:
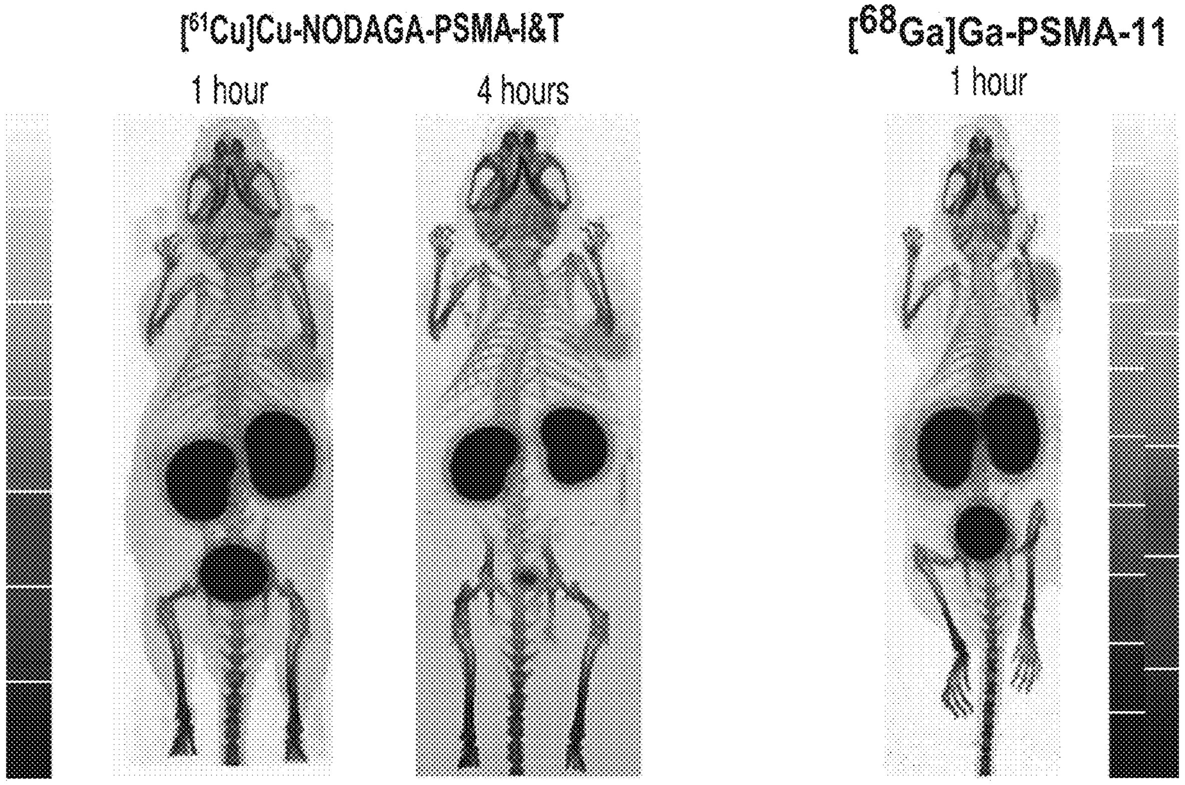

FIG. 31, shows [$^{61}$Cu]Cu-NODAGA-PSMA-I&T (1 and 4 hours) vs. [$^{68}$Ga]Ga-PSMA-11 distribution at 1 hour in a mouse model.

Figure 32A:
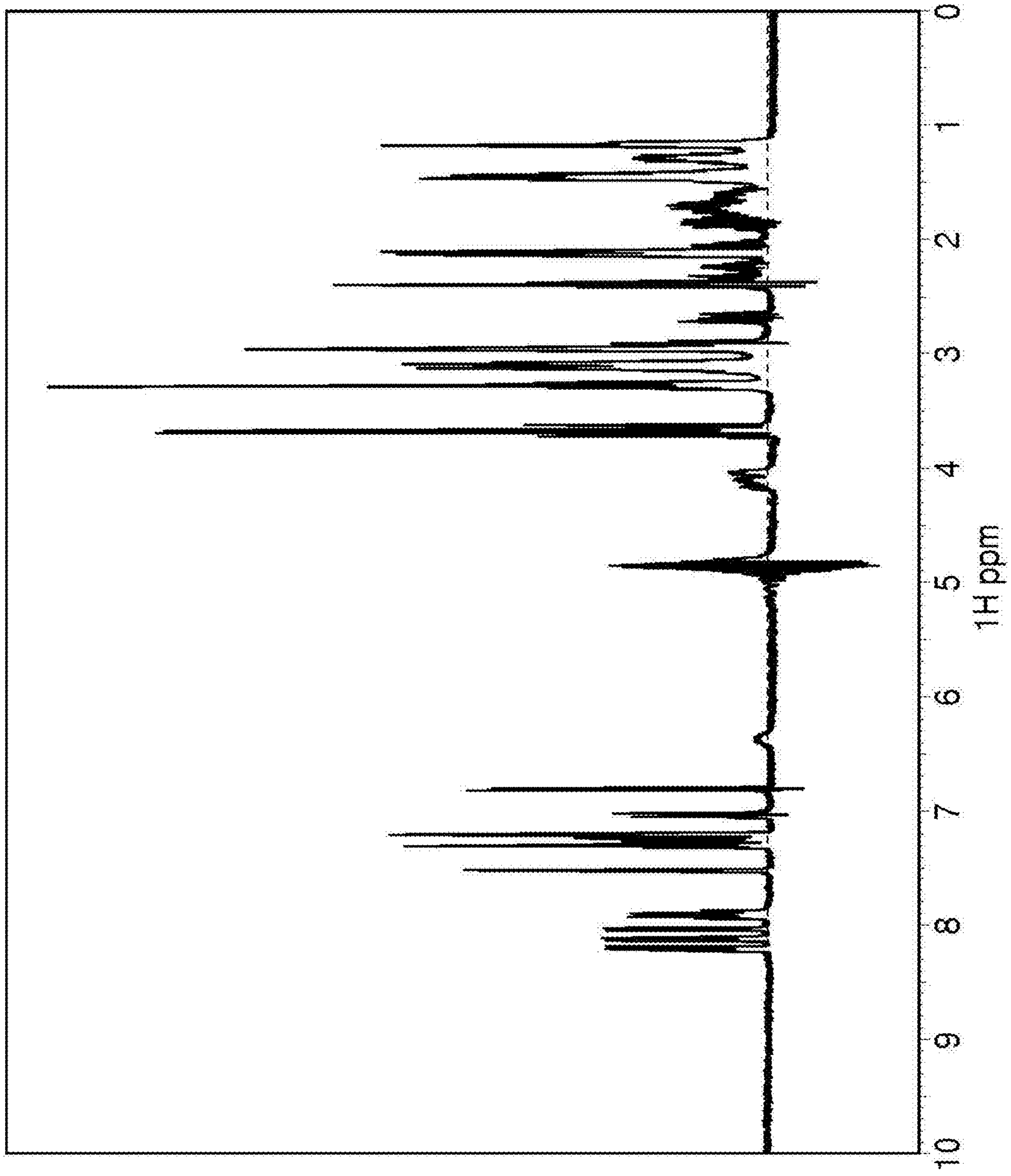

FIGS. 32A-C provide $^{1}$H-NMR data for NODAGA-PSMA-I&T. FIG. 32A shows the $^{1}$H-NMR spectrum, and FIGS. 32B and 32C show the chemical shifts and fragments associated with each residue of NODAGA-PSMA-I&T.

Figure 33:
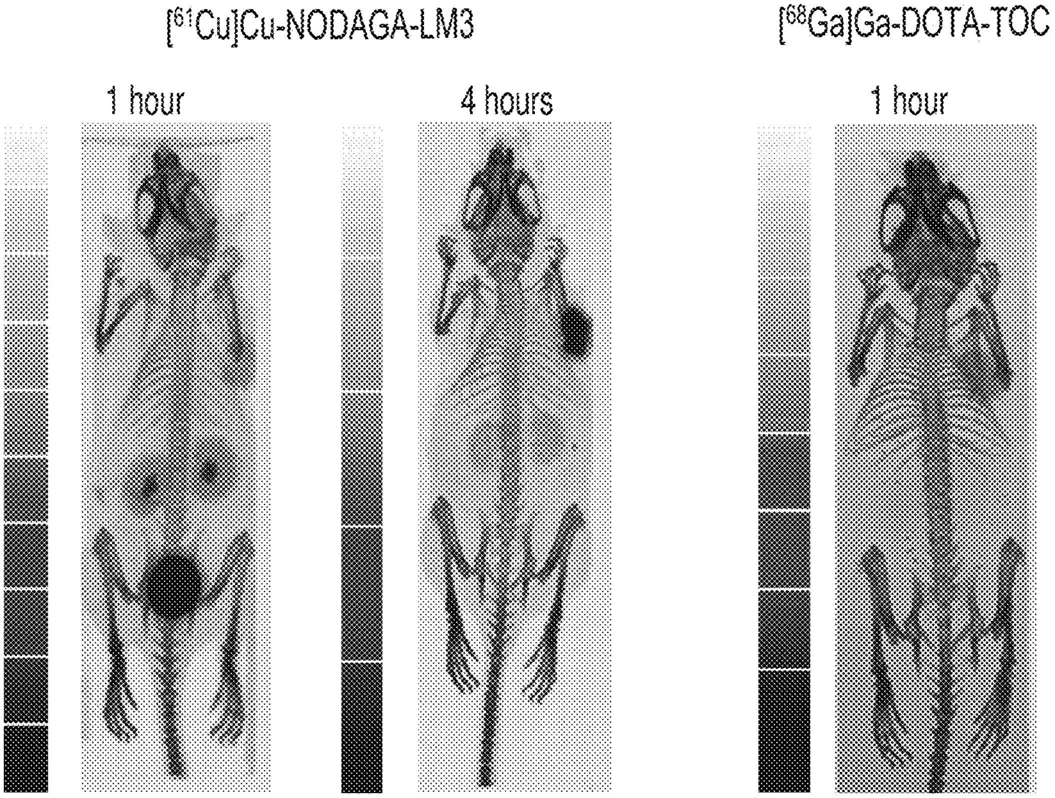

FIG. 33, shows [$^{61}$Cu]Cu-NODAGA-LM3 distribution after 1 hour and 4 hours, the images taken by PET/CT, vs. [$^{68}$Ga]Ga-DOTA-TOC distribution after 1 hour, image taken by PET.

Figure 34:
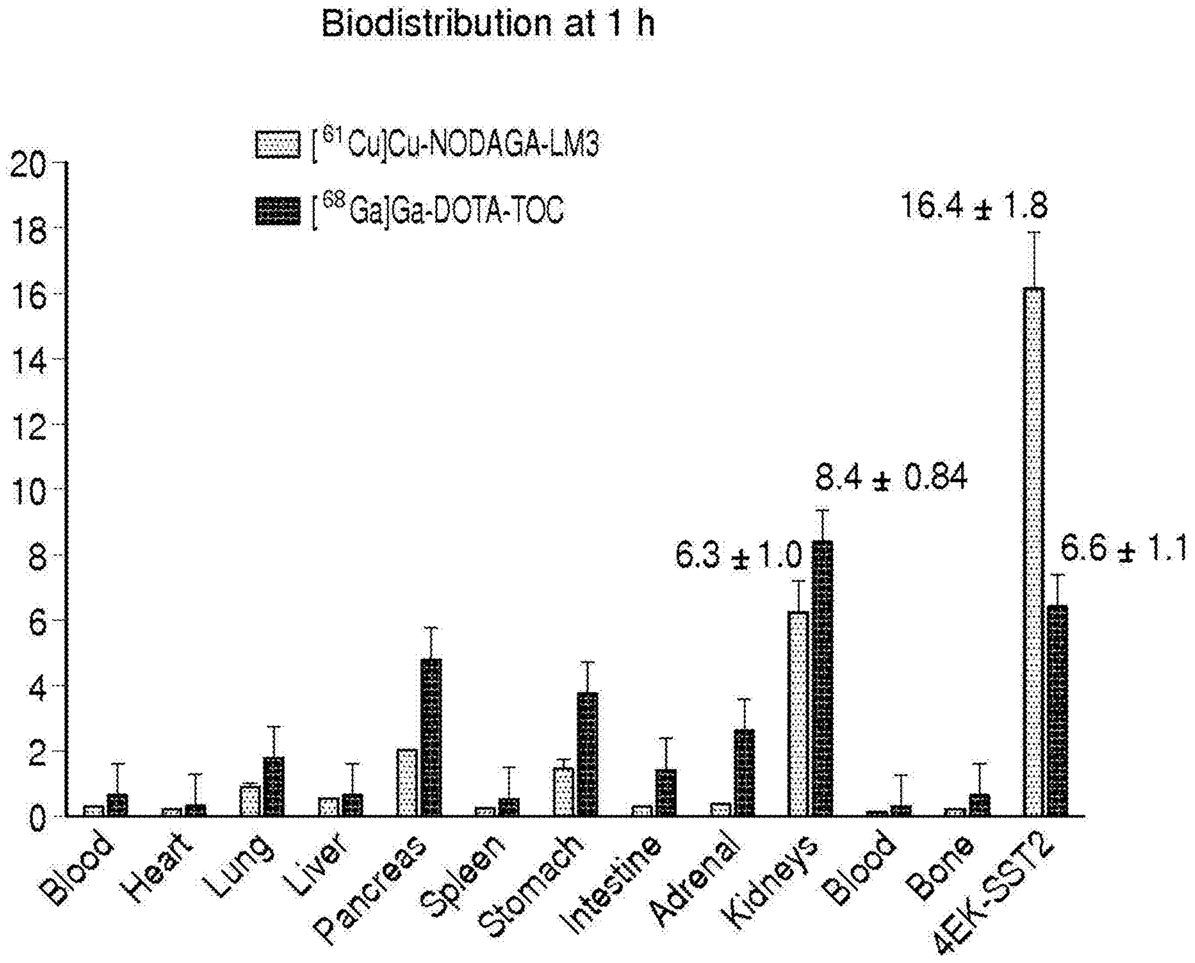

FIG. 34, shows [$^{61}$Cu]Cu-NODAGA-LM3 vs. [$^{68}$Ga]Ga-DOTA-TOC compound distribution after 1 hour in several organs.

Figure 35:
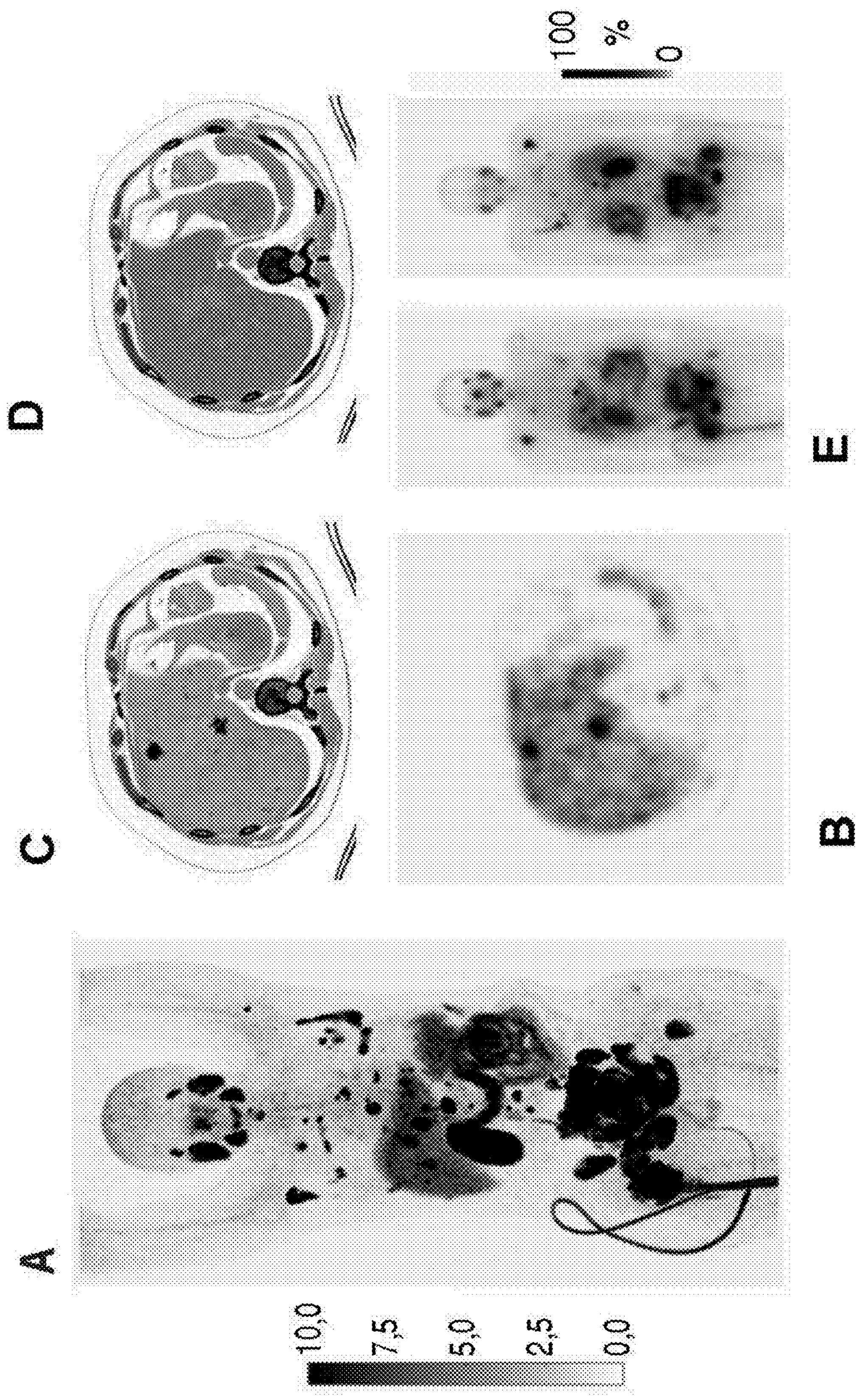

FIG. 35, panels A-E, show PET/CT images and planar scintigraphy of a 48 year old patient with metastatic castration resistant prostate cancer with disease progression following abiraterone and docetaxel therapy and scheduled to undergo [$^{61}$Cu]Cu-NODAGA-PSMA-I&T therapy. The patient is also status post left nephrectomy. Maximum intensity projection images (panel A) show intense tracer uptake by multiple osseous, pelvic lymph node, and liver metastases. Transaxial sections through the liver of PET (panel B), fused PET and CT (panel B), and CT (panel C) demonstrate two PSMA-positive liver lesions with focal tracer uptake. Non-contrast enhanced CT images (panel D). Planar anterior and post-treatment images 24 h after administration [$^{177}$Lu]Lu-PSMA-I&T show a similar distribution of radioactivity as the PET images (panel E).

Figure 36:
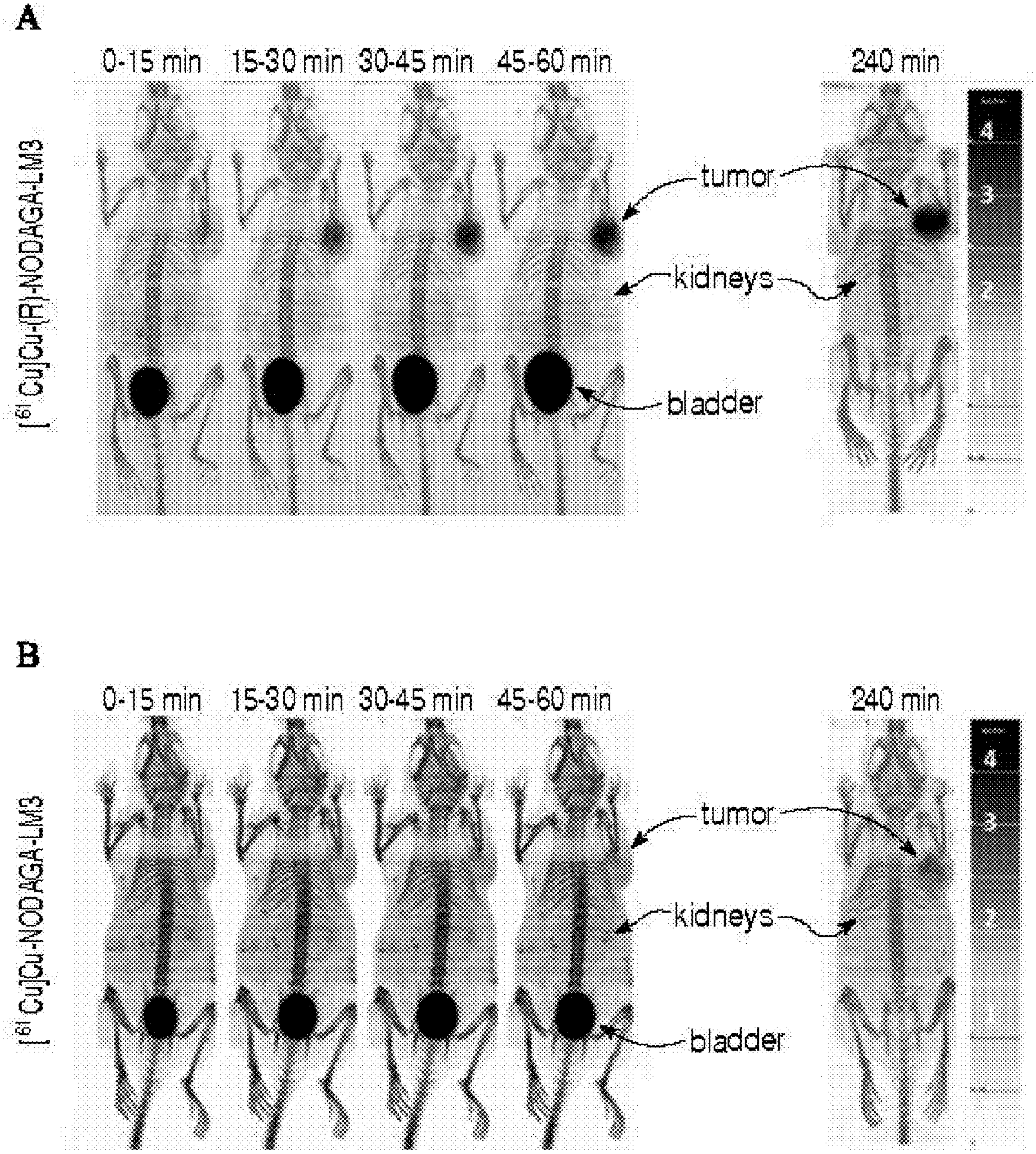

FIG. 36, panels A and B. show dynamic PET/CT scans of [$^{61}$Cu]Cu-(R)-NODAGA-LM3 (panel A) and [$^{61}$Cu]Cu-NODAGA-LM3 (panel B) in mice bearing SST2-positive xenografts. Static image at 240 minutes is also presented.

Figure 37:
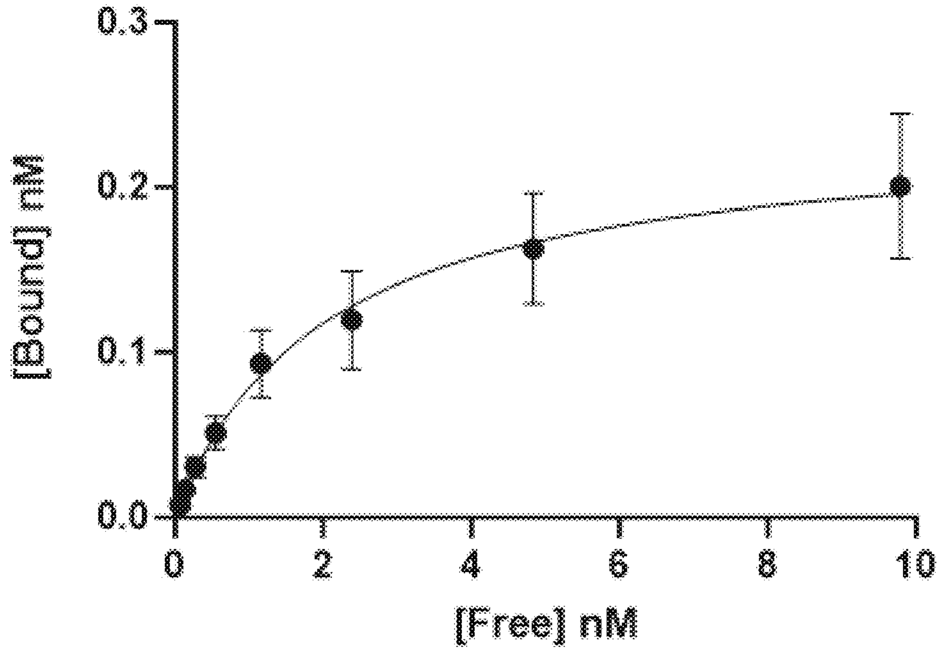

FIG. 37 shows saturation binding of [$^{61}$Cu]Cu-NODAGA-LM3. Bmax ranging between 0.2082 to 0.2711 nM, with a $k_D$ ranging between 1.409 to 2.917 nM.

4. DETAILED DESCRIPTION

4.1. Definitions

When describing the embodiments of the present disclosure, which include compounds and pharmaceutically acceptable salts thereof, pharmaceutical compositions containing such compounds and methods of using such compounds and compositions, the following terms, if present, have the following meanings unless otherwise indicated.

It will be understood by those within the art that, in general, terms used herein, and especially in the appended claims (e.g., bodies of the appended claims) are generally intended as “open” terms (e.g., the term “including” should be interpreted as “including but not limited to,” the term “having” should be interpreted as “having at least,” the term “includes” should be interpreted as “includes but is not limited to,” etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases “at least one” and “one or more” to introduce claim recitations. However, the use of such phrases should not be construed to imply that the introduction of a claim recitation by the indefinite articles “a” or “an” limits any particular claim containing such introduced claim recitation to embodiments containing only one such recitation, even when the same claim includes the introductory phrases “one or more” or “at least one” and indefinite articles such as “a” or “an” (e.g., “a” and/or “an” should be interpreted to mean “at least one” or “one or more”); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of “two recitations,” without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

As used herein, the term "alkyl" refers to both straight and branched chain $C_1$-$C_{30}$ hydrocarbons and includes both saturated and unsaturated hydrocarbons. The use of designations such as, for example, "$C_1$-$C_{20}$" is intended to refer to an alkyl (e.g., straight or branched chain and inclusive of alkenes and alkyls) having the recited range carbon atoms. In certain embodiments, an alkyl group has 1 to 10 carbon atoms ("$C_1$-$C_{10}$ alkyl"). In certain embodiments, an alkyl group has 1 to 9 carbon atoms ("$C_1$-$C_9$ alkyl"). In certain embodiments, an alkyl group has 1 to 8 carbon atoms ("$C_1$-$C_8$ alkyl"). In certain embodiments, an alkyl group has 1 to 7 carbon atoms ("$C_1$-$C_7$ alkyl"). In certain embodiments, an alkyl group has 1 to 6 carbon atoms ("$C_1$-$C_6$ alkyl"). In certain embodiments, an alkyl group has 1 to 5 carbon atoms ("$C_1$-$C_5$ alkyl"). In certain embodiments, an alkyl group has 1 to 4 carbon atoms ("$C_1$-$C_4$ alkyl"). In certain embodiments, an alkyl group has 1 to 3 carbon atoms ("$C_1$-$C_3$ alkyl"). In certain embodiments, an alkyl group has 1 to 2 carbon atoms ("$C_1$-$C_2$ alkyl"). In certain embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like. Representative straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like.

As used herein, the term "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_2$-$C_{20}$ alkenyl"). In certain embodiments, alkenyl does not contain any triple bonds. In certain embodiments, an alkenyl group has 2 to 10 carbon atoms ("$C_2$-$C_{10}$ alkenyl"). In certain embodiments, an alkenyl group has 2 to 9 carbon atoms ("$C_2$-$C_9$ alkenyl"). In certain embodiments, an alkenyl group has 2 to 8 carbon atoms ("$C_2$-$C_8$ alkenyl"). In certain embodiments, an alkenyl group has 2 to 7 carbon atoms ("$C_2$-$C_7$ alkenyl"). In certain embodiments, an alkenyl group has 2 to 6 carbon atoms ("$C_2$-$C_6$ alkenyl"). In certain embodiments, an alkenyl group has 2 to 5 carbon atoms ("$C_2$-$C_5$ alkenyl"). In certain embodiments, an alkenyl group has 2 to 4 carbon atoms ("$C_2$-$C_4$ alkenyl"). In certain embodiments, an alkenyl group has 2 to 3 carbon atoms ("$C_2$-$C_3$ alkenyl"). In certain embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, the terms "alkylene," "alkenylene," and "alkynylene" refer to a divalent radical of an alkyl, alkenyl, or alkynyl group, respectively. When a range or number of carbons is provided for a particular "alkylene," "alkenylene," or "alkynylene," it is understood that the range or number refers to the range or number of carbons in the linear carbon divalent chain. "Alkylene," "alkenylene," and "alkynylene" groups may be substituted or unsubstituted with one or more substituents as described herein.

As used herein, the term "aryl" refers to aromatic groups (e.g., monocyclic, bicyclic and tricyclic structures) containing six to ten carbons in the ring portion. The aryl groups may be optionally substituted through available carbon atoms and in certain embodiments may include one or more heteroatoms such as oxygen, nitrogen or sulfur. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl).

As used herein, "halo" and "halogen" refer to an atom selected from fluorine (fluoro, F), chlorine (chloro, Cl), bromine (bromo, Br), and iodine (iodo, I).

As used herein, "heteroaryl" refers to a radical of a 5-10 membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. “Heteroaryl” includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. “Heteroaryl” also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

As used herein, the term “heterocyclyl” or “heterocyclic” refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon (“3-10 membered heterocyclyl”). In heterocyclyl groups that contain one or more nitrogen atoms, the point of attachment can be a carbon or nitrogen atom, as valency permits. A heterocyclyl group can either be monocyclic (“monocyclic heterocyclyl”) or a fused, bridged or spiro ring system such as a bicyclic system (“bicyclic heterocyclyl”), and can be saturated or can be partially unsaturated. Heterocyclyl bicyclic ring systems can include one or more heteroatoms in one or both rings. “Heterocyclyl” also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms “heterocycle,” “heterocyclyl,” “heterocyclyl ring,” “heterocyclic group,” “heterocyclic moiety,” and “heterocyclic radical,” may be used interchangeably. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

As used herein, the term “substituted”, whether preceded by the term “optionally” or not, means that at least one hydrogen present on a group (e.g., a hydrogen attached to a carbon or nitrogen atom of a group) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a “substituted” group has a substituent at one or more substitutable positions of the group, and when more than one position in any given structure is substituted, the substituent is either the same or different at each position.

When a range of values is listed, it is intended to encompass each value and sub-range within the range. For example, “$C_1$-$C_6$ alkyl” is intended to encompass, $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

In typical embodiments, the present disclosure is intended to encompass the compounds disclosed herein, and the pharmaceutically acceptable salts, pharmaceutically acceptable esters, tautomeric forms, polymorphs, and prodrugs of such compounds. In certain embodiments, the present disclosure includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., Enantiomers, Racemates and Resolutions (Wiley Interscience, New York, 1981); Wilen et al., Tetrahedron 33:2725 (1977); Eliel, Stereochemistry of Carbon Compounds (McGraw-Hill, N Y, 1962); and Wilen, Tables of Resolving Agents and Optical Resolutions p. 268 (E. L. Eliel, Ed., Univ. of Notre Dame Press, Notre Dame, IN 1972). The present disclosure additionally encompasses compounds described herein as individual isomers substantially free of other isomers, and alternatively, as mixtures of various isomers.

With respect to chemical structures that include a chelated metal, the structure as drawn is not intended to define the coordination sphere. Further, the presence or absence of a proton on an ionizable binding moiety is not intended to be definitive. A person of skill in the art will be able to determine the coordination sphere, oxidation states and degree of ionization on a case by case basis.

4.2. Compounds

An aspect of the present disclosure is the provision of compounds comprising one or more chelating moieties and one or more targeting moieties covalently linked through L, which is a bond or a divalent or polyvalent linker moiety and, optionally, a copper radionuclide (*Cu). In embodiments comprising a copper radionuclide, the compounds are considered “radiolabelled” for use in diagnostic and/or therapeutic applications. These compounds are also referred to herein as “targeted chelator construct” and are precursors to the radiolabelled compounds, also referred to as “radiotracers.” It is understood herein that when a particular compound, e.g., radiotracer, is described herein as comprising a particular radioisotope or radionuclide (e.g., $^{61}$Cu) that the compound is isotopically enriched in that isotope at the indicated position.

The terms radiocopper (also referred to herein as Cu*, herein), copper radionuclide and copper radionuclide are used interchangeably herein and refer to an isotope of copper that undergoes spontaneous radioactive decay.

Embodiments of the presently disclosed compounds comprise radiocopper selected from: $^{60}$Cu, $^{61}$Cu, $^{62}$Cu, $^{64}$Cu, and $^{67}Cu$. In certain embodiments, radiocopper is selected from $^{61}Cu$, $^{64}Cu$, and $^{67}Cu$. In certain embodiments, radiocopper is $[^{61}Cu]Cu$. In certain embodiments, radiocopper is $^{67}Cu$.

Certain embodiments of the presently disclosed radiotracers comprise radiocopper (Cu*), wherein *Cu is in a (II) oxidation state.

In embodiments of the present disclosure, the provided compound comprises one or more chelating moieties and one or more targeting moieties covalently linked to the one or more chelating moieties through L, which is a bond or a divalent or polyvalent linker moiety and, optionally, a copper radionuclide (*Cu).

In certain embodiments, a compound is provided, wherein the compound is of Formula X:

Formula X

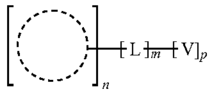

or is a pharmaceutically acceptable salt thereof, wherein:

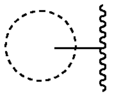

is a chelating moiety;

L is a bond or a linker moiety that connects the chelating moeity to a targeting moiety;

V is the targeting moiety;

n is an integer selected from 1 to 10;

m is an integer selected from 1 to 10; and p is an integer selected from 1 to 10.

In certain embodiments, a compound is of Formula X* is provided:

Formula X*

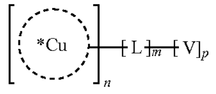

or is a pharmaceutically acceptable salt thereof, wherein:

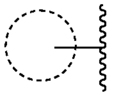

is a chelating moiety;

Cu is selected from: $^{61}Cu$, $^{62}Cu$, $^{64}Cu$, and $^{67}Cu$;

L is a bond or a linker moiety that connects the chelating moeity to a targeting moiety;

V is the targeting moiety;

n is an integer selected from 1 to 10;

m is an integer selected from 1 to 10; and p is an integer selected from 1 to 10.

In certain embodiments of a compound of Formula X, p an integer from 1 to 2, 1 to 3, 1 to 4, 1 to 5, 1 to 6, 1 to 7, 1 to 8, or 1 to 9. In certain embodiments, p is an integer from 2 to 3, 2 to 4, 2 to 5, 2 to 6, 2 to 7, 2 to 8, or 2 to 9. In certain embodiments, p is an integer from 3 to 5, 3 to 7, 5 to 7, 5 to 10, or 7 to 10. In certain embodiments of, p is 2, 3, 4, 5, 6, 7, 8, 9, or 10. In certain embodiments, p is 2, 3, or 4. In certain embodiments, p is 1. In certain embodiments, p is 2. In certain embodiments, p is 3. In certain embodiments, p is 4.

In certain embodiments of a compound of Formula X, m an integer from 1 to 2, 1 to 3, 1 to 4, 1 to 5, 1 to 6, 1 to 7, 1 to 8, or 1 to 9. In certain embodiments, m is an integer from 2 to 3, 2 to 4, 2 to 5, 2 to 6, 2 to 7, 2 to 8, or 2 to 9. In certain embodiments, m is an integer from 3 to 5, 3 to 7, 5 to 7, 5 to 10, or 7 to 10. In certain embodiments of, m is 2, 3, 4, 5, 6, 7, 8, 9, or 10. In certain embodiments, m is 2, 3, or 4. In certain embodiments, m is 1. In certain embodiments, m is 2. In certain embodiments, m is 3. In certain embodiments, m is 4.

In certain embodiments of a compound of Formula X, n is 1, m is 2, and p is 2 such that the chelating moiety is polyvalent, such that 2 L moieties link 2 V targeting moieties to a divalent chelator. In certain embodiments of a compound of Formula X, n is 1, m is 3, and p is 3 such that the chelating moiety is polyvalent, such that 3 L moieties link 3 V targeting moieties to a trivalent chelator. In certain embodiments, each of the L moieties are the same. In certain embodiments, at least one of the L moieties is different. In certain embodiments, each of the V moieties are the same. In certain embodiments, at least one of the V moieties is different.

In certain embodiments of a compound of Formula X, n is 1, m and p are each the same integer and greater than 1, such as an integer from 2 to 10, wherein the chelating moiety is polyvalent. In certain embodiments, n is 2, 3, 4, 5, 6, 7, 8, 9, or 10. In certain embodiments, m is an integer from 1 to 2, 1 to 3, 1 to 4, 1 to 5, 1 to 6, 1 to 7, 1 to 8, or 1 to 9. In certain embodiments, m is an integer from 2 to 3, 2 to 4, 2 to 5, 2 to 6, 2 to 7, 2 to 8, or 2 to 9. In certain embodiments, m is an integer from 3 to 5, 3 to 7, 5 to 7, 5 to 10, or 7 to 10.

In certain embodiments of a compound of Formula X (wherein it is understood herein that Formula X embraces subgenera Formula X1), wherein n is 1, m is 1, and p is 1, wherein L is divalent and links the chelating moiety to the targeting moiety. In certain embodiments, wherein n is greater than 1, such as an integer from 2 to 10, L is polyvalent and links one or more chelating moieties to the targeting moiety. In certain embodiments, wherein n is 1, m is 2, and p is 2, the chelating moiety is polyvalent (e.g., divalent), and each of the two linker moieties (L) link each of the two targeting moieties (V) to the divalent chelator. In certain embodiments, wherein n is 1, m is 3, and p is 3, the chelating moiety is polyvalent, and each of the three linker moieties (L) link each of the three targeting moieties (V) to the trivalent chelator. In certain embodiments, n is 2, 3, 4, 5, 6, 7, 8, 9, or 10. In certain embodiments, m is an integer from 1 to 2, 1 to 3, 1 to 4, 1 to 5, 1 to 6, 1 to 7, 1 to 8, or 1 to 9. In certain embodiments, m is an integer from 2 to 3, 2 to 4, 2 to 5, 2 to 6, 2 to 7, 2 to 8, or 2 to 9. In certain embodiments, m is an integer from 3 to 5, 3 to 7, 5 to 7, 5 to 10, or 7 to 10.

In certain embodiments of a compound of Formula X, wherein n is 1, m is 2, and p is 2, wherein each L is divalent and links each of the two targeting moieties to the chelating moiety. In certain embodiments, n is 1, m is 1, p is 3 where L is polyvalent and links three of the targeting moieties (V) to the chelating moiety. In certain embodiments, n is 1, m is 1, and p is 4 where L is polyvalent and links each of the four targeting moieties to the chelating moiety.

In certain embodiments, the radiocopper is selected from $^{61}Cu$, $^{64}Cu$, and $^{67}Cu$, particularly $^{61}Cu$ or $^{67}Cu$.

Some embodiments of the presently disclosed radiotracers comprise radiocopper (Cu*), wherein the *Cu is in a (II) oxidation state.

In certain embodiments, the compound is according to Formula A:

Formula A

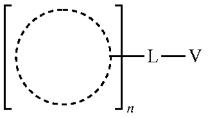

or is a pharmaceutically acceptable salt thereof wherein:

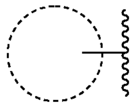

is the chelating moiety;

L is a bond or a linker moiety that connects the chelating moeity to a targeting moiety;

V is the targeting moiety;

n is an integer selected from 1 to 10.

In certain embodiments, the compound is according to Formula A*:

Formula A*

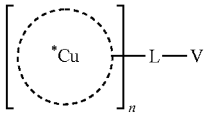

or is a pharmaceutically acceptable salt thereof wherein:

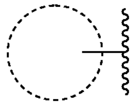

is the chelating moiety;

Cu is optional, and if present, is selected from: $^{61}Cu$, $^{62}Cu$, $^{64}Cu$, or $^{67}Cu$;

L is a bond or a linker moiety that connects the chelating moeity to a targeting moiety;

V is the targeting moiety;

n is an integer selected from 1 to 10.

In certain embodiments of a compound of Formula X, X*, A, and A*, n is an integer from 1 to 2, 1 to 3, 1 to 4, 1 to 5, 1 to 6, 1 to 7, 1 to 8, or 1 to 9. In certain embodiments, n is an integer from 2 to 3, 2 to 4, 2 to 5, 2 to 6, 2 to 7, 2 to 8, or 2 to 9. In certain embodiments, n is an integer from 3 to 5, 3 to 7, 5 to 7, 5 to 10, or 7 to 10. In certain embodiments of, n is 2, 3, 4, 5, 6, 7, 8, 9, or 10. In certain embodiments, n is 2, 3, or 4. In certain embodiments, n is 1. In certain embodiments, n is 2. In certain embodiments, n is 3. In certain embodiments, n is 4.

4.2.1. Chelating Moiety

A chelating moiety comprises two or more binding moieties that are available to form several bonds with a single metal ion. A chelating moiety according to the present disclosure (symbolized by

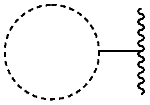

where the line shows the point of attachment) is not particularly limited.

In certain embodiments of a compound of Formula X, X*, A, and A*, the chelating moiety is selected from any known chelator of copper known in the art. In certain embodiments, the chelating moiety is able to complex Cu (II) with relatively fast coordination kinetics, high biological stability and inertness. The known chelating moiety may be modified, derivatized or otherwise functionalized to facilitate covalent bonding to one or more targeting moieties, optionally via one or more linker moieties. In certain embodiments, one or more linker moieties are used to facilitate covalent bonding between a chelating moiety and one or more targeting moiety.

In embodiments of the present disclosure, the term chelating moiety generally encompasses both a coordinated and uncoordinated state. That is, the chelating moiety may be chelated to a metal, and is considered coordinated to, e.g., a copper radionuclide, or may not be chelated to a metal, e.g., a copper radionuclide, and is considered uncoordinated. In certain embodiments, when the chelating moiety is coordinated to radiocopper, the term "chelated-copper complex" is used herein.

In certain embodiments of a compound of Formula X, X*, A, and A*, the chelating moiety comprises a binding moiety, i.e., a chemical group (e.g., from one to ten atoms, e.g., three atoms of a carboxylate group) that contributes to binding of a metal ion to form a coordination complex. In some examples, the binding moiety is capable of ionic, dative, and/or coordinate bonding. In certain embodiments, the chelating moiety comprises from 2-8 binding moieties. In certain embodiments, the chelating moiety comprises 4, 5, 6, 7, or 8 binding moieties. In certain embodiments, the chelating moiety comprises 6 binding moieties.

In certain embodiments of a compound of Formula X, X*, A, and A*, the binding moieties are selected from thiol groups, amine groups, and carboxylate groups. In certain embodiments, one or more of the binding moieties comprise tertiary amines. In further of these embodiments, ≥ three of the binding moieties comprise tertiary amines, e.g., wherein three tertiary amines form a cyclic ring around the metal center.

In certain embodiments of a compound of Formula X, X*, A or A*of the compounds of Formula X or A, the chelating moiety the chelating moiety is selected from DOTAGA (1,4,7,10-tetraazacyclododececane, 1-(glutaric acid)-4,7,10-triacetic acid), DOTA (1,4,7,10-tetraazacyclododecane-1,4,7,10-tetraacetic acid), DOTASA (1,4,7,10-tetraazacyclododecane-1-(2-succinic acid)-4,7,10-triacetic acid), CB-DO2A (10-bis(carboxymethyl)-1,4,7,10-tetraazabicyclo[5.5.2]tetradecane), DEPA (7-[2-(Bis-carboxymethylamino)-ethyl]-4,10-bis-carboxymethyl-1,4,7,10-tetraaza-cyclododec-1-yl-acetic acid)), 3p-C-DEPA (2-[(carboxymethyl)][5-(4-nitrophenyl-1-[4,7,10-tris(carboxymethyl)-1,4,7,10-tetraazacyclododecan-1-yl]pentan-2-yl)amino]acetic acid)), TCMC (2-(4-isothiocyanotobenzyl)-1,4,7,10-tetraaza-1,4,7,10-tetra-(2-carbamonyl methyl)-cyclododecane), oxo-DO3A (1-oxa-4,7,10-triazacyclododecane-5-S-(4-isothiocyanatobenzyl)-4,7,10-triacetic acid), p-NH2-Bn-Oxo-DO3A (1-Oxa-4,7,10-tetraazacyclododecane-5-S-(4-aminobenzyl)-4,7,10-triacetic acid), TE2A ((1,8-N,N'-bis-(carboxymethyl)-1,4,8,11-tetraazacyclotetradecane), MM-TE2A, DM-TE2A, CB-TE2A (4,11-bis(carboxymethyl)-1,4,8,11-tetraazabicyclo[6.6.2]hexadecane), CB-TE1A1P (4,8,11-tetraazacyclotetradecane-1-(methanephosphonic acid)-8-(methanecarboxylic acid), CB-TE2P (1,4,8,11-tetraazacyclotetradecane-1,8-bis(methanephosphonic acid), TETA (1,4,8,11-tetraazacyclotetradecane-1,4,8,11-tetraacetic acid), NOTA (1,4,7-triazacyclononane-N,N',N''-triacetic acid), NODA (1,4,7-triazacyclononane-1,4-diacetate), NODAGA (1,4,7-triazacyclononane-1-glutaric acid-4,7-acetic acid) (also known as NOTAGA), NODA Desferoxamine (1,4,7-triazacyclononane-1,4-diyl)diacetic acid DFO), NETA ([4-[2-(bis-carboxymethylamino)-ethyl]-7-carboxymethl-[1,4,7]triazonan-1-yl}-acetic acid), TACN-TM (N,N',N'', tris(2-mercaptoethyl)-1,4,7-triazacyclononane), Diamsar (1,8-Diamino-3,6,10,13,16,19-hexaazabicyclo(6,6,6)eicosane, 3,6,10,13,16,19-Hexaazabicyclo[6.6.6]eicosane-1,8-diamine), Sarar (1-N-(4-aminobenzyl)-3,6,10,13,16,19-hexaazabicyclo[6.6.6]eicosane-1,8-diamine), AmBaSar (4-((8-amino-3,6,10,13,16,19-hexaazabicyclo [6.6.6] icosane-1-ylamino) methyl) benzoic acid), and 4,4'-((3,6,10,13,16,19-hexaazabicyclo[6.6.6]ico-sane-1,8-diylbis(aza-nediyl))bis(methylene)) dibenzoic acid (BaBaSar).

In certain embodiments of a compound of Formula X, X*, A, and A*, the chelating moiety is selected from DOTAGA, DOTA, NOTA, NODAGA, and NODA.

In certain embodiments of a compound of Formula X, X*, A, and A*, the chelating moiety is NODAGA. In certain embodiments of a compound of Formula A, the chelating moiety is R-NODAGA. In certain embodiments of a compound of Formula X or A, wherein L is a bond, the chelating moiety is NODAGA.

In further embodiments of a compound of Formula X, X*, A, and A*, the chelating moiety comprises a structure selected from those shown below, wherein it is noted is may be considered that these structures further comprise a linker moiety. There is some flexibility regarding which atoms comprise a chelating moiety and which comprise a linker used to attach the chelating moiety to one or more targeting ligands. For example, the chelating moiety of the present embodiments shown below may include the complete amide group (—(C═O)NH—) or it may include only the carbonyl —(C═O)— such that an —NH—, if present, is considered to be part of a linker group:

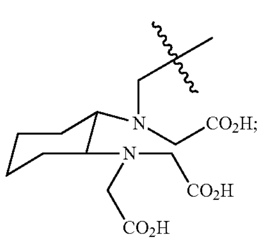

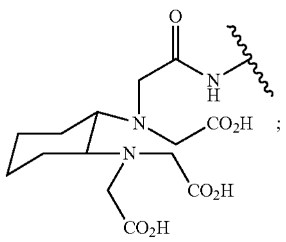

-continued

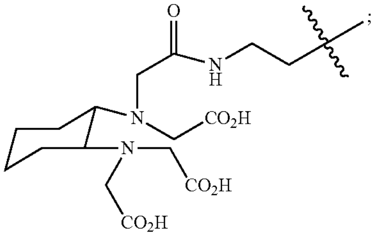

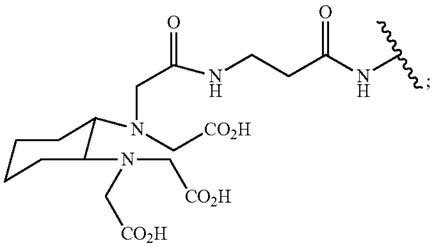

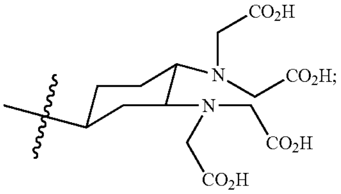

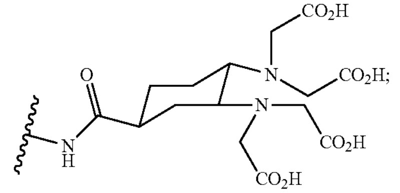

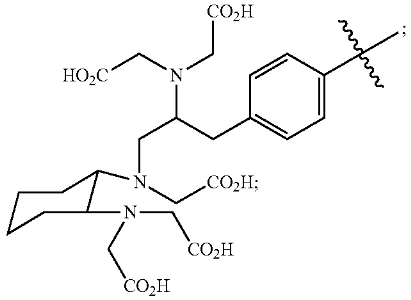

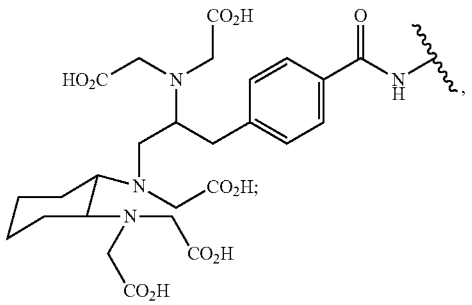

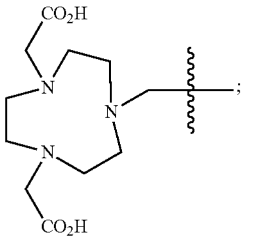

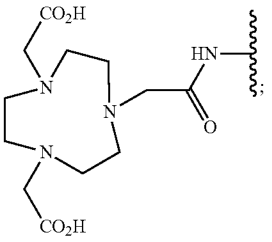

-continued
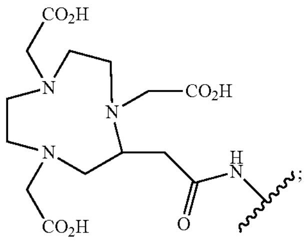
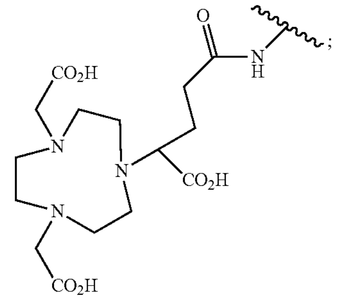
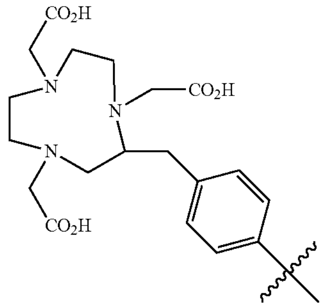
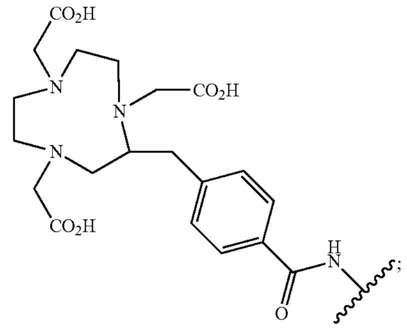
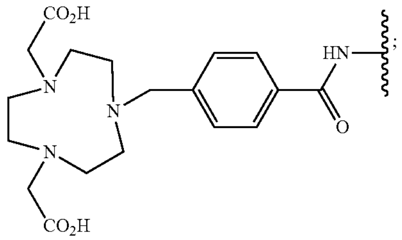
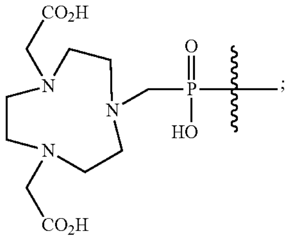
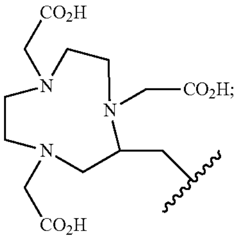
-continued
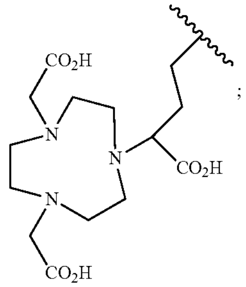
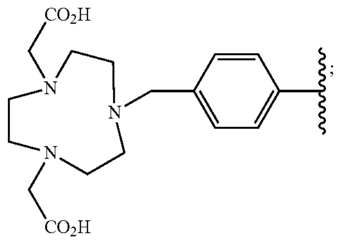
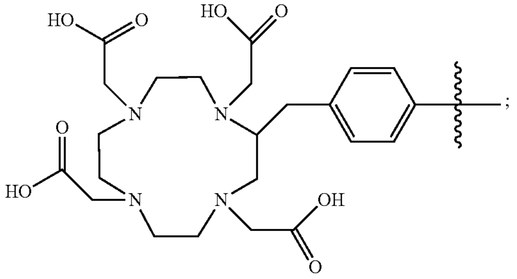
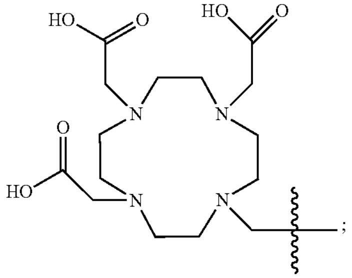
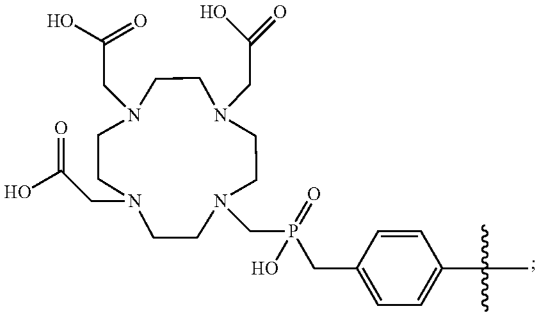
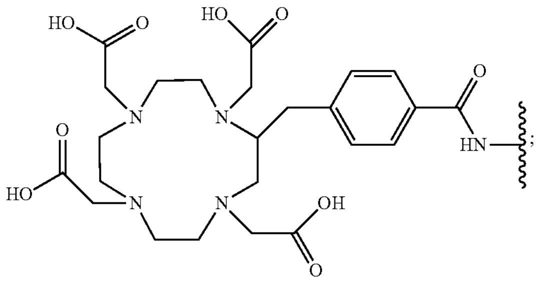
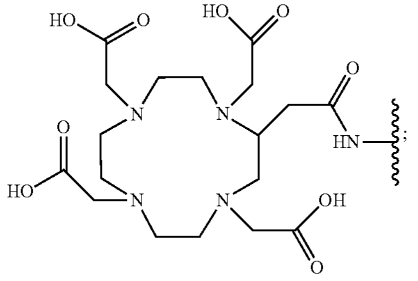

-continued
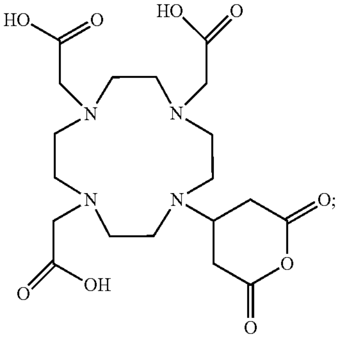
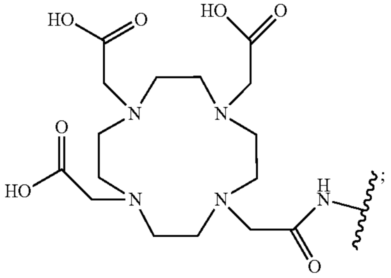
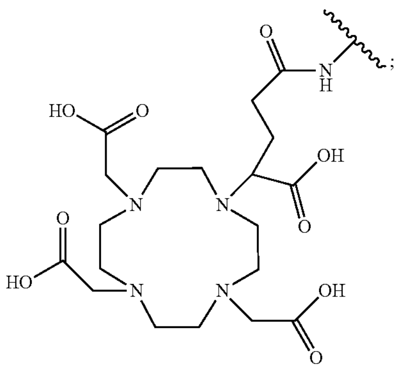
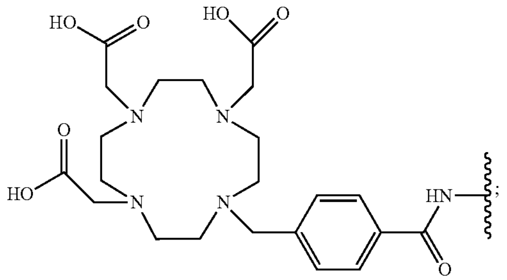
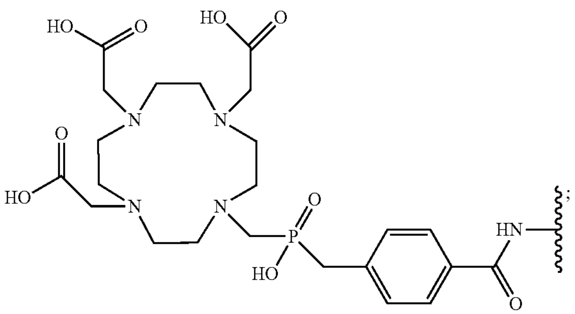
-continued
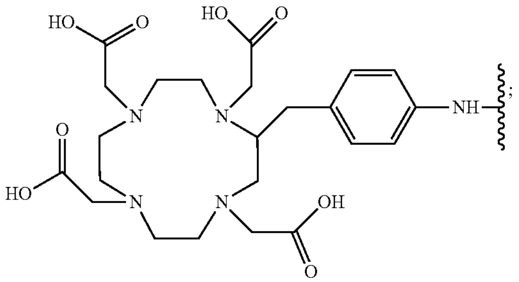
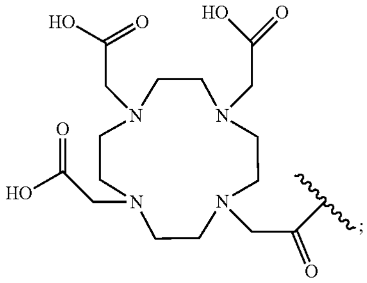
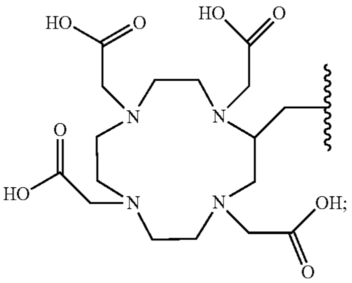
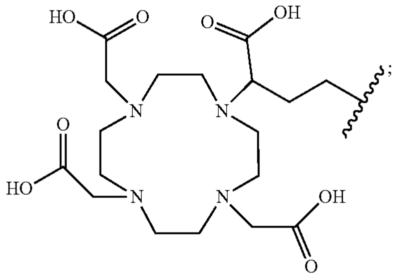
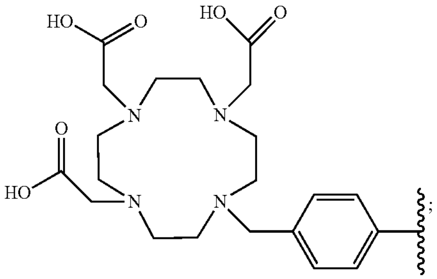
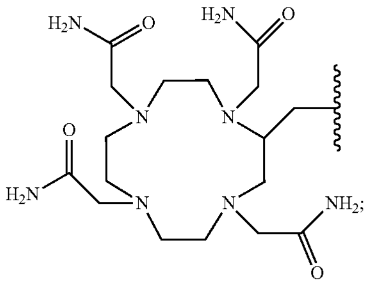

-continued

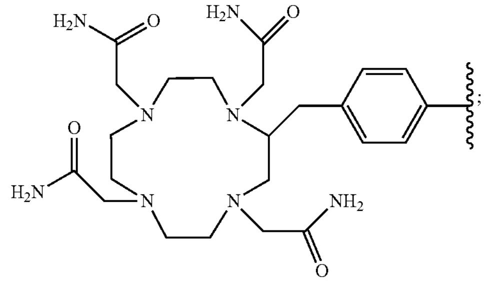

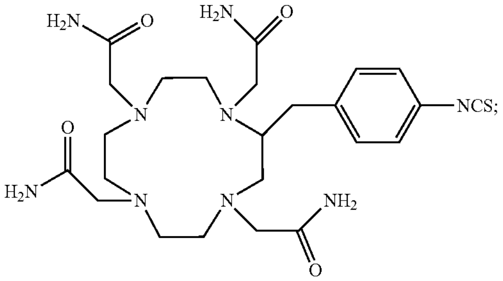

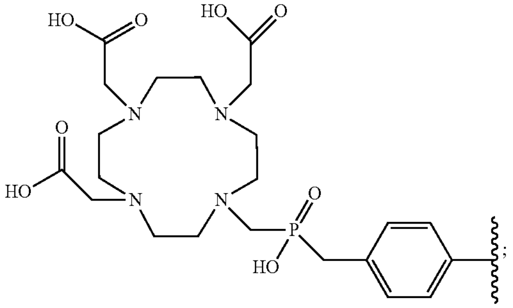

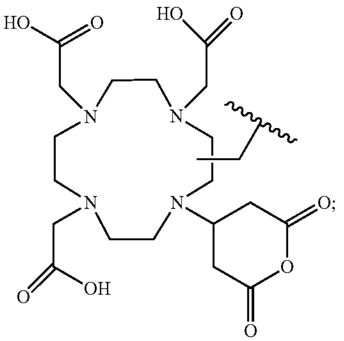

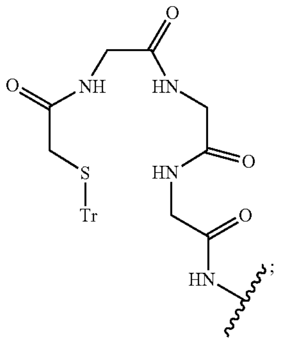

-continued

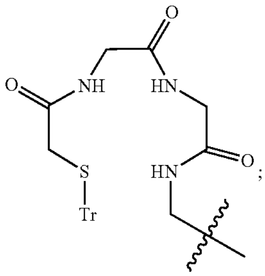

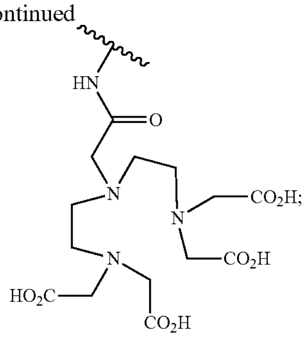

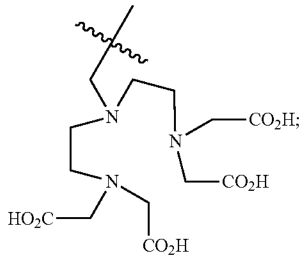

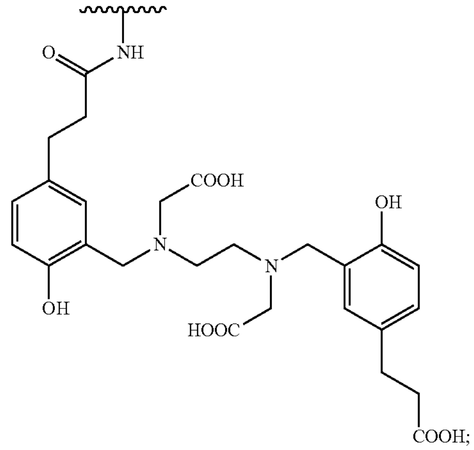

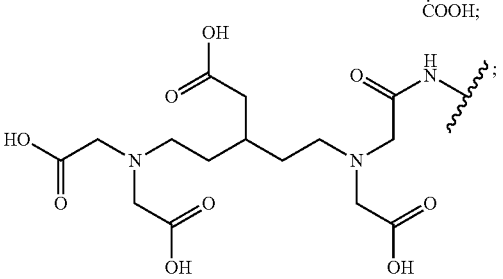

In certain embodiments of a compound of Formula X, X*, A, and A*, the chelating moiety comprises. 2,2',2"-(1,4,7-triazonane-1,4,7-triyl)tri acetic acid (NOTA); 2-(4,7-bis(carboxymethyl)-1,4,7-triazonan-1-yl)succinic acid (NODASA); 2-(4,7-bis(carboxymethyl)-1,4,7-triazonan-1-yl) pentanedioic acid (NODAGA); or 2,2'((2-(7-bis-(carboxymethyl)-1,4,7-triazonan-1-yl)ethyl)azanediyl) diacetic acid (NETA). In certain embodiments, the chelating moiety comprises derivatives of these moieties, such as functional derivatives and derivatives that allow a linker moiety to be covalently attached.

In certain embodiments of a compound of Formula X, X*, A, and A*, the chelating moiety comprises NOTA. In certain embodiments, the chelating moiety comprises NODASA. In certain embodiments, the chelating moiety comprises NODAGA. In certain embodiments, the chelating moiety comprises NETA.

In certain embodiments of a compound of Formula X, X*, A, and A*, the chelating moiety comprises: DOTA (1,4,7,10-tetraazacyclododecane-1,4,7,10-tetraacetic acid), DOTAGA (1,4,7,10-tetraazacyclododecane, 1-(glutaric acid)-4,7,10-triacetic acid), HBED, HBED-CC TFP, or H2DEDPA, as illustrated below. In certain embodiments, the chelating moiety comprises derivatives of these moieties, such as functional derivatives and derivatives that allow a linker moiety to be covalently attached.

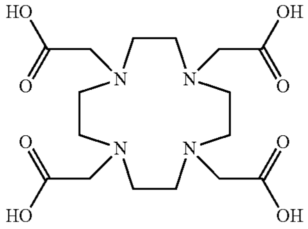

DOTA

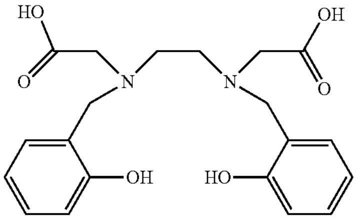

HBED

-continued

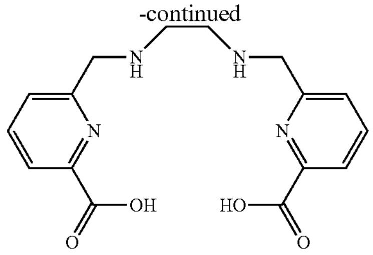

$H_2$DEDPA

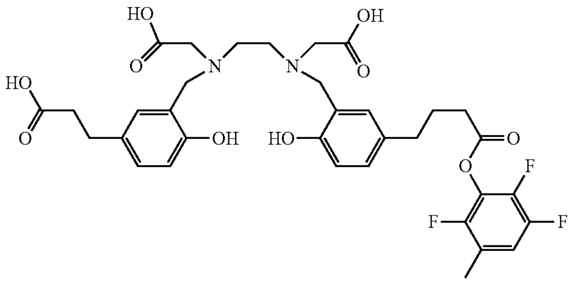

HBED-CC TFP

In certain embodiments of a compound of Formula X, X*, A, and A*, the chelating moiety comprises DOTA. In another certain embodiments, the chelating moiety comprises DOTAGA. In certain embodiments, the chelating moiety comprises derivatives of these moieties, such as functional derivatives and derivatives that allow a linker moiety to be covalently attached.

In certain embodiments of a compound of Formula X, X*, A, and A*, the chelating moiety is selected from a structure selected from NOTA, NODAGA, NODASA, DOTA, DOTAGA, or DOTASA, such as those shown in the table immediately below, wherein a single point of attachment to targeting moiety, optionally via a linker moiety, is shown. Also contemplated are embodiments where each illustrated chelating moiety is further modified to be a divalent or multivalent chelating moiety. In certain embodiments, one or more available carboxylate carbonyl carbons is a point of attachment to a second, and optionally a third, targeting moiety (optionally via a linker moiety) thus replacing the hydroxyl group. In certain embodiments, a methylene carbon is a point of attachment for a second, and optionally a third, targeting moiety (optionally via a linker moiety).

| Common Name | Structure of chelating moiety with conjugation site marked | Chemical name of chelating moiety before conjugation |
|---|---|---|
| NOTA | 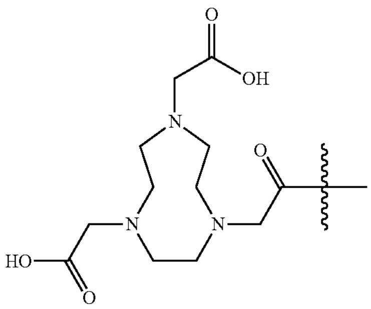 [SMILES: *C(=O)CN1CCN(CC(=O)O)CCN(CC(=O)O)CC1] | 1,4,7-Triazacyclononane-1,4,7-triacetic acid |

-continued

| Common Name | Structure of chelating moiety with conjugation site marked | Chemical name of chelating moiety before conjugation |
|---|---|---|
| NODAGA | 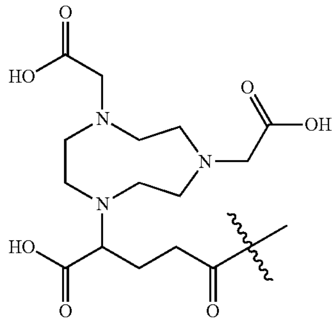 [SMILES: *C(=O)CCC(C(=O)O)N1CCN(CC(=O)O)CCN(CC(=O)O)CC1] | 2,2'-(7-(1-carboxy-4-oxopentyl)-1,4,7-triazonane-1,4-diyl)diacetic acid |
| NODASA | 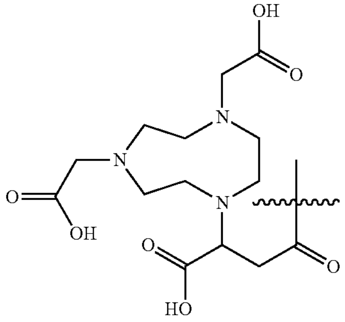 [SMILES: *C(=O)CC(C(=O)O)N1CCN(CC(=O)O)CCN(CC(=O)O)CC1] | 2-(4,7-bis(carboxymethyl)-1,4,7-triazonan-1-yl)succinic acid |
| DOTA | 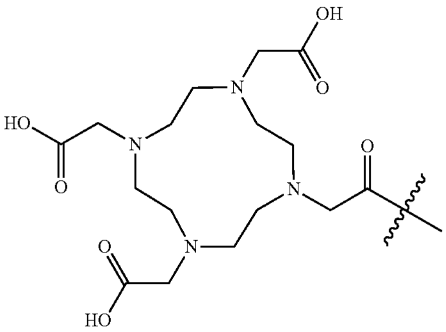 [SMILES: *C(=O)CN1CCN(CC(=O)O)CCN(CC(=O)O)CCN(CC(=O)O)CC1] | (1,4,7,10-tetraazacyclododecane-1,4,7,10-tetraacetic acid) |
| DOTAGA | 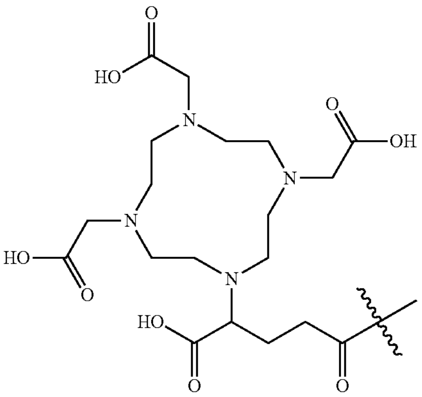 [SMILES: *C(=O)CCC(C(=O)O)N1CCN(CC(=O)O)CCN(CC(=O)O)CCN(CC(=O)O)CC1] | (1,4,7,10-tetraazacyclododecane,1-(glutaric acid)-4,7,10-triacetic acid) |

-continued

| Common Name | Structure of chelating moiety with conjugation site marked | Chemical name of chelating moiety before conjugation |
|---|---|---|
| DOTASA | 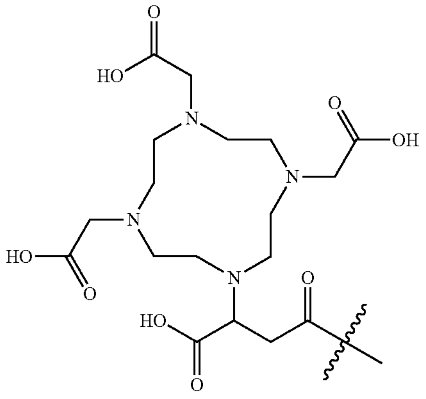 [SMILES: *C(=O)CC(C(=O)O)N1CCN(CC(=O)O)CCN(CC(=O)O)CCN(CC(=O)O)CC1] | (1,4,7,10-tetraazacyclododecane,1-(succinic acid)-4,7,10-triacetic acid) |

In certain embodiments of a compound of Formula X, X*, A, and A*, the chelating moiety comprises a structure according to Formula 1:

Formula 1

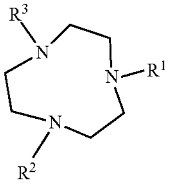

wherein:

$R^1$, $R^2$, and $R^3$ are individually a $C_{2-6}$ alkyl, optionally substituted with one or more substituents selected from oxo, thiol, hydroxyl, $C_{1-3}$ alkoxy, $C_{1-3}$ carboxy, and $C_{1-3}$ alkyl thiol, including deprotonated variants thereof depending on chelation with *Cu;

wherein ≥one of $R^1$, $R^2$, and $R^3$ comprise a point of attachment to the linker moiety (when L is a linker moiety) or to the targeting moiety (when L is a bond).

In certain embodiments of a compound of Formula X, X*, A, and A*, the chelating moiety comprises a structure according to Formula 1':

Formula 1'

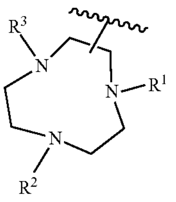

wherein:

$R^1$, $R^2$, and $R^3$ are individually a $C_{2-6}$ alkyl, optionally substituted with one or more substituents selected from oxo, thiol, hydroxyl, $C_{1-3}$ alkoxy, $C_{1-3}$ carboxy, and $C_{1-3}$ alkyl thiol, including deprotonated variants thereof depending on chelation with *Cu;

wherein  denotes the point of attachment to the linker moiety (when L is a linker moiety) or to the targeting moiety (when L is a bond).

In certain embodiments of a compound of Formula X, X*, A, and A*, the chelating moiety comprises a structure according to Formula 1'a Formula 1'a

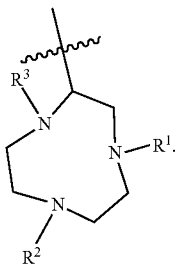

In certain embodiments of a compound of Formula X, X*, A, and A*, the chelating moiety comprises a structure according to Formula 2:

Formula 2

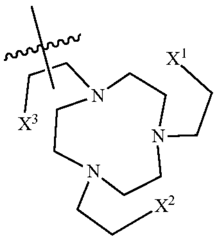

wherein $X^1$, $X^2$, and $X^3$ are individually selected from, —OH, —$NH_2$, and —SH, including deprotonated variants thereof depending on chelation with *Cu;

wherein any methylene is optionally substituted with oxo, thiol, or hydroxyl; and wherein  denotes the point of attachment to the linker moiety (when L is a linker moiety) or to the targeting moiety (when L is a bond).

In certain embodiments of a compound of Formula X, X*, A, and A*, the chelating moiety comprises a structure according to Formula 2':

Formula 2'

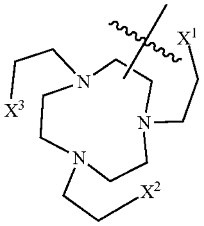

wherein $X^1$, $X^2$, and $X^3$ are individually selected from —OH, —$NH_2$, and —SH, including deprotonated variants thereof depending on chelation with *Cu;

wherein any methylene is optionally substituted with oxo, thiol or hydroxyl; and wherein  denotes the point of attachment to the linker moiety (when L is a linker moiety) or to the targeting moiety (when L is a bond).

In certain embodiments of a compound of Formula X, X*, A, and A*, the chelating moiety comprises a structure according to Formula 2i, 2'i, 2ii, or 2iii:

Formula 2i

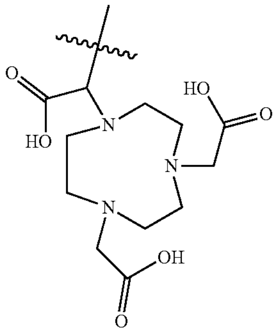

Formula 2'i

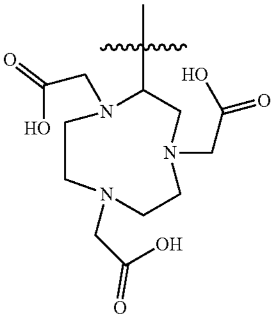

Formula 2ii

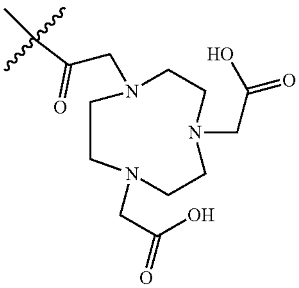

-continued

Formula 2iii

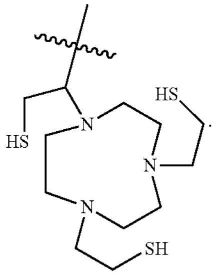

In certain embodiments of a compound of Formula X, X*, A, and A*, the chelating moiety comprises a structure according to Formula 2iR, 2'iR, or 2iiR:

Formula 2iR

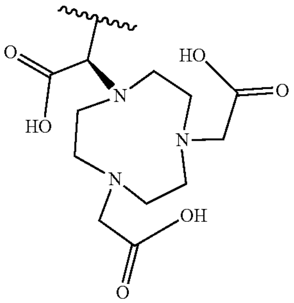

In certain embodiments of a compound of Formula X, X*, A, and A*, the chelating moiety comprises a structure according to Formula 3:

Formula 3

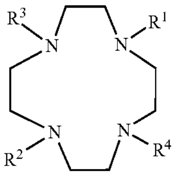

wherein:

$R^1$, $R^2$, $R^3$ and $R^4$ are individually a $C_{2-6}$ alkyl, optionally substituted with one or more substituents selected from oxo, thiol, hydroxyl, $C_{1-3}$ alkoxy, $C_{1-3}$ carboxy, and $C_{1-3}$ alkyl thiol, including deprotonated variants thereof depending on chelation with *Cu;

wherein ≥one of $R^1$, $R^2$, $R^3$ and $R^4$ comprise a point of attachment to the linker moiety (when L is a linker moiety) or to the targeting moiety (when L is a bond).

In certain embodiments of a compound of Formula X, X*, A, and A*, the chelating moiety comprises a structure according to Formula 3':

Formula 3'

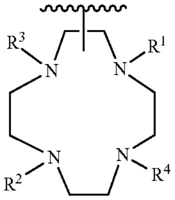

wherein:

$R^1$, $R^2$, $R^3$, and $R^4$ are individually a $C_{2-6}$ alkyl, optionally substituted with one or more substituents selected from oxo, thiol, hydroxyl, $C_{1-3}$ alkoxy, $C_{1-3}$ carboxy, and $C_{1-3}$ alkyl thiol, including deprotonated variants thereof depending on chelation with *Cu;

wherein ⌇ denotes the point of attachment to the linker moiety (when L is a linker moiety) or to the targeting moiety (when L is a bond).

In certain embodiments of a compound of Formula X, X*, A, and A*, the chelating moiety comprises a structure according to Formula 2:

Formula 4

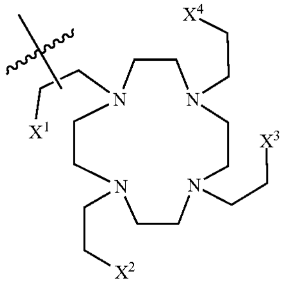

wherein $X^1$, $X^2$, $X^3$, and $X^4$ are individually selected from, —OH, —$NH_2$, and —SH, including deprotonated variants thereof depending on chelation with *Cu;

wherein any methylene is optionally substituted with oxo, thiol, or hydroxyl; and wherein ⌇ denotes the point of attachment to the linker moiety (when L is a linker moiety) or to the targeting moiety (when L is a bond).

In certain embodiments of a compound of Formula X, X*, A, and A*, the chelating moiety comprises a structure according to Formula 4':

Formula 4'

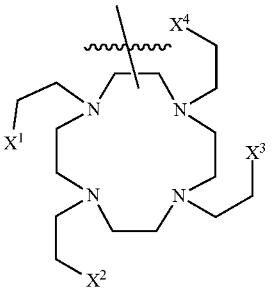

wherein $X^1$, $X^2$, $X^3$, and $X^4$ are individually selected from —OH, —$NH_2$, and —SH, including deprotonated variants thereof depending on chelation with *Cu;

wherein any methylene is optionally substituted with oxo, thiol or hydroxyl; and wherein ⌇ denotes the point of attachment to the linker moiety (when L is a linker moiety) or to the targeting moiety (when L is a bond).

In certain embodiments of a compound of Formula X, X*, A, and A*, the chelating moiety comprises a structure according to Formula 4i, 4'i, or 4ii:

Formula 4i

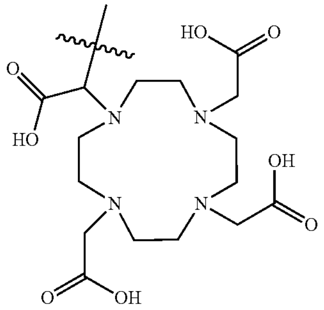

Formula 4'1

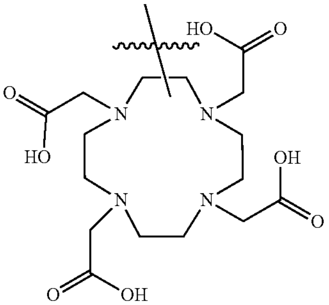

Formula 4ii

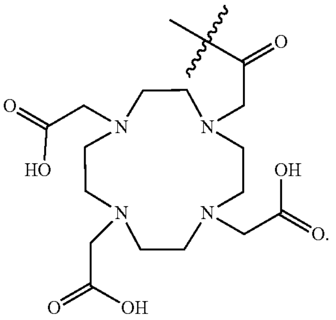

In certain embodiments of a compound of Formula X, X*, A, and A*, the chelating moiety comprises a structure according to Formula 4iR or 4iiR.

Formula 4iR

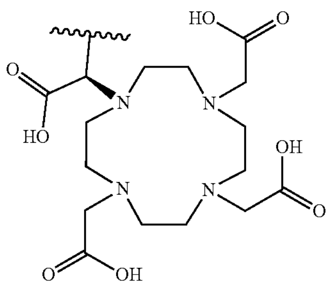

In various embodiments of the chelating moieties as described herein as Formulas 1-4, inclusive of all enumerated subgenera, the chelating moiety further comprises one or more selected from methylene ($—CH_2—$) and carbonyl ($—C(=O)—$). In certain embodiments, the chelating moiety further comprises one methylene and one carbonyl, e.g., $—CH_2—C(=O)—$.

Also contemplated are embodiments of the chelating moieties as described herein as Formulas 1-4, inclusive of all enumerated subgenera, where each illustrated chelating moiety is further modified to be a divalent or multivalent chelating moiety. In certain embodiments, one or more available carboxylate carbonyl carbons is a point of attachment to a second, and optionally a third, targeting moiety (optionally via a linker moiety) thus replacing the hydroxyl group. In certain embodiments, a methylene carbon is a point of attachment for a second, and optionally a third, targeting moiety (optionally via a linker moiety).

4.2.2. Chelated Moiety

In certain embodiments of a compound of Formula X*and A*, compounds of the present disclosure comprise a chelating moiety that is chelated to a radionuclide such as radio copper, i.e., the chelating moiety further comprises a radionuclide metal, alternatively phrase, the chelating moiety is complexed to a radionuclide metal center. In the embodiments provided below, the bonds depicted as lines between the binding moieties and the metal center are provided for illustrative purposes only as these interactions are dynamic and dependent on the environment.

In certain embodiments of a compound of Formula X*and A*, the chelated-copper complex, i.e., comprising the chelating moiety and a copper radionuclide, comprises a structure according to Formula I:

Formula I

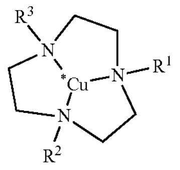

wherein:

$R^1$, $R^2$, and $R^3$ are individually a $C_{2-6}$ alkyl, optionally substituted with one or more substituents selected from oxo, thiol, hydroxyl, $C_{1-3}$ alkoxy, $C_{1-3}$ carboxy, and $C_{1-3}$ alkyl thiol, including deprotonated variants thereof depending on chelation with *Cu;

wherein ≥one of $R^1$, $R^2$, and $R^3$ comprise a point of attachment to the linker moiety (when L is a linker moiety) or to the targeting moiety (when L is a bond).

In certain embodiments of a compound of Formula X*and A*, the chelated-copper complex comprises a structure according to Formula I':

Formula I'

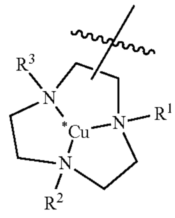

wherein:

$R^1$, $R^2$, and $R^3$ are individually a $C_{2-6}$ alkyl, optionally substituted with one or more substituents selected from oxo, thiol, hydroxyl, $C_{1-3}$ alkoxy, $C_{1-3}$ carboxy, and $C_{1-3}$ alkyl thiol, including deprotonated variants thereof depending on chelation with *Cu;

wherein denotes the point of attachment to the linker moiety (when L is a linker moiety) or to the targeting moiety (when L is a bond).

In certain embodiments of a compound of Formula X*and A*, the chelated-copper complex comprises a structure according to Formula II:

Formula II

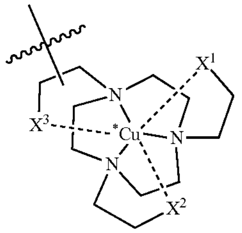

wherein $X^1$, $X^2$, and $X^3$ are individually selected from —OH, $—NH_2$, and —SH, including deprotonated variants thereof depending on chelation with *Cu;

wherein any methylene is optionally substituted with oxo, thiol, or hydroxyl; and wherein denotes the point of attachment to the linker moiety (when L is a linker moiety) or to the targeting moiety (when L is a bond).

In certain embodiments of a compound of Formula X*and A*, the chelated-copper complex comprises a structure according to Formula II':

Formula II'

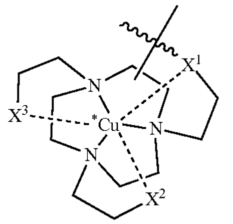

wherein $X^1$, $X^2$, and $X^3$ are individually selected from —OH, $—NH_2$, and —SH, including deprotonated variants thereof depending on chelation with *Cu;

wherein any methylene is optionally substituted with oxo, thiol, or hydroxyl; and wherein  denotes the point of attachment to the linker moiety (when L is a linker moiety) or to the targeting moiety (when L is a bond).

In certain embodiments of a compound of Formula X*and A*, the chelated-copper complex comprises a structure according to Formula IIi, II'i, IIii, or IIiii:

Formula IIi

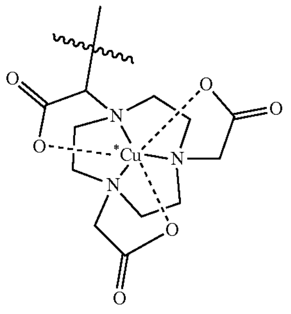

Formula II'i

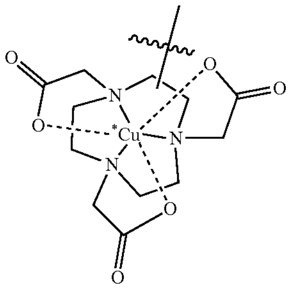

Formula IIii

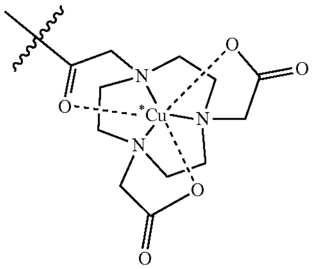

Formula IIiii

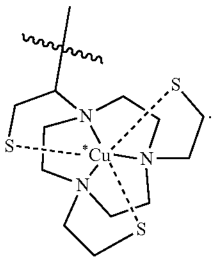

4.2.3. Linker Moiety

In certain embodiments of a compound of Formula X, X*, A, and A*, the linker moiety (L) is a bond or a single or multi-atom linkage between a chelating moiety and a targeting moiety. Alternatively, the linker moiety is not particularly limited and may be any linker known in the field of bioconjugation including linkers known in the construction of antibody drug conjugates. The linker moiety may be selected according to ease of synthesis, lability of the linker moiety, solubility of the radiotracer, and other considerations.

In certain embodiments of a compound of Formula X, X*, A, and A*, L is divalent, such as when n is 1 in Formula X or A as described herein. In other embodiments, L is polyvalent and thereby linking multiple chelating moieties to a targeting moiety, such as when n is greater than 1, e.g., an integer from 2-10 in Formula X or A as described herein.

In certain embodiments of a compound of Formula X, X*, A, and A*, L comprises one or more chemical entities selected from an amino acid, a sequence of amino acid acids, a 5- to 7-membered carbocyclic or heterocyclic group, or a cyclic heterocycles or acyclic organic molecule, any of which may optionally comprise one or more functional groups selected from ketones, amides, alkyne, azide, amine, and isothiocyanate.

In certain embodiments of a compound of Formula X, X*, A and A*L is a bond such that the targeting moiety is bound directly to the chelating moiety or to a plurality of chelating moieties.

In certain embodiments of a compound of Formula X, X*, A and A*L is a divalent linker. In certain embodiments, L is a cleavable divalent linker. Cleavable linkers include linkers that are cleaved by intracellular metabolism following internalization, e.g., cleavage via hydrolysis, reduction, or enzymatic reaction. In certain embodiments, L is a non-cleavable divalent linker. Non-cleavable linkers include linkers that release an attached payload via lysosomal degradation following internalization.

In certain embodiments of a compound of Formula X, X*, A, and A*, L is selected from an acid-labile linker, a hydrolysis-labile linker, an enzymatically cleavable linker, a reduction labile linker, a self-immolative linker, and a non-cleavable linker.

In certain embodiments of a compound of Formula X, X*, A, and A*, L comprises one or more peptides, amino acids, glucuronides, succinimide-thioethers, methylene units, carbonyl units, polyethylene glycol (PEG) units, hydrazones, mal-caproyl units, dipeptide units, valine-citrulline units, para-aminobenzyl (PAB) units, or a combination thereof.

In certain embodiments of a compound of Formula X, X*, A, and A*, L comprises one or more amino acids. Suitable amino acids include natural, non-natural, standard, non-standard, proteinogenic, non-proteinogenic, and L- or D-α-amino acids. In certain embodiments, the L linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combinations thereof. In certain embodiments, L comprises a peptide of up to 3 amino acids, up to 5 amino acids, up to 7 amino acids, up to 10 amino acids, or up to 15 amino acids. In certain embodiments, L comprises a peptide of 1 to 3 amino acids, 2 to 4 amino acids, 1 to 5 amino acids, 2 to 5 amino acids, 3 to 5 amino acids, 3-7 amino acids, 5-10 amino acids, 5-15 amino acids, or 10-15 amino acids. In certain embodiments, L is or comprises suberic acid-D-Lysine-D-phenylalanine-3-iodo-D-tyrosine (Sub-k-f-(I-y))=32-amino-29-benzyl-33-(4-hydroxy-3-iodophenyl)-5,13,20,28,31-pentaoxo-4,6,12,21,27,30-hexaazatritriacontane-1,3,7,26-tetracarboxylic acid.

In certain embodiments of a compound of Formula X, X*, A, and A*, L is a bivalent linker group or linking moiety. In certain embodiments, L is or comprises

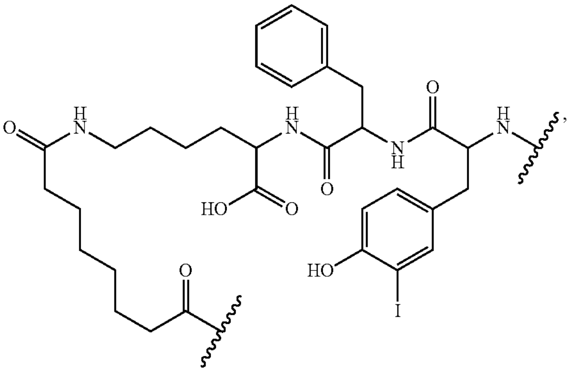
,
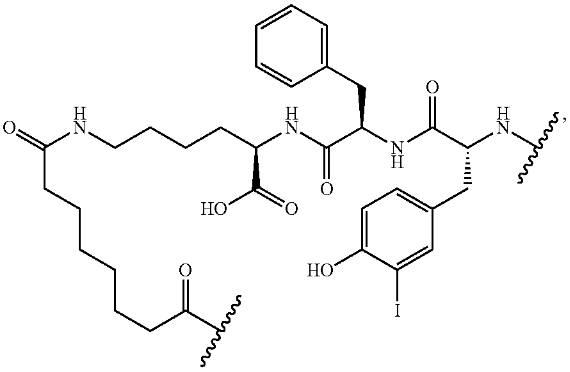
,
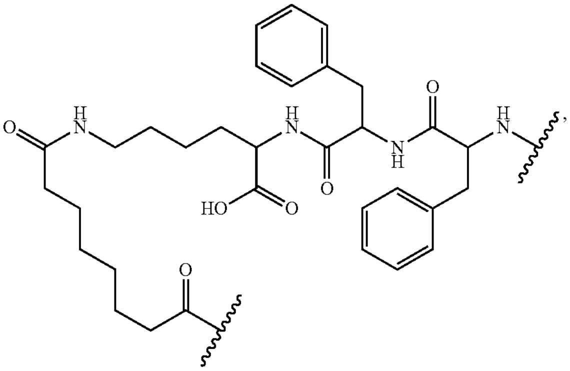
,
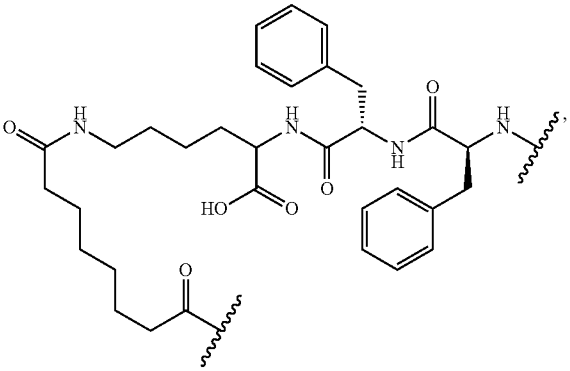
,
-continued
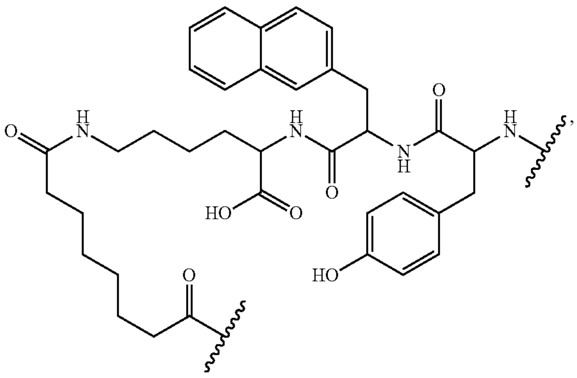
,
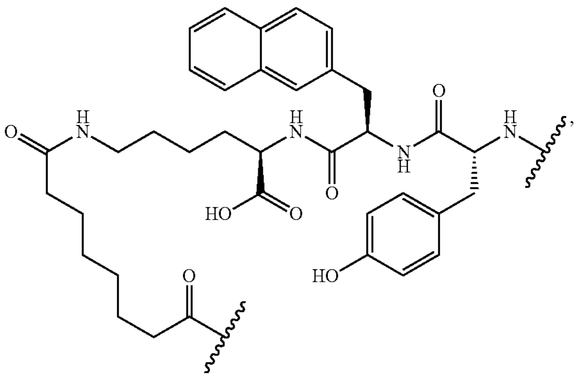
,
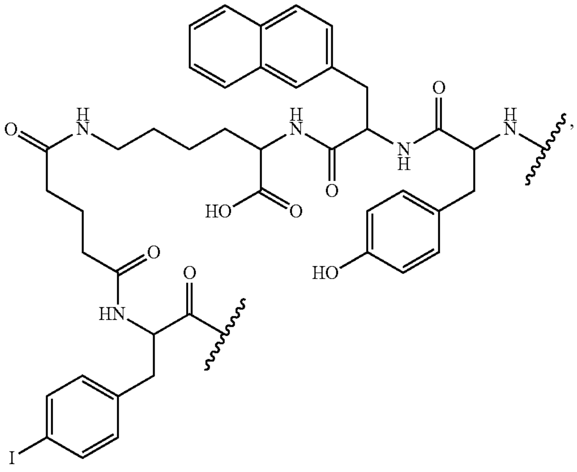
,
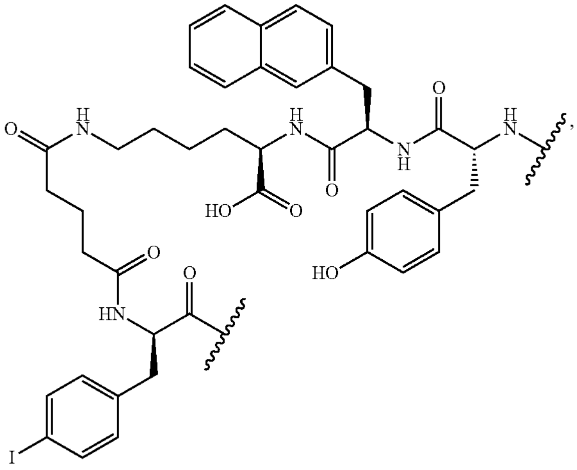
, -continued
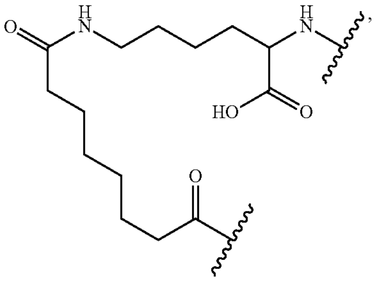
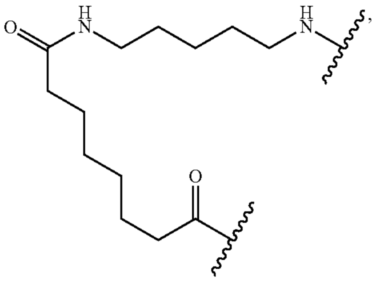
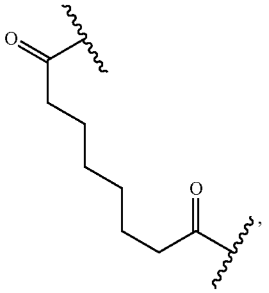
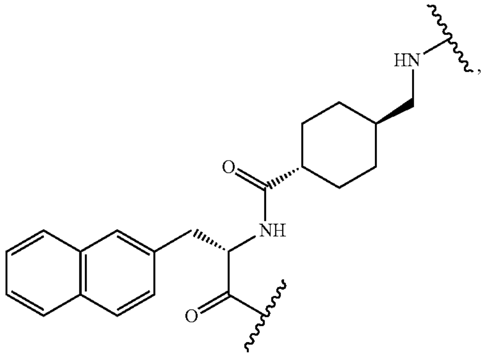
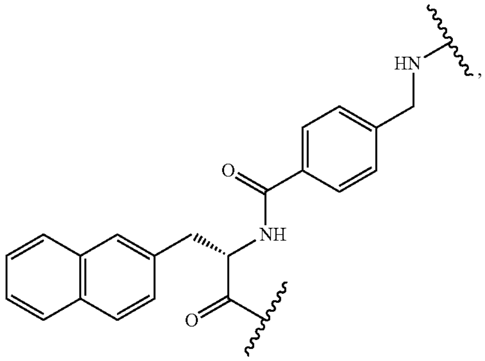
and
-continued
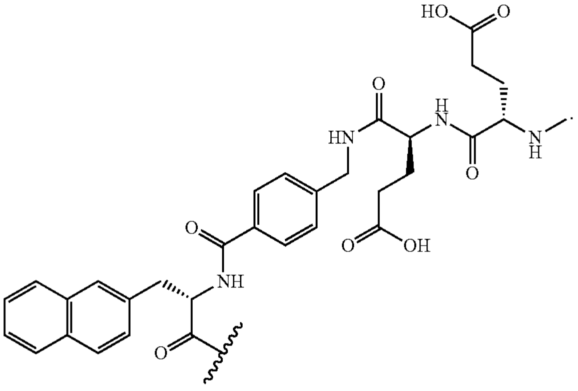 [SMILES: *C(=O)[C@H](Cc1ccc2ccccc2c1)NC(=O)c1ccc(CNC(=O)[C@H](CCC(=O)O)NC(=O)[C@H](CCC(=O)O)NC)cc1]
In certain embodiments of a compound of Formula X, X*, A, and A*, L is or comprises
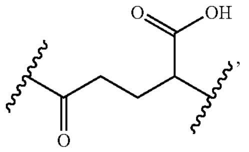
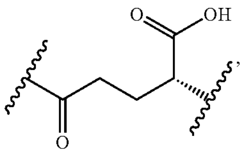
and
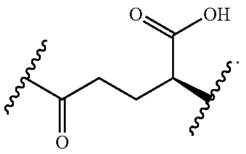
In certain embodiments, L is or comprise
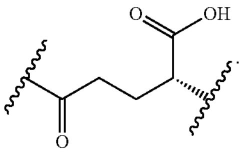 [SMILES: *C(=O)CC[C@@H](*)C(=O)O]
In certain embodiments, L is or comprises
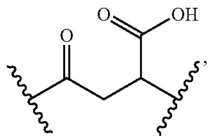
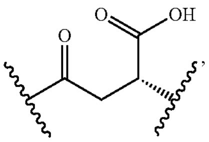
and
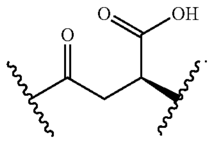
In certain embodiments of a compound of Formula X, X*, A, and A*, L is or comprises one or more of a carbonyl, an amine, an amide, an ester, an ether, ethylene diamine ( 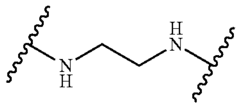 ), 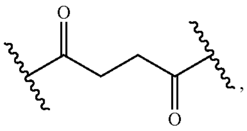,

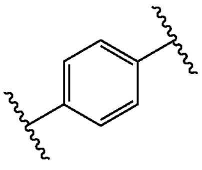 or 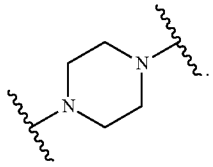.

In certain embodiments, L is or comprises

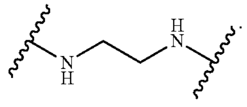 [SMILES: *NCCN*].

In certain embodiments, L is or comprises

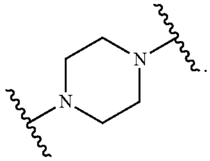 [SMILES: *N1CCN(*)CC1].

Suitable linkers are disclosed in U.S. Patent Application Publication No. US2011/0064657 A1, for "Labeled Inhibitors of Prostate Specific Membrane Antigen (PSMA), Biological Evaluation, and Use as Imaging Agents," published Mar. 17, 2011, to Pomper et al., and U.S. Patent Application Publication No. US2012/0009121 A1, for "PSMA-Targeting Compounds and Uses Thereof," published Jan. 12, 2012, to Pomper et al, each of which is incorporated by reference in its entirety.

4.2.4. Targeting Moiety

The targeting moiety (V) for use with the present disclosure is not particularly limited, as long as one or more of the targeting moiety is amenable to conjugation to a chelating moiety as described herein and wherein the targeting moiety interacts with a cell surface target.

In certain embodiments of a compound of Formula X, X*, A, and A*, the targeting moiety is selected from a peptide, protein, or small organic molecule that binds with a cell surface receptor, e.g., expressed by malignant or premalignant cells; cells in the tumor microenvironment, such as blood vessels, cancer-associated fibroblasts, the stromal matrix and immune cells, inflammatory tissues; and/or sites of tissue remodeling at sites of a myocardial infarct or fibrosis in interstitial lung disease.

In certain embodiments of a compound of Formula X, X*, A, and A*, the targeting moiety is one that is known to target a PSMA (Prostate-Specific Membrane Antigen), SSTR (Somatostatin receptor) and FAP (Fibroblast activation protein).

In certain embodiments of a compound of Formula X, X*, A, and A*, the targeting moiety is one that is known to be suitable for use with $^{68}Ga$, $^{225}Ac$, or $^{177}Lu$ radionuclides. In certain embodiments, the targeting moiety has been used to produce radiotracers for use in medical imaging or therapy or both.

In certain embodiments of a compound of Formula X, X*, A, and A*, the targeting moiety is a peptide. The peptide may comprise natural or unnatural amino acids or combinations thereof. In certain embodiments, the peptide consists of several amino acids linked together with peptide bonds. In other embodiments, the peptide may comprise as many as 50 amino acids. In certain embodiments, the targeting moiety is a peptide of up to 10 amino acids, up to 15 amino acids, up to 20 amino acids, up to 25 amino acids, up to 30 amino acids, up to 35 amino acids, up to 40 amino acids, or up to 45 amino acids. In certain embodiments, the targeting moiety is a peptide of 4-10 amino acids, 5-15 amino acids, 10-20 amino acids, 15-25 amino acids 20-30 amino acids, 25-35 amino acids, 30-40 amino acids, 35-45 amino acids 40-50 amino acids.

In certain embodiments of a compound of Formula X, X*, A, and A*, the targeting moiety is specifically recognized by a molecular target (e.g., a peptide or protein) expressed, e.g., commonly overexpressed, on the surface of cancer cells or in cancer microenvironment.

In certain embodiments of a compound of Formula X, X*, A, and A*, the targeting moiety comprises a cognate molecule to a tumor-specific antigen (TSA) that is found associated cancer cells only, and not on healthy cells. In certain embodiments, the targeting moiety comprises a cognate to tumor-associated antigens (TAA), which have elevated levels on tumor cells, but are also expressed at lower levels on healthy cells.

In certain embodiments of a compound of Formula X, X*, A and A*of the targeted chelator constructs and radiotracers of the present disclosure, the targeting moiety comprises neurotensin or a functional derivative thereof. In certain embodiments, the targeting moiety comprises a molecule that binds to epidermal growth factor receptor 2 (HER2). In certain embodiments, the targeting moiety comprises a molecule that binds to prostate-specific antigen (PSA) also known as gamma-seminoprotein or kallikrein-3 (KLK3). In certain embodiments, the targeting moiety comprises a molecule that binds to tyrosinase-related protein-2 (TRP2), also known as DOPAchrome tautomerase. In certain embodiments, the targeting moiety comprises a molecule that binds to epithelial cell adhesion molecule (EpCAM). In certain embodiments, the targeting moiety comprises a molecule that binds to Glypican-3 (GPC3). In certain embodiments, the targeting moiety comprises a molecule that binds to mesothelin (MSLN), integrin $\alpha v\beta 3$, prostate-specific membrane antigen (PSMA). In certain embodiments, the targeting moiety comprises a molecule that binds to somatostatin receptor (SSTR). In certain embodiments, the targeting moiety comprises a molecule that binds to fibroblast activation protein (FAP). In certain embodiments, the targeting moiety comprises a molecule that binds to epidermal growth factor receptor (EGFR).

4.2.4.1.1 Targets: Neurotensin Receptors

In certain embodiments of a compound of Formula X, X*, A, and A*, the targeting moiety comprises neurotensin (NT) or a functional derivative thereof. In certain embodiments, targeting moiety comprising neurotensin has been previously demonstrated to have the potential to target tumors such as: pancreatic cancer, colorectal cancer, lung cancer, prostate cancer or breast cancer. In certain embodiments, the targeting moiety comprises (pGlu-Leu-Tyr-Glu-Asn-Lys-Pro-Arg-Arg-Pro-Tyr-Ile-Leu). In certain embodiments, the targeting moiety comprises 2-[[5-(2,6-dimethoxyphenyl)-1-

(4-(N-(3-dimethylaminopropyl)-N-methylcarbamoyl)-2-isopropylphenyl)-1H-pyrazole3-carbonyl]amino] adamantane-2-carboxylic acid U.S. Pat. No. 9,868,707B2.

4.2.4.1.2 Targets: Integrin αvβ3

Integrins, consisting of two noncovalently bound transmembrane a and R subunits, are an important molecular family involved in tumor angiogenesis. Integrin αvβ3 is highly expressed on activated endothelial cells, new-born vessels as well as some tumor cells, but is not present in resting endothelial cells and most normal organ systems, making it a suitable target for anti-angiogenic therapy.

In embodiments of a compound of Formula X, X*, A, and A*, the targeting moiety comprises a molecule that binds to integrin αvβ3 or αvβ5. In certain embodiments, the targeting moiety comprises LM609/Avastin, CNTO 95, c7E3 Fab, 17E6, Abegrin, or a functional derivative of any of these.

In certain embodiments of a compound of Formula X, X*, A, and A*, the targeting moiety comprises a peptide that binds to a αvβ3 integrin. In certain embodiments, the targeting moiety is selected from an RGD peptide, SC-68448, SCH221153, and S-247 (as depicted below). In certain embodiments, the targeting moiety comprises a dimeric RGD peptide E-[c(RGDfK)]$_2$, formed by two cyclic pentapeptides c(RGDfK) linked via a glutamic acid residue. In certain embodiments, the targeting moiety comprises c(RGDfV). In these embodiments, f stands for D-phenylalanine. In certain embodiments, the targeting moiety comprises cilengitide, a cyclized RGD-containing pentapeptide, c(RGDf[NMe]V) (as depicted below). In certain embodiments, the targeting moiety comprises a disintegrin, a family of low molecular weight (47-84 amino acids) RGD containing cysteine-rich peptides derived from viper venoms.

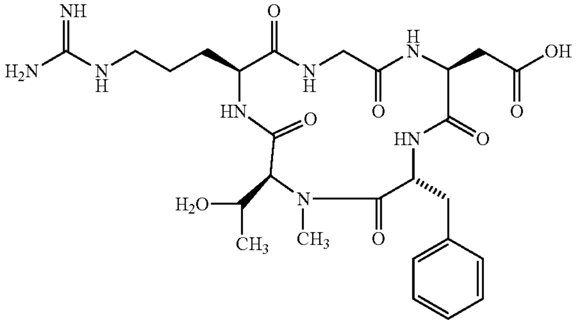

Cilengitide

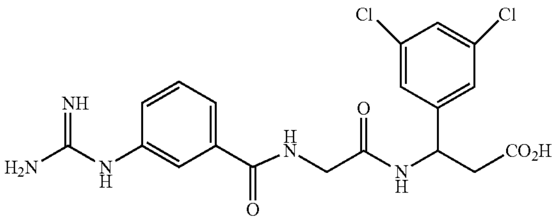

SC-68448

-continued

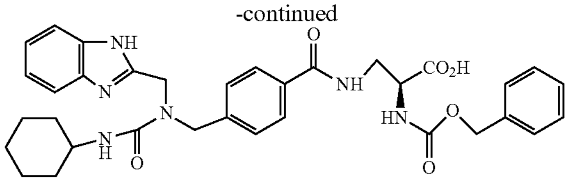

SCH221153

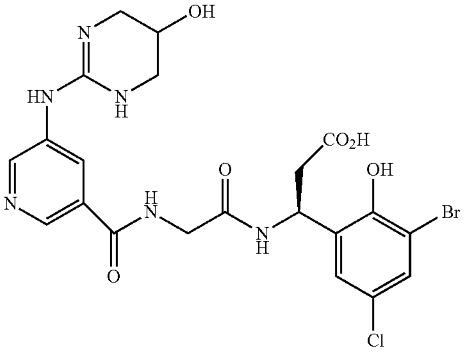

S-247

4.2.4.1.3 Targets: PSMA

Prostate-specific membrane antigen (PSMA) is a 750-amino-acid type II transmembrane glycoprotein that is highly expressed on prostate adenocarcinomas, exhibits only limited expression in benign and extraprostatic tissues, and thus represents an ideal target for the diagnosis and management of prostate cancer.

In certain embodiments of a compound of Formula X, X*, A, and A*, the targeting moiety comprises a peptide that binds to a urea-based prostate-specific membrane antigen (PSMA). In certain embodiments, the targeting moiety comprises a PSMA inhibitor based on an L-Lysine-urea-glutamate, such as Lys-urea-Glu, or a KuE motif.

In certain embodiments of a compound of Formula X, X*, A, and A*, V is a targeting moiety. In certain embodiments, V is a moiety selected from the group consisting of

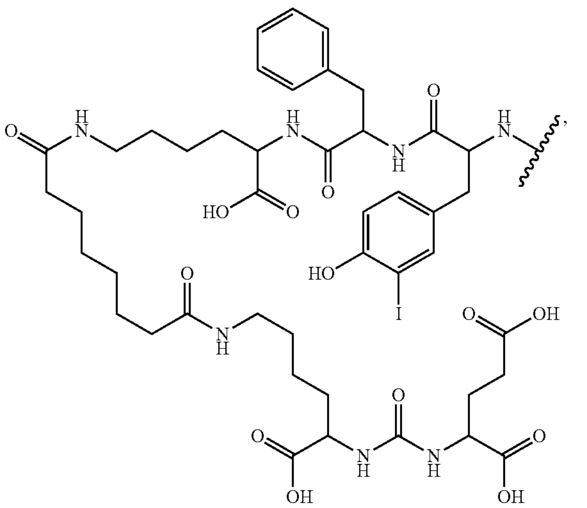

-continued
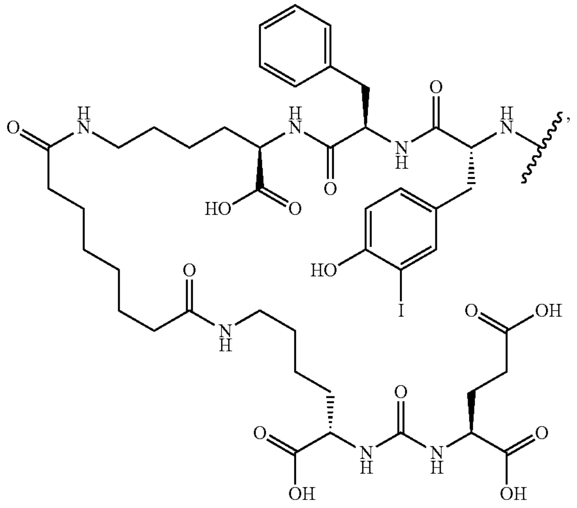
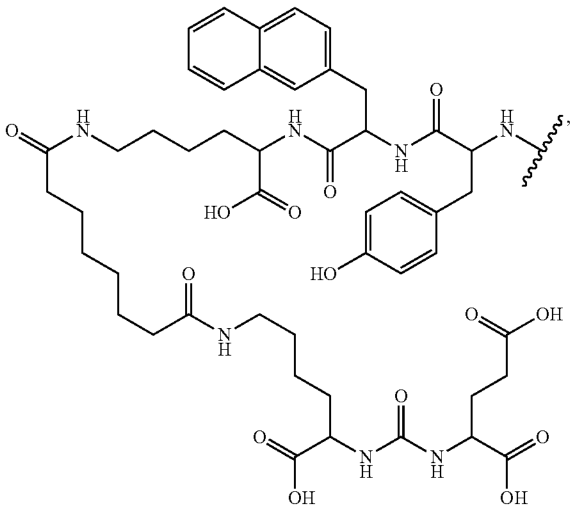
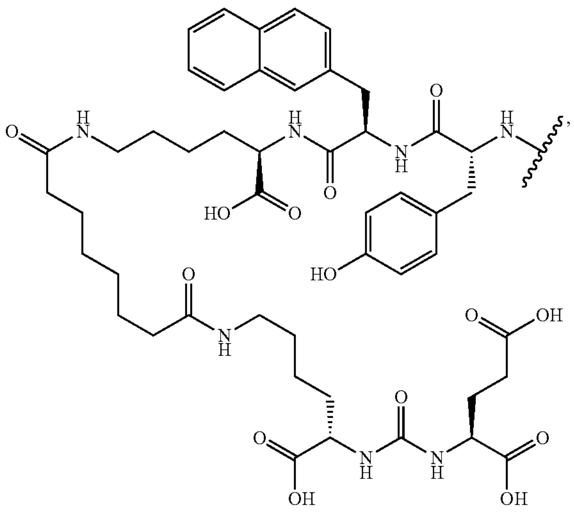
-continued
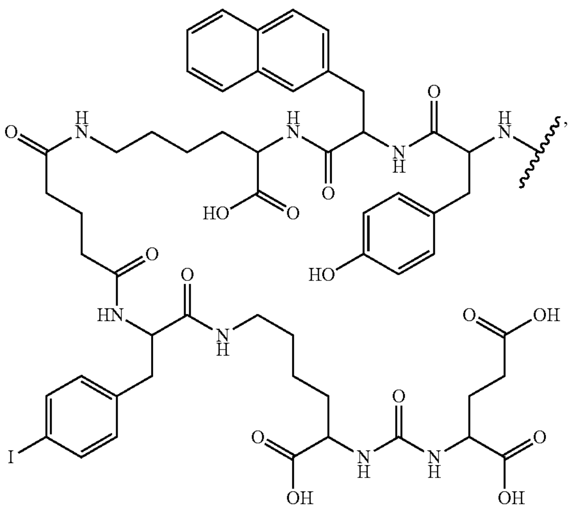
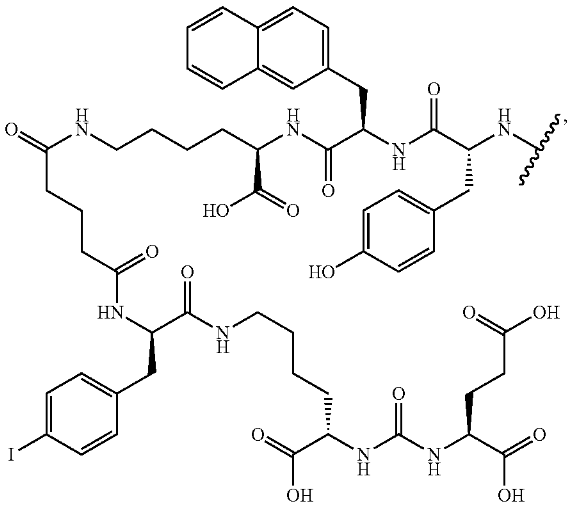
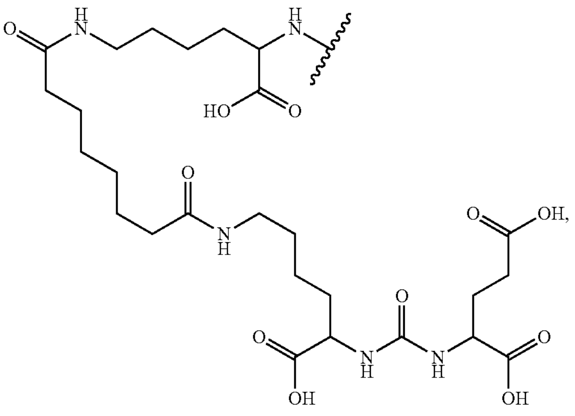

-continued
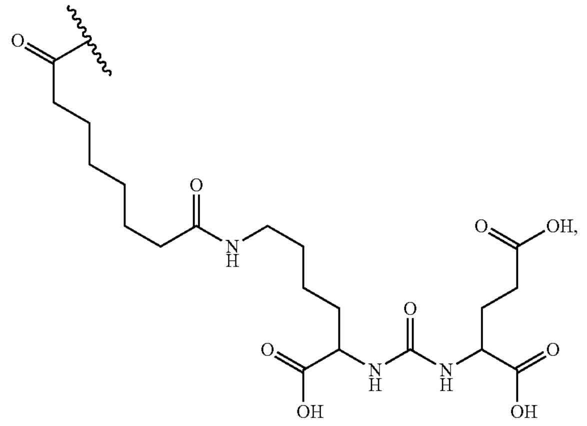
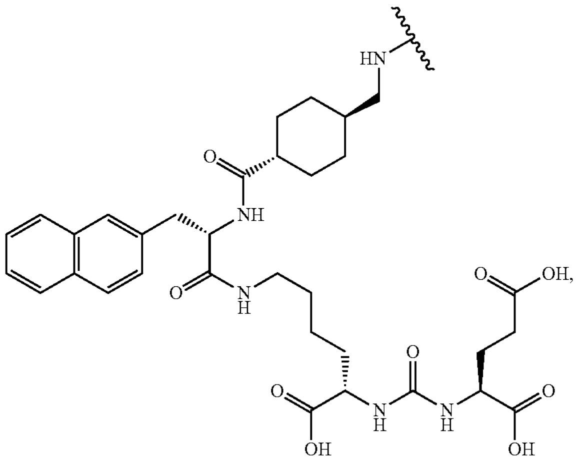
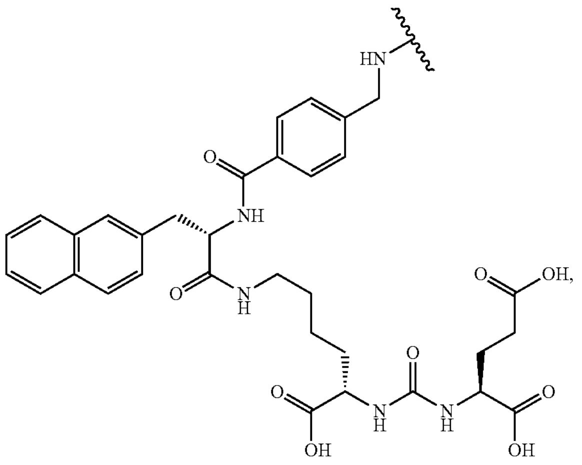
-continued
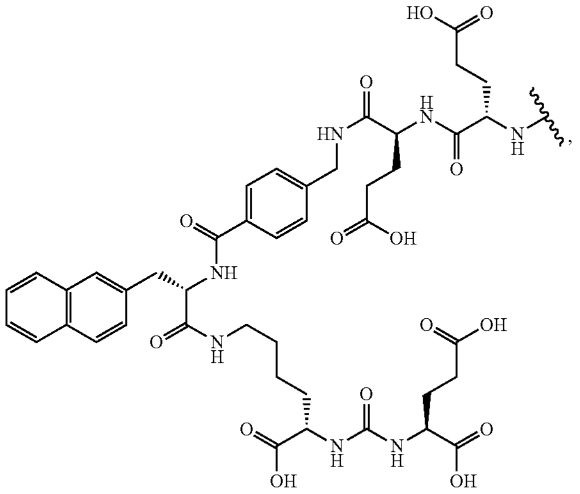
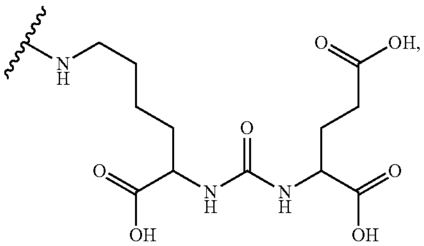 [SMILES: *NCCCCC(NC(=O)NC(CCC(=O)O)C(=O)O)C(=O)O]
and
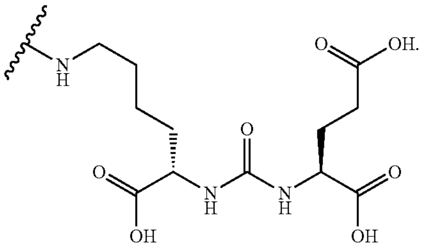 [SMILES: *NCCCC[C@H](NC(=O)N[C@@H](CCC(=O)O)C(=O)O)C(=O)O]
In certain embodiments of a compound of Formula X, X*, A, and A*, the targeting moiety comprises
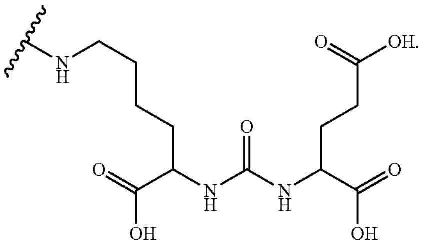
In certain embodiments of a compound of Formula X, X*, A, and A*, the targeting moiety comprises

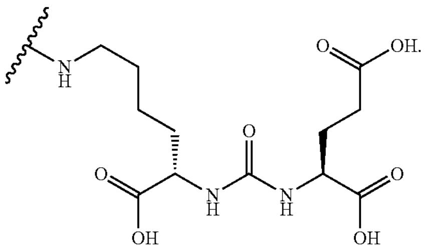

In certain embodiments of a compound of Formula X, X*, A, and A*, the targeting moiety comprises

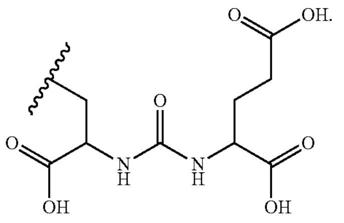 [SMILES: *CC(NC(=O)NC(CCC(=O)O)C(=O)O)C(=O)O]

L is

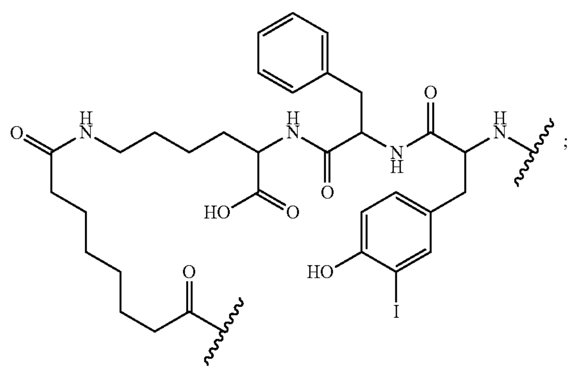

V is a targeting moiety that binds to PSMA; n is 1; m is 1; and p is 1.

In certain embodiments, the compound of Formula X is of Formula 10:

Formula 10

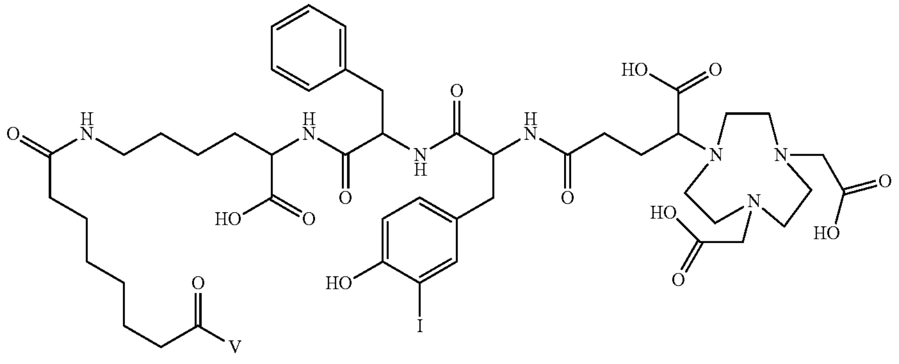

In certain embodiments of a compound of Formula X, X*, A, and A*, the targeting moiety comprises

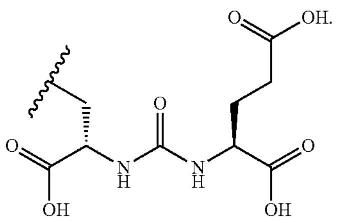 [SMILES: *C[C@H](NC(=O)N[C@@H](CCC(=O)O)C(=O)O)C(=O)O]

In certain embodiments, the compound is of Formula X:

Formula X

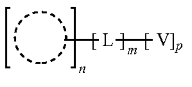

or is a pharmaceutically acceptable salt thereof, wherein: the chelating moiety is NODAGA;

or is a pharmaceutically acceptable salt thereof; wherein V comprises a targeting moiety that binds to PSMA.

In certain embodiments, the compound is of Formula X*:

Formula X*

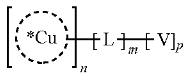

or is a pharmaceutically acceptable salt thereof, wherein: the chelating moiety is NODAGA;

*Cu is a copper radionuclide selected from $^{61}Cu$, $^{62}Cu$, $^{64}Cu$, and $^{67}Cu$;

L is

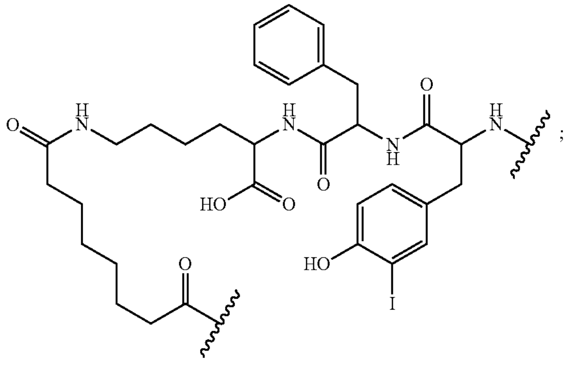 [SMILES: *NC(Cc1ccc(O)c(I)c1)C(=O)NC(Cc1ccccc1)C(=O)NC(CCCCNC(=O)CCCCCCC(*)=O)C(=O)O]

V is a targeting moiety that binds to PSMA; n is 1; m is 1; and p is 1.

In certain embodiments, a compound comprising a copper atom chelated by the compound of embodiment 1, wherein the compound is a structure of Formula 10*:

Formula 10*

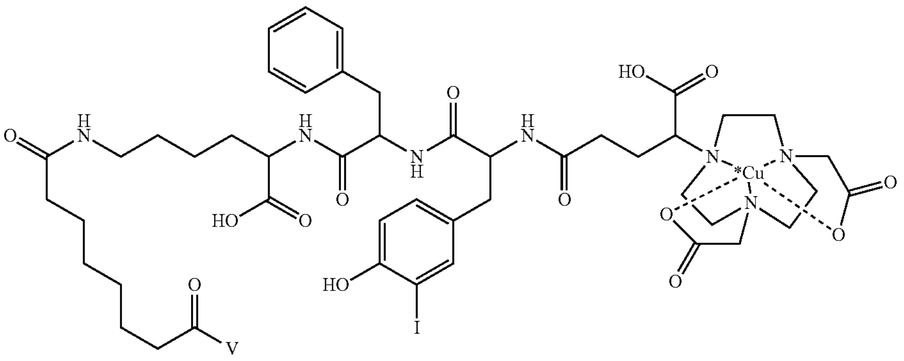

or is a pharmaceutically acceptable salt thereof;

wherein *Cu is a copper radionuclide selected from $^{61}Cu$, $^{62}Cu$, $^{64}Cu$, and $^{67}Cu$.

4.2.4.1.4 Targets: SSTR

Neuroendocrine tumors (NETs) are neoplasms arising most often in the GI tract, pancreas, or lung. Diagnosis of NETs is often delayed until the disease is advanced, because of the variable and nonspecific nature of the initial symptoms. Surgical resection for cure is therefore not an option for most patients. Somatostatin analogues represent the cornerstone of therapy for patients with NETs.

In certain embodiments of a compound of Formula X, X*, A, and A*, the targeting moiety comprises a targeting moiety, SST, that targets the somatostatin receptor 2 (SSTR2). In certain embodiments, the targeting moiety comprises a somatostatin analogue (SSA). In certain embodiments, the targeting moiety comprises a cyclic octapeptide analogue of somatostatin, such as D-Phe-c(Cys-Tyr-D-Trp-Lys-Thr-Cys)-Thr(ol) ($Tyr^3$-octreotide) and D-Phe-c(Cys-Tyr-D-Trp-Lys-Thr-Cys)-Thr ($Tyr^3$-octreotate). In certain embodiments, the targeting moiety comprises D-Phe-c(Cys-Tyr-D-Trp-Lys-Thr-Cys)Thr(ol), i.e., TOC. In certain embodiments, the targeting moiety is according to Structure 1, below where denotes a point of attachment to a chelating moiety or linker.

Structure 1

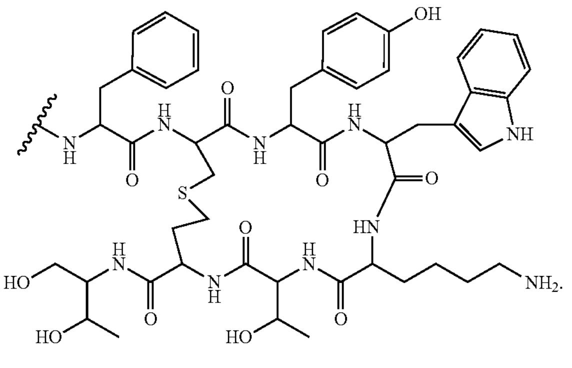

TOC

In certain embodiments of a compound of Formula X, X*, A, and A*, the targeting moiety comprises p-Cl-Phe-cyclo (D-Cys-Tyr-D-4-amino-Phe(carbamoyl)-Lys-Thr-Cys)D-Tyr-$NH_2$, i.e., LM3. LM3 is well known in this field (Fani M et al., J Nucl Med 2011; 52:1110-8), and easily available from commercial sources or by routine synthesis. In certain embodiments, the targeting moiety is according to Structure 2, below where denotes a point of attachment to a chelating moiety or linker.

Structure 2

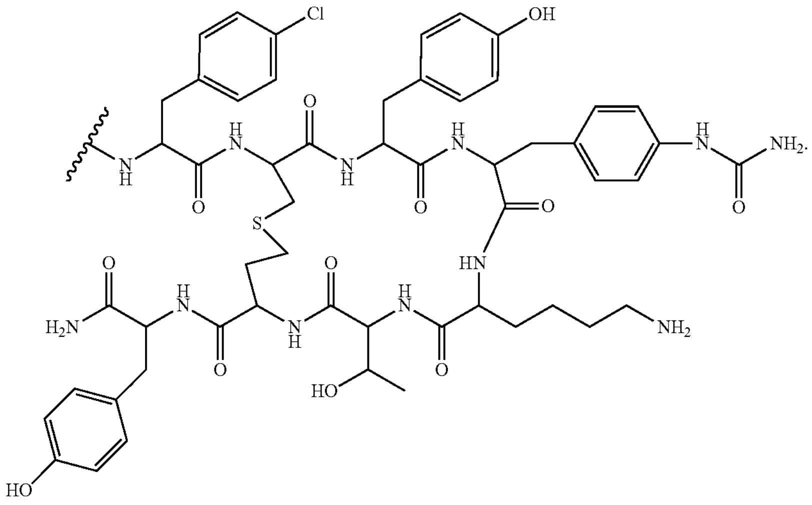

LM3

In certain embodiments, the compound is of Formula X:

Formula X

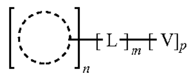

or is a pharmaceutically acceptable salt thereof, wherein: the chelating moiety is NODAGA;

L is linker moiety; V is a targeting moiety SST that binds to SSTR; n is 1; m is 1; and p is 1.

In certain embodiments, the compound is of Formula X In certain embodiments, the compound of Formula X* is of Formula 20:

Formula 20

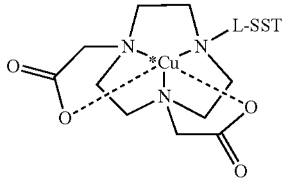

or is a pharmaceutically acceptable salt thereof;

wherein:

*Cu is a copper radionuclide selected from $^{61}Cu$, $^{62}Cu$, and $^{67}Cu$;

L is a bond or a linker moiety; and

SST is a targeting moiety that binds to a somatostatin receptor.

4.2.4.1.5 Targets FAP

In certain embodiments of a compound of Formula X, X*, A, and A*, the targeting moiety comprises a peptide cognate to fibroblast-activation-protein (FAP). FAP is overexpressed by cancer-associated fibroblasts of several tumor entities. In certain embodiments of the radiotracers of the present disclosure, the targeting moiety comprises a FAP-inhibitor structure, such as Val-boroPro, linagliptin, FAPI-02, or functional derivatives of any of these. Also included are FAP cognates disclosed in Roy et al., Design and validation of fibroblast activation protein alpha targeted imaging and therapeutic agents, Theranostics 2020, 10 (13), 5778-5789, which is incorporated herein by reference in its entirety, including, but not limited to:

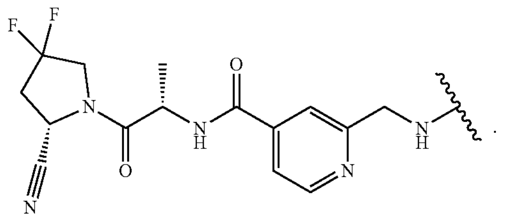 [SMILES: *NCc1cc(C(=O)N[C@@H](C)C(=O)N2CC(F)(F)C[C@H]2C#N)ccn1]

Suitable FAP inhibitors are disclosed in International PCT Patent Application No. WO2019/154886 for FAP Inhibitor, to Haberkorn et al., published Aug. 15, 2019, which is incorporated herein by reference in its entirety.

The present disclosure provides compositions comprising compounds, wherein the compound is of Formula 30:

(Formula 30)

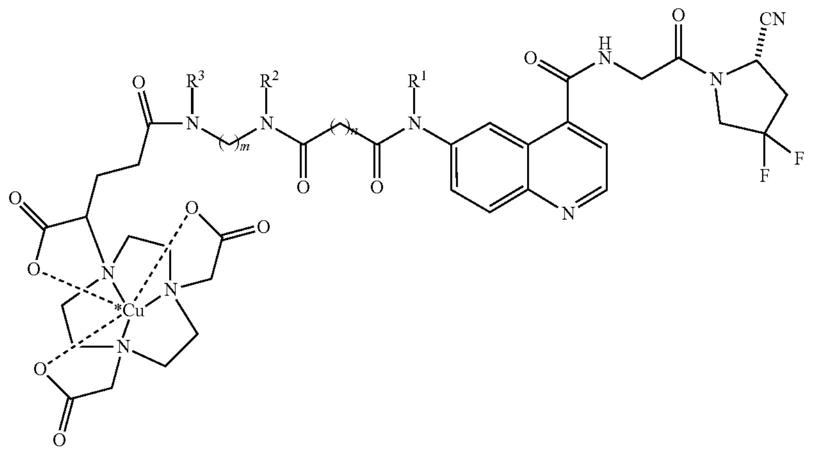

wherein:

$R^1$ is $R^a$;

$R^2$ and $R^3$ are each $R^a$ or together form a $C_{2-9}$ heterocycle with the nitrogen atoms to which they are attached;

$R^a$, independently for each occurrence, is selected from H, $C_{1-10}$ alkyl, $C_{2-10}$ alkenyl, $C_{3-10}$ alkynyl, $C_{3-10}$ cycloalkyl, $C_{6-10}$ aryl, $C_{2-9}$ heterocyclyl, or $C_{5-9}$ heteroaryl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl;

n is an integer from 1 to 20; and m is an integer from 1 to 20;

*Cu is a copper radionuclide selected from $^{61}Cu$, $^{62}Cu$, $^{64}Cu$, and $^{67}Cu$;

or is a pharmaceutically acceptable salt thereof,

In certain embodiments of a compound of Formula 30, $R^1$ is H. In certain embodiments of a compound of Formula 30, $R^1$ is selected from $C_{1-10}$ alkyl, $C_{2-10}$ alkenyl, $C_{3-10}$ alkynyl, $C_{3-10}$ cycloalkyl, $C_{6-10}$ aryl, $C_{2-9}$ heterocyclyl, or $C_{5-9}$ heteroaryl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl. In certain embodiments of a compound of Formula 30, $R^1$ is selected from H, $C_{1-10}$ alkyl, $C_{2-10}$ alkenyl, $C_{3-10}$ alkynyl, $C_{3-10}$ cycloalkyl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl.

In certain embodiments of a compound of Formula 30, $R^1$ is selected from H and $C_{1-10}$ alkyl. In certain embodiments of a compound of Formula 30, $R^1$ is H. In certain embodiments of a compound of Formula 30, $R^1$ is $C_{1-10}$ alkyl. In certain embodiments of a compound of Formula 30, $R^1$ is $C_1$-$C_6$ alkyl. In certain embodiments of a compound of Formula 30, R is selected from methyl, ethyl, propyl, isopropyl, butyl, isobutyl, pentyl and hexyl. In certain embodiments of a compound of Formula 30, $R^1$ is methyl.

In certain embodiments of a compound of Formula 30, $R^2$ is H. In certain embodiments of a compound of Formula 30, $R^2$ is selected from $C_{1-10}$ alkyl, $C_{2-10}$ alkenyl, $C_{3-10}$ alkynyl, $C_{3-10}$ cycloalkyl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl.

In certain embodiments of a compound of Formula 30, $R^3$ is H. In certain embodiments of a compound of Formula 30, $R^3$ is selected from $C_{1-10}$ alkyl, $C_{2-10}$ alkenyl, $C_{3-10}$ alkynyl, $C_{3-10}$ cycloalkyl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl.

In certain embodiments of a compound of Formula 30, $R^2$ and $R^3$ together form a $C_{2-9}$ heterocycle with the nitrogen atoms to which they are attached. In certain embodiments of a compound of Formula 30, the $C_{2-9}$ heterocycle is a 5-, 6-, or 7-membered heterocycle. In certain embodiments of a compound of Formula 30, the $C_{2-9}$ heterocycle is a 5-membered heterocycle selected from a pyrrolidine, pyrazolidine, and imidazoline. In certain embodiments of a compound of Formula 30, the $C_{2-9}$ heterocycle is a 6-membered heterocycle selected from a piperazine, hexahydropyrimidine, hexahydropyridazine, 1,2,3-triazinane, 1,2,4-triazinane, and 1,3,5-triazinane. In certain embodiments of a compound of Formula 30, the $C_{2-9}$ heterocycle is a piperazine.

In certain embodiments of a compound of Formula 30, n is an integer from 1 to 10. In certain embodiments of a compound of Formula 30, n is an integer from 1 to 5. In certain embodiments of a compound of Formula 30, n is 1, 2, 3, 4, or 5. In certain embodiments of a compound of Formula 30, n is 2.

In certain embodiments of a compound of Formula 30, m is an integer from 1 to 10. In certain embodiments of a compound of Formula 30, m is an integer from 1 to 5. In certain embodiments of a compound of Formula 30, m is 1, 2, 3, 4, or 5. In certain embodiments of a compound of Formula 30, m is 2.

In certain embodiments of a compound of Formula 30, *Cu is a copper radionuclide selected from $^{61}Cu$, $^{62}Cu$, $^{64}Cu$, and $^{67}Cu$. In certain embodiments of a compound of Formula 30, *Cu is $^{61}Cu$. In certain embodiments of a compound of Formula 30, *Cu is $^{62}Cu$. In certain embodiments of a compound of Formula 30, *Cu is $^{64}Cu$. In certain embodiments of a compound of Formula 30, *Cu is $^{62}Cu$. In certain embodiments of a compound of Formula 30, *Cu is $^{67}Cu$.

In certain embodiments of a compound of Formula 30, $R^1$ is selected from H and $C_{1-10}$ alkyl, $R^2$ is H, $R^3$ is H, n is an integer from 1 to 20, m is an integer from 1 to 20, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ is H, $R^3$ is H, n is an integer from 1 to 10, m is an integer from 1 to 10, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ is H, $R^3$ is H, n is an integer from 1 to 5, m is an integer from 1 to 5, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ is H, $R^3$ is H, n is 2, m is 2, and *Cu is a copper radionuclide selected from $^{61}Cu$ and $^{67}Cu$.

In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, n is an integer from 1 to 20, m is an integer from 1 to 20, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, n is an integer from 1 to 10, m is an integer from 1 to 10, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, n is an integer from 1 to 5, m is an integer from 1 to 5, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, n is 2, m is 2, and *Cu is a copper radionuclide selected from $^{61}Cu$ and $^{67}Cu$.

In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 5-, 6-, or 7-membered heterocycle, n is an integer from 1 to 20, m is an integer from 1 to 20, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 5-, 6-, or 7-membered heterocycle, n is an integer from 1 to 10, m is an integer from 1 to 10, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 5-, 6-, or 7-membered heterocycle, n is an integer from 1 to 5, m is an integer from 1 to 5, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 5-, 6-, or 7-membered heterocycle, n is 2, m is 2, and *Cu is a copper radionuclide selected from $^{61}Cu$ and $^{67}Cu$.

In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 6-membered heterocycle, n is an integer from 1 to 20, m is an integer from 1 to 20, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 6-membered heterocycle, n is an integer from 1 to 10, m is an integer from 1 to 10, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 6-membered heterocycle, n is an integer from 1 to 5, m is an integer from 1 to 5, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a 6-membered heterocycle, n is 2, m is 2, and *Cu is a copper radionuclide selected from $^{61}Cu$ and $^{67}Cu$.

In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a piperazine, m is an integer from 1 to 20, n is an integer from 1 to 20, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a piperazine, m is an integer from 1 to 10, n is an integer from 1 to 10, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a piperazine, m is an integer from 1 to 5, n is an integer from 1 to 5, and *Cu is a copper radionuclide selected from $^{61}Cu$ and $^{67}Cu$. In certain embodiments of a compound of Formula 30, $R^1$ is selected from H and $C_{1-10}$ alkyl, $R^2$ and $R^3$ together form a $C_{2-9}$ heterocycle with the nitrogen atoms to which they are attached, wherein the $C_{2-9}$ heterocycle is a piperazine, m is 2, n is 2, and *Cu is a copper radionuclide selected from $^{61}Cu$ and $^{67}Cu$.

In certain embodiments of a compound of Formula 30, $R^2$ and $R^3$ together form a piperazine with the nitrogen atoms to which they are attached and m is 2, thereby providing a compound of Formula 30a:

(Formula 30a)

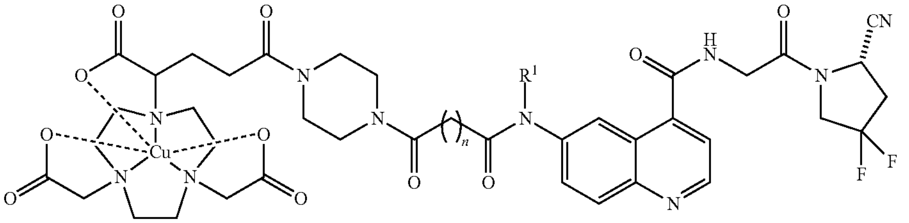

or a pharmaceutically acceptable salt thereof, wherein $R^1$, n, and *Cu are as described above for Formula 30.

In certain embodiments of a compound of Formula 30a, $R^1$ is H. In certain embodiments of a compound of Formula 30a, $R^1$ is selected from $C_{1-10}$ alkyl, $C_{2-10}$ alkenyl, $C_{3-10}$ alkynyl, $C_{3-10}$ cycloalkyl, $C_{6-10}$ aryl, $C_{2-9}$ heterocyclyl, or $C_{5-9}$ heteroaryl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl.

In certain embodiments of a compound of Formula 30a, $R^1$ is selected from H, $C_{1-10}$ alkyl, $C_{2-10}$ alkenyl, $C_{3-10}$ alkynyl, $C_{3-10}$ cycloalkyl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl.

In certain embodiments of a compound of Formula 30a, $R^1$ is selected from H and $C_{1-10}$ alkyl. In certain embodiments of a compound of Formula 30a, $R^1$ is H. In certain embodiments of a compound of Formula 30a, $R^1$ is $C_{1-10}$ alkyl. In certain embodiments of a compound of Formula 30a, $R^1$ is $C_1$-$C_6$ alkyl. In certain embodiments of a compound of Formula 30a, R is selected from methyl, ethyl, propyl, isopropyl, butyl, isobutyl, pentyl and hexyl. In certain embodiments of a compound of Formula 30a, $R^1$ is methyl.

In certain embodiments of a compound of Formula 30a, n is an integer from 1 to 10. In certain embodiments of a compound of Formula 30a, n is an integer from 1 to 5. In certain embodiments of a compound of Formula 30a, n is 1, 2, 3, 4, or 5. In certain embodiments of a compound of Formula 30a, n is 2.

In certain embodiments of a compound of Formula 30a, *Cu is a copper radionuclide selected from $^{61}Cu$, $^{62}Cu$, $^{64}Cu$, and $^{67}Cu$. In certain embodiments of a compound of Formula 30a, *Cu is $^{61}Cu$. In certain embodiments of a compound of Formula 30a, *Cu is $^{62}Cu$. In certain embodiments of a compound of Formula 30a, *Cu is $^{64}Cu$. In certain embodiments of a compound of Formula 30a, *Cu is $^{62}Cu$. In certain embodiments of a compound of Formula 30a, *Cu is $^{67}Cu$.

In certain embodiments of a compound of Formula 30a, $R^1$ is selected from H and $C_{1-10}$ alkyl, n is an integer from 1 to 20, and *Cu is a copper radionuclide selected from $^{61}Cu$ and $^{67}Cu$. In certain embodiments of a compound of Formula 30a, $R^1$ is selected from H and $C_{1-10}$ alkyl, n is an integer from 1 to 10, and *Cu is a copper radionuclide selected from $^{61}Cu$ and $^{67}Cu$. In certain embodiments of a compound of Formula 30a, $R^1$ is selected from H and $C_{1-10}$ alkyl, n is an integer from 1 to 5, and *Cu is a copper radionuclide selected from $^{61}Cu$ and $^{67}Cu$. In certain embodiments of a compound of Formula 30a, $R^1$ is selected from H and $C_{1-10}$ alkyl, n is 2, and *Cu is a copper radionuclide selected from $^{61}Cu$ and $^{67}Cu$.

In certain embodiments of a compound of Formula 30, $R^2$ and $R^3$ are H and m is 2, thereby providing a compound of Formula 30b:

(Formula 30b)

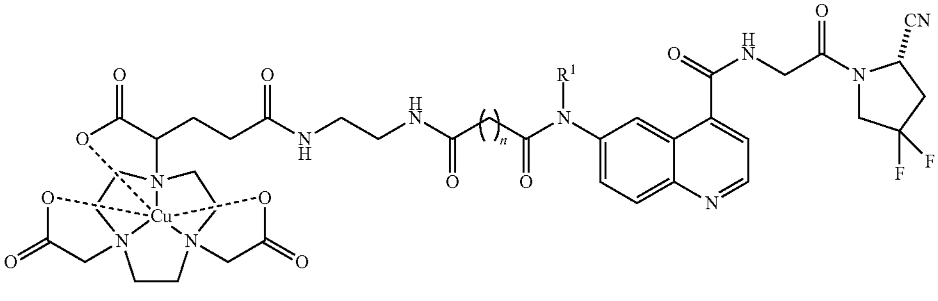

or a pharmaceutically acceptable salt thereof, wherein $R^1$, n, and *Cu are as described above for Formula 30.

In certain embodiments of a compound of Formula 30b, $R^1$ is H. In certain embodiments of a compound of Formula 30b, $R^1$ is selected from $C_{1-10}$ alkyl, $C_{2-10}$ alkenyl, $C_{3-10}$ alkynyl, $C_{3-10}$ cycloalkyl, $C_{6-10}$ aryl, $C_{2-9}$ heterocyclyl, or $C_{5-9}$ heteroaryl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl.

In certain embodiments of a compound of Formula 30b, $R^1$ is selected from H, $C_{1-10}$ alkyl, $C_{2-10}$ alkenyl, $C_{3-10}$ alkynyl, $C_{3-10}$ cycloalkyl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —$OP(O)(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl.

In certain embodiments of a compound of Formula 30b, $R^1$ is selected from H and $C_{1-10}$ alkyl. In certain embodiments of a compound of Formula 30b, $R^1$ is H. In certain embodiments of a compound of Formula 30b, $R^1$ is $C_{1-10}$ alkyl. In certain embodiments of a compound of Formula 30b, $R^1$ is $C_1$-$C_6$ alkyl. In certain embodiments of a compound of Formula 30b, R is selected from methyl, ethyl, propyl, isopropyl, butyl, isobutyl, pentyl and hexyl. In certain embodiments of a compound of Formula 30b, $R^1$ is methyl.

In certain embodiments of a compound of Formula 30b, n is an integer from 1 to 10. In certain embodiments, n is an integer from 1 to 5. In certain embodiments, n is 1, 2, 3, 4, or 5. In certain embodiments, n is 2.

In certain embodiments of a compound of Formula 30b, *Cu is a copper radionuclide selected from $^{61}Cu$, $^{62}Cu$, $^{64}Cu$, and $^{67}Cu$. In certain embodiments of a compound of Formula 30b, *Cu is $^{61}Cu$. In certain embodiments of a compound of Formula 30b, *Cu is $^{62}Cu$. In certain embodiments of a compound of Formula 30b, *Cu is $^{64}Cu$. In certain embodiments of a compound of Formula 30b, *Cu is $^{62}Cu$. In certain embodiments of a compound of Formula 30b, *Cu is $^{67}Cu$.

In certain embodiments of a compound of Formula 30b, $R^1$ is selected from H and $C_{1-10}$ alkyl, n is an integer from 1 to 20, and *Cu is a copper radionuclide selected from $^{61}Cu$ and $^{67}Cu$. In certain embodiments of a compound of Formula 30b, $R^1$ is selected from H and $C_{1-10}$ alkyl, n is an integer from 1 to 10, and *Cu is a copper radionuclide selected from $^{61}Cu$ and $^{67}Cu$. In certain embodiments of a compound of Formula 30b, $R^1$ is selected from H and $C_{1-10}$ alkyl, n is an integer from 1 to 5, and *Cu is a copper radionuclide selected from $^{61}Cu$ and $^{67}Cu$. In certain embodiments of a compound of Formula 30b, $R^1$ is selected from H and $C_{1-10}$ alkyl, n is 2, and *Cu is a copper radionuclide selected from $^{61}Cu$ and $^{67}Cu$.

In certain embodiments of a compound of Formula X, X*, A, and A*, the targeting moiety comprises (S)-6-amino-N-(2-(2-cyano-4,4-difluoropyrrolidin-1-yl)-2-oxoethyl)quinoline-4-carboxamide). In certain embodiments, the targeting moiety and linker moiety are according to F1, F2, F3, F4 depicted in the table below where  denotes a point of attachment to a chelating moiety.

| derived from | targeting moiety |
|---|---|
| F1 | 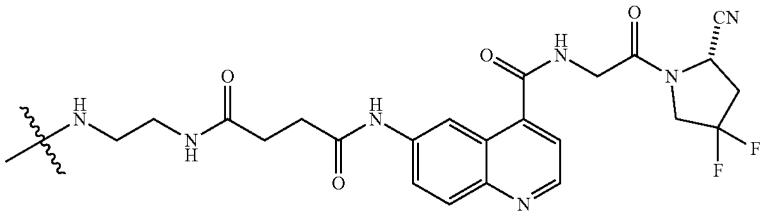 [SMILES: *NCCNC(=O)CCC(=O)Nc1ccc2nccc(C(=O)NCC(=O)N3CC(F)(F)C[C@H]3C#N)c2c1] |
| F2 | 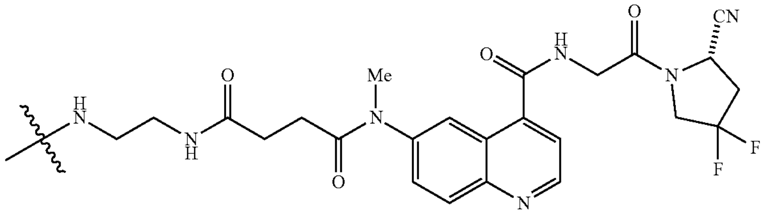 [SMILES: *NCCNC(=O)CCC(=O)N(C)c1ccc2nccc(C(=O)NCC(=O)N3CC(F)(F)C[C@H]3C#N)c2c1] |

-continued

| derived from | targeting moiety |
|---|---|
| F3 | 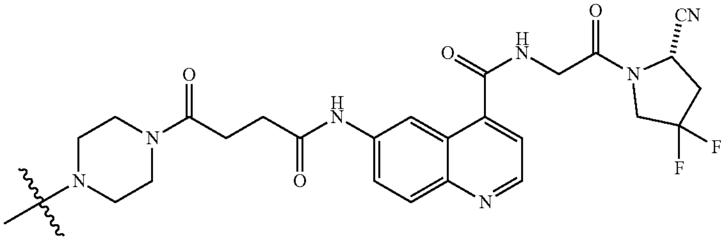 [SMILES: *N1CCN(C(=O)CCC(=O)Nc2ccc3nccc(C(=O)NCC(=O)N4CC(F)(F)C[C@H]4C#N)c3c2)CC1] |
| F4 | 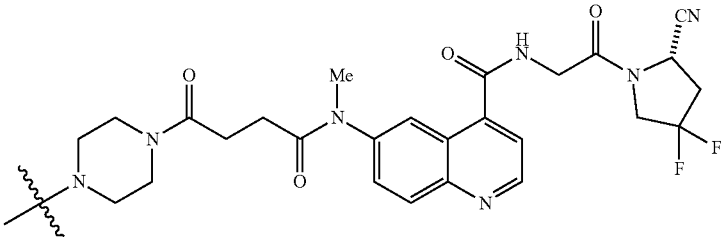 [SMILES: *N1CCN(C(=O)CCC(=O)N(C)c2ccc3nccc(C(=O)NCC(=O)N4CC(F)(F)C[C@H]4C#N)c3c2)CC1] |

4.2.4.2 Exemplified Compounds

In certain embodiments of a compound of Formula X, and A, the compound is one of Structures 1-19 or is a pharmaceutically acceptable salt thereof. In certain embodiments Cu* is in a II oxidation state and selected from $^{61}Cu$, $^{62}Cu$, $^{64}Cu$, and $^{67}Cu$. In certain embodiments, Cu* is $^{61}Cu$. In certain embodiments, Cu* is $^{67}Cu$.

Structure 1

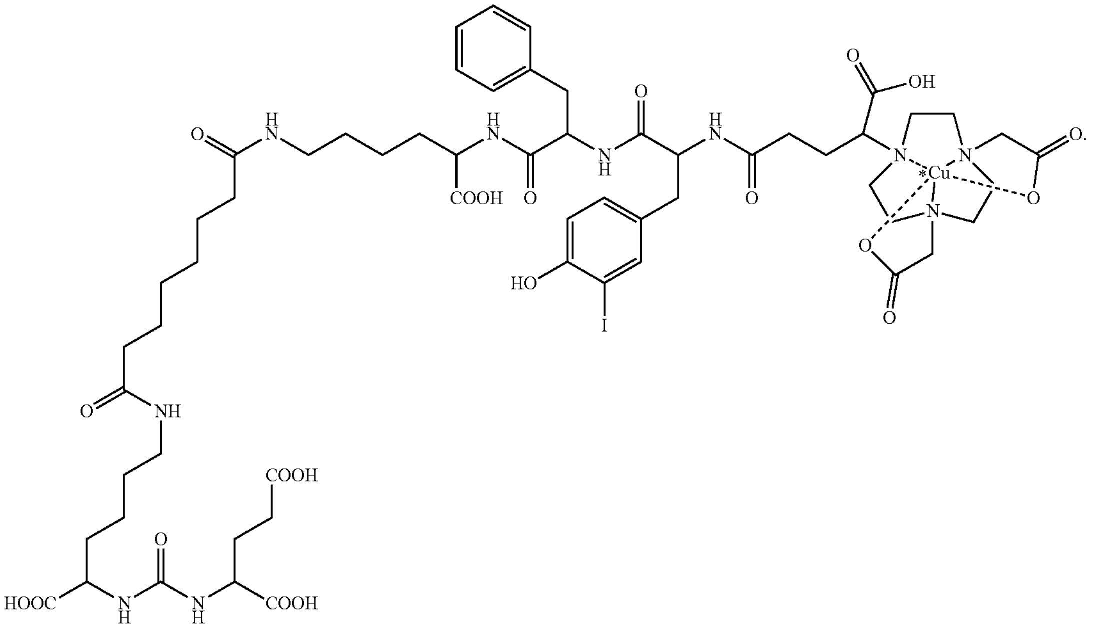

*Cu-NODAGA-PSMA-I&T

-continued
Structure 2
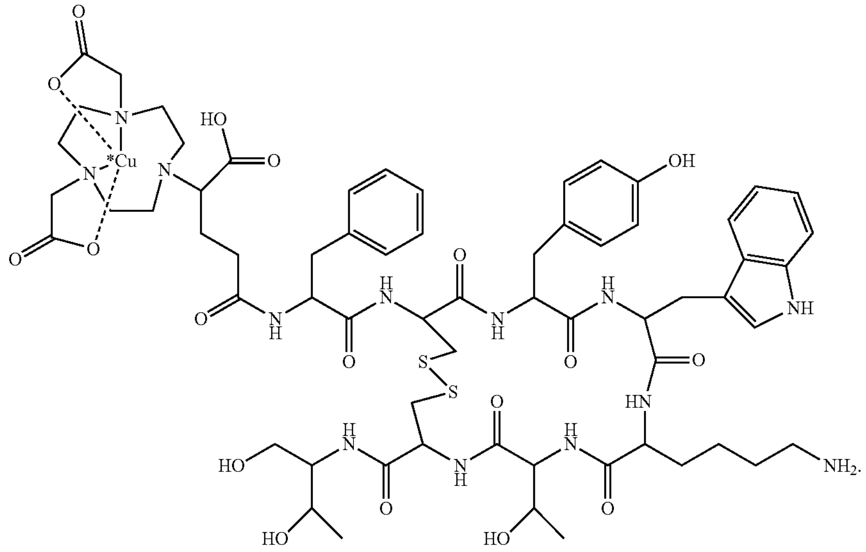
*Cu-NODAGA-TOC
Structure 3
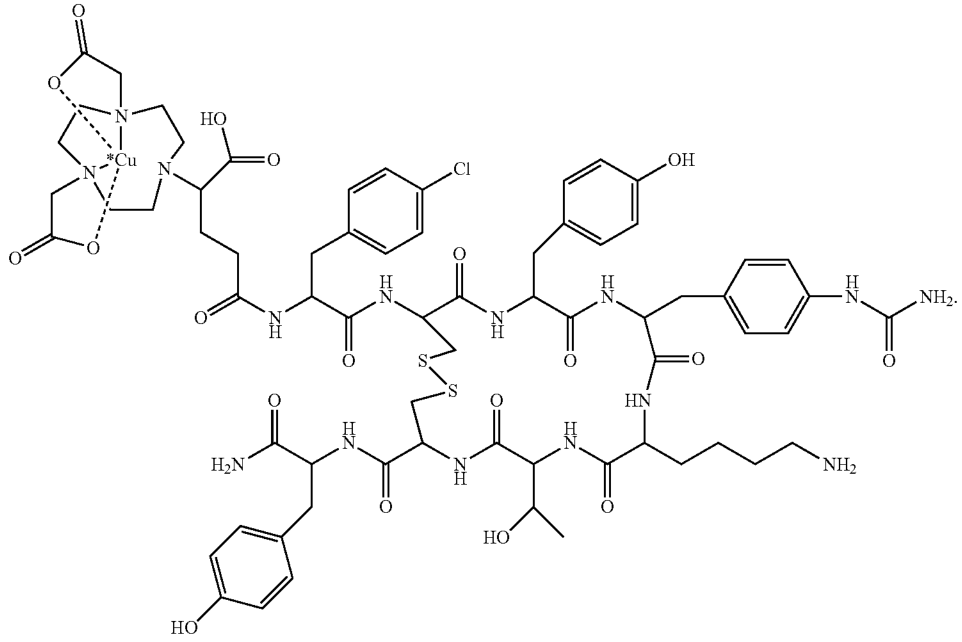
*Cu-NODAGA-LM3

-continued
Structure 4
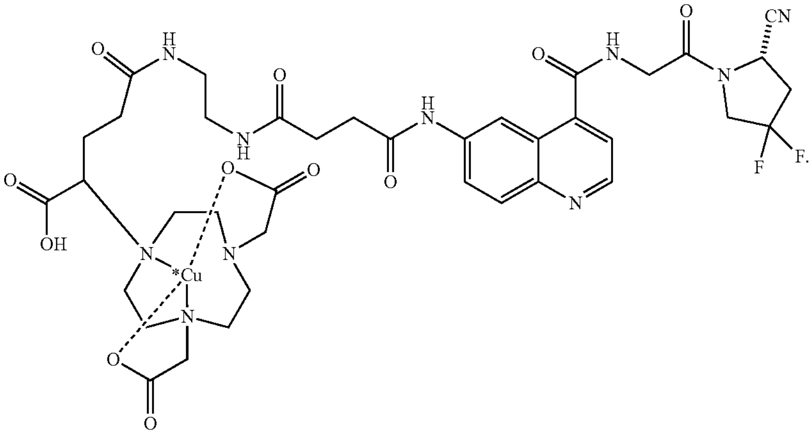
*Cu-NODAGA-F1
Structure 5
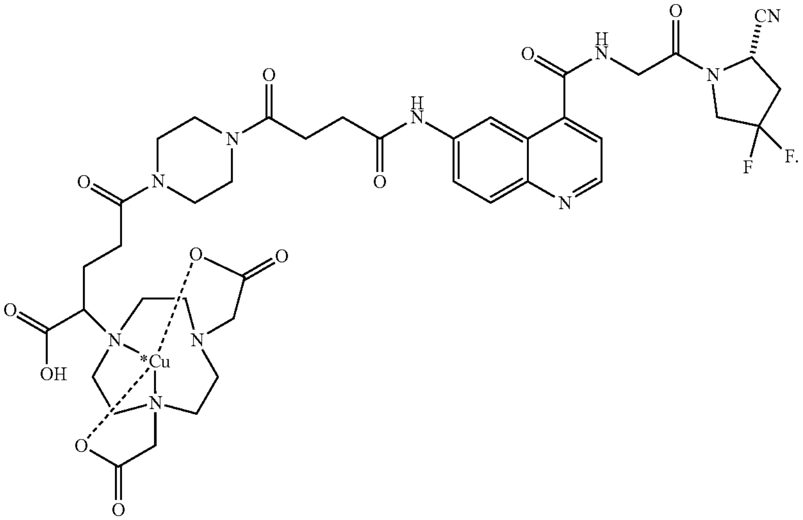
*Cu-NODAGA-F3
Structure 6
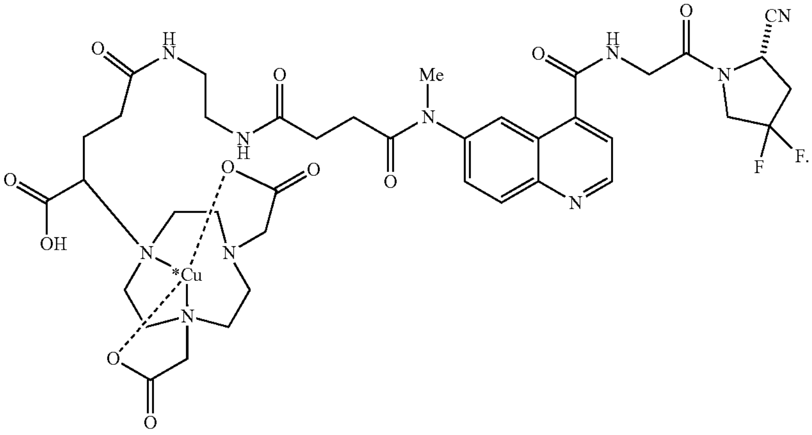
*Cu-NODAGA-F2

-continued
Structure 7
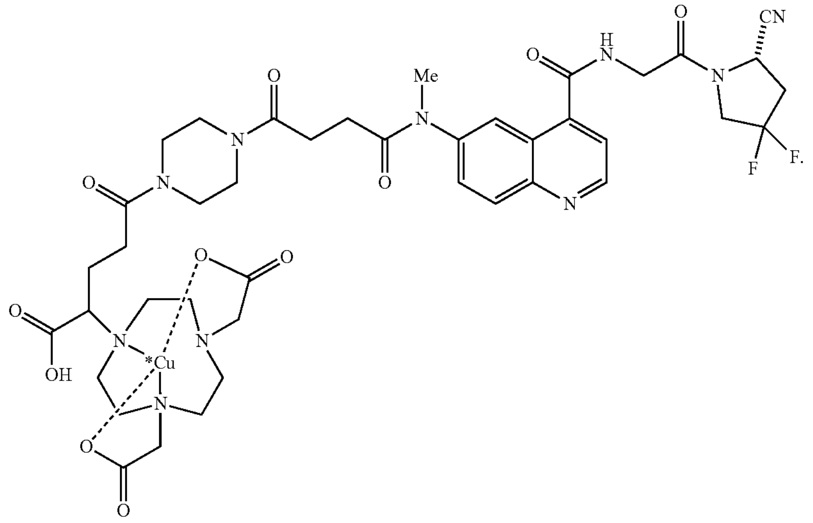
*Cu-NODAGA-F4
Structure 8
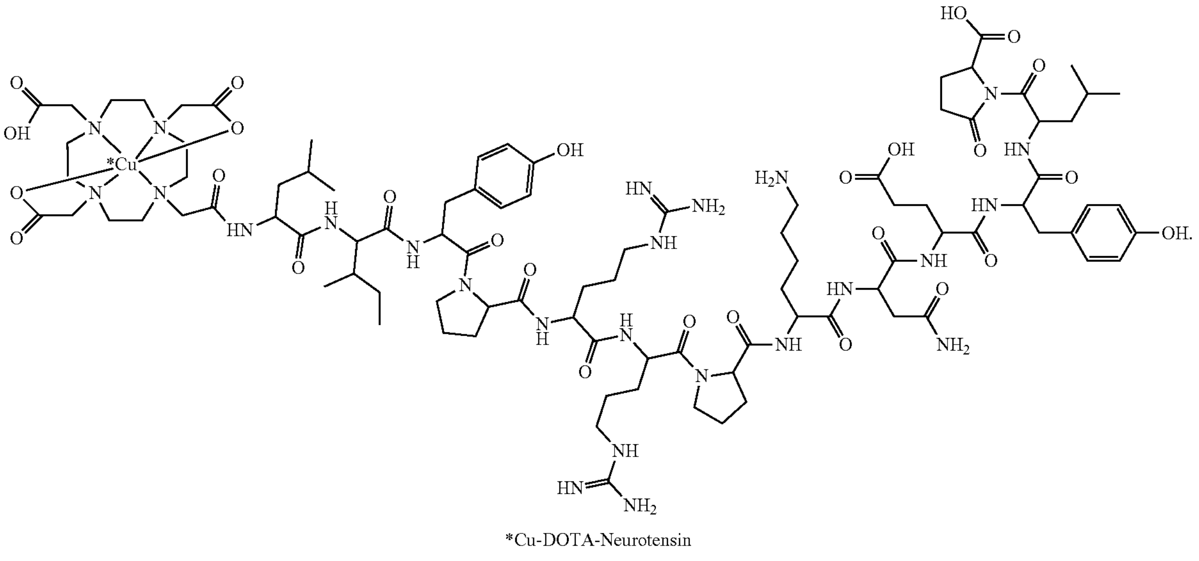
*Cu-DOTA-Neurotensin -continued
Structure 9
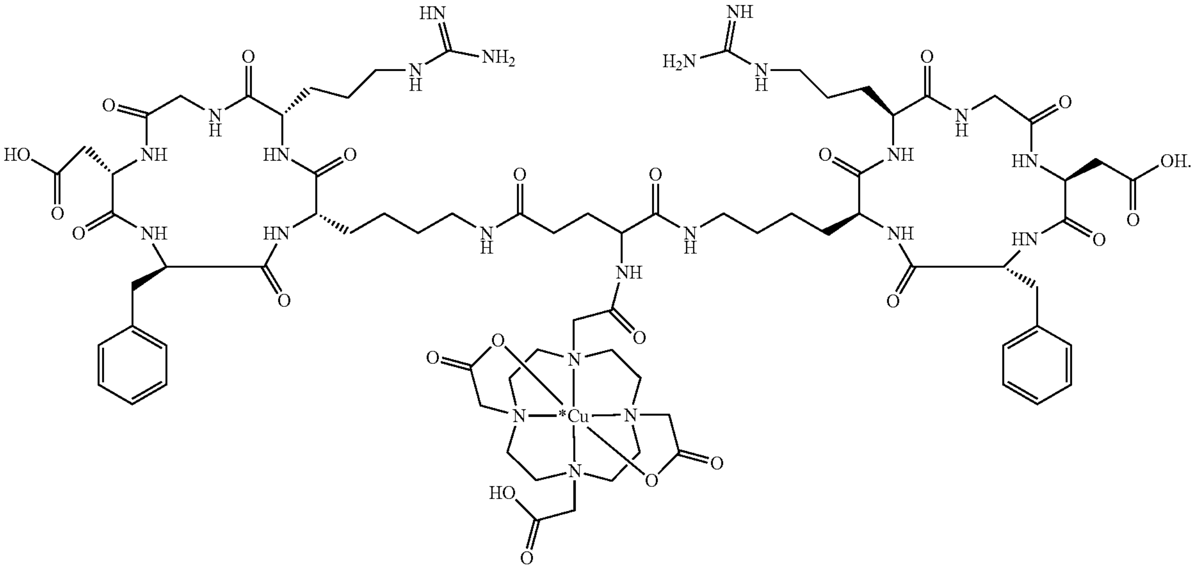
*Cu-DOTA-E-[c(RGDfK)]$_2$
Structure 10
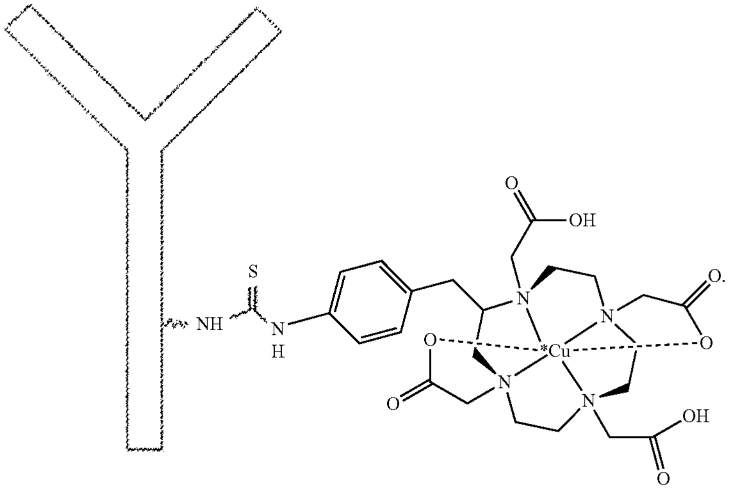
*Cu-DOTAGA-HER2
Structure 11
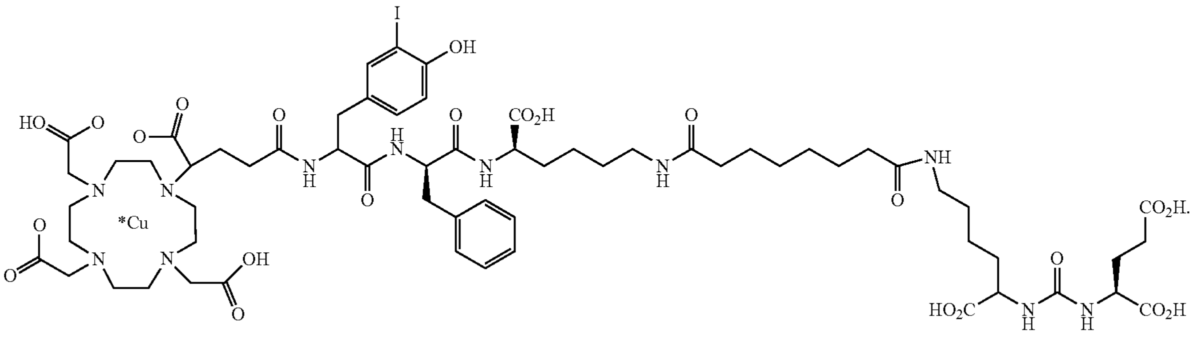
*Cu-DOTAGA-PSMA-I&T In certain embodiments, the composition for use in medical imaging and/or therapy comprises a targeted chelator construct known in the art to be useful in chelating certain radionuclides, e.g., $^{64}Cu$, $^{68}Ga$, or $^{177}Lu$, for use in medical imaging or therapy.

Such targeted chelator constructs include compounds of Structures 8-14, shown below.

Structure 12

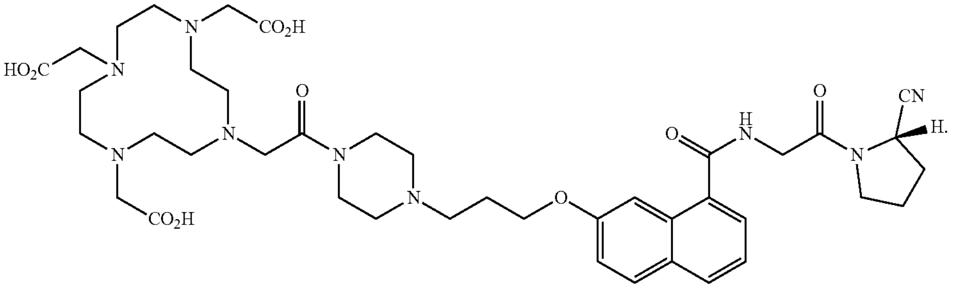

DOTA-FABI-02

Structure 13

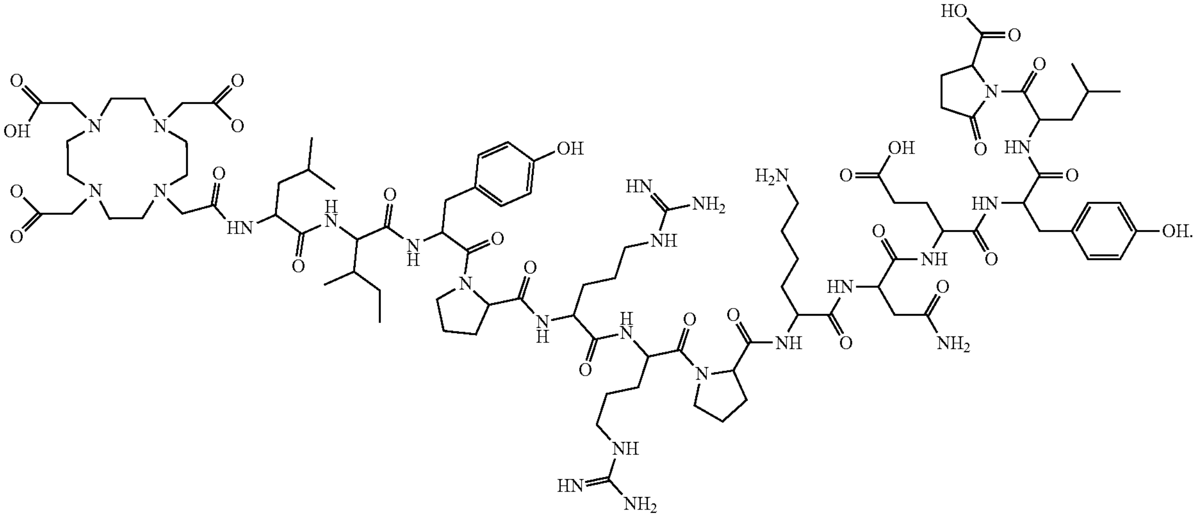

DOTA-NT

Structure 14

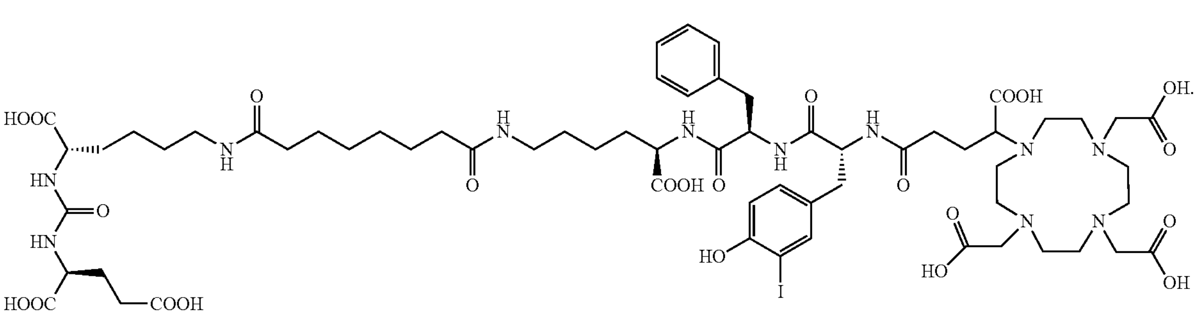

DOTAGA-PSMA-I&T

-continued
Structure 15
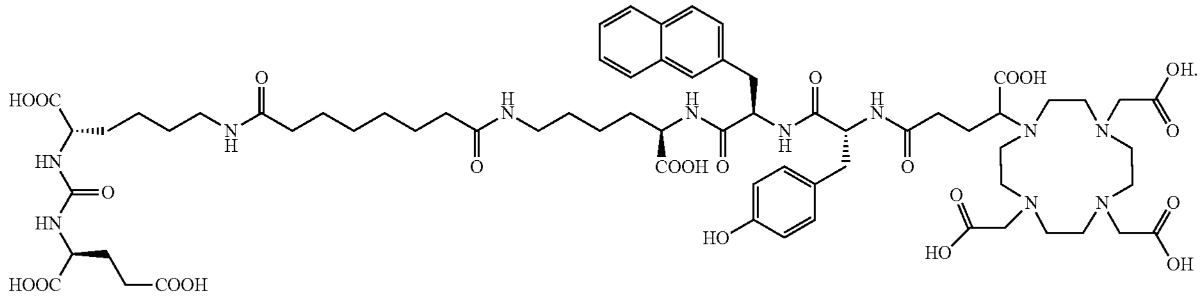
DOTAGA-PSMA 10
Structure 16
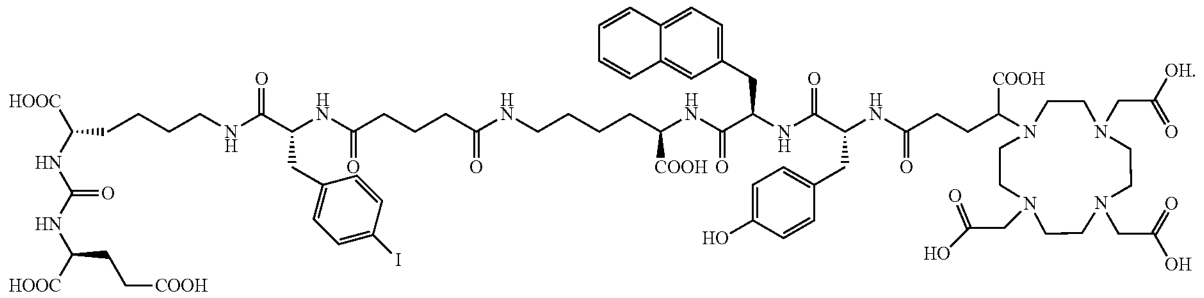
DOTAGA-PSMA 11
Structure 17
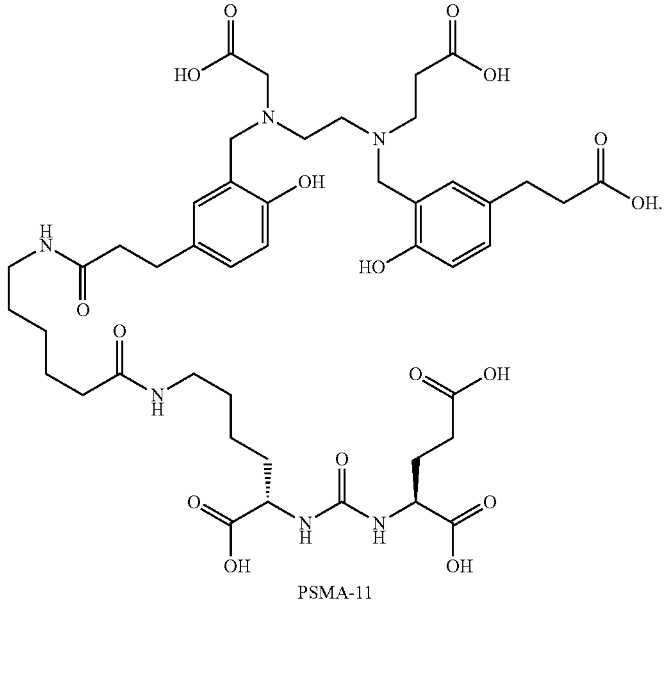
PSMA-11

-continued

Structure 18

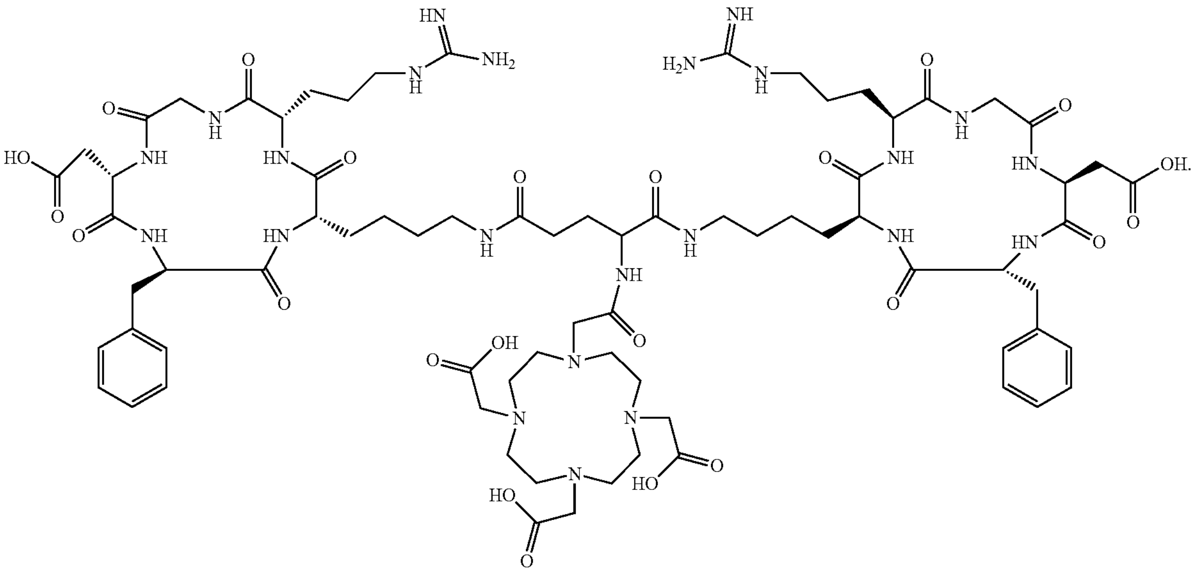

DOTA-E-[c(RDKfD)]2

Structure 19

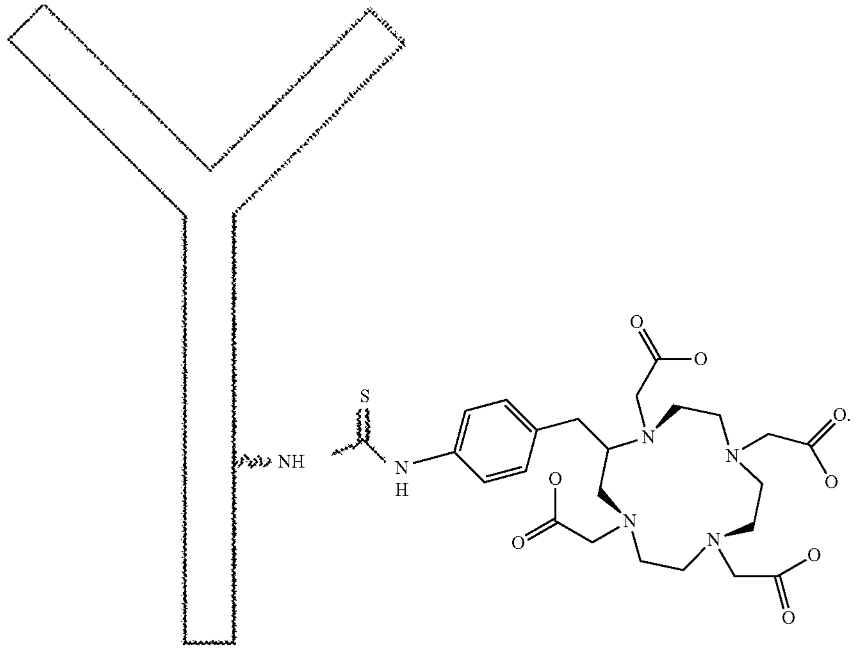

DOTA-HER2

In certain embodiments of the compound of Formula X and A, the compounds is selected from Structures 1-19 above, or is a pharmaceutically acceptable salt thereof, wherein the chelating moiety is replaced by any chelating moiety known to chelate Ga, Lu, or Cu, or chelating moieties exemplified in the Section entitled Chelating Moieties, herein.

In certain embodiments of the compound of Formula X and A, the compounds is selected from one of Structures 15-24, shown below, or is a pharmaceutically acceptable salt thereof.

| Structure # | Name | Targeted chelator construct |
|---|---|---|
| 15 | DOTAGA-PSMA-I&T | 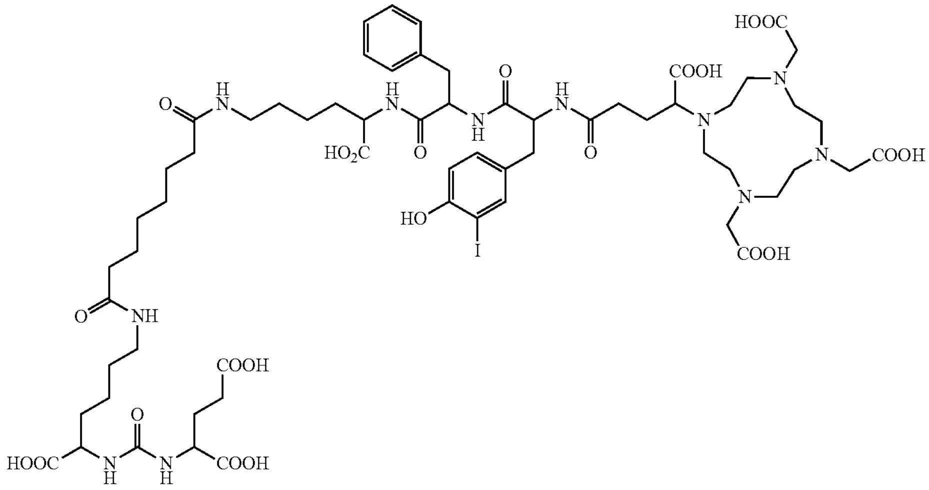 [SMILES: O=C(O)CCC(NC(=O)NC(CCCCNC(=O)CCCCCCC(=O)NCCCCC(NC(=O)C(Cc1ccccc1)NC(=O)C(Cc1ccc(O)c(I)c1)NC(=O)CCC(C(=O)O)N1CCN(CC(=O)O)CCN(CC(=O)O)CCN(CC(=O)O)CC1)C(=O)O)C(=O)O)C(=O)O] |
| 16 | NODAGA-PSMA-I&T | 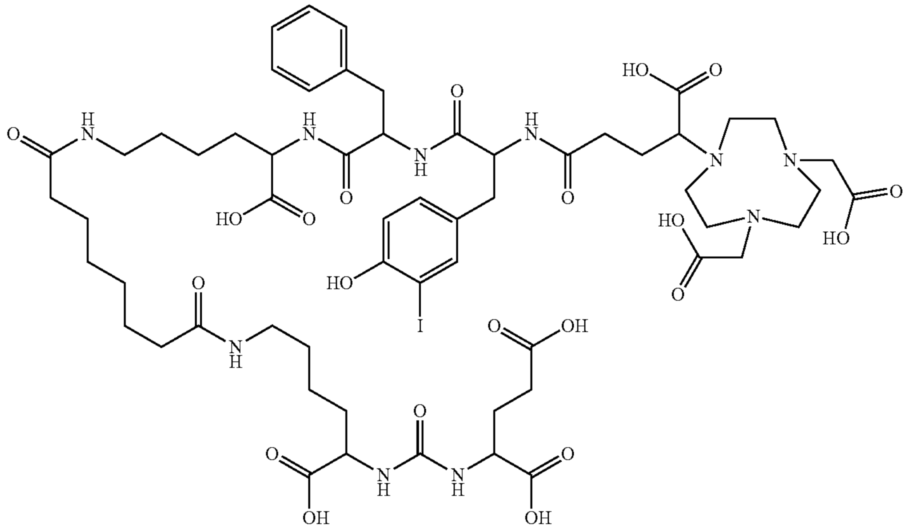 [SMILES: O=C(O)CCC(NC(=O)NC(CCCCNC(=O)CCCCCCC(=O)NCCCCC(NC(=O)C(Cc1ccccc1)NC(=O)C(Cc1ccc(O)c(I)c1)NC(=O)CCC(C(=O)O)N1CCN(CC(=O)O)CCN(CC(=O)O)CC1)C(=O)O)C(=O)O)C(=O)O] |
| 17 | DOTA-TOC | 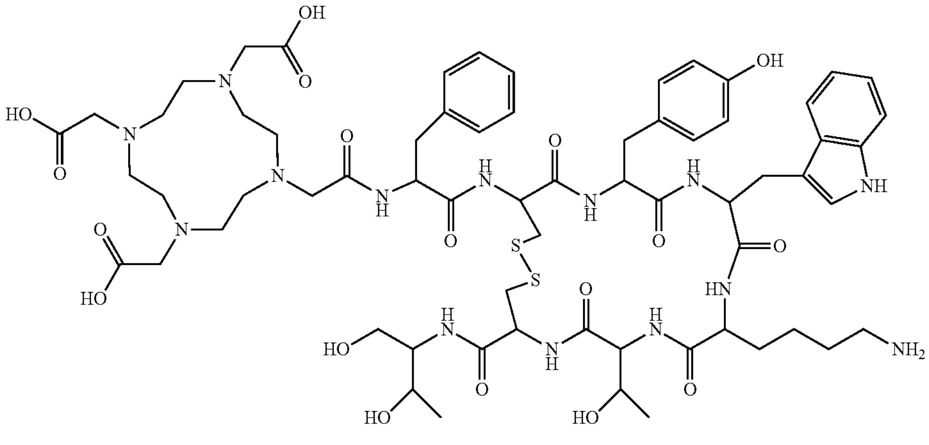 [SMILES: CC(O)C(CO)NC(=O)C1CSSCC(NC(=O)C(Cc2ccccc2)NC(=O)CN2CCN(CC(=O)O)CCN(CC(=O)O)CCN(CC(=O)O)CC2)C(=O)NC(Cc2ccc(O)cc2)C(=O)NC(Cc2c[nH]c3ccccc23)C(=O)NC(CCCCN)C(=O)NC(C(C)O)C(=O)N1] |

-continued
| Structure # | Name | Targeted chelator construct |
|---|---|---|
| 18 | NODAGA-TOC | 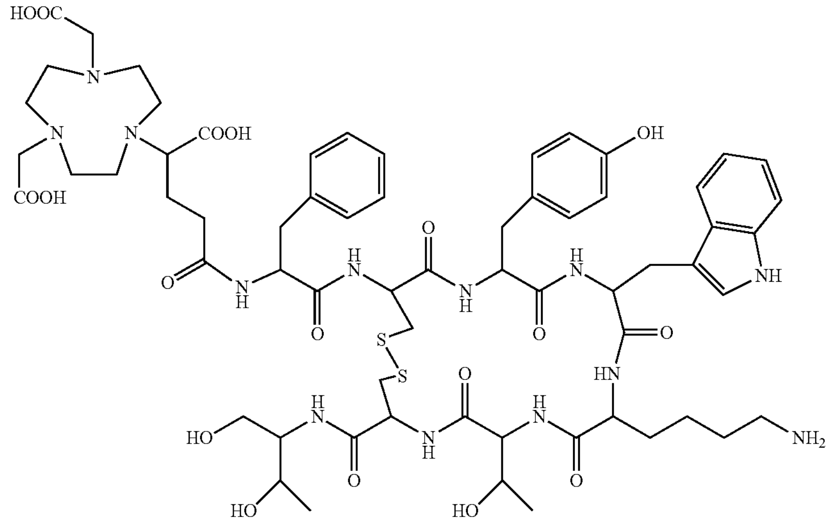 [SMILES: CC(O)C(CO)NC(=O)C1CSSCC(NC(=O)C(Cc2ccccc2)NC(=O)CCC(C(=O)O)N2CCN(CC(=O)O)CCN(CC(=O)O)CC2)C(=O)NC(Cc2ccc(O)cc2)C(=O)NC(Cc2c[nH]c3ccccc23)C(=O)NC(CCCCN)C(=O)NC(C(C)O)C(=O)N1] |
| 19 | NODAGA-LM3 | 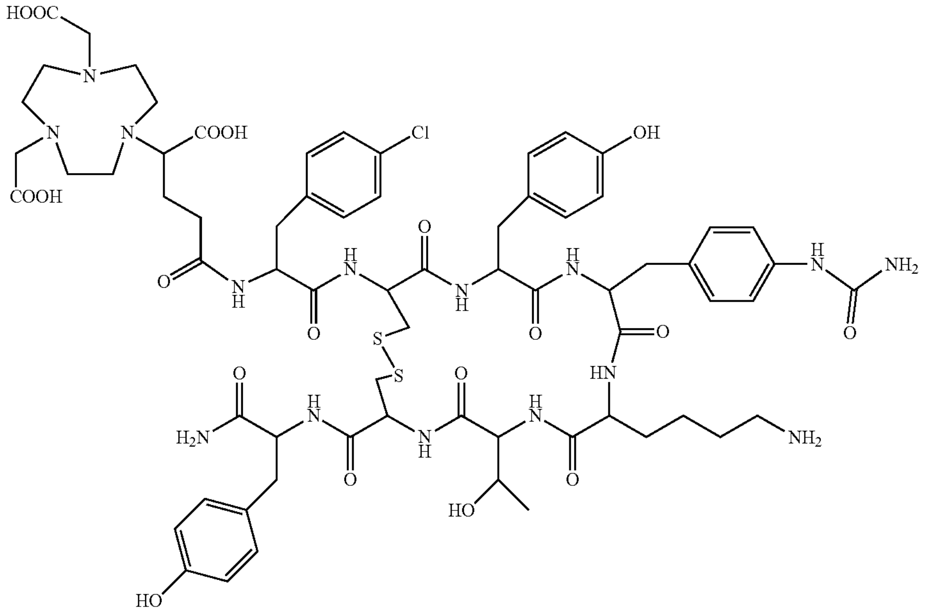 [SMILES: CC(O)C1NC(=O)C(CCCCN)NC(=O)C(Cc2ccc(NC(N)=O)cc2)NC(=O)C(Cc2ccc(O)cc2)NC(=O)C(NC(=O)C(Cc2ccc(Cl)cc2)NC(=O)CCC(C(=O)O)N2CCN(CC(=O)O)CCN(CC(=O)O)CC2)CSSCC(C(=O)NC(Cc2ccc(O)cc2)C(N)=O)NC1=O] |
| 20 | NODAGA-F1 | 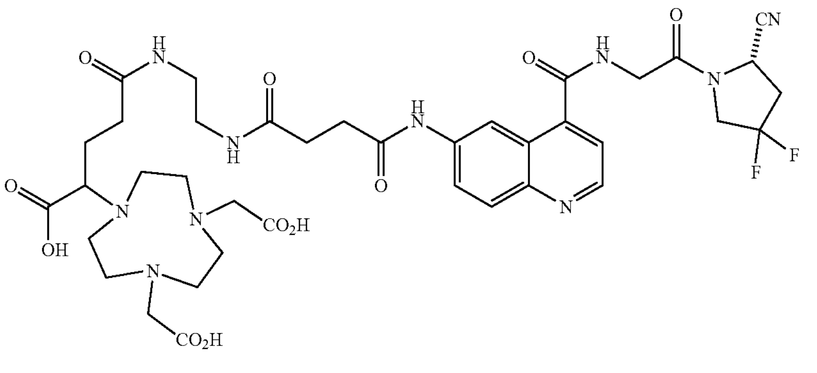 [SMILES: N#C[C@@H]1CC(F)(F)CN1C(=O)CNC(=O)c1ccnc2ccc(NC(=O)CCC(=O)NCCNC(=O)CCC(C(=O)O)N3CCN(CC(=O)O)CCN(CC(=O)O)CC3)cc12] |

-continued
| Structure # | Name | Targeted chelator construct |
|---|---|---|
| 21 | NODAGA-F2 | 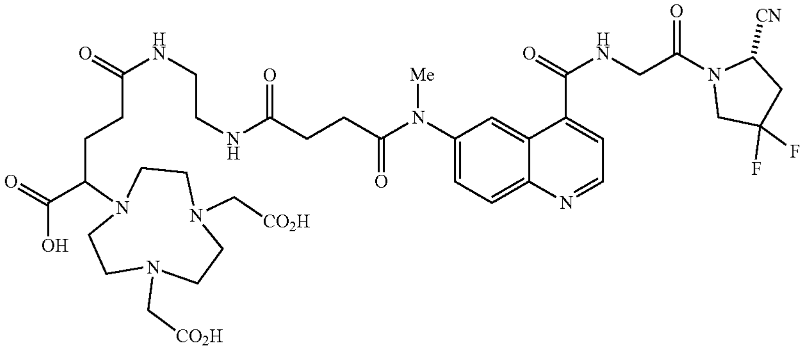 [SMILES: CN(C(=O)CCC(=O)NCCNC(=O)CCC(C(=O)O)N1CCN(CC(=O)O)CCN(CC(=O)O)CC1)c1ccc2nccc(C(=O)NCC(=O)N3CC(F)(F)C[C@H]3C#N)c2c1] |
| 22 | NODAGA-F3 | 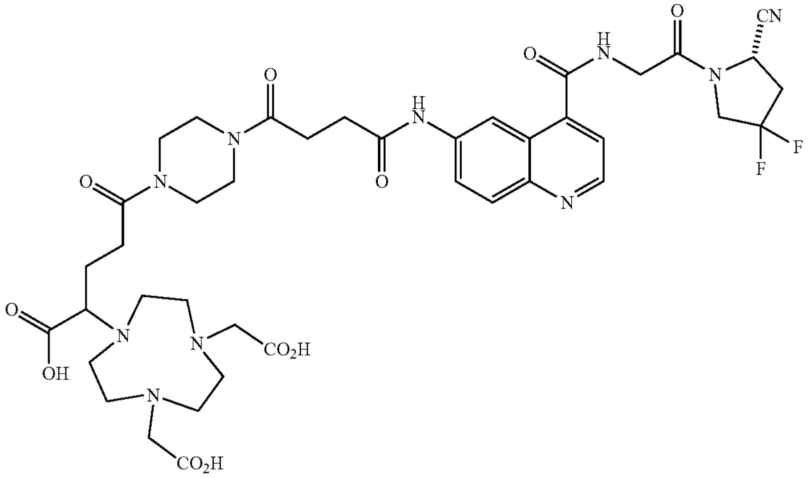 [SMILES: N#C[C@@H]1CC(F)(F)CN1C(=O)CNC(=O)c1ccnc2ccc(NC(=O)CCC(=O)N3CCN(C(=O)CCC(C(=O)O)N4CCN(CC(=O)O)CCN(CC(=O)O)CC4)CC3)cc12] |

-continued

| Structure # | Name | Targeted chelator construct |
|---|---|---|
| 23 | NODAGA-F4 | 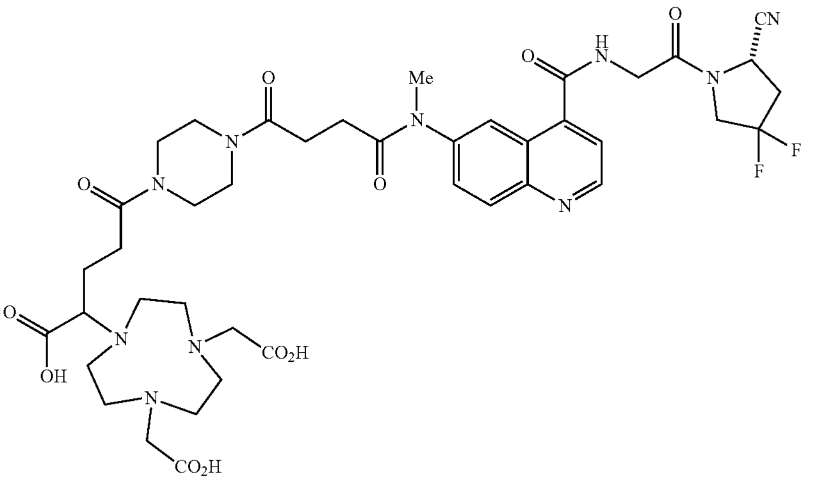 [SMILES: CN(C(=O)CCC(=O)N1CCN(C(=O)CCC(C(=O)O)N2CCN(CC(=O)O)CCN(CC(=O)O)CC2)CC1)c1ccc2nccc(C(=O)NCC(=O)N3CC(F)(F)C[C@H]3C#N)c2c1] |
| 24 | NODAGA-FAP-46 | 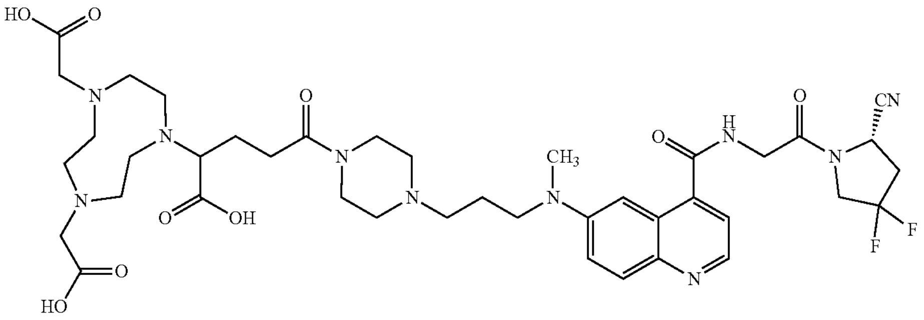 [SMILES: CN(CCCN1CCN(C(=O)CCC(C(=O)O)N2CCN(CC(=O)O)CCN(CC(=O)O)CC2)CC1)c1ccc2nccc(C(=O)NCC(=O)N3CC(F)(F)C[C@H]3C#N)c2c1] |

In certain embodiments of the compound of Formula X* and A*, the compounds is selected from one of Structures 25-34, shown below, or is a pharmaceutically acceptable salt thereof.

In certain embodiments, a diagnostic radiotracer is selected from compounds 25-34.

| Cmpd. No. | Name | Structure |
|---|---|---|
| 25 | [61]Cu]Cu-NODAGA-PSMA-I&T | 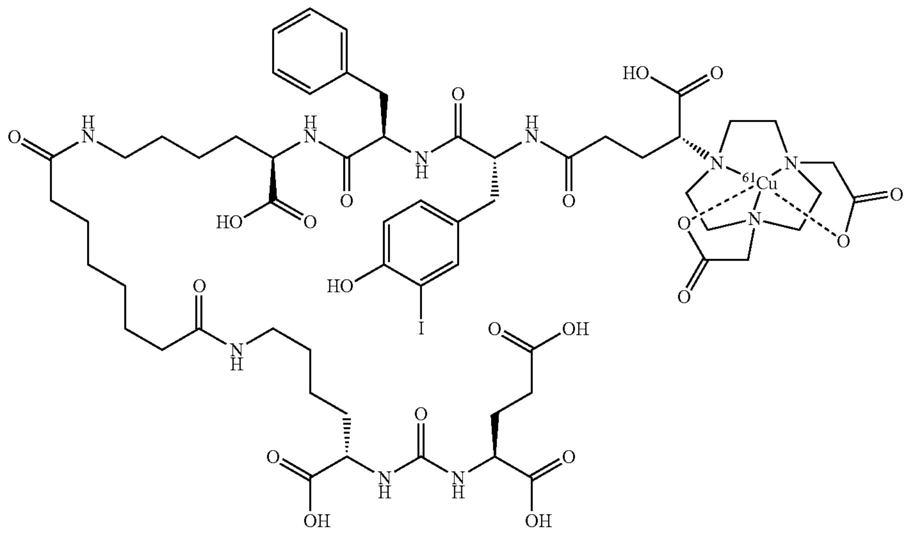 |

-continued
| Cmpd. No. | Name | Structure |
| --- | --- | --- |
| 26 | [$^{61}$Cu]Cu-NODAGA-TOC | 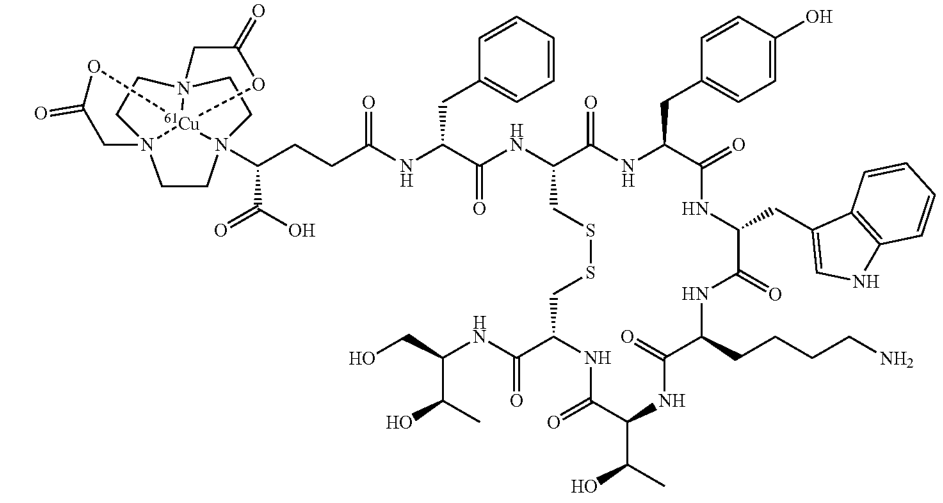 |
| 27 | [$^{61}$Cu]Cu-NODAGA-LM3 | 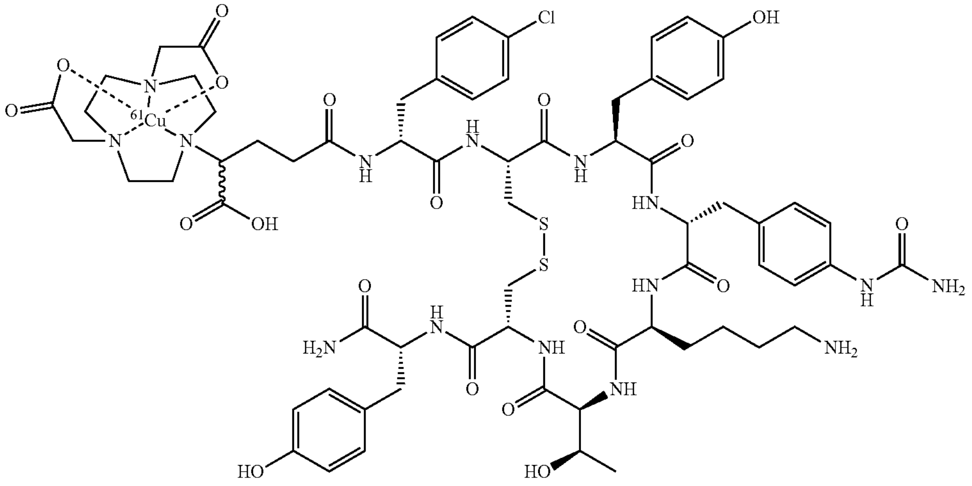 |
| 28 | [$^{61}$Cu]Cu-(R)-NODAGA-LM3 | 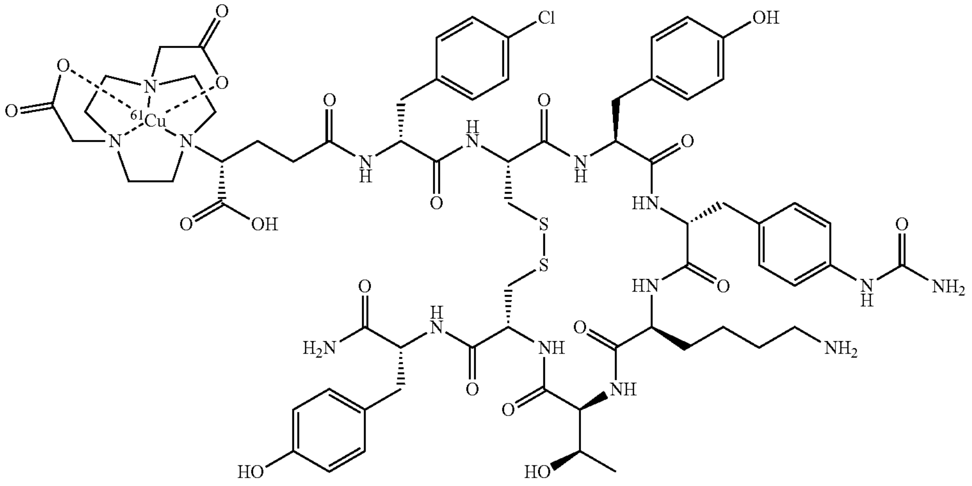 |

-continued
| Cmpd. No. | Name | Structure |
|---|---|---|
| 29 | [61]Cu]Cu-NODAGA-F1 | 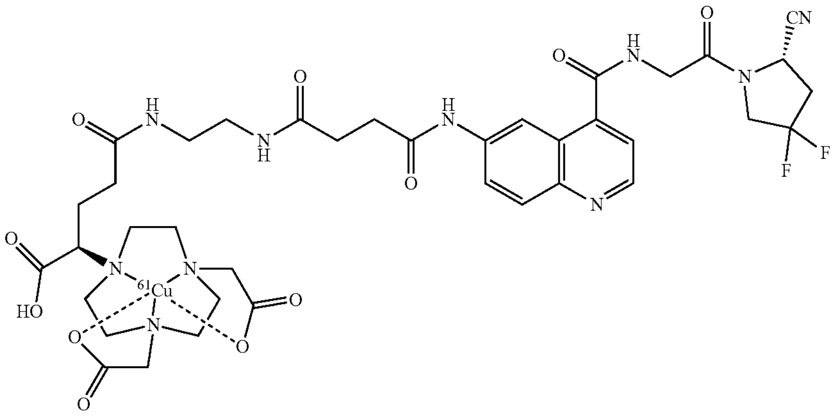 |
| 30 | [61]Cu]Cu-NODAGA-F2 | 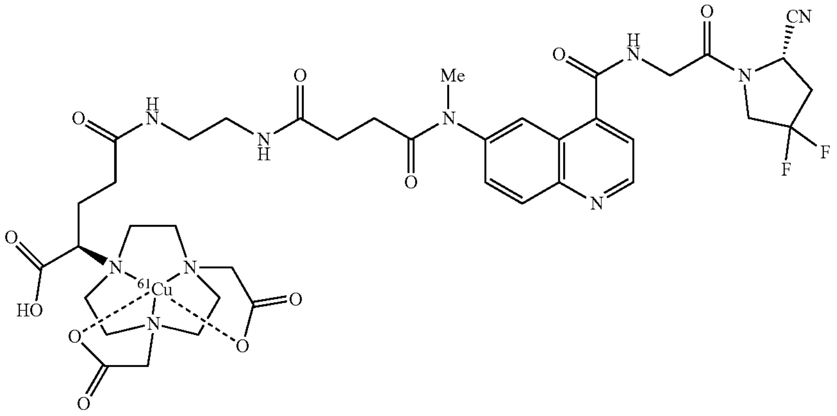 |
| 32 | [61]Cu]Cu-NODAGA-F3 | 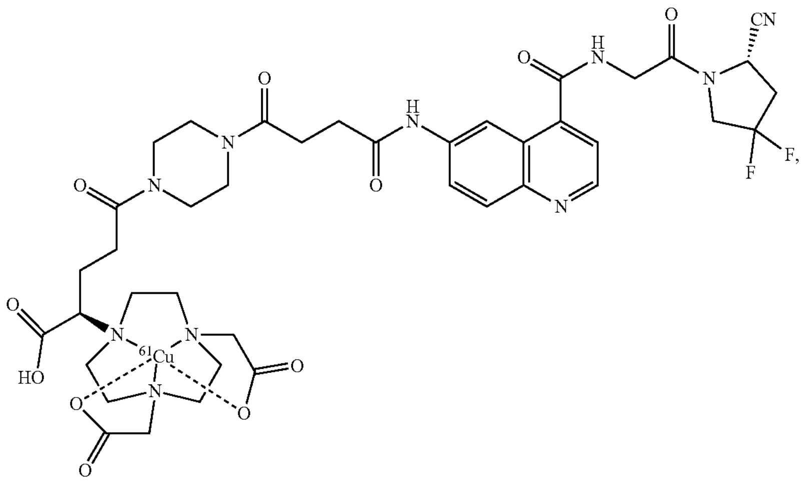 |

-continued
| Cmpd. No. | Name | Structure |
|---|---|---|
| 33 | [61Cu]Cu-NODAGA-F4 | 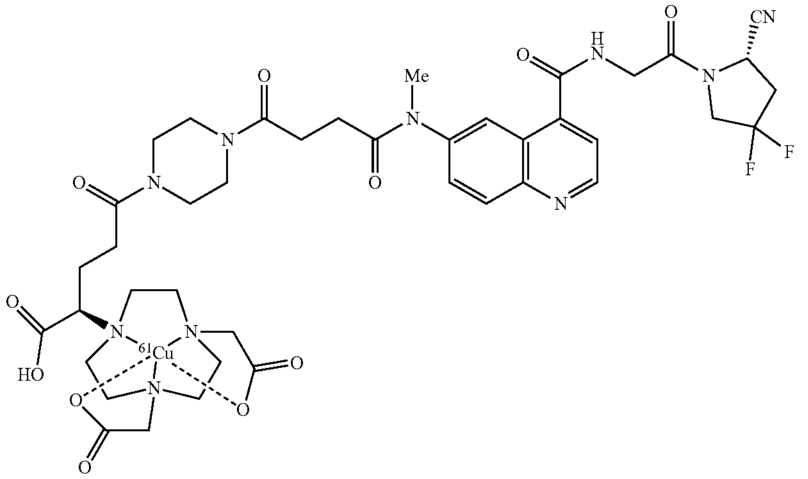 and |
| 34 | [61Cu]Cu-NODAGA-FAPI-46 | 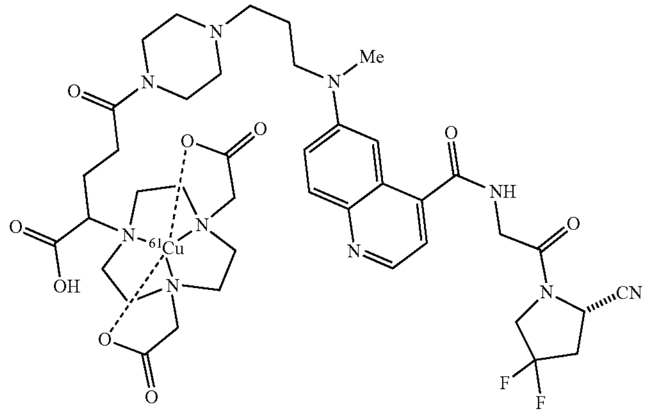 |
In certain embodiments of the compound of Formula X* and A*, the compounds is selected from one of Structures 35-43, shown below, or is a pharmaceutically acceptable salt thereof. In certain embodiments, the compound is a therapeutic radiotracer.

| Cmpd. No. | Name | Structure |
|---|---|---|
| 35 | [67]Cu]Cu-NODAGA-PSMA-I&T | 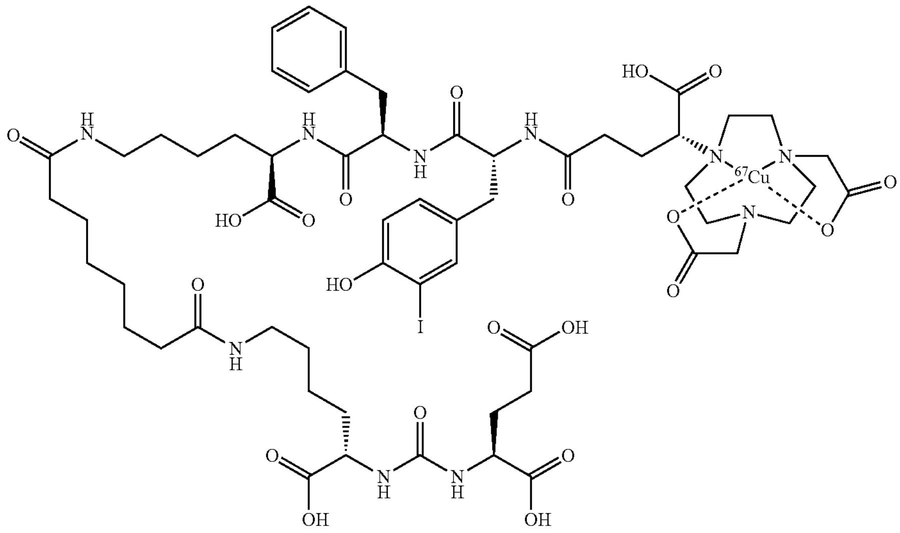 |
| 36 | [67]Cu]Cu-NODAGA-TOC | 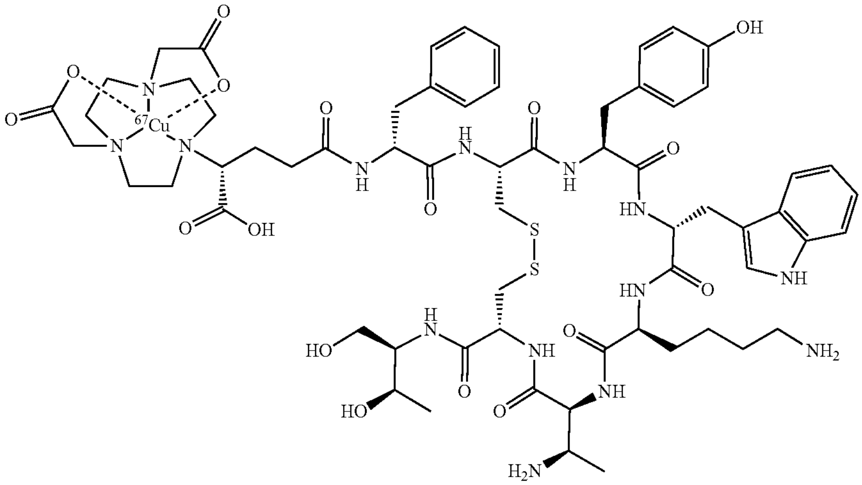 |
| 37 | [67]Cu]Cu-NODAGA-LM3 | 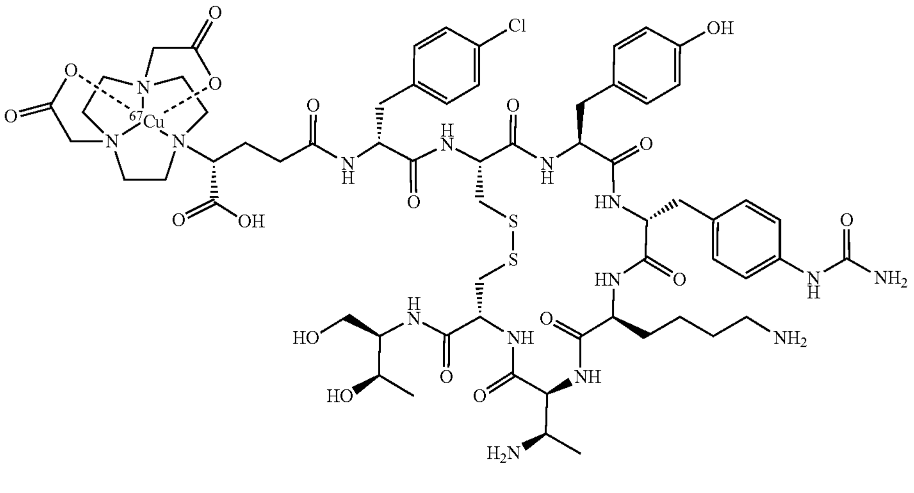 |

-continued
| Cmpd. No. | Name | Structure |
|---|---|---|
| 38 | [67Cu]Cu-(R)NODAGA-LM3 | 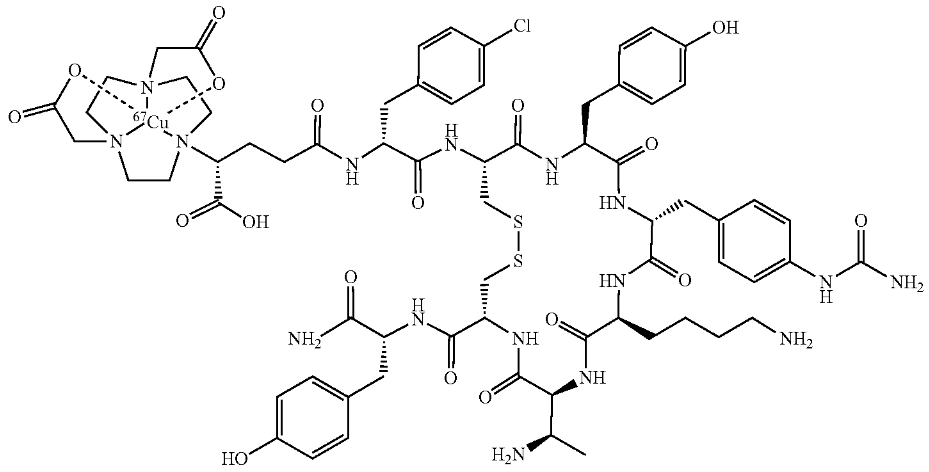 |
| 39 | [67Cu]Cu-NODAGA-F1 | 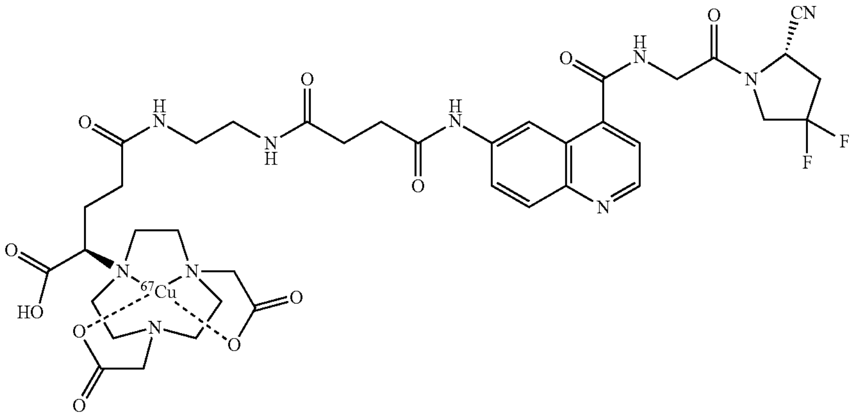 |
| 40 | [67Cu]Cu-NODAGA-F2 | 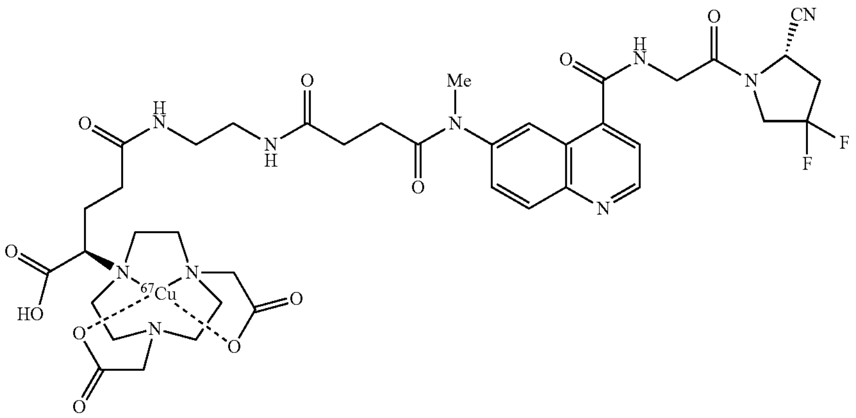 |

-continued

| Cmpd. No. | Name | Structure |
|---|---|---|
| 41 | [67Cu]Cu-NODAGA-F3 | 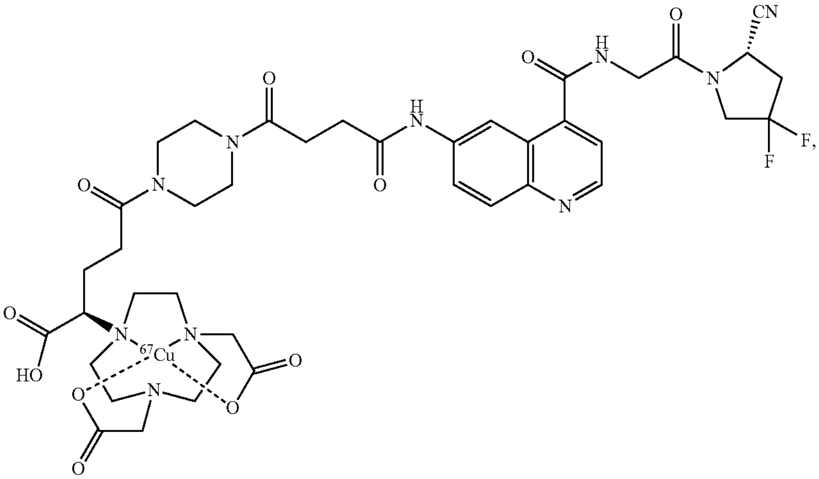 , and |
| 42 | [67Cu]Cu-NODAGA-F4 | 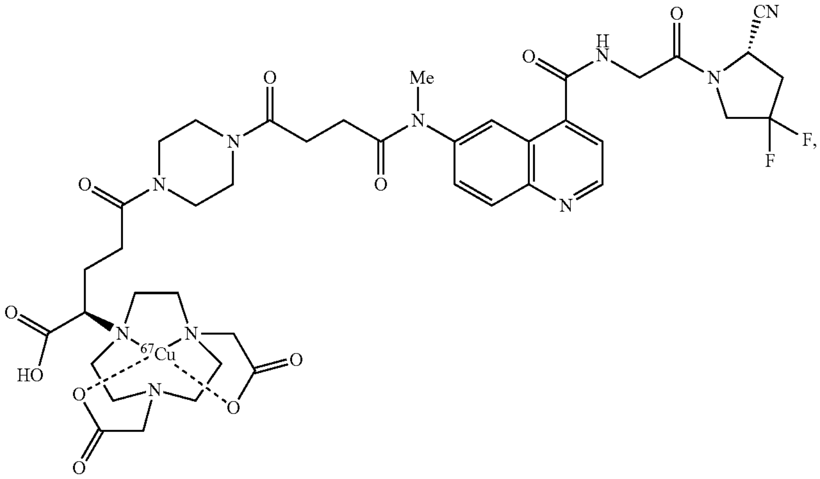 , and |
| 43 | [67Cu]Cu-NODAGA-FAPI-46 | 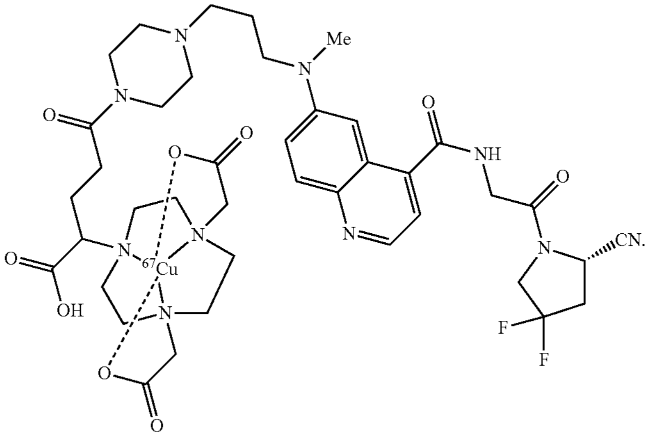 . |

4.3. Pharmaceutical Compositions

An aspect of the present disclosure is the provision of a high purity pharmaceutical composition comprising a compound of Formula X*, Formula A* or a pharmaceutically acceptable salt thereof. In certain embodiments, these compositions are for use in medical imaging (diagnostic imaging) and/or therapy. In another aspect, the present invention provides pharmaceutical compositions comprising a compound of the present disclosure, including Formula X* and A* and examples in combination with a pharmaceutically acceptable excipient (e.g., carrier).

The pharmaceutical compositions include optical isomers, diastereomers, or pharmaceutically acceptable salts of the inhibitors disclosed herein.

A "pharmaceutically acceptable carrier", as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethylcellulose, and polyvinylpyrrolidone. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g., to reduce metabolic degradation).

In certain embodiments, a compound as described herein can be incorporated into a pharmaceutical composition for administration by methods known to those skilled in the art and described herein for provided compounds.

In certain embodiments, the pharmaceutical compositions according to the present disclosure comprise a compound of Formula X, X*, A, and A*, the composition further comprises a pharmaceutically acceptable excipient.

In certain embodiments, pharmaceutical compositions according to the present disclosure characterized by one or more of the activity and purity characteristics as described below.

4.3.1. Radioactivity

The term "radioactivity" (also referred to as activity, or total activity) as used herein refers to a physical quantity defined as the number of radioactive transformations per second that occur in a particular radionuclide. The unit of radioactivity used herein is the becquerel (symbol Bq), which is defined equivalent to reciprocal seconds (1/seconds or $s^{-1}$).

4.3.2. Molar Activity

The term "molar activity" as used herein refers to the amount of radioactivity (e.g., number of nuclear disintegrations per second) per unit mole of the radiolabeled compound, and is expressed in Bq/mol, e.g., GBq/μmol and is used where the molecular weight of the labelled material is known.

In certain embodiments, the compositions has a molar activity of 1 to 280 MBq/nmol, e.g., 5 to 265 MBq/nmol, 10 to 250 MBq/nmol, 15 to 235 MBq/nmol, 20 to 220 MBq/nmol, 25 to 205 MBq/nmol, 30 to 190 MBq/nmol, 35 to 175 MBq/nmol, 40 to 160 MBq/nmol, 45 to 150 MBq/nmol, 50 to 135 MBq/nmol, 55 to 120 MBq/nmol, 1 to 50 MBq/nmol, 2 to 48 MBq/nmol, 4 to 46 MBq/nmol, 6 to 44 MBq/nmol, 8 to 42 MBq/nmol, 10 to 40 MBq/nmol, 12 to 38 MBq/nmol, 14 to 36 MBq/nmol, 16 to 34 MBq/nmol, 18 to 32 MBq/nmol, 20 to 30 MBq/nmol, or 22 to 28 MBq/nmol. In certain embodiments, the composition has a molar activity of 24 MBq/nmol±3 MBq/nmol.

In certain embodiments, the composition has a molar activity of ≥35 MBq/nmol, ≥40 MBq/nmol, ≥45 MBq/nmol, ≥50 MBq/nmol, ≥55 MBq/nmol, ≥60 MBq/nmol, ≥65 MBq/nmol, ≥70 MBq/nmol, ≥75 MBq/nmol, ≥80 MBq/nmol, ≥85 MBq/nmol, ≥90 MBq/nmol, ≥95 MBq/nmol, ≥100 MBq/nmol, ≥105 MBq/nmol, ≥110 MBq/nmol, ≥115 MBq/nmol, ≥120 MBq/nmol, ≥125 MBq/nmol, ≥130 MBq/nmol, ≥135 MBq/nmol, ≥140 MBq/nmol, ≥145 MBq/nmol, ≥150 MBq/nmol, ≥155 MBq/nmol, ≥160 MBq/nmol, ≥165 MBq/nmol, ≥170 MBq/nmol, ≥175 MBq/nmol, ≥180 MBq/nmol, ≥185 MBq/nmol, ≥190 MBq/nmol, ≥195 MBq/nmol, or ≥200 MBq/nmol.

In certain embodiments, the composition has a molar activity of 1 to 250 MBq/nmol, for example, 1 to 200 MBq/nmol, 1 to 150 MBq/nmol, 1 to 100 MBq/nmol, 1 to 50 MBq/nmol, 50 to 250 MBq/nmol, 50 to 200 MBq/nmol, 50 to 150 MBq/nmol, 50 to 100 MBq/nmol, 100 to 250 MBq/nmol, 100 to 150 MBq/nmol, 150 to 250 MBq/nmol, 150 to 200 MBq/nmol, or 200 to 250 MBq/nmol. In certain embodiments, the radiotracer composition is characterized by molar activity of 1 to 150 MBq/nmol.

In certain embodiments, the composition has a molar activity of ≥90 MBq/nmol, ≥88 MBq/nmol, ≥86 MBq/nmol, ≥84 MBq/nmol, ≥82 MBq/nmol, ≥80 MBq/nmol, ≥78 MBq/nmol, ≥76 MBq/nmol, ≥74 MBq/nmol, ≥72 MBq/nmol, ≥70 MBq/nmol, ≥68 MBq/nmol, ≥66 MBq/nmol, ≥64 MBq/nmol, ≥62 MBq/nmol, ≥60 MBq/nmol, ≥58 MBq/nmol, ≥56 MBq/nmol, ≥54 MBq/nmol, ≥52 MBq/nmol, ≥50 MBq/nmol, ≥48 MBq/nmol, ≥46 MBq/nmol, ≥44 MBq/nmol, or ≥42 MBq/nmol.

In certain embodiments of the composition, the composition has a molar activity of ≥3 MBq/nmol, ≥4 MBq/nmol, ≥5 MBq/nmol, ≥6 MBq/nmol, ≥7 MBq/nmol, ≥8 MBq/nmol, ≥9 MBq/nmol, ≥10 MBq/nmol, ≥11 MBq/nmol, ≥12 MBq/nmol, ≥13 MBq/nmol, ≥14 MBq/nmol, ≥15 MBq/nmol, ≥16 MBq/nmol, ≥17 MBq/nmol, ≥18 MBq/nmol, or ≥19 MBq/nmol.

In certain embodiments of the composition, the composition has a molar activity of ≥3 MBq/nmol, ≥5 MBq/nmol, ≥10 MBq/nmol, ≥15 MBq/nmol, ≥20 MBq/nmol, ≥25 MBq/nmol, ≥30 MBq/nmol, ≥35 MBq/nmol, ≥40 MBq/nmol, ≥45 MBq/nmol, ≥50 MBq/nmol, ≥55 MBq/nmol, ≥60 MBq/nmol, ≥65 MBq/nmol, ≥70 MBq/nmol, ≥75 MBq/nmol, ≥80 MBq/nmol, ≥85 MBq/nmol, ≥90 MBq/nmol, ≥95 MBq/nmol, ≥100 MBq/nmol, ≥105 MBq/nmol, ≥110 MBq/nmol, ≥115 MBq/nmol, ≥120 MBq/nmol, ≥125 MBq/nmol, 130 MBq/nmol, 135 MBq/nmol, 140 MBq/nmol, 145 MBq/nmol, 150 MBq/nmol, 155 MBq/nmol, ≥160 MBq/nmol, ≥165 MBq/nmol, ≥170 MBq/nmol, ≥175 MBq/nmol, ≥180 MBq/nmol, ≥185 MBq/nmol, ≥190 MBq/nmol, ≥195 MBq/nmol, ≥200 MBq/nmol, ≥205 MBq/nmol, ≥210 MBq/nmol, ≥215 MBq/nmol, 220≥MBq/nmol, ≥225 MBq/nmol, ≥230 MBq/nmol, ≥235 MBq/nmol, ≥240 MBq/nmol, ≥245 MBq/nmol, ≥250 MBq/nmol, ≥255 MBq/nmol, ≥260 MBq/nmol, ≥265 MBq/nmol, ≥270 MBq/nmol, ≥275 MBq/nmol, or ≥280 MBq/nmol. In certain embodiments, the composition has a molar activity of ≥24 MBq/nmol.

In certain embodiments, the composition has a molar activity of 1 to 250 MBq/nmol, for example, 1 to 200 MBq/nmol, 1 to 150 MBq/nmol, 1 to 100 MBq/nmol, 1 to 50 MBq/nmol, 50 to 250 MBq/nmol, 50 to 200 MBq/nmol, 50 to 150 MBq/nmol, 50 to 100 MBq/nmol, 100 to 250 MBq/nmol, 100 to 150 MBq/nmol, 150 to 250 MBq/nmol, 150 to 200 MBq/nmol, or 200 to 250 MBq/nmol.

4.3.3. Activity Concentration

The term "activity concentration" as used herein refers to the total amount of radioactivity per unit volume. In certain embodiments, activity concentration is expressed in Bq/L or magnitudes thereof (e.g., MBq/mL).

In certain embodiments, a composition provided is characterized by an activity concentration of ≥8 MBq/mL. In certain embodiments, a composition provided herein is characterized by an activity concentration of 8 to 10 MBq/mL, 10 to 20 MBq/mL, 20 to 30 MBq/mL, 30 to 40 MBq/mL, 40 to 50 MBq/mL, 50 to 60 MBq/mL, 60 to 70 MBq/mL, 70 to 80 MBq/mL, 80 to 90 MBq/mL, 90 to 100 MBq/mL, 100 to 110 MBq/mL, 110 to 120 MBq/mL, 120 to 130 MBq/mL, 130 to 140 MBq/mL, 140 to 150 MBq/mL, 150 to 160 MBq/mL, 160 to 170 MBq/mL, 170 to 180 MBq/mL, 180 to 190 MBq/mL, 190 to 200 MBq/mL, 200 to 210 MBq/mL, 210 to 220 MBq/mL, 220 to 230 MBq/mL, 230 to 240 MBq/mL, 240 to 250 MBq/mL, 250 to 260 MBq/mL, 260 to 270 MBq/mL, 270 to 280 MBq/mL, 280 to 290 MBq/mL, 290 to 300 MBq/mL, 300 to 310 MBq/mL, 310 to 320 MBq/mL, 320 to 330 MBq/mL, 330 to 340 MBq/mL, 340 to 350 MBq/mL, 350 to 360 MBq/mL, 360 to 370 MBq/mL, 370 to 380 MBq/mL, 380 to 390 MBq/mL, 390 to 400 MBq/mL, 400 to 410 MBq/mL, 410 to 420 MBq/mL, 420 to 430 MBq/mL, 430 to 440 MBq/mL, 440 to 450 MBq/mL, 450 to 460 MBq/mL, 460 to 470 MBq/mL, 470 to 480 MBq/mL, 480 to 490 MBq/mL, 490 to 500 MBq/mL, 500 to 510 MBq/mL, 510 to 520 MBq/mL, 520 to 530 MBq/mL, 530 to 540 MBq/mL, 540 to 550 MBq/mL, 550 to 560 MBq/mL, 560 to 570 MBq/mL, 570 to 580 MBq/mL, 580 to 590 MBq/mL, 590 to 600 MBq/mL, 600 to 610 MBq/mL, 610 to 620 MBq/mL, 620 to 630 MBq/mL, 630 to 640 MBq/mL, 640 to 650 MBq/mL, 650 to 660 MBq/mL, 660 to 670 MBq/mL, 670 to 680 MBq/mL, 680 to 690 MBq/mL, 690 to 700 MBq/mL, 700 to 710 MBq/mL, 710 to 720 MBq/mL, 720 to 730 MBq/mL, 730 to 740 MBq/mL, 740 to 750 MBq/mL, 750 to 760 MBq/mL, 760 to 770 MBq/mL, 770 to 780 MBq/mL, 780 to 790 MBq/mL, 790 to 800 MBq/mL, 800 to 810 MBq/mL, 810 to 820 MBq/mL, 820 to 830 MBq/mL, 830 to 840 MBq/mL, 840 to 850 MBq/mL, 850 to 860 MBq/mL, 860 to 870 MBq/mL, 870 to 880 MBq/mL, 880 to 890 MBq/mL, 890 to 900 MBq/mL, 900 to 910 MBq/mL, 910 to 920 MBq/mL, 920 to 930 MBq/mL, 930 to 940 MBq/mL, 940 to 950 MBq/mL, 950 to 960 MBq/mL, 960 to 970 MBq/mL, 970 to 980 MBq/mL, 980 to 990 MBq/mL, or 990 to 1000 MBq/mL.

In certain embodiments, a composition provided is characterized by an activity concentration of ≥8 MBq/mL. In certain embodiments, a composition provided is characterized by an activity concentration of 5 to 500 MBq/mL, 20 to 480 MBq/mL, 40 to 460 MBq/mL, 60 to 440 MBq/mL, 80 to 420 MBq/mL, 100 to 400 MBq/mL, 120 to 380 MBq/mL, 140 to 360 MBq/mL, 160 to 340 MBq/mL, 180 to 320 MBq/mL, or 200 to 300 MBq/mL.

In certain embodiments, a composition provided is characterized by an activity concentration of ≥3 MBq/mL, ≥4 MBq/mL, ≥5 MBq/mL, ≥6 MBq/mL, ≥7 MBq/mL, ≥8 MBq/mL, ≥9 MBq/mL, ≥10 MBq/mL, ≥12 MBq/mL, ≥15 MBq/mL, ≥20 MBq/mL, ≥25 MBq/mL, ≥30 MBq/mL, ≥35 MBq/mL, ≥40 MBq/mL, ≥45 MBq/mL, ≥50 MBq/mL, ≥55 MBq/mL, ≥60 MBq/mL, ≥65 MBq/mL, ≥70 MBq/mL, ≥75 MBq/mL, ≥80 MBq/mL, ≥85 MBq/mL, ≥90 MBq/mL, ≥95 MBq/mL, ≥100 MBq/mL, ≥105 MBq/mL, ≥110 MBq/mL, ≥115 MBq/mL, ≥120 MBq/mL, ≥125 MBq/mL, 130 MBq/mL, 135 MBq/mL, 140 MBq/mL, 145 MBq/mL, 150 MBq/mL, 155 MBq/mL, ≥160 MBq/mL, ≥165 MBq/mL, ≥170 MBq/mL, ≥175 MBq/mL, ≥180 MBq/mL, ≥185 MBq/mL, ≥190 MBq/mL, ≥195 MBq/mL, ≥200 MBq/mL, ≥205 MBq/mL, ≥210 MBq/mL, ≥215 MBq/mL, 220≥MBq/mL, ≥225 MBq/mL, ≥230 MBq/mL, ≥235 MBq/mL, ≥240 MBq/mL, ≥245 MBq/mL, ≥250 MBq/mL, ≥255 MBq/mL, ≥260 MBq/mL, ≥265 MBq/mL, ≥270 MBq/mL, ≥275 MBq/mL, or ≥280 MBq/mL.

In certain embodiments, the activity concentration of the resulting pharmaceutical composition may be diluted (e.g., by a factor of 3 to 10) as long as the activity concentration is ≥8 MBq/mL. In certain embodiments, a composition has an activity concentration 8 to 20 MBq/mL, 9 to 19 MBq/mL, 10 to 18 MBq/mL, 11 to 19 MBq/mL, 12 to 18 MBq/mL, 13 to 15 MBq/mL, 14 to 15 MBq/mL, 8 to 14 MBq/mL, 8 to 13 MBq/mL, 8 to 12 MBq/mL, 8 to 11 MBq/mL, 8 to 10 MBq/mL, 8 to 9 MBq/mL, 9 to 14 MBq/mL, 10 to 13 MBq/mL, or 11 to 12 MBq/mL.

In certain embodiments, a pharmaceutical formulation composition provided is characterized by an activity concentration 0.3 to 0.75 GBq/mL.

4.3.4. Radiochemical Purity

"Radiochemical purity," as understood herein, is the ratio, given as a percent, of radioactivity from the desired radionuclide in the radiopharmaceutical composition (e.g., the desired radionuclide that is chelated in a radiotracer as described herein) to the total radioactivity of the composition that comprises the radiopharmaceutical. It is important to know that the majority of the radioactive isotope is attached to the tracer construct and is not free or attached to another chemical entity as these forms may have a different biodistribution. Radiochemical purity (RCP) measurements establish the content of impurities labelled with the same radionuclide used to prepare a radiopharmaceutical, but with a different chemical form. For most radiopharmaceuticals the lower limit of radiochemical purity is 95%, that is, at least 95% of the radioactive isotope must be attached to the ligand. Radiochemical purity determination can be carried out by a variety of chromatographic methods.

Radiochemical purity is determined according to methods well known to those of skill in the art, e.g., radio-HPLC, iTLC and/or γ-spectrometry. As is understood in the art, determination of radiochemical purity is not strictly quantitative, and it is calculated as the ratio between the peak area of the desired radiopharmaceutical and the overall area of all the detected peaks in the radiochromatogram (corrected for decay). The instrument used to determine radiochemical purity with HPLC (radio-HPLC) is a radiometric detector (radiodetector), which has an in-line detector connected in series with a UV or other physicochemical detector. The radiometric detector can be a Geiger-Müller probe, a scintillation detector, or a PIN diode. As compared with radio-HPLC it has the big advantage that all applied radioactivity is detected and there are no concerns with recovery.

In certain embodiments, the composition is characterized by radiochemical purity of ≥90%. In certain embodiments, the composition is characterized by radiochemical purity of ≥91%, ≥92%, ≥93%, ≥94%, 95%, ≥96%, ≥97%, ≥98%, or ≥99%. In certain embodiments, the composition is characterized by radiochemical purity ≥90%. In certain embodiments, the composition is characterized by radiochemical purity of ≥95%. In certain embodiments, the composition is characterized by radiochemical purity of ≥96%. In certain embodiments, the composition is characterized by radiochemical purity of ≥98%.

In certain embodiments, the composition provided is characterized by a radiochemical purity of ≥94.0%, ≥94.5%, ≥95.0%, ≥95.5%, ≥96.0%, ≥96.5%, ≥97.0%, ≥97.5%, ≥98.0%, ≥98.5%, ≥99.0%, or ≥99.5%.

In certain embodiments, the composition provided is characterized by a radiochemical purity of ≥95.2%, ≥95.4%, ≥95.6%, ≥95.8%, ≥96%, ≥96.2%, ≥96.4%, ≥96.6%, ≥96.8%, ≥97%, ≥97.2%, ≥97.4%, ≥97.6%, ≥97.8%, ≥98%, ≥98.2%, ≥98.4%, ≥98.6%, ≥98.8%, ≥99%, ≥99.2%, ≥99.4%, ≥99.6%, or ≥99.8%.

4.3.5. Radionuclidic Purity

The term "radionuclidic purity" as used herein refers to the ratio, expressed as a percentage, of the radioactivity of the desired radionuclide to the total radioactivity of the sample, e.g., the starting material used to prepare a radiolabeled pharmaceutical. As reported herein, unless otherwise specified, radionuclidic purity is determined by high resolution gamma spectroscopy (e.g., high-purity germanium (HPGe) detector) on a sample after expiration, e.g. >8 hours or ≥3 weeks) and is then extrapolated (e.g., using the TENDLE-2019 database according to procedures well known in the art), and reported herein as the value at the end of synthesis (EoB+2 hours) of the radionuclide.

In certain embodiments, the composition is characterized by radionuclidic purity of the compound at end of synthesis ≥85%, for example, of ≥86%, ≥87%, ≥88%, ≥89%, ≥90%, ≥91%, ≥92%, ≥93%, ≥94%, ≥95%, ≥96%, ≥97%, ≥98%, or of ≥99%.

In certain embodiments, the composition is characterized by radionuclidic purity of the compound at end of synthesis ≥90.5%, e.g., ≥91%, ≥91.5%, ≥92%, ≥92.5%, ≥93%, ≥93.5%, ≥94%, ≥94.5%, 95% 95.5%, ≥96%, ≥96.5%, ≥97%, ≥97.5%, ≥98%, ≥98.5%, ≥99% or ≥99.5%.

In certain embodiments, the composition is characterized by a radionuclidic purity of ≥95.1%, e.g., ≥95.2%, ≥95.3%, ≥95.4%, ≥95.5%, ≥95.6%, ≥95.7%, ≥95.8%, ≥95.9%, ≥96%, ≥96.1%, ≥96.2%, ≥96.3%, ≥96.4%, ≥96.5%, ≥96.6%, ≥96.7%, ≥96.8%, ≥96.9%, ≥97%, ≥97.1%, ≥97.2%, ≥97.3%, ≥97.4%, ≥97.5%, ≥97.6%, ≥97.7%, ≥97.8%, ≥97.9%, ≥98%, ≥98.1%, ≥98.2%, ≥98.3%, ≥98.4%, ≥98.5%, ≥98.6%, ≥98.7%, ≥98.8%, ≥98.9%, ≥99%, ≥99.1%, ≥99.2%, ≥99.3%, ≥99.4%, ≥99.5%, ≥99.6%, ≥99.7%, ≥99.8%, or ≥99.9%.

In certain embodiments, the composition is characterized by radionuclidic purity of ≥97% (at end of synthesis). In certain embodiments, the composition is characterized by radionuclidic purity of ≥93%, ≥94%, ≥95%, ≥96%, ≥98%, or ≥99% (at end of synthesis).

4.3.6. Formulations

Compounds of the present invention can be prepared and administered in a wide variety of oral, parenteral, and topical dosage forms. Thus, the compounds of the present invention can be administered by injection (e.g., intravenously, intramuscularly, intracutaneously, subcutaneously, intraduodenally, or intraperitoneally). In certain embodiments, compounds of the present disclosure are administered orally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer compounds of the invention. Accordingly, the present invention also provides pharmaceutical compositions comprising pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is finely divided solid in a mixture with the finely divided active component. In tablets, the active component is mixed with the carrier having the necessary binding properties in suitable proportions and compacted in the shape and size desired.

4.3.7. Effective Dosages

Pharmaceutical compositions provided by the present disclosure include compositions wherein the active ingredient is contained in a therapeutically effective amount, i.e., in an amount effective to achieve its intended purpose. The actual amount effective for a particular application will depend, inter alia, on the condition being treated or images generated. For example, when administered in methods to treat cancer, such compositions will contain an amount of active ingredient effective to achieve the desired result (e.g., imaging cancerous tissue and/or decreasing an amount of cancerous tissue in a subject).

The dosage and frequency (single or multiple doses) of compound administered can vary depending upon a variety of factors, including route of administration; size, age, sex, health, body weight, body mass index, and diet of the recipient; nature and extent of the symptoms of the disease being treated (e.g., the disease responsive treatment; and complications from any disease or treatment regimen. Other therapeutic regimens or agents can be used in conjunction with the methods and compounds of the invention.

For any provided compound or test agent, the diagnostically effective or therapeutically effective amount can be initially determined from cell culture assays and/or animal testing. Target concentrations will be those concentrations of active compound(s) that are capable of diagnosing, monitoring, and/or treating cancer in a patient or subject.

Therapeutically effective amounts for use in humans may be determined from animal models. For example, a dose for humans can be formulated to achieve a concentration that has been found to be effective in animals. The dosage in humans can be adjusted by monitoring cancerous growth, proliferation, and/or metastasis and adjusting the dosage upwards or downwards, as described above.

Dosages may be varied depending upon the requirements of the patient and the compound being employed. The dose administered to a patient, in the context of the present invention, should be sufficient to affect a beneficial therapeutic response in the patient over time. The size of the dose also will be determined by dose escalation tests during clinical trial phases.

In one aspect, compounds provided herein display one or more improved pharmacokinetic (PK) properties (e.g., Cmax, tmax, Cmin, t½, AUC, CL, bioavailability, etc.) when compared to a reference compound. In certain embodiments, a reference compound is aPSMA, SSTR2, or FAP PET radiotracer.

In certain embodiments, a compound of the disclosure or a pharmaceutical composition comprising the same is provided as a unit dose. In certain embodiments, a compound of the disclosure or a radiopharmaceutical composition comprising the same is provided as a unit dose (e.g., molar activity).

In certain embodiments, pharmaceutical compositions of the present disclosure are administered with loop diuretics (e.g., furosemide). In certain embodiments, a pharmaceutical composition of the present disclosure is administered to a subject that is also administered any one of spironolactone, bumetanide, ethacrynic acid, torasemide, hydrochlorothiazide, furosemide, or metolazone.

In certain embodiments, a pharmaceutical composition of the present disclosure is administered to a subject that is also administered any one of the drugs selected from lysine, gelofusine, docetaxel, everolimus, abiraterone acetate, enzalutamide, olaparib, temozolomide, acetazolamide, or succinylacetone.

4.4. Methods of Use

The present disclosure provides compounds and pharmaceutical compositions comprising the same for use in medicine, i.e., for use in treatment, imaging, diagnosing, companion diagnosing, etc. The present disclosure further provides the use of any compounds described herein for targeted radiotherapy, which would be beneficial to diagnosis and/or treatment of cancer.

In certain embodiments, the compounds or pharmaceutical compositions of the present disclosure are administered to a subject once a day, twice a day, daily, or every other day. In certain embodiments, the compounds or pharmaceutical compositions of the present disclosure are administered to a subject twice a week, once a week, every ten days, every two weeks, every three weeks, every four weeks, once a month, every six weeks, every eight weeks, every three months, every four months, every six months, every eight months, every nine months, or annually. The dosage and frequency (single or multiple doses) of compound or pharmaceutical composition administered can vary depending upon a variety of factors, including route of administration; size, age, sex, health, body weight, body mass index, and diet of the recipient; nature and extent of the symptoms of the disease being treated (e.g., the disease responsive treatment) and complications from any disease or treatment regimen. Other therapeutic regimens or agents can be used in conjunction with the methods and compounds of the invention.

For any provided compound or pharmaceutical composition, the effective amount (e.g., the diagnostically effective or therapeutically effective amount) can be initially determined from cell culture assays and/or animal testing. Target concentrations will be those concentrations of active compound(s) that are capable of diagnosing, monitoring, and/or treating cancer in a patient or subject.

Therapeutic efficacy of the compound may be determined from animal models. The dosage in humans can be adjusted during the clinical trials via dose escalation studies by monitoring safety and efficacy.

Dosages may be varied depending upon the requirements of the patient and the compound or pharmaceutical composition being employed. The dose administered to a patient, in the context of the present invention, should be sufficient to affect a beneficial therapeutic response in the patient over time. The size of the dose also will be determined by the existence, nature, and extent of any adverse side effects.

In one aspect, compounds provided herein display one or more improved pharmacokinetic (PK) properties (e.g., Cmax, tmax, Cmin, t1/2, AUC, CL, bioavailability, etc.) when compared to a reference compound.

In some embodiments, a compound of the disclosure or a pharmaceutical composition comprising the same is provided as a unit dose.

In a further aspect, the present disclosure provides a novel radiotracer and/or a novel radiotracer composition as provided herein above for use in a method of imaging, diagnosing and/or staging cancer. In certain embodiments, the cancer is selected from breast cancer (e.g., triple-negative breast cancer), pancreatic cancer, small intestine cancer, colon cancer, gastric cancer, rectal cancer, lung cancer (e.g., non-small cell lung cancer), head and neck cancer, ovarian cancer, hepatocellular carcinoma, epithelial cancer, esophageal cancer, hypopharynx cancer, nasopharynx cancer, larynx cancer, myeloma cells, bladder cancer, cholangiocellular carcinoma, clear cell renal carcinoma, neuroendocrine tumor, oncogenic osteomalacia, sarcoma, CUP (carcinoma of unknown primary), thymus carcinoma, desmoid tumors, glioma, astrocytoma, cervix carcinoma, and prostate cancer.

In certain embodiments, the cancer is prostate cancer. Prostate cancer is not the only cancer to express PSMA. Nonprostate cancers known to demonstrate PSMA expression include breast, lung, colorectal, and renal cell carcinoma. Thus, any compound described herein having a PSMA binding moiety can be used in the diagnosis, imaging or treatment of a cancer having PSMA expression. Preferred indications are the detection or staging of cancer, such as, but not limited high grade gliomas, lung cancer and especially prostate cancer and metastasized prostate cancer, the detection of metastatic disease in patients with primary prostate cancer of intermediate-risk to high-risk, and the detection of metastatic sites, even at low serum PSA values in patients with biochemically recurrent prostate cancer. Another preferred indication is the imaging and visualization of neoangiogensis.

In terms of medical indications to be subjected to therapy, especially radiotherapy, cancer is a preferred indication. Prostate cancer is a particularly preferred indication.

In certain embodiments, the methods comprise administering to a subject in need thereof (e.g., a subject such as a human patient) any of the compounds described herein or a pharmaceutically acceptable salt thereof. In certain embodiments, the methods comprise administering a compound of Formula X*, A*, 10* a compound of structures 24-36 provided herein or a pharmaceutically acceptable salt or composition of any of these, to a subject in need thereof. In certain embodiments, the method comprises administering a pharmaceutical composition comprising a compound of Formula X* or A*, a compound of structures 24-36 provided or a pharmaceutically acceptable salt to a subject in need thereof.

4.4.1.1 Imaging and Diagnosis

In an aspect of the present disclosure, methods of generating an image of a subject, e.g., a certain region or part of the body, are provided, the method comprising administering to the subject a compound described herein comprising a radionuclide. In certain embodiments, the radionuclide is selected from $^{60}$Cu, $^{61}$Cu, $^{62}$Cu, $^{64}$Cu, and $^{67}$Cu. In certain embodiments, the radionuclide is $^{61}$Cu. In certain embodiments, the radionuclide is $^{67}$Cu.

In certain embodiments, methods of generating one or more images of a subject are provided (e.g., of a certain region or part of the subject's body) comprising administering to the subject an effective amount of a compound comprising a radionuclide described herein, or a pharmaceutical composition comprising the same, and generating one or more images of at least a part of the subject's body. In certain embodiments, two or more images of a subject are generated, such as, for example, three or more images, four or more images, or five or more images. In certain embodiments, a diagnostically effective amount of the compound comprising a radionuclide or pharmaceutical composition comprising the same is administered to the subject, i.e., an amount sufficient to identify (visually or computationally) localization of the radionuclide within regions or parts of the subject's body. In some embodiments, the radionuclide is a metal radionuclide. In certain embodiments, the radionuclide is selected from $^{60}$Cu, $^{61}$Cu, $^{62}$Cu, $^{64}$Cu, and $^{67}$Cu. In some embodiments, the radionuclide is $^{61}$Cu.

In certain embodiments, the one or more images are generated using positron emission tomography (PET). In certain embodiments, the one or more images are generated using PET-computer tomography (PET-CT). In certain embodiments, the one or more images are generated using single-photon emission computerized tomography (SPECT).

In certain embodiments, the image is generated using PET or PET-CT, wherein the radionuclide is $^{61}$Cu. In certain embodiments, the image is generated using SPECT wherein the radionuclide is $^{61}$Cu or $^{67}$Cu.

In certain embodiments, after the one or more images are generated, the method further comprises determining the presence or absence of a disease in a subject based on the presence or absence of localization of the radionuclide in the one or more images of the subject's body.

In another aspect of the present disclosure, a method of monitoring the effect of cancer treatment on a subject afflicted with cancer is provided, the method comprising administering to a subject a compound described herein comprising a radionuclide, detecting the localization of the compound in the subject using, e.g., PET or SPECT, and determining the effects of the cancer treatment. In certain embodiments, the compound is administered to the subject and localization is observed at multiple time points, i.e., at an earlier time point (e.g., before cancer treatment begins (t=0)) and at a later time point, e.g., 1 month after commencing treatment, 2 months after commencing treatment, 3 months after commencing treatment, 4 months after commencing treatment, 5 months after commencing treatment, or 6 or more months after commencing treatment. The cancer treatment is determined to be beneficial (i.e., a positive effect) if less localization is observed at the later time point compared to the earlier time point. The cancer treatment is determined to not be beneficial (i.e., a negative effect) if more localization is observed at the later time point compared to the earlier time point. The cancer treatment is determined to not have an effect if there is no difference in localization at the later time point compared to the earlier time point.

In certain embodiments, the disease to be detected includes cancers, such as somatostatin receptor expressing tumors like neuroendocrine tumors, prostate cancer, malignant meningiomas, epithelial cancers which overexpress FAP including non-small cell lung cancer, triple-negative breast cancer, colorectal carcinoma, gastric cancer, ovarian cancer, and pancreatic cancer; myocardial infarct and interstitial lung disease. In certain embodiments, the cancer is selected from breast cancer (e.g., triple-negative breast cancer), pancreatic cancer, small intestine cancer, colon cancer, gastric cancer, rectal cancer, lung cancer (e.g., non-small cell lung cancer), head and neck cancer, ovarian cancer, hepatocellular carcinoma, epithelial cancer, esophageal cancer, hypopharynx cancer, nasopharynx cancer, larynx cancer, myeloma cells, bladder cancer, cholangiocellular carcinoma, clear cell renal carcinoma, neuroendocrine tumor, oncogenic osteomalacia, sarcoma, CUP (carcinoma of unknown primary), thymus carcinoma, desmoid tumors, glioma, astrocytoma, cervix carcinoma, and prostate cancer.

In another aspect of the present disclosure, a method of monitoring the effect of cancer treatment on a subject afflicted with cancer is provided. The method comprises administering to a subject an effective amount of a compound comprising a radionuclide described herein or a pharmaceutical composition comprising the same; detecting localization of the radionuclide in the subject using, e.g., PET, PET-CT, or SPECT; and determining the effects of the cancer treatment. In certain embodiments, the compound comprising a radionuclide or pharmaceutical composition comprising the same is administered to the subject and localization is observed at multiple time points, i.e., at an earlier time point (e.g., before cancer treatment begins (t=0)) and at a later time point, e.g., 2 weeks after commencing treatment, 3 weeks after commencing treatment, 1 month after commencing treatment, 2 months after commencing treatment, 3 months after commencing treatment, 4 months after commencing treatment, 5 months after commencing treatment, or 6 or more months after commencing treatment. In certain but not all embodiments, the cancer treatment is determined to be beneficial (i.e., a positive effect) if less localization is observed at the later time point compared to the earlier time point. In certain but not all embodiments, the cancer treatment is determined to not be beneficial (i.e., a negative effect) if more localization is observed at the later time point compared to the earlier time point. In certain but not all embodiments, the cancer treatment is determined to not have an effect if there is no difference in localization at the later time point compared to the earlier time point.

4.4.1.2 Therapy

In an aspect of the present disclosure, a method of treating a disease in a patient afflicted with a disease is provided, the method comprising administering to the patient an effective amount of compound or pharmaceutical composition described herein.

In certain embodiments, a method of providing radionuclide therapy to a cancer patient in need thereof is provided, the method comprising administering to the cancer patient an effective amount of the high purity radiotracer composition as described herein, wherein *Cu is $^{64}$Cu or $^{67}$Cu.

In certain embodiments, the compound administered is of Formula X, wherein the compound comprises a radionuclide selected from $^{64}$Cu and $^{67}$Cu. Such embodiments are useful in treating cancers, e.g., breast cancer (e.g., triple-negative breast cancer), pancreatic cancer, small intestine cancer, colon cancer, gastric cancer, rectal cancer, lung cancer (e.g., non-small cell lung cancer), head and neck cancer, ovarian cancer, hepatocellular carcinoma, epithelial cancer, esophageal cancer, hypopharynx cancer, nasopharynx cancer, larynx cancer, myeloma cells, bladder cancer, cholangiocellular carcinoma, clear cell renal carcinoma, neuroendocrine tumor, oncogenic osteomalacia, sarcoma, CUP (carcinoma of unknown primary), thymus carcinoma, desmoid tumors, glioma, astrocytoma, cervix carcinoma, and prostate cancer.

In further embodiments of the above methods, the cancer is selected from somatostatin receptor expressing tumors like neuroendocrine tumors, prostate cancer, malignant meningiomas, epithelial cancers which overexpress FAP including non-small cell lung cancer, triple-negative breast cancer, head and neck cancer, colorectal carcinoma, gastric cancer, ovarian cancer, and pancreatic cancer.

4.4.1.3 Theranostics

In an aspect of the present disclosure, a theranostic method comprises the use of a pair of *Cu radiotracers ("theranostic pair"), as provided herein, for both imaging/diagnosis of a disease and for treating the disease in the same patient, wherein the theranostic pair of radiotracers differ only in the radionuclide, i.e., they are different radioisotopes. In certain embodiments, the theranostic pair comprises a $\gamma$ or positron emitting radionuclide in the radiotracer for imaging/diagnosis (e.g., with PET, PET-CT, or SPECT) and a R emitting radionuclide in the radiotracer for therapy.

In certain embodiments, the theranostic pair comprises $^{61}Cu$ (for imaging/diagnosis) and $^{67}Cu$ (for therapy). In certain embodiments, this is referred to as a $^{61/67}Cu$ theranostic pair.

Certain embodiments of the theranostic method comprise the administration of a diagnostic form of the radiotracer (e.g., wherein *Cu is $^{61}Cu$ for PET or wherein *Cu is $^{67}Cu$ for SPECT), enabling expression of the therapeutic target to be visualized in vivo with a companion imaging method before switching to the radiolabeled therapeutic counterpart, e.g., wherein *Cu is 64Cu or $^{67}Cu$.

In certain embodiments, a theranostic method comprises:

(a) administering to a subject an effective amount of a compound comprising a $^{61}Cu$ radionuclide described herein or a pharmaceutical composition comprising the same;

(b) generating one or more images of the subject (e.g., of a certain region or part of the subject's body); and (c) administering to the subject an effective amount of a compound comprising a $^{67}Cu$ radionuclide described herein or a pharmaceutical composition comprising the same, wherein the compounds of step (a) and (c) differ only in radioisotopic identity.

In certain embodiments, the amount of compound comprising a $^{61}Cu$ radionuclide described herein or pharmaceutical composition comprising the same administered in step (a) is effective to generate one or more images of subject (i.e., a "detectably effective amount"). In certain embodiments, the amount of compound comprising a $^{61}Cu$ radionuclide described herein or pharmaceutical composition comprising the same administered in step (a) is effective to diagnose the presence or absence of a disease (i.e., a "diagnostically effective amount").

In certain embodiments, the method further comprises determining, via the one or more images of the subject, the presence or absence of a disease in the subject based on the presence or absence of localization of the $^{61}Cu$ radionuclide in the subject's body. In instances where the subject is not determined to have a disease, step (c) in the method is not performed.

In certain embodiments, the method further comprises calculating an effective therapeutic amount of the compound comprising a $^{67}Cu$ radionuclide described herein to administer to the subject in step (c). In certain embodiments, the method further comprises calculating an effective therapeutic dose of the compound comprising a $^{67}Cu$ radionuclide described herein to administer to the subject in step (c).

In certain embodiments, the amount of compound comprising a $^{67}Cu$ radionuclide described herein or a pharmaceutical composition comprising the same administered in step (c) is effective therapeutically to treat the disease in the subject (i.e., a "therapeutically effective amount").

In certain embodiments, a theranostic method comprises:

(a) generating one or more images of a subject (e.g., of a certain region or part of the subject's body), comprising administering to the subject an effective amount of a compound comprising a $^{61}Cu$ radionuclide described herein or a pharmaceutical composition comprising the same;

(b) determining, via the one or more images of the subject, the presence or absence of a disease in the subject based on the presence or absence of localization of the $^{61}Cu$ radionuclide in the subject's body; and (c) administering to the subject, when the presence of a disease in the subject is determined, an effective amount of a compound comprising a $^{67}Cu$ radionuclide described herein, or a pharmaceutical composition comprising the same, wherein the compounds in step (a) and (c) differ only in the radionuclide identity.

4.5. Methods of Making Compositions

In certain embodiments, the method of making the compounds and compositions according to Formulas X* and A* as provided herein comprises the step of (a) combining a high purity radiocopper solution with:

(b) a compound as provided herein, e.g., according to Formula X, e.g., Formula A, wherein the compound comprises *Cu.

In certain embodiments, the combining occurs in a reaction time of 15 min at elevated temperature (80-95° C.). In certain embodiments, the combining occurs in a reaction time of 15 min at room temperature. In certain embodiments, the combining occurs in a reaction time 2-5 min at room temperature. In certain of these embodiments, the combining occurs in a suitable buffer solution (e.g., ammonium acetate buffer, 0.5M, pH=8).

In certain embodiments, no further purification step is necessary to remove uncomplexed $^{61}Cu$ the reaction mixture, allowing direct use of the formed compound.

4.5.1. Radiolabeling Yield (Radiochemical Yield)

Radiochemical yield is the amount of activity in the product expressed as the percentage (%) of starting activity used in the considered process (e.g., synthesis, separation, etc.). The quantity of both must relate to the same radionuclide and be decay corrected to the same point in time before the calculation is made (see also Appendix A). It should be understood, that under this definition, the radiochemical yield is only related to the considered radionuclide, and it does not include compounds labelled with all radionuclides that may undergo the same reaction as the radionuclide of interest (e.g., $^{68}Ge$ in $^{68}Ga$ preparations). 'Radiochemical yield', calculated using decay-corrected radioactivity values for products and starting compounds, is identical to the concept of 'chemical yield'. Logically, the reference time for correction of decay must be identical to describe a particular reaction, irrespective of whether it is chosen to be the end of the radionuclide production, the end of bombardment, the start of synthesis, the end of synthesis, or any other convenient reference time point.

In certain embodiments, a composition of the present disclosure is characterized by radiolabeling yield at the end of labeling of ≥80%. In further embodiments, the composition is characterized by radiolabeling ≥95% or greater. In further embodiments, the composition is characterized by radiolabeling yield of ≥95% at room temperature.

In certain embodiments, the composition provided is characterized by a radiolabeling yield of greater than 85%, e.g., greater than 85.5%, 86.0%, 86.5%, 87.0%, 87.5%, 88.0%, 88.5%, 89.0%, 89.5%, 90.0%, 90.5%, 91.0%, 91.5%, 92.0%, 92.5%, 93.0%, 93.5%, 94.0%, 94.5%, 95.0%, 95.5%, 96.0%, 96.5%, 97.0%, 97.5%, 98.0%, 98.5%, 99.0%, or 99.5%. In certain embodiments, the composition is characterized by radiolabeling yield of greater than 90%. In certain embodiments, the composition is characterized by radiolabeling yield of greater than 92%. In certain embodiments, the composition is characterized by radiolabeling yield of greater than 95%.

4.5.2. Properties of Radionuclide Starting Material

Highly pure compositions comprising one or more copper radionuclides Cu*, such as 6° Cu, $^{61}$Cu, $^{62}$Cu, $^{64}$Cu, and $^{67}$Cu are produced though the deuteron, proton, or alpha particle bombardment of a target coin comprising a highly pure Nb backing and a target coating comprising stable nickel or zinc isotopes and using a particle accelerator such as a medical cyclotron. For example, methods for preparing highly pure compositions comprising a copper radionuclide are described in U.S. Provisional Patent Application No. 63/409,684, filed Sep. 23, 2022, which is hereby incorporated by reference in its entirety.

In certain embodiments, the radiocopper solution comprises radiocopper dissolved as its chloride salt. In certain embodiments, the irradiated target material is dissolved with an HCl solution. In certain embodiments, the HCl solution is ≥4M, ≥5 M or ≥6M.

In various embodiments, the radionuclide composition has a radionuclidic purity at end of synthesis (EOB plus 2 hours) is ≥95.0%. In certain embodiments, the high-purity composition comprises a $^{6x}$Cu radionuclide, e.g., $^{61}$Cu, $^{64}$Cu, or $^{67}$Cu. In certain embodiments, the high-purity composition comprises $^{64}$Cu, for example, for use as a therapeutic agent. In other embodiments, the high-purity composition comprises $^{67}$Cu. In certain embodiments, the high-purity composition comprises $^{61}$Cu, for example, for use as a radiotracer, such as in diagnostic imaging.

In various embodiments, the high-purity composition comprises $^{61}$Cu and has a radionuclidic purity at end of synthesis of ≥97.0%.

In certain embodiments, the radionuclide composition, e.g., a high-purity radionuclide, comprising $^{61}$Cu, $^{64}$Cu, or $^{67}$Cu, particularly $^{61}$Cu, is characterized by one of more of the following purity requirements:

$^{110m}$Ag≤0.1 Bq/g;
$^{108m}$Ag≤0.1 Bq/g; and
$^{109}$Cd≤0.1 Bq/g.

Considering radiocobalt impurities, the $^{64}$Ni(p,α) reaction produces $^{61}$Co (t½=1.649 h), with other radiocobalt impurities (e.g., $^{55}$Co, etc.) arising largely from the small quantities of other (A≠64) Ni isotopes in the isotopically enriched starting material. In the context of $^{61}$Cu, however, among other reactions on other Ni isotopes, the dominant $^{61}$Ni(p,α) and $^{60}$Ni(d,α) reactions will give rise to long lived $^{58}$Co (t½=70.86 d) producing 0.05% and 0.11% of $^{58}$Co relative activity compared with $^{61}$Cu, respectively. As such, efficient purification of the radionuclide composition from radiocobalt by-products may prove to be even more important in the context of $^{61}$Cu purification. In considering QC of $^{61}$Cu, Section 2.6 of the IAEA Radioisotopes and Radiopharmaceuticals Reports No. 1 [INTERNATIONAL ATOMIC ENERGY AGENCY, Cyclotron produced radionuclides: Emerging positron emitters for medical applications: $^{64}$Cu and $^{124}$I, Radioisotopes and Radiopharmaceuticals Reports 1, IAEA, Vienna (2016) 63, incorporated herein in its entirety] presents in great detail on $^{64}$Cu radionuclidic purity, and molar activity.

In certain embodiments, the high-purity radionuclide composition is produced via the deuteron irradiation of natural nickel or $^{60}$Ni, or via the proton irradiation of $^{61}$Ni, wherein the composition comprises one or more of the following:

$^{56}$Co≤1500 Bq/g;
$^{57}$Co≤100 Bq/g;
$^{58}$Co≤15000 Bq/g; and
$^{60}$Co≤15 Bq/g.

In certain embodiments, the high-purity radionuclide composition is produced via the deuteron irradiation of natural nickel or $^{60}$Ni, or via the proton irradiation of $^{61}$Ni, wherein the composition comprises two or more of the following:

$^{56}$Co≤1500 Bq/g;
$^{57}$Co≤100 Bq/g;
$^{58}$Co≤15000 Bq/g;
$^{60}$Co≤15 Bq/g; and/or
having two or more of the following:
$^{110m}$Ag≤1 Bq/g;
$^{108m}$Ag≤1 Bq/g; and
$^{109}$Cd≤1 Bq/g.

In certain embodiments, the high-purity radionuclide composition is produced via the deuteron irradiation of natural nickel or $^{60}$Ni, or via the proton irradiation of $^{61}$Ni, wherein the radionuclide is not a Cu radionuclide and the composition comprises one or more of the following:

$^{110m}$Ag≤0.1 Bq/g;
$^{108m}$Ag≤0.1 Bq/g; and
$^{109}$Cd≤0.1 Bq/g.

4.5.2.1 Specific Activity of radionuclide

Specific activity measurements are provided for the [$^{61}$Cu]$CuCl_2$ starting material to produce the pharmaceutical compositions of the present disclosure. Methods of determining specific activity are known in the art, In certain embodiments, a composition provided is characterized by a specific activity of ≥0.5 GBq/mg, e.g., ≥1 GBq/mg, ≥1.5 GBq/mg, ≥2.0 GBq/mg, ≥3.0 GBq/mg, ≥4.0 GBq/mg, ≥5.0 GBq/mg, ≥6.0 GBq/mg, ≥7.0 GBq/mg, ≥8.0 GBq/mg, ≥9.0 GBq/mg, or ≥10.0 GBq/mg.

In certain embodiments, a composition provided herein as a specific activity of 0.5 to 10.0 GBq/mg, for example, 1.0 to 10.0 GBq/mg, 2.0 to 10.0 GBq/mg, 3.0 to 10.0 GBq/mg, 4.0 to 10.0 GBq/mg, 5.0 to 10.0 GBq/mg, 6.0 to 10.0 GBq/mg, 7.0 To 10.0 GBq/mg, 8.0 to 10.0 GBq/mg, 9.0 to 10.0 GBq/mg, 0.5 to 5.0 GBq/mg, 1.0 to 5.0 GBq/mg, 2.0 to 5.0 GBq/mg, 3.0 to 5.0 GBq/mg, or 4.0 to 5.0 GBq/mg.

In certain embodiments, t a composition provided herein as a specific activity of 0.5 to 1.9 GBq/mg, 0.55 to 1.85 GBq/mg, 0.6 to 1.8 GBq/mg, 0.65 to 1.75 GBq/mg, 0.7 to 1.7 GBq/mg, 0.75 to 1.65 GBq/mg, 0.8 to 1.6 GBq/mg, 0.85 to 1.55 GBq/mg, 0.9 to 1.5 GBq/mg, 0.95 to 1.45 GBq/mg, 1 to 1.4 GBq/mg, 1.05 to 1.35 GBq/mg, 1.1 to 1.3 GBq/mg, 1.15 to 1.25 GBq/mg, 0.6 to 1.3 GBq/mg, 0.65 to 1.25 GBq/mg, 0.7 to 1.2 GBq/mg, 0.75 to 1.15 GBq/mg, 0.8 to 1.1 GBq/mg, or 0.85 to 1.05 GBq/mg.

In certain embodiments, a composition provided herein as a specific activity of at least 0.5 GBq/mg, e.g., at least 1 GBq/mg, at least 1.5 GBq/mg, at least 2.0 GBq/mg, at least 3.0 GBq/mg, at least 4.0 GBq/mg, at least 5.0 GBq/mg, at least 6.0 GBq/mg, at least 7.0 GBq/mg, at least 8.0 GBq/mg, at least 9.0 GBq/mg, or at least 10.0 GBq/mg.

In certain embodiments, a composition provided herein as a specific activity from 0.5 GBq/mg to 10.0 GBq/mg, such as, for example, from 1.0 GBq/mg to 10.0 GBq/mg, from 2.0 GBq/mg to 10.0 GBq/mg, from 3.0 GBq/mg to 10.0 GBq/mg, from 4.0 GBq/mg to 10.0 GBq/mg, from 5.0 GBq/mg to 10.0 GBq/mg, from 6.0 GBq/mg to 10.0 GBq/mg, from 7.0 GBq/mg to 10.0 GBq/mg, from 8.0 GBq/mg to 10.0 GBq/mg, from 9.0 GBq/mg to 10.0 GBq/mg, from 0.5 GBq/mg to 5.0 GBq/mg, from 1.0 GBq/mg to 5.0 GBq/mg, from 2.0 GBq/mg to 5.0 GBq/mg, from 3.0 GBq/mg to 5.0 GBq/mg, or from 4.0 GBq/mg to 5.0 GBq/mg.

In certain embodiments, a composition provided herein as a specific activity from 0.5 GBq/mg to 1.9 GBq/mg, from 0.55 GBq/mg to 1.85 GBq/mg, from 0.6 GBq/mg to 1.8 GBq/mg, from 0.65 GBq/mg to 1.75 GBq/mg, from 0.7 GBq/mg to 1.7 GBq/mg, from 0.75 GBq/mg to 1.65 GBq/mg, from 0.8 GBq/mg to 1.6 GBq/mg, from 0.85 GBq/mg to 1.55 GBq/mg, from 0.9 GBq/mg to 1.5 GBq/mg, from 0.95 GBq/mg to 1.45 GBq/mg, from 1 GBq/mg to 1.4 GBq/mg, from 1.05 GBq/mg to 1.35 GBq/mg, from 1.1 GBq/mg to 1.3 GBq/mg, from 1.15 GBq/mg to 1.25 GBq/mg, from 0.6 GBq/mg to 1.3 GBq/mg, from 0.65 GBq/mg to 1.25 GBq/mg, fromis characterized by a specific activity of 0.7 to 1.2 GBq/mg, 0.75 to 1.15 GBq/mg, 0.8 to 1.1 GBq/mg, or 0.85 GBq/mg to 1.05 GBq/mg.

In certain embodiments a composition provided herein as a specific activity from 0.7 GBq/mg to 1.2 GBq/mg, from 0.75 GBq/mg to 1.15 GBq/mg, from 0.8 GBq/mg to 1.1 GBq/mg, or from 0.85 GBq/mg to 1.05 GBq/mg.

In certain embodiments, a composition provided is characterized by a specific activity of ≥0.5 GBq/mg, e.g., ≥1 GBq/mg, ≥1.5 GBq/mg, ≥2.0 GBq/mg, ≥3.0 GBq/mg, ≥4.0 GBq/mg, ≥5.0 GBq/mg, ≥6.0 GBq/mg, ≥7.0 GBq/mg, ≥8.0 GBq/mg, ≥9.0 GBq/mg, or ≥10.0 GBq/mg.

In certain embodiments, a composition provided herein as a specific activity of 0.5 to 10.0 GBq/mg, for example, 1.0 to 10.0 GBq/mg, 2.0 to 10.0 GBq/mg, 3.0 to 10.0 GBq/mg, 4.0 to 10.0 GBq/mg, 5.0 to 10.0 GBq/mg, 6.0 to 10.0 GBq/mg, 7.0 To 10.0 GBq/mg, 8.0 to 10.0 GBq/mg, 9.0 to 10.0 GBq/mg, 0.5 to 5.0 GBq/mg, 1.0 to 5.0 GBq/mg, 2.0 to 5.0 GBq/mg, 3.0 to 5.0 GBq/mg, or 4.0 to 5.0 GBq/mg.

In certain embodiments, t a composition provided herein as a specific activity of 0.5 to 1.9 GBq/mg, 0.55 to 1.85 GBq/mg, 0.6 to 1.8 GBq/mg, 0.65 to 1.75 GBq/mg, 0.7 to 1.7 GBq/mg, 0.75 to 1.65 GBq/mg, 0.8 to 1.6 GBq/mg, 0.85 to 1.55 GBq/mg, 0.9 to 1.5 GBq/mg, 0.95 to 1.45 GBq/mg, 1 to 1.4 GBq/mg, 1.05 to 1.35 GBq/mg, 1.1 to 1.3 GBq/mg, 1.15 to 1.25 GBq/mg, 0.6 to 1.3 GBq/mg, 0.65 to 1.25 GBq/mg, 0.7 to 1.2 GBq/mg, 0.75 to 1.15 GBq/mg, 0.8 to 1.1 GBq/mg, or 0.85 to 1.05 GBq/mg.

In certain embodiments, a composition provided herein as a specific activity of at least 0.5 GBq/mg, e.g., at least 1 GBq/mg, at least 1.5 GBq/mg, at least 2.0 GBq/mg, at least 3.0 GBq/mg, at least 4.0 GBq/mg, at least 5.0 GBq/mg, at least 6.0 GBq/mg, at least 7.0 GBq/mg, at least 8.0 GBq/mg, at least 9.0 GBq/mg, or at least 10.0 GBq/mg.

In certain embodiments, a composition provided herein as a specific activity from 0.5 GBq/mg to 10.0 GBq/mg, such as, for example, from 1.0 GBq/mg to 10.0 GBq/mg, from 2.0 GBq/mg to 10.0 GBq/mg, from 3.0 GBq/mg to 10.0 GBq/mg, from 4.0 GBq/mg to 10.0 GBq/mg, from 5.0 GBq/mg to 10.0 GBq/mg, from 6.0 GBq/mg to 10.0 GBq/mg, from 7.0 GBq/mg to 10.0 GBq/mg, from 8.0 GBq/mg to 10.0 GBq/mg, from 9.0 GBq/mg to 10.0 GBq/mg, from 0.5 GBq/mg to 5.0 GBq/mg, from 1.0 GBq/mg to 5.0 GBq/mg, from 2.0 GBq/mg to 5.0 GBq/mg, from 3.0 GBq/mg to 5.0 GBq/mg, or from 4.0 GBq/mg to 5.0 GBq/mg.

In certain embodiments, a composition provided herein as a specific activity from 0.5 GBq/mg to 1.9 GBq/mg, from 0.55 GBq/mg to 1.85 GBq/mg, from 0.6 GBq/mg to 1.8 GBq/mg, from 0.65 GBq/mg to 1.75 GBq/mg, from 0.7 GBq/mg to 1.7 GBq/mg, from 0.75 GBq/mg to 1.65 GBq/mg, from 0.8 GBq/mg to 1.6 GBq/mg, from 0.85 GBq/mg to 1.55 GBq/mg, from 0.9 GBq/mg to 1.5 GBq/mg, from 0.95 GBq/mg to 1.45 GBq/mg, from 1 GBq/mg to 1.4 GBq/mg, from 1.05 GBq/mg to 1.35 GBq/mg, from 1.1 GBq/mg to 1.3 GBq/mg, from 1.15 GBq/mg to 1.25 GBq/mg, from 0.6 GBq/mg to 1.3 GBq/mg, from 0.65 GBq/mg to 1.25 GBq/mg, fromis characterized by a specific activity of 0.7 to 1.2 GBq/mg, 0.75 to 1.15 GBq/mg, 0.8 to 1.1 GBq/mg, or 0.85 GBq/mg to 1.05 GBq/mg.

In certain embodiments a composition provided herein as a specific activity from 0.7 GBq/mg to 1.2 GBq/mg, from 0.75 GBq/mg to 1.15 GBq/mg, from 0.8 GBq/mg to 1.1 GBq/mg, or from 0.85 GBq/mg to 1.05 GBq/mg.

In certain embodiments, a composition provided is characterized by a specific activity of ≥0.5 GBq/μg, e.g., ≥1 GBq/μg, ≥1.5 GBq/μg, ≥2.0 GBq/μg, ≥3.0 GBq/μg, ≥4.0 GBq/μg, ≥5.0 GBq/μg, ≥6.0 GBq/μg, ≥7.0 GBq/μg, ≥8.0 GBq/μg, 9.0 GBq/μg, or ≥10.0 GBq/μg.

In certain embodiments, a composition provided herein as a specific activity of 0.5 to 10.0 GBq/μg, for example, 1.0 to 10.0 GBq/μg, 2.0 to 10.0 GBq/μg, 3.0 to 10.0 GBq/μg, 4.0 to 10.0 GBq/μg, 5.0 to 10.0 GBq/μg, 6.0 to 10.0 GBq/μg, 7.0 To 10.0 GBq/μg, 8.0 to 10.0 GBq/μg, 9.0 to 10.0 GBq/μg, 0.5 to 5.0 GBq/μg, 1.0 to 5.0 GBq/μg, 2.0 to 5.0 GBq/μg, 3.0 to 5.0 GBq/μg, or 4.0 to 5.0 GBq/μg.

In certain embodiments, t a composition provided herein as a specific activity of 0.5 to 1.9 GBq/μg, 0.55 to 1.85 GBq/μg, 0.6 to 1.8 GBq/g, 0.65 to 1.75 GBq/μg, 0.7 to 1.7 GBq/μg, 0.75 to 1.65 GBq/μg, 0.8 to 1.6 GBq/μg, 0.85 to 1.55 GBq/μg, 0.9 to 1.5 GBq/μg, 0.95 to 1.45 GBq/μg, 1 to 1.4 GBq/μg, 1.05 to 1.35 GBq/μg, 1.1 to 1.3 GBq/μg, 1.15 to 1.25 GBq/μg, 0.6 to 1.3 GBq/μg, 0.65 to 1.25 GBq/μg, 0.7 to 1.2 GBq/μg, 0.75 to 1.15 GBq/μg, 0.8 to 1.1 GBq/μg, or 0.85 to 1.05 GBq/μg.

In certain embodiments, a composition provided herein as a specific activity of at least 0.5 GBq/μg, e.g., at least 1 GBq/μg, at least 1.5 GBq/μg, at least 2.0 GBq/μg, at least 3.0 GBq/μg, at least 4.0 GBq/μg, at least 5.0 GBq/μg, at least 6.0 GBq/μg, at least 7.0 GBq/μg, at least 8.0 GBq/μg, at least 9.0 GBq/μg, or at least 10.0 GBq/μg.

In certain embodiments, a composition provided herein as a specific activity from 0.5 GBq/μg to 10.0 GBq/μg, such as, for example, from 1.0 GBq/μg to 10.0 GBq/μg, from 2.0 GBq/μg to 10.0 GBq/μg, from 3.0 GBq/μg to 10.0 GBq/μg, from 4.0 GBq/μg to 10.0 GBq/μg, from 5.0 GBq/μg to 10.0 GBq/μg, from 6.0 GBq/μg to 10.0 GBq/μg, from 7.0 GBq/μg to 10.0 GBq/μg, from 8.0 GBq/μg to 10.0 GBq/μg, from 9.0 GBq/μg to 10.0 GBq/μg, from 0.5 GBq/μg to 5.0 GBq/μg, from 1.0 GBq/μg to 5.0 GBq/μg, from 2.0 GBq/μg to 5.0 GBq/μg, from 3.0 GBq/μg to 5.0 GBq/μg, or from 4.0 GBq/μg to 5.0 GBq/μg.

In certain embodiments, a composition provided herein as a specific activity from 0.5 GBq/μg to 1.9 GBq/μg, from 0.55 GBq/μg to 1.85 GBq/μg, from 0.6 GBq/μg to 1.8 GBq/μg, from 0.65 GBq/μg to 1.75 GBq/μg, from 0.7 GBq/μg to 1.7 GBq/μg, from 0.75 GBq/μg to 1.65 GBq/μg, from 0.8 GBq/μg to 1.6 GBq/μg, from 0.85 GBq/μg to 1.55 GBq/μg, from 0.9 GBq/μg to 1.5 GBq/μg, from 0.95 GBq/μg to 1.45 GBq/μg, from 1 GBq/μg to 1.4 GBq/μg, from 1.05 GBq/μg to 1.35 GBq/μg, from 1.1 GBq/μg to 1.3 GBq/μg, from 1.15 GBq/μg to 1.25 GBq/μg, from 0.6 GBq/μg to 1.3 GBq/μg, from 0.65 GBq/μg to 1.25 GBq/μg, from is characterized by a specific activity of 0.7 to 1.2 GBq/μg, 0.75 to 1.15 GBq/μg, 0.8 to 1.1 GBq/μg, or 0.85 GBq/μg to 1.05 GBq/μg.

In certain embodiments a composition provided herein as a specific activity from 0.7 GBq/μg to 1.2 GBq/μg, from 0.75

GBq/μg to 1.15 GBq/μg, from 0.8 GBq/μg to 1.1 GBq/μg, or from 0.85 GBq/μg to 1.05 GBq/μg.

4.5.2.2 Chemical Purity

In certain embodiments, the radionuclide composition is characterized for "chemical purity," which is understood herein as the molar percent of the identified or desired radionuclide to all metals in the sample. The radionuclide compositions prepared by the disclosed methods herein exhibit high chemical purity, which facilitates the production of radiopharmaceuticals with high radiochemical purity. Radiochemical purity, as understood herein, is the ratio or percent of reactivity from the desired radionuclide in the radiopharmaceutical to the total radioactivity of the sample that includes the radiopharmaceutical. Non-radioactive isotopes of metals ("cold" metals) will not contribute to the total radioactivity of a sample, but they can compete with the desired radionuclide for inclusion in the radiopharmaceutical, e.g., competing for chelation sites in the radiopharmaceutical.

In certain embodiments, the radionuclide composition according to the present disclosure has a chemical purity of ≥99.0% by mole. In certain embodiments, the radionuclide composition is prepared according to the methods provided herein.

In certain embodiments, the radionuclidic composition is an aqueous solution and is characterized by one or more of the following:

Fe≤2 μg/L;

$^{69}$Cu and $^{65}$Cu together are ≤1 μg/L;

Zn(II)≤2 μg/L;

Sn(IV)≤0.01 μg/L;

Ti(IV)≤0.01 μg/L;

Al(III)≤2 μg/L;

As≤1 μg/L;

Ni≤1 μg/L; and wherein any one of Cr, Cd, Co, and Y is ≤0.1 μg/mL.

In certain embodiments, the radionuclidic composition is by comprising Fe≤2 μg/L. In certain embodiments, iron is present in ≤3 μg/L, ≤2.9 μg/L, ≤2.8 μg/L, ≤2.7 μg/L, ≤2.6 μg/L, ≤2.5 μg/L, 2.4 μg/L, 2.3 μg/L, 2.2 μg/L, 2.1 μg/L, 2 μg/L, ≤1.9 μg/L, 1.8 μg/L, 1.7 μg/L, 1.6 μg/L, 1.5 μg/L, 1.4 μg/L, 1.3 μg/L, 1.2 μg/L, ≤1.1 μg/L, ≤1 μg/L, 0.9 μg/L, ≤0.8 μg/L, ≤0.7 μg/L, ≤0.6 μg/L, ≤0.5 μg/L, ≤0.4 μg/L, ≤0.3 μg/L, ≤0.2 μg/L, or ≤0.1 μg/L.

In certain embodiments, the radionuclidic composition is characterized by comprising Cu (non-radioactive)≤1 μg/L. In certain embodiments, Cu (non-radioactive ) is present in ≤2 μg/L, ≤1.9 μg/L, ≤1.8 μg/L, ≤1.7 μg/L, ≤1.6 μg/L, ≤1.5 μg/L, ≤1.4 μg/L, ≤1.3 μg/L, ≤1.2 μg/L, ≤1.1 μg/L, ≤1 μg/L, 0.9 μg/L, 0.8 μg/L, 0.7 μg/L, 0.6 μg/L, 0.5 μg/L, 0.4 μg/L, 0.3 μg/L, ≤0.2 μg/L, or ≤0.1 μg/L.

In certain embodiments, the radionuclidic composition is characterized by comprising Ni ≤1 μg/L. In certain embodiments, nickel is present in ≤4.5 μg/L, ≤4.4 μg/L, ≤4.3 μg/L, ≤4.2 μg/L, ≤4.1 μg/L, 4 μg/L, 3.9 μg/L, 3.8 μg/L, ≤3.7 μg/L, 3.6 μg/L, ≤3.5 μg/L, 3.4 μg/L, ≤3.3 μg/L, 3.2 μg/L, 3.1 μg/L, 3 μg/L, 2.9 μg/L, ≤2.8 μg/L, ≤2.7 μg/L, ≤2.6 g/L, ≤2.5 μg/L, ≤2.4 μg/L, 2.3 μg/L, ≤2.2 μg/L, 2.1 μg/L, 2 μg/L, 1.9 μg/L, 1.8 μg/L, 1.7 μg/L, ≤1.6 μg/L, 1.5 μg/L, 1.4 μg/L, 1.3 μg/L, ≤1.2 μg/L, ≤1.1 μg/L, 1 μg/L, ≤0.9 μg/L, ≤0.8 μg/L, ≤0.7 μg/L, ≤0.6 μg/L, ≤0.5 μg/L, ≤0.4 μg/L, ≤0.3 μg/L, ≤0.2 μg/L, or ≤0.1 μg/L.

In certain embodiments, the radionuclide composition is an embodiment as described above, further characterized by one or more of: an activity concentration of 0.60-0.66 GBq/mL at EoB+2 hours; a molar activity of 10-100 MBq/nmol at EoB+2 hours; and an activity of ≥500 MBq at EoB+2 hrs. An embodiment, as described above, further characterized by one or more of: an activity concentration of ≥25 MBq/mL at EoB+2 hours, a molar activity of 10-150 MBq/nmol at EoB+2 hours, and an activity of ≥150 MBq at the EoB+2 hrs.

An embodiment as described above, further characterized by one or more of: an activity concentration of 0.60-0.66 GBq/mL at EoB+2 hours; a molar activity of 10-100 MBq/nmol at EoB+2 hours; and an activity at end of synthesis of ≥500 MBq.

4.5.3. Activity Concentration

Activity concentration is the total amount of radioactivity per unit volume of the [$^{61}$Cu]$CuCl_2$ starting material.

In certain embodiments, ≥0.5 GBq/mL, e.g., ≥1 GBq/mL, ≥1.5 GBq/mL, ≥2.0 GBq/mL, ≥3.0 GBq/mL, ≥4.0 GBq/mL, ≥5.0 GBq/mL, ≥6.0 GBq/mL, ≥7.0 GBq/mL, ≥8.0 GBq/mL, ≥9.0 GBq/mL, or ≥10.0 GBq/mL.

In certain embodiments, a composition provided is characterized by an activity concentration 0.5 to 10.0 GBq/mL, for example, 1.0 to 10.0 GBq/mL, 2.0 to 10.0 GBq/mL, 3.0 to 10.0 GBq/mL, 4.0 to 10.0 GBq/mL, 5.0 to 10.0 GBq/mL, 6.0 to 10.0 GBq/mL, 7.0 to 10.0 GBq/mL, 8.0 to 10.0 GBq/mL, 9.0 to 10.0 GBq/mL, 0.5 to 5.0 GBq/mL, 1.0 to 5.0 GBq/mL, 2.0 to 5.0 GBq/mL, 3.0 to 5.0 GBq/mL or 4.0 to 5.0 GBq/mL.

In certain embodiments, a composition provided is characterized by an activity concentration of 0.5 to 1.9 GBq/mL, 0.55 to 1.85 GBq/mL, 0.6 to 1.8 GBq/mL, 0.65 to 1.75 GBq/mL, 0.7 to 1.7 GBq/mL, 0.75 to 1.65 GBq/mL, 0.8 to 1.6 GBq/mL, 0.85 to 1.55 GBq/mL, 0.9 to 1.5 GBq/mL, 0.95 to 1.45 GBq/mL, 1 to 1.4 GBq/mL, 1.05 to 1.35 GBq/mL, 1.1 to 1.3 GBq/mL, 1.15 to 1.25 GBq/mL, 0.6 to 1.3 GBq/mL, 0.65 to 1.25 GBq/mL, 0.7 to 1.2 GBq/mL, 0.75 to 1.15 GBq/mL, 0.8 to 1.1 GBq/mL, or 0.85 to 1.05 GBq/mL.

In certain embodiments, a pharmaceutical formulation composition provided is characterized by an activity concentration 0.3 to 0.75 GBq/mL.

The activity concentration of the resulting pharmaceutical composition will be diluted by a factor of 3 to 10 as long as the activity concentration is ≥8 MBq/mL. In certain embodiments, a composition provided is characterized by an activity concentration 8 to 20 MBq/mL, 9 to 19 MBq/mL, 10 to 18 MBq/mL, 11 to 19 MBq/mL, 12 to 18 MBq/mL, 13 to 15 MBq/mL, 14 to 15 MBq/mL, 8 to 14 MBq/mL, 8 to 13 MBq/mL, 8 to 12 MBq/mL, 8 to 11 MBq/mL, 8 to 10 MBq/mL, 8 to 9 MBq/mL, 9 to 14 MBq/mL, 10 to 13 MBq/mL, or 11 to 12 MBq/mL.

4.6. Enumerated Embodiments

Enumerated Embodiments Group A

Embodiment 1a: A compound, wherein the compound is of Formula X*:

Formula X*

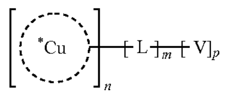

or is a pharmaceutically acceptable salt thereof, wherein:

the chelating moiety is NODAGA;

Cu is $^{61}Cu$ or $^{67}Cu$;

L is;

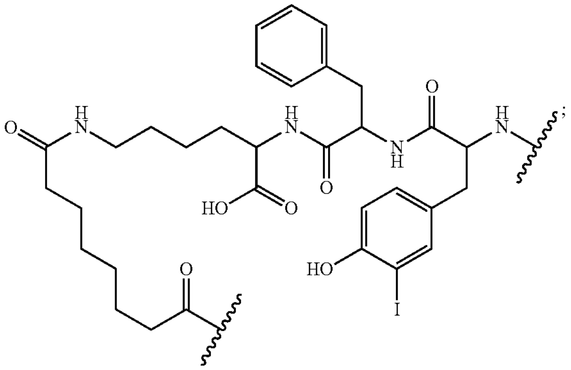 [SMILES: *NC(Cc1ccc(O)c(I)c1)C(=O)NC(Cc1ccccc1)C(=O)NC(CCCCNC(=O)CCCCCCC(*)=O)C(=O)O]

V is a targeting moiety that binds to PSMA;

n is 1;

L is

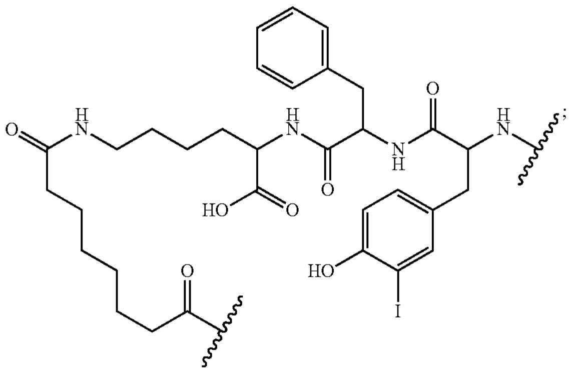 [SMILES: *NC(Cc1ccc(O)c(I)c1)C(=O)NC(Cc1ccccc1)C(=O)NC(CCCCNC(=O)CCCCCCC(*)=O)C(=O)O]

V is a targeting moiety that binds to PSMA;

n is 1;

m is 1; and p is 1.

Embodiment 1. A compound of any preceding embodiment, wherein the compound is of Formula 10:

Formula 10

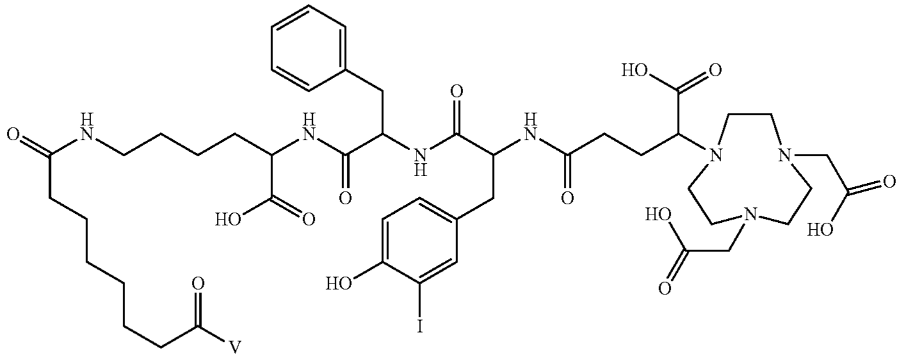

m is 1; and p is 1.

Embodiment 1b: A compound of any preceding embodiment, wherein the compound is of Formula X:

Formula X

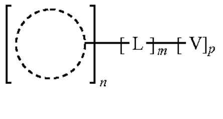

or is a pharmaceutically acceptable salt thereof, wherein:

the chelating moiety is NODAGA;

Cu is a copper radionuclide selected from $^{61}Cu$, $^{62}Cu$, $^{64}Cu$, and $^{67}Cu$;

or is a pharmaceutically acceptable salt thereof;

wherein V comprises a targeting moiety that binds to PSMA.

Embodiment 2. The compound of any preceding embodiment, wherein V comprises means for binding PSMA.

Embodiment 3. The compound of any preceding embodiment, wherein V comprises the structure:

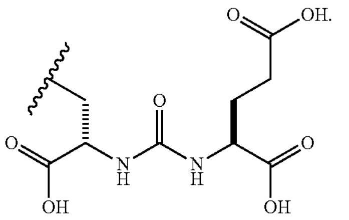 [SMILES: *C[C@H](NC(=O)N[C@@H](CCC(=O)O)C(=O)O)C(=O)O]

Embodiment 4. The compound of any preceding embodiment, wherein the compound is of the structure:

or is a pharmaceutically acceptable salt thereof.

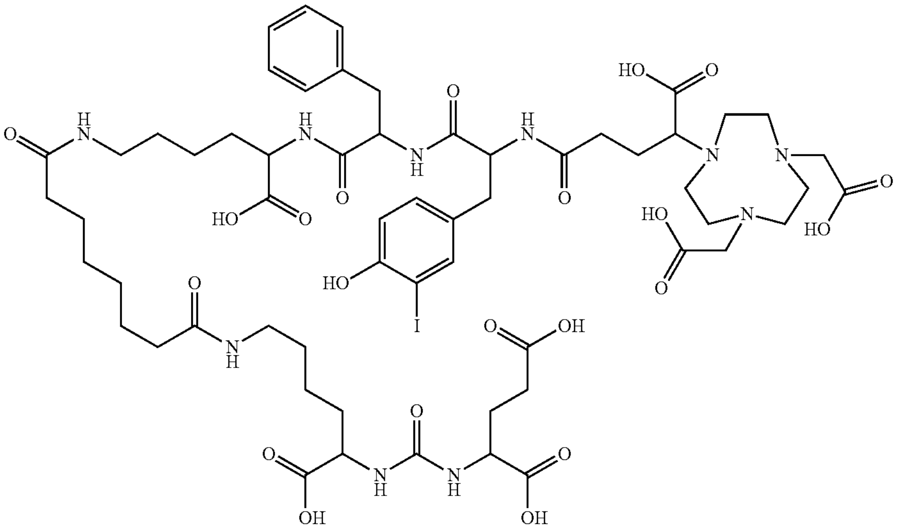 [SMILES: O=C(O)CCC(NC(=O)NC(CCCCNC(=O)CCCCCCC(=O)NCCCCC(NC(=O)C(Cc1ccccc1)NC(=O)C(Cc1ccc(O)c(I)c1)NC(=O)CCC(C(=O)O)N1CCN(CC(=O)O)CCN(CC(=O)O)CC1)C(=O)O)C(=O)O)C(=O)O]

Embodiment 5. The compound of any preceding embodiment, wherein the compound is of the structure:

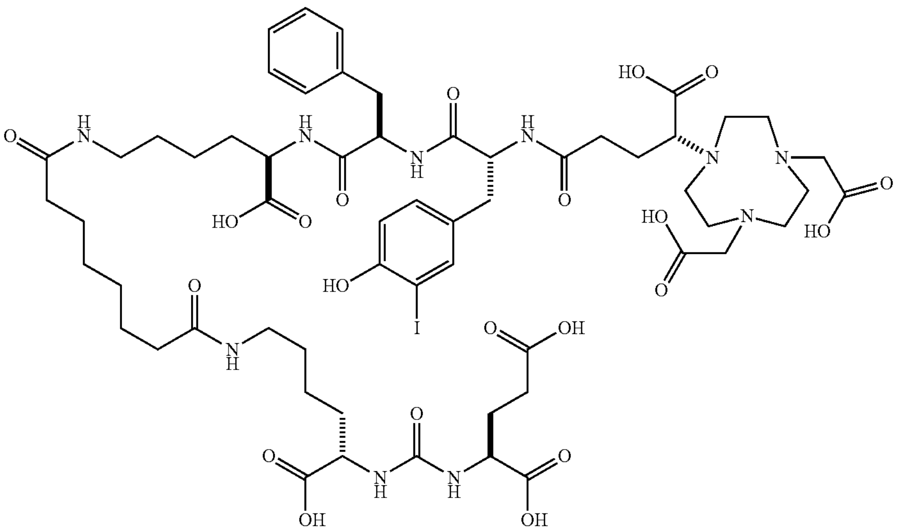

or is a pharmaceutically acceptable salt thereof.

Embodiment 6a: A compound of any preceding embodiment, wherein the compound is of Formula X*:

Formula X*

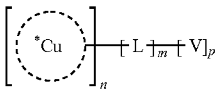

or is a pharmaceutically acceptable salt thereof, wherein:

the chelating moiety is NODAGA;

*Cu is a copper radionuclide selected from $^{61}Cu$, $^{62}Cu$, $^{64}Cu$, and $^{67}Cu$;

L is

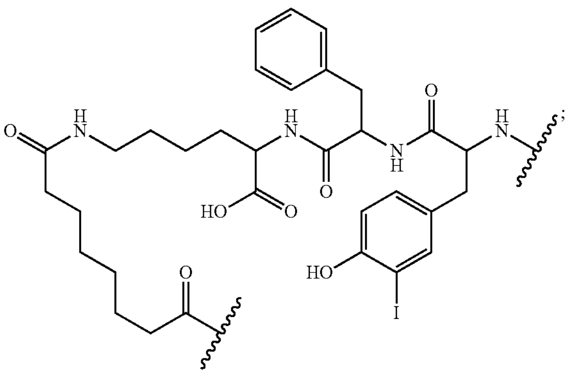 [SMILES: *NC(Cc1ccc(O)c(I)c1)C(=O)NC(Cc1ccccc1)C(=O)NC(CCCCNC(=O)CCCCCCC(*)=O)C(=O)O]

V is a targeting moiety that binds to PSMA;
n is 1;
m is 1; and
p is 1.

Embodiment 6. A compound of any preceding embodiment comprising a copper atom chelated by the compound of embodiment 1, wherein the compound is a structure of Formula 10*:

Formula 10*

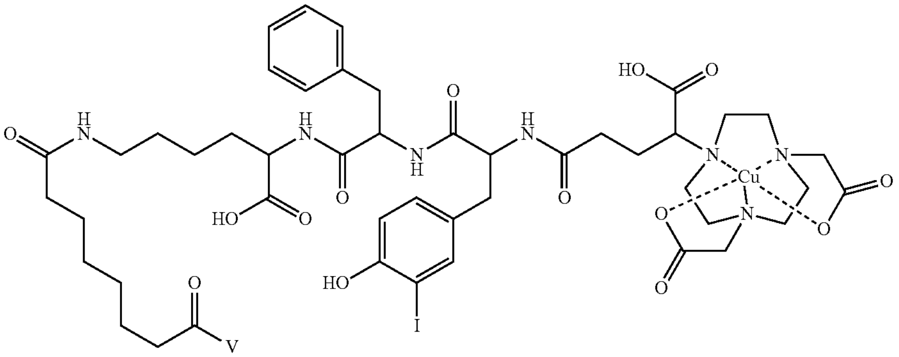

or is a pharmaceutically acceptable salt thereof;

wherein *Cu is a copper radionuclide selected from $^{61}Cu$, $^{62}Cu$, $^{64}Cu$, and $^{67}Cu$.

Embodiment 7. The compound of embodiment 6a or 6, wherein *Cu is $^{61}Cu$.

Embodiment 8. The compound of embodiment 6a or 6, wherein *Cu is $^{67}Cu$.

Embodiment 9. The compound of any preceding embodiment, wherein V comprises the structure:

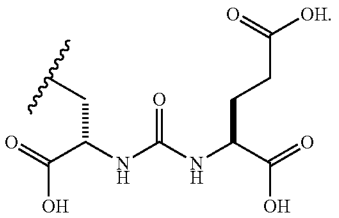 [SMILES: *C[C@H](NC(=O)N[C@@H](CCC(=O)O)C(=O)O)C(=O)O]

Embodiment 10. The compound of embodiments 1-6 and 8-9, wherein the compound is of the structure:

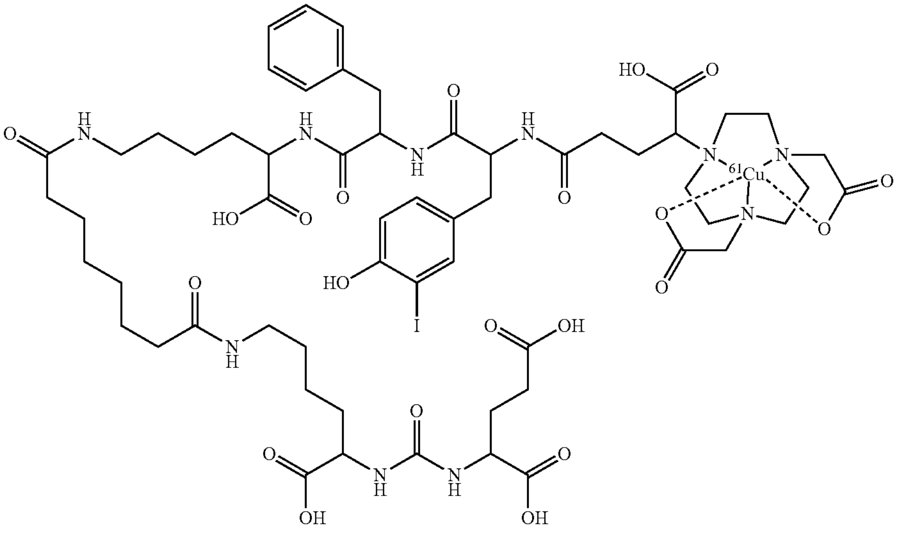

or is a pharmaceutically acceptable salt thereof.

Embodiment 11. The compound of embodiments 1-7 and 9, wherein the compound is of the structure:
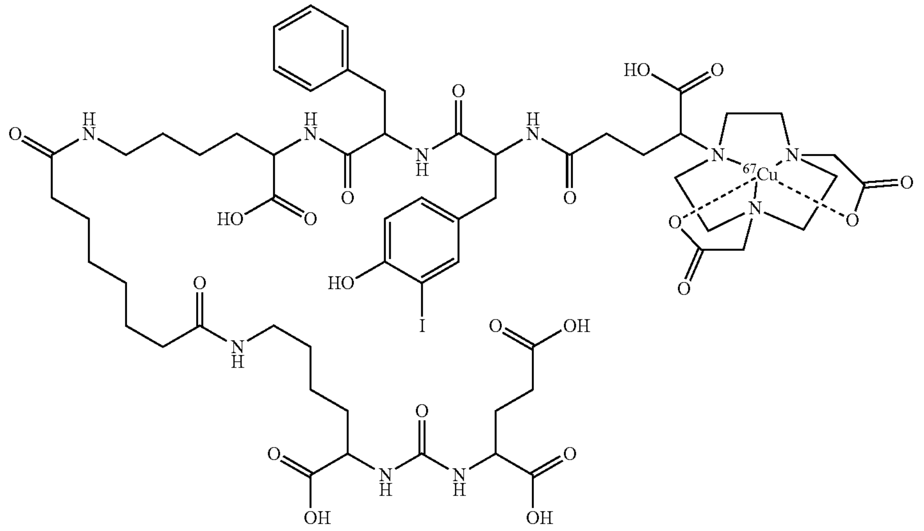
or is a pharmaceutically acceptable salt thereof.
Embodiment 12. The compound of embodiment 10, wherein the compound is of the structure:
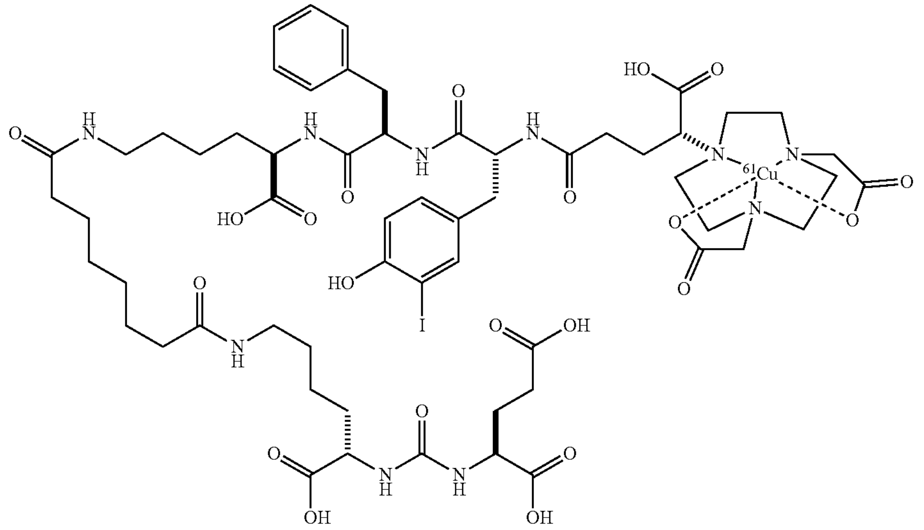
or is a pharmaceutically acceptable salt thereof.
Embodiment 13. The compound embodiment 11, wherein the compound is of the structure:

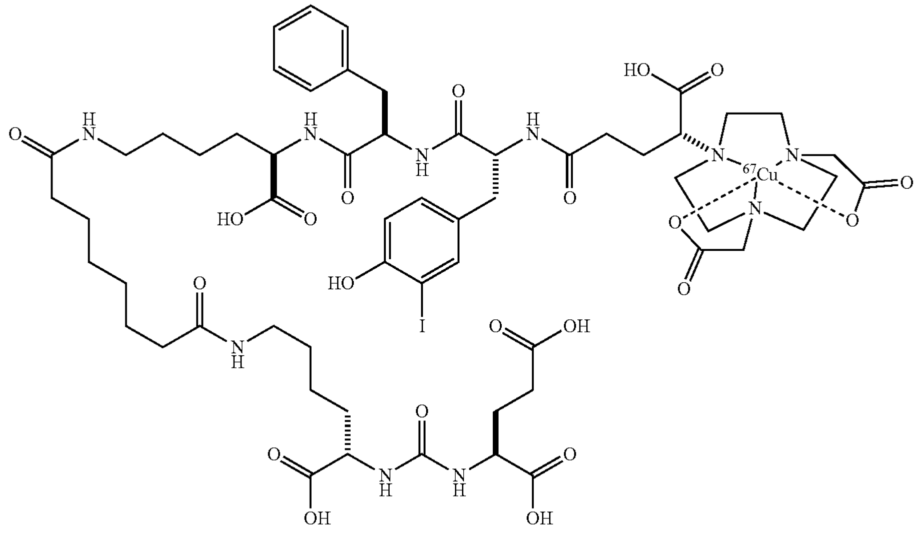

or is a pharmaceutically acceptable salt thereof.

Embodiment 14. A pharmaceutical composition comprising a compound of any preceding embodiment and a pharmaceutically acceptable excipient, wherein the composition is characterized by one or more of:

molar activity of ≥3 MBq/nmol;

radiochemical purity ≥91%;

activity concentration of ≥8 MBq/mL;

radionuclidic purity of the compound at end of synthesis (EoB plus 2 hours) ≥95%; and pH of 4-7.

Embodiment 15. The composition of any preceding embodiment, wherein the composition is characterized by a molar activity of ≥3 MBq/nmol, e.g., ≥10 MBq/nmol, from 10 to 250 MBq/nmol, from 20 to 250 MBq/nmol, from 50 to 250 MBq/nmol, from 50 to 200 MBq/nmol, from 50 to 150 MBq/nmol, from 50 to 100 MBq/nmol, from 100 to 250 MBq/nmol, from 100 to 150 MBq/nmol, from 150 to 250 MBq/nmol, from 150 to 200 MBq/nmol, or from 200 to 250 MBq/nmol.

Embodiment 16. The composition of any preceding embodiment, wherein the composition is characterized by radiochemical purity of ≥91%, e.g., ≥95%, ≥95.5%, ≥96%, ≥96.5%, ≥97%, ≥97.5%, ≥98%, ≥98.5%, ≥99%, or ≥99.5%.

Embodiment 17. The composition of any preceding embodiment, wherein the composition is characterized by activity concentration of ≥8 MBq/mL, e.g., 8 to 400 MBq/mL, 8 to 350 MBq/mL, 8 to 300 MBq/mL, 8 to 250 MBq/mL, 8 to 200 MBq/mL, 8 to 150 MBq/mL, 8 to 100 MBq/mL, 8 to 100 MBq/mL 8 to 50 MBq/mL, 8 to 25 MBq/mL, or 8 to 15 MBq/mL.

Embodiment 18. The composition of any preceding embodiment, wherein the composition is characterized by radionuclidic purity of the compound at end of synthesis of ≥95%, e.g., ≥95.5%, ≥96%, ≥96.5%, ≥97%, ≥97.5%, ≥98%, ≥98.5%, ≥99%, ≥99.1%, ≥99.2%, ≥99.3%, ≥99.4%, ≥99.5%, ≥99.6%, ≥99.7%, ≥99.8%, ≥99.9%, or ≥99.99%.

Embodiment 19. The composition of any preceding embodiment, wherein the composition is characterized by radionuclidic purity of the sum of radiocobalt compounds at end of synthesis (EoB plus 2 hours) of ≤0.05%, e.g., ≤0.04%, ≤0.03%, ≤0.02%, or ≤0.01%.

Embodiment 20. The composition of any preceding embodiment, wherein the composition is characterized by pH of 4-7.

Embodiment 21. A composition comprising a compound of any preceding embodiment and a pharmaceutically acceptable excipient, wherein the composition is characterized by one or more of:

molar activity of ≥20 MBq/nmol;

radiochemical purity of ≥91%;

activity concentration of 8 to 100 MBq/mL;

radionuclidic purity of the compound at end of synthesis (EoB plus 2 hours) of ≥95%; and pH of 4-7.

Embodiment 22. The composition of any preceding embodiment, wherein the composition is characterized by a molar activity of ≥20 MBq/nmol, e.g., from 20 to 250 MBq/nmol, from 50 to 250 MBq/nmol, from 50 to 200 MBq/nmol, from 50 to 150 MBq/nmol, from 50 to 100 MBq/nmol, from 100 to 250 MBq/nmol, from 100 to 150 MBq/nmol, from 150 to 250 MBq/nmol, from 150 to 200 MBq/nmol, or from 200 to 250 MBq/nmol.

Embodiment 23. The composition of any preceding embodiment, wherein the composition is characterized by radiochemical purity of ≥91%, e.g., ≥95%, ≥95.5%, ≥96.0%, ≥96.5%, ≥97.0%, ≥97.5%, ≥98.0%, ≥98.5%, ≥99.0%, or ≥99.5%.

Embodiment 24. The composition of any preceding embodiment, wherein the composition is characterized by activity concentration of 8 to 100 MBq/mL, e.g., 8 to 15 MBq/mL.

Embodiment 25. The composition of any preceding embodiment, wherein the composition is characterized by radionuclidic purity of the compound at end of synthesis of ≥95.0%, e.g., ≥95.5%, ≥96%, ≥96.5%, ≥97%, ≥97.5%, ≥98%, ≥98.5%, ≥99%, ≥99.1%, ≥99.2%, ≥99.3%, ≥99.4%, ≥99.5%, ≥99.6%, ≥99.7%, ≥99.8%, or ≥99.9%.

Embodiment 26. The composition of any preceding embodiment, wherein the composition is characterized by radionuclidic purity of the sum of radiocobalt compounds at end of synthesis (EoB plus 2 hours) of ≤0.05%, e.g., ≤0.04%, ≤0.03%, ≤0.02%, or ≤0.01%.

Embodiment 27. A method of generating one or more images of a subject, comprising: administering to the subject an effective amount of a composition according to embodiment 14; and generating one or more images of at least a part of the subject's body.

Embodiment 28. The method of embodiment 27, wherein the one or more images is generated using positron emission tomography (PET) or single-photon emission computerized tomography (SPECT).

Embodiment 29. A method of treating cancer a patient, comprising administering to the patient an effective amount of the composition of embodiment 21.

Embodiment 30. A theranostic method comprising:

(a) administering to a subject an effective amount of a composition according to embodiment 14;

(b) generating one or more images of at least part a of the subject's body; and (c) administering to the subject an effective amount of a composition comprising the compound of any preceding embodiment.

Enumerated Embodiments Group B

Embodiment 1a. A pharmaceutical composition comprising a compound and a pharmaceutically acceptable excipient, wherein the compound is of Formula X*:

Formula X*

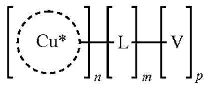

or is a pharmaceutically acceptable salt thereof, wherein: the chelating moiety is NODAGA;

Cu is a copper radionuclide selected from $^{61}Cu$, $^{62}Cu$, $^{64}Cu$, and $^{67}Cu$;

L is linker moiety; V is a targeting moiety SST that binds to SSTR; n is 1; m is 1; and p is 1.

Embodiment 1. A pharmaceutical composition comprising a compound and a pharmaceutically acceptable excipient, wherein the compound is of Formula 20:

Formula 20

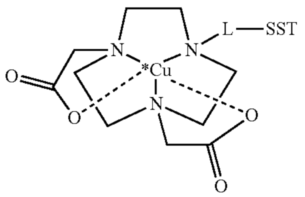

or is a pharmaceutically acceptable salt thereof;

wherein:

Cu is a copper radionuclide selected from $^{61}Cu$, $^{62}Cu$, and $^{67}Cu$;

L is a bond or a linker moiety; and

SST is a targeting moiety that binds to a somatostatin receptor.

Embodiment 2. The composition of embodiment 1, wherein the composition is characterized by one or more of:

molar activity of ≥3 MBq/nmol;

radiochemical purity ≥91%;

activity concentration of ≥8 MBq/mL;

radionuclidic purity of the compound at end of synthesis (EoB plus 2 hours) ≥95%; and pH of 4-7.

Embodiment 3. The composition of any preceding embodiment, wherein the composition is characterized by molar activity of ≥3 MBq/nmol, e.g., ≥10 MBq/nmol, from 10 to 250 MBq/nmol, from 20 to 250 MBq/nmol, from 50 to 250 MBq/nmol, from 50 to 200 MBq/nmol, from 50 to 150 MBq/nmol, from 50 to 100 MBq/nmol, from 100 to 250 MBq/nmol, from 100 to 150 MBq/nmol, from 150 to 250 MBq/nmol, from 150 to 200 MBq/nmol, or from 200 to 250 MBq/nmol.

Embodiment 4. The composition of any preceding embodiment, wherein the composition is characterized by radiochemical purity of ≥91%, e.g., ≥95%, ≥95.5%, ≥96%, ≥96.5%, ≥97%, ≥97.5%, ≥98%, ≥98.5%, ≥99%, or ≥99.5%.

Embodiment 5. The composition of any preceding embodiment wherein the composition is characterized by activity concentration of ≥8 MBq/mL, e.g., 8 to 400 MBq/mL, 8 to 350 MBq/mL, 8 to 300 MBq/mL, 8 to 250 MBq/mL, 8 to 200 MBq/mL, 8 to 150 MBq/mL, 8 to 100 MBq/mL, 8 to 100 MBq/mL 8 to 50 MBq/mL, 8 to 25 MBq/mL, or 8 to 15 MBq/mL.

Embodiment 6. The composition of any preceding embodiment, wherein the composition is characterized by radionuclidic purity of the compound at end of synthesis of ≥95%, e.g., ≥95.5%, ≥96%, ≥96.5%, ≥97%, ≥97.5%, ≥98%, ≥98.5%, ≥99%, ≥99.1%, ≥99.2%, ≥99.3%, ≥99.4%, ≥99.5%, ≥99.6%, ≥99.7%, ≥99.8%, ≥99.9%, or ≥99.99%.

Embodiment 7. The composition of any preceding embodiment, wherein the composition is characterized by pH of 4-7.

Embodiment 8. The composition of any preceding embodiment, wherein SST comprises means for binding a somatostatin receptor.

Embodiment 9. The composition of any preceding embodiment, wherein SST comprises the structure:

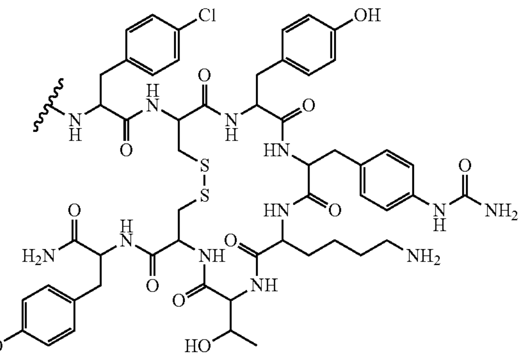

Embodiment 10. The composition of any preceding embodiment, wherein SST comprises the structure:

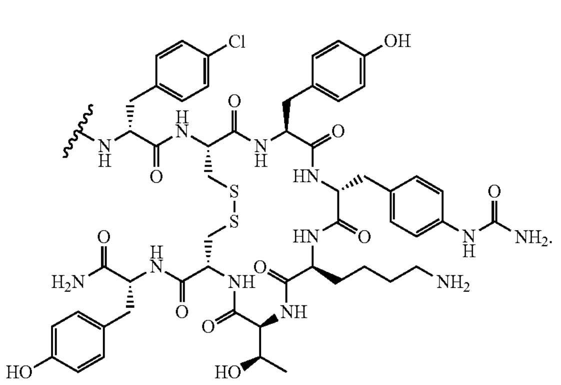 [SMILES: *N[C@H](Cc1ccc(Cl)cc1)C(=O)N[C@H]1CSSC[C@@H](C(=O)N[C@H](Cc2ccc(O)cc2)C(N)=O)NC(=O)[C@H]([C@@H](C)O)NC(=O)[C@H](CCCCN)NC(=O)[C@@H](Cc2ccc(NC(N)=O)cc2)NC(=O)[C@H](Cc2ccc(O)cc2)NC1=O]

Embodiment 11. The composition of any preceding embodiment, wherein the compound is of the structure:

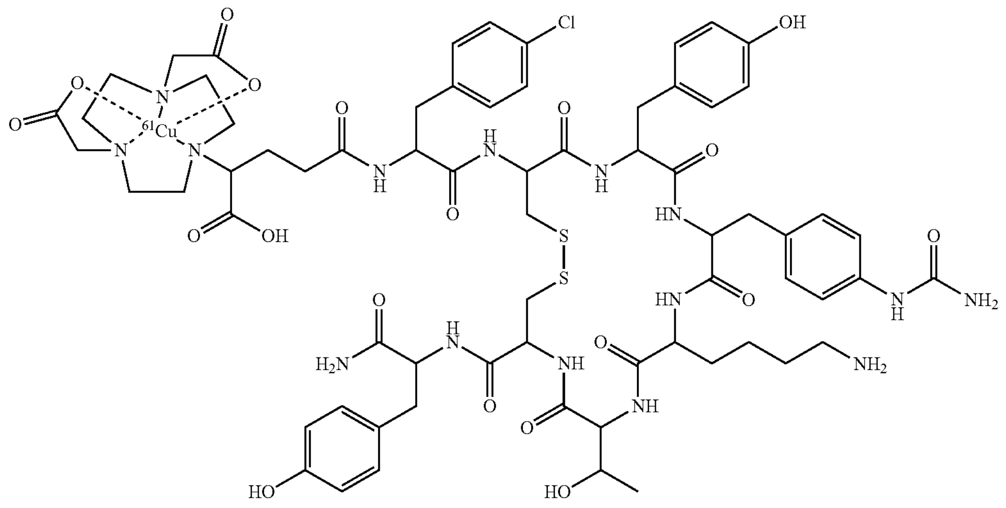

or is a pharmaceutically acceptable salt thereof.

Embodiment 12. The composition of any preceding embodiment, wherein the compound is of the structure:

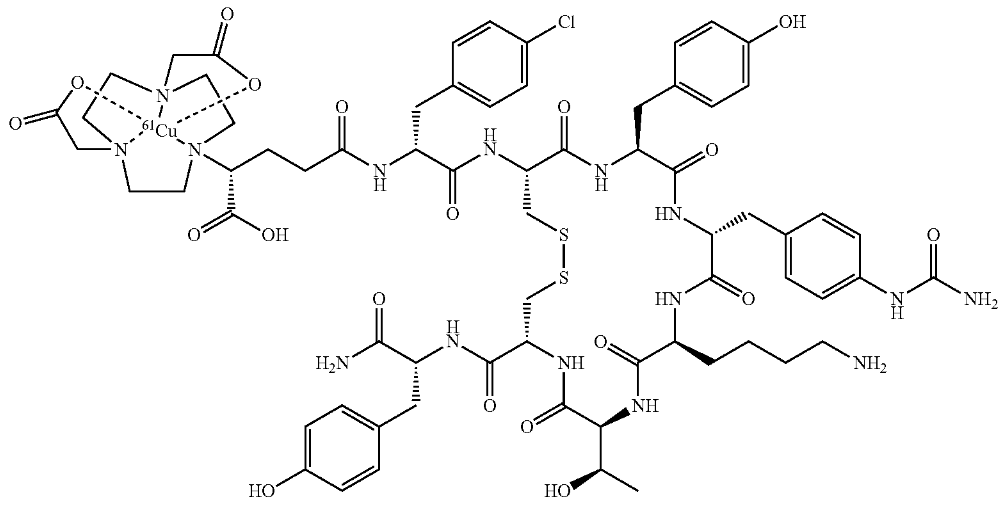

or is a pharmaceutically acceptable salt thereof.

Embodiment 13. The composition of any preceding embodiment, wherein the compound is of the structure:

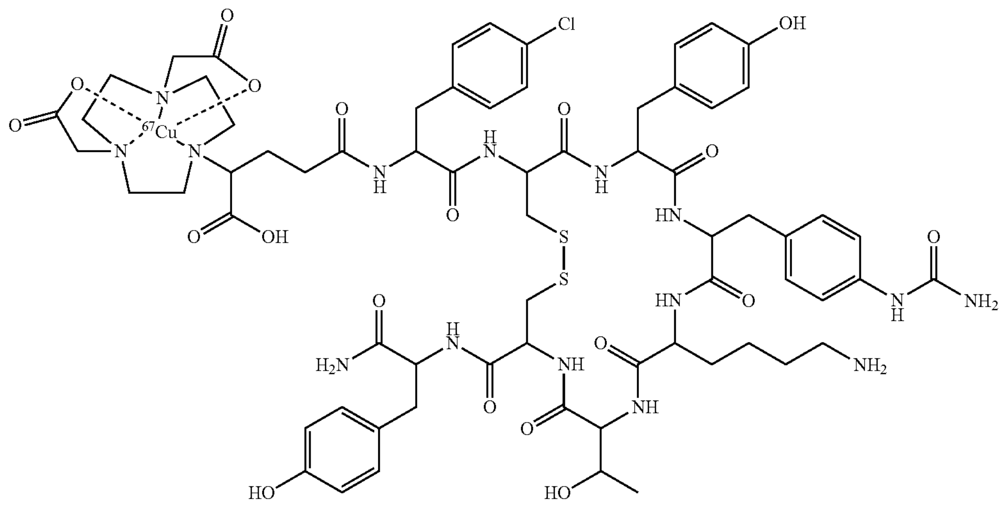

or is a pharmaceutically acceptable salt thereof.

Embodiment 14. The composition of any preceding embodiment, wherein the compound is of the structure:

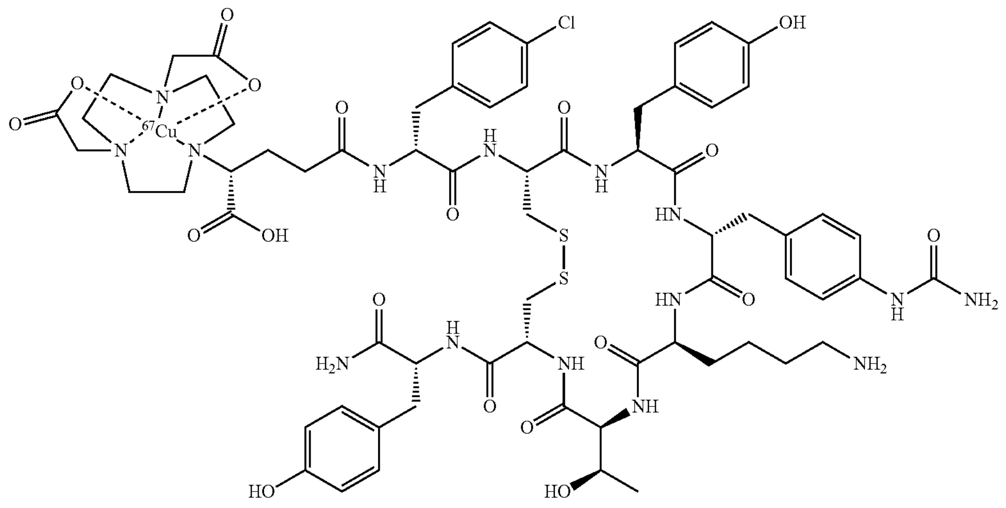

or is a pharmaceutically acceptable salt thereof.

Embodiment 15. A method of generating one or more images of a subject, comprising:

(a) administering to the subject an effective amount of the composition according to embodiment 11; and (b) generating one or more images of at least a part of the subject's body.

Embodiment 16. The method of embodiment 14, wherein the one or more images is generated using photon emission tomography (PET).

Embodiment 17. The method of embodiment 14, wherein the one or more images is generated using single-photon emission computerized tomography (SPECT).

Embodiment 18. A theranostic method comprising:

(a) administering to a subject an effective amount of a first pharmaceutical composition, wherein the composition is according to embodiment 11;

(b) generating one or more images of at least part a of the subject's body;

(c) administering to the subject an effective amount of a second pharmaceutical composition comprising a compound, wherein the compound is of Formula 20 as defined in embodiment 1 or is a pharmaceutically acceptable salt thereof.

Enumerated Embodiments Group C

Embodiment 1. A pharmaceutical composition comprising a compound and a pharmaceutically acceptable excipient, wherein the compound is of Formula 30:

Formula 30

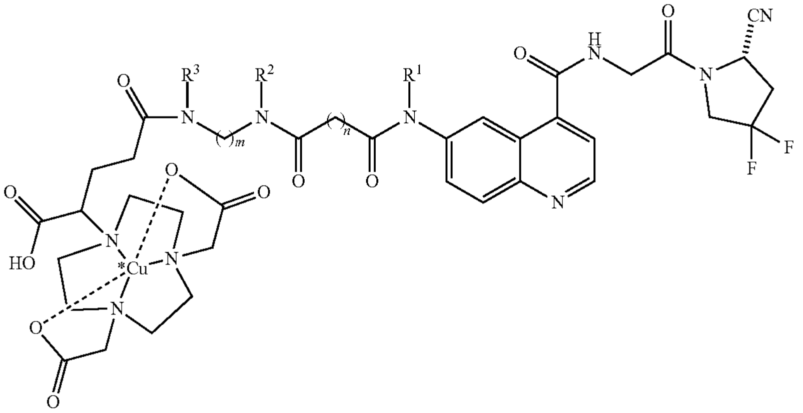

wherein:

$R^1$ is $R^a$;

$R^2$ and $R^3$ are each $R^a$ or together form a $C_{2-9}$ heterocycle with the nitrogen atoms to which they are attached; $R^a$, independently for each occurrence, is selected from H, $C_{1-10}$ alkyl, $C_{2-10}$ alkenyl, $C_{3-10}$ alkynyl, $C_{3-10}$ cycloalkyl, $C_{6-10}$ aryl, $C_{2-9}$ heterocyclyl, or $C_{5-9}$ heteroaryl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —OP(O)$(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl;

n is an integer from 1 to 20;

m is an integer from 1 to 20; and

*Cu is a copper radionuclide selected from $^{61}Cu$, $^{62}Cu$, $^{64}Cu$, and $^{67}Cu$;

or is a pharmaceutically acceptable salt thereof; and wherein the composition is characterized by one or more of:

molar activity of ≥3 MBq/nmol;

radiochemical purity ≥91%;

activity concentration of ≥8 MBq/mL; and radionuclidic purity of the compound at end of synthesis (EoB plus 2 hours) ≥95%.

Embodiment 2. The composition of embodiment 1, wherein $R^1$ is methyl or H.

Embodiment 3. The composition of embodiment 1 or 2, wherein $R^2$ is H and $R^3$ is H.

Embodiment 4. The composition of embodiment 1 or 2, wherein $R^2$ and $R^3$ together form a $C_{2-9}$ heterocycle with the nitrogen atoms to which they are attached.

Embodiment 5. The composition of embodiment 4, wherein the $C_{2-9}$ heterocycle is a 6-membered heterocycle selected from a piperazine, hexahydropyrimidine, hexahydropyridazine, 1,2,3-triazinane, 1,2,4-triazinane, and 1,3,5-triazinane.

Embodiment 6. The composition of any one of embodiments 1-5, wherein the radionuclide is selected from $^{61}Cu$ and $^{67}Cu$.

Embodiment 7. The composition of any one of embodiments 1-6, wherein the compound is of Formula 30a or Formula 30b:

(Formula 30a)

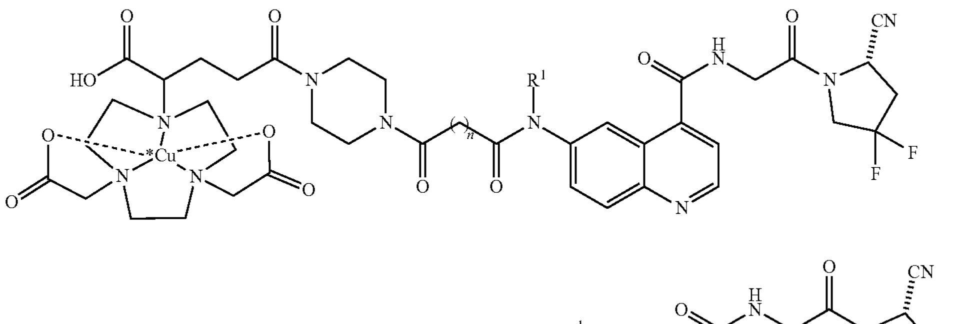

(Formula 30b)

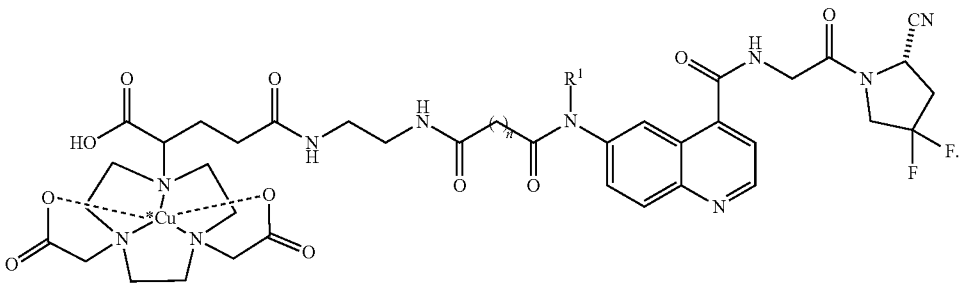

Embodiment 8. The composition of embodiment 7, wherein $R^1$ is H or methyl.
Embodiment 9. The composition of embodiment 7 or 8, wherein the radionuclide is selected from $^{61}Cu$ and $^{67}Cu$.
Embodiment 10. The composition of any one of embodiments 1-9, wherein the compound is selected from:
| Compound | Structure |
|---|---|
| *Cu-NODAGA-F1 | 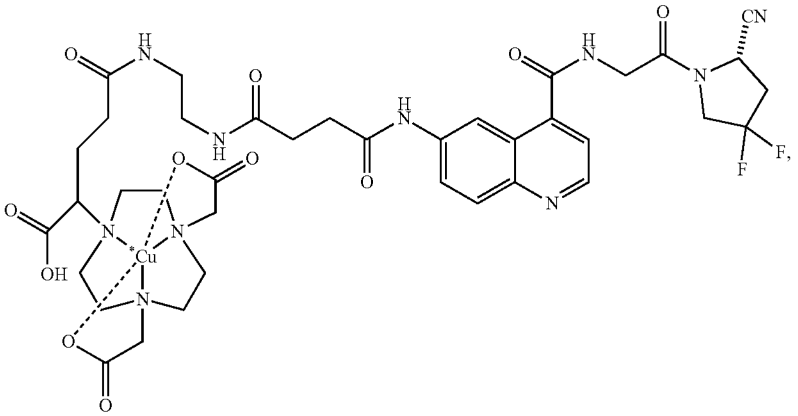 , |
| *Cu-NODAGA-F2 | 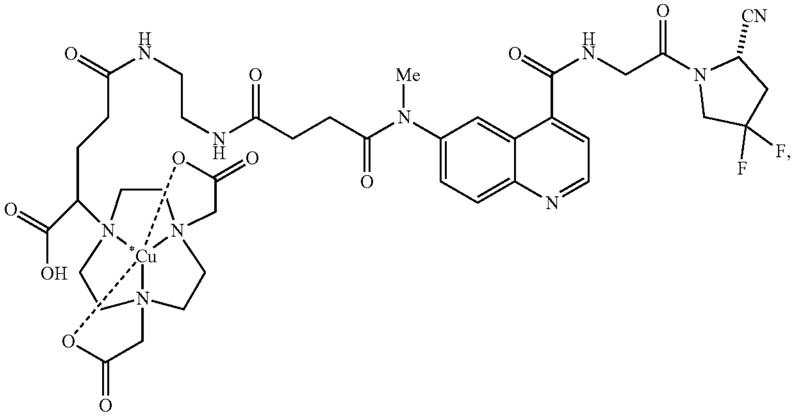 , |
| *Cu-NODAGA-F3 | 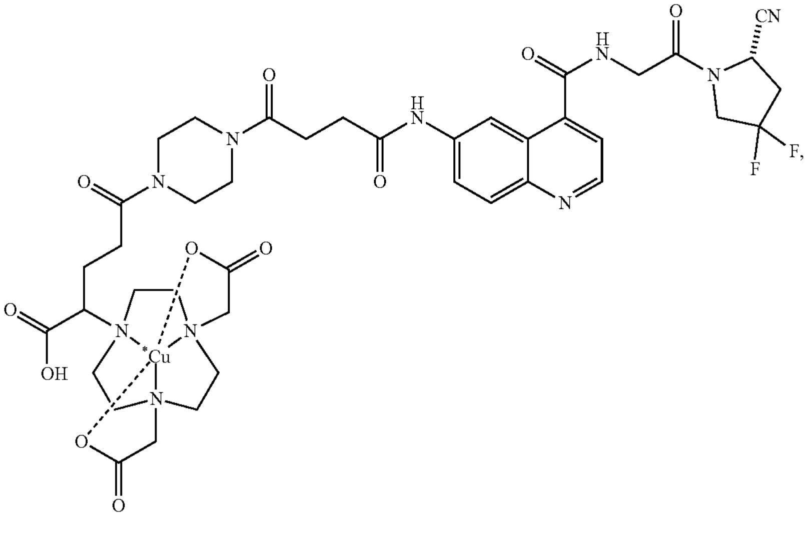 , and |

-continued

| Compound | Structure |
| --- | --- |
| *Cu-NODAGA-F4 | 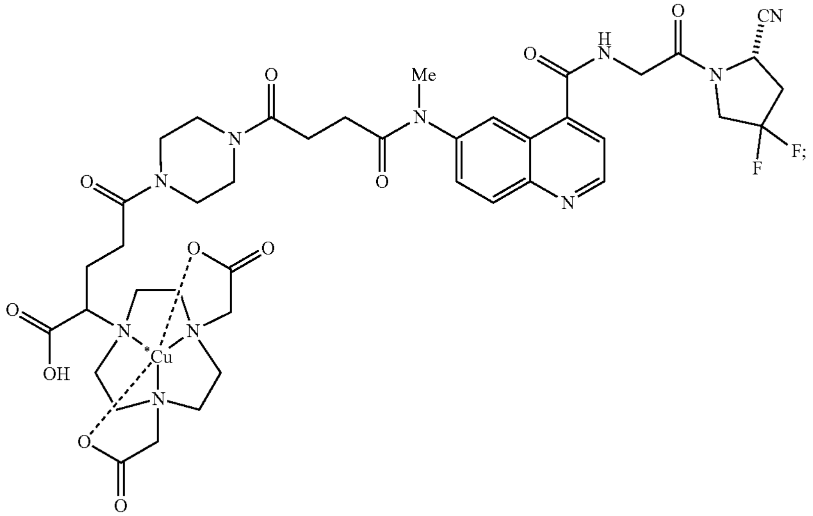 |

or is a pharmaceutically acceptable salt thereof.

Embodiment 11. The composition of any one of embodiments 1-10, wherein the composition has a molar activity of ≥3 MBq/nmol, e.g., ≥10 MBq/nmol, from 10 to 250 MBq/nmol, from 20 to 250 MBq/nmol, from 50 to 250 MBq/nmol, from 50 to 200 MBq/nmol, from 50 to 150 MBq/nmol, from 50 to 100 MBq/nmol, from 100 to 250 MBq/nmol, from 100 to 150 MBq/nmol, from 150 to 250 MBq/nmol, from 150 to 200 MBq/nmol, or from 200 to 250 MBq/nmol.

Embodiment 12. The composition of any one of embodiments 1-11, wherein the composition has a radiochemical purity of ≥91%, e.g., ≥95%, ≥95.5%, ≥96%, ≥96.5%, ≥97%, ≥97.5%, ≥98%, ≥98.5%, ≥99%, or ≥99.5%.

Embodiment 13. The composition of any one of embodiments 1-12, wherein the composition has an activity concentration of ≥8 MBq/mL, e.g., 8 to 400 MBq/mL, 8 to 350 MBq/mL, 8 to 300 MBq/mL, 8 to 250 MBq/mL, 8 to 200 MBq/mL, 8 to 150 MBq/mL, 8 to 100 MBq/mL, 8 to 100 MBq/mL 8 to 50 MBq/mL, 8 to 25 MBq/mL, or 8 to 15 MBq/mL.

Embodiment 14. The composition of any one of embodiments 1-13, wherein the composition is characterized by radionuclidic purity of the compound at end of synthesis of ≥95%, e.g., ≥95.5%, ≥96%, ≥96.5%, ≥97%, ≥97.5%, ≥98%, ≥98.5%, ≥99%, ≥99.1%, ≥99.2%, ≥99.3%, ≥99.4%, ≥99.5%, ≥99.6%, ≥99.7%, ≥99.8%, ≥99.9%, or ≥99.99%.

Embodiment 15. The composition of any one of embodiments 1-14, wherein the composition has a pH from 4 to 7.

Embodiment 16. A method of generating one or more images of a subject comprising: administering to the subject an effective amount of composition of any one of embodiments 1-15, wherein the radionuclide is $^{61}$Cu; and generating one or more images of at least a part of the subject's body.

Embodiment 17. The method of embodiment 16, wherein the one or more images are generated using positron emission tomography (PET), PET-computer tomography (PET-CT), or single-photon emission computerized tomography (SPECT).

Embodiment 18. The method of embodiment 16 or 17, wherein the one or more images are generated using PET-CT.

Embodiment 19. A method of treating a disease in a patient in need thereof, comprising administering to the patient an effective amount of a composition of embodiment 1, wherein the radionuclide is $^{67}$Cu.

Embodiment 20. The method of embodiment 19, wherein the disease is selected from cancers, inflammatory diseases, infectious diseases, and immune diseases.

Embodiment 21. The method of embodiment 19 or 20, wherein the disease is cancer.

Embodiment 22. The method of embodiment 20 or 21, wherein the cancer is selected from breast cancer, pancreatic cancer, small intestine cancer, colon cancer, gastric cancer, rectal cancer, lung cancer, head and neck cancer, ovarian cancer, hepatocellular carcinoma, epithelial cancer, esophageal cancer, hypopharynx cancer, nasopharynx cancer, larynx cancer, myeloma cells, bladder cancer, cholangiocellular carcinoma, clear cell renal carcinoma, neuroendocrine tumor, oncogenic osteomalacia, sarcoma, CUP (carcinoma of unknown primary), thymus carcinoma, desmoid tumors, glioma, astrocytoma, cervix carcinoma, and prostate cancer.

Embodiment 23. A theranostic method comprising:

(a) administering to a subject an effective amount of a first pharmaceutical composition, wherein the composition is according to embodiment 1, wherein the radionuclide is $^{61}$Cu;

(b) generating one or more images of the subject; and (c) administering to the subject an effective amount of a second pharmaceutical composition comprising a compound, wherein the compound is of Formula 30:

Formula 30

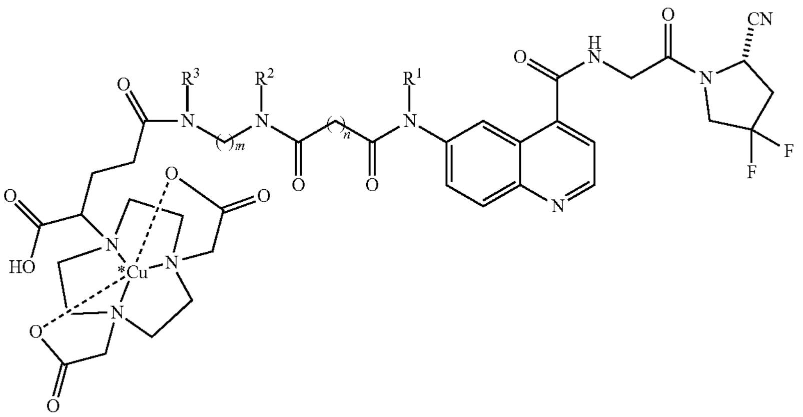

wherein:

$R^1$ is $R^a$;

$R^2$ and $R^3$ are each $R^a$ or together form a $C_{2-9}$ heterocycle with the nitrogen atoms to which they are attached;

$R^a$, independently for each occurrence, is selected from H, $C_{1-10}$ alkyl, $C_{2-10}$ alkenyl, $C_{3-10}$ alkynyl, $C_{3-10}$ cycloalkyl, $C_{6-10}$ aryl, $C_{2-9}$ heterocyclyl, or $C_{5-9}$ heteroaryl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —OP(O)$(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl;

n is an integer from 1 to 20;

m is an integer from 1 to 20; and

*Cu is $^{67}$Cu, or is a pharmaceutically acceptable salt thereof.

Embodiment 24. The method of embodiment 23, wherein:

(a) the compound of the first pharmaceutical composition is $^{61}$[Cu]Cu-NODAGA-F1 and the compound of the second pharmaceutical composition is $^{67}$[Cu]Cu-NODAGA-F1;

(b) the compound of the first pharmaceutical composition is $^{61}$[Cu]Cu-NODAGA-F2 and the compound of the second pharmaceutical composition is $^{67}$[Cu]Cu-NODAGA-F2;

(c) the compound of the first pharmaceutical composition is $^{61}$[Cu]Cu-NODAGA-F3 and the compound of the second pharmaceutical composition is $^{67}$[Cu]Cu-NODAGA-F3; or (d) the compound of the first pharmaceutical composition is $^{61}$[Cu]Cu-NODAGA-F4 and the compound of the second pharmaceutical composition is $^{67}$[Cu]Cu-NODAGA-F4.

Embodiment 25. The method of embodiment 23 or 24, further comprising determining, via the one or more images of the subject, the presence or absence of a disease in the subject based on the presence or absence of localization of the $^{61}$Cu radionuclide of the first compound in the subject's body.

Embodiment 26. The method of embodiment 25, wherein the disease is selected from cancers, inflammatory diseases, infectious diseases, and immune diseases.

Embodiment 27. The method of any one of embodiments 23-27, wherein the one or more images are generated by using positron emission tomography (PET), PET-computer tomography (PET-CT), or single-photon emission computerized tomography (SPECT).

Embodiment 28. A method of making the composition of embodiment 1 comprising combining a high purity radiocopper solution with a compound of Formula 40:

Formula 40

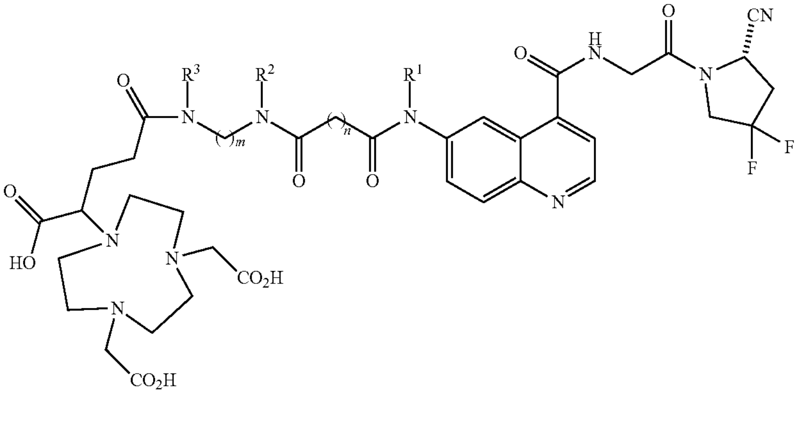

wherein $R^1$ is $R^a$;

$R^2$ and $R^3$ are each $R^a$ or together form a $C_{2-9}$ heterocycle with the nitrogen atoms to which they are attached;

$R^a$, independently for each occurrence, is selected from H, $C_{1-10}$ alkyl, $C_{2-10}$ alkenyl, $C_{3-10}$ alkynyl, $C_{3-10}$ cycloalkyl, $C_{6-10}$ aryl, $C_{2-9}$ heterocyclyl, or $C_{5-9}$ heteroaryl, optionally substituted by one or more substituents selected from —OH, —OR', =O, =S, —SH, —SR', —$NH_2$, —NHR', —$N(R')_2$, —NHCOR', —NR'COR', halogen, —CN, —$CO_2H$, —$CO_2R'$, —CHO, —COR', —$CONH_2$, —CONHR', —$CON(R')_2$, —$NO_2$, —OP(O)$(OH)_2$, —$SO_3H$, —$SO_3R'$, —SOR', and —$SO_2R'$, wherein R', independently for each occurrence, is $C_{1-10}$ alkyl or $C_{3-10}$ cycloalkyl;

n is an integer from 1 to 20;

m is an integer from 1 to 20; and wherein the high purity radiocopper solution is characterized by one or more of the following:

a chemical purity of ≥99% by mole and/or:

Fe≤2 mg/L;

$^{69}$Cu and $^{65}$Cu together are ≤1 mg/L;

Zn≤2 mg/L;

Sn≤0.01 mg/L;

Ti≤0.01 mg/L;

Al≤2 mg/L;

As≤1 mg/L;

Ni≤1 mg/L; and wherein any one of Cr, Cd, Co, and Y is ≤0.1 mg/mL.

Embodiment 29. The method of embodiment 28, wherein the high purity radiocopper solution is [$^{61}$Cu]$CuCl_2$.

Embodiment 30. The method of embodiment 28 or 29, wherein the high purity radiocopper solution and compound of Formula 40 are combined at a temperature from 80-95° C.

5. EXAMPLES

Summary of Experimental Observations

In view of the increasing clinical demand for PSMA-targeted PET imaging, the production capacity of the generator produced $^{68}$Ga-tracers (2-3 patient doses) was very limited. $^{18}$F-labeled derivatives are an alternative, but this comes at the cost of the facile chelator-based kit radiolabeling and the possibility of a therapeutic companion (theranostics); options not offered with $^{18}$F. In addition, the pitfalls of $^{18}$F-PSMA radiotracers raise concerns. $^{61}$Cu can be produced in cyclotrons in large scale, allows kit-based radiolabeling and has a distribution radius bigger than $^{68}$Ga or $^{18}$F due to the longer half-life. This enables, in addition, delayed imaging that can result to improved image contrast, compared to the existing PSMA radiotracers, without additional radiation burden for the patient.

As a proof of concept, $^{61}$Cu was chelated to a targeting moiety (e.g., PSMA-I&T, SS analogues, or FAP inhibitors) through a chelator (e.g., NODAGA) and a linker moiety. Herein it was reported that the targeted chelator construct was labelled with $^{61}$Cu at room temperature within minutes, rendering the procedure to produce a PET tracer fast and simple, following a "mix and shake" approach, without the need of costly infrastructure, like module-assisted radiosynthesis or purification systems (routinely used in $^{18}$F and often for $^{68}$Ga radiotracers). The method gives an added flexibility to the radio pharmacist/practitioner to produce multiple (more than three) patient doses with one shipment of $^{61}$Cu onsite in a working day (in contrast to $^{68}$Ga, 1-3 doses maximum).

Through the NODAGA chelator, a construct having the same targeting moiety (PSMA-I&T, somatostatin analogues, or FAP inhibitors) can be conjugated to create a radiotracer comprising a therapeutic radionuclide of the same chemical element, namely $^{67}$Cu, which was a beta emitter and useful in radiotherapy. By virtue of being the same chemical element, $^{67}$Cu was bound by a chelator and the targeting moiety in the very same chemical manner as $^{61}$Cu. leading to the chemically identical radiotherapeutic version of a companion radiotracer [$^{67}$Cu]Cu-NODAGA-PSMA-I&T, [$^{67}$Cu]Cu-NODAGA-LM3, [$^{67}$Cu]Cu-NODAGA-F1, [$^{67}$Cu]Cu-NODAGA-F2, [$^{67}$Cu]Cu-NODAGA-F3, and [$^{67}$Cu]Cu-NODAGA-F4, and [$^{67}$Cu]Cu-NODAGA-FAPI-46. These therapeutic compounds have identical properties and total-body distribution as the PET radiotracer, including antigen-targeting lesions. In addition, $^{67}$Cu has a shorter half-compared to $^{177}$Lu, ($t_{1/2}$ $^{67}$Cu=2.6 days vs $^{177}$Lu=6.7 days), while having very similar energy of the beta particles. Thus, $^{67}$Cu might fit better to the pharmacokinetics of the proposed tracers, it may allow shorter time intervals between treatment cycles and last but not least, it was expected to have lower radiation burden for the patient and better logistics regarding waste management in the hospitals.

Highly Pure [$^{61}$Cu]$CuCl_2$

Due to the relatively short half-lives ($t_{1/2}$ $^{68}$Ga=68 min; $^{18}$F=110 min) and physical properties of the radionuclides, the key challenges in the PET tracer industry remain a) the imaging quality, b) reliability of supply and distribution of the radiopharmaceutical at low cost and c) low radiation burden to the patient. The distinctive advantage of using $^{61}$Cu as a positron emitter, e.g., in a PET tracer, will not only ensure a) good imaging quality due to its physical properties (low mean positron energy) but also the possibility of delayed imaging, expected to improve the diagnostic sensitivity due to the washout of radioactivity from the background, thus improved image contrast, b) a large distribution radius due to its relatively long half-life ($t_{1/2}$ $^{61}$Cu=205.5 min) while c) still keeping the radiation burden to the patient at a minimum. Provided herewith is an enabling description of new processes to produce highly pure $^{61}$Cu, in the form of [$^{61}$Cu]$CuCl_2$, to be used in radiopharmaceutical applications, e.g., as a positron emitter in a PET tracer, in high activity concentration and volumes. Until now, the use of $^{61}$Cu, particularly highly pure $^{61}$Cu, in radiotracers has not been recorded.

Trace metals and cold copper compete with $^{61}$Cu to bind a chelator (for example, NODAGA) in this order: cold Cu(II) (i.e., stable isotopes)>Zn(II)>Fe(III)>Sn(IV)>Ti(IV)>Al(III.). The competition from these trace metals and cold copper decreases the tracer's radiolabeling yield and radiochemical purity significantly, see *Innovative Complexation Strategies for the Introduction of Short-lived PET Isotopes into Radiopharmaceuticals* (p. 105). Frequent sources of trace metals are the raw nickel metal powder itself, especially isotopically enriched nickel, reagents, and any metals in instruments used, such as iron. The purification process (ion-exchange columns) removes much of the trace metals except for cold (of particular relevance are stable isotopes $^{69}$Cu and $^{65}$Cu), which passes through into the product fraction by being the same element as the desired $^{61}$Cu. One way of preventing cold copper contamination and the associated reduction in chemical purity is to pass the dissolved nickel raw material (stable isotopes) through the process and separate the cold copper from the nickel before plating (see FIG. 8 for ICP-MS analysis) and Table 4 display the chemical purity of the [$^{61}Cu$]$CuCl_2$ by either bombardment of $^{nat}Ni$ or $^{61}Ni$ on a niobium backing and the resulting impurity profile.

TABLE 4

Chemical Purity of $^{61}Cu$ transmuted from $^{nat}Ni$ vs. $^{61}Ni$

| | ng/MBq | |
|---|---|---|
| | Cu-61 from nat-Ni | Cu-61 from Ni-61 |
| Aluminum (Al) | 1.1 | 0.3 |
| Cobalt (Co) | N/D | 0.2 |
| Copper (Cu) | 0.3 | 0.6 |
| Iron (Fe) | 1.6 | 1.5 |
| Lead (Pb) | 0.4 | 0.7 |
| Nickel (Ni) | 3.4 | 0.1 |
| Zinc (Zn) | 0.7 | 0.1 |

Radionuclidic Purity

Radionuclidic purity is important in radiopharmacy since any radionuclidic impurities increase the radiation dose received by the patient and may also degrade the quality of any imaging procedure performed. For example, if significant levels of other radionuclides are present then biological distribution may be altered. Radionuclide samples contain some contaminants arising the production process or the decay of the primary radioisotope. Radionuclide impurities can occur as a result of the manufacturing process, for example, for nuclides produced by cyclotron there can be contaminants due to impurities in the target or by the energy of the reaction. In order to control the effects of these contaminants on the radiation dose received by the patient, limits are set on the maximum levels of contamination allowed. These limits are defined by governmental agencies, e.g., in pharmacopoeia monographs, and vary depending upon the radionuclide concerned and the physical decay characteristics of the likely contaminants. Measurement of radionuclidic purity may be performed high resolution using gamma-ray spectroscopy on samples well after bombardment. The activity of the long lived isotopes is then extrapolated back to EoB or EoS or even at expiration. High activity emitted from long lived radionuclidic impurities greatly increases the cost and complexity of managing the disposal of all consumables that come into contact with the nuclide composition.

Through the deuteron irradiation of natural nickel and $^{60}Ni$, and proton irradiation of $^{61}Ni$, long-lived isotopes of cobalt are produced: $^{56}Co$, $^{57}Co$, $^{58}Co$ and $^{60}Co$. Other long-lived radionuclides such as $^{110m}Ag$, $^{108m}Ag$ and $^{109}Cd$ are produced through the irradiation of commonly used silver backing material, which are dissolved along with starting material during the purification process. Due to their long half-lives, the proportion of these radionuclides increases with time compared to the $^{61}Cu$, decreasing the radionuclidic purity of the product, especially at later time points when using $^{nat}Ni$ as a starting material. Though most cobalt isotopes can be separated in the purification process, the $^{110m}Ag$, $^{108m}Ag$ and $^{109}Cd$ end up in the $^{61}Cu$ fraction and nickel solution that is further used in recycling of irradiated target coating. The long-lived radionuclides become problematic when considering the radiation burden to the patient and the accumulation of radioactive waste. Third-party coin manufacturers did not publish the contamination from the non-niobium coin backings (e.g., silver). As provided by the present disclosure, the method of making and using coins comprising niobium represents an advantage, e.g., in view of the radionuclidic and chemical purity of samples produced following subatomic particle bombardment, isolation, and purification. A detailed comparison of the known $^{61}Cu$ products (prepared via Ag backings and prior art methods of plating the target) to $^{61}Cu$ as provided by the present disclosure is provided below.

With these factors in mind, a niobium backing material was chosen due to its inert nature to acids at room temperature and at elevated temperatures. This characteristic allows the niobium backing material to resist the acid medium used during the dissolution and purification process. By doing so, higher radionuclidic and chemical purity can be achieved in the radiometal aqueous solution, eventually resulting in higher purity for the radiopharmaceutical prepared from the desired $^{61}Cu$ isotope. Although plating methods of niobium exist, the element has not yet been used for radionuclide production due to the poor adhesion of the plated Ni material (as discussed above). The Ni (or $^{68}Zn$ for the production of $^{68}Ga$) requires sufficient adhesion for the coin to survive thermal loads (1200 W) during irradiation and pneumatic shuttle acceleration at 5 bar to 7 bar of pressure and abrupt stop at the head. On the other hand, however, the plated Ni (or Zn) must dissolve sufficiently during the dissolution and purification process. Attempts were made to plasma-coat niobium backings for plating nickel (Ni). However, this process resulted in losses and incomplete dissolution of Ni from the niobium backing. The thermal processes involved in plasma coating altered the grain structure of the niobium backing material, leading to a strong bond between the plated nickel and niobium. This strong bond made it difficult for the nickel to fully dissolve, causing losses. The plasma coating process itself resulted in very high losses in target coating, rendering the process not viable for use, especially with very expensive highly enriched target metals. The main reference to this summary is the IAEA documentation regarding cyclotron radionuclide production, *IAEA RADIOISOTOPES AND RADIOPHARMACEUTICALS, REPORTS, No.* 1. (INTERNATIONAL ATOMIC ENERGY AGENCY VIENNA, 2016) Additionally, a monetary evaluation regarding the procurement costs of niobium utilized as a backing material displays a 40% lower cost in comparison to commonly used backing materials such as gold, silver, and platinum where costs range from €80 to €120 per backing material (single coin).

Parallel to this, elements pertaining to the radiochemical purity of the labelling process are controlled by manufacturing the plating solution under controlled conditions described herein. By procuring the plating solution from a raw base material of, e.g., nickel, the possibility of contamination is now independent from outside sources and suppliers. Such material and equipment used in these cases are inert glass beakers and falcon tubes (ensured to not contain any undesirable substances), TraceSelect pure water, pure reagents (trace-metal grade), inert coin adapter and electrolytic cell (on the electroplating unit), etc. Through this, the contaminants of trace metals can be minimized reduced or avoided all together. This difference between 99.9% purity and 99.99% purity plays a role in the resulting chemical purity of a radionuclide and therefore in the radiochemical purity of a radiopharmaceutical prepared from the radionuclide, where the presence of cold Cu, Zn, Fe, Sn, Ti, or Al or any salt thereof are an issue as they will compete for binding to the chelator in the tracer along with the desired radionuclide ($^{61}Cu$).

Robustness of plating is tested through a drop and scratch test. This assessment ensures that the electrodeposited substrate on the backing will survive mechanical impacts of the shuttling system and establishes an increased probability of survivability under the cyclotron beam.

In certain embodiments, coins are irradiated with 8.4 MeV deuterons for an average duration of 120 mins at a range of 40 μA to 45 μA or with 13.2 MeV deuterons at 40 μA to 45 μA using an ARTMS or GE shuttling system on a GE PET Trace cyclotron.

In certain embodiments, the coins are irradiated with 8.4 MeV deuterons for an average duration of 120 mins at a range of 40 μA to 45 μA or with 10 μA to 100 μA 13 MeV protons using an ARTMS or GE shuttling system on a GE PET Trace cyclotron.

Dissolution of Ni from the niobium backing is undergone via the utilization of a dissolution system in 10 M HCl. The subsequent $^{61}$Cu is then purified with two subsequent ion exchange resins in a FASTlab synthesis unit. The processing time for these purifications can reach up to 60 minutes.

The resulting [$^{61}$Cu]$CuCl_2$ solution of the plated material has an average activity of 1.7-4.5 GBq. This activity is measured using a dose calibrator and its radionuclidic purity by a calibrated gamma spectrometer e.g., at PSI in Switzerland.

Gamma spectrometry measurements were performed to identify any radionuclidic impurities, particularly long-lived radionuclides. These results indicate an 89.3% and 94% reduction in impurities for $^{nat}$Ni and $^{61}$Ni on niobium backing materials with respect to silver backing materials when utilizing the methods disclosed herein. ICP-MS measurements are performed on the product of cold dissolutions by Labor Veritas in Switzerland to monitor elemental impurities present in the product according to ICH-Q3D. All detected impurities are within regulated ICH-Q3D concentrations (see ICH-Q3D Guidelines, pg 25).

The plating of highly enriched $^{61}$Ni is also enabled with the same plating parameters as described above, for a higher yield and industrial production using proton irradiation (typically at A to 100 μA, 13 MeV protons for 20 minutes to 2 hours and up to one half-life of $^{61}$Cu).

Following automated transportation of the irradiated coin from the cyclotron to the hot cell docking station, the capsule was transferred to a QIS dissolution unit with tongs. The transmuted target metal was dissolved from the niobium backing material using 1:1 7M HCl: 30% $H_2O_2$ (ultratrace analysis, Merck) (4 mL). The acid-peroxide mixture is circulated, immersing the coin and target metal surface to dissolve all irradiated elements at 2 mL/min for about 23 minutes at about 60° C. When the target metal was fully dissolved, acidic solution containing the dissolved metal was withdrawn and the QIS system was flushed with 10M HCl (3 mL). The combined acidic solutions were then fed forward to the FASTlab purification unit.

Novel $^{61}$Cu Radiotracers

Radiotracers comprising PSMA-I&T,SS (somatostatin) analogues, and FAP inhibitors in combination with $^{61}$Cu have not been reported. Accordingly, NODAGA-PSMA-I&T, NODAGA-LM3, NODAGA-F1, NODAGA-F2, NODAGA-F3, and NODAGA-F4, as discussed herein, are new precursors or intermediates. Likewise, the radiotracers [$^{61}$Cu]Cu-NODAGA-PSMA-I&T, [$^{61}$Cu]Cu-NODAGA-LM3, [$^{61}$Cu]Cu-NODAGA-F1, [$^{61}$Cu]Cu-NODAGA-F2, [$^{61}$Cu]Cu-NODAGA-F3, [$^{61}$Cu]Cu-NODAGA-F4, [$^{61}$Cu]Cu-NODAGA-FAPI-46 are also novel.

[$^{61}$Cu]Cu-NODAGA-PSMA-I&T: A New Radiotracer for PET Imaging of Prostate Cancer In the last few years, radiotracers targeting prostate-specific membrane antigen (PSMA) have influenced imaging and management of prostate cancer. $^{68}$Ga-labeled urea-based PSMA inhibitors are the most commonly used radiotracers in this disease entity. $^{18}$F-labeled derivatives have become an alternative mainly for meeting the increasing demand for PSMA-targeted PET imaging. This comes, however, at the cost of the facile chelator-based kit radiolabeling and the possibility of a therapeutic companion (theranostics); options possible with radiometals. As an alternative, in certain embodiments, herein is disclosed cyclotron-produced $^{61}$Cu ($E\beta^+$mean=500 keV, $E\beta^+$max=1216 keV, $t_{1/2}$=3.34 h) that combines the attractive logistics of $^{18}$F, chelator based radiochemistry, and further therapeutic options (e.g., $^{67}$Cu). Here it is reported the first preclinical data on [$^{61}$Cu]Cu-NODAGA-PSMA-I&T radiotracers.

[$^{61}$Cu]$CuCl_2$ was produced from an irradiated Ni-target at the University Hospital Zurich cyclotron followed by cassette based automated separation as described previously (1). DOTAGA-(I-y)fk(Sub-KuE) (PSMA-I&T, herein DOTAGA-PSMA-I&T) (2) and NODAGA-(I-y)fk(Sub-KuE) (NODAGA-PSMA-I&T) were labeled with [$^{61}$Cu]$CuCl_2$ in ammonium acetate buffer, pH 8 at room temperature (95° C. for a DOTAGA chelator). Both [$^{61}$Cu]Cu-PSMA radiotracers were evaluated head-to-head in vitro using LNCaP cells and by dynamic and static PET/CT imaging and biodistribution studies in LNCaP-xenografted nude mice.

[$^{61}$Cu]Cu-NODAGA-PSMA-I&T and [$^{61}$Cu]Cu-DOTAGA-PSMA-I&T were prepared at a molar activity of 24 MBq/nmol, without the need of post-purification. [$^{61}$Cu]Cu-NODAGA-PSMA-I&T was more hydrophilic than [$^{61}$Cu]Cu-DOTAGA-PSMA-I&T (log D=−2.95±0.08 and −2.69±0.44, respectively). In vitro, both radiotracers showed similar PSMA-mediated cellular uptake (approx. 35% after 2 h at 37° C.), with 50-60% being internalized. PET/CT images of [$^{61}$Cu]Cu-NODAGA-PSMA-I&T vs [$^{61}$Cu]Cu-DOTAGA-PSMA-I&T indicated clear differences. [$^{61}$Cu]Cu-NODAGA-PSMA-I&T accumulated in the tumor, increasing from 15 up to 60 min p.i., and in the kidneys. Kidney uptake could be reduced by modulating the injected mass. [$^{61}$Cu]Cu-DOTAGA-PSMA-I&T showed lower tumor, but also lower kidney uptake, than [$^{61}$Cu]Cu-NODAGA-PSMA-I&T, and high activity in the liver. The accumulation in the liver may be due to in vivo instability of the [$^{61}$Cu]Cu-DOTAGA complex. Comprehensive biodistribution studies of both radiotracers in LNCaP xenografts are presented.

The NODAGA chelator is confirmed to be a perfect match for [$^{61}$Cu]Cu-based radiotracers compared with the DOTAGA chelator. [$^{61}$Cu]Cu-NODAGA-PSMA-I&T showed better characteristics, including but not limited to higher tumor uptake and lower background activity than [$^{61}$Cu]Cu-DOTAGA-PSMA-I&T, potentially attributed to its higher in vivo stability. [$^{61}$Cu]Cu-NODAGA-PSMA-I&T is, therefore, the potential candidate for clinical translation of [$^{61}$Cu]Cu-based PSMA-targeted PET imaging.

[$^{61}$Cu]Cu-PSMA-I&T Versus [$^{68}$Ga]Ga-PSMA-I&T for PET Imaging of Prostate Cancer Prostate-specific membrane antigen (PSMA)-targeting is highly relevant-targeting is highly relevant in prostate cancer for detection and therapy (theranostics). A number of low molecular-weight PSMA inhibitors have been developed for this purpose, with [$^{68}$Ga]Ga-PSMA-11 being recently approved. Others, like [$^{68}$Ga]Ga-PSMA-617 and [$^{68}$Ga]Ga-PSMA-I&T, offer additionally the possibility of theranostics when labeled with $^{177}$Lu. In view of the increasing clinical demand, the production capacity of the generator produced $^{68}$Ga-tracers (2-3 patient doses) raises certain concerns. A valuable alternative is $^{61}Cu$ ($E\beta^+$ mean=500 keV, $E\beta^+$ max=1216 keV, $t_{1/2}$=3.34 h). $^{61}Cu$ can be produced in cyclotrons in large scale, while its lower energy and longer half-life (enabling delayed imaging), compared to $^{68}Ga$, may result to refined imaging quality. In addition, $^{61}Cu$ has the therapeutic companion $^{67}Cu$. Herein it is reported the comparison of [$^{61}Cu$]Cu-PSMA versus [$^{68}Ga$]Ga-PSMA, based on PSMA-I&T.

The chelator DOTAGA on PSMA-I&T (herein referred as DOTAGA-PSMA-I&T) was replaced with NODAGA for labeling with $^{61}Cu$, due to the stable Cu-NODAGA complex in vivo, compared to Cu-DOTAGA. [$^{61}Cu$]$CuCl_2$ was produced from irradiated Ni target at the University Hospital Zurich cyclotron followed by cassette-based automated separation, as described previously (1). [$^{61}Cu$]Cu-NODAGA-PSMA-I&T was evaluated head-to-head with [$^{68}Ga$]Ga-DOTAGA-PSMA-I&T in terms of lipophilicity, in vitro cellular uptake in LNCaP cells, PET/CT imaging and quantitative biodistribution in LNCaP-xenografted nude mice. Results: The two radiotracers were prepared at molar activities of 24-30 MBq/nmol. [$^{61}Cu$]Cu-NODAGA-PSMA-I&T, compared with [$^{68}Ga$]Ga-DOTAGA-PSMA-I&T, showed higher hydrophilicity (log D=−2.95±0.08 and −2.79±0.41, respectively) and higher cellular uptake in vitro (26.6±0.9% after 1 h at 37° C., with 12±1.9% being internalized versus 20.6±2.3% cellular uptake and 9.8±1.3% internalized fraction, respectively). PET/CT images 1 h p.i. revealed the same biodistribution pattern for both radiotracers, which was characterized by accumulation mainly in the tumor—with [$^{61}Cu$]Cu-NODAGA-PSMA-I&T showing higher uptake—and in the kidneys. The biodistribution pattern of [$^{61}Cu$]Cu-NODAGA-PSMA-I&T was the same on PET/CT images at 4 h p.i. The kidney uptake of [$^{61}Cu$] Cu-NODAGA-PSMA-I&T could be reduced significantly, 96% to 72% to 34% IA/g at 1 h p.i. by increasing the injected amount, 200 to 400 to 1000 pmol, respectively. Conclusion: [$^{61}Cu$]Cu-NODAGA-PSMA-I&T compared well with [$^{68}Ga$]Ga-DOTAGA-PSMA-I&T on PET/CT images in terms of total body distribution, while showing higher tumor uptake and offering the possibility of delayed images. [$^{61}Cu$] Cu-NODAGA-PSMA-I&T is considered for clinical evaluation versus established [$^{68}Ga$]Ga-PSMA tracers. References: 1.J. Svedjehed et al., EJNMMI Radiopharmacy and Chemistry 2020; 5:21.

Provided herein are methods of making target coins for use in a medical cyclotron (particle accelerator), methods of using this coin to produce high purity radiocopper compositions; methods of making targeted chelator constructs and methods of preparing the radiotracers using the high purity radiocopper compositions. Also provided herein are extensive in-vitro and in-vivo characterization of [$^{61}Cu$]Cu-NODAGA-PSMA-I&T, [$^{61}Cu$]Cu-NODAGA-TOC, [$^{61}Cu$] Cu-NODAGA-LM3, [$^{61}Cu$]Cu-NODAGA-F1, [$^{61}Cu$]Cu-NODAGA-F2, [$^{61}Cu$]Cu-NODAGA-F3, [$^{61}Cu$]Cu-NODAGA-F4 and [$^{61}Cu$]Cu-NODAGA-FAPI-46 constructs in various pre-clinical studies; including direct comparison of [$^{61}Cu$]Cu-NODAGA-PSMA-I&T with the following radiotracers currently in clinically use: [$^{68}Ga$]Ga-PSMA-I&T, [$^{68}Ga$]Ga-PSMA-11 and [$^{18}F$]F-PSMA-1007. (For the known structure of [$^{18}F$]F-PSMA-1007, see Katzschmann et al. 2021 Pharmaceuticals 14(3):188) Also provided is a direct comparison of [$^{61}Cu$]Cu-NODAGA-TOC vs. [$^{61}Cu$]Cu-NODAGA-LM3 vs. [$^{68}Ga$]Ga-DOTA-TOC (currently in clinical use) and the process development of radiotracers [$^{61}Cu$]Cu-NODAGA-PSMA-I&T and [$^{61}Cu$] Cu-NODAGA-LM3 in preparation for a phase I clinical trial (on-going).

5.1. Example 1. High Purity [$^{61}Cu$]$CuCl_2$ from Ni/Nb Target Coins

5.1.1. Preparing Plating Solution

5.1.1.1 Preparation of Buffer Solution

Ammonium Chloride (4.6 g, Aldrich: 326372, Trace Select) was weighed into a clean (no metal) Falcon Tube (50 mL), and the previously cleaned magnetic stirring bar was added. 6 mL of Trace Select water (Honeywell 95305) was added in one aliquot to flush walls of the Falcon in case any salt sticks to the Falcon tube walls. 1 mL of ammonium hydroxide 28% (Sigma 338818) was added with a 1000 μL pipette with a respective pipette tip, 8× times. The lid of the Falcon was closed, and the Falcon is, in turns, vortexed (1-2 minutes) (immersion in an ultra-sonic bath was a possible alternative for 1-2 minutes) and shaken, until all salt was dissolved. The Falcon tube can also be warmed (e.g., by rolling between hands) to improve solubility, temperature (e.g., around 23° C., preferably between 23-25° C.). After complete dissolution of the salt, the pH acceptance criteria, pH range 9.28-9.62, needs to be verified by pH measurement of the solution at RT, e.g., with and electronic pH meter. The Falcon tube was closed with parafilm and stored at room temperature. Prior to use, any solid salt formation was redissolved.

5.1.1.2 Preparation of Nickel Nitrate Plating Solution

A 50 mL glass beaker was washed with nitric acid (Trace Select) followed by water (Trace Select). In a fume hood, the beaker was dried by placing it on a heating plate set to 150° C. To the beaker was added 210 μg of natural (isotopic distribution) nickel (powder, Sigma-Aldrich <50 μm, 99.7% trace metals basis, essentially free from any impurities, except iron. The copper impurity amounts to <0.3 ppm.) were weighed into the beaker and 4 mL of 65% nitric acid were added using a pipette. The beaker was placed back on the active heating plate and the stirring was set to 300 rpm. Ensure the ventilation of the fume hood was functioning properly (evolution of $NO_2$). During the dissolution, the solution turns green. The solution was reduced by evaporation to a volume of ≈600 μL and taken from the heating plate to cool down to room temperature. The remaining solution was transferred to a 50 mL metal-free Falcon tube. The glass beaker was rinsed with a total of 2.8 mL of Trace Select water, in steps of 0.8 mL, 1 mL, and 1 mL, where each step was transferred to the Falcon tube before the adding the next washing fraction. Buffer solution (4 mL), 11 mL of Trace Select water, and 3 mL of ammonium hydroxide 28% (Sigma 338818) were added to the Falcon tube. The pH of the solution was measured and adjusted to the required pH by adding ammonium hydroxide 28% (Aldrich 338818) using sterile B-Braun syringes.

5.1.1.3 Examples of Suitable Starting Material to Prepare $^{60}Ni$ and $^{61}Ni$ Electroplating Solutions The following are example lots of $^{60}Ni$ and $^{61}Ni$ (certificate as provided by Isoflex, USA, March 2018):

TABLE 5

| | | | | | | | | | | | |
|---|---|---|---|---|---|---|---|---|---|---|---|
| Isotope | $^{61}Ni$ | | | | | | | | | | |
| Enrichment | 86.20% | | | | | | | | | | |
| Form | Metal ingot/powder | | | | | | | | | | |
| Certificate | 6275 | | | | | | | | | | |
| Isotopic distribution | Isotope | Ni-58 | Ni-60 | Ni-61 | Ni-62 | Ni-64 | | | | | |
| | Content (%) | 1.17 | 0.8 | 86.2 | 11.7 | 0.14 | | | | | |
| Chemical admixtures | Element | Al | Bi | Ca | Cd | Co | Cr | Cu | Fe | K | µg |
| | Content (ppm) | 10 | <10 | 20 | 10 | <10 | <10 | 20 | 40 | <10 | <50 |
| | Element | Mo | Mn | Na | Pb | Si | Sn | Zn | | | |
| | Content (ppm) | <8 | <50 | <10 | <10 | 20 | 30 | 50 | | | |

TABLE 6

| | | | | | | | | | | | |
|---|---|---|---|---|---|---|---|---|---|---|---|
| Isotope | $^{61}Ni$ | | | | | | | | | | |
| Enrichment | 99.39% | | | | | | | | | | |
| Form | Metal powder | | | | | | | | | | |
| Certificate | TBD/not specified | | | | | | | | | | |
| Isotopic | Isotope | Ni-58 | Ni-60 | Ni-61 | Ni-62 | Ni-64 | | | | | |
| distribution | Content (%) | 0.01 | 0.29 | 99.39 | 0.29 | 0.02 | | | | | |
| Chemical | Element | Al | Co | Cr | Cu | Fe | µg | Mn | Pb | Si | Ti |
| admixtures | Content (ppm) | 12 | <10 | <10 | 14 | <10 | <10 | <10 | <10 | <10 | <10 |
| | Element | Zn | C | S | | | | | | | |
| | Content (ppm) | <10 | 157 | <10 | | | | | | | |

TABLE 7

| | | | | | | | | | | | |
|---|---|---|---|---|---|---|---|---|---|---|---|
| Isotope | $^{60}Ni$ | | | | | | | | | | |
| Enrichment | 99.31% | | | | | | | | | | |
| Form | metal powder | | | | | | | | | | |
| Certificate | TBD/not specified | | | | | | | | | | |
| Isotopic | Isotope | Ni-58 | Ni-60 | Ni-61 | Ni-62 | Ni-64 | | | | | |
| distribution | Content (%) | 0.21 | 99.31 | 0.46 | 0.015 | 0.005 | | | | | |
| Chemical | Element | Al | Co | Cr | Cu | Fe | µg | Mn | Pb | Si | Ti |
| admixtures | Content (ppm) | <10 | 70 | 20 | 25 | <10 | <10 | <10 | <10 | 15 | <10 |
| | Element | Zn | C | S | P | | | | | | |
| | Content (ppm) | 15 | 114 | 20 | 30 | | | | | | |

The samples of natural nickel from Sigma-Aldrich were essentially free from any impurities, except iron. The copper impurity amounts to <0.3 ppm. Please see certificate of analysis as described in Example 2. Additional suitable sources of natural Ni include:

Nickel powder, <50 µm, 99.7% trace metals basis

Nickel rod, diam. 6.35 mm, =99.99% trace metals basis

Nickel foil, thickness 0.5 mm, 99.98% trace metals 5.1.1.4 Preparation of Zinc Nitrate Plating Solution A 50 mL glass beaker was washed with nitric acid (Trace Select) followed by water (Trace Select). In a fume hood, the beaker was dried by placing it on a heating plate set to 150° C. 210 µg of natural (isotopic distribution) zinc (zinc powder, Sigma-Aldrich <10 µm, >98%) were weighed into the beaker and 4 mL of 65% nitric acid were added using a pipette. The beaker was placed back on the active heating plate and the stirring was set to 300 rpm. Ensure the ventilation of the fume hood was functioning properly (evolution of $NO_2$). During the dissolution, the solution turns green. The solution was reduced by evaporation to a volume of ≈600 µL and taken from the heating plate to cool down to room temperature. The remaining solution was transferred to a 50 mL metal-free Falcon tube. The glass beaker was rinsed with a total of 2.8 mL of Trace Select water, in steps of 0.8 mL, 1 mL, and 1 mL, where each step was transferred to the Falcon tube before the adding the next washing fraction. 4 mL of the buffer solution (prepared in Section 5.2.1.1), 11 mL of Trace Select water, and 3 mL of ammonium hydroxide 28% (Sigma 338818) were added to the Falcon tube. The pH of the solution was measured and adjusted to the required pH by adding ammonium hydroxide 28% (Aldrich 338818) using sterile B-Braun syringes.

5.1.2. Electroplating the Backing Surface

A disc shaped niobium backing was obtained from high purity Nb as described herein and (28 mm×1.0 mm) was cleaned with ethanol (high-purity) and inserted in a Comecer Electroplating Unit V21204. A platinum wire anode was positioned so that the distance relative to the coin surface was between about 1 and 3 mm, adjusted by a polymer spacer. The coin mass was determined to be 5.25 grams. Niobium backing (22 mm×1.0 mm weighs 3.3 g). The plating solution was charged to the electrolyte container and attached to the apparatus. The voltage was set to 4.5V. The current reading after 5 min stabilization was 180 μA. The duty cycle for pump was set to 45%. The plating liquid turned from blue to transparent, slow decrease of current to 160 μA was observed over the period of 120 minutes. The plating process was stopped. The coin was taken out of the electrolytic cell and its weight was measured. The coin also underwent microscopic evaluation, FIGS. 1 and 2 using a DINOLite digital microscope to observe the crystal structure and homogeneity of the surface. The coin (FIG. 2) was stored in a metal-free Falcon tube under a nitrogen atmosphere.

5.1.3. Results of the Electroplating

Figure 1:
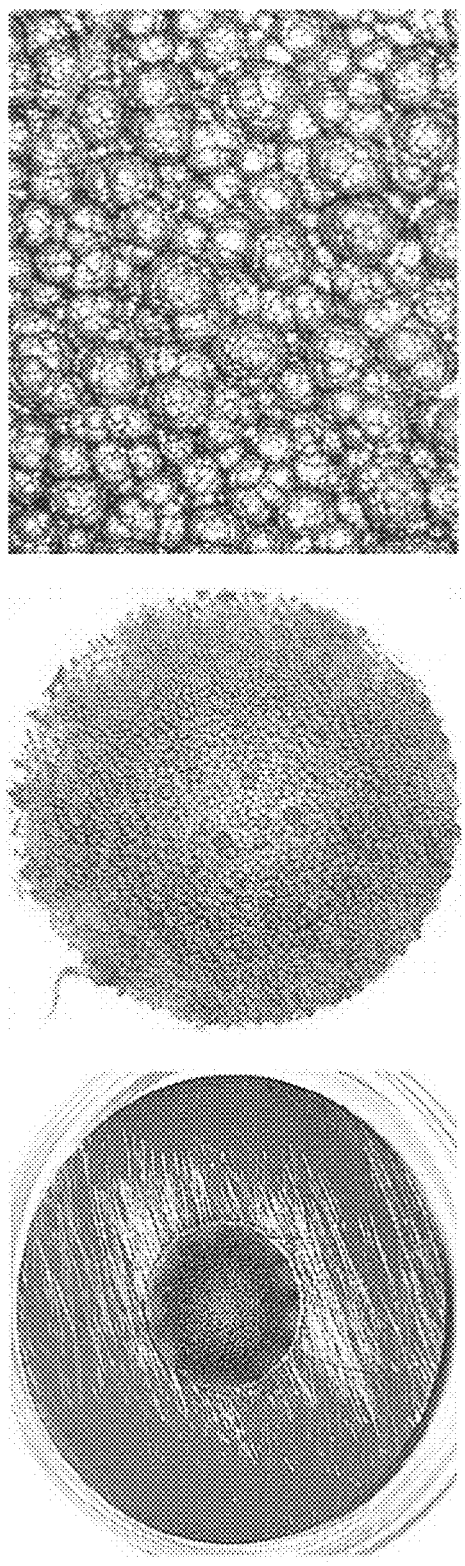
FIG. 1 illustrates with increasing magnification homogenous nickel coating having durable adhesion to a niobium coin upon completion of electroplating, as evaluated using a DINOLite digital microscope. Panel A, 20× magnification; panel B, 50× magnification; panel C, 250× magnification.
Figure 2:
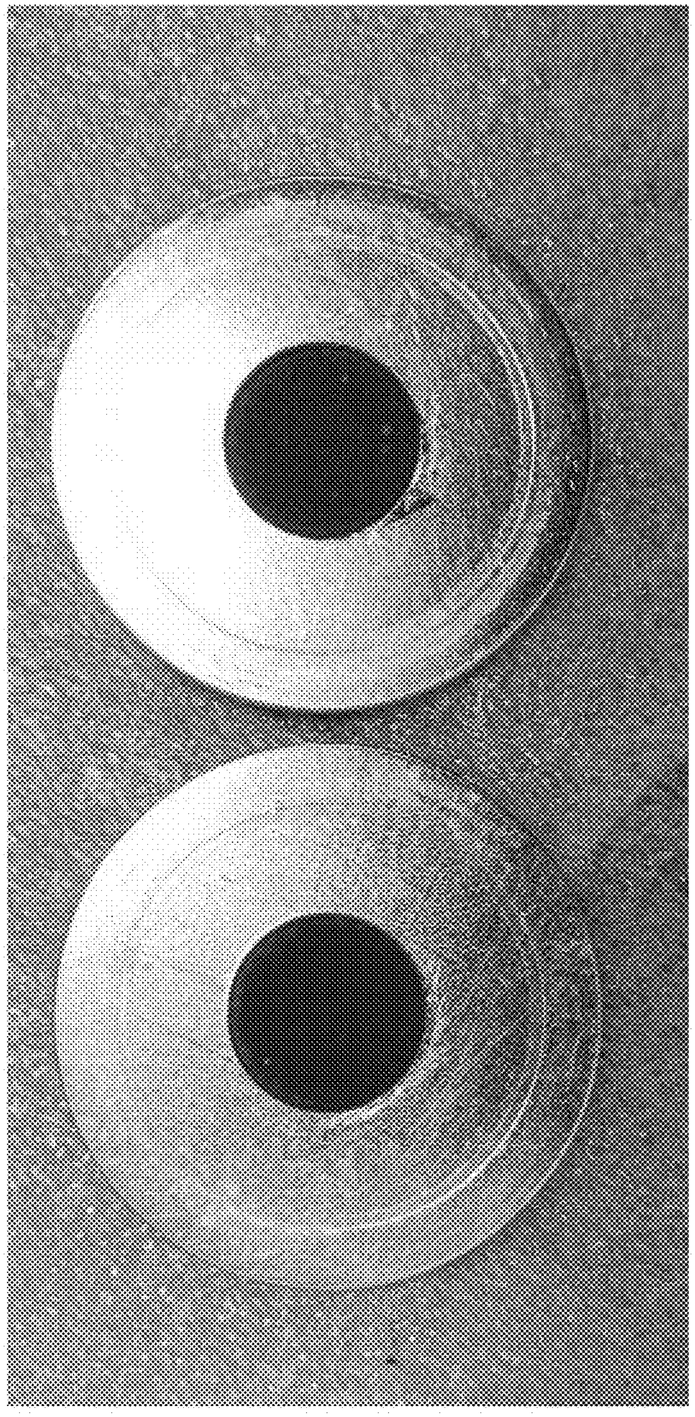
FIG. 2 shows samples of the coin provided according to the present disclosure with nickel deposited in the center of a niobium backing.

Upon completion of electroplating, the coin underwent a microscopic evaluation using a DINOLite digital microscope to observe the crystal structure and homogeneity of the surface. As can be seen in FIG. 1 (panels A-C), a homogenous target coating having durable adhesion was obtained, see also FIG. 2.

5.1.4. General Guidelines for High-purity [$^{61}$Cu]$Cl_2$ Production

The purpose of this example was to enable the bulk production of Copper-61 ($^{61}$Cu) from the deuteron irradiation of natural nickel and/or enriched $^{60}$Ni. This effort was a proof of concept, and, therefore, there were no benchmarked specifications for $^{61}$Cu. However, we optimize target performance, target geometry/material use, irradiation parameters, and chemical processing methods to produce [$^{61}$Cu]$CuCl_2$ following enriched $^{60}$Ni irradiation, or, scaled accordingly for $^{nat}$Ni irradiation. There were no pharmacopoeia specifications for radio-copper explicitly, however, test QC methods include assessment of radionuclidic purity and molar activity (to demonstrate usability of the extracted [$^{61}$Cu]$CuCl_2$).

This example considers use of two different types of targets, natural nickel ($^{nat}$Ni) targets and highly enriched Nickel-60 ($^{60}$Ni) targets both of which were suitable for deuteron bombardment. However, $^{nat}$Ni was cheap and available in high-purity while $^{60}$Ni was still costly and requires efficiency measures. If even higher yields were desired, target preparation efforts may be directly translated into the proton-based $^{61}$Ni(p,n)$^{61}$Cu route, however, given the cost of enriched $^{61}$Ni (c.a. $25 USD/μg), such an approach imposes the need for target recycling.

The set of guidelines below enable all types of targets in the production of $^{61}$Cu, including the production of high-purity [$^{61}$Cu]$CuCl_2$ from the Nb coins with a Zn or Ni (any isotopic enrichment) coating electroplated thereon as provided herein. Specific details are also provided for deuteron, and proton irradiations, respectively. This protocol was followed to generate all the $^{61}$Cu-compositions evaluated in the following examples.

| | |
|---|---|
| Target Backing Geometry | Flat coin - disc-shaped. The dimensions of the target backing form are:<br>Coin backing:<br>Diameter Ø = 20-30 ± 0.1 mm<br>Thickness H = 1.5 mm<br>Target Ni layer or coating<br>a. Diameter 13 mm (deuteron) or 10 mm (proton)<br>b. Mass 70-100 μg, e.g, around 100 ± 40 μg (deuteron) or around 50 ± 20 μg (proton)<br>c. Thickness (H) full density (d = 8.9)<br>i. $H_{min}$ = 0.1 mm; $H_{max}$ = 0.14 mm corresponding to 70-100 μg deposited<br>Tolerances/finishes unless otherwise stated are as follows:<br>Surface finish: Ra 1.6<br>General tolerance: ISO 2768-m<br>Sharp edges and corners according to ISO 13 715 |
| Target Backing Surface | Optional - Surface treated with abrasion by pink corundum grindstone - free of impurities |
| Target Backing Material | Niobium foil, 99.8% (metals basis), 1.0 mm (0.04 in) thick, annealed, Stock No.: 10257<br>Lot No.: C15P07 |

| Element | ppm |
|---|---|
| Carbon | 24 |
| Hydrogen | 1 |
| Molybdenum | 2 |
| Nickel | 4 |
| Silicon | 1 |
| Titanium | 2 |
| Zirconium | 3 |
| Iron | 1 |
| Hafnium | 2 |
| Nitrogen | 14 |
| Oxygen | 56 |

-continued

| | | |
|---|---|---|
| | Tantalum | 785 |
| | Tungsten | 4 |
| Target Backing Material | Niobium 99.9% typical certificate of analysis results, Goodfellows Product nr. 931-627-20 | |
| | Element | ppm |
| | B | <10 ppm |
| | Ni | <5 ppm |
| | O | 100 ppm |
| | Si | 100 ppm |
| | Zr | <10 ppm |
| | Ta | 500 ppm |
| | H | <10 ppm |
| | W | <100 ppm |
| | C | 25 ppm |
| | N | 20 ppm |
| | Fe | 30 ppm |
| | Cu | <5 ppm |
| | Mo | 10 ppm |
| | Ti | <10 ppm |
| Transfer system compatibility | As the target can be automatically transferred to/from the cyclotron by means of a pneumatic target transfer system, it was critical that the deposited Ni was robust to direct air flow and abrupt mechanical movements.<br>In certain embodiments, the target coating remains adhered to the backing during pneumatic transfer both to and from the cyclotron. Such a pneumatic system was typically fed by a compressed air connection of ~6-7 bar, and at minimum, 360 SLPM flow. Such a system was "push-push", and therefore, compressed air was typically blown on both the front and rear sides of the coin, respectively, depending on the direction of transfer. The coin will also come to an abrupt stop as it reaches the target station or hot cell.<br>In certain embodiments, suitable tests that indicate target durability include the following, whereby the total mass loss for all tests combined should be negligible (e.g. <1 µg): Visual inspection, gentle knocking/tapping on a countertop on top of white paper to check for loosening of target coating grains, gently rubbing an acid-washed Teflon spatula against the deposited target coating and checking for loosening of target coating grains, and/or placing and gently pressing down on a piece of Scotch tape against the target coating.<br>If there was access to the cyclotron apparatus, it was recommended to transfer the coin back/forth multiple times and ensure target coating stability (i.e., no mass loss). Such a test may be performed with a degrader in place. | |
| Method of Production | Electrodeposition from bath with a significantly high pH (e.g., 9.9-10.8) | |
| Target Metal Form | To withstand the deposited beam power, the target metal was preferably metallic nickel (not, e.g., nickel oxide).<br>Depending on the means of target preparation (e.g. electroplating), the raw nickel starting material need not necessarily be metallic. However, methods used for preparing $^{nat}$Ni targets should ultimately be directly translatable to preparation of $^{60}$Ni or $^{61}$Ni targets. At present, it was understood that enriched Ni was typically in the form of a salt. | |
| Target Additives | The use of binders must not necessary be avoided if they are absent of the final metallic coin and if an assessment on a case-by-case basis to understand potential impact to product quality has been done (e.g. ICP-MS on the binder material.<br>Any reagents used for target preparation (e.g. electroplating reagents) must be of the highest quality, in particular, with regards to trace metals. | |
| Metal Content | Preferably, the highest grades of reagents should be used, to avoid trace metals contamination of the target coating, as more than a tenth of a microgram per 100 µg of target metal (that is, 1 ppm of the target metal) is already a significant contamination that may render the coin unusable for production of high-purity radionuclides. In the case of the production of radiocopper it is not accepted to add more than 0.1 ppm of cold Cu as this would reduce the purity of the prepared radionuclide composition.<br>Preferably, max level of impurities allowed to be added by the process to the initial nickel:<br>Copper (Cu): 0.1 ppm<br>High affinity metals (Ga, Lu, Pb, Y): 0.1 ppm<br>Zinc and cobalt (Zn, Co): 0.3 ppm<br>Transition and other metals (Cd, Cr, Al, Mn, Mo, Sn, Ti, V . . .): 1 ppm on a case by case<br>Iron (Fe): 10 ppm<br>Family I and II (K, Ba, µg, Be . . .): 1000 ppm<br>The metal coins were analyzed on a batch per batch basis by dissolution in nitric acid to assess the metal contamination within the coin that were not | |

-continued

| | |
|---|---|
| | found in the starting nickel metal and thus originate from the process.<br>The amount suggested above were a good, albeit not strict, guide since chemical purification following irradiation will, in turn, further remove some of these impurities. The ultimate specification on this front will therefore be an iterative process as the Cu/Ni separation chemistry is refined. However, the process shall not significantly add impurities that were not in the originating pure nickel material.<br>It is preferable that cold Cu should be minimized in the deposited Ni since this will follow the chemistry of any $^{61}$Cu and cannot be separated post-irradiation. Any such cold Cu will directly compete with $^{61}$Cu during radiolabeling of the pharmaceutical. Methods of removing Cu from the dissolved target metal are well known. |
| Density of Target | To withstand the deposited beam power, the Ni target should preferably be of reasonably high volumetric density (e.g. approximately ≥90% or, ≥8.0 g/cm$^3$). |
| Power Rating | The power rating for the target, including the combined deposited Ni and plate should preferably be:<br>≥420 W (deuterons)<br>≥820 W (protons) |
| Loading Mass of Target | The loading mass vs. the deposited mass of Ni (i.e. deposition efficiency) relates not to technical specifications, but rather, to cost. In the case of $^{nat}$Ni deposition, loading efficiency will not have a significant impact on the cost of $^{61}$Cu. However, losses should be minimized in considering the translation to enriched $^{6x}$Ni. For $^{60}$Ni, losses should be maintained below ~10%, and for $^{61}$Ni, below ~1%. Some techniques such as magnetron sputtering are thus not possible for enriched nickel but are satisfactory for $^{nat}$Ni. |
| Mass/thickness of Nickel | For deuterons (i.e. $^{nat}$Ni or $^{60}$Ni), the thickness should be appropriate for stopping the deuterons, with a maximum 10% variability in material deposition. Such thicknesses equate to:<br>≥100 μm (assuming 100% density)<br>≥70 μg or ≥89 μg/cm$^2$ (assuming 10 mm diameter)<br>For protons (i.e. $^{61}$Ni), one may wish to selectively limit the deposited material to optimize the balance between material cost, yield, and backing material activation. With a maximum 10% variability in material deposition, four examples are noted below.<br>$^{61}$Ni Scenario #1 (11→9 MeV)<br>78 μm (assuming 100% density)<br>55 μg or 69 μg/cm$^2$ (assuming 10 mm diameter well)<br>$^{61}$Ni Scenario #1 (12→8 MeV)<br>155 μm (assuming 100% density)<br>108 μg or 138 μg/cm$^2$ (assuming 10 mm diameter well)<br>$^{61}$Ni Scenario #1 (13→7 MeV)<br>233 μm (assuming 100% density)<br>163 μg or 208 μg/cm$^2$ (assuming 10 mm diameter well)<br>$^{61}$Ni Scenario #1 (13→4 MeV)<br>309 μm (assuming 100% density)<br>216 μg or 275 μg/cm$^2$ (assuming 10 mm diameter well) |
| Isotopic enrichment | The $^{6x}$Cu radioisotopes which will be coproduced during production of $^{61}$Cu (t ½ = 3.339 h) include:<br>$^{57}$Cu (t ½ = 0.196 s) $^{58}$Cu (t ½ = 3.204 s)<br>$^{59}$Cu (t ½ = 81.5 s) $^{60}$Cu (t ½ = 23.7 m)<br>$^{62}$Cu (t ½ = 9.673 m) $^{64}$Cu (t ½ = 12.701 h)<br>From a practical handling point of view, all but $^{60}$Cu and $^{64}$Cu are likely to have decayed prior to use. Only $^{64}$Cu will have any impact on the possible shelf-life of $^{61}$Cu.<br>In addition to the production of Cu radioisotopes, other radionuclides (e.g. Co and Ni) will also be produced, the ratio of which will depend on the isotopic composition, and whether undergoing deuteron or proton irradiation. As these byproducts are chemically different from copper, such radionuclides may be removed during $^{61}$Cu purification/processing. For example, The Cu-61 was purified from metal and radiometal impurities via a GE Healthcare FASTlab 2 module through a tributyl phosphate resin cartridge and a tertiary-amine-based weak ionic exchange resin containing long-chained alcohols. |
| Any other requirements | Niobium is preferred over silver for its better resistance to corrosion, its low amount of activation on irradiation and for its high melting temperature that permits the deposit of nickel by other processes such as melting or heat sintering. However, silver possesses a higher thermal conductivity and may be suitable for certain embodiments.<br>For target backing manufacture, the following sheet of niobium is suitable for laser cutting:<br>http://www.Goodfellow.com<br>NB000400 Niobium Foil, Size: 150 × 150 mm Thickness: 1.5 mm, Purity: 99.9%, Temper: Annealed, Quality: LT<br>From one sheet up to 25 target backings can be manufactured. |

5.1.5. Purification and Characterization of $[^{61}Cu]CuCl_2$ and Waste Streams

The solid target irradiated material was dissolved in a total volume of 7 mL of 6 M HCl with the addition of 30% hydrogen peroxide via a dissolution chamber.

Separation and purification was accomplished using a cassette-based FASTlab platform using a TBP (tributylphosphate-based) resin (1 mL) (particle size 50-100 μm; pre-packed, Triskem) then a weakly basic (tertiary amine; TK201) resin (2 mL) (particle size 50-100 μm; pre-packed, Triskem) each of which were pre-conditioned with $H_2O$ (7 mL) and HCl (10M, 7 mL). The cassette reagent vials were prepared using concentrated HCl (Optima Grade, Fischer Scientific), NaCl (ACS, Fischer Scientific) and milli-Q water (Millipore system, 18 MΩ-cm resistivity). 6M HCl (2×4.2 mL), 5M NaCl in 0.05 M HCl (4.2 mL). The subsequent $^{61}Cu$ was then purified with two subsequent ion exchange resins in a FASTlab synthesis unit.

1) The acid-adjusted dissolution solution (approx. 7 mL) was loaded over both columns in series and directed into a "Ni collection fraction". The TBP resin acted as a guard column as it quantitatively retained $Fe^{3+}$ ions, while the $Cu^{2+}$ and $Co^{2+}$ complexes were quantitatively retained on the tertiary amine (TK201) resin.
2) Both columns were washed with 6M HCl (4 mL) to maximize Ni recovery for future recycling.
3) The TK201 column was washed with 4.5M HCl (5.5 mL) to elute the majority of cobalt salts.
4) The TK201 column was washed with 5M NaCl in 0.05M HCl (4 mL) to decrease residual acid on the resin and further remove any residual cobalt salts.
5) The TK201 column was washed with of 0.05M HCl (3 mL) to quantitatively elute the $[^{61}Cu]CuCl_2$.

The resulting $[^{61}Cu]CuCl_2$ solution of the plated material has an average activity of 1.0-4.5 GBq. This activity was measured using a dose calibrator from Comecer and its radionuclidic purity by a gamma spectrometer at PSI in Switzerland.

Gamma spectrometry measurements were performed to identify any radionuclidic impurities, particularly long-lived radionuclides. These results indicate a 89.3% and 94% reduction in impurities for $^{nat}Ni$ and $^{61}Ni$ on niobium backing materials with respect to silver backing materials when utilizing the methods disclosed herein. ICP-MS measurements were performed on the product of cold dissolutions by Labor Veritas in Switzerland to monitor elemental impurities present in product according to ICH-Q3D. All detected impurities were within regulated ICH-Q3D concentrations (see ICH-Q3D Guidelines, pg 25).

The plating of highly enriched $^{61}Ni$ was also enabled with the same plating parameters as described above, for a higher yield and industrial production using proton irradiation (typically at 80 μA to 100 μA, 13 MeV protons for 1 hour to 2 hours and up to one half-life of $^{61}Cu$).

5.1.6. Purity and Activity Evaluations of $[^{61}Cu]CuCl_2$ Compositions Prepared from $^{nat}Ni(d,n)^{61}Cu$ and $^{60}Ni(d,n)^{61}Cu$ Using Nb-Backed Coins This example presents information on the activity of the produced $^{61}Cu$ generated using the Nb backing, Ni electrodeposited coins of the present disclosure; alongside cobalt radioisotopes, that were produced with deuteron irradiation using the coin comprising a natural nickel target and the coin comprising enriched $^{60}Ni$ as target, i.e., $^{nat}Ni(d,n)^{61}Cu$ and $^{60}Ni(d,n)^{61}Cu$, respectively. The irradiated materials were dissolved and purified as described in Example 3.

The obtained and purified $^{61}Cu$ product and waste generated during purification from the products of deuteron irradiation of natural nickel/Nb coin and $^{60}Ni$/Nb coin, respectively, was processed and analysed by gamma-spectrometry and presented below.

TENDL-2019 based thick target yield calculations using isotopic abundancy of natural nickel/Nb coin and enriched $^{60}Ni$/Nb coin, respectively.

5.1.7. Radiocobalt Content

Table 8 contains activities of cobalt radioisotopes in the different fractions post FASTlab purification as a mean of three measurements (n=3 irradiations) using $^{nat}Ni$/Nb target coin. The activities were extrapolated to a 3 h and 50 μA beam at EoB (end of bombardment)+2 h. The activity of $[^{61}Cu]CuCl_2$ in these irradiations was determined experimentally and confirmed to be ~80% of TENDL-2019 based estimates.

Activity of produced $^{61}Cu$ for irradiation with deuteron at 8.4 MeV, 3 h at 50 μA at 80% efficiency (EoB+2 h): 3052 MBq. Also see FIG. 3 for the change in cobalt radioisotopes with time along with the corresponding change in $^{61}Cu$ purity.

TABLE 8

| Cobalt isotopes: natNi/Nb target coin | | | | |
|---|---|---|---|---|
| Radionuclide | Cu fraction [Bq] | Ni fraction [Bq] | Co-waste I + II [Bq] | Half-life [days] |
| $^{56}Co$ | 118345 | 2696 | 2458071 | 77 |
| $^{57}Co$ | 0 | 0 | 474 | 272 |
| $^{58}Co$ | 95395 | 2145 | 1940192 | 71 |
| $^{60}Co$ | 124 | 3 | 2602 | 1925 |

Table 9 contains calculated activities of cobalt radioisotopes that would be obtained by using 99% enriched $^{60}Ni$ as target metal. The activities were extrapolated to a 3 h and 50 μA beam at EoB (end of bombardment)+2 h. The activity of $^{61}Cu$ was calculated accordingly.

Activity of produced $^{61}Cu$ with deuteron irradiation at 8.4 MeV, 3 h at 50 μA at 80% efficiency (EoB+2 h): 11.552 MBq. Also see FIG. 4 for the change in cobalt radioisotopes with time and the corresponding change in $^{61}Cu$ purity.

TABLE 9

| Cobalt isotopes: enriched $^{60}Ni$/Nb target coin. | | | | |
|---|---|---|---|---|
| Radionuclide | $^{61}Cu$ fraction [Bq] | Separated Ni [Bq] | Separated Co-waste I + II [Bq] | Half-life [days] |
| $^{56}Co$ | 365 | 8 | 7583 | 77 |
| $^{57}Co$ | 0 | 0 | 1793 | 272 |
| $^{58}Co$ | 242909 | 5463 | 4940424 | 71 |
| $^{60}Co$ | 0.5 | 0 | 11 | 1925 |

5.1.7.1 Activity and Chemical Purity

Based on measured activities (MBq) at different beam currents (μA) and timescales (5-60 minutes), the measured activity resulting from deuteron bombardment of $^{nat}Ni$, $^{60}Ni$ and proton bombardment of $^{61}Ni$ using the process described herein was found to be approximately >80% of the theoretical activity calculated using the TENDL-19 cross section database.

The activity of radiocobalt and other long-lived radionuclides was measured post-release (>3 weeks after bombardment). The EOB activity of the long-lived impurities was then extrapolated.

In Table 10, the extrapolated radiocobalt activity content and $^{61}Cu$ purity of [$^{61}Cu$]$CuCl_2$ solution produced by $^{nat}Ni$ as target metal for a 50 µA, 3 h deuteron irradiation after FASTlab purification were presented.

TABLE 10

Natural Ni/Nb Target Coin- Extrapolation of $^{61}Cu$ activity and purity in produced [$^{61}Cu$]$CuCl_2$ solution.

| Hours post EoB | Co species activity in Cu fraction [Bq] | $^{61}Cu$ activity [MBq] | $^{64}Cu$ activity [MBq] | % Purity $^{61}Cu$ | % Purity PET nuclides $^{61}Cu$ + $^{64}Cu$ | % non-Cu radionuclides |
|---|---|---|---|---|---|---|
| 0 | 213864 | 4622 | 70 | | 99.995% | 0.00456% |
| 1 | 213784 | 3756 | 66 | 98.261% | 99.994% | 0.00559% |
| 2 | 213704 | 3052 | 63 | 97.979% | 99.993% | 0.00686% |
| 3 | 213624 | 2479 | 59 | 97.652% | 99.992% | 0.00841% |
| 4 | 213544 | 2015 | 56 | 97.274% | 99.990% | 0.01031% |
| 5 | 213465 | 1637 | 53 | 96.837% | 99.987% | 0.01263% |
| 6 | 213385 | 1330 | 50 | 96.332% | 99.985% | 0.01545% |
| 7 | 213305 | 1081 | 48 | 95.750% | 99.981% | 0.01890% |
| 8 | 213225 | 878 | 45 | 95.081% | 99.977% | 0.02309% |
| 9 | 213145 | 714 | 43 | 94.312% | 99.972% | 0.02817% |
| 10 | 213066 | 580 | 41 | 93.432% | 99.966% | 0.03434% |

Less than 0.03% non-Cu radioisotopes ($^{56}Co$ and $^{58}Co$) will be left in the copper fraction, assuming a product expiry time, e.g., >3 weeks post EoB. This value was lower than the limit allowed for Ga-68 cyclotron-produced as found in the Pharmacopeia (*0.1% at expiry for non-Ga radioisotopes):

The $^{64}Cu$ originating from $^{nat}Ni$ irradiation (content ~5% at expiry) will be the main impurity, reducing the radioisotopic purity of $^{61}Cu$ product at longer irradiation times or shelf-life (illustrated as the grey curve in FIG. 3).

In Table 11 and after FASTlab purification. FIG. 4, shows the extrapolated radiocobalt activity content and $^{61}Cu$ purity of the produced [$^{61}Cu$]$CuCl_2$ solution.

TABLE 11

$^{60}Ni$/Nb Target coin - Extrapolation of $^{61}Cu$ activity and purity in produced [$^{61}Cu$]$CuCl_2$ solution.

| Hours post EoB | Co species activity in Cu fraction [Bq] | $^{61}Cu$ activity [MBq] | $^{64}Cu$ activity [MBq] | % Purity $^{61}Cu$ | % Purity PET nuclides $^{61}Cu$ + $^{64}Cu$ | % non-Cu radionuclides |
|---|---|---|---|---|---|---|
| 0 | 243275 | 17498 | 0.378 | | 99.999% | 0.00139% |
| 1 | 243176 | 14217 | 0.358 | 99.996% | 99.998% | 0.00171% |
| 2 | 242977 | 11552 | 0.339 | 99.995% | 99.998% | 0.00210% |
| 3 | 242680 | 9386 | 0.321 | 99.994% | 99.997% | 0.00259% |
| 4 | 242285 | 7627 | 0.304 | 99.993% | 99.997% | 0.00318% |
| 5 | 241792 | 6197 | 0.288 | 99.991% | 99.996% | 0.00390% |
| 6 | 241201 | 5035 | 0.272 | 99.990% | 99.995% | 0.00479% |
| 7 | 240514 | 4091 | 0.258 | 99.988% | 99.994% | 0.00588% |
| 8 | 239731 | 3324 | 0.244 | 99.985% | 99.993% | 0.00721% |
| 9 | 238853 | 2701 | 0.231 | 99.983% | 99.991% | 0.00884% |
| 10 | 237882 | 2195 | 0.219 | 99.979% | 99.989% | 0.01084% |

Less than 0.01% non-Cu radioisotopes ($^{56}Co$ and $^{58}Co$) were left in the Cu fraction, assuming a product expiry time of 8 h post EoB. This value was ten times lower than the allowed limit for $^{68}Ga$ cyclotron-produced as found in the Pharmacopeia (0.1% at expiry for non-Ga radioisotopes*).

Less than 0.02% $^{64}Cu$ was left in the copper fraction at an expiry time of 8 h post EoB, one hundred times lower than the specification required for $^{68}Ga$ (2% Ga radioisotopes were allowed for $^{68}Ga$).

5.1.8. Purity of Produced [$^{61}Cu$]$CuCl_2$ from Ni/Nb Target Coins: Comparison with Commercially Available Radionuclides In Table 12, a comparison of the regulatory specifications on the purity of commercially available radionuclides were given along with the characteristics of the high purity [$^{61}Cu$]$CuCl_2$ produced from deuteron irradiation of natNi/Nb and enriched $^{60}Ni$/Nb target coin (50 µA, 3 h) and after FASTlab purification were presented.

TABLE 12

Comparison between commercially available radionuclides and [$^{61}$Cu]$CuCl_2$ solution produced from irradiation of $^{nat}$Ni/Nb coins and enriched $^{60}$Ni/Nb coins.

| Radionuclide | % Purity at EoB + 2 hours | % Max radioisotopes of same element at EoB + 2 hours | % Max other radioisotopes at EoB + 2 hours | Dominant impurities | % Purity at expiry | % Max other radioisotopes at expiry |
|---|---|---|---|---|---|---|
| $^{111}$In[1] | 99.93% | 0.075% | | $^{65}$Zn, $^{114m}$In | 99.85% | 0.15% |
| $^{18}$F[2] | | | | $^{56}$Co | 99.90% | 0.10% |
| $^{18}$F [3] | | | | $^{56}$Co | 99.99% | 0.01% |
| $^{68}$Ga cyclotron[4] | 98% | 2% | 0.10% | | | |
| $^{68}$Ga generator[5] | 99.90% | | 0.001% | $^{68}$Ge | | |
| $^{177}$Lu[6] | 99.90% | 0.05% | | | | |
| $^{61}$Cu from $^{nat}$Ni | 97.27% (EoB + 4 h) | 3.16% | 0.013% | $^{56}$Co, $^{58}$Co | 95.08% (EoB + 8 h) | 5% |
| $^{61}$Cu from $^{60}$Ni | 99.99% (EoB + 4 h) | 0.009% | 0.004% | $^{56}$Co, $^{58}$Co | 99.98% (EoB + 8 h) | 0.02% |

As the first notable comparison, cyclotron production of $^{68}$Ga from proton irradiation also produces long lived radionuclides, (see, e.g., Applied Radiation and Isotopes, 65(10), 1101-1107, IAEA-TECDOC-1863 Gallium-68 Cyclotron Production)-notably $^{65}$Zn (half-life=244 days) from the $^{66}$Zn (p,pn)$^{65}$Zn decay. With a roughly 0.36500 of $^{66}$Zn in an enriched $^{68}$Zn starting target metal, about 770 Bq of $^{65}$Zn will be produced from a 50 μA, 3 h beam with an energy of 13 MeV in a thick target (TENDL-2019 based calculations). Using natural Zn with 27.700 abundancy in $^{66}$Zn, 58 kBq of $^{65}$Zn will be produced in one run of 50 μA for 3 h beam. The isotopic purity of Zn in the target metal is, thus, very important.

Similar with [$^{61}$Cu]$CuCl_2$ production, cyclotron production of [$^{64}$Cu]$CuCl_2$ from proton irradiation also produces long-lived cobalt radionuclides, namely, $^{55}$Co, $^{57}$Co, $^{58}$Co, and $^{60}$Co. (See, e.g., Nuclear Medicine & Biology, Vol. 24, pp. 35-43, 1997; Applied Radiation and Isotopes 68 (2010) 5-13) By operating with a degraded beam of below 13 MeV, $^{60}$Co (from $^{64}$Ni(p,na)$^{60}$Co) was reduced to 1 Bq per run of 50 μA, 3 h. With beam energies below 13 MeV, $^{55}$Co, formed from the $^{58}$Ni(p,α)$^{55}$Co reaction, will remain the main impurity (half-life=17.53 hours). The 170 Bq of the long-lived $^{57}$Co was formed in about 170 Bq in these conditions mostly from $^{60}$Ni(p,α)$^{57}$Co.

Note: These estimates were computed from thick target yields using TENDL-2019 cross section data and isotopic abundancy of enriched $^{64}$Ni as follows: 0.00376% $^{58}$Ni, 0.00298% $^{60}$Ni, 0.0058% $^{61}$Ni, 0.135% $^{62}$Ni, 99.858% $^{64}$Ni.

Example 1B. Enriched $^{61}$Ni as Target Metal on Nb Backed Coins $^{61}$Cu was produced through the proton bombardment of $^{61}$Ni electroplated Nb backed coin via cyclotron equipped with a solid target system irradiating a highly pure Niobium coin plated with highly pure $^{61}$Ni (purity 99.42%). The proton beam currents used were up to 100 μA, and beam energy of 13 MeV. An aluminum beam degrader was used.

The solid target irradiated material was dissolved in a total volume of 7 mL of 6M HCl with the addition of 30% $H_2O_2$ in a heated dissolution chamber. The $^{61}$Cu was purified from metal and radiometal impurities via a GE Healthcare FAST-lab 2 module through a tributyl phosphate resin cartridge and a tertiary-amine-based weak ionic exchange resin containing long-chained alcohols. The product was finally eluted in an ISO class 5 environment in 3 mL 0.05 M HCl through a sterile filter Millex 4 mm Durapore PVDF 0.22 μm into a sterile evacuated vial. The vial was handled with care using the appropriate shielding and can be stored at room temperature until use using appropriate shielding for transport and handling.

TABLE 13

Specifications of [$^{61}$Cu]$CuCl_2$.

| Parameter | Test Method | Specification |
|---|---|---|
| Appearance | Visual inspection | Clear, colorless solution, free from particulate matter |
| Volume | Weight measurement | 3 ± 0.3 mL |
| Activity concentration (EoS) | Dose calibrator | 0.30-2 GBq/mL |
| pH value | pH paper strips | 1-1.6 |
| Radiochemical purity | Radio-TLC | ≥99% (as [$^{61}$Cu]$CuCl_2$) |
| Radionuclidic identity | γ-Spectrometry (in lab at EoB + 90 minutes) | γ-photons with energy peaks at: 283 keV ± 20 keV 511 ± 20 keV (eventually sum peak at 1022 keV ± 20 keV) 656 keV ± 20 keV |
| | Half-life via dose calibrator | 200 ± 20 min |
| Radionuclidic purity | γ-Spectrometry (sent out, evaluated >3 weeks, values extrapolated to in lab at EoB + 90 minutes) | ≥99.9% |

TABLE 13-continued

Specifications of $[^{61}Cu]CuCl_2$.

| Parameter | Test Method | Specification |
|---|---|---|
| Bacterial endotoxin content | LAL test (Endosafe) | ≤17.5 EU/mL |
| Chemical purity | ICP-MS (sent out, evaluated >3weeks, values relevant to in lab at EoB + 90 minutes as these do not change with time) | Sum of impurities ≤ 15 μg/GBq<br>Cu ≤ 0.5 μg/GBq<br>Al ≤ 2 μg/GBq<br>Co ≤ 1 μg/GBq<br>Fe ≤ 3 μg/GBq<br>Pb ≤ 1 μg/GBq<br>Ni ≤ 2 μg/GBq<br>Zn ≤ 1 μg/GBq |

*post-release (≥3 weeks)
#measured periodically

As shown in Table 14 and FIG. 5, commercially available $[^{61}Cu]CuCl_2$ contains radionuclidic impurities, particularly high levels of $^{56}$ Co and $^{58}Co$, in addition to $^{110m}Ag$ and $^{109}Cd$. Elimination of Ag and Cd isotopes from the Cu-61 product by replacing silver with niobium as backing material. There was a nine-fold reduction of $^{56}Co$ isotopes for natNi and >2000× reduction for Ni-61 (less shielding of radioactive waste is required). 50% reduction of long-lived cobalt isotopes (earlier final disposal of the produced waste) was also observed. It was clear from the data below, that the radionuclidic purity of $[^{61}Cu]CuCl_2$ produced by the methods of the present disclosure was shown to be superior to previously known methods and products. The high levels of long-lived Co, Ag, and Cd radionuclides pose a radiation burden for the patient and a radioactive waste issue for consumables that have come in contact with the $[^{61}Cu]CuCl_2$ product during radiopharmaceutical manufacturing and radiolabeling.

TABLE 14

Detailed radionuclidic impurities present in commercially available $^{61}Cu$ compared to high-purity $[^{61}Cu]Cl_2$ of the present disclosure, expressed in Bq/g.

| | | Coin | | |
|---|---|---|---|---|
| | | Ext. Coins | Present Coins | |
| Elements | $T_{1/2}$ | nat-Ni on Ag | nat-Ni on Nb<br>Bq/g | $^{61}Ni$ on Nb |
| Co-56 | 77.23 days | 5269.2 | 539.5 | 2.3 |
| Co-57 | 271.74 days | 1.8 | 1.5 | 1.2 |
| Co-58 | 70.86 days | 4586.8 | 503.8 | 588.5 |
| Co-60 | 5.27 years | 5.9 | 2.8 | 0.9 |
| Ag-108m | 439 years | 0.9 | N/D | N/D |
| Ag-110m | 249.86 days | 1.5 | N/D | N/D |
| Cd-109 | 462.6 days. | 10 | N/D | N/D |

The total radionuclidic impurity profile was summed and displayed below in Table 15 and FIG. 6, showing an 83% decrease in radionuclidic impurities. When present in the $[^{61}Cu]CuCl_2$ product, these impurities can cause a radiation burden for the patient, waste issues, and degrade the quality of the radiopharmaceutical. They can also interfere with the chelation process by competing with $^{61}Cu$, which affects the accurate radiolabeling of the tracer. An 89.3% reduction of impurities was observed upon changing the backing material from silver to the niobium backing provided herein and using the Ni plating methods described herein.

Additional reduction of 46% was observed when using Ni-61 as starting material.

TABLE 15 compares the sum of radionuclidic impurities in the produced $[^{61}Cu]CuCl_2$ stemming from the irradiation of commercially available coins compared to impurities produced by the coins of the present disclosure, expressed in Bq/g.

| | Coin | | |
|---|---|---|---|
| | Ext. Coins | Present Coins | |
| | natNi on Ag. | nat-Ni on Nb | $^{61}Ni$ on Nb |
| Bq/g | 9876 ± 1.5 | 1057 ± 1.8 | 593 ± 0.2 |

Consequent to the purity of the $^{6}Cu$ at EoB an EoS EoB+2, long-live radionuclidic impurities decay slower and, thus, increase in concentration in relation to $^{61}Cu$ at longer timescales. Thus, the impurity profile may vary greatly based on the isotopic enrichment of the raw material, purity, method, and process of producing a coin, which influences the type and amount of radionuclidic impurities in the finished $[^{61}Cu]CuCl_2$ product.

FIG. 7. contrasts the radionuclidic purity of $[^{61}Cu]CuCl_2$ solution produced with commercially available natNi target metal on a Ag backing compared to the radionuclidic purity of $[^{61}Cu]CuCl_2$ solution produced by irradiation of Ni target metal electroplated according to the present disclosure on high purity Nb backing when assessed by gamma spectrometry in Bq/g (summed radionuclidic impurities) at t=0 h and at t=12 h. The presented data highlight the superior quality of the $[^{61}Cu]CuCl_2$ solution when produced by irradiation of Ni target coatings electroplated according to the present disclosure on high purity Nb backing, where the purity after 12 hours is still well above the purity limits set by pharmacopeia for similar radionuclides for medical use.

TABLE 16

Radionuclidic purity of $[^{61}Cu]CuCl_2$ stemming from the irradiation of commercially available coins or material to $[^{61}Cu]CuCl_2$ produced through method of the present disclosure. Radionuclidic purity of commercially available $^{61}Cu$ compared to high-purity $[^{61}Cu]CuCl_2$ of the present disclosure as measured at EOS and EOS + 12 hours.

| | Ext. Coins | Present Coins | |
|---|---|---|---|
| Coin | nat-Ni on Ag | nat-Ni on Nb | $^{61}Ni$ on Nb |
| Purity % t = 0 h | 99.998 | 99.999 | 99.9999 |
| Purity % t = 12 h | 99.978 | 99.993 | 99.999 |

5.1.9. Endotoxin Determination by Limulus Amebocyte Lysate (LAL Test)

The bacterial endotoxins were determined by LAL test using the Charles River Endosafe™-PTS system.

During dispensing of the [$^{61}$Cu]$CuCl_2$ solution, an aliquot of 1 mL was dispensed for quality control tests. The tests were carried out in a non-classified quality control laboratory. The solution was composed of [$^{61}$Cu]$CuCl_2$, 0.05 M HCl(aq).

TABLE 17

LAL-tested [$^{61}$Cu]$CuCl_2$ solution.

| Material | Description |
|---|---|
| Endosafe ™-PTS cartridge sensitivity 5-0.05 Eu/mL | Charles River PTS2005F. Disposable test cartridge used as platform for the rapid kinetic chromogenic LAL test. Pre-loaded with all the reagents required to perform the test. |
| Endotoxin free water | Charles River W120 |
| Endotoxin-free pipette tips | Sarstedt Biosphere Quality Tips, 70.762.200 (100-1000 μL); 70.3031.305 (250 uL); 70.1114.200 (0.5-20 μL) |
| Endotoxin-free dilution tubes | Charles River TL1000 |
| Endotoxin-free TRIS buffer | Charles River 100 mM TRIS buffer BT105 |

The [$^{61}$Cu]$CuCl_2$ solution (pH 1.3) was diluted before the analysis using LAL reagent water and a buffer in order to reach a pH value in the range 6-7.6. To adjust the pH, TRIS buffer was added to the [$^{61}$Cu]$CuCl_2$ solution.

A dilution was prepared of the [$^{61}$Cu]$CuCl_2$ to be tested mixing the reagents in the endotoxin-free dilution tubes as follows: dilution factor (1:75); [$^{61}$Cu]$CuCl_2$ sample (10 μL); TRIS buffer (40 μL); water (700 μL). Mix for about 30 seconds.

5.1.10. Conclusion

The experimental activities of $^{6}$Cu produced after deuteron irradiation are about 80% of the theoretical yield as calculated from TENDL-2019 cross section data.

The main long-lived nuclides in the radioactive waste fraction from cyclotron production of $^{61}$Cu are radiocobalt species of $^{56}$Co, $^{57}$Co, $^{58}$Co, and $^{60}$Co. After four years, $^{56}$Co, $^{57}$Co, and $^{58}$Co are calculated to have decayed below regulatory clearance limits, LL*, leaving only $^{60}$Co. *Clearance limits (LL) means the value corresponding to the activity concentration level of a material below which handling of this material is no longer subject to mandatory licensing or supervision.

To improve the yield and purity of the [$^{61}$Cu]$CuCl_2$ product, target coins with 99% enriched $^{60}$Ni or $^{61}$Ni can be used. Using these targets, the extrapolated purity of [$^{61}$Cu]$CuCl_2$ product will be higher as $^{64}$Cu will not be formed as a radioisotopic impurity. Additionally, the $^{56}$Co and $^{60}$Co contents will be reduced by a factor of 100. On the other hand, $^{57}$Co amounts will quadruple (but is in low activity) and $^{58}$Co amounts will be doubled (but will decay below LL before $^{56}$Co/$^{58}$Co).

Example 2A—Preparation of NODAGA-PSMA-I&T

General Analytical reversed-phase high performance liquid chromatography (RP-HPLC) is performed on a Nucleosil 100 $C_{18}$ (5 m, 125×4.0 mm) column (CS GmbH, Langerwehe, Germany) using a Sykam gradient HPLC System (Sykam GmbH, Eresing, Germany). The peptides are eluted applying different gradients of 0.1% (v/v) trifluoroacetic acid (TFA) in H2O (solvent A) and 0.1% TFA (v/v) in acetonitrile (solvent B) at a constant flow of 1 mL/min (specific gradients are cited in the text). UV detection is performed at 220 nm using a 206 PHD UV-Vis detector (Linear™ Instruments Corporation, Reno, USA). Both retention times tR as well as the capacity factors K' are cited in the text. Preparative RP-HPLC is performed on the same HPLC system using a Multospher 100 RP 18-5 (250×20 mm) column (CS GmbH, Langerwehe, Germany) at a constant flow of 9 mL/min. Radio-HPLC of the radioiodinated reference ligand is carried out using a Nucleosil 100 C18 (5 μm, 125×4.0 mm) column.

Synthesis of Carboxyl-Protected Lys-Urea-Glu-Core (KuE)

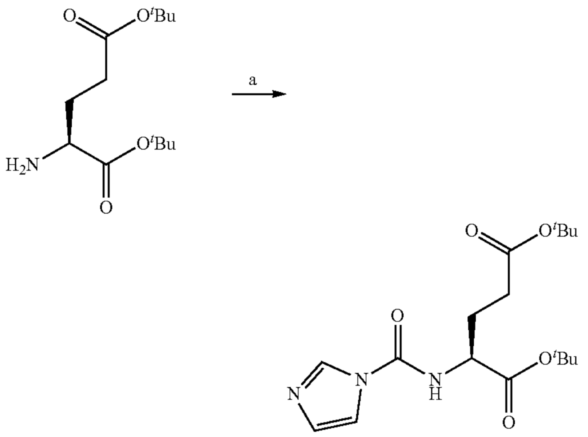

Step a. (S)-di-tert-butyl 2-(1H-imidazole-1-carboxamido) pentanedioate (1) is synthesized from the di-tert-butyl ester of glutamic acid. It is reacted with carbonyldiimidazole (CDI) under anhydrous conditions in the presence of triethylamine (TEA) to form the intermediate acylimidazole derivatives. HPLC (10% to 90% B in 15 min): tR=12.2 min; K'=5.78. Calculated monoisotopic mass for 1 ($C_{17}H_{27}N_3O_5$): 353.4; found: m/z=376.0 [M+Na]+.

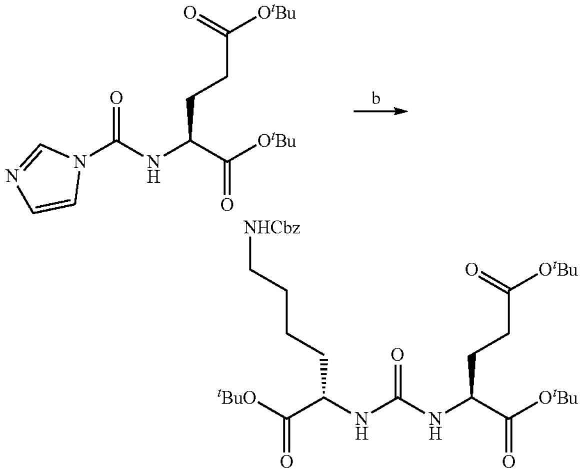

Step b. Cbz-(OtBu)KuE(OtBu)$_2$ (2): A solution of 3.40 g (9.64 mmol, 1.0 eq) 1 in 45 mL 1,2-dichloroethane (DCE) is cooled to 0° C., and 2.69 mL (19.28 mmol, 2.0 eq) of triethylamine (TEA), and 3.59 g (9.64 mmol, 1.0 eq) of Cbz-Lys-OtBu HCl is added under vigorous stirring. The reaction mixture is heated to 40° C. overnight. The solvent is removed in vacuo, and the crude product is purified via silica gel flash-chromatography using an eluent mixture of ethyl acetate/hexane/TEA (500/500/0.8 (v/v/v)). Upon solvent evaporation, 4.80 g of 2 are obtained as a colourless, sticky oil (yield: 80% based on L-di-tert-butyl glutamate HCl). HPLC (40% to 100% B in 15 min): tR=14.3 min; K'=8.53. Calculated monoisotopic mass for 2 ($C_{32}H_{51}N_3O_9$): 621.8; found: m/z=622.2 [M+H]+, 644.3 [M+Na]+.

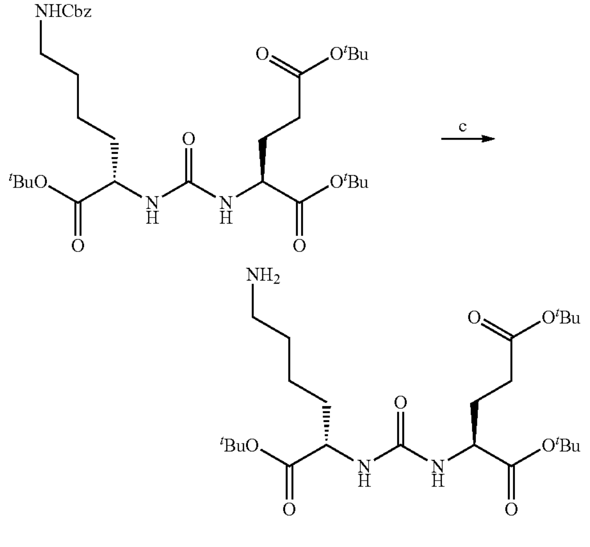

Step c. (OtBu)KuE(OtBu)$_2$ (3): For Cbz deprotection, 6.037 g (9.71 mmol, 1.0 eq) of 2 is dissolved in 150 mL of ethanol (EtOH), and 0.6 g (1.0 mmol, 0.1 eq) of Palladium on activated charcoal (10%) is added. After purging the flask with H2, the solution is stirred overnight under light $H_2$-pressure (balloon). The crude product is filtered through Celite, the solvent is evaporated in vacuo, and the desired product is obtained as a waxy solid (4.33 g, 91.5% yield). HPLC (10% to 90% B in 15 min): tR=12.6 min; K'=6.41. Calculated monoisotopic mass for 3 ($C_{24}H_{45}N_3O_7$): 487.6; found: m/z=488.3 [M+H]+, 510.3 [M+Na]+.

Synthesis of Protected Sub-KuE Conjugate

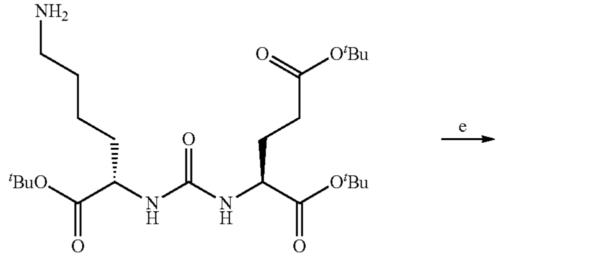

-continued

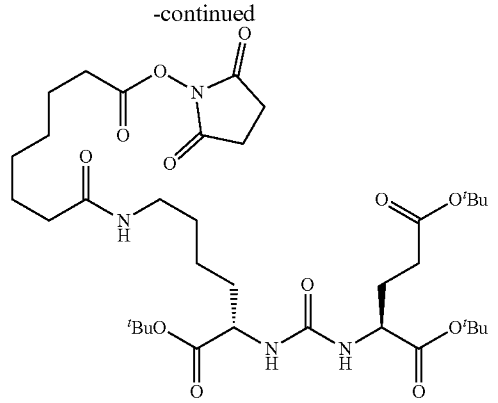

NHS-Sub-(OtBu)KuE(OtBu)$_2$ (4): 3 (40 μg, 0.08 mmol, 1 eq) is dissolved in 500 μL N,N-dimethylformamide (DMF), and 57 μL (0.41 mmol, 5 eq) of TEA is added. This solution is added dropwise (within 30 min) to a solution of 33.2 μg (0.09 mmol, 1.1 eq) of disuccinimidyl suberate (DSS). After stirring for an additional 2 h at room temperature (RT), the reaction mixture is concentrated in vacuo, diluted with ethyl acetate and extracted with water (twice). The organic phase is dried over $Na_2SO_4$, filtered and evaporated to dryness. Due to sufficient purity of the crude 4, it is used for the following reaction step without further purification. HPLC (10% to 90% B in 15 min): tR=16.9 min; K'=8.39. Calculated monoisotopic mass for 4 ($C_{36}H_{60}N_4O_{12}$): 740.4; found: m/z=741.2 [M+H]+, 763.4 [M+Na]+.

Synthesis of Peptidic Linker

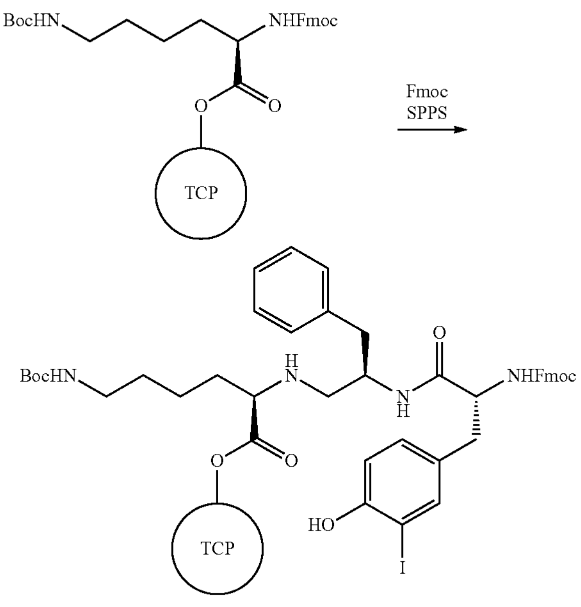

Fmoc-3-iodo-D-Tyr-D-Phe-D-Lys(Boc) (Fmoc-(I-y)fk): Fmoc-Lys (Boc)-OH (1.5 eq) is dissolved in dry dichloromethane (DCM), and N,N-diisopropylethylamine (DIPEA) (1.25 eq) is added. Dry TCP resin is suspended and stirred at RT for 5 min. Another 2.5 eq of DIPEA is added, and stirring is continued for 90 min. Then, 1 mL methanol (MeOH) per gram resin is added to cap unreacted tritylchloride groups. After 15 min, the resin is filtered off, washed twice with DCM, DMF and MeOH, respectively, and dried in vacuo. Final load of resin-bound Fmoc-Lys(Boc)-OH is calculated from the weight difference.

Assembly of the peptide sequence H2N-3-iodo-D-Tyr-D-Phe-on resin-bound Lys(Boc) is performed according to a standard Fmoc-protocol using 1.5 eq of 1-hydroxybenzotriazole(HOBt) and O-(1H-benzotriazol-1-yl)-N,N,N',N'-tetramethyluronium-tetrafluoroborate (TBTU) as coupling reagents and 4.5 eq DIPEA. After coupling of the last amino acid, the resin is washed, dried and stored in a desiccator until further functionalization.

Coupling of Chelating Moiety

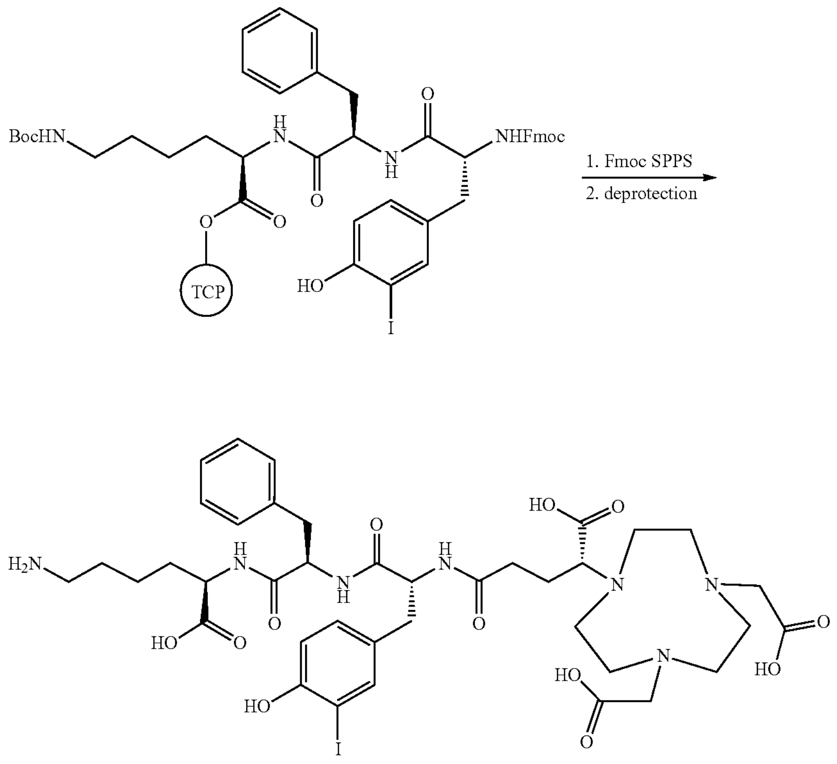

Fmoc-3-iodo-D-Tyr-D-Phe-D-Lys(Boc)-TCP resin is allowed to pre-swell in N-methyl-pyrrolidon (NMP) for 30 min. After cleavage of the N-terminal Fmoc-protecting group using 20% piperidine in DMF (v/v), the resin is washed eight times with NMP.

NODAGA-iodo-D-Tyr-D-Phe-D-Lys (NODAGA-(I-y)fk, 5): For 38 μmol of resin-bound peptide, 31 μg of NODAGA-tris-tBu-ester (57 μmol, 1.5 eq), 108 μg of O-(7-azabenzotriazol-1-yl)-N,N,N',N'-tetramethyluronium hexafluorophosphate (HATU; 0.28 μmol, 5 eq) and 87 μL of DIPEA (570 μmol, 15 eq) in NMP are added to the resin. After 72 h of shaking, the resin is washed with NMP and DCM. HPLC (10% to 90% B in 15 min): tR=8.2 min; K'=4.13. Calculated monoisotopic mass for 5 ($C_{39}H_{54}IN_7O_{12}$): 939.29;

Cleavage from the resin (2×30 min) and concomitant tBu-deprotection is performed using a mixture (v/v/v) of 95% TFA, 2.5% triisobutylsilane (TIBS) and 2.5% water. The combined product solutions are then concentrated, the crude peptide is precipitated using diethyl ether and is dried in vacuo. Due to sufficient purity of the crude products, they are used for the following reaction step without further purification.

Condensation of the Chelator-Conjugated Peptides and the PSMA Binding Motif

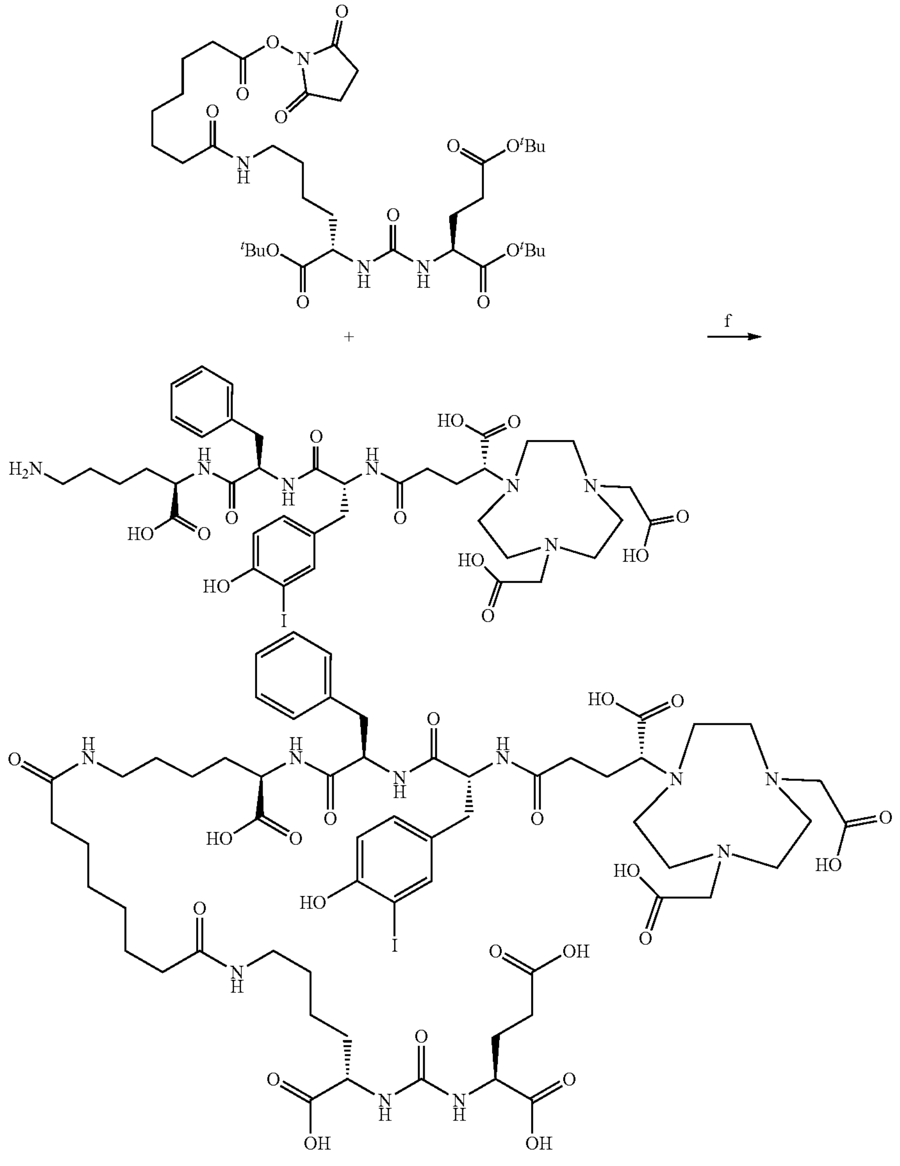

NODAFA-PSMA-I&T

NODAGA-(I-y)fk(Sub-KuE) (6): To a solution of 5 (15 μg, 18 μmol, 1 eq) and TEA (13 μL, 90 μmol, 5 eq) dissolved in 600 μL of DMF is slowly added 13 μg of 4 (18 μmol, 1 eq) dissolved in 400 μL of DMF. After stirring for 2 h at RT, the reaction mixture is evaporated to dryness. Subsequent removal of tBu-protecting groups is carried out by dissolving the crude product in TFA and stirring for 40 min. After precipitation in diethyl ether, the crude product is dissolved in water and purified using preparative RP-HPLC (25% to 40% B in 20 min). HPLC (10% to 90% B in 15 min): tR=10.3 min; K'=5.44. Calculated monoisotopic mass for 10 ($C_{59}H_{85}IN_{10}O_{21}$): 1396.5. See FIG. 32A-C for $^{1}$H-NMR spectrum and associate chemical shifts.

Alternatively, HPLC analysis was performed on a Waters XBridge Peptide BEH C18, 250×4.6 mm, 3.5 μm column; eluent A: water (0.1% $H_3PO_4$); eluent B: acetonitrile (0.1% $H_3PO_4$); 10% B to 90% linearly over 15 minutes at 1 mL/min; detection at 215 nm; retention time, 12.4 minutes.

MALDI-TOF calc. $[MH]^+$ 1397.5 m/z. Found 1397.8 m/z. Here performed in linear positive mode with cyano hydroxycinnamic acid as matrix.

Example 2—Complexation of Natural Copper ($^{nat}$Cu) to NODAGA-, DOTAGA- and DOTA-Targeted Chelator Constructs of PSMA Ligands, Somatostatin Analogues and FAP Ligands The $^{nat}$Cu complexes were prepared by incubating each targeted chelator constructs with 1.5-fold excess of $^{nat}$-$CuCl_2$×$2H_2O$ in ammonium acetate buffer, 0.5 M, pH 8 at 95° C. for 15 min (for the NODAGA-constructs, NODAGA-PSMA-I&T, NODAGA-TOC, NODAGA-LM3, NODAGA-F1, NODAGA-F2, NODAGA-F3, NODAGA-F4, and NODAGA-FAPI-46) or 30 min (for the DOTAGA- and DOTA-constructs, DOTAGA-PSMA-I&T and DOTA-TOC). Uncomplexed $^{nat}$Cu ions were eliminated by SepPak C-18 purification. The $^{nat}$Cu-complexes were eluted with methanol, evaporated to dryness, re-dissolved in water and lyophilized. The purity of all complexes was confirmed by liquid chromatography and mass spectrometry (LC-MS). Table 13 presents the retention time (tR), and the obtained mass (mass-to-charge ratio, m/z) of the ion $[M+2H]^{2+}$ in comparison to the theoretical mass, confirming the identity of the formed $^{nat}$Cu-complexed conjugates.

TABLE 13

Analytical data of $^{nat}$Cu-constructs. The analysis was performed on a LC-MS (Shimadzu LC2020) system using Waters X Bridge C18 5 μm, 150 × 4.6 mm column and a gradient of 15-65% acetonitrile (0.1% TFA)/water (0.1% TFA) in 15 min, at a flow rate of 2 mL/min. For F1, F2, F3, and F4, the analysis was performed on a LC-MS (Shimadzu LC2020) system using Gemini C6 Phenyl 5 μm, 250 × 4.6 mm column and a gradient of 15-80% acetonitrile (0.1% TFA)/water (0.1% TFA) in 15 min, at a flow rate of 2 mL/min. Table 13: Analytical for $^{nat}$Cu complexed targeted constructs targeted

| $^{nat}$Cu-complexed targeted constructs | m/z calculated | m/z measured | tR (min) |
|---|---|---|---|
| $^{nat}$Cu-DOTAGA-PSMA-I&T | 780.9 | 780.9 | 11.19 |
| $^{nat}$Cu-NODAGA-PSMA-I&T | 730.4 | 730.8 | 11.20 |
| $^{nat}$Cu-DOTA-TOC | 742.6 | 742.5 | 10.61 |
| $^{nat}$Cu-NODAGA-TOC | 728.1 | 728.0 | 10.96 |
| $^{nat}$Cu-NODAGA-LM3 | 792.3 | 792.6 | 10.92 |
| $^{nat}$Cu-NODAGA-F1 | 920.2 | 920.3 | 9.77 |
| $^{nat}$Cu- NODAGA-F3 | 946.9 | 946.5 | 9.94 |
| $^{nat}$Cu-NODAGA-F2 | 934.2 | 934.2 | 9.44 |
| $^{nat}$Cu-NODAGA-F4 | 960.1 | 960.1 | 10.46 |

m/z = mass-to-charge ratio of the ion $[M^{+2}H]^{2+}$; tR = retention time

Example 3—$^{61}$Cu-Labelling of NODAGA-, DOTAGA- and DOTA-Radiotracers of PSMA Ligands and Somatostatin Analogues and of FAPI Inhibitors An aliquot of NODAGA-, DOTAGA- or DOTA-targeted chelator construct (3-6 nmol, 1 μg/mL in water) was diluted in 0.25-0.30 mL of ammonium (or sodium) acetate (0.5 M pH 8), followed by the addition of 0.1-0.7 mL $[^{61}Cu]CuCl_2$ in 0.05 M HCl (70-240 MBq). The reaction mixture was incubated for 15 min at different temperatures, depending on the chelator; the NODAGA-constructs (NODAGA-PSMA-I&T, NODAGA-TOC, NODAGA-LM3, NODAGA-F1, NODAGA-F2, NODAGA-F3, NODAGA-F4, and NODAGA-FAPI-46) were incubated at room temperature (approx. 20-25° C.), while the DOTAGA and DOTA-constructs (DOTAGA-PSMA-I&T and DOTA-TOC) were incubated at 95° C. The pH of the reaction was between 5 and 6.

$[^{61}Cu]$Cu-NODAGA PSMA-I&T Preparation and Test Methods

During dispensing of the $[^{61}Cu]$Cu-NODAGA PSMA-I&T solution, an aliquot of 1 mL is dispensed for quality control tests. The tests are carried out in a non-classified quality control laboratory.

The solution is composed of $[^{61}Cu]$Cu-NODAGA PSMA-I&T, 0.05 M HCl, 0.5 M sodium acetate with ascorbic acid 20 μg/mL and 0.9% NaCl sterile solution for injection.

The specifications for the $[^{61}Cu]$Cu-NODAGA PSMA-I&T solution, as well as the test methods are listed in Table 14 (quality parameters tested before release (or distribution) of the physical product) and Table 15 (quality parameters tested after release).

TABLE 14

Specifications of the $[^{61}Cu]$Cu-NODAGA-PSMA-I&T solution tested before release

| Parameter | Test method | Specification |
|---|---|---|
| Appearance | Visual inspection (Ph. Eur. 2.9.20) | Clear, colorless solution |
| pH value | pH indicator paper strips or pH-meter (Ph. Eur. 2.2.3) | 5.0-7.0 |
| Radioactive concentration | Dose calibrator (Ph. Eur. 2.2.66/Calculation) | 8-30 MBq/mL |
| Identification $[^{61}Cu]$Cu-NODAGA PSMA-I&T | HPLC-UV | Complies |
| Radiochemical purity $[^{61}Cu]$Cu-NODAGA-PSMA-I&T | Radio-HPLC | ≥95% |
| Radiochemical purity $[^{61}Cu]$Cu-NODAGA-PSMA-I&T | Radio-TLC (Reversed-Phase) (Ph. Eur. 2.2.27) | ≥95% |
| Content free $^{61}$Cu (II) | Radio-TLC (Reversed-Phase) (Ph. Eur. 2.2.27) | ≤5% |
| Sterile filter integrity | Bubble point test | 3.0-4.5 bar |
| Bacterial endotoxins content | Kinetic chromogenic LAL test (Ph. Eur. 2.6.14) | <17.5 EU/mL |
| Radionuclidic identity | γ-Spectrometry (Ph. Eur. 2.2.66) | γ-photons with energy peak at 511 ± 30 ke V (eventually sum peak at 1022 keV + 283 keV and 656 ke V) |
| Radionuclidic identity | Half-life (Ph. Eur. 0125) | 200 ± 20 min |

TABLE 15

Specifications of the $[^{61}Cu]$Cu-NODAGA-PSMA-I&T solution tested after release

| Parameter | Test method | Specification |
|---|---|---|
| Radionuclidic purity $^{61}$Cu | γ-Spectrometry (Ph. Eur. 2.2.66) | ≥99.99% |
| Radionuclidic purity (RNP) $[^{56,57,58,60}Co]$Co | γ-Spectrometry (Ph. Eur. 2.2.66) | ≤0.01% |
| Sterility | Sterility test (Ph. Eur. 2.6.1) | No microbial growth |

Scheme 1. $^{61}$Cu-labeling reaction of NODAGA-PSMA-I&T, NODAGA-TOC, NODAGA-LM3, NODAGA-F1, NODAGA-F3, NODAGA-F2, and NODAGA-F4.
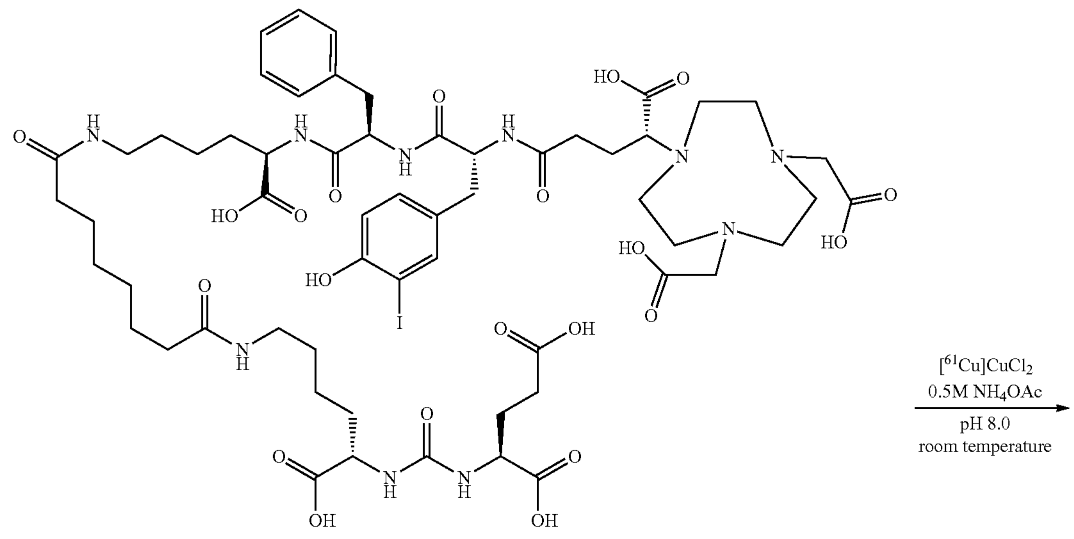
NODAFA-PSMA-I&T
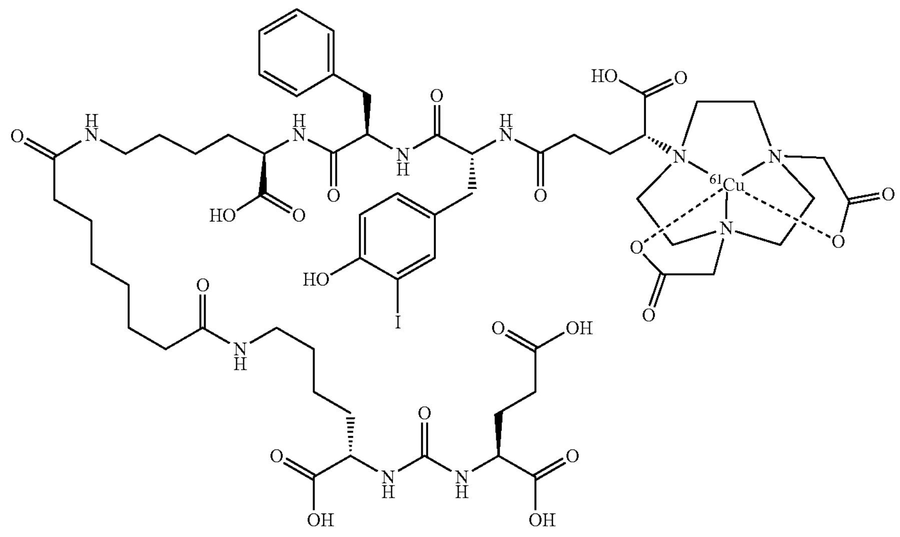
[$^{61}$Cu]Cu-NODAGA-PSMA-I&T -continued
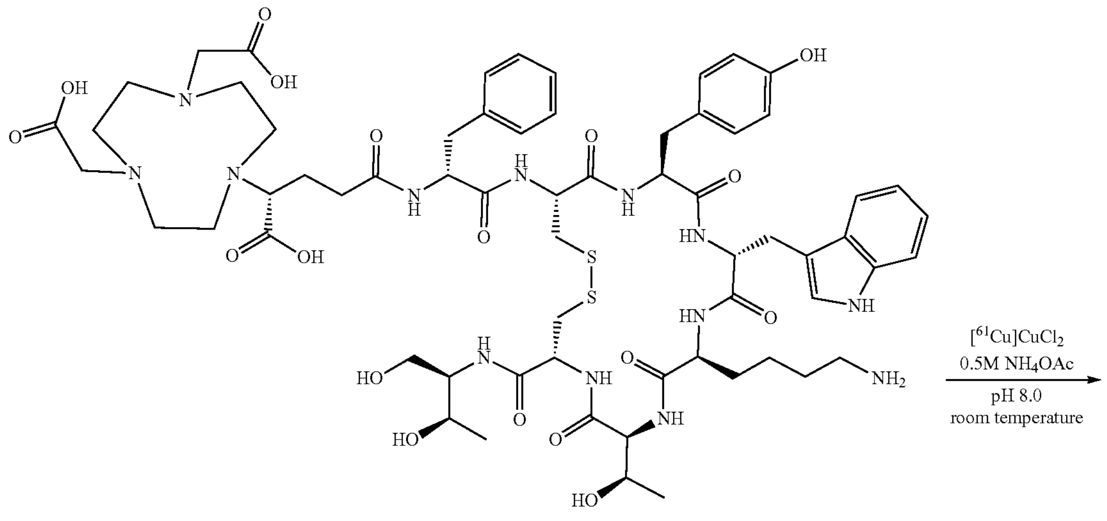
NODAGA-TOC
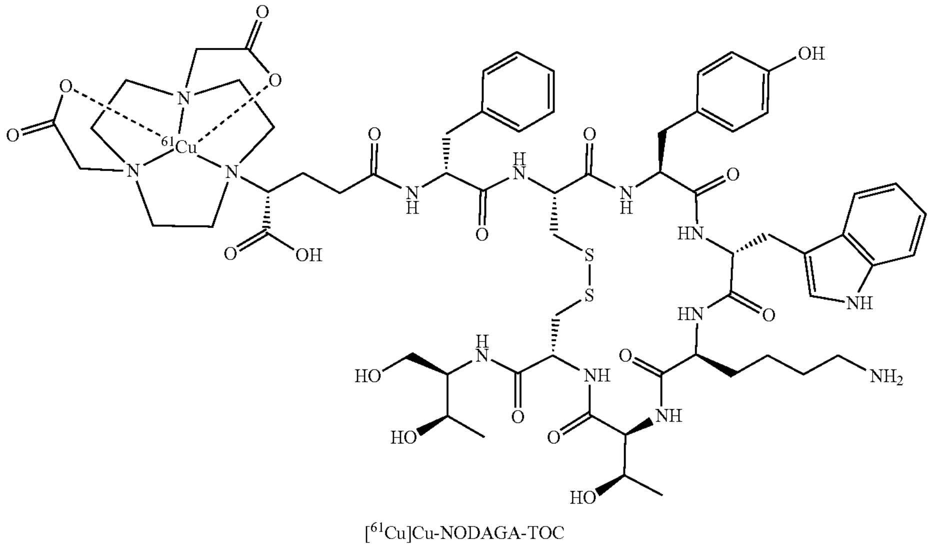
[$^{61}$Cu]Cu-NODAGA-TOC
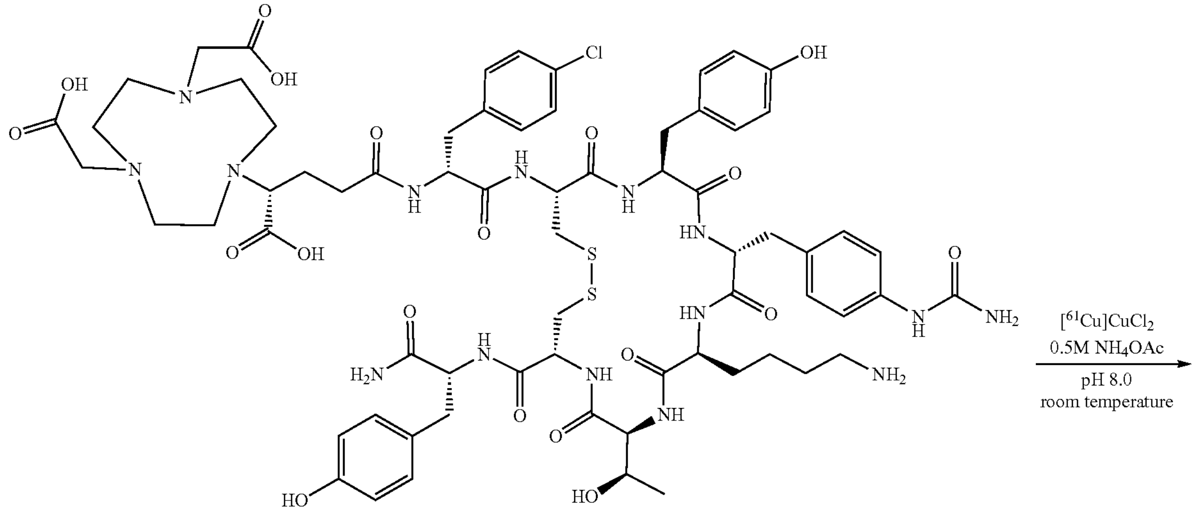
NODAGA-LM3

-continued
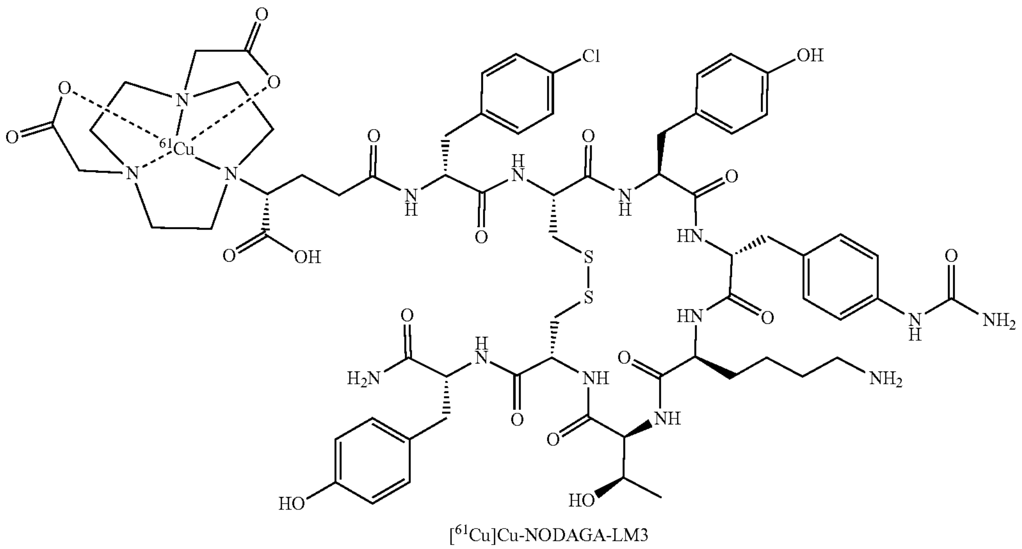
$[^{61}Cu]Cu$-NODAGA-LM3
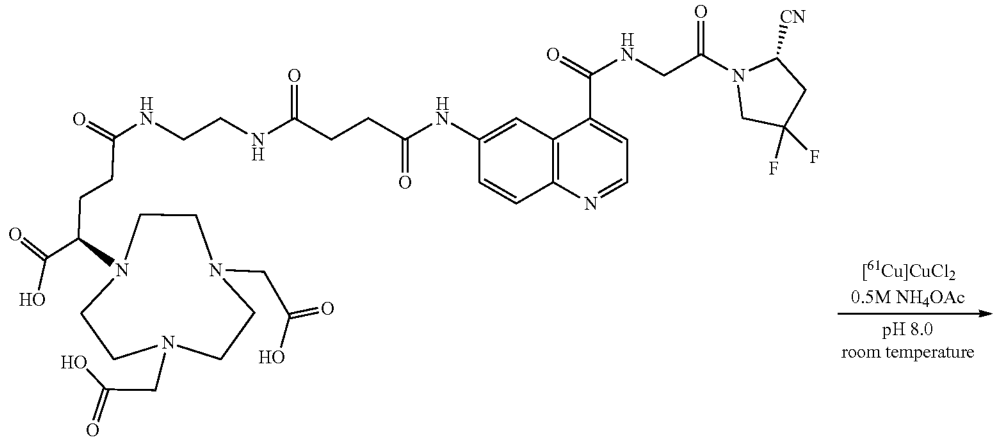
NODAGA-F1
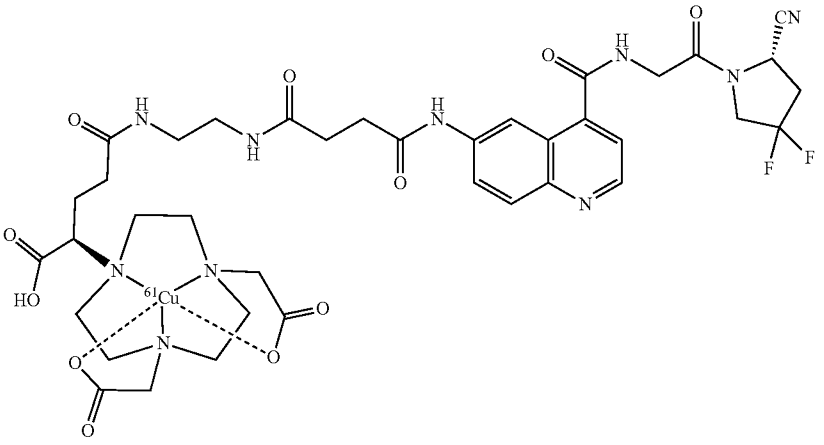
$[^{61}Cu]Cu$-NODAGA-F1

-continued
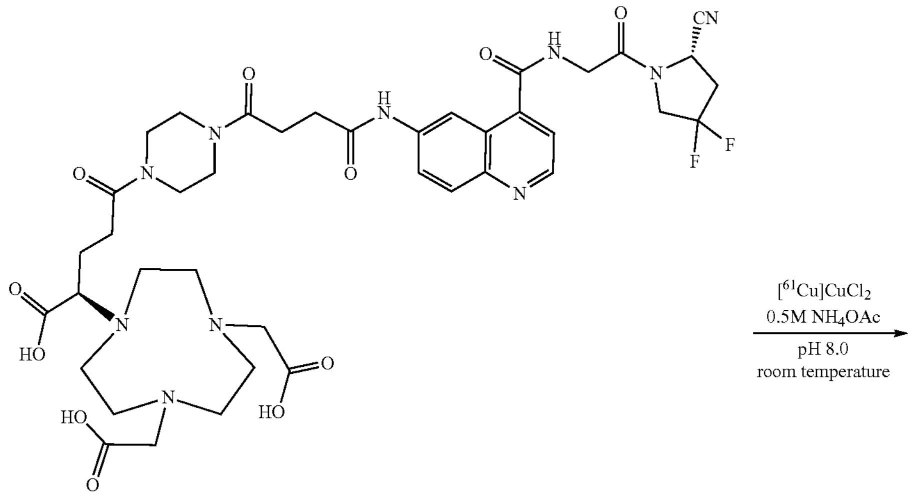
NODAGA-F3
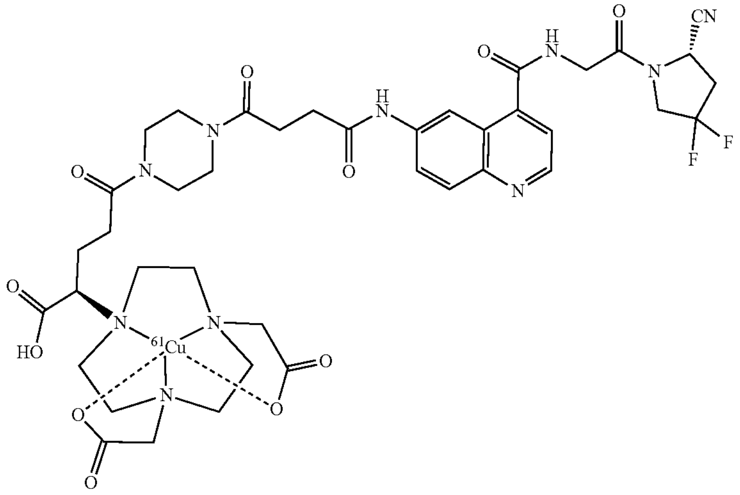
[$^{61}$Cu]Cu-NODAGA-F3
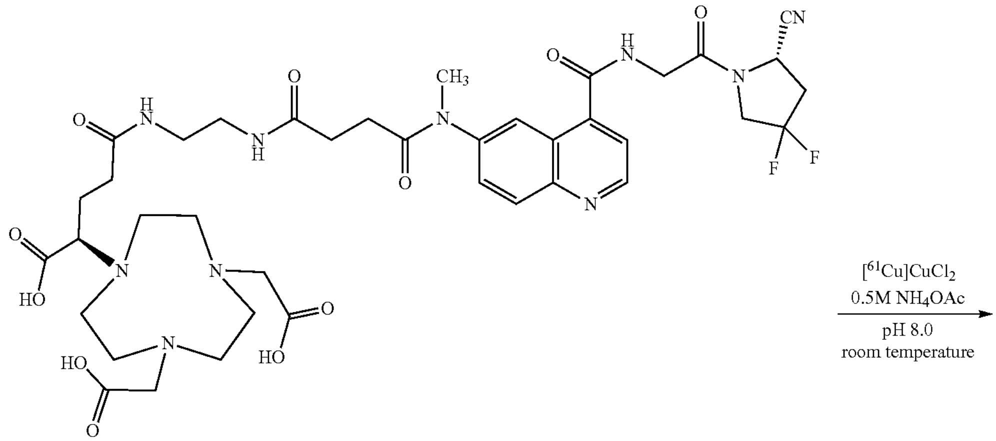
NODAGA-F2

-continued

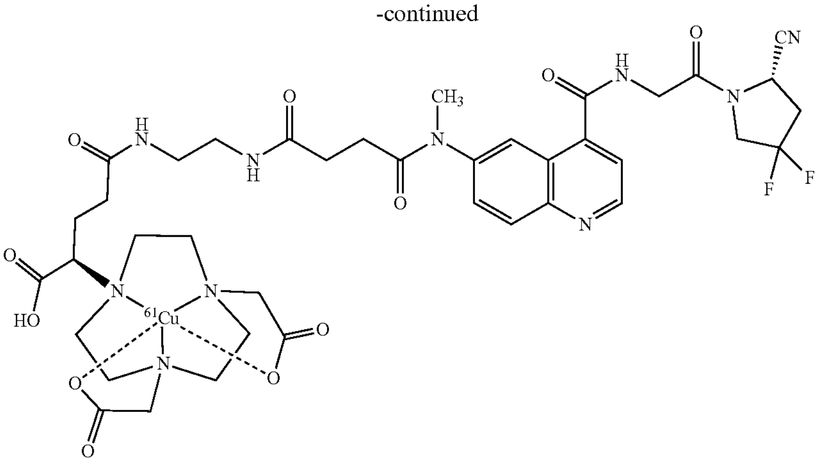

[$^{61}$Cu]Cu-NODAGA-F2

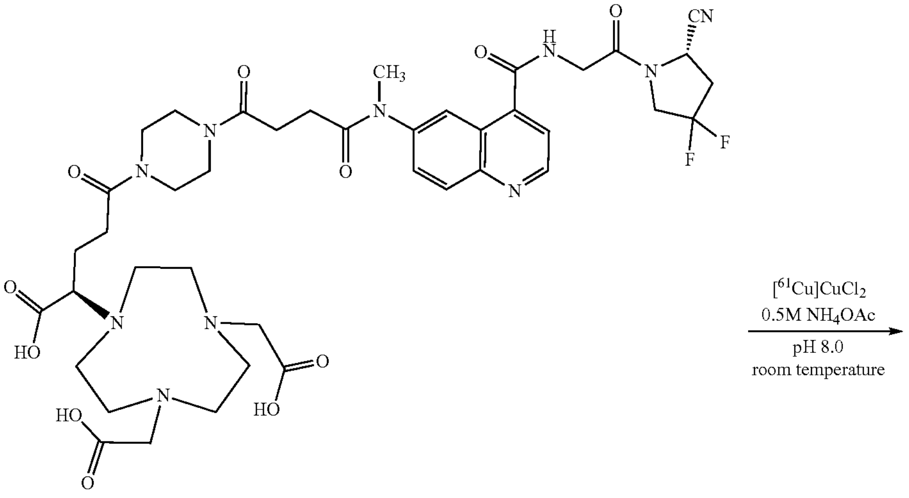

NODAGA-F4

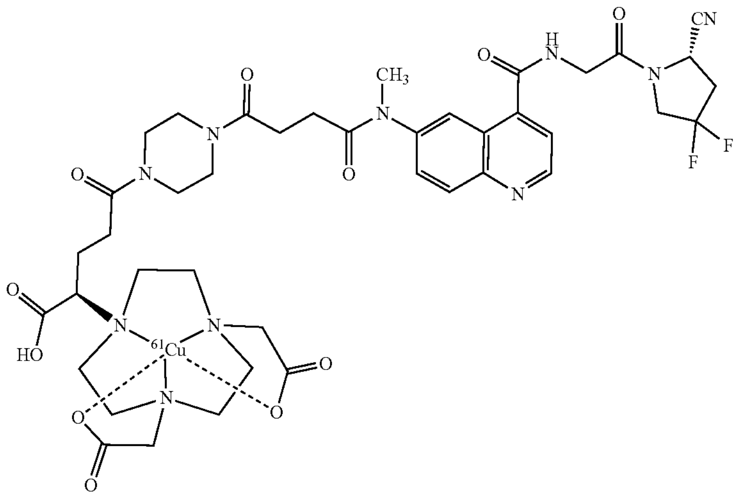

[$^{61}$Cu]Cu-NODAGA-F4

Quality control was performed on a reverse-phase high performance liquid chromatography (RP-PLC) connected to a radio-detector (radio-HPLC). The results of the radio-HPLC are provided in Table 16 below.

[$^{61}$Cu]Cu-DOTAGA-PSMA-I&T and [$^{61}$Cu]Cu-NODAGA-PSMA-I&T were prepared at a molar activity of 24 MBq/nmol, without the need of post-labeling purification.

TABLE 16

Radiochemical purity and retention time (tR) of the $^{61}$Cu-radiotracers using standard HPLC methodology with increasing gradient concentration of aqueous acetonitrile with formic acid (Shimadzu LC-20A Prominence HPLC system) equipped with a radioactivity-HPLC-flow-monitor (Elysia-Raytest Gabi Star) Column (125.4.6 Nucleosil 100-5-C18 AB).

| Radiotracer | Radiochemical purity | tR (min) |
|---|---|---|
| [$^{61}$Cu]Cu-DOTAGA-PSMA-I&T | ≥97% | 7.2 ± 0.2 |
| [$^{61}$Cu]Cu-NODAGA-PSMA-I&T | ≥98% | 7.1 ± 0.2 |
| [$^{61}$Cu]Cu-DOTA-TOC | ≥98% | 9.8 ± 0.2 |
| [$^{61}$Cu]Cu-NODAGA-TOC | ≥98% | 10.2 ± 0.2 |
| [$^{61}$Cu]Cu-NODAGA-LM3 | ≥98% | 10.7 ± 0.2 |
| [$^{61}$Cu]Cu-NODAGA-F1 | ≥98% | 5.9 ± 0.2 |
| [$^{61}$Cu]Cu-NODAGA-F3 | ≥97% | 6.1 ± 0.2 |
| [$^{61}$Cu]Cu-NODAGA-F2 | ≥98% | 6.1 ± 0.2 |
| [$^{61}$Cu]Cu-NODAGA-F4 | ≥98% | 6.4 ± 0.2 |
| 61Cu -NODAGA-FAPI-46 | ≥95% | 5.7 ± 0.2 |

All constructs were labeled with $^{61}$Cu in very high yield and purity. No further purification step was necessary to remove uncomplexed $^{61}$Cu from the reaction mixture, allowing direct use of the formed radiotracer.

Example 4—Lipophilicity of [61Cu]Cu-Labeled NODAGA-, DOTAGA- and DOTA-Radiotracers of PSMA Ligands, Somatostatin Analogs and FAPI Ligands and Comparison with their $^{68}$Ga Counterparts and Reference Radiotracers The lipophilic/hydrophilic character of the radiotracers was assessed by the determination of the distribution coefficient (D), expressed as log D (pH=7.4), between an aqua and an organic phase following the "shake-flask" method. The radiotracer (1 μM) was added to a 50:50 pre-saturated mixture of 1-octanol and phosphate buffered saline (PBSpH 7.4). The solution was vortexed for 30 min and then centrifuged at 3,000 rpm to achieve a phase separation. Aliquots from each phase were collected and measured in a gamma-counter. The distribution coefficient was calculated as the average of the logarithmic values of the ratio between the radioactivity in the organic and the PBS phase. The results are summarized in Table 17.

Table 17. Lipophilicity expressed as the log distribution coefficient D (log D(Octanol/PBS pH7.4)) of $^{61}$Cu-radiotracers versus $^{68}$Ga-radiotracers (reference radiotracers). Results are means standard deviation from a minimum of two separate experiments, each in triplicates.

TABLE 17

Lipophilicity of Radiotracers

| Radiotracer | log D(O/PBS pH 7.4) |
|---|---|
| [$^{61}$Cu]Cu-DOTAGA-PSMA-I&T | −2.69 ± 0.44 |
| [$^{61}$Cu]Cu-NODAGA-PSMA-I&T | −2.95 ± 0.08 |
| [$^{68}$Ga]Ga-DOTAGA-PSMA-I&T | −2.79 ± 0.41 |
| [$^{68}$Ga]Ga-NODAGA-PSMA-I&T | −2.85 ± 0.29 |
| [$^{68}$Ga]Ga-PSMA-11* | −3.89 ± 0.19 |
| [$^{18}$F]PSMA-1007# | −3.02 ± 0.11 |
| [$^{61}$Cu]Cu-DOTA-TOC | −2.81 ± 0.29 |
| [$^{61}$Cu]Cu-NODAGA-TOC | −2.60 ± 0.24 |
| [$^{61}$Cu]Cu-NODAGA-LM3 | −2.42 ± 0.04 |
| [$^{68}$Ga]Ga-DOTA-TOC | −3.18 ± 0.11 |
| [$^{68}$Ga]Ga-NODAGA-TOC | −2.48 ± 0.30 |
| [$^{61}$Cu]Cu-NODAGA-F1 | −3.17 ± 0.28 |
| [$^{61}$Cu]Cu-NODAGA-F3 | −3.32 ± 0.44 |
| [$^{61}$Cu]Cu-NODAGA-F2 | −3.09 ± 0.08 |
| [$^{61}$Cu]Cu-NODAGA-F4 | −3.12 ± 0.16 |
| [$^{61}$Cu]Cu-NODAGA-FAPI-46 | −3.10 ± 0.34 |
| [$^{68}$Ga]Ga-FAPI-46 | −3.01 ± 0.18 |

*[$^{68}$Ga]Ga-PSMA-11 is known and published in Carlucci et al. J. Nucl. Med. 62:149-155.
#[$^{18}$F]PSMA-1007 is known and published in Cardinale et al. J. Nucl. Med. 2017:58:425-431.

The lipophilicities of [$^{61}$Cu]Cu-NODAGA-PSMA-I&T and [$^{61}$Cu]Cu-DOTAGA-PSMA-I&T are in the same level. Both $^{61}$Cu-labeled PSMA radiotracers are more lipophilic than [$^{68}$Ga]Ga-PSMA-11, and [$^{18}$F]F-PSMA-1007, approved PET tracer for PSMA imaging (Hennrich U and Eder M Pharmaceuticals 2021; 14:713). Higher lipophilicity than the one of [$^{68}$Ga]Ga-PSMA-11 is reported to be beneficial for PSMA-based radiotracers (Wirtz M et al., EJNMMI Rese 2018). Additionally, $^{61}$Cu complexation did not influence significantly the lipophilic/hydrophilic character of the radiotracers, being in the same level with their $^{68}$Ga-counterparts. Similarly, the lipophilicity of [$^{61}$Cu]Cu-NODAGA-TOC and [$^{61}$Cu]Cu-DOTA-TOC is in the same level, being more lipophilic than the clinically used [$^{68}$Ga]Ga-DOTA-TOC, while [$^{61}$Cu]Cu-NODAGA-LM3 is the most lipophilic among them. The lipophilicity of all $^{61}$Cu-labeled FAPI constructs are about the same as each other.

Example 5—Binding Affinity of $^{nat}$Cu-Complexed NODAGA-, DOTAGA- and DOTA-Constructs of PSMA Ligands and Somatostatin Analogs and Comparison to Reference Compounds The affinity was measured via the determination of the $IC_{50}$ (concentration of the test construct causing 50% inhibition of the specific binding of a reference radioligand for the same molecular target). See FIG. 9.

In the case of the PSMA constructs, the radioiodinated ((S)-1-carboxy-5-(4-(-$^{125}$I-iodo-benzamido)pentyl)carbamoyl)-L-glutamic acid ([$^{125}$I-BA]KuE) was used as reference radioligand. The assay was performed on LNCaP cells seeded in 24-well plates (1.5×105 cells/well). The cells were incubated with increased concentrations of each $^{nat}$Cu-complexed conjugates (ranging from 0.1 up to 100 nM) in the presence of 0.2 nM [$^{125}$I-BA]KuE. After 1 hour incubation on ice, the unbound (free) [$^{125}$I-BA]KuE was collected by removing the medium and the cells were detached with NaOH 1 M for counting (bound radioligand). Non-specific binding was defined as the amount of binding activity in the presence of the blocking agent 2-(phosphonomethyl)pentanedioic acid (2-PMPA) in high excess (10 μM).

In the case of the somatostatin constructs, the $^{125}$I-labeled Tyr-somatostatin-14 ($^{125}$I-SS-14) was used as reference radioligand. The assay was performed on HEK cell membranes expressing the human SST2 (HEK-SST2) cell membrane suspension on 96-well plates. The membranes were incubated with increased concentrations of each $^{nat}$Cu-construct (ranging from 0.001 up to 100 nM) in the presence of 0.05 nM $^{125}$I-SS-14. After 1 hour incubation at 37° C., filtration on a Brandel 48-well Cell Harvester followed. The filters containing the membranes (bound radioligand) were collected for measurement. Non-specific binding was defined as the amount of binding activity in the presence of SS-14 in 1,000-fold excess.

Quantification of the free and bound radioligand was performed in a gamma-counter. The data were analyzed by GraphPad Prism 9 Software and the $IC_{50}$ values were determined using the "log(inhibitor) vs response" equation based on the specific binding=total−non-specific binding. The $IC_{50}$ values were expressed in nM and they are reported in Table 18.

Table 18. $IC_{50}$ values were determined by competitive assays. The PSMA constructs were assessed in LNCaP cells after 1 hour incubation on ice using the radioligand [$^{125}$I-BA]KuE at a concentration of 0.2 nM and the somatostatin constructs were assessed on HEK-SST2 membranes after 1 hour incubation at 37° C. using the radioligand [$^{125}$I]-Tyr-somatostatin-14 at a concentration of 0.05 nM. The results are expressed as means standard deviation (SD) from a minimum of two separate experiments, each in triplicates.

TABLE 18

| $IC_{50}$ values determined by competitive assays. | |
|---|---|
| $^{nat}$Cu-complexed construct | $IC_{50}$ (nM) |
| $^{nat}$Cu-DOTAGA-PSMA-I&T | 11.2 ± 2.3 |
| $^{nat}$Cu-NODAGA-PSMA-I&T | 9.3 ± 1.8 |
| $^{nat}$Ga-PSMA-11 | 2.4 ± 0.4 |
| $^{nat}$Cu-DOTA-TOC | 0.23 ± 0.02 |
| $^{nat}$Cu-NODAGA-TOC | 0.34 ± 0.04 |
| NODAGA-LM3 | 17.8 ± 2.0 |
| $^{nat}$Cu-NODAGA-LM3 | 17.7 ± 2.2 |
| $^{nat}$Ga-DOTA-TOC | 0.18 ± 0.02 |
| Somatostatin-14 | 0.11 ± 0.02 |

Between the two $^{nat}$Cu-complexed PSMA constructs and the two $^{nat}$Cu-complexed TOC somatostatin analogs, the exchange of the chelator from DOTAGA (reference construct DOTAGA-PSMA-I&T used in the clinics) and DOTA (reference construct DOTA-TOC used in the clinics) to the chelator NODAGA (NODAGA-PSMA-I&T and NODAGA-TOC, respectively) does not hamper the affinity of the $^{nat}$Cu-complexed constructs for their molecular target (PSMA and SST2, respectively). The $IC_{50}$ values of the $^{nat}$Cu-complexed NODAGA constructs are in a similar low nanomolar range, indicating very high affinity, as for the corresponding DOTAGA and DOTA constructs and also for the references molecules, $^{nat}$Ga-PSMA-11 (in the case of the PSMA I&T constructs) and $^{nat}$Ga-DOTA-TOC and the natural hormone, somatostatin-14 (in the case of the TOC and LM3 constructs), respectively.

Complexation of Cu (or radiolabeling with $^{61}$Cu) does not hamper the affinity of the NODAGA-LM3 construct for its molecular target (SST2), as suggested by the $IC_{50}$ values of the NODAGA-LM3 and $^{nat}$Cu-NODAGA-LM3 that remain the same.

Example 6—In Vitro Cellular Uptake of the $^{61}$Cu-Radiotracers

The cellular uptake was studied in vitro using intact cells seeded in 6-well plates overnight. On the day of the experiment, the cells were washed and incubated with each of the exemplified [$^{61}$Cu]Cu-radiotracer at different time points, either alone or in the presence of a blocking agent to distinguish between specific and non-specific uptake. At each investigated time point, the medium containing the unbound (free) radiotracer was removed, followed by two washing steps with ice-cold phosphate-buffered saline. The cells were then treated 2×5 min with ice-cold glycine solution (0.05 M, pH 2.8) to detach the cell surface-bound radiotracer (acid released). Afterwards, the cells containing the internalized radiotracer were detached with 1 M NaOH at 37° C. and collected for measurement. The amount of specific cell surface-bound and internalized radiotracer is expressed as percentage of the total applied activity, after subtracting the non-specific values.

[$^{61}$Cu]Cu-DOTAGA-PSMA-I&T and [$^{61}$Cu]Cu-NODAGA-PSMA-I&T (0.5 nM) were assessed in LNCaP cells and compared to their [$^{68}$Ga]Ga-counterparts. 2-(phosphonomethyl)-pentanedioic acid (2-PMPA, 10 μM) was used to determine non-specific binding (FIG. 14).

[$^{61}$Cu]Cu-DOTA-TOC and [$^{61}$Cu]Cu-NODAGA-TOC (2.5 nM) were assessed in HEK-SST2 cells and compared to their [$^{68}$Ga]Ga-counterparts. Somatostatin-14 (SS-14, 25 μM) was used to determine non-specific binding.

[$^{61}$Cu]Cu-NODAGA-F1, [$^{61}$Cu]Cu-NODAGA-F3, [$^{61}$Cu]Cu-NODAGA-F2, [$^{61}$Cu]Cu-NODAGA-F4, and [$^{61}$Cu]Cu-NODAGA-FAPI-46 (0.2 nM) were assessed in HT-1080.hFAP (FAP-positive) and HT-1080.wt (FAP-negative) cells.

Internalization and cell-surface bound fractions for the tested radiotracers are reported in Table 19, Table 20, and Table 21.

Cellular uptake and distribution between cell surface (cell membrane bound) and internalized fractions of $^{61}$Cu-labeled PSMA-I&T constructs versus their $^{68}$Ga counterparts (Table 19). The values are expressed as % of the applied activity and refer to the specific uptake calculated after subtracting the non-specific values (measured in the presence of 10 μM 2-PMPA) from the total values (specific=total−non specific).

TABLE 19

| Cellular uptake and distribution | | | | |
|---|---|---|---|---|
| Time Point [min] | [$^{61}$Cu]Cu-DOTAGA-PSMA-I&T | [$^{61}$Cu]Cu-NODAGA-PSMA-I&T | [$^{68}$Ga]Ga-DOTAGA-PSMA-I&T | [$^{68}$Ga]Ga-NODAGA-PSMA-I&T |
| Cell surface fraction | | | | |
| 5 | 3.7 ± 0.5 | 4.3 ± 0.7 | 4.3 ± 0.2 | 4.7 ± 0.9 |
| 15 | 8.1 ± 0.7 | 8.2 ± 1.0 | 8.6 ± 0.8 | 7.4 ± 1.2 |
| 30 | 11.6 ± 1.0 | 10.7 ± 1.0 | 9.5 ± 0.5 | 8.8 ± 1.3 |
| 60 | 13.4 ± 0.8 | 10.8 ± 1.8 | 10.8 ± 1.1 | 9.3 ± 1.9 |
| 120 | 14.7 ± 1.0 | 10.2 ± 1.8 | 10.0 ± 0.5 | n.d. |
| Internalized fraction | | | | |
| 5 | 0.7 ± 0.1 | 1.2 ± 0.2 | 0.7 ± 0.1 | 0.6 ± 0.3 |
| 15 | 2.8 ± 0.2 | 3.9 ± 0.4 | 2.6 ± 0.2 | 2.1 ± 0.5 |
| 30 | 6.2 ± 0.5 | 7.0 ± 1.1 | 5.0 ± 0.2 | 4.4 ± 0.6 |
| 60 | 13.3 ± 0.5 | 11.7 ± 1.6 | 9.8 ± 1.3 | 8.8 ± 1.0 |
| 120 | 21.3 ± 0.9 | 17.6 ± 2.8 | 15.4 ± 2.1 | n.d. |

n.d. not determined

The $^{61}$Cu-labeled PSMA radiotracers showed time-dependent uptake in PSMA-expressing cells with approx. equal distribution between the cell surface (membrane) fraction and the internalized fraction at 37° C. [$^{61}$Cu]Cu-NODAGA-PSMA-&T showed slightly, but not significantly, lower cell surface bound and internalization than [$^{61}$Cu]Cu-DOTAGA-PSMA-I&T. The cellular uptake of both $^{61}$Cu-labeled PSMA radiotracer constructs was in the same range as their $^{68}$Ga-counterparts. The above findings lead to the conclusion that overall, the PSMA-mediated cellular uptake in vitro is not hampered by exchanging the chelator or the radionuclide.

Table 20. Cellular uptake and distribution between cell surface (cell membrane bound) and internalized fractions of $^{61}$Cu-labeled somatostatin analogs versus their $^{68}$Ga counterparts. The values are expressed as 00 of the applied activity and refer to the specific uptake calculated after subtracting the non-specific values (measured in the presence of 25 μM somatostatin-14) from the total values (specific=total−non specific).

TABLE 20

| Cellular uptake and distribution | | | | |
|---|---|---|---|---|
| Time Point [min] | [61Cu]Cu-DOTA-TOC | [61Cu] Cu-NODAGA-TOC | [68Ga]Ga-DOTA-TOC | [68Ga]Ga-NODAGA-TOC |
| Cell surface fraction | | | | |
| 30 | 2.3 ± 0.2 | 2.0 ± 0.3 | 3.6 ± 0.6 | 2.6 ± 0.3 |
| 60 | 2.2 ± 0.4 | 2.2 ± 0.4 | 2.7 ± 0.6 | 3.0 ± 0.6 |
| 120 | 1.8 ± 0.5 | 2.0 ± 0.4 | 2.7 ± 0.5 | 2.8 ± 0.7 |
| 240 | 1.6 ± 0.4 | 1.4 ± 0.7 | 3.2 ± 0.6 | 2.9 ± 0.6 |
| Internalized fraction | | | | |
| 30 | 39.1 ± 1.8 | 27.7 ± 4.0 | 33.9 ± 4.3 | 27.4 ± 0.9 |
| 60 | 56.8 ± 1.1 | 38.9 ± 2.0 | 52.8 ± 2.4 | 35.3 ± 4.2 |
| 120 | 71.7 ± 1.4 | 55.0 ± 3.1 | 66.1 ± 2.8 | 46.6 ± 3.8 |
| 240 | 76.7 ± 1.4 | 69.5 ± 2.9 | 77.5 ± 6.0 | 61.4 ± 5.6 |

The $^{61}$Cu-labeled TOC radiotracers were almost entirely internalized on SST2-expressing cells at 37° C. in a time-dependent manner, with only a negligible amount remaining on the cell surface (cell membrane). The observations herein between the two $^{61}$Cu-radiotracers and the comparison with their corresponding $^{68}$Ga-counterparts, are in agreement with the findings above for the PSMA constructs.

Table. Cellular uptake and distribution between cell surface (cell membrane bound) and internalized fractions of $^{61}$Cu-labeled FAPI analogs. The values are expressed as % of the applied activity and refer to the specific uptake calculated after subtracting the non-specific values (measured in the presence of the non-FAP expressing cell line HT-1080.wt) from the total values (specific=total−non specific).

TABLE 21

| Cellular uptake and distribution | | | | | |
|---|---|---|---|---|---|
| Time Point [min] | [61Cu]Cu-NODAGA-F1 | [61Cu]Cu-NODAGA-F3 | [61Cu]Cu-NODAGA-F2 | [61Cu]Cu-NODAGA-F4 | [61Cu]Cu-NODAGA-FAPI-46 |
| Cell surface fraction | | | | | |
| 15 | 1.2 ± 0.3 | 0.9 ± 0.3 | 1.2 ± 0.6 | 1.0 ± 0.7 | 0.9 ± 0.3 |
| 60 | 1.4 ± 0.3 | 1.2 ± 0.4 | 1.4 ± 0.5 | 1.4 ± 0.4 | 1.2 ± 0.4 |
| 240 | 1.3 ± 0.2 | 1.4 ± 0.4 | 1.3 ± 0.5 | 0.9 ± 0.6 | 1.7 ± 0.4 |
| Internalized fraction | | | | | |
| 30 | 26.2 ± 3.5 | 26.6 ± 4.9 | 20.7 ± 5.5 | 22.2 ± 7.4 | 24.3 ± 2.3 |
| 60 | 29.9 ± 1.8 | 36.9 ± 5.3 | 27.0 ± 6.9 | 22.2 ± 5.1 | 36.1 ± 1.6 |
| 240 | 29.3 ± 1.8 | 39.4 ± 4.8 | 28.3 ± 7.5 | 17.4 ± 4.4 | 50.0 ± 6.0 |

The $^{61}$Cu-labeled FAP radiotracers were fast and almost entirely internalized on cell expressing the human FAP at 37° C., with only a negligible amount remaining on the cell surface (cell membrane).

Example 7—Tumor Xenografts

Athymic nude Foxn1nu/Foxn1+ mice, 4-6 weeks old, were injected subcutaneously in the flank with LNCaP cells (107 cells/200 μL) suspended 1:1 culture medium and Matrigel, or with HEK-SST2 cells (107 cells/100 μL) suspended in sterile phosphate-buffered saline, or dual with HT-1080.hFAP cells (5×106 cells/100 μL, right shoulder) and with HT-1080.wt (5×106 cells/100 μL, left shoulder). The tumors were allowed to grow for 1-3 weeks before commencement of the experiments. The LNCap xenografts were used for the evaluation of the PSMA-based radiotracers, the SST2 xenografts for the somatostatin-based radiotracers and the HT-1080.hFAP and HT-1080.wt for the FAP inhibitor-based radiotracers.

Example 8—PET/CT Imaging

Tumor xenografted mice were injected intravenously into the tail vein with the tested radiotracer. LNCap xenografts were injected with 100 μL/400 pmol/4-8 MBq $^{61}$Cu-labeled PSMA radiotracers, the HEK-SST2 xenografts with 100 μL/200 pmol/3-5 MBq $^{61}$Cu-labeled somatostatin radiotracers and the HT-1080 xenografts with 100 μL/500 pmol/10-12 MBq $^{61}$Cu-labeled FAP-inhibitor radiotracers. Mice were anesthetized with 1.5% isoflurane and dynamic PET scans were acquired during 1 hour upon injection of the radiotracer. The mice were euthanized by $CO_2$ at 4 hours p.i., the bladder was mechanically emptied, and static PET scans were acquired for 30 min. PET images were acquired using the β-CUBE PET scanner system (MOLECUBES, Gent, Belgium) and they were decay corrected and reconstructed with the VivoQuant software version 4.0. The CT was imaged supine, headfirst, using the NanoSPECT/CT™ scanner (Bioscan Inc.). Topograms and helical CT scans of the whole mouse were first acquired using the following parameters: X-ray tube current: 177 μA, X-ray tube voltage 45 kVp, 90 seconds and 180 frames per rotation, pitch 1. CT images were reconstructed using CTReco (version r1.146), with a standard filtered back projection algorithm (exact cone beam) and post-filtered (RamLak, 100% frequency cut-off), resulting in a pixel size of 0.2 mm. Co-registered PET/CT images were visualized using maximum intensity projection (MIP) with InVivoScope (version 1.43, Bioscan Inc.). The results are presented in the Examples that follow.

Example 9—Biodistribution Studies

Quantitative biodistribution studies were conducted in tumor xenografted mice after intravenous injection into the tail vein of the tested radiotracer as follow: [$^{61}$Cu]Cu-DOTAGA-PSMA-I&T and [$^{61}$Cu]Cu-NODAGA-PSMA-I&T at injected amounts of 100 μL/200 pmol/1.5-3.5 MBq in LNCaP xenografts, [$^{61}$Cu]Cu-NODAGA-TOC or [$^{61}$Cu] Cu-DOTA-TOC at injected amounts of 100 uL/200 pmol/1.5-4.5 MBq in HEK-SST2 xenografts and [$^{61}$Cu]Cu-NODAGA-F1, [$^{61}$Cu]Cu-NODAGA-F3, [$^{61}$Cu]Cu-NODAGA-F2, [$^{61}$Cu]Cu-NODAGA-F4 or [$^{61}$Cu]Cu-NODAGA-FAPI-46 at injected amounts of 100 uL/500 pmol/0.8-1.2 MBq in HT-1080.hFAP and HT-1080.wt xenografts. The mice were randomly distributed in groups and euthanized at 1 and at 4 hours post-injection. The organs of interest were collected, rinsed, blotted, weighed and counted in a gamma counter. The results are expressed as percentage of injected activity per gram (0% IA/g), representing the mean±standard deviation of n=4-8 mice per group and they were obtained by extrapolation from counts of an aliquot taken from the injected solution as standard.

The results are presented in Table 22, Table 23, and Table 24A, 24B, and 24C.

TABLE 22

Biodistribution data of [$^{61}$Cu]Cu-NODAGA-PSMA-I&T and [$^{61}$Cu]Cu-DOTAGA-PSMA-I&T in LNCaP xenografts at 1 hour and 4 hours post-injection. Results are expressed as mean of the % injected activity per gram of tissue (% IA/g) ± standard deviation (SD).

| | [$^{61}$Cu]Cu-NODAGA-PSMA-I&T* | | [$^{61}$Cu]Cu-DOTAGA-PSMA-I&T# | |
|---|---|---|---|---|
| Organ | 1 hour | 4 hours | 1 hour | 4 hours |
| Blood | 0.28 ± 0.06 | 0.10 ± 0.03 | 2.06 ± 0.24 | 1.12 ± 0.24 |
| Heart | 0.45 ± 0.15 | 0.22 ± 0.05 | 3.73 ± 0.32 | 2.08 ± 0.33 |
| Lung | 1.69 ± 0.45 | 0.74 ± 0.19 | 6.35 ± 0.35 | 4.67 ± 0.76 |
| Liver | 1.02 ± 0.28 | 0.72 ± 0.11 | 19.3 ± 3.3 | 13.9 ± 2.2 |
| Pancreas | 0.97 ± 0.36 | 0.45 ± 0.09 | 2.82 ± 0.67 | 1.71 ± 0.23 |
| Spleen | 6.04 ± 1.87 | 1.28 ± 0.39 | 4.64 ± 1.35 | 2.95 ± 0.73 |
| Stomach | 1.13 ± 0.20 | 0.66 ± 0.15 | 7.77 ± 0.62 | 7.10 ± 0.97 |
| Intestine | 2.11 ± 0.78 | 1.06 ± 0.50 | 8.95 ± 0.62 | 7.74 ± 1.76 |
| Adrenal | 17.3 ± 3.26 | 8.32 ± 2.87 | 9.35 ± 1.50 | 6.46 ± 2.38 |
| Kidneys | 118 ± 13 | 91 ± 10 | 57 ± 6 | 22.1 ± 2.2 |
| Muscle | 1.12 ± 0.32 | 0.50 ± 0.22 | 1.00 ± 0.05 | 0.48 ± 0.08 |
| Bone | 2.73 ± 0.91 | 1.34 ± 0.48 | 2.31 ± 0.36 | 1.69 ± 0.25 |
| Salivary glands | 2.01 ± 0.33 | 0.52 ± 0.06 | 5.60 ± 1.39 | 2.31 ± 0.19 |
| LNCaP-tumor | 14.0 ± 5.0 | 10.7 ± 3.3 | 6.06 ± 0.25 | 4.88 ± 0.63 |
| Ratios | | | | |
| Tumor/Blood | 55.8 ± 20.0 | 109 ± 43 | 2.97 ± 0.23 | 4.56 ± 1.49 |
| Tumor/Liver | 14.9 ± 4.9 | 15.4 ± 5.7 | 0.32 ± 0.05 | 0.35 ± 0.05 |
| Tumor/Kidney | 0.13 ± 0.03 | 0.12 ± 0.03 | 0.11 ± 0.01 | 0.22 ± 0.04 |
| Tumor/Muscles | 13.6 ± 3.75 | 25.4 ± 12.0 | 6.08 ± 0.22 | 10.5 ± 2.8 |

*n = 8, #n = 4

[$^{61}$Cu]Cu-NODAGA-PSMA-I&T and [$^{61}$Cu]Cu-DOTAGA-PSMA-J&T showed high accumulation in PSMA-positive (LNCaP) tumor and PSMA-positive tissues, such as the kidneys and the salivary glands. [$^{61}$Cu]Cu-NODAGA-PSMA-J&T showed higher tumor uptake and also higher kidney uptake, compared to [$^{61}$Cu]Cu-DOTAGA-PSMA-I&T, which in turn showed undesirably higher uptake in the liver, stomach, intestine and also in the blood, which contribute overall to higher background. Between the two radiotracers, [$^{61}$Cu]Cu-NODAGA-PSMA-&T showed superiority because of the higher tumor uptake and the improved tumor-to-non tumor organ ratios (besides tumor-to-kidneys at 4 hours). Between the two investigating time points of 1 and 4 hours after injection, 4 hours showed to be advantageous because of the significantly improved tumor-to-background ratios, see FIG. 12.

TABLE 23

Biodistribution studies of [$^{61}$Cu]Cu-NODAGA-TOC and [$^{61}$Cu]Cu-DOTA-TOC in HEK-SST2 xenografts at 1 hour and 4 hours post-injection. Results are expressed as mean of the % injected activity per gram of tissue (% IA/g) ± standard deviation (SD).

| | [$^{61}$Cu]Cu-NODAGA-TOC | | [$^{61}$Cu]Cu-DOTA-TOC | |
|---|---|---|---|---|
| Organ | 1 hour* | 4 hours# | 1 hour¥ | 4 hours * |
| Blood | 0.22 ± 0.04 | 0.04 ± 0.02 | 0.38 ± 0.09 | 0.21 ± 0.04 |
| Heart | 0.16 ± 0.04 | 0.07 ± 0.03 | 0.63 ± 0.07 | 0.49 ± 0.06 |
| Lung | 1.09 ± 0.20 | 0.51 ± 0.24 | 1.96 ± 0.16 | 1.25 ± 0.08 |
| Liver | 0.29 ± 0.04 | 0.27 ± 0.09 | 3.59 ± 0.49 | 2.52 ± 0.56 |
| Pancreas | 2.59 ± 0.49 | 0.60 ± 0.21 | 4.29 ± 0.50 | 0.68 ± 0.07 |
| Spleen | 0.22 ± 0.05 | 0.10 ± 0.04 | 0.55 ± 0.08 | 0.37 ± 0.09 |
| Stomach | 2.34 ± 0.43 | 1.22 ± 0.25 | 4.34 ± 0.50 | 2.09 ± 0.50 |
| Intestine | 0.92 ± 0.12 | 0.65 ± 0.23 | 2.94 ± 0.15 | 2.06 ± 0.92 |
| Adrenal | 0.99 ± 0.17 | 0.67 ± 0.26 | 2.05 ± 0.58 | 1.14 ± 0.50 |
| Kidneys | 12.5 ± 2.25 | 4.36 ± 0.92 | 5.32 ± 0.58 | 2.33± 0.39 |
| Muscle | 0.16 ± 0.06 | 0.07 ± 0.04 | 0.19 ± 0.05 | 0.16 ± 0.08 |
| Bone | 0.46 ± 0.17 | 0.31 ± 0.11 | 0.60 ± 0.16 | 0.50 ± 0.19 |

TABLE 23-continued

Biodistribution studies of [$^{61}$Cu]Cu-NODAGA-TOC and [$^{61}$Cu]Cu-DOTA-TOC in HEK-SST2 xenografts at 1 hour and 4 hours post-injection. Results are expressed as mean of the % injected activity per gram of tissue (% IA/g) ± standard deviation (SD).

| | [$^{61}$Cu]Cu-NODAGA-TOC | | [$^{61}$Cu]Cu-DOTA-TOC | |
|---|---|---|---|---|
| Organ | 1 hour* | 4 hours# | 1 hour¥ | 4 hours * |
| Pituitary | 3.80 ± 1.35 | 2.97 ± 0.95 | 3.00 ± 1.32 | 2.43 ± 1.27 |
| SST2-tumor | 8.88 ± 3.19 | 7.39 ± 1.36 | 7.44 ± 2.33 | 6.85 ± 2.48 |
| Ratios | | | | |
| Tumor/Blood | 40 | 185 | 20 | 33 |
| Tumor/Liver | 31 | 27 | 2.1 | 2.7 |
| Tumor/Kidney | 0.7 | 1.7 | 1.4 | 2.9 |
| Tumor/Muscles | 56 | 106 | 39 | 43 |

*n = 5, #n = 7, ¥n = 4

[$^{61}$Cu]Cu-NODAGA-PSMA-I&T and [$^{61}$Cu]Cu-DOTAGA-PSMA-I&T showed high accumulation in SST2-positive (HEK-SST2) tumor and SST2-positive tissues, such as the stomach and the pancreas and elimination via the kidneys. [$^{61}$Cu]Cu-NODAGA-TOC showed higher kidney uptake, compared to [$^{61}$Cu]Cu-DOTA-TOC, which in turn showed undesirably higher uptake in the liver, stomach, pancreas and intestine and also in the blood, which contribute overall to higher background. Between the two radiotracers, [$^{61}$Cu]Cu-NODAGA-TOC showed superiority because of the improved tumor-to-non tumor organ ratios (besides tumor-to-kidney). Between the two investigating time points, 4 hours after injection showed to be advantageous compared to 1 hour, because of the significantly improved tumor-to-background ratios.

The observations in the PSMA-xenografts and in the SST2-xenografs are in line and representative of the superiority of the [$^{61}$Cu]Cu-NODAGA chelate vs [$^{61}$Cu]Cu-DOTAGA or [$^{61}$Cu]Cu-DOTA chelate in combination with different targeting moieties and for the advantages of with $^{61}$Cu (half-life 3.33 hours) vs $^{68}$Ga (half-life 68 min) that is routinely used in clinics, by means of imaging at 4 hours instead of 1 hour.

[$^{61}$Cu]Cu-NODAGA-F1 showed high accumulation in FAP-positive (HT-1080.hFAP) tumor and murine-FAP-positive tissues, such as synovial tissues in the joints (e.g., joint associated with a femur).

TABLE 24A

Biodistribution studies of [$^{61}$Cu]Cu-NODAGA-F1 and [$^{61}$Cu]Cu-NODAGA-F3 in HT-1080.hFAP and HT-1080.wt xenografts at 1 hour and 4 hours post-injection. Results are expressed as mean of the % injected activity per gram of tissue (% IA/g) ± standard deviation (SD).

| Organ | [$^{61}$Cu]Cu-NODAGA-F1, 1 h | [$^{61}$Cu]Cu-NODAGA-F1, 4 h | [$^{61}$Cu]Cu-NODAGA-F3, 1 h | [$^{61}$Cu]Cu-NODAGA-F3, 4 h |
|---|---|---|---|---|
| Blood | 2.3 ± 0.1 | 1.2 ± 0.3 | 1.7 ± 0.1 | 0.9 ± 0.0 |
| Heart | 1.2 ± 0.3 | 0.7 ± 0.1 | 0.7 ± 0.1 | 0.5 ± 0.0 |
| Lung | 1.8 ± 0.0 | 0.8 ± 0.2 | 1.2 ± 0.1 | 0.7 ± 0.1 |
| Liver | 1.5 ± 0.0 | 1.0 ± 0.2 | 0.9 ± 0.1 | 0.7 ± 0.1 |
| Pancreas | 2.5 ± 0.3 | 1.4 ± 0.2 | 1.6 ± 0.2 | 0.9 ± 0.0 |
| Spleen | 0.8 ± 0.1 | 0.5 ± 0.1 | 0.5 ± 0.1 | 0.3 ± 0.0 |
| Stomach | 1.1 ± 0.2 | 0.7 ± 0.1 | 0.8 ± 0.1 | 0.5 ± 0.0 |
| Intestine | 1.7 ± 0.4 | 1.1 ± 0.4 | 0.8 ± 0.2 | 0.4 ± 0.1 |
| Adrenal | 2.3 ± 0.5 | 1.4 ± 0.2 | 2.1 ± 0.6 | 1.4 ± 0.3 |
| Kidney | 2.4 ± 0.3 | 1.5 ± 0.5 | 1.6 ± 0.3 | 1.0 ± 0.2 |
| Muscle | 2.6 ± 0.7 | 1.3 ± 0.1 | 2.1 ± 0.8 | 1.1 ± 0.1 |
| Femur | 10.9 ± 1.1 | 4.2 ± 1.5 | 5.4 ± 1.2 | 3.7 ± 0.3 |
| HT1080.hFAP | 12.6 ± 1.5 | 7.1 ± 3.0 | 7.9 ± 0.9 | 6.4 ± 2.0 |
| HT1080.wt | 4.5 ± 0.6 | 2.1 ± 0.5 | 4.0 ± 2.2 | 1.8 ± 0.3 |
| tumor mass | 0.1 ± 0.0 | 0.2 ± 0.2 | 0.1 ± 0.0 | 0.1 ± 0.1 |

TABLE 24B

Biodistribution studies of [$^{61}$Cu]Cu-NODAGA-F2 and [$^{61}$Cu]Cu-NODAGA-F4 in HT-1080.hFAP and HT-1080.wt xenografts at 1 hour and 4 hours post-injection. Results are expressed as mean of the % injected activity per gram of tissue (% IA/g) ± standard deviation (SD).

| Organ | [$^{61}$Cu]Cu-NODAGA-F2, 1 h | [$^{61}$Cu]Cu-NODAGA-F2, 4 h | [$^{61}$Cu]Cu-NODAGA-F4, 1 h | [$^{61}$Cu]Cu-NODAGA-F4, 4 h |
|---|---|---|---|---|
| Blood | 1.2 ± 0.1 | 0.5 ± 0.1 | 1.4 ± 0.1 | 0.4 ± 0.1 |
| Heart | 0.6 ± 0.1 | 0.3 ± 0.0 | 0.6 ± 0.0 | 0.2 ± 0.0 |
| Lung | 0.8 ± 0.1 | 0.4 ± 0.0 | 0.9 ± 0.1 | 0.3 ± 0.0 |
| Liver | 0.6 ± 0.1 | 0.6 ± 0.1 | 0.6 ± 0.1 | 0.4 ± 0.0 |
| Pancreas | 1.1 ± 0.2 | 0.5 ± 0.0 | 1.1 ± 0.1 | 0.4 ± 0.1 |
| Spleen | 0.4 ± 0.1 | 0.2 ± 0.0 | 0.4 ± 0.0 | 0.2 ± 0.0 |
| Stomach | 0.6 ± 0.1 | 0.3 ± 0.1 | 0.5 ± 0.0 | 0.2 ± 0.0 |
| Intestine | 0.5 ± 0.1 | 0.3 ± 0.1 | 0.5 ± 0.2 | 0.3 ± 0.1 |
| Adrenal | 1.5 ± 0.3 | 0.3 ± 0.1 | 1.1 ± 0.2 | 0.5 ± 0.1 |
| Kidney | 1.1 ± 0.1 | 1.0 ± 0.1 | 1.8 ± 0.2 | 1.1 ± 0.1 |
| Muscle | 0.9 ± 0.1 | 0.4 ± 0.1 | 0.8 ± 0.2 | 0.4 ± 0.1 |
| Femur | 2.4 ± 0.3 | 1.6 ± 0.3 | 3.2 ± 0.8 | 1.2 ± 0.1 |
| HT1080.hFAP | 3.5 ± 1.0 | 4.0 ± 0.6 | 7.4 ± 1.6 | 3.0 ± 0.8 |
| HT1080.wt | 1.4 ± 0.2 | 0.9 ± 0.1 | 1.7 ± 0.2 | 0.6 ± 0.0 |
| tumor mass | 0.4 ± 0.1 | 0.3 ± 0.1 | 0.3 ± 0.1 | 0.3 ± 0.1 |

TABLE 24C

Biodistribution studies of [$^{61}$Cu]Cu-NODAGA-FAPI-46 in HT-1080.hFAP and HT-1080.wt xenografts at 1 hour and 4 hours post-injection. Results are expressed as mean of the % injected activity per gram of tissue (% IA/g) ± standard deviation (SD).

| Organ | [$^{61}$Cu]Cu-NODAGA-FAPI-46, 1 h | [$^{61}$Cu]Cu-NODAGA-FAPI-[6]Cu]Cu-46, 4 h |
|---|---|---|
| Blood | 2.6 ± 0.1 | 1.5 ± 0.1 |
| Heart | 1.1 ± 0.0 | 0.7 ± 0.1 |
| Lung | 1.5 ± 0. | 1.0 ± 0.1 |
| Liver | 0.9 ± 0.0 | 0.8 ± 0.2 |
| Pancreas | 2.0 ± 0.2 | 1.6 ± 0.1 |
| Spleen | 0.7 ± 0.1 | 0.5 ± 0.1 |
| Stomach | 1.0 ± 0.1 | 0.6 ± 0.1 |
| Intestine | 1.0 ± 0.4 | 0.6 ± 0.2 |
| Adrenal | 2.2 ± 0.1 | 2.0 ± 0.2 |
| Kidney | 1.5 ± 0.1 | 1.0 ± 0.1 |
| Muscle | 1.7 ± 0.1 | 1.4 ± 0.2 |
| Femur | 6.5 ± 0.4 | 4.6 ± 0.4 |
| HT1080.hFAP | 8.4 ± 1.4 | 7.7 ± 0.4 |
| HT1080.wt | 3.1 ± 0.0 | 2.5 ± 0.2 |
| tumor mass | 0.1 ± 0.0 | 0.2 ± 0.0 |

[$^{61}$Cu]Cu-NODAGA-F1, [$^{61}$Cu]Cu-NODAGA-F3, [$^{61}$Cu]Cu-NODAGA-F2, [$^{61}$Cu]Cu-NODAGA-F4, and [$^{61}$Cu]Cu-NODAGA-FAPI-46 showed high accumulation in FAP-positive (HT-1080.hFAP) tumor and murine-FAP-positive tissues, such as synovial tissues in the joints (e.g., joint associate with a femur).

Example 10—Specificity Studies

The specificity of [$^{61}$Cu]Cu-NODAGA-PSMA-I&T and [$^{61}$Cu]Cu-DOTAGA-PSMA-I&T was assessed in LNCaP xenografted mice, firstly injected with 1.3 μmol (300 μg) of 2-Phosphonomethyl pentanedioic acid (2-PMPA) as the blocking agent, followed by the injection of the radiotracer e.g. [$^{61}$Cu]Cu-DOTAGA-PSMA-I&T (100 μL/400 pmol/4-8 MBq) or [$^{61}$Cu]Cu-NODAGA-PSMA-I&T (100 μL/400 pmol/4-8 MBq). One-hour post injection PET/CT images were acquired as described in Example 8. In addition, PET/CT image of xenografts after injection of [$^{61}$Cu]$CuCl_2$ (100 μL/7 MBq) was acquired in order to assess the total body distribution of free (uncomplexed)$^{61}$Cu. The results are shown in FIG. 10, panels A and B. L=liver; K=kidneys; T=tumor; Bl=bladder; I=intestine.

The significantly lower uptake of [$^{61}$Cu]Cu-NODAGA-PSMA-I&T and [$^{61}$Cu]Cu-DOTAGA-PSMA-I&T in PSMA-positive tumors and kidneys in xenografts pre-injected with 2-PMPA illustrates the PSMA-mediated uptake (specificity) (FIG. 12, panel A and B). The PET/CT images of uncomplexed $^{61}$Cu (FIG. 12, panel C) shows accumulation in the abdomen, especially liver and intestine, which is comparable to the uptake seen on the PET/CT images of [$^{61}$Cu]Cu-DOTAGA-PSMA-I&T (in addition to tumor and kidneys), but not to the total body distribution of the [$^{61}$Cu]Cu-NODAGA-PSMA-I&T (FIG. 11, panels A and B). Similar are the observations for the [$^{61}$Cu]Cu-DOTA-TOC (PET/CT image (FIG. 13, panels A and B) shares features with [$^{61}$Cu]$CuCl_2$), compared to [$^{61}$Cu]Cu-NODAGA-TOC (FIG. 13, panels C and D) or [$^{61}$Cu]Cu-(R)-NODAGA-LM3 (FIG. 13, panels E and F). This direct comparison is an indication of the high in vivo stability, and thus superiority, of the [$^{61}$Cu]Cu-NODAGA radiotracers contrary to the low in vivo stability of the [$^{61}$Cu]Cu-DOTAGA and [$^{61}$Cu]Cu-DOTA radiotracers.

Example 11—Pharmacokinetics in Non-Tumor Bearing Mice

Pharmacokinetic studies of [$^{61/64}$Cu]Cu-NODAGA-PSMA-I&T (Table 25) and [$^{61}$Cu]/[$^{64}$Cu]Cu-NODAGA-TOC (Table 26) were performed in healthy female BALB/c mice from 1 hour up to 24 hour after injection of 100 μL/200 pmol/4 MBq of the corresponding radiotracer. $^{61}$Cu (half-life 3.33 hours) was used for the time points of 1 and 4 hours and $^{64}$Cu (half-life 12.7 hours) for the time points of 12 and 24 hours. The biodistribution at the investigate time points was performed as described in the Example 9. The data were combined with the results obtained from the groups of xenografts at 1 hour and 4 hours p.i., as the biodistribution in nude mice was the same as in the healthy mice. The results were expressed as described in the Example 10.

TABLE 25

Biodistribution data of [$^{61}$Cu]/[$^{64}$Cu]Cu-NODAGA-PSMA-I&T at 1, 4, 12, and 24 hours after injection. Results are expressed as mean of the % injected activity per gram of tissue (% IA/g) ± standard deviation (SD).

| Organ | 1 hour* | 4 hours# | 12 hours¥ | 24 hours¥ |
|---|---|---|---|---|
| Blood | 0.33 ± 0.09 | 0.11 ± 0.03 | 0.11 ± 0.01 | 0.08 ± 0.01 |
| Heart | 0.49 ± 0.12 | 0.25 ± 0.06 | 0.26 ± 0.05 | 0.21 ± 0.02 |
| Lung | 1.49 ± 0.45 | 0.68 ± 0.22 | 0.52 ± 0.11 | 0.32 ± 0.12 |
| Liver | 1.12 ± 0.25 | 0.88 ± 0.25 | 0.96 ± 0.18 | 0.84 ± 0.11 |
| Pancreas | 1.37 + 0.90 | 0.55 ± 0.16 | 0.28 ± 0.04 | 0.17 ± 0.03 |
| Spleen | 9.33 ± 3.81 | 2.35 ± 1.45 | 1.40 ± 0.57 | 0.58 ± 0.15 |
| Stomach | 1.12 ± 0.15 | 0.72 ± 0.15 | 0.52 ± 0.03 | 0.31 ± 0.05 |
| Intestine | 2.11 ± 0.85 | 1.12 ± 0.48 | 0.94 ± 0.41 | 0.46 ± 0.11 |
| Adrenal | 14.38 ± 4.39 | 7.31 ± 2.76 | 2.99 ± 0.93 | 1.17 ± 0.22 |
| Kidneys | 124 ± 21 | 94 ± 12 | 60 ± 9 | 16.1 ± 4.9 |
| Muscles | 0.99 ± 0.30 | 0.45 ± 0.18 | 0.25 ± 0.05 | 0.08 ± 0.02 |
| Femur | 2.48 ± 0.97 | 1.34 ± 0.38 | 0.50 ± 0.10 | 0.20 ± 0.05 |
| Salivary glands | 1.89 ± 0.28 | 0.58 ± 0.12 | 0.39 ± 0.05 | 0.22 ± 0.05 |

*n = 16,
#n = 13,
¥n = 5

[$^{61/64}$Cu]Cu-NODAGA-PSMA-I&T had fast blood clearance and high accumulation in the kidneys due to the excretion route and the expression of PSMA. Other organs with considerable uptake are the adrenals, spleen and intestine. Within 24 hours the radiotracer is washed out from all organs, but the kidneys.

TABLE 26

Biodistribution data of [$^{61/64}$Cu]Cu-NODAGA-TOC at 1, 4, 12, and 24 hours after injection. Results are expressed as mean of the % injected activity per gram of tissue (% IA/g) ± standard deviation (SD).

| Organ | 1 hour* | 4 hours# | 12 hours¥ | 24 hours¥ |
|---|---|---|---|---|
| Blood | 0.24 ± 0.08 | 0.04 ± 0.02 | 0.04 ± 0.01 | 0.03 ± 0.00 |
| Heart | 0.17 ± 0.03 | 0.07 ± 0.02 | 0.09 ± 0.02 | 0.07 ± 0.02 |
| Lung | 1.07 ± 0.17 | 0.50 ± 0.24 | 0.51 ± 0.12 | 0.27 ± 0.09 |
| Liver | 0.35 ± 0.08 | 0.28 ± 0.08 | 0.37 ± 0.09 | 0.26 ± 0.02 |
| Pancreas | 2.71 ± 0.40 | 0.60 ± 0.19 | 0.14 ± 0.03 | 0.07 ± 0.01 |
| Spleen | 0.23 ± 0.04 | 0.10 ± 0.03 | 0.10 ± 0.02 | 0.07 ± 0.02 |
| Stomach | 2.62 ± 0.48 | 1.35 ± 0.26 | 0.75 ± 0.19 | 0.26 ± 0.04 |

TABLE 26-continued

Biodistribution data of [$^{61/64}$Cu]Cu-NODAGA-TOC at 1, 4, 12, and 24 hours after injection. Results are expressed as mean of the % injected activity per gram of tissue (% IA/g) ± standard deviation (SD).

| Organ | 1 hour* | 4 hours# | 12 hours¥ | 24 hours¥ |
|---|---|---|---|---|
| Intestine | 0.96 ± 0.12 | 0.69 ± 0.19 | 0.57 ± 0.07 | 0.31 ± 0.05 |
| Adrenal | 1.06 ± 0.24 | 0.63 ± 0.22 | 0.32 ± 0.20 | 0.18 ± 0.10 |
| Kidneys | 17.2 ± 4.46 | 7.64 ± 3.85 | 2.46 ± 0.85 | 0.66 ± 0.15 |
| Muscles | 0.16 ± 0.05 | 0.07 ± 0.03 | 0.02 ± 0.01 | 0.01 ± 0.00 |
| Femur | 0.45 ± 0.14 | 0.28 ± 0.11 | 0.11 ± 0.04 | 0.06 ± 0.01 |
| Pituitary | 3.39 ± 1.11 | 2.71 ± 1.84 | 0.48 ± 0.25 | 0.43 ± 0.29 |

*n = 10,
#n = 12,
¥n = 5

[$^{61/64}$Cu]Cu-NODAGA-TOC had a very fast blood clearance and it was essentially excreted almost entirely from the body within 24 hours.

Example 12—In Vivo Comparison of the [61Cu]Cu-NODAGA Radiotracers with Reference Compounds The biodistribution of the [$^{61}$Cu]Cu-NODAGA radiotracers was compared with the reference compounds used in patients under identical experimental conditions. The mice were randomly distributed in groups, injected with the radiotracer under investigation and euthanized at 1 and at 4 hours post-injection of the radiotracers under investigation. The organs of interest were collected, rinsed, blotted, weighed and counted in a gamma counter. The results are expressed as percentage of injected activity per gram (% IA/g), representing the mean±standard deviation of all mice per group and they were obtained by extrapolation from counts of an aliquot taken from the injected solution as standard. Table 27 and FIG. 31 and FIG. 32 show the direct comparison of [$^{61}$Cu]Cu-NODAGA-PSMA-I&T (100 μL/200 pmol/1.5-3.5 MBq) vs [$^{68}$Ga]Ga-PSMA-11 (100 μL/200 pmol/3-5 MBq), vs [$^{18}$F]PSMA-1007 (100 μL/70 pmol/15 MBq), Table 28 shows the direct comparison of [$^{61}$Cu]Cu-NODAGA-TOC vs [$^{68}$Ga]Ga-DOTA-TOC at 1 hour after injection, and FIG. 33 and FIG. 34 show the direct comparison of [$^{61}$Cu]Cu-NODAGA-LM3 vs [$^{68}$Ga]Ga-DOTA-TOC at 1 hour after injection.

TABLE 27

Comparative biodistribution of [$^{61}$Cu]Cu-NODAGA-PSMA-I&T versus [$^{68}$Ga]Ga-PSMA-11 in LNCap xenograft mice at 1 h after injection and versus [$^{18}$F]PSMA-1007 in LNCap xenograft mice at 1 h and 4 h after injection and selective tumor-to-non tumor organ ratios. Results are expressed as mean of the % injected activity per gram of tissue (% IA/g) ± standard deviation (SD).

| | [$^{61}$Cu]Cu-NODAGA-PSMA-I&T* | | [$^{68}$Ga]Ga-PSMA-11# | [$^{18}$F]PSMA-1007 | |
|---|---|---|---|---|---|
| Organ | 1 h | 4 h | 1 h | 1 h | 4 h |
| Blood | 0.28 ± 0.06 | 0.10 ± 0.03 | 0.25 ± 0.07 | 0.41 ± 0.11 | 0.17 ± 0.04 |
| Heart | 0.45 ± 0.15 | 0.22 ± 0.05 | 0.32 ± 0.10 | 1.25 ± 0.29 | 0.53 ± 0.23 |
| Lung | 1.69 ± 0.45 | 0.74 ± 0.19 | 1.43 ± 0.43 | 2.08 ± 0.24 | 1.61 ± 0.58 |
| Liver | 1.02 ± 0.28 | 0.72 ± 0.11 | 0.54 ± 0.27 | 0.93 ± 0.26 | 0.32 ± 0.16 |
| Pancreas | 0.97 ± 0.36 | 0.45 ± 0.09 | 0.70 ± 0.12 | 1.32 ± 0.58 | 0.80 ± 0.32 |
| Spleen | 6.04 ± 1.87 | 1.28 ± 0.39 | 6.38 ± 1.37 | 11.0 ± 1.1 | 8.33 ± 2.11 |
| Stomach | 1.13 ± 0.20 | 0.66 ± 0.15 | 0.69 ± 0.11 | 0.75 ± 0.15 | 0.47 ± 0.16 |
| Intestine | 2.11 ± 0.78 | 1.06 ± 0.50 | 1.52 ± 0.60 | 1.04 ± 0.33 | 0.43 ± 0.22 |
| Adrenal | 17.3 ± 3.26 | 8.32 ± 2.87 | 19.2 ± 5.35 | 7.18 ± 2.20 | 8.03 ± 2.66 |
| Kidney | 118 ± 13 | 90.9 ± 10.1 | 159 ± 31 | 100 ± 17 | 132 ± 9 |
| Muscle | 1.12 ± 0.32 | 0.50 ± 0.22 | 0.90 ± 0.36 | 0.53 ± 0.09 | 0.27 ± 0.11 |
| Bone | 2.73 ± 0.91 | 1.34 ± 0.48 | 3.69 ± 1.86 | 0.94 ± 0.13 | 0.62 ± 0.11 |
| Salivary gland | 2.01 ± 0.33 | 0.52 ± 0.06 | 1.56 ± 0.31 | 2.54 ± 0.72 | 1.62 ± 0.43 |

TABLE 27-continued

Comparative biodistribution of [$^{61}$Cu]Cu-NODAGA-PSMA-I&T versus [$^{68}$Ga]Ga-PSMA-11 in LNCap xenograft mice at 1 h after injection and versus [$^{18}$F]PSMA-1007 in LNCap xenograft mice at 1 h and 4 h after injection and selective tumor-to-non tumor organ ratios. Results are expressed as mean of the % injected activity per gram of tissue (% IA/g) ± standard deviation (SD).

| | [$^{61}$Cu]Cu-NODAGA-PSMA-I&T* | | [$^{68}$Ga]Ga-PSMA-11# | [$^{18}$F]PSMA-1007 | |
|---|---|---|---|---|---|
| Organ | 1 h | 4 h | 1 h | 1 h | 4 h |
| LNCaP-tumor | 14.0 ± 5.0 | 10.7 ± 3.3 | 10.2 ± 1.53 | 9.70 ± 2.57 | 6.28 ± 2.19 |
| Ratios | 1 h | 4 h | 1 h | 1 h | 4 h |
| Tumor/Blood | 55.8 ± 20.0 | 109 ± 43 | 45.3 ± 19.7 | 25.8 ± 11.5 | 42.7 ± 16.4 |
| Tumor/Liver | 14.9 ± 4.9 | 15.4 ± 5.7 | 23.5 ± 12.5 | 11.3 ± 4.5 | 18.4 ± 8.5 |
| Tumor/Kidney | 0.13 ± 0.03 | 0.12 ± 0.03 | 0.07 ± 0.02 | 0.10 ± 0.03 | 0.04 ± 0.01 |
| Tumor/Muscles | 13.6 ± 3.75 | 25.4 ± 12.0 | 13.6 ± 8.3 | 19.2 ± 6.5 | 20.1 ± 2.5 |

[$^{61}$Cu]Cu-NODAGA-PSMA-I&T compares fairly with the reference radiotracer [$^{68}$Ga]Ga-PSMA-11 which is used in the clinics at 1 hour after injection (FIG. 31). However, [$^{61}$Cu]Cu-NODAGA-PSMA-I&T offers the possibility of images at 4 hours after injection where the tumor-to-background ratios are significantly increasing. This is expected to results in a significantly better image contrast and thus improved diagnostic sensitivity. [$^{61}$Cu]Cu-NODAGA-PSMA-I&T compares also fairly with the other reference radiotracer used in the clinics, [$^{18}$F]PSMA-1007, with some exceptions, such as the higher and persistent spleen uptake of [$^{18}$F]PSMA-1007 at 1 h and 4 h p.i. At the later time point of investigation (4 h p.i.) [$^{61}$Cu]Cu-NODAGA-PSMA-I&T has higher tumor uptake than the clinically used [$^{18}$F]PSMA-1007 (10.7±3.3 vs 6.28±2.19% IA/g, p=0.0145) and better tumor-to-background (tumor-to-blood and tumor-to-muscles) ratio.

TABLE 28

Comparative biodistribution of [$^{61}$Cu]Cu-NODAGA-TOC versus [$^{68}$Ga]Ga-DOTA-TOC in HEK-SST2 xenograft mice at 1 h after injection and selective tumor-to-non tumor organ ratios. Results are expressed as mean of the % injected activity per gram of tissue (% IA/g) ± standard deviation (SD).

| Organ | [$^{61}$Cu]Cu-NODAGA-TOC | [$^{68}$Ga]Ga-DOTA-TOC# |
|---|---|---|
| Blood | 0.22 ± 0.04 | 0.63 ± 0.09 |
| Heart | 0.16 ± 0.04 | 0.27 ± 0.03 |
| Lung | 1.09 ± 0.20 | 1.68 ± 0.32 |
| Liver | 0.29 ± 0.04 | 0.58 ± 0.07 |
| Pancreas | 2.59 ± 0.49 | 4.77 ± 1.16 |
| Spleen | 0.22 ± 0.05 | 0.42 ± 0.05 |
| Stomach | 2.34 ± 0.43 | 3.73 ± 0.36 |
| Intestine | 0.92 ± 0.12 | 1.39 ± 0.28 |
| Adrenal | 0.99 ± 0.17 | 2.57 ± 0.78 |
| Kidney | 12.5 ± 2.25 | 8.37 ± 0.84 |
| Muscle | 0.16 ± 0.06 | 0.23 ± 0.09 |
| Bone | 0.46 ± 0.17 | 0.49 ± 0.07 |
| Pitituty | 3.80 ± 1.35 | 3.29 ± 0.63 |
| HEK-SST2 | 8.88 ± 3.19 | 6.64 ± 1.11 |
| Ratios | 1 hour (4 hours) | 1 hour |
| Tumor/Blood | 40 (185) | 11 |
| Tumor/Liver | 31 (27) | 12 |
| Tumor/Kidney | 0.7 (1.7) | 0.8 |
| Tumor/Muscles | 56 (106) | 29 |

*n = 5,
#n = 4

[$^{61}$Cu]Cu-NODAGA-TOC compares well with the reference radiotracer [$^{68}$Ga]Ga-DOTA-TOC, which is used in the clinics, providing higher tumor-to-background ratios at 1 hour after injection, improving further at 4 hours after injection, see FIG. 34.

Overall, the [$^{61}$Cu]Cu-NODAGA radiotracers are suitable for 4 hours imaging due to their lasting tumor uptake and their high in vivo stability (see Example 10) and at the same time due to their lower background (see Examples 8 and 9), compared to [$^{61}$Cu]Cu-DOTAGA or [$^{61}$Cu]Cu-DOTA radiotracers, independent of the targeting moiety. Imaging at 4 hours is advantageous versus 1 hour that is performed routinely with $^{68}$Ga due to the improved image contrast when [$^{61}$Cu]Cu-NODAGA chelates are used in combination with a targeting moiety.

Example 13: Synthesis of FAP Inhibitors

5.1.11. Synthesis of (S)-N1-(2-aminoethyl)-N4-(4-((2-(2-cyano-4,4-difluoropyrrolidin-1-yl)-2-oxoethyl)carbamoyl)quinolin-6-yl)succinimide (1)

Step 1: (S)-6-amino-N-(2-(2-cyano-4,4-difluoropyrrolidin-1-yl)-2-oxoethyl)quinoline-4-carboxamide (A)

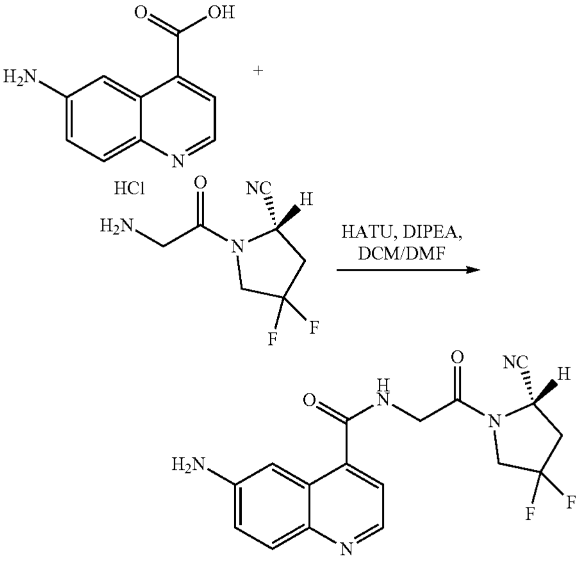

The two precursors (purchased from AstaTech) were dissolved together with HATU in DMF and then DCM was added. DIPEA was added dropwise and the reaction was monitored via LC/MS. The reaction was complete after less than 1 h. The crude product was concentrated, diluted with Water/ACN 85:15 and directly purified via HPLC (LCMS-2020 Shimadzu system equipped with a Gemini C-6 Phenyl column (10×250 mm, 5 μm particle size). The gradient used was 5-80% solvent B in 15 min (A=$H_2O$ [0.1% TFA], B=ACN [0.1% TFA]) at a flow rate of 5.0 mL/min) to provide A as a pure red powder (38 μg, 84% yield).

Step 2: Synthesis of (S)-4-((4-((2-(2-cyano-4,4-difluoropyrrolidin-1-yl)-2-oxoethyl)carbamoyl)quinolin-6-yl)amino)-4-oxobutanoic acid (B)

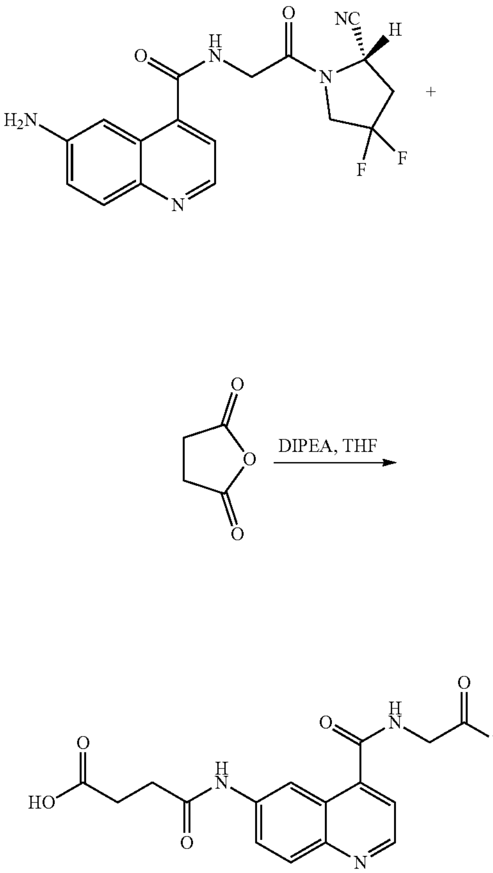

(S)-6-amino-N-(2-(2-cyano-4,4-difluoropyrrolidin-1-yl)-2-oxoethyl)quinoline-4-carboxamide (A) and succinic anhydride were dissolved in THF. DIPEA was added dropwise and the reaction was mixed overnight and checked via LC/MS. The crude product was directly purified HPLC (LCMS-2020 Shimadzu system equipped with a Gemini C-6 Phenyl column (10×250 mm, 5 μm particle size). The gradient used was 5-80% solvent B in 8 min (A=$H_2O$ [0.1% TFA], B=ACN [0.1% TFA]) at a flow rate of 5.0 mL/min) to afford B as a yellow powder (32.7 μg, 68% yield).

Step 3: (S)-N1-(2-aminoethyl)-N4-(4-((2-(2-cyano-4,4-difluoropyrrolidin-1-yl)-2-oxoethyl)carbamoyl)quinolin-6-yl)succinimide (F1)

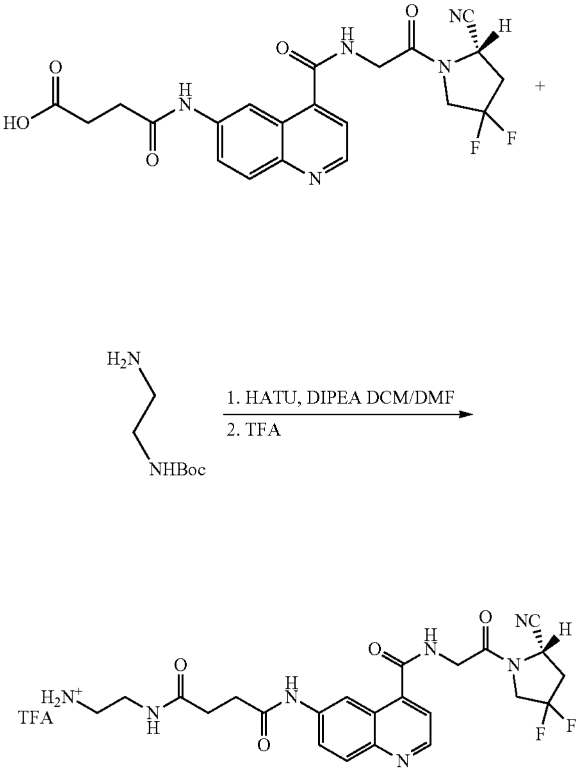

(S)-6-amino-N-(2-(2-cyano-4,4-difluoropyrrolidin-1-yl)-2-oxoethyl)quinoline-4-carboxamide (B) and succinic anhydride were dissolved in THF. DIPEA was added dropwise and the reaction was mixed overnight and checked via LC/MS. The crude product was directly purified via HPLC (5 to 80% in 8 minutes) to afford F1 as a yellow powder (32.7 μg, 68% yield).

5.1.12. Synthesis of (S)-N1-(2-aminoethyl)-N4-(4-((2-(2-cyano-4,4-difluoropyrrolidin-1-yl)-2-oxoethyl)carbamoyl)quinolin-6-yl)-N4-methylsuccinamide (2)

F2 was prepared as shown in Scheme 2:

Scheme 2

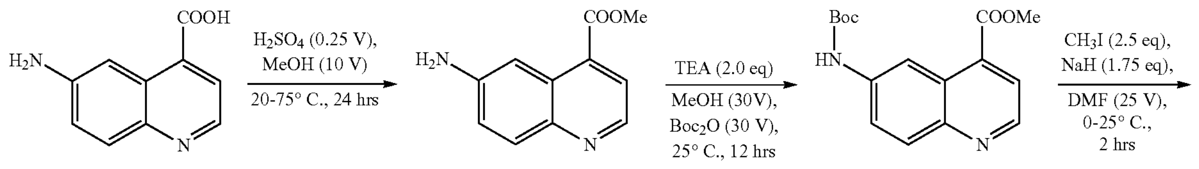

A B C

-continued
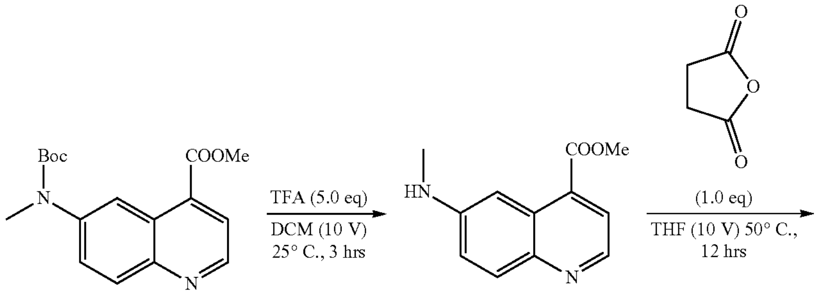
D E
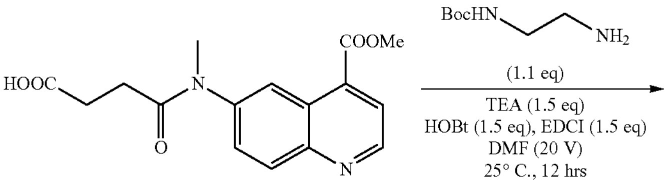
F
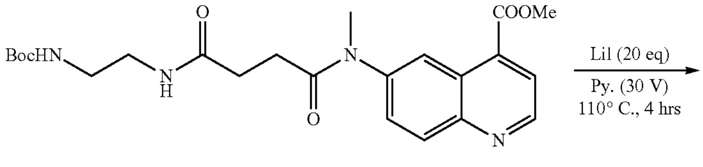
G
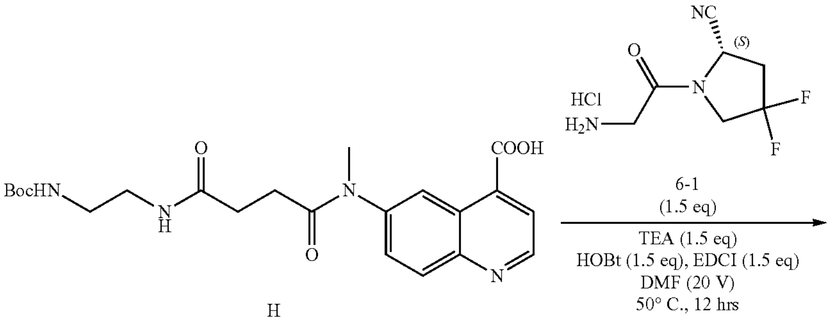
H
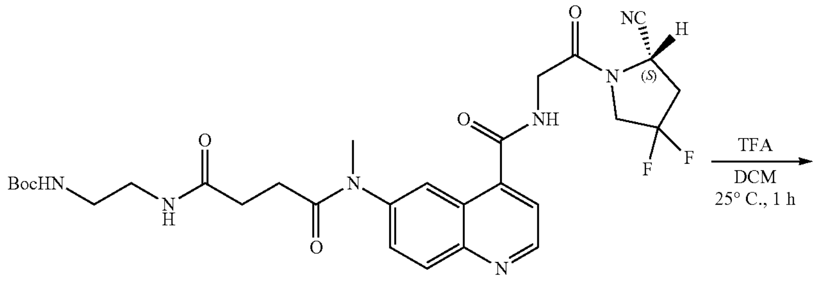
I
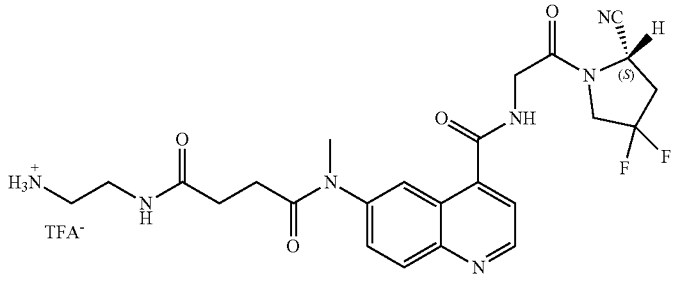
F2

Step 1: To a mixture of compound A (4.17 g, 22.2 mmol) in MeOH (84.0 mL) was added SOCl2 (26.4 g, 222 mmol, 16.1 mL) in one portion at 0-5° C. under N2. The reaction was stirred at 0-5° C. for 0.5 h. The mixture was heated to 75° C. and stirred for 12 hrs. The mixture was added SOCl2 (26.4 g, 222 mmol, 16.1 mL) and stirred for 12 hrs at 75° C. The mixture was added SOCl2 (26.4 g, 222 mmol, 16.1 mL) and stirred for 12 hrs at 75° C. The mixture was added SOCl2 (13.2 g, 111 mmol, 8.04 mL) and stirred for 12 hrs at 75° C. LC-MS showed one main peak with desired mass was detected. The mixture was concentrated in vacuum. The crude product was triturated with MeCN (300 mL) at 20° C. for 1 hr to afford compound B (7.05 g, crude) as a brown solid. 1H NMR: (400 MHz, DMSO-d6) δ 8.81 (d, J=4.8 Hz, 1H), 8.27 (d, J=8.8 Hz, 1H), 8.10 (d, J=4.8 Hz, 1H), 7.82 (s, 1H), 7.67 (d, J=8.0 Hz, 1H), 3.98 (s, 3H). LC-MS (LCMS-2020 Shimadzu system equipped with a Gemini C-6 Phenyl column (3.5×250 mm, 5 μm particle size). The gradient used was 5-80% solvent B in 8 min (A=$H_2O$ [0.1% TFA], B=ACN [0.1% TFA]) at a flow rate of 1.0 mL/min, product: RT=1.262 min).

Step 2: To a solution of B (7.02 g, 34.7 mmol) in MeOH (100 mL), Boc2O (100 mL) was added TEA (7.03 g, 69.4 mmol), the mixture was stirred at 25° C. for 12 hrs. LCMS showed compound B consumed and one peak of desired MS was detected. The mixture was concentrated in vacuum. The residue was purified by column chromatography (SiO2, Petroleum ether/Ethyl acetate=100/1 to 1/1, compound C Rf=0.35) to obtain compound C (4.36 g, 41.5% yield) as a brown solid. 1H NMR: (400 MHz, CDCl3) δ 8.89 (d, J=4.4 Hz, 1H), 8.78 (d, J=2.4 Hz, 1H), 8.11 (d, J=9.2 Hz, 1H), 7.96-7.89 (m, 2H), 6.83 (s, 1H), 4.04 (s, 3H), 1.57 (s, 9H).

Step 3: To a solution of compound C (3.36 g, 11.1 mmol) in DMF (84.0 mL) was added NaH (778 μg, 19.5 mmol, 60% purity) in portions at 0° C., the mixture was stirred at 25° C. for 20 mins. MeI (3.94 g, 27.8 mmol) was added to the reaction mixture at 25° C. and stirred at 25° C. for 2 hrs. LCMS (ET60385-17-P1A3, Product RT=0.562 min) showed compound C consumed and one peak of desired MS was detected. The reaction mixture was cooled to 0° C. and quenched with brine (80.0 mL), extracted with EtOAc (3×100 mL). The organic layer was dried over sodium sulfate, filtered and concentrated in vacuum to obtain compound D (4.78 g, crude) as a brown solid.

Step 4: To a solution of compound D (4.78 g, 15.1 mmol) in DCM (50.0 mL) was added dropwise TFA (8.61 g, 75.5 mmol), the mixture was stirred at 25° C. for 12 hrs. LCMS showed compound D consumed and one peak of desired MS was detected. The reaction mixture was quenched with saturated $NaHCO_3$ (50.0 mL), extracted with DCM (3×40.0 mL). The organic layer was dried over sodium sulfate, filtered and concentrated in vacuum. The residue was purified by column chromatography (SiO2, Petroleum ether/Ethyl acetate=100/1 to 1/1, product Rf=0.40).to obtain compound E (2.51 g, 76.8% yield) as a brown solid. 1H NMR: ET60385-19-P1A1 (400 MHz, CDCl3) δ 8.67 (d, J=4.4 Hz, 1H), 7.94 (d, J=9.2 Hz, 1H), 7.85 (d, J=4.4 Hz, 1H), 7.80 (d, J=2.4 Hz, 1H), 7.17-7.14 (m, 1H), 4.02 (s, 3H), 3.01 (s, 3H).

Step 5: To a solution of compound E (500 μg, 2.31 mmol) in THE (4.00 mL) was added tetrahydrofuran-2,5-dione (231 μg, 2.31 mmol), the reaction mixture was stirred at 50° C. for 12 hrs. LCMS showed compound E consumed and one peak of desired MS was detected. The mixture was concentrated in vacuum to obtain compound F (716 μg, crude) as a brown solid. 1H NMR: ET60385-43-P1A1 (400 MHz, CDCl3) δ 9.10 (d, J=4.0 Hz, 1H), 8.77 (d, J=2.4 Hz, 1H), 8.28 (d, J=8.8 Hz, 1H), 8.03 (d, J=4.0 Hz, 1H), 7.66-7.64 (m, 1H), 4.06 (s, 3H), 3.42 (s, 3H), 2.69-2.66 (m, 2H), 2.51-2.50 (m, 2H).

Step 6: To a solution of compound F (716 μg, 2.26 mmol) in DMF (7.00 mL) was added TEA (343 μg, 3.40 mmol), HOBt (458 μg, 3.40 mmol), EDCI (650 μg, 3.40 mmol) and tert-butyl N-(2-aminoethyl)carbamate (398 μg, 2.49 mmol), the reaction mixture was stirred at 25° C. for 12 hrs. LCMS showed compound F consumed and one peak of desired MS was detected. The reaction mixture was quenched with saturated $NaHCO_3$ (15.0 mL), extracted with DCM (25.0 mL×3) washed with brine (15.0 mL). The organic layer was dried over sodium sulfate, filtered and concentrated in vacuum to obtain compound G (1.33 g, crude) as a brown solid.

Step 7: To a solution of compound G (1.33 g, 2.90 mmol) in Py. (20.0 mL) was added LiI (7.86 g, 58.6 mmol), the mixture was stirred at 110° C. for 4 hrs. LCMS showed compound G consumed and one peak of desired MS was detected. The mixture was concentrated in vacuum. The residue was purified by prep-HPLC (column: Welch Xtimate C18 250*100 mm #10 um; mobile phase: [water ($NH_4HCO_3$)-ACN]; B %: 1%-30%, 20 min) to obtain compound H (647 μg, 50.1% yield) as an off-white solid.

Step 8: To a solution of compound H (617 μg, 1.39 mmol) in DMF (6.00 mL) was added DIEA (717 μg, 5.55 mmol), HATU (791 μg, 2.08 mmol) and compound 6-1 (587 μg, 2.08 mmol, 80% purity, HCl), the mixture was stirred at 25° C. for 1 hr. LCMS showed compound H consumed and one peak of desired MS was detected. The reaction mixture was quenched with saturated $NaHCO_3$ (15.0 mL), extracted with DCM (25.0 mL×3) washed with brine (15.0 mL). The organic layer was dried over sodium sulfate, filtered and concentrated in vacuum. to obtain compound I (2.70 g, crude) as a brown solid.

Step 9: To a solution of compound I (2.70 g, 4.39 mmol) in DCM (10.0 mL) was added TFA (41.5 g, 364 mmol), the mixture was stirred at 25° C. for 1 hr. LCMS (ET60385-61-P1A4, Product RT=0.490 min) showed compound I consumed and one peak of desired MS was detected. The mixture was concentrated in vacuum. The residue was purified by prep-HPLC (column: Welch Xtimate C18 250*100 mm #10 um; mobile phase: [water ($NH_4HCO_3$)-ACN]; B %: 5%-35%, 20 min) to obtain compound F2 (260 μg, 11.1% yield, 97.3% purity) as a brown solid. LCMS (LCMS-2020 Shimadzu system equipped with a Gemini C-6 Phenyl column (3.5×250 mm, 5 μm particle size). The gradient used was 5-80% solvent B in 8 min (A=$H_2O$ [0.1% TFA], B=ACN [0.1% TFA]) at a flow rate of 1.0 mL/min, Product RT=0.493 min).

5.1.13. Synthesis of (S)—N-(2-(2-cyano-4,4-difluoropyrrolidin-1-yl)-2-oxoethyl)-6-(4-oxo-4-(piperazin-1-yl)butanamido)quinoline-4-carboxamide (F3)

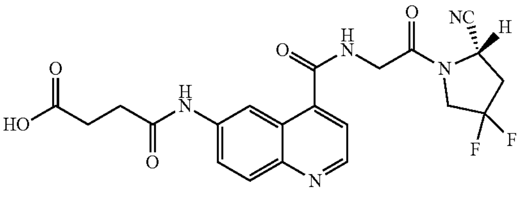

+

-continued

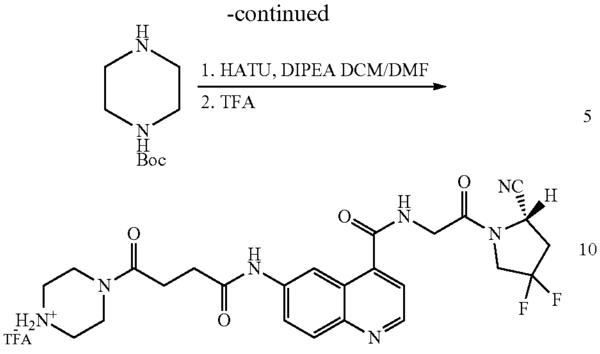

(S)-4-((4-((2-(2-cyano-4,4-difluoropyrrolidin-1-yl)-2-oxoethyl)carbamoyl)quinolin-6-yl)amino)-4-oxobutanoic acid, HATU and the amine were dissolved in DCM and DMF. DIPEA was added dropwise and the reaction was checked. When all the coupling occurred, the crude product was concentrated a bit and then TIPS was added. TFA was added dropwise and the mixture was checked via LC/MC until completion. Crude product (F3) was used as such.

5.1.14. Synthesis of (S)-(fN-(2-(2-cyano-4,4-difluoropyrrolidin-1-yl)-2-oxoethyl)-6-(N-methyl-4-oxo-4-(piperazin-1-yl)butanamido)quinoline-4-carboxamide (F4)

F4 was prepared as shown in Scheme 3:

Scheme 3

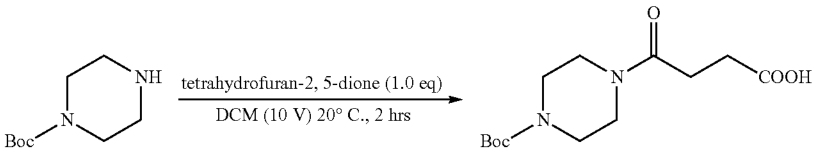

J

K

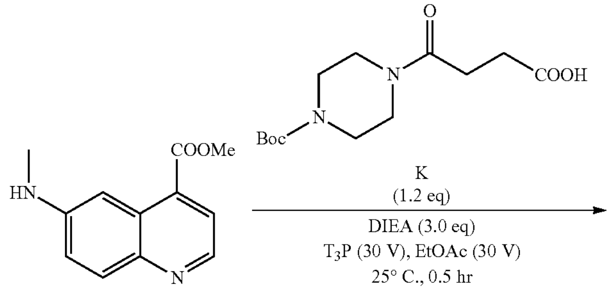

L

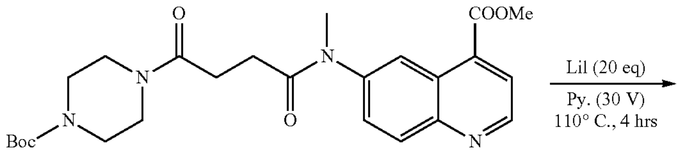

M

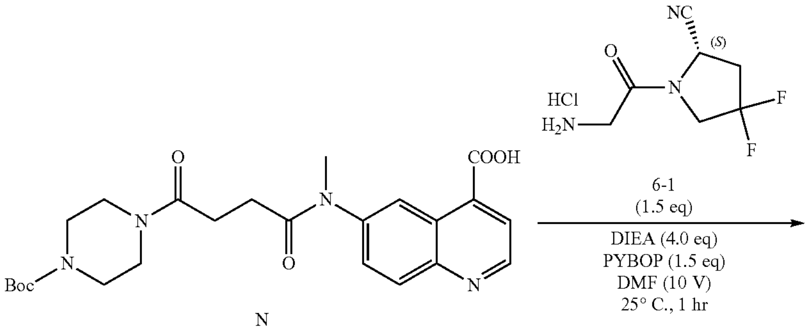

N

-continued

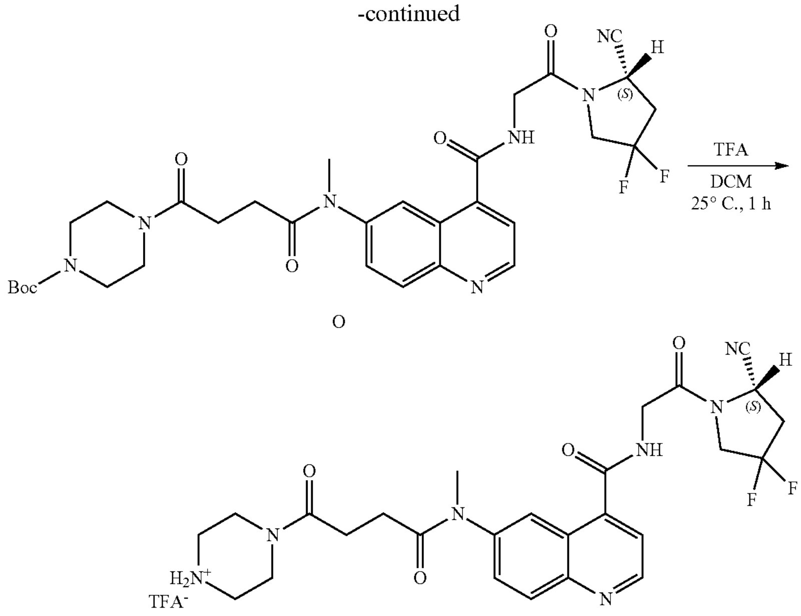

F4

Step 1: To a mixture of compound J (10.0 g, 53.7 mmol) in DCM (70.0 mL) was added tetrahydrofuran-2,5-dione (5.37 g, 53.7 mmol). The mixture was stirred for 2 hrs at 20° C. TLC (dichloromethane/methanol/AcOH=9/1/0.01, compound J Rf=0.0) showed the reaction was completed. The mixture was concentrated in vacuum. The residue was purified by silica gel chromatography (dichloromethane/methanol=100/1, 9/1) to afford compound K (4.75 g, 30.9% yield) as a white solid. 1H NMR: (400 MHz, $CDCl_3$) δ 10.56-11.09 (m, 1H), 3.53-3.62 (m, 2H), 3.45 (s, 4H), 3.36-3.42 (m, 2H), 2.60-2.73 (m, 4H), 1.45 (s, 9H).

Step 2: To a solution of compound L (300 μg, 1.39 mmol) in EtOAc (10.0 mL) was added DIEA (537 μg, 4.16 mmol), compound K (476 μg, 1.66 mmol) and T3P (11.2 g, 17.7 mmol, 50% purity), the reaction mixture was stirred at 25° C. for 0.5 hr. LCMS showed compound L consumed and one peak of desired MS was detected. Then reaction mixture is diluted with EtOAc (20.0 mL), washed with water (60.0 mL), saturated $NaHCO_3$ (60.0 mL), and brine (20.0 mL). The organic phase is dried over $Na_2SO_4$ and concentrated in vacuum to obtain compound M (716 μg, crude) as brown oil.

Step 3: To a solution of compound M (716 μg, 1.48 mmol) in Py. (20.0 mL) was added LiI (3.96 g, 29.5 mmol), the mixture was stirred at 110° C. for 4 hrs. LCMS showed compound M consumed and one peak of desired MS was detected. The mixture was concentrated in vacuum. The residue was purified by prep-HPLC (column: Welch Xtimate C18 250*100 mm #10 um; mobile phase: [water ($NH_4HCO_3$)-ACN]; B %: 1%-30%, 20 min) to obtain compound N (460 μg, 64.4% yield, 97.4% purity) as an off-white solid. LCMS (LCMS (LCMS-2020 Shimadzu system equipped with a Gemini C-6 Phenyl column (3.5×250 mm, 5 μm particle size). The gradient used was 5-80% solvent B in 8 min (A=$H_2O$ [0.1% TFA], B=ACN [0.1% TFA]) at a flow rate of 1.0 mL/min, Product RT=0.596 min)

Step 4: To a solution of compound N (460 μg, 977 umol) in DMF (5.00 mL) was added DIEA (505 μg, 3.91 mmol), PYBOP (763 μg, 1.47 mmol) and compound 6-1 (330 μg, 1.47 mmol, HCl), the mixture was stirred at 25° C. for 1 hr. LCMS showed one peak of desired MS was detected. The reaction mixture was quenched with saturated $NaHCO_3$ (15.0 mL), extracted with DCM (25.0 mL×3) washed with brine (15.0 mL). The organic layer was dried over $Na_2SO_4$, filtered and concentrated in vacuum to obtain compound O (2.10 g, crude) as brown oil.

Step 5: To a solution of compound O (2.10 g, 3.27 mmol) in DCM (10.0 mL) was added TFA (15.4 g, 135 mmol), the mixture was stirred at 25° C. for 1 hr. LCMS showed compound O consumed and one peak of desired MS was detected. The mixture was concentrated in vacuum. The residue was purified by prep-HPLC (column: Welch Xtimate C18 250*70 mm #10 um; mobile phase: [water ($NH_4HCO_3$)-ACN]; B %: 0%-40%, 20 min) to obtain compound F4 (196 μg, 11.0% yield) as an off-white solid.

5.1.15. Synthesis of FAPI-46

FAPI-46 was prepared as shown in Scheme 4:

Scheme 4

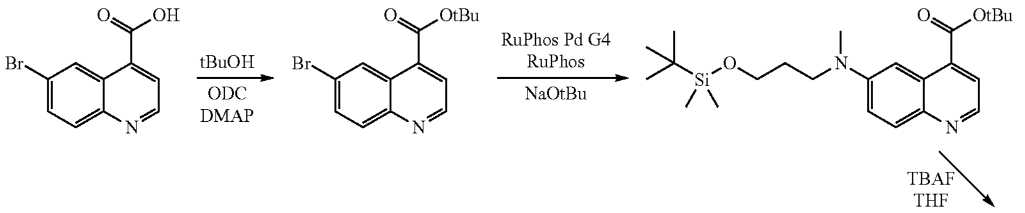

-continued

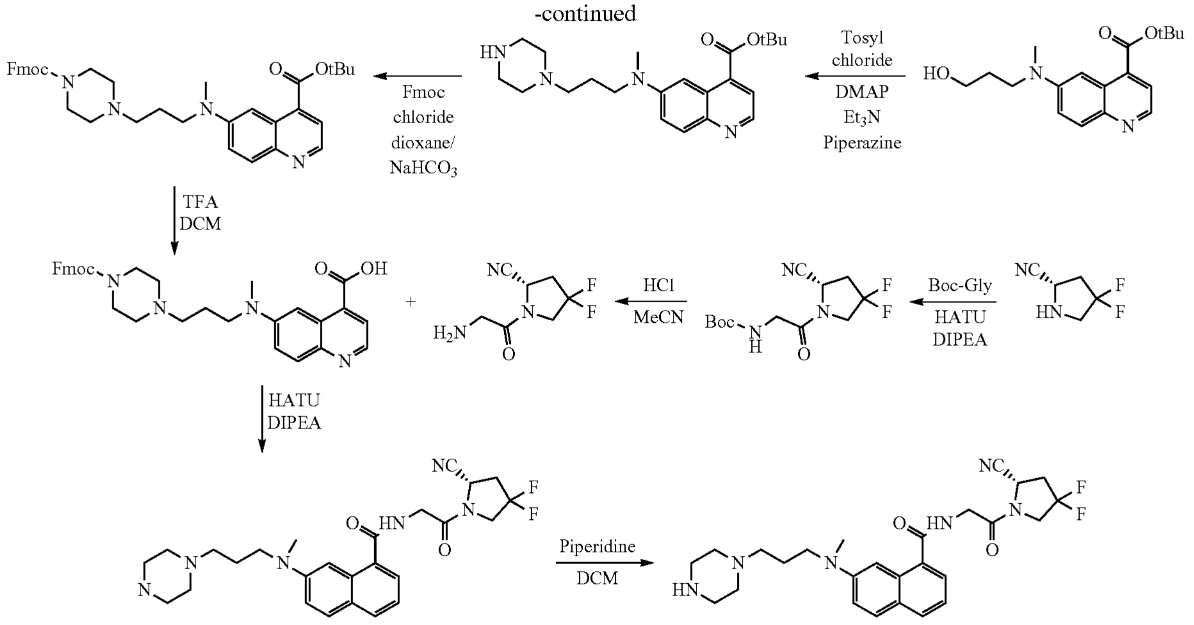

FAPI-46 can also be prepared according to the method described in WO 2019/154886A1.

Example 14: Synthesis of FAPI-NODAGA Targeted Chelator Constructs

5.1.16. Synthesis of 2,2'-(7-((R)-1-carboxy-4-((2-(4-((4-((2-((S)-2-cyano-4,4-difluoropyrrolidin-1-yl)-2-oxoethyl)carbamoyl)quinolin-6-yl)amino)-4-oxobutanamido)ethyl)amino)-4-oxobutyl)-1,4,7-triazonane-1,4-diyl)diacetic acid ((R)-NODAGA-F1)

To the (S)-N1-(2-aminoethyl)-N4-(4-((2-(2-cyano-4,4-difluoropyrrolidin-1-yl)-2-oxoethyl)carbamoyl)quinolin-6-yl) succinimide (F1) crude solution, DIPEA was added dropwise to neutralize TFA. Then, HATU and NODAGA-Tris (tBu) were added dropwise as DMSO solution (150 μL). The reaction was complete after a few minutes. The crude product was concentrated and purified via HPLC. To the pure material, DCM, TIPS and TFA were added, and the reaction was left for 1 day until completion and purified via HPLC to obtain 15.8 μg of (R)-NODAGA-F1 as a pale yellow powder (Yield: 51%).

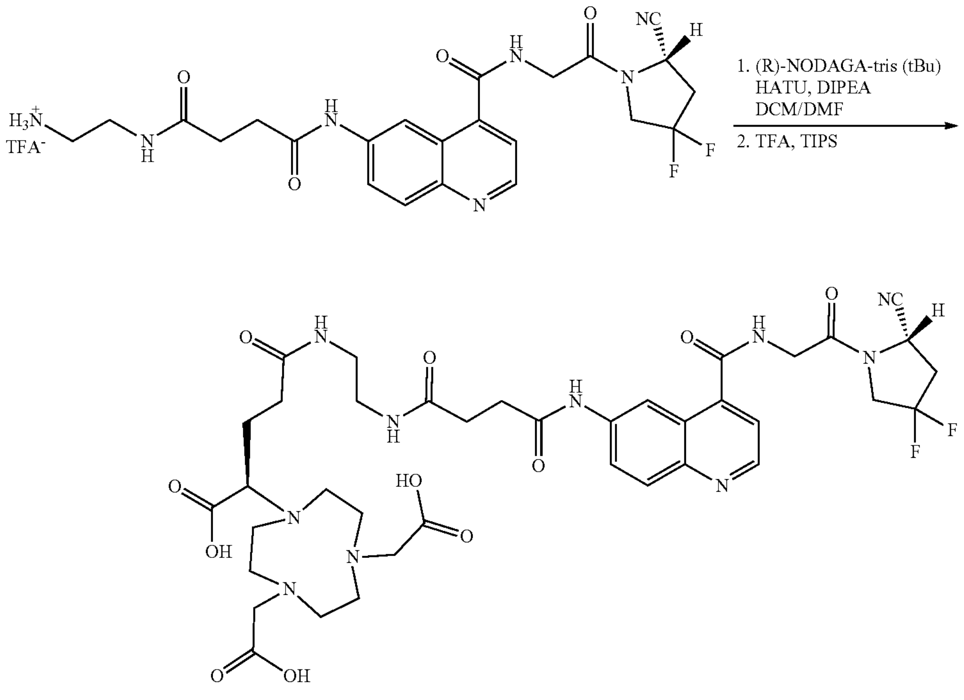

5.1.17. Synthesis of 2,2'-(7-((R)-1-carboxy-4-((2-(4-((4-((2-((S)-2-cyano-4,4-difluoropyrrolidin-1-yl)-2-oxoethyl)carbamoyl)quinolin-6-yl)(methyl)amino)-4-oxobutanamido)ethyl)amino)-4-oxobutyl)-1,4,7-triazonane-1,4-diyl)diacetic acid ((R)-NODAGA-F2)
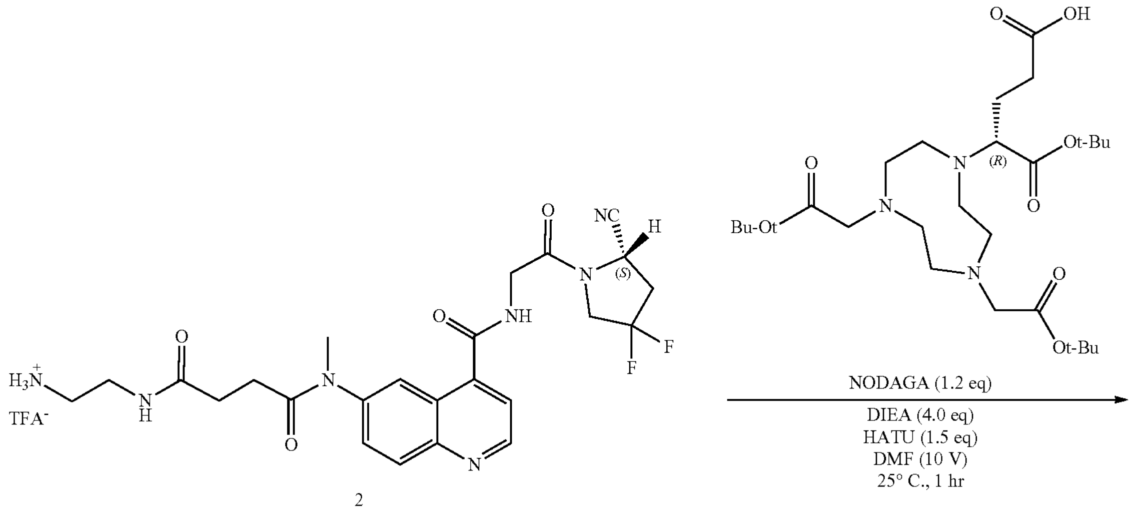
2
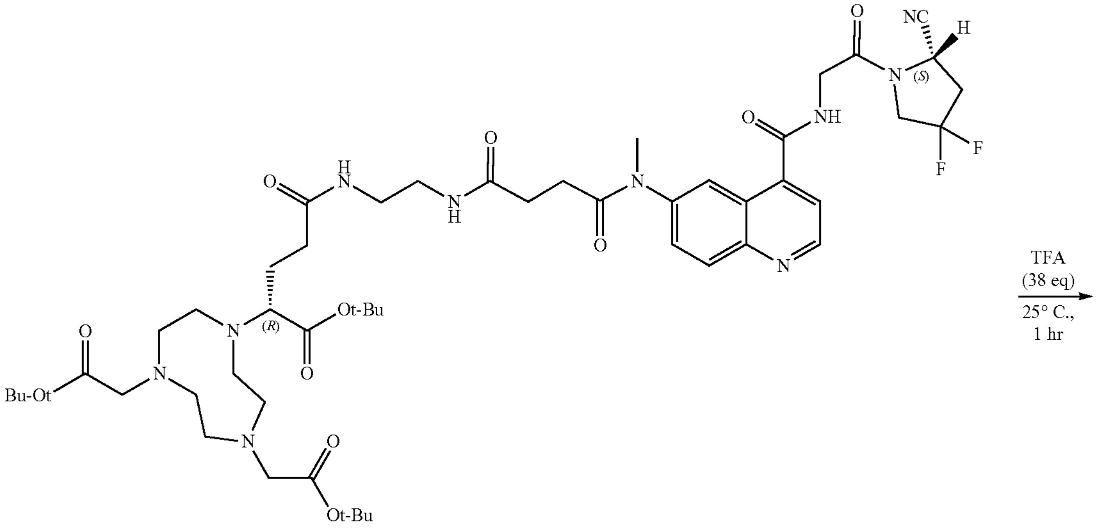
R -continued

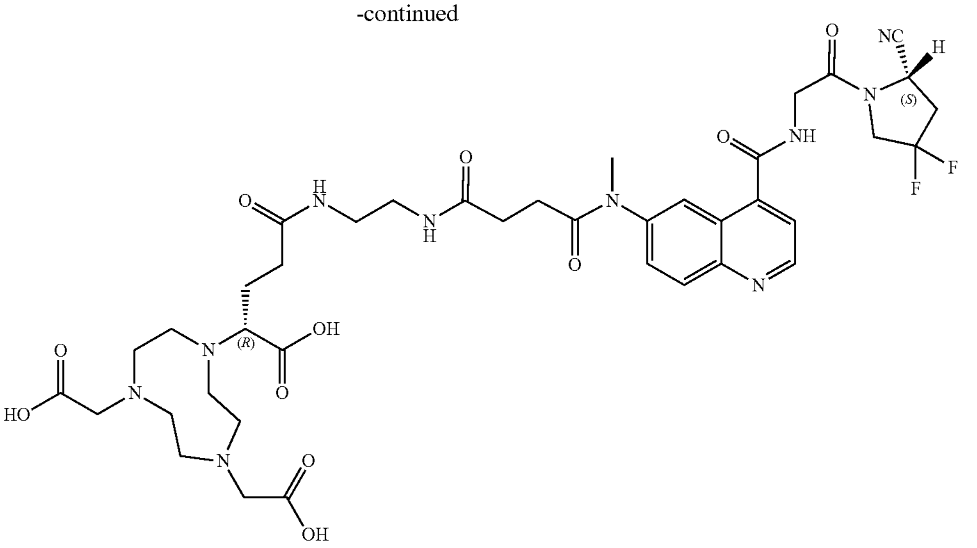

NODAGA-F2

Step 1: To a solution of compound F2 (80.0 μg, 155 μmol) in DMF (1.00 mL) was added DIEA (80.2 μg, 620 μmol), HATU (121 μg, 232 μmol) and NODAGA-Tris(tBu) (101 μg, 186 μmol), the mixture was stirred at 25° C. for 1 hr. LCMS showed compound F2 consumed and one peak of desired MS was detected. The reaction mixture was quenched with saturated $NaHCO_3$ (4.00 mL), extracted with DCM (10.0 mL×3) washed with brine (10.0 mL). The organic layer was dried over sodium sulfate, filtered and concentrated in vacuum to obtain R (310 μg, crude) was obtained as brown oil.

Step 2: To a solution of compound R (310 μg, 297 μmol) in TFA (1.29 g, 11.3 mmol) at 25° C., the mixture was stirred at 25° C. for 1 hr. LCMS showed compound R consumed and one peak of desired MS was detected. The mixture was concentrated in vacuum. The crude product on notebook page ET60385-73 (220 μg, crude) and ET60385-78 (206 μg, crude) was combined for further purification. The residue was purified by prep-HPLC (column: C18-1 150*30 mm*5 um; mobile phase:[water (TFA)-ACN]; B %: 5%-35%, 20 min) to obtain (R)-NODAGA-F2 (10.01 μg, 3.30% yield, 96.9% purity, TFA) a brown solid. 1H NMR: ET60385-73-P1A2 (400 MHz, D2O) 6 9.14 (d, J=5.2 Hz, 1H), 8.32-9.30 (m, 2H), 8.02-7.98 (m, 2H), 5.18-5.14 (m, 1H), 4.38 (s, 2H), 4.33-4.24 (m, 1H), 4.20-4.10 (m, 1H), 3.76 (s, 4H), 3.51-3.31 (m, 4H), 3.25-3.12 (m, 12H), 3.03-2.87 (m, 6H), 2.49 (s, 3H), 2.30 (t, J=7.2 Hz, 2H), 2.03-1.85 (m, 1H). LCMS (ET60385-73-P1Z1, Product RT=1.610 min).

5.1.18. Synthesis of 2,2'-(7-((R)-1-carboxy-4-(4-(4-((4-((2-((S)-2-cyano-4,4-difluoropyrrolidin-1-yl)-2-oxoethyl)carbamoyl)quinolin-6-yl)amino)-4-oxobutanoyl)piperazin-1-yl)-4-oxobutyl)-1,4,7-triazonane-1,4-diyl)diacetic acid ((R)-NODAGA-F3)

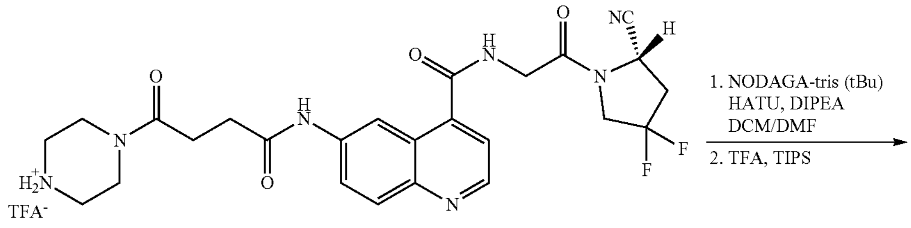

3

-continued

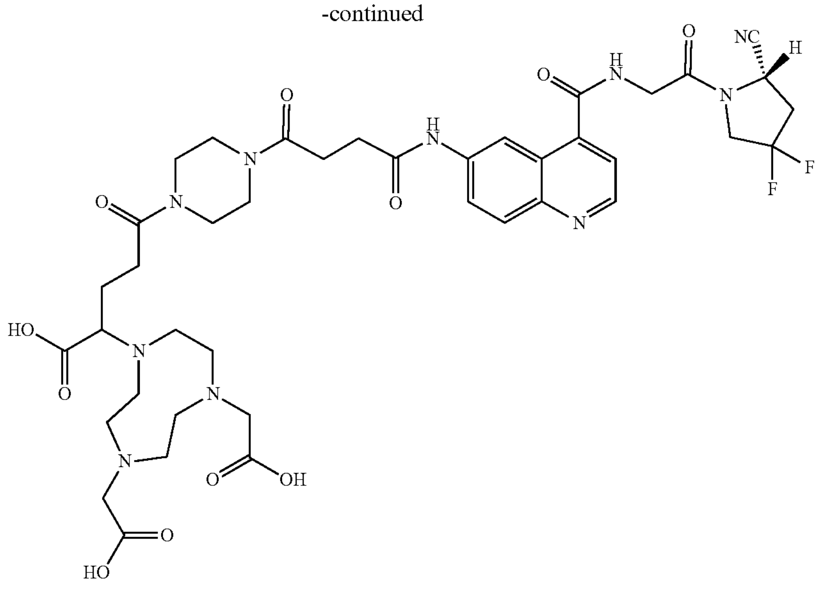

NODAGA-F3

To the (S)—N-(2-(2-cyano-4,4-difluoropyrrolidin-1-yl)-2-oxoethyl)-6-(4-oxo-4-(piperazin-1-yl)butanamido)quinoline-4-carboxamide (F3) crude solution, DIPEA was added dropwise to neutralize TFA. Then, HATU and NODAGA-Tris(TBu) were added dropwise as DMSO solution (150 μL). The reaction was complete after a few minutes. The crude product was concentrated and purified via HPLC. To the pure material, DCM, TIPS and TFA were added and the reaction was left for 1 day until completion and purified via HPLC to obtain 15.8p g of (R)-NODAGA-F3 a pale yellow powder (Yield: 26%).

5.1.19. Synthesis of 2,2'-(7-((R)-1-carboxy-4-(4-(4-((4-((2-((S)-2-cyano-4,4-difluoropyrrolidin-1-yl)-2-oxoethyl)carbamoyl)quinolin-6-yl)(methyl)amino)-4-oxobutanoyl)piperazin-1-yl)-4-oxobutyl)-1,4,7-triazonane-1,4-diyl)diacetic acid ((R)-NODAGA-F4)

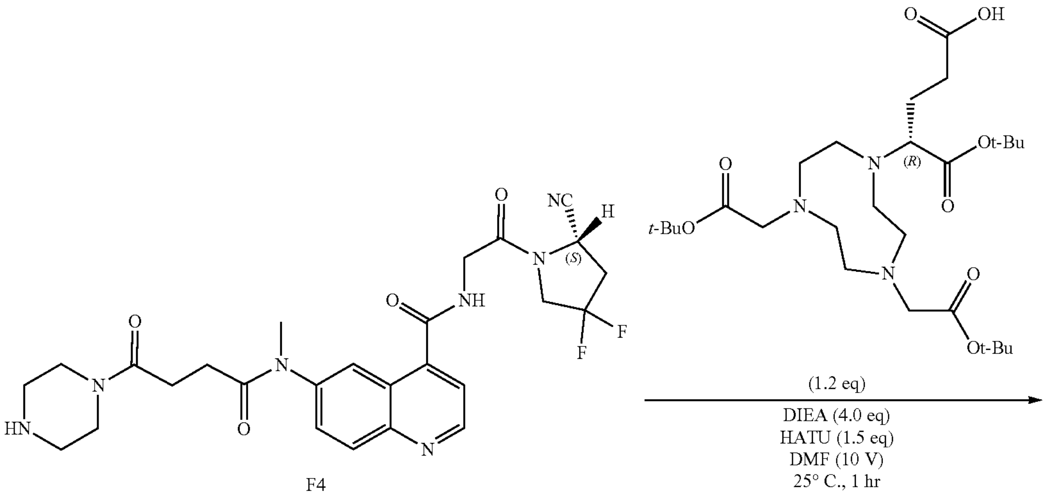

F4

-continued

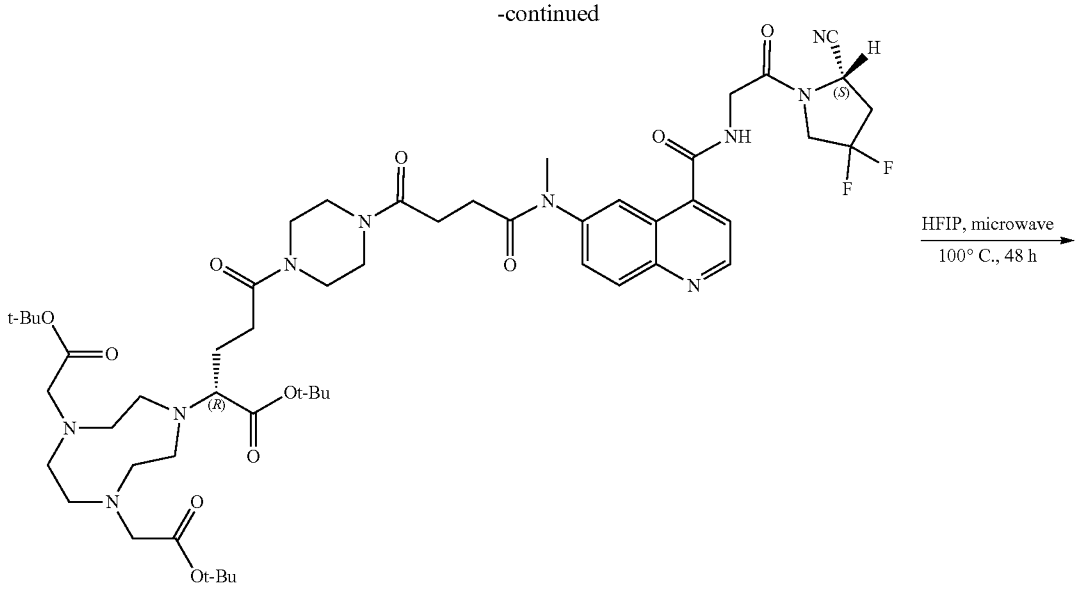

S

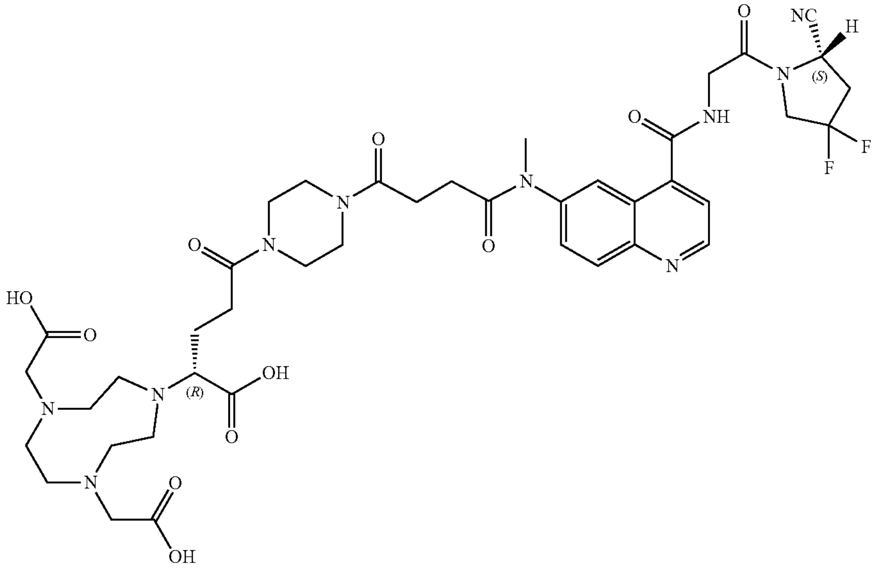

(*R*)-NODAGA-F4

Step 1: To a solution of compound F4 (40.0 μg, 73.8 μmol) in DMF (0.50 mL) was added DIEA (9.55 μg, 73.8 μmol), HATU (57.6 μg, 110 μmol) and NODAGA-Tris(tBu) (48.1 μg, 88.6 μmol). The mixture was stirred at 25° C. for 1 hr. LCMS showed one peak of desired MS was detected. The mixture was concentrated in vacuum. The residue was purified by prep-HPLC (column: Waters Xbridge Prep OBD C18 150*40 mm*10 um; mobile phase: [water ($NH_4HCO_3$)-ACN]; B %: 50%-90%, 8 min) to obtain compound S (28.0 μg, 35.5% yield) as a white solid.

Step 2: Compound S (28.0 μg, 26.2 μmol) was taken up into a microwave tube in HFIP (4.41 μg, 26.2 μmol). The sealed tube was heated at 100° C. for 48 hrs under microwave. LCMS showed compound S consumed and one peak of desired MS was detected. The mixture was concentrated in vacuum. The residue was purified by prep-HPLC (column: Phenomenex Luna C18 75*30 mm*3 um; mobile phase: [water (TFA)-ACN]; B %: 5%-30%, 8 min) to obtain (R)-NODAGA-F4 (9.01 μg, 36.9% yield, 96.6% purity, TFA) as an off-white solid. 1H NMR: (400 MHz, D20) 6 9.10 (d, J=4.8 Hz, 1H), 8.31-8.27 (m, 2H), 8.00-7.97 (m, 2H), 5.15-5.12 (m, 1H), 4.35 (s, 2H), 4.26-4.22 (m, 1H), 4.17-4.15 (m, 1H), 3.75 (s, 4H), 3.60-3.50 (m, 9H), 3.22-3.09 (m, 18H), 2.67-2.58 (m, 6H), 2.07-1.96 (m, 2H). LCMS (ET56076-48-P1Z2, Product RT=1.640 min)

5.1.20. Synthesis of 2,2'-(7-(1-carboxy-4-(4-(3-((4-((2-((S)-2-cyano-4,4-difluoropyrrolidin-1-yl)-2-oxoethyl)carbamoyl)quinolin-6-yl)(methyl)amino)propyl)piperazin-1-yl)-4-oxobutyl)-1,4,7-triazonane-1,4-diyl)diacetic acid (NODAGA-FAPI-46)

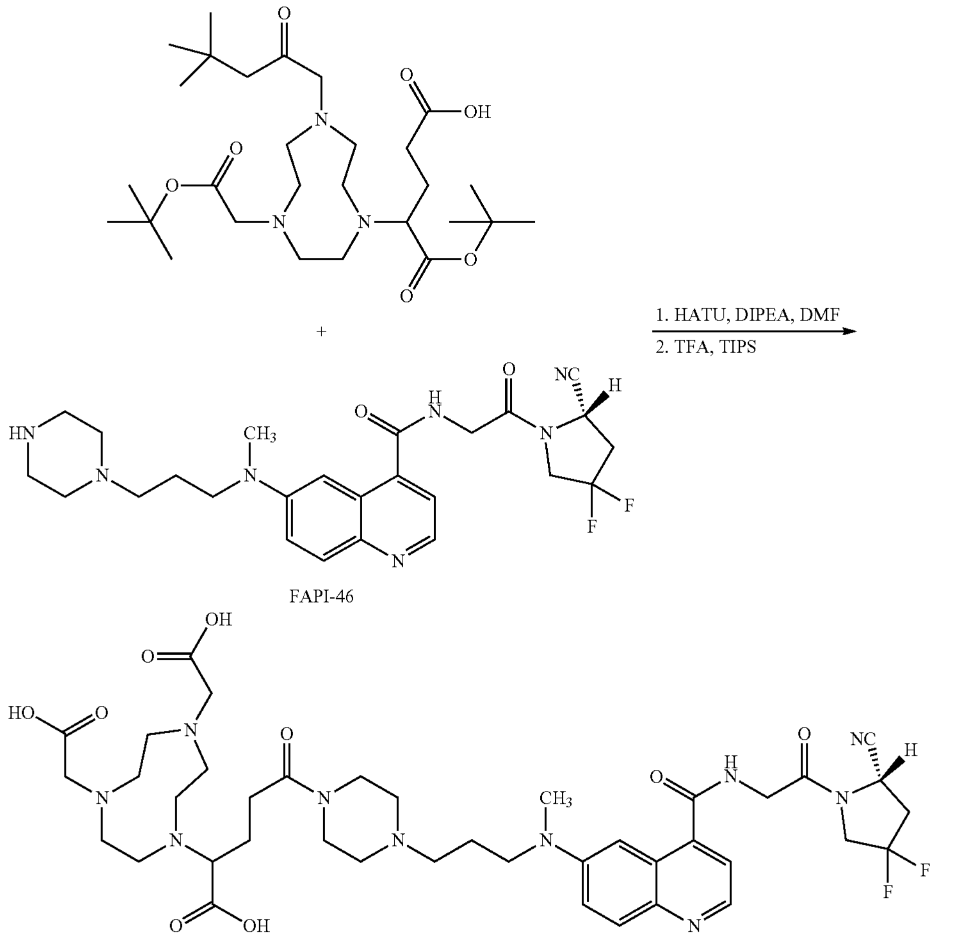

FAPI-46

NODAGA-FAPI-46

(S)—N-(2-(2-cyano-4,4-difluoropyrrolidin-1-yl)-2-oxoethyl)-6-(4-oxo-4-(piperazin-1-yl)butanamido)quinoline-4-carboxamide, (R)-NODAGA(tris)tBu and HATU were dissolved in DCM+100 μL of DMF. DIPEA was added dropwise and the reaction was stirred for 2 h until completion (checked via LC/MS, method 15 to 80% in ACN). When no starting material was left and only a peak related to the product mass was observable (m/z=1025), TIPS and TFA (600 μL) were added. After 48 h, the reaction was complete. The crude was purified via HPLC (10-65% CAN in 15 min, rt=9.5) to afford 6.8 μg of a red powder (Yield: 36%).

Example 15: Radiolabeling FAP Targeted Chelator Constructs

[$^{61}$Cu]Cu-NODAGA-F1 and $^{61}$Cu-NODAGA-F3

An aliquot of conjugate (3-6 nmol, 1 μg/mL in water) was diluted in 0.25-0.30 mL of ammonium (or sodium) acetate (0.5 M pH 8), followed by the addition of 0.1-0.7 mL [$^{61}$Cu]$CuCl_2$ in 0.05 M HCl (70-240 MBq). The reaction mixture was incubated for 15 min at room temperature (approx. 20-25° C.). The pH of the reaction was between 5 and 6. Quality control was performed on a reverse-phase high performance liquid chromatography (RP-HPLC) connected to a radio-detector (radio-HPLC). The results of the radio-HPLC are provided in Table 29 below.

[$^{61}$Cu]Cu-NODAGA-F2 and [$^{61}$Cu]Cu-NODAGA-F4

$^{61}$Cu-labeled conjugates were prepared by incubating 1.5-3 nmol of the corresponding conjugate (as a 1 μg/mL solution) in 125-300 μL of ammonium acetate (0.5 M, pH 8) with 50-200 μL of [$^{61}$Cu]$CuCl_2$ in 0.05 M HCl (33-70 MBq). A pH check was performed in order to guarantee the necessary conditions for the reaction (pH≥5). The reaction mixture was incubated for 10 min at room temperature. Quality control and stability studies were performed by Radio-HPLC on a Shimadzu SCL-40 connected to a GABI radioactivity-HPLC-flow-monitor 7-spectrometer (Elysia-raytest, Straubenhardt, Germany). Radioligands were analyzed using Phenomenex Jupiter Proteo C12 (90 Å, 250×4.6 mm) column using the gradient 15-80% B in 8 min (A=H2O [0.1% TFA], B=ACN [0.1% TFA]) with a flow rate of 1 mL/min. The results of the radio-HPLC are provided in Table 29 below.

TABLE 29

| Radiochemical purity and retention time (tR) of the [$^{61}$Cu]Cu-labeled radiotracers | | |
|---|---|---|
| Radiotracer | Radiochemical purity | $t_R$ (min) |
| [$^{61}$Cu]Cu-NODAGA-F1 | ≥98% | 5.9 ± 0.2 |
| [$^{61}$Cu]Cu-NODAGA-F2 | ≥98% | 6.1 ± 0.2 |
| [$^{61}$Cu]Cu-NODAGA-F3 | ≥97% | 6.1 ± 0.2 |
| [$^{61}$Cu]Cu-NODAGA-F4 | ≥98% | 6.4 ± 0.2 |
| [$^{61}$Cu]Cu-NODAGA-FAPI-46 | ≥95% | 5.7 ± 0.2 |

All conjugates were labeled with $^{61}$Cu, obtaining high radiochemical purity. No further purification step was necessary to remove uncomplexed $^{61}$Cu from the reaction mixture, allowing direct use of the formed radiotracer.

Example 16: Partition Coefficient (Log D) of FAPI Radiotracers

The lipophilic/hydrophilic character of the radiotracers was assessed by the determination of the distribution coefficient (D), expressed as log D (pH=7.4), between an aqua and an organic phase following the "shake-flask" method. In a pre-lubricated Eppendorf tube, a pre-saturated mixture of 500 μL of 1-octanol and 500 μL of PBS pH 7.4 (phosphate-buffered saline) were added. An aliquot of 10 pmol in 10 μL of the radioligand was added to this mixture, shaken for 30 min, and then centrifuged at 3000 rcf for 10 min to achieve phase separation. Aliquots of 100 μL were removed from the 1-octanol and from the PBS phases, and the activity was measured in a γ-counter. The partition coefficient was calculated as the average log ratio value of the radioactivity in the organic fraction and PBS fraction. The results are presented in Table 30 and in FIG. 17.

TABLE 30

| Lipophilicity expressed as the log distribution coefficient D (log DO/PBS pH 7.4) of $^{61}$Cu-labeled conjugates versus $^{68}$Ga-labeled conjugates (reference radiotracers). | |
|---|---|
| Radiotracer | log $D_{(O/PBS\ pH\ 7.4)}$ |
| [$^{61}$Cu]Cu-NODAGA-F1 | −3.17 ± 0.28 |
| [$^{61}$Cu]Cu-NODAGA-F3 | −3.32 ± 0.39 |
| [$^{61}$Cu]Cu-NODAGA-F2 | −3.09 ± 0.08 |
| [$^{61}$Cu]Cu-NODAGA-F4 | −3.12 ± 0.16 |
| [$^{61}$Cu]Cu-NODAGA-FAPI-46 | −3.10 ± 0.34 |
| [$^{68}$Ga]Ga-FAPI-46 | −3.01 ± 0.18 |

Results are means±standard deviation from a minimum of two separate experiments, each in triplicates.

Example 17: In Vitro hFAP Inhibition Assay—FAPI Radiotracers

The enzymatic activity of hFAP on the substrate Z-Gly-Pro-AMC was measured at room temperature on a microtiter plate reader, monitoring the fluorescence at an excitation wavelength of 360 nm and an emission wavelength of 465 nm. The assay was performed by mixing the substrate (20 μM), hFAP (200 μM, constant), and the inhibitors in assay buffer (50 mM Tris, 1 M NaCl, 1 μg/mL BSA, pH=7.5), with serial dilution of the inhibitors ranging from 250 nM to 2 fM, 1:2 in a total volume of 20 μL. FAPI-46 was used as positive control. Experiments were performed in triplicate, and the mean fluorescence values were fitted using Graph Pad Prism 9 (equation used: Y=Bottom+(Top−Bottom)/(1+((X^HillSlope)/($IC_{50}$^HillSlope)))). The $IC_{50}$ value is defined as the concentration of inhibitor required to reduce the enzyme activity by 50% after the addition of the substrate. The results are presented in Table 31 and FIG. 18.

TABLE 31

| In Vitro Inhibition Assay | | |
|---|---|---|
| Compound | $IC_{50}$ (pM) | 95% CI (pM) |
| [$^{nat}$Cu]Cu-NODAGA-F1 | 141.3 | 71.9 to 230.0 |
| [$^{nat}$Cu]Cu-NODAGA-F3 | 40.1 | 26.2 to 54.4 |
| [$^{nat}$Cu]Cu-NODAGA-F2 | 120.5 | 88.0 to 157.8 |
| [$^{nat}$Cu]Cu-NODAGA-F4 | 105.1 | 63.3 to 149.4 |

Example 18: In Vitro Cellular Uptake—FAPI Radiotracers

The cellular uptake was studied in vitro using intact cells seeded in 6-well plates overnight. On the day of the experiment, the cells were washed and incubated with each $^{61}$Cu-labeled conjugate at different time points, either alone or in the presence of a blocking agent to distinguish between specific and non-specific uptake. At each investigated time point, the medium containing the unbound (free) radiotracer was removed, followed by two washing steps with ice-cold phosphate-buffered saline. The cells were then treated 2×5 min with ice-cold glycine solution (0.05 M, pH 2.8) to detach the cell surface-bound radiotracer (acid released). Afterwards, the cells containing the internalized radiotracer were detached with 1 M NaOH at 37° C. and collected for measurement. The amount of specific cell surface-bound and internalized radiotracer is expressed as percentage of the total applied activity, after subtracting the non-specific values. [$^{61}$Cu]Cu-NODAGA-F1, [$^{61}$Cu]Cu-NODAGA-F3, [$^{61}$Cu]Cu-NODAGA-F2, [$^{61}$Cu]Cu-NODAGA-F4, and [$^{61}$Cu]Cu-NODAGA-FAPI-46 (0.2 nM) were assessed in HT-1080.hFAP (FAP-positive) and HT-1080.wt (FAP-negative) cells. Internalization and cell surface-bound fractions for the tested radiotracers are reported in Table 32. The values are expressed as % of the applied activity and refer to the specific uptake calculated after subtracting the non-specific values (measured in the presence of the non-FAP expressing cell line HT-1080.wt) from the total values (specific=total−non-specific).

TABLE 32

| Cellular uptake and distribution | | | | | |
|---|---|---|---|---|---|
| Time Point [min] | [$^{61}$Cu]Cu-NODAGA-F1 | [$^{61}$Cu]Cu-NODAGA-F2 | [$^{61}$Cu]Cu-NODAGA-F3 | [$^{61}$Cu]Cu-NODAGA-F4 | [$^{61}$Cu]Cu-NODAGA-FAPI-46 |
| | | Cell surface fraction | | | |
| 15 | 1.2 ± 0.3 | 1.2 ± 0.6 | 0.9 ± 0.3 | 1.0 ± 0.7 | 0.9 ± 0.3 |
| 60 | 1.4 ± 0.3 | 1.4 ± 0.5 | 1.2 ± 0.4 | 1.4 ± 0.4 | 1.2 ± 0.4 |
| 240 | 1.3 ± 0.2 | 1.3 ± 0.5 | 1.4 ± 0.4 | 0.9 ± 0.6 | 1.7 ± 0.4 |

TABLE 32-continued

| Cellular uptake and distribution | | | | | |
|---|---|---|---|---|---|
| Time Point [min] | [$^{61}$Cu]Cu-NODAGA-F1 | [$^{61}$Cu]Cu-NODAGA-F2 | [$^{61}$Cu]Cu-NODAGA-F3 | [$^{61}$Cu]Cu-NODAGA-F4 | [$^{61}$Cu]Cu-NODAGA-FAPI-46 |
| | Internalized fraction | | | | |
| 30 | 26.2 ± 3.5 | 20.7 ± 5.5 | 26.6 ± 4.9 | 22.2 ± 7.4 | 24.3 ± 2.3 |
| 60 | 29.9 ± 1.8 | 27.0 ± 6.9 | 36.9 ± 5.3 | 22.2 ± 5.1 | 36.1 ± 1.6 |
| 240 | 29.3 ± 1.8 | 28.3 ± 7.5 | 39.4 ± 4.8 | 17.4 ± 4.4 | 50.0 ± 6.0 |

Upon thawing, HT-1080.hFAP (FAP-positive), HT-1080.wt (FAP-negative), HEK-293.hFAP and HEK-293.wt cells were kept in culture in MEM medium supplemented with fetal bovine serum (10%, FBS) and Penicillin-Streptomycin (1%) at 37° C. and 5% CO2. For passaging, cells were detached using Trypsin-EDTA 0.05% when reaching 90% confluency and re-seeded at a dilution of 1:4/1:12 (HT-1080) or 1:10/1:20 (HEK-293).

HT-1080.hFAP and HT-1080.wt cells were seeded in a 24-well plate at a concentration of 1.8×105 cells/well in 400 μL of medium 24 hours before the experiment. The cells were then preconditioned in 360 μL of assay medium (MEM medium without supplements) at 37° C. for 60 min. 40 μL of a 2 nM solution of $^{61}$Cu-labeled radioligand was added and the cells were incubated at 37° C. The cellular uptake was interrupted at different time points (15 min, 1 hour and 4 hours), by washing twice with ice-cold PBS. Cell surface-bound radioligand was obtained by washing cells twice with ice-cold glycine buffer (pH 2.8), followed by a collection of the internalized fraction with 1 M NaOH. The activity in each fraction was measured in a γ-counter (Cobra II). The results are expressed as a percentage of the applied radioactivity, after subtracting the non-specific uptake in the HT-1080.wt cells (FIG. 19, panels A-D and FIG. 20).

Example 19: Saturation Binding Experiment—FAP Targeted Radiotracers

Cell Membrane Preparation: HEK-293.hFAP cells were grown to confluence, mechanically disaggregated, washed with PBS (pH 7.4) and re-suspended in 20 mM of homogenization Tris buffer (pH 7.5) containing 1.3 mM EDTA, 0.25 M sucrose, 0.7 mM bacitracin, 5 μM soybean trypsin inhibitor, and 0.7 mM PMSF. The cells were homogenized using Ultra-Turrax, and the homogenized suspension was centrifuged at 500×g for 10 min at 4° C. The supernatant was collected in centrifuge tubes (Beckman Coulter Inc., Brea, CA, USA). This procedure was then repeated 5 times. The collected supernatant was centrifuged in an ultra-centrifuge (Beckman) at 4° C. for 55 min at 49,000× g. Then, the pellet was re-suspended in 10 mM ice-cold HEPES buffer (pH 7.5), aliquoted, and stored at −80° C. The protein concentration of those membrane suspensions was determined by the Bradford method, BSA as the standard.

Saturation Experiment: The association profiles of $^{61}$Cu-labeled radioligands were studied at different concentrations, ranging from 0.075 to 50 nM, in HEK-293.hFAP cell membranes at 37° C. Each assay tube contained 170 μL of binding buffer (20 mM HEPES, pH 7.4, containing 4 mM $\mu gCl_2$, 0.2% BSA, 20 μg/L bacitracin, 20 μg/L PMSF and 200,000 KIU/L aprotinin). The incubation was initiated by adding 30 μL of radioligand solution at 10 times the final concentration and 100 μL of cell membrane suspension to yield 10 μg of protein per well. For the determination of the non-specific binding, 140 μL of the above binding buffer was added along with 30 μL of FAPI-46 to obtain (0.1 mM). Bound fractions were plotted versus the corresponding radioligand concentration at equilibrium. The dissociation constant (KD) and maximal binding capacity (Bmax) values were calculated using GraphPad Software Inc., Prism 7, San Diego, CA, USA (Table 33 and FIG. 21).

TABLE 33

| In Vitro Saturation Binding | | |
|---|---|---|
| Compound | $B_{max}$ | $K_D$ (nM) |
| [$^{61}$Cu]Cu-NODAGA-F1 | 8.6-9.2 | 1.7-2.2 |
| [$^{61}$Cu]Cu-NODAGA-F3 | 7.3-8.1 | 1.2-1.8 |
| [$^{61}$Cu]Cu-NODAGA-F2 | 7.7-8.4 | 1.4-2.0 |
| [$^{61}$Cu]Cu-NODAGA-F4 | 9.1-9.8 | 3.0-3.9 |
| [$^{61}$Cu]-NODAGA-FAPI-46 | 9.0-10.3 | 2.3-3.8 |

Example 20: Mice Studies—FAP Targeted Radiotracers

All animal experiments were conducted in accordance with Swiss animal welfare laws and regulations under the license number 30515 granted by the Veterinary Office (Department of Health) of the Canton Basel-Stadt.

Tumor Implantation: Female athymic nude-Foxn1nu/Foxn1+ mice (Envigo, The Netherlands), 4-6 weeks old, were injected subcutaneously with 5-10×106 of HT-1080.hFAP cells suspended in 100 μL of PBS on the right shoulder or on the right flank, while 5-10×106 HT-1080.wild-type cells suspended in 100 μL of PBS were injected on the contralateral shoulder or flank. The tumors were allowed to grow to an average volume of 100-200 mm3.

Biodistribution Studies: The xenografted mice were randomized (n=5 per group) and injected intravenously via the tail vein with the $^{61}$Cu-labeled radioligands (100 μL, 500 pmol, 0.8-1 MBq). Mice were euthanized 1 h and 4 h p.i. by $CO_2$ asphyxiation. Organs of interest and blood were collected, rinsed of excess blood, blotted dry, weighed, and counted in a γ-counter. The samples were counted against a suitably diluted aliquot of the injected solution as the standard and the results are expressed as the percentage of the injected activity per gram of tissue (0% I.A./g)±SD. Results are shown in Tables 35A and 35B and FIGS. 22-27.

TABLE 35A

| Biodistribution data | | | | |
|---|---|---|---|---|
| | [$^{61}$Cu]Cu-NODAGA-F1 | | [$^{61}$Cu]Cu-NODAGA-F2 | |
| Organ | 1 hour | 4 hours | 1 hour | 4 hours |
| Blood | 2.3 ± 0.1 | 1.2 ± 0.3 | 1.2 ± 0.1 | 0.5 ± 0.1 |
| Heart | 1.2 ± 0.3 | 0.7 ± 0.1 | 0.6 ± 0.1 | 0.3 ± 0.0 |
| Lung | 1.8 ± 0.0 | 0.8 ± 0.2 | 0.8 ± 0.1 | 0.4 ± 0.0 |
| Liver | 1.5 ± 0.0 | 1.0 ± 0.2 | 0.6 ± 0.1 | 0.6 ± 0.1 |
| Pancreas | 2.5 ± 0.3 | 1.4 ± 0.2 | 1.1 ± 0.2 | 0.5 ± 0.0 |
| Spleen | 0.8 ± 0.1 | 0.5 ± 0.1 | 0.4 ± 0.1 | 0.2 ± 0.0 |
| Stomach | 1.1 ± 0.2 | 0.7 ± 0.1 | 0.6 ± 0.1 | 0.3 ± 0.1 |
| Intestine | 1.7 ± 0.4 | 1.1 ± 0.4 | 0.5 ± 0.1 | 0.3 ± 0.1 |
| Adrenal | 2.3 ± 0.5 | 1.4 ± 0.2 | 1.5 ± 0.3 | 0.3 ± 0.1 |
| Kidneys | 2.4 ± 0.3 | 1.5 ± 0.5 | 1.1 ± 0.1 | 1.0 ± 0.1 |
| Muscle | 2.6 ± 0.7 | 1.3 ± 0.1 | 0.9 ± 0.1 | 0.4 ± 0.1 |
| Femur | 10.9 ± 1.1 | 4.2 ± 1.5 | 2.4 ± 0.3 | 1.6 ± 0.3 |
| HT-1080.hFAP | 12.6 ± 1.5 | 7.1 ± 3.0 | 3.5 ± 1.0 | 4.0 ± 0.6 |
| HT-1080.wt | 4.5 ± 0.6 | 2.1 ± 0.5 | 1.4 ± 0.2 | 0.9 ± 0.1 |
| Tumor mass | 0.1 ± 0.0 | 0.2 ± 0.2 | 0.4 ± 0.1 | 0.3 ± 0.1 |

*n = 5

TABLE 35B

| Biodistribution data | | | | |
|---|---|---|---|---|
| | [$^{61}$Cu]Cu-NODAGA-F3 | | [$^{61}$Cu]Cu-NODAGA-F4 | |
| Organ | 1 hour | 4 hours | 1 hour | 4 hours |
| Blood | 1.7 ± 0.1 | 0.9 ± 0.0 | 1.4 ± 0.1 | 0.4 ± 0.1 |
| Heart | 0.7 ± 0.1 | 0.5 ± 0.0 | 0.6 ± 0.0 | 0.2 ± 0.0 |
| Lung | 1.2 ± 0.1 | 0.7 ± 0.1 | 0.9 ± 0.1 | 0.3 ± 0.0 |
| Liver | 0.9 ± 0.1 | 0.7 ± 0.1 | 0.6 ± 0.1 | 0.4 ± 0.0 |
| Pancreas | 1.6 ± 0.2 | 0.9 ± 0.0 | 1.1 ± 0.1 | 0.4 ± 0.1 |
| Spleen | 0.5 ± 0.1 | 0.3 ± 0.0 | 0.4 ± 0.0 | 0.2 ± 0.0 |
| Stomach | 0.8 ± 0.1 | 0.5 ± 0.0 | 0.5 ± 0.0 | 0.2 ± 0.0 |
| Intestine | 0.8 ± 0.2 | 0.4 ± 0.1 | 0.5 ± 0.2 | 0.3 ± 0.1 |
| Adrenal | 2.1 ± 0.6 | 1.4 ± 0.3 | 1.1 ± 0.2 | 0.5 ± 0.1 |
| Kidneys | 1.6 ± 0.3 | 1.0 ± 0.2 | 1.8 ± 0.2 | 1.1 ± 0.1 |
| Muscle | 2.1 ± 0.8 | 1.1 ± 0.1 | 0.8 ± 0.2 | 0.4 ± 0.1 |
| Femur | 5.4 ± 1.2 | 3.7 ± 0.3 | 3.2 ± 0.8 | 1.2 ± 0.1 |
| HT-1080.hFAP | 7.9 ± 0.9 | 6.4 ± 2.0 | 7.4 ± 1.6 | 3.0 ± 0.8 |
| HT-1080.wt | 4.0 ± 2.2 | 1.8 ± 0.3 | 1.7 ± 0.2 | 0.6 ± 0.0 |
| Tumor mass | 0.1 ± 0.0 | 0.1 ± 0.1 | 0.3 ± 0.1 | 0.3 ± 0.1 |

[$^{61}$Cu]Cu-NODAGA-F1 showed high accumulation in FAP-positive (HT-1080.hFAP) tumor and murine-FAP-positive tissues, such as synovial tissue in the joints (e.g., joints associated with a femu).

PET/CT Imaging: Mice bearing FAP-positive and FAP-negative xenografts were injected intravenously with $^{61}$Cu-labeled radioligands of the present disclosure or $^{61}$Cu-NODAGA-FAPI-46 (100 μL/500 pmol/6-12 MBq). Mice were anesthetized with 1.5% isoflurane and dynamic PET scans were acquired during 1 hour upon injection of the radiotracer. The mice were euthanized by $CO_2$ at 4 hours p.i., and static PET scans were acquired for 30 min.

PET/CT images were acquired using β-CUBE PET scanner system (Molecubes, Gent, Belgium), with a spatial resolution of 0.85 mm and an axial field-of-view of 13 cm. Dynamic PET scans were acquired for 60 min. All PET scans were decay corrected and reconstructed into a 192×192×384 matrix by an ordered subsets maximization expectation (OSEM) algorithm using 30 iterations, a voxel size of 400×400×400 μm a 15 min per frame. CT data was used to apply attenuation correction on the PET data. The CT was imaged supine, head first, using the NanoSPECT/CT™ scanner (Bioscan Inc.). Topograms and helical CT scans of the whole mouse were first acquired using the following parameters: X-ray tube current: 177 μA, X-ray tube voltage 45 kVp, 90 seconds and 180 frames per rotation, pitch 1. CT images were reconstructed using CTReco (version r1.146), with a standard filtered back projection algorithm (exact cone beam) and post-filtered (RamLak, 100% frequency cut-off), resulting in a pixel size of 0.2 mm. Co-registered PET/CT images were visualized using maximum intensity projection (MIP) with VivoQuant software (version 4.0). (FIGS. 15, 16, 28-30).

Remaining PET activity in the mouse body 4 h p.i. prior to the 4 h scan was determined (Table 36). [$^{61}$Cu]Cu-NODAGA-FAPI-46 and [$^{61}$Cu]Cu-NODAGA-F1 showed the highest retention in the body, while [$^{61}$Cu]Cu-NODAGA-F4 presented the lowest value. Due to the physical characteristic of the radionuclide, [$^{68}$Ga]Ga-FAPI-46 was not evaluated 4 h p.i.

TABLE 36

| In Vitro PET Remaining Activity | | | |
|---|---|---|---|
| | Injected Activity (MBq) | Activity left after 4 h (MBq) | Percentage of activity left |
| [$^{61}$Cu]Cu-NODAGA-F1 | 10.07 | 1.85 | 18.4% |
| [$^{61}$Cu]Cu-NODAGA-F3 | 7.65 | 0.86 | 11.2% |
| [$^{61}$Cu]Cu-NODAGA-F2 | 12.12 | 1.31 | 10.8% |
| [$^{61}$Cu]Cu-NODAGA-F4 | 10.34 | 0.76 | 7.4% |
| [$^{61}$Cu]Cu-NODAGA-FAPI-46 | 7.25 | 1.34 | 18.9% |
| [$^{68}$Ga]Ga-FAPI-46 | 12.23 | / | / |

Example 21. [$^{61}$Cu]Cu-NODAGA-PSMA-I&T in Humans

Radiopharmaceutical preparation: The reaction is carried out in a GE Healthcare FASTlab 2 module. A 40 μg (28 nmol) aliquot of lyophilized NODAGA-PSMA-I&T (piCHEM, Austria) was dissolved in up to 6 mL 0.5 M sodium acetate (pH 8) and ascorbic acid (20 μg/mL), and transferred to a reaction vial. Then [$^{61}$Cu]$CuCl_2$ in 0.05 M hydrochloric acid (0.3-1.0 GBq/mL) (3 mL) was added to the NODAGA-PSMA-I&T solution, reaching a pH between 4.5 and 6.5. The obtained reaction solution was incubated for 10 min at room temperature (approx. 20-25 C) and dispensed to the product vial (20 mL sterile evacuated vial) over a sterile Cathivex-GV 25 mm PVDF 0.22 m filter. The product was finally diluted with 0.900 sodium chloride for injection (B. Braun, Germany) up to 12 mL. Quality controls are performed to verify compliance with the specifications reported in Table 37. [$^{61}$Cu]Cu-NODAGA-PSMA-I&T is produced with high radiochemical purity (≥950%). Therefore, no further purification step is necessary. All the chemicals used are trace metal grade.

TABLE 37

| Specifications of [$^{61}$Cu]Cu-NODAGA-PSMA-I&T. | | |
|---|---|---|
| Parameter | Test Method | Values |
| Appearance | Visual inspection | Colorless, clear solution |
| Bacterial endotoxin content | LAL test | <17.5 EU/mL |
| Free $^{61}$Cu | Radio-TLC test | ≤5% |
| pH | pH strips | 5.0-7.0 |
| Activity concentration | Dose calibrator | 8-15 MBq/mL |
| Radiochemical purity | Radio-TLC test | ≥95% |
| | Radio-HPLC test | ≥95% |
| Radionuclidic identity | Gamma-spectrometry# | Peaks at 511 ± 30 keV and 656 ± 30 keV |
| Radionuclidic purity* $^{56}$Co, $^{57}$Co, $^{58}$Co, $^{60}$Co | Gamma-spectrometry# | ≤0.01% (in sum) |
| Radionuclidic purity* $^{61}$Cu | Gamma-spectrometry# | ≥99.99% |
| Molar Activity | Dose calibrator measurement | 16-80 MBq/nmol |
| Sterile filter integrity | Bubble point test | 3.0-4.5 bar |
| Sterility* | Sterility test | No microbial growth |

*after release (i.e., analytic validations are complete and a provided pharmaceutical composition is to be administered to a patient).
#Gamma Spec data is obtained from [$^{61}$Cu]$CuCl_2$ starting material.

Patient Injection

A [$^{61}$Cu]Cu-NODAGA-PSMA-I&T dose of 2.84 mCi (104 MBq) was administered intravenously to a 48-years old patient with known metastatic prostate cancer. The patient was coadministered 10 μg furosemide (Lasix®, Sanofi-Aventis, Frankfurt, Germany). The imaging was performed at 3 hours following radiotracer administration on a Biograph Vision 600 (Siemens, Germany) PET/CT scanner. These images, shown in FIG. 35, were obtained from the skull to mid-thigh and reconstructed into multiplanar PT, CT, and fused PET/CT images. CT was used for attenuation correction.

Results

Radiotracer accumulation was noted in multi-focal osseous and hepatic metastases, as well as in the expected physiologic distribution of PSMA-targeted tracers in the lacrimal glands, salivary glands, liver, spleen, kidneys, ureters, bladder, and proximal small bowel, FIG. 35.

Example 22—Biodistribution Studies on [61Cu]Cu-NODAGA-LM3 and [$^{61}$Cu]Cu-(R)-)NODAGA-LM3

Quantitative biodistribution studies were conducted in HEK-SST2 tumor-xenografted mice after intravenous injection into the tail vein of the tested radiotracer as follows: [$^{61}$Cu]Cu-NODAGA-LM3 and [$^{61}$Cu]Cu-(R)-NODAGA-LM3 at injected amounts of 100 μL/20 pmol/1.0-1.2 MBq (100 μL, 20 pmol, 1.0-1.2 MBq). The mice were randomly distributed in groups and euthanized at 4 hours post-injection. The organs of interest were collected, rinsed, blotted, weighed, and their respective radioactivity was counted in a gamma counter. Table 39 tabulates the results expressed as percentage of injected activity per gram (0% IA/g), representing the mean±standard deviation of n=4 mice per group and they were obtained by extrapolation from counts of an aliquot taken from the injected solution as standard. PET/CT imaging of [$^{61}$Cu]Cu-NODAGA-LM3 and [$^{61}$Cu]Cu-(R)-) NODAGA-LM3 was performed as described in Example 8 for [$^{61}$Cu]Cu-labeled somatostatin radiotracers in HEK-SST2 xenografts (100 μL/200 pmol/3-5 MBq). Dynamic PET/CT imaging was performed from 0 to 60 min after injection and static PET/CT imaging was performed at 240 min after injection, see FIG. 36.

TABLE 39

Biodistribution data of [$^{61}$Cu]Cu-NODAGA-LM3 and [$^{61}$Cu]Cu-(R)-NODAGA-LM3 in HEK-SST2 xenografts at 4 hours post-injection. Results are expressed as mean of the % injected activity per gram of tissue (% IA/g) ± standard deviation (SD).

| Organ | [$^{61}$Cu]Cu-NODAGA-LM3 | [$^{61}$Cu]Cu-(R)NODAGA-LM3 | p values |
|---|---|---|---|
| Blood | 0.11 ± 0.02 | 0.10 ± 0.01 | |
| Heart | 0.13 ± 0.02 | 0.17 ± 0.02 | |
| Lung | 0.32 ± 0.05 | 0.42 ± 0.05 | |
| Liver | 0.44 ± 0.06 | 0.73 ± 0.06 | |
| Pancreas | 0.43 ± 0.12 | 0.44 ± 0.24 | 0.94 |
| Spleen | 0.14 ± 0.01 | 0.17 ± 0.02 | |
| Stomach | 0.68 ± 0.15 | 0.78 ± 0.14 | 0.36 |
| Intestine | 0.43 ± 0.08 | 0.58 ± 0.13 | |
| Adrenal | 0.60 ± 0.15 | 0.61 ± 0.18 | |
| Kidneys | 4.59 ± 0.41 | 3.87 ± 0.51 | 0.07 |
| Muscle | 0.06 ± 0.02 | 0.10 ± 0.02 | |
| Bone | 0.31 ± 0.07 | 0.42 ± 0.12 | |
| Pituitary | 2.96 ± 0.62 | 3.64 ± 0.31 | 0.15 |
| SSTR2-tumor | 20.39 ± 4.20 | 18.97 ± 2.11 | 0.57 |

[$^{61}$Cu]Cu-NODAGA-LM3, the construct prepared from a enantiomeric mixture of (S)NODAGA and (R)NODAGA moieties, and [$^{61}$Cu]Cu-(R)NODAGA-LM3, the construct prepared from enantiomerically pure R enantiomer of NODAGA, showed high accumulation in SST2-positive (HEK-SST2) tumor and SST2-positive tissues, such as the stomach and the pancreas and elimination via the kidneys. Uptake in the remaining organs was low, resulting in a high tumor-to-background ratio. The [$^{61}$Cu]Cu-NODAGA-LM3 results were statistically evaluated vs [$^{61}$Cu]Cu-(R) NODAGA-LM3 results via unpaired two-tailed t test and did not show statistical difference (p values >0.05) for tumor, kidneys, and the SST positive organs such as the pancreas, stomach and pituitary.

Based on these data, it can be asserted that the enantiomerically pure composition displays the same pharmacokinetics as the mixture of enantiomers. The biodistribution and high tumor-to-background ratio observed in the SST2-xenograft data are supportive of the superiority of the SSTR2 antagonist vs SSTR2 agonists, in combination with high stability afforded by use of the stable NODAGA chelator for copper.

The uptake of [$^{61}$Cu]Cu-NODAGA-LM3 in the excretion organs is low, this leads to an improved tumor-to-background contrast. The diastereomeric mixture, [$^{61}$Cu]Cu-NODAGA-LM3, and the pure [$^{61}$Cu]Cu-(R)-NODAGA-LM3 constructs show the same distribution pattern (FIG. 36).

Example 23: Saturation Binding Experiment—[61Cu]Cu-NODAGA-LM3

Cell Membrane Preparation: HEK-SST2 cells were grown to confluence, mechanically disaggregated, washed with PBS (pH 7.4) and re-suspended in 20 mM of homogenization Tris buffer (pH 7.5) containing 1.3 mM EDTA, 0.25 M sucrose, 0.7 mM bacitracin, 5 μM soybean trypsin inhibitor, and 0.7 mM PMSF. The cells were homogenized using Ultra-Turrax, and the homogenized suspension was centrifuged at 500×g for 10 min at 4° C. The supernatant was collected in centrifuge tubes (Beckman Coulter Inc., Brea, CA, USA). This procedure was then repeated 5 times. The collected supernatant was centrifuged in an ultra-centrifuge (Beckman) at 4° C. for 55 min at 49,000× g. Then, the pellet was re-suspended in 10 mM ice-cold HEPES buffer (pH 7.5), aliquoted, and stored at −80° C. The protein concentration of those membrane suspensions was determined by the Bradford method, BSA as the standard.

Saturation Experiment: The association profiles of [$^{61}$Cu] Cu-NODAGA-LM3 was studied at different concentrations, ranging from 0.075 to 10 nM, in HEK-SST2 cell membranes at 37° C. Each assay tube contained 170 μL of binding buffer (20 mM HEPES, pH 7.4, containing 4 mM $\mu gCl_2$, 0.2% BSA, 20 μg/L bacitracin, 20 μg/L PMSF and 200,000 KIU/L aprotinin). The incubation was initiated by adding 30 μL of radioligand solution at 10 times the final concentration and 100 μL of cell membrane suspension to yield 10 μg of protein per well. For the determination of the non-specific binding, 140 μL of the above binding buffer was added along with 1,000-fold excess of NODAGA-LM3 to obtain (final concentration 0.1 μM). Bound fractions were plotted versus the corresponding radioligand concentration at equilibrium. The dissociation constant (KD) and maximal binding capacity (Bmax) values were calculated using GraphPad Software Inc., Prism 7, San Diego, CA, USA (FIG. 37)

6. EQUIVALENTS AND INCORPORATION BY REFERENCE

While the provided disclosure has been particularly shown and described with reference to a preferred embodiment and various alternate embodiments, it will be understood by persons skilled in the relevant art that various changes in form and details can be made therein without departing from the spirit and scope of the provided disclosure.

All references, issued patents, and patent applications cited within the body of the instant specification, are hereby incorporated by reference in their entirety, for all purposes. In particular, U.S. Provisional Patent Application Nos. 63/409,684 (filed Sep. 23, 2022); 63/409,687 (filed Sep. 23, 2022); 63/416,479 (filed Oct. 14, 2022); 63/520,329 (filed Aug. 17, 2023); and 63/520,323 (filed Aug. 17, 2023) are hereby incorporated by reference in their entirety. Additionally, the following U.S. non-provisional patent applications are also incorporated by reference in their entirety:

the application titled "SOLID TARGET SYSTEMS FOR THE PRODUCTION OF HIGH PURITY RADIONUCLIDE COMPOSITIONS" filed Sep. 25, 2023 as U.S. patent application Ser. No. 18/474,211; and the application titled "FIBROBLAST ACTIVATION PROTEIN (FAP) INHIBITORS, FAP CONJUGATES, AND DIAGNOSTIC AND THERAPEUTIC USES THEREOF" filed Sep. 25, 2023 as U.S. patent application Ser. No. 18/474,209.

What is claimed is:

1. A pharmaceutical composition comprising a compound and a pharmaceutically acceptable excipient, wherein the compound is of Formula X*:

Formula X*

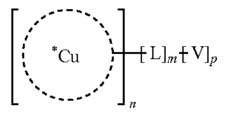

or is a pharmaceutically acceptable salt thereof; wherein:

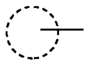

is a chelating moiety;

the chelating moiety is NODAGA;

*Cu is $^{61}$Cu obtained by deuteron irradiation of $^{nat}$Ni or $^{60}$Ni on a niobium backing or by proton irradiation of $^{61}$Ni on a niobium backing;

L comprises

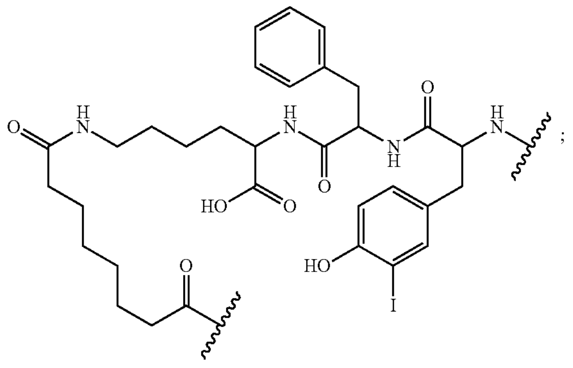 [SMILES: *NC(Cc1ccc(O)c(I)c1)C(=O)NC(Cc1ccccc1)C(=O)NC(CCCCNC(=O)CCCCCCC(*)=O)C(=O)O]

V is a targeting moiety that binds to PSMA;

n is 1;

m is 1; and p is 1, and wherein, (a) the composition is characterized at end of synthesis by radiochemical purity of ≥95%;

(b) the composition is characterized at end of synthesis by radionuclidic purity for $^{61}$Cu of ≥99.999%;

(c) the $^{61}$Cu is characterized at end of synthesis by sum of radionuclidic impurities of ≤6000 Bq/g;

(d) the $^{61}$Cu is characterized at end of synthesis+12 hours by radionuclidic purity of ≥99.985%; or (e) the $^{61}$Cu is characterized at end of synthesis by $^{56}$Co activity concentration of ≤800 Bq/g and $^{58}$Co activity concentration of ≤800 Bq/g.

2. The composition of claim 1, wherein the compound is Formula 10*:
Formula 10*
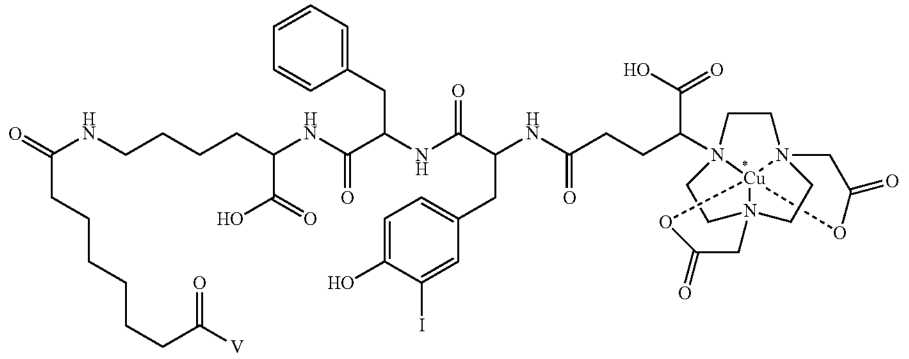
or is a pharmaceutically acceptable salt thereof.
3. The composition of claim 2, wherein V comprises the structure:
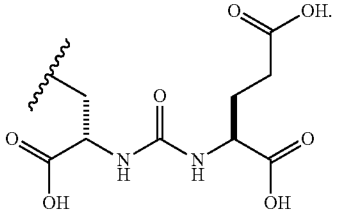 [SMILES: *C[C@H](NC(=O)N[C@@H](CCC(=O)O)C(=O)O)C(=O)O]
4. The composition of claim 2, wherein the compound is of the structure:
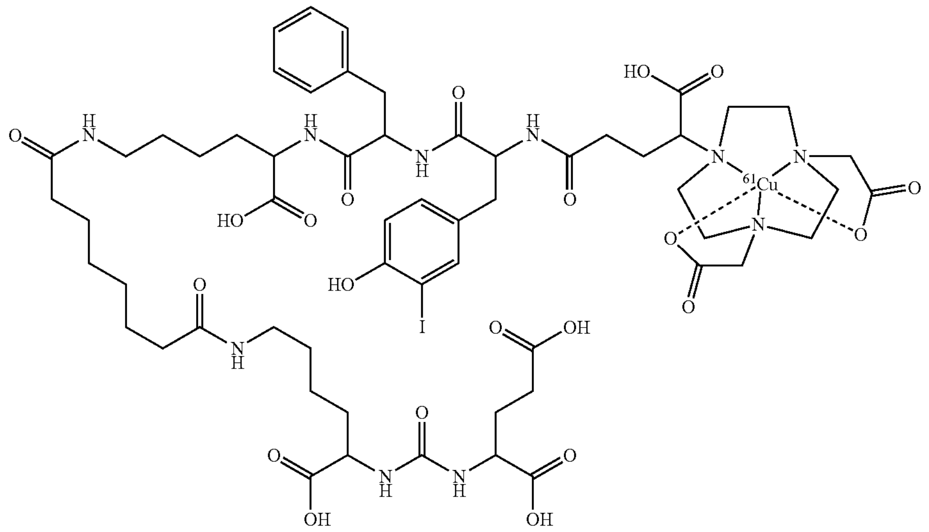
or is a pharmaceutically acceptable salt thereof.

5. The composition of claim 2, wherein the compound is of the structure:

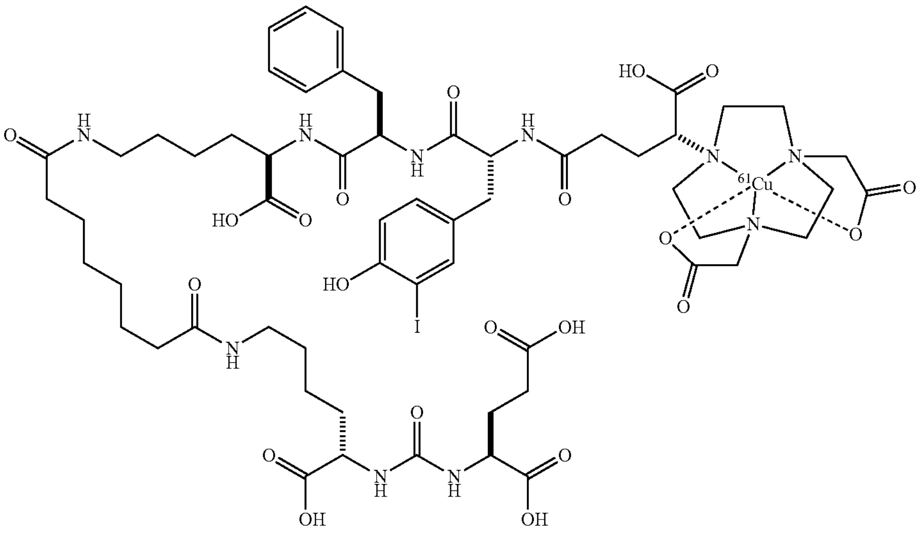

or is a pharmaceutically acceptable salt thereof.

6. The composition of claim 2, wherein the composition is characterized at end of synthesis by radiochemical purity of ≥97%.

7. The composition of claim 2, wherein the composition is characterized at end of synthesis by radiochemical purity of ≥98%.

8. The composition of claim 2, wherein the composition is characterized at end of synthesis by radiochemical purity of ≥99%.

9. The composition of claim 2, wherein the composition is characterized by pH of 4-7.

10. The composition of claim 2, wherein the composition is characterized at end of synthesis by radionuclidic purity of the sum of radiocobalt of ≤0.05%.

11. A method of generating one or more images of a subject, comprising:

administering to the subject an effective amount of a composition according to claim 2; and generating one or more images of at least a part of the subject's body.

12. The method of claim 11, wherein the one or more images is generated using positron emission tomography (PET) or single-photon emission computerized tomography (SPECT).

13. A method of detecting PSMA-receptor-expressing tumors in a human subject, the method comprising;

administering to the subject an effective amount of the composition of claim 2; and generating one or more images of a part of a subject's body.

14. A theranostic method comprising:

(a) administering to a subject an effective amount of the composition according to claim 2;

(b) generating one or more images of at least a part of the subject's body; and (c) administering to the subject an effective amount of a composition comprising a compound, wherein the compound is of the structure:

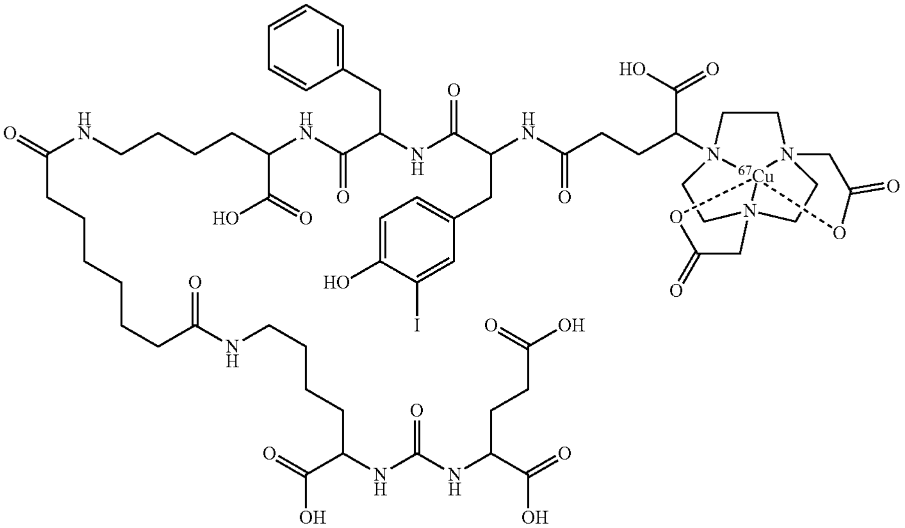

or is a pharmaceutically acceptable salt thereof.

15. A method of treating a cancer that expresses a PSMA receptor, the method comprising:

administering to the subject a diagnostically effective amount of the composition of claim 2;

generating one or more images of at least a part of a subject's body;

administering a therapeutically effective amount of a compound, wherein the compound is of the structure:

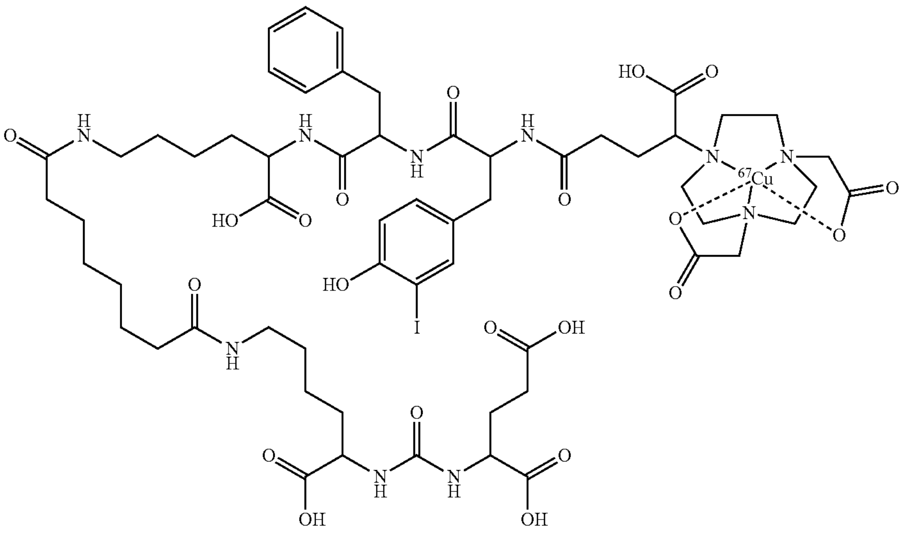

or is a pharmaceutically acceptable salt thereof.

16. The method of claim 15, wherein the cancer is prostate cancer.

17. The composition of claim 2, wherein the composition at end of synthesis is characterized by one or more of:

a $^{110}$mAg specific activity ≤0.1 Bq/g;

a $^{108}$mAg specific activity ≤0.1 Bq/g; or a $^{109}$Cd specific activity ≤0.1 Bq/g.

18. The composition of claim 2, wherein the composition at end of synthesis is characterized by having:

a $^{56}$Co specific activity ≤1500 Bq/g;

a $^{57}$Co specific activity ≤100 Bq/g;

a $^{58}$Co specific activity ≤15000 Bq/g; and a $^{60}$Co specific activity ≤15 Bq/g.

19. The composition of claim 2, wherein the chemical purity of the composition at end of synthesis is characterized by having Al≤1.2 ng/MBq;

Co≤0.2 ng/MBq;

Fe≤1.7 ng/MBq;

Pb≤0.8 ng/MBq; or

Zn≤0.8 ng/MBq.

20. The composition of claim 2, wherein the composition at end of synthesis is characterized by activity concentration of ≥8 MBq/mL.

21. The composition of claim 2, wherein the composition at end of synthesis is characterized by activity concentration of 8-15 MBq/mL.

22. The composition of claim 2, wherein the $^{61}$Cu is characterized at end of synthesis by radionuclidic purity of ≥99.9999%.

23. The composition of claim 2, wherein the composition is characterized at end of synthesis by radionuclidic purity of the sum of radiocobalt of ≤0.01%.

24. The composition of claim 2, wherein the 61 Cu is characterized at end of synthesis by $^{56}$Co activity concentration of ≤80 Bq/g.

25. The composition of claim 2, wherein the $^{61}$Cu is characterized at end of synthesis by $^{56}$Co activity concentration of ≤8 Bq/g.

26. The composition of claim 2, wherein the $^{61}$Cu is characterized at end of synthesis by sum of radionuclidic impurities of ≤4000 Bq/g.

27. The composition of claim 2, wherein the $^{61}$Cu is characterized at end of synthesis by sum of radionuclidic impurities of ≤2000 Bq/g.

28. The composition of claim 2, wherein the composition is characterized at end of synthesis by radiochemical purity of ≥95%.

29. The composition of claim 2, wherein the composition is characterized at end of synthesis by radionuclidic purity for 61Cu of ≥99.999%.

30. The composition of claim 2, wherein the $^{61}$Cu is characterized at end of synthesis by sum of radionuclidic impurities of ≤6000 Bq/g.

31. The composition of claim 2, wherein the $^{61}$Cu is characterized at end of synthesis+12 hours by radionuclidic purity of ≥99.985%.

32. The composition of claim 2, wherein the $^{61}$Cu is characterized at end of synthesis by $^{56}$Co activity concentration of ≤800 Bq/g and $^{58}$Co activity concentration of ≤800 Bq/g.

33. The composition of claim 2, wherein (a) the composition is characterized at end of synthesis by radiochemical purity of ≥ 95%;

(b) the composition is characterized at end of synthesis by radionuclidic purity for 61Cu of ≥99.999%;

(c) the $^{61}$Cu is characterized at end of synthesis by sum of radionuclidic impurities of ≤6000 Bq/g;

(d) the $^{61}$Cu is characterized at end of synthesis+12 hours by radionuclidic purity of ≥99.985%; and (e) the $^{61}$Cu is characterized at end of synthesis by $^{56}$Co activity concentration of ≤800 Bq/g and $^{58}$Co activity concentration of ≤800 Bq/g.

34. The composition of claim 2, wherein (a) the composition is characterized at end of synthesis by radiochemical purity of >95%;

(b) the composition is characterized at end of synthesis by radionuclidic purity for $^{61}Cu$ of ≥99.999%;

(d) the $^{61}Cu$ is characterized at end of synthesis+12 hours by radionuclidic purity of ≥99.985%; and (e) the $^{61}Cu$ is characterized at end of synthesis by $^{56}Co$ activity concentration of ≤800 Bq/g and $^{58}Co$ activity concentration of ≤800 Bq/g.

35. The composition of claim 2, wherein (a) the composition is characterized at end of synthesis by radiochemical purity of ≥95%;

(b) the composition is characterized at end of synthesis by radionuclidic purity for 61Cu of ≥99.999%;

(c) the $^{61}Cu$ is characterized at end of synthesis by sum of radionuclidic impurities of ≤6000 Bq/g; and (d) the $^{61}Cu$ is characterized at end of synthesis+12 hours by radionuclidic purity of ≥99.985%.

36. The composition of claim 2, wherein, (a) the composition is characterized at end of synthesis by radiochemical purity of 95%;

(b) the composition is characterized at end of synthesis by radionuclidic purity for $^{61}Cu$ of ≥99.999%; and (d) the $^{61}Cu$ is characterized at end of synthesis+12 hours by radionuclidic purity of ≥99.985%.

37. The composition of claim 2, wherein (a) the composition is characterized at end of synthesis by radiochemical purity of ≥ 95%; and (b) the composition is characterized at end of synthesis by radionuclidic purity for 61Cu of ≥99.999%.

38. The composition of claim 5, wherein the composition is characterized at end of synthesis by radiochemical purity of ≥97%.

39. The composition of claim 5, wherein the composition is characterized at end of synthesis by radiochemical purity of ≥98%.

40. The composition of claim 5, wherein the composition is characterized at end of synthesis by radiochemical purity of ≥99%.

41. The composition of claim 5, wherein the composition is characterized by pH of 4-7.

42. The composition of claim 5, wherein the composition is characterized at end of synthesis by radionuclidic purity of the sum of radiocobalt of ≤0.05%.

43. The composition of claim 5, wherein the composition at end of synthesis is characterized by one or more of:

a $^{110}$mAg specific activity ≤0.1 Bq/g;

a $^{108}$mAg specific activity ≤0.1 Bq/g; or a $^{109}Cd$ specific activity ≤0.1 Bq/g.

44. The composition of claim 5, wherein the composition at end of synthesis is characterized by having:

a $^{56}Co$ specific activity ≤1500 Bq/g;

a $^{57}Co$ specific activity ≤100 Bq/g;

a $^{58}Co$ specific activity ≤15000 Bq/g; and a $^{60}Co$ specific activity ≤15 Bq/g.

45. The composition of claim 5, wherein the chemical purity of the composition at end of synthesis is characterized by having Al≤1.2 ng/MBq;

Co≤0.2 ng/MBq;

Fe≤1.7 ng/MBq;

Pb≤0.8 ng/MBq; or

Zn≤0.8 ng/MBq.

46. The composition of claim 5, wherein the composition at end of synthesis is characterized by activity concentration of ≥8 MBq/mL.

47. The composition of claim 5, wherein the composition at end of synthesis is characterized by activity concentration of 8-15 MBq/mL.

48. The composition of claim 5, wherein the $^{61}Cu$ is characterized at end of synthesis by radionuclidic purity of ≥99.9999%.

49. The composition of claim 5, wherein the composition is characterized at end of synthesis by radionuclidic purity of the sum of radiocobalt of ≤0.01%.

50. The composition of claim 5, wherein the $^{61}Cu$ is characterized at end of synthesis by $^{56}Co$ activity concentration of ≤80 Bq/g.

51. The composition of claim 5, wherein the $^{61}Cu$ is characterized at end of synthesis by $^{56}Co$ activity concentration of ≤8 Bq/g.

52. The composition of claim 5, wherein the $^{61}Cu$ is characterized at end of synthesis by sum of radionuclidic impurities of ≤4000 Bq/g.

53. The composition of claim 5, wherein the $^{61}Cu$ is characterized at end of synthesis by sum of radionuclidic impurities of ≤2000 Bq/g.

54. The composition of claim 5, wherein the composition is characterized at end of synthesis by radiochemical purity of ≥95%.

55. The composition of claim 5, wherein the composition is characterized at end of synthesis by radionuclidic purity for 61Cu of ≥99.999%.

56. The composition of claim 5, wherein the $^{61}Cu$ is characterized at end of synthesis by sum of radionuclidic impurities of ≤6000 Bq/g.

57. The composition of claim 5, wherein the $^{61}Cu$ is characterized at end of synthesis+12 hours by radionuclidic purity of ≥99.985%.

58. The composition of claim 5, wherein the $^{61}Cu$ is characterized at end of synthesis by $^{56}Co$ activity concentration of ≤800 Bq/g and $^{58}Co$ activity concentration of ≤800 Bq/g.

59. The composition of claim 5, wherein (a) the composition is characterized at end of synthesis by radiochemical purity of ≥95%;

(b) the composition is characterized at end of synthesis by radionuclidic purity for 61Cu of ≥99.999%;

(c) the $^{61}Cu$ is characterized at end of synthesis by sum of radionuclidic impurities of ≤6000 Bq/g;

(d) the $^{61}Cu$ is characterized at end of synthesis+12 hours by radionuclidic purity of ≥99.985%; and (e) the $^{61}Cu$ is characterized at end of synthesis by $^{56}Co$ activity concentration of ≤800 Bq/g and $^{58}Co$ activity concentration of ≤800 Bq/g.

60. The composition of claim 5, wherein (a) the composition is characterized at end of synthesis by radiochemical purity of ≥95%;

(b) the composition is characterized at end of synthesis by radionuclidic purity for 61Cu of ≥99.999%;

(d) the $^{61}Cu$ is characterized at end of synthesis+12 hours by radionuclidic purity of ≥99.985%; and (e) the $^{61}Cu$ is characterized at end of synthesis by $^{56}Co$ activity concentration of ≤800 Bq/g and $^{58}Co$ activity concentration of ≤800 Bq/g.

61. The composition of claim 5, wherein (a) the composition is characterized at end of synthesis by radiochemical purity of ≥95%;

(b) the composition is characterized at end of synthesis by radionuclidic purity for 61Cu of ≥99.999%;

(c) the $^{61}Cu$ is characterized at end of synthesis by sum of radionuclidic impurities of ≤6000 Bq/g; and (d) the $^{61}Cu$ is characterized at end of synthesis+12 hours by radionuclidic purity of ≥99.985%.

62. The composition of claim 5, wherein (a) the composition is characterized at end of synthesis by radiochemical purity of ≥95%;

(b) the composition is characterized at end of synthesis by radionuclidic purity for 61Cu of ≥99.999%; and (d) the $^{61}Cu$ is characterized at end of synthesis+12 hours by radionuclidic purity of ≥99.985%.

63. The composition of claim 5, wherein (a) the composition is characterized at end of synthesis by radiochemical purity of ≥95%; and (b) the composition is characterized at end of synthesis by radionuclidic purity for 61Cu of ≥99.999%.

64. A method of generating one or more images of a subject, comprising:

administering to the subject an effective amount of a composition according to claim 5; and generating one or more images of at least a part of the subject's body.

65. The method of claim 64, wherein the one or more images is generated using positron emission tomography (PET) or single-photon emission computerized tomography (SPECT).

66. A method of detecting PSMA-receptor-expressing tumors in a human subject, the method comprising;

administering to the subject an effective amount of the composition of claim 5; and generating one or more images of a part of a subject's body.

67. A theranostic method comprising:

(a) administering to a subject an effective amount of the composition according to claim 5;

(b) generating one or more images of at least a part of the subject's body; and (c) administering to the subject an effective amount of a composition comprising a compound, wherein the compound is of the structure:

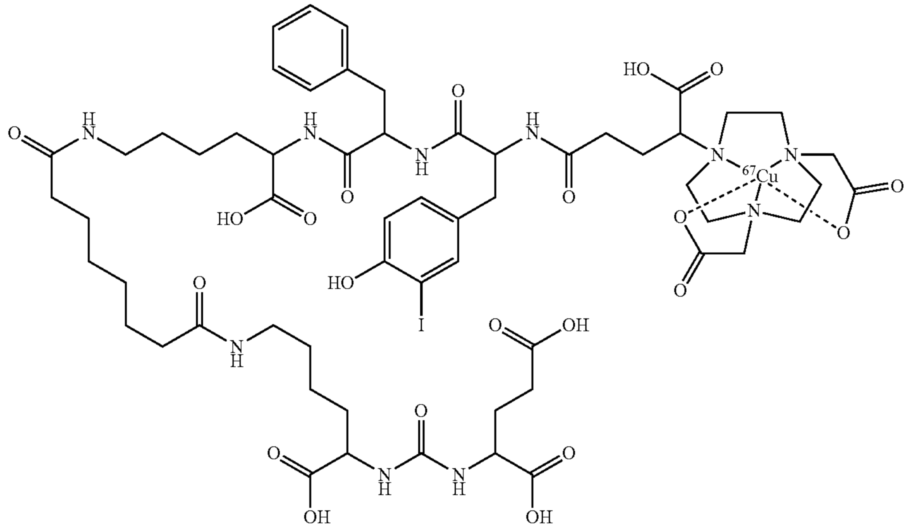

or is a pharmaceutically acceptable salt thereof.

68. A method of treating a cancer that expresses a PSMA receptor, the method comprising:

administering to the subject a diagnostically effective amount of the composition of claim 5;

generating one or more images of at least a part of a subject's body;

administering a therapeutically effective amount of a compound, wherein the compound is of the structure:

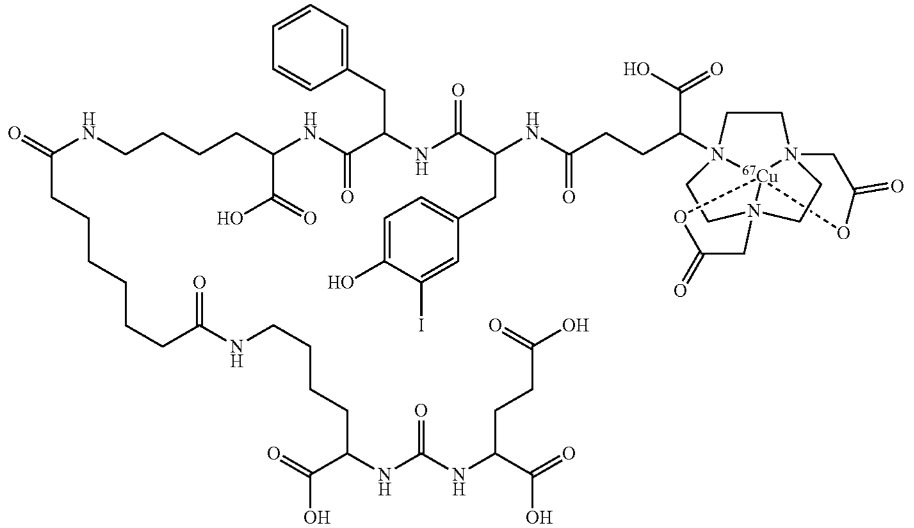

or is a pharmaceutically acceptable salt thereof.

69. The method of claim 68, wherein the cancer is prostate cancer.

* * * * *